United States Patent
Boss et al.

(10) Patent No.: US 11,839,613 B2
(45) Date of Patent: *Dec. 12, 2023

(54) PYRIMIDINE DERIVATIVES AS PGE2 RECEPTOR MODULATORS

(71) Applicant: IDORSIA PHARMACEUTICALS LTD, Allschwil (CH)

(72) Inventors: Christoph Boss, Allschwil (CH); Olivier Corminboeuf, Allschwil (CH); Heinz Fretz, Gunten (CH); Isabelle Lyothier, Allschwil (CH); Davide Pozzi, Allschwil (CH); Sylvia Richard-Bildstein, Allschwil (CH); Hervé Siendt, Allschwil (CH); Thierry Sifferlen, Allschwil (CH)

(73) Assignee: Idorsia Pharmaceuticals Ltd, Allschwil (CH)

( * ) Notice: Subject to any disclaimer, the term of this patent is extended or adjusted under 35 U.S.C. 154(b) by 50 days.

This patent is subject to a terminal disclaimer.

(21) Appl. No.: 16/614,209

(22) PCT Filed: May 17, 2018

(86) PCT No.: PCT/EP2018/062844
§ 371 (c)(1),
(2) Date: Nov. 15, 2019

(87) PCT Pub. No.: WO2018/210988
PCT Pub. Date: Nov. 22, 2018

(65) Prior Publication Data
US 2021/0113559 A1    Apr. 22, 2021

(30) Foreign Application Priority Data

May 18, 2017    (WO) ................. PCT/EP2017/061989

(51) Int. Cl.
| | |
|---|---|
| A61K 31/506 | (2006.01) |
| A61K 45/06 | (2006.01) |
| C07D 409/12 | (2006.01) |
| C07D 409/14 | (2006.01) |
| C07D 239/26 | (2006.01) |
| A61K 31/505 | (2006.01) |

(Continued)

(52) U.S. Cl.
CPC .......... *A61K 31/506* (2013.01); *A61K 31/505* (2013.01); *A61K 31/5355* (2013.01); *A61K 45/06* (2013.01); *A61P 35/00* (2018.01); *C07D 239/26* (2013.01); *C07D 401/12* (2013.01); *C07D 401/14* (2013.01); *C07D 403/12* (2013.01); *C07D 405/12* (2013.01); *C07D 405/14* (2013.01); *C07D 409/12* (2013.01); *C07D 409/14* (2013.01); *C07D 413/12* (2013.01); *C07D 413/14* (2013.01); *C07D 417/14* (2013.01)

(58) Field of Classification Search
None
See application file for complete search history.

(56) References Cited

U.S. PATENT DOCUMENTS

| | | |
|---|---|---|
| 5,948,786 A | 9/1999 | Fujiwara et al. |
| 9,518,044 B2 | 12/2016 | Jiang et al. |

(Continued)

FOREIGN PATENT DOCUMENTS

| | | |
|---|---|---|
| WO | WO 2001/072302 | 10/2001 |
| WO | WO 2002/032422 | 4/2002 |

(Continued)

OTHER PUBLICATIONS

Take et al., Prostaglandin E Receptor 4 Antagonist in Cancer Immunotherapy: Mechanisms of Action. Frontiers in Immunology, 2020, 11, p. 1-7.*

(Continued)

*Primary Examiner* — Po-Chih Chen
(74) *Attorney, Agent, or Firm* — Hoxie & Associates LLC

(57) ABSTRACT

The present invention relates to pyrimidine derivatives of formula (I)

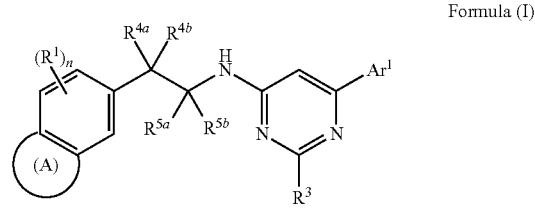

Formula (I)

wherein $(R^1)_n$, $R^3$, $R^{4a}$, $R^{4b}$, $R^{5a}$, $R^{5b}$ and $Ar^1$ are as described in the description and their use in the treatment of cancer by modulating an immune response comprising a reactivation of the immune system in the tumor. The invention further relates to novel benzofurane and benzothiophene derivatives of formula (II) and their use as pharmaceuticals, to their preparation, to pharmaceutically acceptable salts thereof, and to their use as pharmaceuticals, to pharmaceutical compositions containing one or more compounds of formula (I), and especially to their use as modulators of the prostaglandin 2 receptors EP2 and/or EP4.

20 Claims, No Drawings

(51) Int. Cl.
  C07D 405/14    (2006.01)
  C07D 405/12    (2006.01)
  C07D 413/14    (2006.01)
  C07D 401/14    (2006.01)
  A61K 31/5355   (2006.01)
  C07D 417/14    (2006.01)
  A61P 35/00     (2006.01)
  C07D 401/12    (2006.01)
  C07D 403/12    (2006.01)
  C07D 413/12    (2006.01)

(56) References Cited

U.S. PATENT DOCUMENTS

| | | |
|---|---|---|
| 11,241,431 B2 | 2/2022 | Fretz et al. |
| 11,325,899 B2 | 5/2022 | Boss et al. |
| 11,446,298 B2 | 9/2022 | Boss et al. |
| 2008/0280891 A1 | 11/2008 | Kelly et al. |
| 2013/0225528 A1 | 8/2013 | Wang et al. |
| 2020/0069686 A1 | 3/2020 | Fretz et al. |
| 2020/0179383 A1 | 6/2020 | Boss et al. |
| 2021/0115031 A1 | 4/2021 | Boss et al. |
| 2022/0175775 A1 | 6/2022 | Fretz et al. |

FOREIGN PATENT DOCUMENTS

| | | |
|---|---|---|
| WO | WO 2002/032900 | 4/2002 |
| WO | WO 2002/050032 | 6/2002 |
| WO | WO 2002/050033 | 6/2002 |
| WO | WO 2002/064564 | 8/2002 |
| WO | WO 2003/086390 | 10/2003 |
| WO | WO 2003/087061 | 10/2003 |
| WO | WO 2003/099857 | 12/2003 |
| WO | WO 2004/067524 | 8/2004 |
| WO | WO 2005/019218 | 3/2005 |
| WO | WO 2005/021508 | 3/2005 |
| WO | WO 2005/026129 | 3/2005 |
| WO | WO 2005/037812 | 4/2005 |
| WO | WO 2005/105732 | 11/2005 |
| WO | WO 2005/105733 | 11/2005 |
| WO | WO 2006/044732 | 4/2006 |
| WO | WO 2006/122403 | 11/2006 |
| WO | WO 2006/128129 | 11/2006 |
| WO | WO 2007/121280 | 10/2007 |
| WO | WO 2007/121578 | 11/2007 |
| WO | WO 2007/143825 | 12/2007 |
| WO | WO 2008/006583 | 1/2008 |
| WO | WO 2008/008059 | 1/2008 |
| WO | WO 2008/017164 | 2/2008 |
| WO | WO 2008/039882 | 4/2008 |
| WO | WO 2008/104055 | 9/2008 |
| WO | WO 2008/116304 | 10/2008 |
| WO | WO 2008/123207 | 10/2008 |
| WO | WO 2008/152093 | 12/2008 |
| WO | WO 2009/005076 | 1/2009 |
| WO | WO 2009/047359 | 4/2009 |
| WO | WO 2009/105220 | 8/2009 |
| WO | WO 2009/139373 | 11/2009 |
| WO | WO 2010/019796 | 2/2010 |
| WO | WO 2010/032123 | 3/2010 |
| WO | WO 2010/034110 | 4/2010 |
| WO | WO 2011/022348 | 2/2011 |
| WO | WO 2011/063181 | 5/2011 |
| WO | WO 2011/144742 | 11/2011 |
| WO | WO 2012/039972 | 3/2012 |
| WO | WO 2012/043634 | 4/2012 |
| WO | WO 2012/066065 | 5/2012 |
| WO | WO 2012/066070 | 5/2012 |
| WO | WO 2012/076063 | 6/2012 |
| WO | WO 2012/103071 | 8/2012 |
| WO | WO 2012/127032 | 9/2012 |
| WO | WO 2012/149528 | 11/2012 |
| WO | WO 2012/177618 | 12/2012 |
| WO | WO 2013/004290 | 1/2013 |
| WO | WO 2013/020945 | 2/2013 |
| WO | WO 2013/090552 | 6/2013 |
| WO | WO 2013/163190 | 10/2013 |
| WO | WO 2014/004229 | 1/2014 |
| WO | WO 2014/004230 | 1/2014 |
| WO | WO 2014/044755 | 3/2014 |
| WO | WO 2014/084778 | 6/2014 |
| WO | WO 2014/086739 | 6/2014 |
| WO | WO 2014/122267 | 8/2014 |
| WO | WO 2014/126746 | 8/2014 |
| WO | WO 2014/186218 | 11/2014 |
| WO | WO 2014/191929 | 12/2014 |
| WO | WO 2014/200075 | 12/2014 |
| WO | WO 2015/033299 | 3/2015 |
| WO | WO 2015/034820 | 3/2015 |
| WO | WO 2015/044900 | 4/2015 |
| WO | WO 2015/058031 | 4/2015 |
| WO | WO 2015/058067 | 4/2015 |
| WO | WO 2015/091475 | 6/2015 |
| WO | WO 2015/094902 | 6/2015 |
| WO | WO 2015/094912 | 6/2015 |
| WO | WO 2015/147020 | 10/2015 |
| WO | WO 2015/167825 | 11/2015 |
| WO | WO 2015/179615 | 11/2015 |
| WO | WO 2015/187089 | 12/2015 |
| WO | WO 2015/195228 | 12/2015 |
| WO | WO 2016/021742 | 2/2016 |
| WO | WO 2016/111347 | 7/2016 |
| WO | WO 2017/014323 | 1/2017 |
| WO | WO 2017/066633 | 4/2017 |
| WO | WO 2017/085198 | 5/2017 |
| WO | WO 2018/013840 | 1/2018 |
| WO | WO 2018/210987 | 11/2018 |
| WO | WO 2018/210992 | 11/2018 |
| WO | WO 2018/210994 | 11/2018 |
| WO | WO 2018/210995 | 11/2018 |

OTHER PUBLICATIONS

Ganesh et al., Peripherally restricted, highly potent, selective, aqueous-soluble EP2 antagonist with anti-inflammatory properties. Molecular Pharmaceutics, 2018, 15, 5809-5817.*

Banik et al., Prostaglandin EP2 receptor antagonist ameliorates neuroinflammation in a two-hit mouse model of Alzheimer's disease. Journal of Neuroinflammation, 2018, 18, p. 1-21.*

Schafer, S., Kolkhof, P. Failure is an option: learning from unsuccessful proof-of-concept trials. Drug Discovery Today. Nov. 2008, 13, 913-916.*

Horig, H., Pullman, W. From bench to clinic and back: Perspective on the 1st IQPC Translational Research conference. Journal of Translational Medicine. Dec. 2004, 2, 44.*

Ahmadi, M. et al., "Prevention of Both Direct and Cross-Priming of Antitumor CD8+ T-Cell Responses following Overproduction of Prostaglandin E2 by Tumor Cells In vivo," Cancer Res, vol. 68(18): 7520-7529 (2008).

Al-Wadei, H.A.N. et al., "Celecoxib and GABA Cooperatively Prevent the Progression of Pancreatic Cancer In Vitro and in Xenograft Models of Stress-Free and Stress-Exposed Mice," Plos One, vol. 7(8)(e43376): 1-11 (2012).

Alaa, M. et al., "Prostaglandin E2 receptor 2 overexpression in squamous cell carcinoma of the lung correlates with $p16^{INK4A}$ methylation and an unfavorable prognosis," International Journal of Oncology, vol. 34: 805-812 (2009).

Attur, M. et al., "Prostaglandin $E_2$ Exerts Catabolic Effects in Osteoarthritis Cartilage: Evidence for Signaling via the EP4 Receptor," J Immunol, vol. 181:5082-5088 (2008).

Babaev, V.R., et al., "Macrophage EP4 Deficiency Increases Apoptosis and Suppresses Early Atherosclerosis," Cell Metabolism, vol. 8: 492-501 (2008).

Badawi, A.F. et al., "Expression of Cyclooxygenase-2 and Peroxisome Proliferator-Activated Receptor-γ and Levels of Prostaglandin $E_2$ And 15-Deoxy-$\Delta^{12,14}$- Prostaglandin $J_2$ in Human Breast Cancer and Metastasis," Int. J. Cancer, vol. 103: 84-90 (2003).

Banu, S.K. et al., "Selective Inhibition of Prostaglandin E2 Receptors EP2 and EP4 Induces Apoptosis of Human Endometriotic Cells

(56) References Cited

OTHER PUBLICATIONS through Suppression of ERK1/2, AKT, NFκB, and β-Catenin Pathways and Activation of Intrinsic Apoptotic Mechanisms," *Mol Endocrinol*, vol. 23(8): 1291-1305 (2009).
Bao, Y-S. et al., "The regulation of CD4+ T cell immune responses toward Th2 cell development by prostaglandin E2," *International Immunopharmacology*, vol. 11: 1599-1605 (2011).
Boyd, M.J. et al., "A novel series of potent and selective $EP_4$ receptor ligands: Facile modulation of agonism and antagonism," *Bioorganic & Medicinal Chemistry Letters*, vol. 21: 484-487 (2011).
Brotons, C. et al., "A Systematic Review of Aspirin in Primary Prevention: Is It Time for a New Approach?" *Am J Cardiovasc Drugs*, vol. 15: 113-133 (2015).
Bryk, R. et al., "Identification of new inhibitors of protein kinase R guided by statistical modeling," *Bioorganic & Medicinal Chemistry Letters*, vol. 21: 4108-4114 (2011).
Caiazzo, E. et al., "Adenosine signalling mediates the anti-inflammatory effects of the COX-2 inhibitor nimesulide," *Biochemical Pharmacology*, vol. 112: 72-81 (2016).
Chen, Q. et al., "A novel antagonist of the prostaglandin $E_2$ $EP_4$ receptor inhibits Th1 differentiation and Th17 expansion and is orally active in arthritis models," *British Journal of Pharmacology*, vol. 160: 292-310 (2010).
Chen, Y. et al., "Prostaglandin $E_2$ and the protein kinase A pathway mediate arachidonic acid induction of c-fos in human prostate cancer cells," *British Journal of Cancer*, vol. 82(12): 2000-2006 (2000).
Chow, L.W-C. et al., "Celecoxib anti-aromatase neoadjuvant (CAAN) trial for locally advanced breast cancer," *Journal of Steroid Biochemistry & Molecular Biology*, vol. 111: 13-17 (2008).
Chuang, P-C. et al., "Inhibition of CD36-Dependent Phagocytosis by Prostaglandin $E_2$ Contributes to the Development of Endometriosis," *The American Journal of Pathology*, vol. 176(2): 850-860 (2010).
Cimino, P.J. et al., "Therapeutic targets in prostaglandin $E_2$ signaling for neurologic disease," *Curr Med Chem.*, vol. 15(19): 1863-1869; pp. 1-15 (2008).
Cipollone, F. et al., "Association Between Prostaglandin E Receptor Subtype EP4 Overexpression and Unstable Phenotype in Atherosclerotic Plaques in Human," *Arterioscler Thromb Vasc Biol.*, vol. 25:1925-1931; Figures I-II; 10 pages (2005).
Clark, P. et al., "MF498 [N-{[4-(5,9-Diethoxy-6-oxo-6,8-dihydro-7H-pyrrolo[3,4-g]quinolin-7-yl)-3-methylbenzyl]sulfonyl}-2-(2-methoxyphenyl)acetamide], a Selective E Prostanoid Receptor 4 Antagonist, Relieves Joint Inflammation and Pain in Rodent Models of Rheumatoid and Osteoarthritis," *The Journal of Pharmacology and Experimental Therapeutics*, vol. 325(2): 425-434 (2008).
Colucci, J. et al., "Discovery of 4-{1-[({1-[4-(trifluoromethyl)benzyl]-1H-indol-7-yl}carbonyl)amino]cyclopropyl}benzoic acid (MF-766), a highly potent and selective $EP_4$ antagonist for treating inflammatory pain," *Bioorganic & Medicinal Chemistry Letters*, vol. 20: 3760-3763 (2010).
Davis, T.W. et al., "COX-2 Inhibitors as Radiosensitizing Agents for Cancer Therapy," *Am J Clin Oncol*, vol. 26(4 Suppl 2): S58-S61 (2003).
Delong, P. et al., "Use of Cyclooxygenase-2 Inhibition to Enhance the Efficacy of Immunotherapy," *Cancer Research*, vol. 63: 7845-7852 (2003).
Demeure, C.E. et al., "Prostaglandin E2 primes naive T cells for the production of anti-inflammatory cytokines," *Eur. J. Immunol.*, vol. 27: 3526-3531 (1997).
Drew, D.A. et al., "Aspirin and colorectal cancer: the promise of precision chemoprevention," *Nature Reviews | Cancer*, vol. 16: 173-186 (2016).
Eberstål, S. et al., "Inhibition of cyclooxygenase-2 enhances immunotherapy against experimental brain tumors." *Cancer immunology, immunotherapy: CII; Lund University*, 26 pages (2012).
Eberstål, S et al., "Intratumoral COX-2 inhibition enhances GM-CSF immunotherapy against established mouse GL261 brain tumors," *Int. J. Cancer*, vol. 134: 2748-2753 (2014).
Elberg, G. et al., "$EP_2$ receptor mediates $PGE_2$-induced cystogenesis of human renal epithelial cells," *Am J Physiol Renal Physiol*, vol. 293:F1622-F1632 (2007).
Esaki, Y. et al., "Dual roles of $PGE_2$-EP4 signaling in mouse experimental autoimmune encephalomyelitis," *PNAS*, vol. 107(27): 12233-12238 (2010).
Falandry, C. et al., "Celecoxib and exemestane versus placebo and exemestane in postmenopausal metastatic breast cancer patients: a double-blind phase III GINECO study," *Breast Cancer Res Treat*, vol. 116: 501-508 (2009).
Fischer, S.M. et al., "Coxibs and Other Nonsteroidal Anti-Inflammatory Drugs in Animal Models of Cancer Chemoprevention," *Cancer Prev Res*, vol. 4(11): 1728-1735 (2011).
Fu, S.L. et al., "Anti-cancer effects of COX-2 inhibitors and their correlation with angiogenesis and invasion in gastric cancer," *World J Gastroenterol*, vol. 10(13): 1971-1974 (2004).
Fulton, A.M. et al., "Targeting Prostaglandin E EP Receptors to Inhibit Metastasis," *Cancer Res*, vol. 66(20): 9794-9797 (2006).
Funahashi, H. et al., "Delayed Progression of Pancreatic Intraepithelial Neoplasia in a Conditional $Kras^{G12D}$ Mouse Model by a Selective Cyclooxygenase-2 Inhibitor," *Cancer Res*, vol. 67(15): 7068-7071 (2007).
Gallo, O. et al., "Prognostic Significance of Cyclooxygenase-2 Pathway and Angiogenesis in Head and Neck Squamous Cell Carcinoma," *Human Pathology*, vol. 33(7): 708-714 (2002).
Ganesh, T., "Evaluation of WO 2012/177618 A1 and US-2014/0179750 A1: novel small molecule antagonists of prostaglandin-$E_2$ receptor EP2," *Expert Opinion on Therapeutic Patents*, vol. 25(7): 837-844 (2015).
Garcia Rodriguez, L. et al., "Coxibs: Pharmacology, Toxicity and Efficacy in Cancer Clinical Trials," *Recent Results in Cancer Research*, vol. 191: 67-93 (2013).
Generali, D. et al., "COX-2 expression is predictive for early relapse and aromatase inhibitor resistance in patients with ductal carcinoma in situ of the breast, and is a target for treatment," *British Journal of Cancer*, vol. 111: 46-54 (2014).
Ghosh, N. et al., "COX-2 as a target for cancer chemotherapy," *Pharmacological Reports*, vol. 62: 233-244 (2010).
Goodwin, J.F. et al., "Beyond DNA repair: DNA-PK function in cancer," *Cancer Discov.*, vol. 4(10): 1126-1139; pp. 1-27 (2014).
Greene, T.W et al., Protective Groups In Organic Synthesis, $3^{rd}$ Edition, 52 pages (1999).
Greenhough, A. et al., "The COX-2/$PGE_2$ pathway: key roles in the hallmarks of cancer and adaptation to the tumour microenvironment," *Carcinogenesis*, vol. 30(3): 377-386 (2009).
Hahn, T. et al., "Short-term dietary administration of celecoxib enhances the efficacy of tumor lysate-pulsed dendritic cell vaccines in treating murine breast cancer," *Int. J. Cancer*, vol. 118: 2220-2231 (2006).
Harris, S.G. et al., "Prostaglandins as modulators of immunity," *TRENDS in Immunology*, vol. 23(3): 144-150 (2002).
Higgins, J.P. et al., "Enhancing immune responses to tumor-associated antigens," *Cancer Biology & Therapy*, vol. 8(15): 1440-1449 (2009).
Hizaki, H. et al., "Abortive expansion of the cumulus and impaired fertility in mice lacking the prostaglandin E receptor subtype $EP_2$," *Proc. Natl. Acad. Sci. USA*, vol. 96: 10501-10506 (1999).
Honda, T. et al., "Prostacyclin-IP signaling and prostaglandin $E_2$-EP2/EP4 signaling both mediate joint inflammation in mouse collagen-induced arthritis," *JEM*, vol. 203(2): 325-335 (2006).
Hoshino, T. et al., "Improvement of cognitive function in Alzheimer's disease model mice by genetic and pharmacological inhibition of the $EP_4$ receptor," *Journal of Neurochemistry*, vol. 120: 795-805 (2012).
Hoskin, D.W. et al., "Inhibition of T cell and natural killer cell function by adenosine and its contribution to immune evasion by tumor cells (Review)," *International Journal of Oncology*, vol. 32: 527-535 (2008).
Jain, S. et al., "Prostaglandin E2 Regulates Tumor Angiogenesis in Prostate Cancer," *Cancer Res*, vol. 68(19): 7750-7759 (2008).

(56) References Cited

OTHER PUBLICATIONS

Jin, J. et al., "Prostaglandin E2 receptor subtype 2 (EP2) regulates microglial activation and associated neurotoxicity induced by aggregated α-synuclein," *Journal of Neuroinflammation*, vol. 4(2): pp. 1-10 (2007).
Kalinski, P., "Regulation of Immune Responses by Prostaglandin $E_2$," *J Immunol*, vol. 188: 21-28 (2012).
Keene, C.D. et al., "Suppressed Accumulation of Cerebral Amyloid β Peptides in Aged Transgenic Alzheimer's Disease Mice by Transplantation with Wild-Type or Prostaglandin $E_2$ Receptor Subtype 2-Null Bone Marrow," *The American Journal of Pathology*, vol. 177(1): 346-354 (2010).
Kennedy, C.R.J. et al., "Salt-sensitive hypertension and reduced fertility in mice lacking the prostaglandin $EP_2$ receptor," *Nature Medicine*, vol. 5(2): 217-220 (1999).
Kim, J.G. et al., "IFN-γ Inhibits the Suppressive Effects of $PGE_2$ on the Production of Tumor Necrosis Factor-α by Mouse Macrophages," *Immunological Investigations*, vol. 29(3): 257-269 (2000).
Kofler, D.M. et al., "Decreased RORC-dependent silencing of prostaglandin receptor EP2 induces autoimmune Th17 cells," *The Journal of Clinical Investigation*, vol. 124(6): 2513-2522 (2014).
Kojima, F. et al., "Prostaglandin $E_2$ activates RAP1 via EP2/EP4 receptors and cAMP-signaling in rheumatoid synovial fibroblasts: Involvement of EPAC1 and PKA: The regulation of Rap1 by $PGE_2$ in RSF," *Prostaglandins Other Lipid Mediat.*, vol. 89(1-2): 26-33; pp. 1-18 (2009).
Kundu, N. et al., "Antagonism of the prostaglandin E receptor EP4 inhibits metastasis and enhances NK function," *Breast Cancer Res Treat.*, vol. 117(2): 235-242; pp. 1-14 (2009).
Kuo, K-T. et al., "Prognostic Role of PGE2 Receptor EP2 in Esophageal Squamous Cell Carcinoma," *Ann Surg Oncol*, vol. 16: 352-360 (2009).
Lee, J. et al., "Selective Inhibition of Prostaglandin E2 Receptors EP2 and EP4 Inhibits Adhesion of Human Endometriotic Epithelial and Stromal Cells Through Suppression of Integrin-Mediated Mechanisms," *Biology of Reproduction*, vol. 88(3): 77; pp. 1-11 (2013).
Lee, J. et al., "Selective blockade of prostaglandin $E_2$ receptors EP2 and EP4 signaling inhibits proliferation of human endometriotic epithelial cells and stromal cells through distinct cell cycle arrest," *Fertility and Sterility*, vol. 93(8): 2498-2506 (2010).
Li, Y. et al., "Hydrogel dual delivered celecoxib and anti-PD-1 synergistically improve antitumor immunity," *OncoImmunology*, vol. 5(2):e1074374-12 (2016).
Liang, X. et al., "The $PGE_2$ EP2 receptor accelerates disease progression and inflammation in a model of amyotrophic lateral sclerosis," *Ann Neurol.*, vol. 64(3): 304-314; pp. 1-18 (2008).
Liang, X. et al., "Function of COX-2 and Prostaglandins in Neurological Disease," *J Mol Neurosci*, vol. 33:94-99 (2007).
Liang, X. et al., "Deletion of the Prostaglandin $E_2$ EP2 Receptor Reduces Oxidative Damage and Amyloid Burden in a Model of Alzheimer's Disease," *The Journal of Neuroscience*, vol. 25(44): 10180-10187 (2005).
Lustberg, M.B. et al., "Phase II Trial of Neoadjuvant Exemestane in Combination With Celecoxib in Postmenopausal Women Who Have Breast Cancer," *Clin Breast Cancer.*, vol. 11(4): 221-227; pp. 1-15 (2011).
Ma, X. et al., "A prostaglandin E (PGE) receptor EP4 antagonist protects natural killer cells from $PGE_2$-mediated immunosuppression and inhibits breast cancer metastasis," *OncoImmunology*, vol. 2(1): e22647-8 (2013).
Mandapathil, M. et al., "Generation and Accumulation of Immunosuppressive Adenosine by Human $CD4^+CD25^{high}FOXP3^+$ Regulatory T Cells," *The Journal of Biological Chemistry*, vol. 285(10): 7176-7186 (2010).
Mandapathil, M. et al., "Adenosine and Prostaglandin $E_2$ Cooperate in the Suppression of Immune Responses Mediated by Adaptive Regulatory T Cells," *The Journal of Biological Chemistry*, vol. 285(36): 27571-27580 (2010).
Markosyan, N. et al., "Mammary Carcinoma Cell Derived Cyclooxygenase 2 Suppresses Tumor Immune Surveillance by Enhancing Intratumoral Immune Checkpoint Activity," *Breast Cancer Research*, vol. 15:R75; pp. 1-13 (2013).
Marugan, J.J. et al., "Evaluation of Quinazoline Analogues as Glucocerebrosidase Inhibitors with Chaperone Activity," *J. Med. Chem.*, vol. 54: 1033-1058 (2011).
Matsumoto, H. et al., "Diversification of Cyclooxygenase-2-Derived Prostaglandins in Ovulation and Implantation," *Biology of Reproduction*, vol. 64: 1557-1565 (2001).
Maubach, K.A. et al., "BGC20-1531, a novel, potent and selective prostanoid $EP_4$ receptor antagonist: a putative new treatment for migraine headache," *British Journal of Pharmacology*, vol. 156: 316-327 (2009).
Medeiros, A.I. et al., "Efferocytosis impairs pulmonary macrophage and lung antibacterial function via $PGE_2/EP2$ signaling," *J. Exp. Med.*, vol. 206(1): 61-68 (2009).
Mitsuhashi, M. et al., "Regulation of interleukin-12 gene expression and its anti-tumor activities by prostaglandin $E_2$ derived from mammary carcinomas," *J Leukoc Biol.*, vol. 76(2): 322-332; pp. 1-21 (2004).
Miyata, Y. et al., "Tumor-associated Stromal Cells Expressing E-prostanoid 2 or 3 Receptors in Prostate Cancer: Correlation With Tumor Aggressiveness and Outcome by Angiogenesis and Lymphangiogenesis," *Urology*, vol. 81(1): 136-142 (2013).
Miyaura, C. et al., "Impaired Bone Resorption to Prostaglandin $E_2$ in Prostaglandin E Receptor EP4-knockout Mice," *The Journal of Biological Chemistry*, vol. 275(26): 19819-19823 (2000).
Montine, T.J. et al., "Neuronal oxidative damage from activated innate immunity is $EP_2$ receptor-dependent," *Journal of Neurochemistry*, vol. 83: 463-470 (2002).
Motz, G.T. et al., "Tumor endothelium FasL establishes a selective immune barrier promoting tolerance in tumors," *Nature Medicine*, vol. 20(6): 607-615; Online Methods, 11 pages (2014).
Mu, L. et al., "Understanding DP receptor antagonism using a CoMSIA approach," *Bioorganic & Medicinal Chemistry Letters*, vol. 21:66-75 (2011).
Murase, A. et al., "Effect of prostanoid $EP_4$ receptor antagonist, CJ-042,794, in rat models of pain and inflammation," *European Journal of Pharmacology*, vol. 580: 116-121 (2008).
Nakanishi, M. et al., "Multifaceted roles of $PGE_2$ in inflammation and cancer[1]," *Semin Immunopathol.*, vol. 35(2): 123-137; pp. 1-23 (2013).
Nakanishi, Y. et al., "COX-2 inhibition alters the phenotype of tumor-associated macrophages from M2 to M1 in $Apc^{Min/+}$ mouse polyps," *Carcinogenesis*, vol. 32(9): 1333-1339 (2011).
Nakao, K. et al., "CJ-023,423, a Novel, Potent and Selective Prostaglandin $EP_4$ Receptor Antagonist with Antihyperalgesic Properties," *The Journal of Pharmacology and Experimental Therapeutics*, vol. 322(2): 686-694 (2007).
Obermajer, N. et al., "Positive feedback between $PGE_2$ and COX2 redirects the differentiation of human dendritic cells toward stable myeloid-derived suppressor cells," *Blood*, vol. 118(20): 5498-5505 (2011).
Obermajer, N. et al., "Key role of the positive feedback between $PGE_2$ and COX2 in the biology of myeloid-derived suppressor cells," *OncoImmunology*, vol. 1(5): 762-764 (2012).
Oshima, H. et al., "Prostaglandin $E_2$ signaling and bacterial infection recruit tumor-promoting macrophages to mouse gastric tumors; $PGE_2$ and infection in tumorigenesis," *Gastroenterology*, vol. 140(2): 596-607; 29 pages (2011).
Peluffo, M.C. et al., "A prostaglandin E2 receptor antagonist prevents pregnancies during a preclinical contraceptive trial with female macaques," *Human Reproduction*, vol. 29(7): 1400-1412 (2014).
Pockaj, B.A. et al., "Reduced T-Cell and Dendritic Cell Function Is Related to Cyclooxygenase-2 Overexpression and Prostaglandin $E_2$ Secretion in Patients With Breast Cancer," *Annals of Surgical Oncology*, vol. 11(3): 328-339 (2004).
Pooler, A.M. et al., "Prostaglandin $E_2$ regulates amyloid precursor protein expression via the EP2 receptor in cultured rat microglia," *Neuroscience Letters*, vol. 362: 127-130 (2004).
Pozzi, A. et al., "Colon Carcinoma Cell Growth Is Associated with Prostaglandin $E_2$/EP4 Receptor-evoked ERK Activation," *The Journal of Biological Chemistry*, vol. 279(28): 29797-29804 (2004).

(56) References Cited

OTHER PUBLICATIONS

Rautio, J., Prodrugs and Targeted Delivery; Towards Better ADME Properties, 23 pages (2010).
Reinold, H. et al., "Spinal inflammatory hyperalgesia is mediated by prostaglandin E receptors of the EP2 subtype," *J. Clin. Invest.*, vol. 115(3): 673-679; 9 pages (2005).
Remington, "Part 5—Pharmaceutics Manufacturing," *The Science and Practice of Pharmacy, 21st Edition*, 5 pages (2005).
Sahin, I.H. et al., "Impact of non-steroidal anti-inflammatory drugs on gastrointestinal cancers: Current state-of-the science," *Cancer Letters*, vol. 345: 249-257 (2014).
Santulli, P. et al., "Hormonal Therapy Deregulates Prostaglandin-Endoperoxidase Synthase 2 (PTGS2) Expression in Endometriotic Tissues," *J Clin Endocrinol Metab*, vol. 99(3): 881-890 (2014).
Schiffmann, S. et al., "$PGE_2$/EP4 signaling in peripheral immune cells promotes development of experimental autoimmune encephalomyelitis," *Biochemical Pharmacology*, vol. 87: 625-635 (2014).
Sharma, S. et al., "Tumor Cyclooxygenase-2/Prostaglandin $E_2$-Dependent Promotion of FOXP3 Expression and $CD4^+CD25^+$ T Regulatory Cell Activities in Lung Cancer," *Cancer Res*, vol. 65(12): 5211-5220 (2005).
Shie, F-S., et al., "Microglial EP2 Is Critical to Neurotoxicity From Activated Cerebral Innate Immunity," *GLIA*, vol. 52: 70-77 (2005).
Sinha, P. et al., "Prostaglandin E2 Promotes Tumor Progression by Inducing Myeloid-Derived Suppressor Cells," *Cancer Res*, vol. 67(9): 4507-4513 (2007).
Specht, C. et al., "Prostaglandins, But Not Tumor-Derived IL-10, Shut Down Concomitant Tumor-Specific Ctl Responses During Murine Plasmacytoma Progression," *Int. J. Cancer*, vol. 91: 705-712 (2001).
Stahl, P.H. et al., Handbook of Pharmaceutical Salts; Properties, Selection, and Use, 330-350; 24 pages (2008).
Stella, V. et al., "Prodrugs: Challenges and Rewards, Part 1," *Biotechnology: Pharmaceutical Aspects*, vol. V, 6 pages (2007).
Stolina, M. et al., "Specific Inhibition of Cyclooxygenase 2 Restores Antitumor Reactivity by Altering the Balance of IL-10 and IL-12 Synthesis," *J Immunol*, vol. 164: 361-370 (2000).
Suzawa, T. et al., "The Role of Prostaglandin E Receptor Subtypes (EP1, EP2, EP3, and EP4) in Bone Resorption: An Analysis Using Specific Agonists for the Respective EPs," *Endocrinology*, vol. 141(4): 1554-1559 (2000).
Takadera, T et al., "Prostaglandin $E_2$ deteriorates N-methyl-D-aspartate receptor-mediated cytotoxicity possibly by activating EP2 receptors in cultured cortical neurons," *Life Sciences*, vol. 78: 1878-1883 (2006).
Terada, N. et al., "Identification of EP4 as a Potential Target for the Treatment of Castration-Resistant Prostate Cancer Using a Novel Xenograft Model," *Cancer Res*, vol. 70(4): 1606-1615; Correction pp. 4785-4786 (2010).
Tilley, S.L. et al., "Reproductive failure and reduced blood pressure in mice lacking the EP2 prostaglandin $E_2$ receptor," *J. Clin. Invest.*, vol. 103(11): 1539-1545 (1999).
Tomita, M. et al., "Effects of Selective Prostaglandin EP4 Receptor Antagonist on Osteoclast Formation and Bone Resorption In Vitro," *Bone*, vol. 30(1): 159-163 (2002).
Toomey, D. et al., "Therapeutic vaccination with dendritic cells pulsed with tumor-derived Hsp70 and a COX-2 inhibitor induces protective immunity against B16 melanoma," *Vaccine*, vol. 26: 3540-3549 (2008).
Veltman, J.D. et al., "COX-2 inhibition improves immunotherapy and is associated with decreased numbers of myeloid-derived suppressor cells in mesothelioma. Celecoxib influences MDSC function," *BMC Cancer*, vol. 10(464): 1-13 (2010).
Volenec, F.J. et al., "Mouse Colostomy Model for Studies on large Bowel Cancer," *Journal of Surgical Oncology*, vol. 13: 39-44 (1980).
Wang, D. et al., "Recent advances in basic science: Prostaglandins And Cancer," *Gut*, vol. 55:115-122 (2006).
Wang, R. et al., "Chemoprevention of Cancers in Gastrointestinal Tract with Cyclooxygenase 2 Inhibitors," *Current Pharmaceutical Design*, vol. 19: 115-125 (2013).
Wang, Y. et al., "Prostaglandin $E_2$ Induces Vascular Endothelial Growth Factor Secretion in Prostate Cancer Cells Through EP2 Receptor-Mediated cAMP Pathway," *Molecular Carcinogenesis*, vol. 46: 912-923 (2007).
Wouters, J. et al., Pharmaceutical Salts and Co-Crystals, 10 pages (2012).
Xin, X. et al., "Targeting COX-2 and EP4 to control tumor growth, angiogenesis, lymphangiogenesis and metastasis to the lungs and lymph nodes in a breast cancer model," *Laboratory Investigation*, vol. 92: 1115-1128 (2012).
Xu, L. et al., "Molecular docking and synthesis of novel quinazoline analogues as inhibitors of transcription factors NF-κB activation and their anti-cancer activities," *Bioorganic & Medicinal Chemistry*, vol. 21: 540-546 (2013).
Xu, S. et al., "An EP4 Antagonist ONO-AE3-208 Suppresses Cell Invasion, Migration, and Metastasis of Prostate Cancer," *Cell Biochem Biophys*, vol. 70: 521-527 (2014).
Yamaguchi, N.H. et al., "Gefitinib and celecoxib in advanced metastatic gastrointestinal tumors: a pilot feasibility study," *J Gastrointest Oncol*, vol. 5(1): 57-66 (2014).
Yang, L. et al., "Host and Direct Antitumor Effects and Profound Reduction in Tumor Metastasis with Selective EP4 Receptor Antagonism," *Cancer Res*, vol. 66(19): 9665-9672 (2006).
Zelenay, S. et al., "Cyclooxygenase-Dependent Tumor Growth through Evasion of Immunity," *Cell*, vol. 162: 1257-1270 (2015).
Zhang, H. et al., "Enhancement of Antitumor Activity by Combination of Tumor Lysate-Pulsed Dendritic Cells and Celecoxib in a Rat Glioma Model," *Oncology research*, vol. 20(10): 447-455; 11 pages (2012).
Zhang, X. et al., Tumor Growth Inhibition by Simultaneously Blocking Epidermal Growth Factor Receptor and Cyclooxygenase-2 in a Xenograft Model, *Clin Cancer Res*, vol. 11(17): 6261-6269 (2005).
Zhang, Y. et al., "PGE2 promotes angiogenesis through EP4 and PKA Cγ pathway," *Blood*, vol. 118(19): 5355-5364 (2011).
Bonavita, E. et al., "Antagonistic Inflammatory Phenotypes Dictate Tumor Fate and Response to Immune Checkpoint Blockade," *Immunity*, 2020, 53, 1215-1229 and e1-e8.
Hong, D. et al., "First-in-human Phase I Study of Immunomodulatory E7046, an Antagonist of PGE2-receptor E-type 4 (EP4), in Patients with Advanced Cancers," Journal for Immuno Therapy of Cancer, 2020, 8:e000222, 12 pages, doi: 10.1136/jitc-2019-000222.

* cited by examiner

PYRIMIDINE DERIVATIVES AS PGE2 RECEPTOR MODULATORS

CROSS REFERENCE TO RELATED APPLICATIONS

This application is a United States Application under 35 U.S.C. 371 claiming benefit of PCT Application No. PCT/EP2018/062844, filed on May 17, 2018, which claims the benefit of PCT Application No. PCT/EP2017/061989, filed on May 18, 2017.

The present invention relates to pyrimidine derivatives of formula (I) and their use in the treatment of cancer by modulating an immune response comprising a reactivation of the immune system in the tumor. The present invention further relates to novel pyrimidine derivatives of formula (II) and their use as pharmaceuticals. The invention also concerns related aspects including processes for the preparation of the compounds, pharmaceutical compositions containing one or more compounds of formula (I)/formula (II), and their use as modulators of the PGE2 receptors EP2 (alias PTGER2, alias PGE2 Receptor EP2 Subtype) and/or EP4 (alias PTGER4, alias EP4R, alias PGE2 Receptor EP4 Subtype). The compounds of formula (I)/formula (II) may especially be used as single agents or in combination with one or more therapeutic agents and/or chemotherapy and/or radiotherapy and/or immunotherapy in the prevention/prophylaxis or treatment of cancers; in particular the prevention/prophylaxis or treatment of melanoma; lung cancer; bladder cancer; renal carcinomas; gastro-intestinal cancers; endometrial cancer; ovarian cancer; cervical cancer; and neuroblastoma.

Prostaglandin E2 (PGE2) is a bioactive lipid that can elicit a wide range of biological effects associated with inflammation and cancer. PGE2 belongs to the prostanoid family of lipids. Cyclooxygenase (COX) is the rate-limiting enzyme in the synthesis of biological mediators termed prostanoids, consisting of prostaglandin PGD2, PGE2, PGF2α, prostacyclin PGI2, and thromboxane TXA2. Prostanoids function via activation of seven transmembrane G-protein-coupled receptors (GPCRs), in particular EP1, EP2, EP3, and EP4 are receptors for PGE2. Activation of both EP2 and EP4 by PGE2 stimulates adenylate cyclase, resulting in elevation of cytoplasmic cAMP levels to initiate multiple downstream events via its prototypical effector Protein kinase A. In addition, PGE2 is also able to signal via PI3K/AKT and Ras-MAPK/ERK signalling Cancers figure among the leading causes of death worldwide. Tumors are comprised of abnormally proliferating malignant cancer cells but also of a functionally supportive microenvironment. This tumor microenvironment is comprised of a complex array of cells, extracellular matrix components, and signaling molecules and is established by the altered communication between stromal and tumor cells. As tumors expand in size, they elicit the production of diverse factors that can help the tumor to grow such as angiogenic factors (promoting ingrowth of blood vessels) or that can help to evade the attack of the host immune response. PGE2 is such an immuno-modulatory factor produced in tumors.

It is well established that COX2, mainly via PGE2, promotes overall growth of tumors and is upregulated and correlates with clinical outcome in a high percentage of common cancers, especially colorectal, gastric, esophageal, pancreatic, breast and ovarian cancer. High COX-2 and PGE2 expression levels are associated with neoplastic transformation, cell growth, angiogenesis, invasiveness, metastasis and immune evasion.

The finding that COX2 is over-expressed and plays an important role in carcinogenesis in gastrointestinal (GI) cancers including among others esophagus, gastric and colorectal cancers has led to the fact that COX-inhibitors (Coxibs), including Celecoxib, and other nonsteroidal anti-inflammatory drugs (NSAID), including aspirin, are among the most studied cancer chemopreventive agents in development today (for review see for example Wang R et al, Curr Pharm Des. 2013; 19(1):115-25; Garcia Rodriguez L A et al, Recent Results Cancer Res. 2013; 191:67-93, Sahin I H et al, Cancer Lett. 2014 Apr. 10; 345(2):249-57; Drew D A et al, Nat Rev Cancer 2016, 16:173; Brotons C et al, Am J Cardiovasc Drugs. 2015 April; 15(2):113)

In addition to COX2 and PGE2, also EP receptors, especially EP2 and EP4, are aberrantly over-expressed in multiple types of cancers, especially in gastro-intestinal (GI) cancers and pancreatic cancer. Furthermore, the over-expression of PGE2 and/or EP2 and/or EP4 correlates with diseases progression in some cancer types such as oesophageal squamous cell carcinoma (Kuo K T et al, Ann Surg Onc 2009; 16(2), 352-60); squamous cell carcinoma of the lung (Alaa M et al, Int J Oncol 2009, 34(3); 805-12); prostate cancer (Miyata Y et al, Urology 2013, 81(1):136-42); Badawi A F and Badr M Z Int J Cancer. 2003, 103(1):84-90); head and neck squamous cell carcinoma (Gallo 0 et al, Hum Pathol. 2002, 33(7):708-14).

In accordance to studies performed with Coxibs, in mice, knockout of either COX1, COX2, microsomal prostaglandin E synthase 1 (mPTGES1), EP2 or EP4 resulted in reduced tumor incidence and progression in different tumor models. Conversely, overexpression of COX2 or mPTGES1 in transgenic mice resulted in increased tumor incidence and tumor burden (for review see Nakanishi M. and Rosenberg D. W., Seminars in Immunopathology 2013, 35: 123-137; Fischer S M et al Cancer Prev Res (Phila) 2011 November; 4(11): 1728-35; Fulton A M et al Cancer Res 2006; 66(20); 9794-97).

Several pharmacological studies to inhibit tumor growth and progression using EP receptor antagonists or COX2 inhibitors in different tumor models have been conducted in mice. Among others, EP antagonists and/or COX2 inhibitors reduced tumor growth and metastasis in experimental models of colorectal cancer (e.g Yang L et al Cancer Res 2006, 66(19), 9665-9672; Pozzi A. et al JBC 279(28); 29797-29804), lung carcinomas (Sharma S et al Cancer Res 2005 65(12), 5211-5220), gastro-intestinal cancer (Oshima H et al Gastroenterology 2011, 140(2); 596-607; Fu S L et al world J Gastroenterol 2004, 10(13); 1971-1974), breast cancer (Kundu N et al, Breast Cancer Res Treat 117, 2009; 235-242; Ma X et al, OncoImmunology 2013; Xin X et al Lab Investigation 2012, 1-14; Markosyan N et al; Breast Cancer Res 2013, 15:R75), prostate cancer (Xu S et al, Cell Biochem Biophys 2014, Terada et al Cancer Res 70(4) 2010; 1606-1615), pancreatic cancer (A-Wadei H A et al, PLOS One 2012, 7(8):e43376; Funahashi H et al, Cancer Res 2007, 67(15):7068-71). COX2 inhibitors were approved for the treatment of familial adenomatous polyposis (FAP) which is an inherited pre-disposition syndrome for colorectal cancer, but later retracted due to cardiovascular side effects.

Mechanistically, PGE2 signalling is mainly involved in the crosstalk between tumor and stromal cells, thereby creating a microenvironment which is favourable for the tumor to grow. In particular, PGE2 signalling via EP2 and EP4 can for example (i) suppress the cytotoxicity and cytokine production of natural killer cells, (ii) skew the polarization of tumor-associated macrophages towards tumor-promoting M2 macrophages (see for example Nakanishi Y et al Carcinogenesis 2011, 32:1333-39), (iii) regulate the activation, expansion and effector function of both Tregs (regulatory T cells) and MDSC (myeloid derived suppressor cells), which are potent immunosuppressive cells that accumulate in tumors both in patients and in experimental animal models (see for example Sharma S et al, Cancer Res 2005, 5(12):5211-20; Sinha P et al Cancer Res 2007, 67(9), 4507-4513; Obermajer N et al, Blood 2011, 118(20):5498-5505); (iv) down-regulate IFN-γ, TNF-α IL-12 and IL-2 expression in immune cells such as natural killer cells, T-cells, dendritic cells and macrophages, impairing the ability of these immune cells to induce tumor cell apoptosis and restrain tumorigenesis (see for example Bao Y S et al, Int Immunopharmacol. 2011; 11(10):1599-605; Kim J G and Hahn Y S, Immunol Invest. 2000; 29(3):257-69; Demeuere C E et al, Eur J Immunol. 1997; 27(12):3526-31; Mitsuhashi M et al, J Leukoc Biol. 2004; 76(2):322-32; Pockaj B A et al, Ann Surg Oncol. 2004; 11(3):328-39; (v) suppress activation, IL-2 responsivness, expansion and cytotoxicity of T-cells thereby contributing to local immunsuppresion (see for example Specht C et al, Int J Cancer 200191:705-712); (vi) inhibit maturation of dendritic cells, their ability to present antigens and to produce IL-12, resulting in abortive activation of cytotoxic T-cells (see for example Ahmadi M et al, Cancer Res 2008, 68(18):7250-9; Stolina M et al, J Immunol 2000, 164:361-70); (vii) regulate tumor angiogenesis (formation of new blood vessels for nutrient and oxygen supply) by enhancing endothelial cell motility and survival as well as by increasing the expression of VEGF (vascular endothelial growth factor) (see for example Zhang Y and Daaka Y, Blood 2011; 118(19):5355-64; Jain S et al, Cancer Res. 2008; 68(19):7750-9; Wang and Klein, Molecular Carcinogenesis 2007, 46:912-923; (viii) enhance tumor cell survival (via PI3K/AKT and MAPK signalling). For review see for example Kalinski P, J Immunol 2012, 188(1), 21-28; Obermajer N et al, Oncoimmunology 1(5), 762-4; Greenhough A et al, carcinogenesis 2009, 30(3), 377-86; Wang D and Dubois R N, Gut 2006, 55, 115-122; Harris S G e al Trends Immunol 2002, 22, 144-150).

Coxibs have been shown to render tumor cells more sensitive to radiation and chemotherapy and several clinical trials have been performed or are ongoing combining Coxibs with radio- and/or chemotherapy (for review see e.g Ghosh N et al, Pharmacol Rep. 2010 March-April; 62(2):233-44; Davis T W et al, Am J Clin Oncol. 2003, 26(4):S58-61; see also Higgins J P et al, Cancer Biol Ther 2009, 8:1440-49).

Furthermore, there is some evidence of additive effects and/or synergy between Coxibs and epidermal growth factor receptor (EGFR) inhibitors (see for example Zhang X et al, Clin Cancer Res. 2005, 11(17):6261-9; Yamaguchi N H et al, J Gastrointest Oncol. 2014, 5(1):57-66); and with aromatase inhibitors (see for example Generali D et al, Br J Cancer. 2014; 111(1):46-54; Lustberg M B et all, Clin Breast Cancer. 2011 August; 11(4):221-7; Falandry C et al, Breast Cancer Res Treat. 2009 August; 116(3):501-8; Chow L W et al, J Steroid Biochem Mol Biol. 2008, 111(1-2):13-7).

Moreover, additive/synergistic effects have been seen in different mouse tumor models when Aspirin (a COX1/2 inhibitor) was combined with and anti-VEGF antibody (Motz G T et al; Nat Med 2014 20(6):607) and this combination is currently under investigation in clinical trials (NCT02659384).

Recently, it has been shown that, if combined, different immunotherapeutic approaches can have enhanced anti-tumor efficacy. Due to the immune-modulatory properties of PGE2, Coxibs have thus also been used in combination with different immunotherapeutic approaches. In particular, additive or even synergistic effects could be observed when Coxibs were combined with dendritic cell vaccination in a rat glioma model and in a mouse mesothelioma or melanoma model (Zhang H et al, Oncol Res. 2013; 20(10):447-55; Veltman J D et al, BMC Cancer. 2010; 10:464; Toomey D et all, Vaccine. 2008 Jun. 25; 26(27-28):3540-9); with granulocyte-macrophage colony-stimulating factor (GM-CSF) in mouse brain tumors (Eberstál S et al, Int J Cancer. 2014 Jun. 1; 134(11):2748-53); with interferon gamma (IFN-γ) in brain tumors (Eberstál S et al, Cancer Immunol Immunother. 2012, 61(8):1191-9); with dendritic cell vaccination or with GM-CSF in a mouse breast cancer model (Hahn T et al, Int J Cancer. 2006, 118(9):2220-31); and with adenoviral interferon beta (IFN-β) therapy in a mouse mesothelioma model (DeLong P et al, Cancer Res. 2003 Nov. 15; 63(22):7845-52). Along these lines, additive or even synergistic effects of Coxibs and/or EP2 and/or EP4 antagonists can also be envisaged with agents acting on cytotoxic T-lymphocyte-associated protein 4 (CTLA-4) such as anti-CTLA-4 antibodies; anti-TIM-3 antibodies, anti-Lag-3 antibodies; anti-TIGIT antibodies; or, in particular, with agents acting on programmed cell death protein 1 (PD1), such as anti-PD1 or anti-PDL1 (programmed cell death ligand 1) antibodies (Yongkui Li et al Oncoimmunology 2016, 5(2):e1074374; Zelenay S et al, Cell 2015, 162; 1-14; WO2013/090552, which indicates a synergistic effect of dual EP2 and EP4 blockade in combination with agents acting on PD1).

Adenosine is another endogenous factor with anti-inflammatory properties that is generated through the activity of ectonucleotidases, CD39 and CD73, expressed on various cell types, including regulatory T cells (Treg) (Mandapathil M et al, J Biol Chem. 2010; 285(10):7176-86). Immune cells also respond to Adenosine, because they bear receptors for ADO, which are mainly of the A2a/A2b type (Hoskin D W, et al, Int J Oncol 2008, 32:527-535). Signaling via Adenosine receptors and EP2/EP4 receptors converges on the cytoplasmic adenylyl cyclase, leading to up-regulation of cAMP. It was shown that Adenosine and PGE2 cooperate in the suppression of immune responses mediated by regulatory T cells (Mandapathil M et al, J Biol Chem. 2010; 285(36):27571-80; Caiazzo E et al, Biochem Pharmacol. 2016; 112:72-81).

Thus, the present EP2 and/or EP4 antagonists may be useful, alone, or in combination with with one or more therapeutic agents and/or chemotherapy and/or radiotherapy and/or immunotherapy; in particular in combination with chemotherapy, radiotherapy, EGFR inhibitors, aromatase inhibitors, anti-angiogenic drugs, adenosine inhibitors, immunotherapy such as especially PD1 and/or PDL1 blockade, or other targeted therapies; for the prevention/prophylaxis or treatment of cancers, notably for the prevention/prophylaxis or treatment of skin cancer including melanoma including metastatic melanoma; lung cancer including non-small cell lung cancer; bladder cancer including urinary bladder cancer, urothelial cell carcinoma; renal carcinomas including renal cell carcinoma, metastatic renal cell carcinoma, metastatic renal clear cell carcinoma; gastro-intestinal cancers including colorectal cancer, metastatic colorectal cancer, familial adenomatous polyposis (FAP), oesophageal cancer, gastric cancer, gallbladder cancer, cholangiocarcinoma, hepatocellular carcinoma, and pancreatic cancer such as pancreatic adenocarcinoma or pancreatic ductal carcinoma; endometrial cancer; ovarian cancer; cervical cancer; neuroblastoma; prostate cancer including castrate-resistant prostate cancer; brain tumors including brain metastases, malignant gliomas, glioblastoma multiforme, medulloblastoma, meningiomas; breast cancer including triple negative breast carcinoma; oral tumors; nasopharyngeal tumors; thoracic cancer; head and neck cancer; leukemias including acute myeloid leukemia, adult T-cell leukemia; carcinomas; adenocarcinomas; thyroid carcinoma including papillary thyroid carcinoma; choriocarcinoma; Ewing's sarcoma; osteosarcoma; rhabdomyosarcoma; Kaposi's sarcoma; lymphoma including Burkitt's lymphoma, Hodgkin's lymphoma, MALT lymphoma; multiple myelomas; and virally induced tumors.

In addition, selective or dual EP2 and/or EP4 antagonists may be useful in several other diseases or disorders responding for example to treatment with COX2 inhibitors, with the advantage that EP2 and/or EP4 antagonists should not possess the potential cardiovascular side effects seen with COX2 inhibitors, which are mainly due to interference with PGI2 and TXA2 synthesis (see for example Boyd M J et al, bioorganic and medicinal chemistry letters 21, 484, 2011). For example, blockade of prostaglandin production by COX inhibitors is the treatment of choice for pain, including especially inflammatory pain and painful menstruation. Thus EP2 and/or EP4 and/or dual EP2/EP4 antagonists may be useful for the treatment of pain, especially inflammatory pain. Evidence from EP2 knockout mice suggest that EP2 antagonists can be used for the treatment of inflammatory hyperalgesia (Reinold H et al, J Clin Invest 2005, 115(3): 673-9). In addition, EP4 antagonists have beneficial effect in vivo in inflammatory pain models (eg Murase A, Eur J Pharmacol 2008; Clark P, J Pharmacol Exp Ther. 2008; Maubach K A Br J Pharmacol. 2009; Colucci J Bioorg Med Chem Lett. 2010, Boyd M J et al, Bioorg Med Chem Lett 2011, Chn Q et al Br J Phramacol 2010, Nakao K et al, J Pharmacol Exp Ther. 2007 August; 322(2):686-94). Administration of an EP2 in combination with an EP4 antagonist showed significant, but partial inhibition of joint inflammation in mouse collagen-induced arthritis model (Honda T et al J Exp Med 2006, 203(2):325-35).

EP2 and/or dual EP2/EP4 antagonists may be of use to decrease female fertility, i.e. they have been shown to prevent pregnancy if used as contraceptive in macaques (Peluffo M C et al Hum Reprod 2014). EP2 knockout mice have decreased fertility, smaller litter sizes and reduced cumulus expansion (Matsumoto et al, Biology of reproduction 2001, 64; 1557-65; Hitzaki et al, PNAS 1999, 96(18), 10501-10506; Tilley S L J Clin Inves 1999, 103(11):1539-45; Kennedy C R et al, Nat Med 1999 5(2):217-20).

There is also rationale that EP2 and/or EP4 antagonists may be of use to prevent or treat endometriosis: for example EP2, EP3 and EP4 and COX2 are overexpressed in endometriosis cell lines and tissues (e.g. Santulli P et al J Clin Endocrinol Metab 2014, 99(3):881-90); antagonist treatment was shown to inhibit the adhesion of endometrial cells in vitro (Lee J et al Biol Reprod 2013, 88(3):77; Lee J et al Fertil Steril 201, 93(8):2498-506); COX2 inhibitors have been shown to reduce endometric lesions in mice via EP2 (Chuang P C et al, Am J Pathol 2010, 176(2):850-60); and antagonist treatment has been shown to induce apoptosis of endometric cells in vitro (Banu S K et al, MOI endocrinol 2009, 23(8) 1291-305).

Dual EP2/EP4 antagonists, or the combination of a selective EP2 antagonists with a selective EP4 antagonist, may be of potential use for autoimmune disorders; e.g. they have been shown to be effective in mouse model for multiple sclerosis (MS) (Esaki Y et al PNAS 2010, 107(27):12233-8; Schiffmann S et al, Biochem Pharmacol. 2014, 87(4): 625-35; see also Kofler D M et al J Clin Invest 2014, 124(6): 2513-22). Activation of EP2/EP 4 signalling in cells in vitro (Kojima F et al Prostaglandins Other Lipid Mediat 2009, 89:26-33) linked dual or selective EP2 and/or EP4 antagonists to the treatment of rheumatoid arthritis. Also, elevated levels of PGE(2) have been reported in synovial fluid and cartilage from patients with osteoarthritis (OA) and it has been shown that PGE2 stimulates matrix degradation in osteoarthritis chondrocytes via the EP4 receptor (Attur M et al, J Immunol. 2008; 181(7):5082-8).

EP4 overexpression is associated with enhanced inflammatory reaction in atherosclerotic plaques of patients (Cipollone F et al, Artherioscler Thromb Vasc Biol 2005, 25(9); 1925-31), thus the use of EP4 and/or dual EP2/EP4 antagonists may be indicated for plaque stabilization and prevention/prophylaxis of acute ischemic syndromes. In addition, EP4 deficiency suppresses early atherosclerosis, by compromising macrophage survival (Babaev V R et al, Cell Metab. 2008 December; 8(6):492-501)

EP2 and/or dual EP2/EP4 antagonists may also be useful in the treatment of pneumonia: intrapulmonary administration of apoptotic cells demonstrated that PGE(2) via EP2 accounts for subsequent impairment of lung recruitment of leukocytes and clearance of *Streptococcus pneumoniae*, as well as enhanced generation of IL-10 in vivo (Medeiros Al et al J Exp Med 2009 206(1):61-8).

EP2 and/or dual EP2/EP4 antagonists may in addition be useful for the treatment of neurodegenerative diseases (for review see Cimino P J et al, Curr Med Chem. 2008; 15(19):1863-9). EP2 receptor accelerates progression of inflammation in a mouse model of amyotrophic lateral sclerosis (ALS) (Liang X et al, Ann Neurol 2008, 64(3): 304-14); COX2 inhibitors have been shown to be neuroprotective in rodent models of stroke, Parkinson disease and ALS (for review see Liang X et al J Mol Neurosci 2007, 33(1):94-9), decreased neurotoxicity was observed in EP2 knockout mice treated with parkinsonian toxican (Jin J et al, J Neuroinflammation 2007, 4:2), PGE2 via EP2 aggravates neurodegeneration in cultured rat cells (Takadera T et al, Life Sci 2006, 78(16): 1878-83); Reduced amyloid burden was observed in Alzheimer's disease mouse model if crossed with EP2 knockout mice (Liang X et al J Neurosci 2005, 25(44):10180-7; Keene C D et al, Am J Pathol. 2010, 177(1):346-54). EP2 null mice are protected from CD14-dependent/innate immunity mediated neuronal damage in neurodegenerative disease (Shie F S et al Glia 2005, 52(1): 70-7); PGE2 via EP2 increases amyloid precursor protein (APP) expression in cultured rat microglial cells (Pooler A M et al Neurosci. Lett. 2004, 362(2):127-30). EP2 antagonist limits oxidative damage from activation of innate immunity (intracranial injection of LPS) in the brain and could be used for Alzheimer or HIV associated dementia (Montine T J et al, J Neurochem 2002, 83(2):463-70). In an Alzheimer's disease mouse model cognitive function could be improved by genetic and pharmacological inhibition of EP4 (Hoshino T et al, J Neurochem 2012, 120(5):795-805).

EP2 and/or dual EP2/EP4 antagonists may also be useful to treat autosomal dominant polycystic kidney disease (ADPKD): PGE2 via EP2 induces cystogenesis of human renal epithelial cells; and EP2 was found to be overexpressed in patient samples (Elberg G et al, Am J Physiol Renal Physiol 2007, 293(5):F1622-32).

EP4 and/or dual EP2/EP4 antagonists may also be useful to treat osteoporosis: PGE2 stimulates bone resorption mainly via EP4 and partially via EP2 (Suzawa T et all, Endocrinology. 2000 April; 141(4):1554-9), EP4 knockout mice show impaired bone resorption (Miyaura C et al, J Biol Chem 2000, 275(26): 19819-23) and an EP4 antagonists showed partial inhibition of PGE(2)-stimulated osteoclastogenesis and osteoclastic bone resorption (Tomita M et al, Bone. 2002 January; 30(1):159-63).

WO2008/152093 discloses selective EP2 receptor modulators which comprise an indole ring linked to the rest of the molecule in position 3, and a pyrimidine moiety which however is not substituted with a directly linked aromatic substituent. WO2006/044732 discloses pyrimidine compounds which are modulators of PGD2 claimed to be useful e.g. in the treatment of allergic diseases; however, for example the exemplified compound CAS 1001913-77-4 has been tested to be inactive on both the EP2 and the EP4 receptor in the in vitro assay set out in the experimental part below. WO2008/006583 discloses pyrimidin derivatives which are ALK-5 inhibitors. WO2006/044732 and WO2008/039882 disclose certain pyrimidine derivatives as protaglandin D2 receptor antagonists. Pyrimidin-2-yl derivatives are disclosed in WO2013/020945, WO2012/127032, WO2011/144742, WO2011/022348, WO2009/105220, Bioorg. Med. Chem 2011, 21(13) 4108-4114 and Bioorg. Med. Chem 2011, 21(1) 66-75. Further compounds which are claimed to be active as anti-cancer agents are disclosed in WO2006/128129, WO2008/008059 and Bioorg. Med. Chem 2013, 21(2), 540-546. WO2012/149528 discloses 2-methyl-pyrimidine derivatives as inhibitors of the inducible form of Phosphofructose-Kinase, thought to useful in the treatment of cancer by decreasing tumor growth by reducing the extremely high rate of glycolysis in cancer cells. WO2018/013840, WO2013/163190 WO2015/058067, and WO2015/058031 disclose certain DNA-PK inhibitors interacting with DNA repair processes. The disclosed compounds are thought to be useful to sensitize cancer cells by directly modulating cancer cell proliferation, and to enhance the efficacy of both cancer chemotherapy and radiotherapy.

The present invention provides novel pyrimidine derivatives of formula (I)/formula (II) which are modulators of the prostaglandin 2 receptors EP2 and/or EP4. Certain compounds of the present invention are dual antagonists of both the EP2 and the EP4 receptor. The present compounds may, thus, be useful for the prevention/prophylaxis or treatment of diseases which respond to the blockage of the EP2 receptors and/or the EP4 receptors such as especially cancers, wherein a particular aspect is the treatment of cancer by modulating an immune response comprising a reactivation of the immune system in the tumor; as well as pain including especially inflammatory pain and painful menstruation; endometriosis; acute ischemic syndromes in atherosclerotic patients; pneumonia; neurodegenerative diseases including amyotrophic lateral sclerosis, stroke; Parkinson disease, Alzheimer's disease and HIV associated dementia; autosomal dominant polycystic kidney disease; and to control female fertility.

1) A first aspect of the invention relates to compounds of the formula (I)

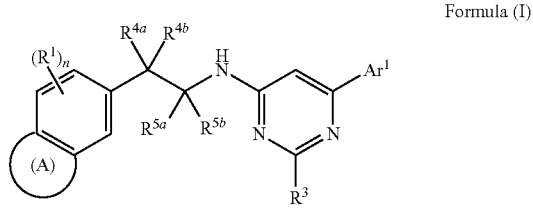

Formula (I)

for use in the treatment of a cancer, wherein said cancer is treated by modulating an immune response comprising a reactivation of the immune system in the tumor;

wherein said cancer is notably a cancer selected from melanoma including metastatic melanoma; lung cancer including non-small cell lung cancer; bladder cancer including urinary bladder cancer, urothelial cell carcinoma; renal carcinomas including renal cell carcinoma, metastatic renal cell carcinoma, metastatic renal clear cell carcinoma; gastrointestinal cancers including colorectal cancer, metastatic colorectal cancer, familial adenomatous polyposis (FAP), oesophageal cancer, gastric cancer, gallbladder cancer, cholangiocarcinoma, hepatocellular carcinoma, and pancreatic cancer such as pancreatic adenocarcinoma or pancreatic ductal carcinoma; endometrial cancer; ovarian cancer; cervical cancer; neuroblastoma; prostate cancer including castrate-resistant prostate cancer; brain tumors including brain metastases, malignant gliomas, glioblastoma multiforme, medulloblastoma, meningiomas; breast cancer including triple negative breast carcinoma; oral tumors; nasopharyngeal tumors; thoracic cancer; head and neck cancer; leukemias including acute myeloid leukemia, adult T-cell leukemia; carcinomas; adenocarcinomas; thyroid carcinoma including papillary thyroid carcinoma; choriocarcinoma; Ewing's sarcoma; osteosarcoma; rhabdomyosarcoma; Kaposi's sarcoma; lymphoma including Burkitt's lymphoma, Hodgkin's lymphoma, MALT lymphoma; multiple myelomas; and virally induced tumors (especially such cancer is selected from melanoma; lung cancer; bladder cancer; renal carcinomas; gastro-intestinal cancers; endometrial cancer; ovarian cancer; cervical cancer; and neuroblastoma); wherein said compound is optionally used in combination with one or more chemotherapy agents and/or radiotherapy and/or targeted therapy;

wherein in compounds of the formula (I):

ring (A) in the fragment:

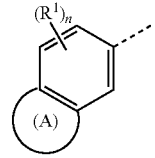

represents an aromatic 5- or 6-membered ring or a non-aromatic 5- to 7-membered ring, which ring (A) is fused to the phenyl group, wherein independently said ring (A) optionally contains one or two heteroatoms independently selected from nitrogen, oxygen, and sulfur (notably such fused group is benzofuranyl, benzothiophenyl, benzothiazolyl, benzoisothiazolyl, indolyl, indazolyl, naphthyl, quinolinyl, isoquinolinyl, 2,3-dihydro-benzo[b]thiophenyl, benzo[1,3]dioxolyl, 1,3-dihydro-isobenzofuranyl, 2,3-dihydro-benzofuranyl, indanyl, 5,6,7,8-tetrahydro-naphthalenyl, 2,3-dihydro-benzo[1,4]dioxinyl, chromanyl, 3,4-dihydro-2H-benzo[1,4]oxazinyl, 1,2,3,4-tetrahydro-quinolinyl, 3,4-dihydro-2H-benzo[b][1,4]dioxepinyl);

wherein said fragment is optionally substituted with $(R^1)_n$; wherein $(R^1)_n$ represents one, two, three, or four optional substituents (i.e. said fragment is unsubstituted, or substituted with one, two, three, or four $R^1$), wherein said substituents $R^1$ are independently selected from $(C_{1-3})$alkyl (especially methyl), $(C_{2-3})$alkenyl (especially vinyl), $(C_{2-3})$alkynyl (especially ethynyl), $(C_{1-3})$alkoxy (especially methoxy, ethoxy, isopropoxy), halogen (especially fluoro, or chloro), —S—($C_{1-3}$)alkyl (especially methylsulfanyl), ($C_{1-3}$)fluoroalkyl (especially trifluoromethyl), ($C_{1-3}$)fluoroalkoxy (especially trifluoromethoxy, difluoromethoxy), cyano, oxo, —$NR^{N7}R^{N8}$ wherein $R^{N7}$ and $R^{N8}$ independently represent hydrogen or ($C_{1-4}$)alkyl (especially methyl);

$R^3$ represents hydrogen, methyl or trifluoromethyl (especially hydrogen);

$R^{4a}$ and $R^{4b}$ independently represent hydrogen, methyl, or $R^{4a}$ and $R^{4b}$ together with the carbon atom to which they are attached represent a cycloprop-1,1-diyl group;

$R^{5a}$ and $R^{5b}$ independently represent hydrogen, methyl, or $R^{5a}$ and $R^{5b}$ together with the carbon atom to which they are attached represent a cycloprop-1,1-diyl group;

$Ar^1$ represents
phenyl, or 5- or 6-membered heteroaryl (notably 5-membered heteroaryl, especially thiophenyl or thiazolyl); wherein said phenyl or 5- or 6-membered heteroaryl independently is mono-, di- or tri-substituted, wherein the substituents are independently selected from
($C_{1-6}$)alkyl (especially methyl, ethyl, n-propyl, isopropyl, n-butyl, isobutyl, 1-methyl-propan-1-yl, tert.-butyl, 3-methyl-butyl);
($C_{1-4}$)alkoxy (especially methoxy, ethoxy, n-propoxy, isopropoxy, n-butoxy, isobutoxy);
($C_{1-3}$)fluoroalkyl, wherein said ($C_{1-3}$)fluoroalkyl is optionally substituted with hydroxy (especially trifluoromethyl, 2,2,2-trifluoro-1-hydroxy-ethyl);
($C_{1-3}$)fluoroalkoxy (especially difluoromethoxy, trifluoromethoxy, 2,2,2-trifluoroethoxy);
halogen (especially fluoro, chloro, bromo);
cyano;
($C_{3-6}$)cycloalkyl, wherein said ($C_{3-6}$)cycloalkyl is unsubstituted or mono-substituted with amino (especially cyclopropyl, 1-amino-cyclopropyl);
($C_{4-6}$)cycloalkyl containing a ring oxygen atom, wherein said ($C_{4-6}$)cycloalkyl containing a ring oxygen atom is unsubstituted or mono-substituted with hydroxy (especially 3-hydroxy-oxetan-3-yl);
($C_{3-6}$)cycloalkyl-oxy (especially cyclobutyl-oxy, cyclopentyl-oxy);
hydroxy;
—$X^1$—CO—$R^{O1}$, wherein
$X^1$ represents a direct bond, ($C_{1-3}$)alkylene (especially —$CH_2$—, —$CH(CH_3)$—, —$C(CH_3)_2$—, —$CH_2$—$CH_2$—), —O—($C_{1-3}$)alkylene-* (especially —O—$CH_2$*, —O—$CH(CH_3)$—*, —O—C($CH_3$)$_2$—*, —O—$CH_2$—$CH_2$—*), —NH—($C_{1-3}$)alkylene-* (especially —NH—$CH_2$*, —NH—$CH(CH_3)$—*), —S—$CH_2$*, —$CF_2$—, —CH=CH—, ethen-1,1-diyl, —CH=CH—, —NH—CO—*, —CO—, or ($C_{3-5}$)cycloalkylene; wherein the asterisks indicate the bond that is linked to the —CO—$R^{O1}$ group; and
$R^{O1}$ represents
—OH;
—O—($C_{1-4}$)alkyl (especially ethoxy, methoxy);
—NH—$SO_2$—$R^{S3}$ wherein $R^{S3}$ represents ($C_{1-4}$)alkyl, ($C_{3-6}$)cycloalkyl wherein the ($C_{3-6}$)cycloalkyl optionally contains a ring oxygen atom, ($C_{3-6}$)cycloalkyl-($C_{1-3}$)alkylene wherein the ($C_{3-6}$)cycloalkyl optionally contains a ring oxygen atom, ($C_{1-3}$)fluoroalkyl, or —$NH_2$;
—O—$CH_2$—CO—$R^{O4}$, wherein $R^{O4}$ represents hydroxy, or ($C_{1-4}$)alkoxy, or —N[($C_{1-4}$)alkyl]$_2$;
—O—$CH_2$—O—CO—$R^{O5}$, wherein $R^{O5}$ represents ($C_{1-4}$)alkyl or ($C_{1-4}$)alkoxy;
—O—$CH_2$—$CH_2$—N[($C_{1-4}$)alkyl]$_2$ (especially —O—$CH_2$—$CH_2$—N($CH_3$)$_2$); or
(5-methyl-2-oxo-[1,3]dioxol-4-yl)-methyloxy-;
[wherein in particular such group —$X^1$—CO—$R^{O1}$ represents —COOH, —CO—O—$CH_3$, —CO—O—$C_2H_5$, —O—$CH_2$—COOH, —O—CH($CH_3$)—COOH, —O—C($CH_3$)$_2$—COOH, —O—$CH_2$—$CH_2$—COOH, —NH—$CH_2$—COOH, —NH—$CH_2$—CO—O—$CH_3$, —NH—CH($CH_3$)—COOH, —CO—NH—$SO_2$—$CH_3$, —CO—NH—$SO_2$—C($CH_3$)$_2$, —CO—NH—$SO_2$-cyclopropyl, —CO—NH—$SO_2$—$C_2H_5$, —CO—NH—$SO_2$—$NH_2$, —CO—O—$CH_2$—COOH, —CO—O—$CH_2$—$CH_2$—N($CH_3$)$_2$, —CO—O—$CH_2$—CO—N($CH_3$)$_2$, —CO—O—$CH_2$—O—CO—O—$C_2H_5$, —CO—O—$CH_2$—O—CO-propyl, (5-methyl-2-oxo-[1,3]dioxol-4-yl)-methyl-O—CO—, —$CH_2$—COOH, —$CH_2$—CO—O—$CH_3$, —$CH_2$—CO—O—$C_2H_5$, —$CH_2$—$CH_2$—COOH, —CH=CH—COOH, —CH=CH—CO—O—$C_2H_5$, —$CF_2$—COOH, —NH—CO—COOH, —CO—COOH, 1-carboxy-cyclopropan-1-yl];
—CO—$CH_2$—OH;

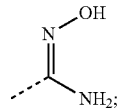

2-hydroxy-3,4-dioxo-cyclobut-1-enyl;
hydroxy-($C_{1-4}$)alkyl (especially hydroxymethyl, 1-hydroxy-ethyl);
dihydroxy-($C_{2-4}$)alkyl (especially 1,2-dihydroxyethyl);
hydroxy-($C_{2-4}$)alkoxy (especially 2-hydroxy-ethoxy);
($C_{1-4}$)alkoxy-($C_{2-4}$)alkoxy (especially 2-methoxy-ethoxy);
($CH_2$)$_r$CO—$NR^{N3}R^{N4}$ wherein r represents the integer 0 or 1; and wherein $R^{N3}$ and $R^{N4}$ independently represent hydrogen, ($C_{1-4}$)alkyl, hydroxy-($C_{2-4}$)alkyl, ($C_{1-3}$)alkoxy-($C_{2-4}$)alkyl, or hydroxy (wherein preferably at least one of $R^{N3}$ and $R^{N4}$ represents hydrogen; and wherein particular examples of such group —CO—$NR^{N3}R^{N4}$ are —CO—$NH_2$, —CO—NH($CH_3$), —CO—NH($C_2H_5$), —$CH_2$—CO—$NH_2$, —CO—NH—$C_2H_4$—OH, —CO—NH—$C_2H_4$—$OCH_3$, or —CO—N($CH_3$)$_2$, —CO—NH-isopropyl, or —CO—NH—OH);
—$X^2$—$NR^{N1}R^{N2}$, wherein $X^2$ represents —($CH_2$)$_m$—, wherein m represents the integer 0 or 1; or $X^2$ represents —O—$CH_2$—$CH_2$—*, wherein the asterisk indicates the bond that is linked to the —$NR^{N1}R^{N2}$ group; and wherein
$R^{N1}$ and $R^{N2}$ independently represent hydrogen, ($C_{1-4}$)alkyl, ($C_{1-4}$)alkoxy-($C_{2-4}$)alkyl, ($C_{3-6}$)cycloalkyl, or ($C_{2-3}$)fluoroalkyl;
or $R^{N1}$ independently represents hydrogen or ($C_{1-4}$)alkyl, and $R^{N2}$ independently represents —CO—H, —CO—($C_{1-3}$)alkyl, —CO—($C_{1-3}$)alkylene-OH, or —CO—O—($C_{1-3}$)alkyl;
or $R^{N1}$ and $R^{N2}$ together with the nitrogen to which they are attached form a 4-, 5- or 6-membered saturated ring optionally containing one ring oxygen or ring sulfur atom, wherein said ring is unsubstituted, or mono-substituted with oxo on a ring carbon atom, or disubstituted with oxo on a ring sulfur atom;

(especially such group —$X^2$—$NR^{N1}R^{N2}$ represents amino, methylamino, ethylamino, propylamino, amino-methyl, methylamino-methyl, isobutylamino-methyl, cyclopropylamino-methyl, cyclobutylamino-methyl, (2-methoxyethyl)amino-methyl, (2,2,2-trifluoro-ethyl)-amino; or —NH—CO—H, —N($C_2H_5$)—CO—H, —NH—CO—$C_2H_5$, —NH—CO—$CH_2$—$CH_2$—OH, —NH—CO—O—$CH_3$, —N($CH_3$)—CO—O—$CH_3$; or pyrrolidin-1-yl, 2-oxo-pyrrolidin-1-yl, 1,1-dioxo-isothiazolidin-2-yl, morpholin-4-yl, azetidin-1-yl, or piperidin-1-yl; or 2-(dimethylamino)-ethoxy);

—NH—CO—$NR^{N5}R^{N6}$ wherein $R^{N5}$ and $R^{N6}$ independently represent hydrogen or ($C_{1-4}$)alkyl (wherein preferably at least one of $R^{N5}$ and $R^{N6}$ represents hydrogen; and wherein particular examples of such group —NH—CO—$NR^{N5}R^{N6}$ are —NH—CO—$NH_2$, —NH—CO—NH—$C_2H_5$);

—$SO_2$—$R^{S1}$ wherein $R^{S1}$ represents hydroxy, ($C_{1-4}$)alkyl (especially methyl), or —$NR^{N7}R^{N8}$ wherein $R^{N7}$ and $R^{N8}$ independently represent hydrogen or ($C_{1-3}$)alkyl (wherein preferably at least one of $R^{N7}$ and $R^{N8}$ represents hydrogen; and wherein particular examples of such group —$SO_2$—$R^{S1}$ are —$SO_2$—$CH_3$, —$SO_2$—$NH_2$, —$SO_2$—OH, —$SO_2$—NH—$CH_3$);

—S—$R^{S2}$ wherein $R^{S2}$ represents ($C_{1-4}$)alkyl (especially methyl, ethyl, n-propyl, isopropyl, isobutyl), ($C_{3-6}$)cycloalkyl optionally containing one ring oxygen atom (especially cyclobutyl, oxetan-3-yl);

—($CH_2$)$_q$-$HET^1$, wherein q represents the integer 0, 1 or 2 (especially q is 0, i.e. $HET^1$ is linked to $Ar^1$ by a direct bond); and wherein $HET^1$ represents 5-oxo-4,5-dihydro-[1,2,4]oxadiazol-3-yl (encompassing its tautomeric form 5-hydroxy-[1,2,4]oxadiazol-3-yl), 3-oxo-2,3-dihydro-[1,2,4]oxadiazol-5-yl (encompassing its tautomeric form 3-hydroxy-[1,2,4]oxadiazol-5-yl), or 5-thioxo-4,5-dihydro-[1,2,4]oxadiazol-3-yl (encompassing its tautomeric form 5-mercapto-[1,2,4]oxadiazol-3-yl);

—($CH_2$)$_p$-HET, wherein p represents the integer 0 or 1 (especially p is 0, i.e. HET is linked to $Ar^1$ by a direct bond); and wherein HET represents a 5- or 6-membered heteroaryl (especially 5-membered heteroaryl selected from oxazolyl, isoxazolyl, oxadiazolyl, thiazolyl, isothiazolyl, thiadiazolyl, imidazolyl, pyrazolyl, triazolyl, and tetrazolyl), wherein said 5- or 6-membered heteroaryl is unsubstituted, or mono- or di-substituted, wherein the substituents are independently selected from ($C_{1-4}$)alkyl (especially methyl), ($C_{1-4}$)alkoxy (especially methoxy), —COOH, hydroxy, hydroxy-($C_{1-3}$)alkyl (especially hydroxymethyl), ($C_{3-5}$)cycloalkyl optionally containing one ring oxygen atom (especially cyclopropyl, oxetan-3-yl), or —$NR^{N9}R^{N10}$ wherein $R^{N9}$ and $R^{N10}$ independently represent hydrogen, ($C_{1-3}$)alkyl (especially methyl), or hydroxy-($C_{2-4}$)alkyl (especially 2-hydroxy-ethyl); (especially such group —($CH_2$)$_p$-HET is 1H-tetrazol-5-yl, 3-hydroxy-isoxazol-5-yl, 2-hydroxy-[1,3,4]oxadiazol-4-yl, 3-amino-isoxazol-5-yl, 2-amino-oxazol-5-yl, 5-amino-[1,3,4]thiadiazol-2-yl, 5-methylamino-[1,3,4]thiadiazol-2-yl, 5-methoxy-[1,2,4]oxadiazol-3-yl, 5-amino-[1,2,4]oxadiazol-3-yl, 5-[(2-hydroxy-ethyl)]-amino)-[1,2,4]oxadiazol-3-yl, 5-hydroxymethyl-[1,2,4]oxadiazol-3-yl, 5-(oxetan-3-yl)-[1,2,4]oxadiazol-3-yl, 1H-imidazol-4-yl, 5-methyl-1H-imidazol-4-yl, 2,5-dimethyl-1H-imidazol-4-yl);

or $Ar^1$ represents 8- to 10-membered bicyclic heteroaryl (notably 9- or 10-membered bicyclic heteroaryl; especially indazolyl, benzoimidazolyl, indolyl, benzotriazolyl, benzofuranyl, benzooxazolyl, quinoxalinyl, isoquinolinyl, quinolinyl, pyrrolopyridinyl, or imidazopyridinyl); wherein said 8- to 10-membered bicyclic heteroaryl independently is unsubstituted, mono-, or di-substituted, wherein the substituents are independently selected from ($C_{1-4}$)alkyl (especially methyl); ($C_{1-4}$)alkoxy (especially methoxy); ($C_{1-3}$)fluoroalkyl (especially trifluoromethyl); ($C_{1-3}$)fluoroalkoxy (especially trifluoromethoxy); halogen; cyano; hydroxy, or —($C_{0-3}$)alkylene-COO$R^{O2}$ wherein $R^{O2}$ represents hydrogen or ($C_{1-4}$)alkyl (especially such group —($C_{0-3}$)alkylene-COO$R^{O2}$ is —COOH); (especially such 8- to 10-membered bicyclic heteroaryl, if unsubstituted, is 1H-benzoimidazol-5-yl, 1H-indol-6-yl, 1H-indol-5-yl, 1H-indol-2-yl, 1H-indazol-5-yl, isoquinolin-7-yl, quinolin-6-yl; or, if substituted, is 3-carboxy-1H-indol-6-yl, 4-carboxy-1H-indol-2-yl, 5-carboxy-1H-indol-2-yl, 6-carboxy-1H-indol-2-yl, 7-carboxy-1H-indol-2-yl, 5-(methoxycarbonyl)-1H-indol-2-yl, 6-(methoxycarbonyl)-1H-indol-2-yl), 6-carboxy-benzofuran-2-yl, 3-carboxy-benzofuran-6-yl, 2-carboxy-benzofuran-5-yl, or 2-carboxy-benzofuran-6-yl);

or $Ar^1$ represents a group of the structure (Ar-III):

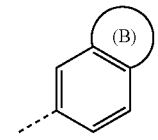

(Ar-III)

wherein ring (B) represents a non-aromatic 5- or 6-membered ring fused to the phenyl group, wherein ring (B) comprises one or two heteroatoms independently selected from nitrogen and oxygen (notably such group (Ar-III) is 2,3-dihydro-benzofuranyl, 2,3-dihydro-1H-indolyl, 2,3-dihydro-benzo[1,4]dioxinyl, 2,3-dihydro-1H-indazolyl, 2,3-dihydro-1H-benzo[d]imidazolyl, 2,3-dihydrobenzo[d]isoxazolyl, 2,3-dihydro-isoindolyl, 2,3-dihydro-benzooxazolyl, 1,2,3,4-tetrahydro-quinazolinyl, 1,2,3,4-tetrahydro-isoquinolinyl, or 1,2,3,4-tetrahydro-phthalazinyl); wherein said ring (B) independently is unsubstituted, mono-, or di-substituted, wherein the substituents are independently selected from oxo, ($C_{1-6}$)alkyl (especially methyl, ethyl, propyl, butyl, isobutyl) and —($C_{0-3}$)alkylene-COO$R^{O3}$ wherein $R^{O3}$ represents hydrogen or ($C_{1-3}$)alkyl (especially such group (Ar-III) is 2-oxo-2,3-dihydro-benzooxazol-6-yl, 3-methyl-2-oxo-2,3-dihydro-benzooxazol-5-yl, 1-methyl-3-oxo-2,3-dihydro-1H-indazol-6-yl, 2-oxo-1,2,3,4-tetrahydro-quinazolin-6-yl, 1-methyl-2-oxo-1,2,3,4-tetrahydro-quinazolin-6-yl, 1-oxo-1,2,3,4-tetrahydro-isoquinolin-6-yl, 1-methyl-2-oxo-1,2,3,4-tetrahydro-quinazolin-7-yl, or 1-oxo-1,2,3,4-tetrahydro-isoquinolin-7-yl).

In a sub-embodiment, $Ar^1$ especially represents
phenyl, or 5- or 6-membered heteroaryl; wherein said phenyl or 5- or 6-membered heteroaryl independently is mono-, di- or tri-substituted (especially di-substituted),
  wherein one of said substituents is selected from $(C_{4-6})$cycloalkyl containing a ring oxygen atom, wherein said $(C_{4-6})$cycloalkyl containing a ring oxygen atom is unsubstituted or mono-substituted with hydroxy; hydroxy;

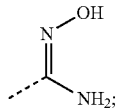

—$X^1$—CO—$R^{O1}$; 2-hydroxy-3,4-dioxo-cyclobut-1-enyl; hydroxy-$(C_{2-4})$alkoxy; —$(CH_2)_r$CO—$NR^{N3}R^{N4}$; —NH—CO—$NR^{N5}R^{N6}$; $SO_2$—$R^{S1}$; —$(CH_2)_q$-$HET^1$; —$(CH_2)_p$-HET;
  and the other of said substituents, if present, independently are selected from $(C_{1-6})$alkyl; $(C_{1-4})$alkoxy; $(C_{1-3})$fluoroalkyl; $(C_{1-3})$fluoroalkoxy; halogen; cyano; $(C_{1-6})$cycloalkyl, wherein said $(C_{1-6})$cycloalkyl is unsubstituted or mono-substituted with amino; $(C_{3-6})$cycloalkyl-oxy; hydroxy; hydroxy-$(C_{1-4})$alkyl; dihydroxy-$(C_{2-4})$alkyl; hydroxy-$(C_{2-4})$alkoxy; $(C_{1-4})$alkoxy-$(C_{2-4})$alkoxy; —$X^2$—$NR^{N1}R^{N2}$; —S—$R^{S2}$; wherein the above groups and substituents are as defined in embodiment 1).
or $Ar^1$ represents 8- to 10-membered bicyclic heteroaryl as defined in embodiment 1); wherein said 8- to 10-membered bicyclic heteroaryl independently is unsubstituted, mono-, or di-substituted, wherein the substituents are independently selected from $(C_{1-4})$alkyl; $(C_{1-4})$alkoxy; $(C_{1-3})$fluoroalkyl; $(C_{1-3})$fluoroalkoxy; halogen; cyano; hydroxy, or —$(C_{0-3})$alkylene-$COOR^{O2}$ wherein $R^{O2}$ represents hydrogen or $(C_{1-4})$alkyl;
or $Ar^1$ represents a group of the structure (Ar-III) as defined in embodiment 1).

2) A second embodiment relates to compounds according to embodiment 1), wherein $R^3$ represents hydrogen.

3) Another embodiment relates to compounds according to embodiment 1), wherein $R^3$ represents methyl.

4) Another embodiment relates to compounds according to any one of embodiments 1) to 3), wherein $R^{4a}$ and $R^{4b}$ both represent hydrogen.

5) Another embodiment relates to compounds according to any one of embodiments 1) to 4), wherein $R^{5a}$ and $R^{5b}$ both represent hydrogen. Particular compounds of formula (I) are compounds wherein $R^{4a}$ and $R^{4b}$ both represent hydrogen; and $R^{5a}$ and $R^{5b}$ both represent hydrogen.

6) Another embodiment relates to compounds according to any one of embodiments 1) to 5), wherein the characteristics defined for the fragment

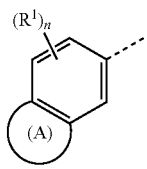

according to embodiments 8), or 17) to 20) below apply mutatis mutandis.

7) Another embodiment relates to compounds according to any one of embodiments 1) to 6), wherein the characteristics defined for the substituent $Ar^1$ according to embodiments 8), or 11) to 16) below apply mutatis mutandis.

8) A second aspect of the invention relates to compounds of the formula (II)

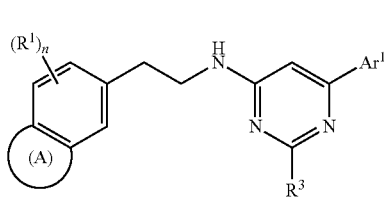

Formula (II)

wherein in compounds of the formula (II)
ring (A) in the fragment:

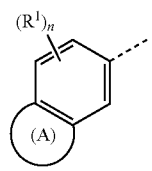

represents an aromatic 5- or 6-membered ring or a non-aromatic 5- to 7-membered ring, which ring (A) is fused to the phenyl group, wherein said ring (A) optionally contains one or two heteroatoms independently selected from nitrogen, oxygen, and sulfur (notably such fused group is benzofuranyl, benzothiophenyl, benzothiazolyl, benzoisothiazolyl, indolyl, indazolyl, naphthyl, quinolinyl, isoquinolinyl, 2,3-dihydro-benzo[b]thiophenyl, benzo[1,3]dioxolyl, 1,3-dihydro-isobenzofuranyl, 2,3-dihydro-benzofuranyl, indanyl, 5,6,7,8-tetrahydro-naphthalenyl, 2,3-dihydro-benzo[1,4]dioxinyl, chromanyl, 3,4-dihydro-2H-benzo[1,4]oxazinyl, 1,2,3,4-tetrahydro-quinolinyl, 3,4-dihydro-2H-benzo[b][1,4]dioxepinyl); wherein said fragment is optionally substituted with $(R^1)_n$; wherein $(R^1)_n$ represents one, two, three, or four optional substituents (i.e. said fragment is unsubstituted, or substituted with one, two, three, or four $R^1$), wherein said substituents $R^1$ are independently selected from $(C_{1-3})$alkyl (especially methyl), $(C_{2-3})$alkenyl (especially vinyl), $(C_{2-3})$alkynyl (especially ethynyl), $(C_{1-3})$alkoxy (especially methoxy, ethoxy, isopropoxy), halogen (especially fluoro, or chloro), —S—$(C_{1-3})$alkyl (especially methylsulfanyl), $(C_{1-3})$fluoroalkyl (especially trifluoromethyl), $(C_{1-3})$fluoroalkoxy (especially trifluoromethoxy, difluoromethoxy), cyano, oxo, —$NR^{N7}R^{N8}$ wherein $R^{N7}$ and $R^{N8}$ independently represent hydrogen or $(C_{1-4})$alkyl (especially methyl);

$R^3$ represents hydrogen, or methyl (especially hydrogen);
$Ar^1$ represents
a phenyl group of the structure (Ar-I):

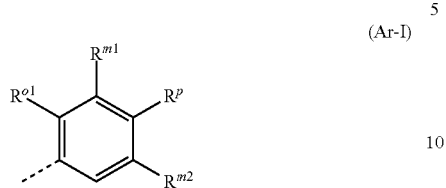

wherein
$R^p$ represents
$(C_{4-6})$cycloalkyl containing a ring oxygen atom, wherein said $(C_{4-6})$cycloalkyl containing a ring oxygen atom is unsubstituted or mono-substituted with hydroxy (especially 3-hydroxy-oxetan-3-yl); hydroxy;
—$X^1$—CO—$R^{O1}$, wherein
$X^1$ represents a direct bond, $(C_{1-3})$alkylene (especially —$CH_2$—, —$CH(CH_3)$—, —$C(CH_3)_2$—, —$CH_2$—$CH_2$—), —O—$(C_{1-3})$alkylene-* (especially —O—$CH_2$—*, —O—$CH(CH_3)$—*, —O—$C(CH_3)_2$—*, —O—$CH_2$—$CH_2$—*), —NH—$(C_{1-3})$alkylene-* (especially —NH—$CH_2$*, —NH—$CH(CH_3)$—*), —S—$CH_2$*, —$CF_2$—, —CH=CH—, ethen-1,1-diyl, —CH=CH—, —NH—CO—*, —CO—, or $(C_{3-5})$cycloalkylene; wherein the asterisks indicate the bond that is linked to the —CO—$R^{O1}$ group; and
$R^{O1}$ represents
-OH;
-O—$(C_{1-4})$alkyl (especially ethoxy, methoxy);
—NH—$SO_2$—$R^{S3}$ wherein $R^{S3}$ represents $(C_{1-4})$alkyl, $(C_{3-6})$cycloalkyl wherein the $(C_{3-6})$cycloalkyl optionally contains a ring oxygen atom, $(C_{3-6})$cycloalkyl-$(C_{1-3})$alkylene wherein the $(C_{3-6})$cycloalkyl optionally contains a ring oxygen atom, $(C_{1-3})$fluoroalkyl, or —$NH_2$;
—O—$CH_2$—CO—$R^{O4}$, wherein $R^{O4}$ represents hydroxy, or $(C_{1-4})$alkoxy, or —N[$(C_{1-4})$alkyl]$_2$;
—O—$CH_2$—O—CO—$R^{O5}$, wherein $R^{O5}$ represents $(C_{1-4})$alkyl or $(C_{1-4})$alkoxy;
-O—$CH_2$—$CH_2$—N[$(C_{1-4})$alkyl]$_2$ (especially —O—$CH_2$—$CH_2$—N$(CH_3)_2$); or
(5-methyl-2-oxo-[1,3]dioxol-4-yl)-methyloxy-;
[wherein in particular such group —$X^1$—CO—$R^{O1}$ represents —COOH, —CO—O—$CH_3$, —CO—O—$C_2H_5$, —O—$CH_2$—COOH, —O—$CH(CH_3)$—COOH, —O—$C(CH_3)_2$—COOH, —O—$CH_2$—$CH_2$—COOH, —NH—$CH_2$—COOH, —NH—$CH_2$—CO—O—$CH_3$, —NH—$CH(CH_3)$—COOH, —CO—NH—$SO_2$—$CH_3$, —CO—NH—$SO_2$—$C(CH_3)_2$, —CO—NH—$SO_2$-cyclopropyl, —CO—NH—$SO_2$—$C_2H_5$, —CO—NH—$SO_2$—$NH_2$, —CO—O—$CH_2$—COOH, —CO—O—$CH_2$—$CH_2$—N$(CH_3)_2$, —CO—O—$CH_2$—CO—N$(CH_3)_2$, —CO—O—$CH_2$—O—CO—O—$C_2H_5$, —CO—O—$CH_2$—O—CO-propyl, (5-methyl-2-oxo-[1,3]dioxol-4-yl)-methyl-O—CO—, —$CH_2$—COOH, —$CH_2$—CO—O—$CH_3$, —$CH_2$—CO—O—$C_2H_5$, —$CH_2$—$CH_2$—COOH, —CH=CH—COOH, —CH=CH—CO—O—$C_2H_5$, —$CF_2$—COOH, —NH—CO—COOH, —CO—COOH, 1-carboxy-cyclopropan-1-yl];

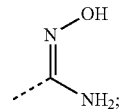

2-hydroxy-3,4-dioxo-cyclobut-1-enyl;
hydroxy-$(C_{1-4})$alkyl (especially hydroxymethyl, 1-hydroxy-ethyl);
hydroxy-$(C_{2-4})$alkoxy (especially 2-hydroxy-ethoxy);
—$(CH_2)_r$CO—$NR^{N3}R^{N4}$ wherein r represents the integer 0 or 1; and wherein $R^{N3}$ and $R^{N4}$ independently represent hydrogen, $(C_{1-4})$alkyl, hydroxy-$(C_{2-4})$alkyl, $(C_{1-3})$alkoxy-$(C_{2-4})$alkyl, or hydroxy (wherein preferably at least one of $R^{N3}$ and $R^{N4}$ represents hydrogen; and wherein particular examples of such group —CO—$NR^{N3}R^{N4}$ are —CO—$NH_2$, —CO—$NH(CH_3)$, —CO—NH$(C_2H_5)$, —$CH_2$—CO—$NH_2$, —CO—NH—$C_2H_4$—OH, —CO—NH—$C_2H_4$—$OCH_3$, or —CO—N$(CH_3)_2$, —CO—NH-isopropyl, or —CO—NH—OH);
—$NR^{N1}R^{N2}$, wherein $R^{N1}$ independently represents hydrogen or $(C_{1-4})$alkyl, and $R^{N2}$ independently represents —CO—H, —CO—$(C_{1-3})$alkyl, or —CO—$(C_{1-3})$alkylene-OH; (especially such group —$(CH_2)_m$—$NR^{N1}R^{N2}$ represents-NH—CO—H, —N$(C_2H_5)$—CO—H, —NH—CO—$C_2H_5$, or —NH—CO—$CH_2$—$CH_2$—OH);
—NH—CO—$NR^{N5}R^{N6}$ wherein $R^{N5}$ and $R^{N6}$ independently represent hydrogen or $(C_{1-4})$alkyl (wherein preferably at least one of $R^{N5}$ and $R^{N6}$ represents hydrogen; and wherein particular examples of such group —NH—CO—$NR^{N5}R^{N6}$ are —NH—CO—$NH_2$, —NH—CO—NH—$C_2H_5$);
—$SO_2$—$R^{S1}$ wherein $R^{S1}$ represents $(C_{1-4})$alkyl (especially methyl), or —$NR^{N7}R^{N8}$ wherein $R^{N7}$ and $R^{N8}$ independently represent hydrogen or $(C_{1-3})$alkyl (wherein preferably at least one of $R^{N7}$ and $R^{N8}$ represents hydrogen; and wherein particular examples of such group —$SO_2$—$R^{S1}$ are —$SO_2$—$CH_3$, —$SO_2$—$NH_2$, —$SO_2$—NH—$CH_3$);
—$(CH_2)_q$-$HET^1$, wherein q represents the integer 0, 1 or 2 (especially q is 0, i.e. $HET^1$ is linked to $Ar^1$ by a direct bond); and wherein $HET^1$ represents 5-oxo-4,5-dihydro-[1,2,4]oxadiazol-3-yl (encompassing its tautomeric form 5-hydroxy-[1,2,4]oxadiazol-3-yl), 3-oxo-2,3-dihydro-[1,2,4]oxadiazol-5-yl (encompassing its tautomeric form 3-hydroxy-[1,2,4]oxadiazol-5-yl), or 5-thioxo-4,5-dihydro-[1,2,4]oxadiazol-3-yl (encompassing its tautomeric form 5-mercapto-[1,2,4]oxadiazol-3-yl);
—$(CH_2)_p$-HET, wherein p represents the integer 0 or 1 (especially p is 0, i.e. HET is linked to $Ar^1$ by a direct bond); and wherein HET represents a 5-membered heteroaryl (especially oxazolyl, isoxazolyl, oxadiazolyl, thiazolyl, isothiazolyl, thiadiazolyl, imidazolyl, pyrazolyl, triazolyl, or tetrazolyl), wherein said 5-membered heteroaryl is unsubstituted, or mono- or di-substituted, wherein the substituents are independently selected from $(C_{1-4})$alkyl (especially methyl), $(C_{1-4})$alkoxy (especially methoxy), —COOH, hydroxy, hydroxy-$(C_{1-3})$alkyl (especially hydroxymethyl), $(C_{3-5})$cycloalkyl optionally containing one ring oxygen atom (especially cyclopropyl, oxetan-3-yl), or —NR$^{N9}$R$^{N10}$ wherein R$^{N9}$ and R$^{N10}$ independently represent hydrogen, $(C_{1-3})$alkyl (especially methyl), or hydroxy-$(C_{2-4})$alkyl (especially 2-hydroxy-ethyl); (especially such group —(CH$_2$)$_p$-HET is 1H-tetrazol-5-yl, 3-hydroxy-isoxazol-5-yl, 2-hydroxy-[1,3,4]oxadiazol-4-yl, 3-amino-isoxazol-5-yl, 2-amino-oxazol-5-yl, 5-amino-[1,3,4]thiadiazol-2-yl, 5-methylamino-[1,3,4]thiadiazol-2-yl, 5-methoxy-[1,2,4]oxadiazol-3-yl, 5-amino-[1,2,4]oxadiazol-3-yl, 5-[(2-hydroxy-ethyl)]-amino)-[1,2,4]oxadiazol-3-yl, 5-hydroxymethyl-[1,2,4]oxadiazol-3-yl, 5-(oxetan-3-yl)-[1,2,4]oxadiazol-3-yl, 1H-imidazol-4-yl, 5-methyl-1H-imidazol-4-yl, 2,5-dimethyl-1H-imidazol-4-yl);

R$^{m1}$ represents
hydrogen;
$(C_{1-6})$alkyl (especially methyl, ethyl, n-propyl, isopropyl, n-butyl, isobutyl);
$(C_{1-4})$alkoxy (especially methoxy, ethoxy, n-propoxy, isopropoxy, n-butoxy, isobutoxy);
$(C_{1-3})$fluoroalkyl (especially trifluoromethyl);
$(C_{1-3})$fluoroalkoxy (especially difluoromethoxy, trifluoromethoxy, 2,2,2-trifluoroethoxy);
halogen (especially fluoro or chloro);
$(C_{3-6})$cycloalkyl (especially cyclopropyl);
$(C_{3-6})$cycloalkyl-oxy (especially cyclopropyl-oxy, cyclobutyl-oxy, cyclopentyl-oxy);
hydroxy;
hydroxy-$(C_{2-4})$alkoxy (especially 2-hydroxy-ethoxy);
—X$^2$—NR$^{N1}$R$^{N2}$, wherein X$^2$ represents a direct bond; or X$^2$ represents —O—CH$_2$—CH$_2$—*, wherein the asterisk indicates the bond that is linked to the —NR$^{N1}$R$^{N2}$ group; and wherein R$^{N1}$ and R$^{N2}$ independently represent hydrogen, $(C_{1-4})$alkyl (especially methyl), or $(C_{3-6})$cycloalkyl (especially cyclopropyl); (especially such group —X$^2$—NR$^{N1}$R$^{N2}$ represents amino, methylamino, ethylamino, propylamino; or 2-(dimethylamino)-ethoxy);
—S—R$^{S2}$ wherein R$^{S2}$ represents $(C_{1-4})$alkyl (especially methyl, ethyl, n-propyl, isopropyl, isobutyl), or $(C_{3-6})$cycloalkyl optionally containing one ring oxygen atom (especially cyclobutyl, oxetan-3-yl);
wherein in a sub-embodiment, R$^{m1}$ especially is different from hydrogen;
R$^{m2}$ represents hydrogen, methyl, fluoro, or chloro; and
R$^{o1}$ represents hydrogen; or, in case R$^{m2}$ represents hydrogen, R$^{o1}$ represents hydrogen or fluoro;
or Ar$^1$ represents a 5-membered heteroaryl group of the structure (Ar-II):

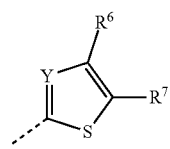

(Ar-II)

wherein
Y represents CR$^8$ wherein R$^8$ represents especially hydrogen, or halogen (notably fluoro, chloro); or Y represents N;
R$^7$ represents
$(C_{4-6})$cycloalkyl containing a ring oxygen atom, wherein said $(C_{4-6})$cycloalkyl containing a ring oxygen atom is unsubstituted or mono-substituted with hydroxy (especially 3-hydroxy-oxetan-3-yl);
—X$^1$—CO—R$^{O1}$, wherein
X$^1$ represents a direct bond, $(C_{1-3})$alkylene (especially —CH$_2$—, —CH(CH$_3$)—, —C(CH$_3$)$_2$—, —CH$_2$—CH$_2$—), —O—$(C_{1-3})$alkylene-* (especially —O—CH$_2$—*, —O—CH(CH$_3$)—*, —O—C(CH$_3$)$_2$—*, —O—CH$_2$—CH$_2$—*), —NH—$(C_{1-3})$alkylene* (especially —NH—CH$_2$*, —NH—CH(CH$_3$)—*), —S—CH$_2$*, —CF$_2$—, —CH=CH—, —CH≡CH—, —NH—CO—*, —CO—, or $(C_{3-5})$cycloalkylene; wherein the asterisks indicate the bond that is linked to the —CO—R$^{O1}$ group; and
R$^{O1}$ represents
—OH;
—O—$(C_{1-4})$alkyl (especially ethoxy, methoxy);
—NH—SO$_2$—R$^{S3}$ wherein R$^{S3}$ represents $(C_{1-4})$alkyl, $(C_{1-6})$cycloalkyl wherein the $(C_{3-6})$cycloalkyl optionally contains a ring oxygen atom, $(C_{3-6})$cycloalkyl-$(C_{1-3})$alkylene wherein the $(C_{3-6})$cycloalkyl optionally contains a ring oxygen atom, $(C_{1-3})$fluoroalkyl, or —NH$_2$;
—O—CH$_2$—CO—R$^{O4}$, wherein R$^{O4}$ represents hydroxy, or $(C_{1-4})$alkoxy, or —N[(C$_{1-4}$)alkyl]$_2$;
—O—CH$_2$—O—CO—R$^{O5}$, wherein R$^{O5}$ represents $(C_{1-4})$alkyl or $(C_{1-4})$alkoxy;
—O—CH$_2$—CH$_2$—N[(C$_{1-4}$)alkyl]$_2$ (especially —O—CH$_2$—CH$_2$—N(CH$_3$)$_2$); or
(5-methyl-2-oxo-[1,3]dioxol-4-yl)-methyloxy-;
[wherein in particular such group —X$^1$—CO—R$^{O1}$ represents —COOH, —CO—O—CH$_3$, —CO—O—C$_2$H$_5$, —O—CH$_2$—COOH, —O—CH(CH$_3$)—COOH, —O—C(CH$_3$)$_2$—COOH, —O—CH$_2$—CH$_2$—COOH, —NH—CH$_2$—COOH, —NH—CH$_2$—CO—O—CH$_3$, —NH—CH(CH$_3$)—COOH, —CO—NH—SO$_2$—CH$_3$, —CO—NH—SO$_2$—C(CH$_3$)$_2$, —CO—NH—SO$_2$-cyclopropyl, —CO—NH—SO$_2$—C$_2$H$_5$, —CO—NH—SO$_2$—NH$_2$, —CO—O—CH$_2$—COOH, —CO—O—CH$_2$—CH$_2$—N(CH$_3$)$_2$, —CO—O—CH$_2$—CO—N(CH$_3$)$_2$, —CO—O—CH$_2$—O—CO—O—C$_2$H$_5$, —CO—O—CH$_2$—O—CO-propyl, (5-methyl-2-oxo-[1,3]dioxol-4-yl)-methyl-O—CO—, —CH$_2$—COOH, —CH$_2$—CO—O—CH$_3$, —CH$_2$—CO—O—C$_2$H$_5$, —CH$_2$—CH$_2$—COOH, —CH=CH—COOH, —CH≡CH—CO—O—C$_2$H$_5$, —CF$_2$—COOH, —NH—CO—COOH, —CO—COOH, 1-carboxy-cyclopropan-1-yl];

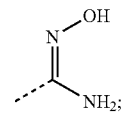

2-hydroxy-3,4-dioxo-cyclobut-1-enyl;
hydroxy-($C_{1-4}$)alkyl (especially hydroxymethyl, 1-hydroxy-ethyl);
hydroxy-($C_{2-4}$)alkoxy (especially 2-hydroxy-ethoxy);
—($CH_2$)$_r$CO—NR$^{N3}$R$^{N4}$ wherein r represents the integer 0 or 1; and wherein R$^{N3}$ and R$^{N4}$ independently represent hydrogen, ($C_{1-4}$)alkyl, hydroxy-($C_{2-4}$)alkyl, ($C_{1-3}$)alkoxy-($C_{2-4}$)alkyl, or hydroxy (wherein preferably at least one of R$^{N3}$ and R$^{N4}$ represents hydrogen; and wherein particular examples of such group —CO—NR$^{N3}$R$^{N4}$ are —CO—NH$_2$, —CO—NH(CH$_3$), —CO—NH($C_2H_5$), —CH$_2$—CO—NH$_2$, —CO—NH—$C_2H_4$—OH, —CO—NH—$C_2H_4$—OCH$_3$, or —CO—N(CH$_3$)$_2$, —CO—NH-isopropyl, or —CO—NH—OH);
—NR$^{N1}$R$^{N2}$, wherein R$^{N1}$ independently represents hydrogen or ($C_{1-4}$)alkyl, and R$^{N2}$ independently represents —CO—H, —CO—($C_{1-3}$)alkyl, or —CO—($C_{1-3}$)alkylene-OH; (especially such group —(CH$_2$)$_m$—NR$^{N1}$R$^{N2}$ represents-NH—CO—H, —N($C_2H_5$)—CO—H, —NH—CO—$C_2H_5$, or —NH—CO—CH$_2$—CH$_2$—OH);
—NH—CO—NR$^{N5}$R$^{N6}$ wherein R$^{N5}$ and R$^{N6}$ independently represent hydrogen or ($C_{1-4}$)alkyl (wherein preferably at least one of R$^{N5}$ and R$^{N6}$ represents hydrogen; and wherein particular examples of such group —NH—CO—NR$^{N5}$R$^{N6}$ are —NH—CO—NH$_2$, —NH—CO—NH—$C_2H_5$);
—SO$_2$—R$^{S1}$ wherein R$^{S1}$ represents ($C_{1-4}$)alkyl (especially methyl), or —NR$^{N7}$R$^{N8}$ wherein R$^{N7}$ and R$^{N8}$ independently represent hydrogen or ($C_{1-3}$)alkyl (wherein preferably at least one of R$^{N7}$ and R$^{N8}$ represents hydrogen; and wherein particular examples of such group-SO$_2$—R$^{S1}$ are —SO$_2$—CH$_3$, —SO$_2$—NH$_2$, —SO$_2$—NH—CH$_3$);
—(CH$_2$)$_q$-HET$^1$, wherein q represents the integer 0, 1 or 2 (especially q is 0, i.e. HET$^1$ is linked to Ar$^1$ by a direct bond); and wherein HET$^1$ represents 5-oxo-4,5-dihydro-[1,2,4]oxadiazol-3-yl (encompassing its tautomeric form 5-hydroxy-[1,2,4]oxadiazol-3-yl), 3-oxo-2,3-dihydro-[1,2,4]oxadiazol-5-yl (encompassing its tautomeric form 3-hydroxy-[1,2,4]oxadiazol-5-yl), or 5-thioxo-4,5-dihydro-[1,2,4]oxadiazol-3-yl (encompassing its tautomeric form 5-mercapto-[1,2,4]oxadiazol-3-yl);
—(CH$_2$)$_p$-HET, wherein p represents the integer 0 or 1 (especially p is 0, i.e. HET is linked to Ar$^1$ by a direct bond); and wherein HET represents a 5-membered heteroaryl (especially oxazolyl, isoxazolyl, oxadiazolyl, thiazolyl, isothiazolyl, thiadiazolyl, imidazolyl, pyrazolyl, triazolyl, or tetrazolyl), wherein said 5-membered heteroaryl is unsubstituted, or mono- or di-substituted, wherein the substituents are independently selected from ($C_{1-4}$)alkyl (especially methyl), ($C_{1-4}$)alkoxy (especially methoxy), —COOH, hydroxy, hydroxy-($C_{1-3}$)alkyl (especially hydroxymethyl), ($C_{3-5}$)cycloalkyl optionally containing one ring oxygen atom (especially cyclopropyl, oxetan-3-yl), or —NR$^{N9}$R$^{N10}$ wherein R$^{N9}$ and R$^{N10}$ independently represent hydrogen, ($C_{1-3}$)alkyl (especially methyl), or hydroxy-($C_{2-4}$)alkyl (especially 2-hydroxy-ethyl); (especially such group —(CH$_2$)$_p$-HET is 1H-tetrazol-5-yl, 3-hydroxy-isoxazol-5-yl, 2-hydroxy-[1,3,4]oxadiazol-4-yl, 3-amino-isoxazol-5-yl, 2-amino-oxazol-5-yl, 5-amino-[1,3,4]thiadiazol-2-yl, 5-methylamino-[1,3,4]thiadiazol-2-yl, 5-methoxy-[1,2,4]oxadiazol-3-yl, 5-amino-[1,2,4]oxadiazol-3-yl, 5-[(2-hydroxy-ethyl)]-amino)-[1,2,4]oxadiazol-3-yl, 5-hydroxymethyl-[1,2,4]oxadiazol-3-yl, 5-(oxetan-3-yl)-[1,2,4]oxadiazol-3-yl, 1H-imidazol-4-yl, 5-methyl-1H-imidazol-4-yl, 2,5-dimethyl-1H-imidazol-4-yl);

R$^6$ represents
($C_{1-6}$)alkyl (especially methyl, ethyl, n-propyl, isopropyl, n-butyl, isobutyl);
($C_{1-4}$)alkoxy (especially methoxy, ethoxy, n-propoxy, isopropoxy, n-butoxy);
($C_{1-3}$)fluoroalkyl (especially trifluoromethyl);
($C_{1-3}$)fluoroalkoxy (especially difluoromethoxy, trifluoromethoxy, 2,2,2-trifluoroethoxy);
halogen (especially fluoro or chloro);
hydroxy;
($C_{3-6}$)cycloalkyl (especially cyclopropyl);
($C_{3-6}$)cycloalkyl-oxy (especially cyclopropyl-oxy, cyclobutyl-oxy, cyclopentyl-oxy);
hydroxy-($C_{2-4}$)alkoxy (especially 2-hydroxy-ethoxy);
—X$^2$—NR$^{N1}$R$^{N2}$, wherein X$^2$ represents a direct bond; or X$^2$ represents —O—CH$_2$—CH$_2$—*, wherein the asterisk indicates the bond that is linked to the —NR$^{N1}$R$^{N2}$ group; and wherein R$^{N1}$ and R$^{N2}$ independently represent hydrogen, ($C_{1-4}$) alkyl, or ($C_{3-6}$)cycloalkyl; (especially such group —X$^2$—NR$^{N1}$R$^{N2}$ represents amino, methylamino, ethylamino, propylamino; or 2-(dimethylamino)-ethoxy);
—S—R$^{S2}$ wherein R$^{S2}$ represents ($C_{1-4}$)alkyl (especially methyl, ethyl, n-propyl, isopropyl, isobutyl), or ($C_{3-6}$)cycloalkyl optionally containing one ring oxygen atom (especially cyclobutyl, oxetan-3-yl);

or Ar$^1$ represents 8- to 10-membered bicyclic heteroaryl (notably 9- or 10-membered bicyclic heteroaryl; especially indazolyl, benzoimidazolyl, indolyl, benzofuranyl, benzooxazolyl, quinoxalinyl, isoquinolinyl, or quinolinyl); wherein said 8- to 10-membered bicyclic heteroaryl independently is mono-substituted with —($C_{0-3}$)alkylene-COOR$^{O2}$ wherein R$^{O2}$ represents hydrogen or ($C_{1-4}$)alkyl (especially methyl) (wherein especially such group —($C_{0-3}$)alkylene-COOR$^{O2}$ is —COOH); (especially such 8- to 10-membered bicyclic heteroaryl is 3-carboxy-1H-indol-6-yl, 4-carboxy-1H-indol-2-yl, 5-carboxy-1H-indol-2-yl, 6-carboxy-1H-indol-2-yl, 7-carboxy-1H-indol-2-yl, 5-(methoxycarbonyl)-1H-indol-2-yl, 6-(methoxycarbonyl)-1H-indol-2-yl), 6-carboxy-benzofuran-2-yl, 3-carboxy-benzofuran-6-yl, 2-carboxy-benzofuran-5-yl, or 2-carboxy-benzofuran-6-yl);

or Ar$^1$ represents a group of the structure (Ar-III):

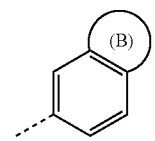

(Ar-III)

which is selected from 2-oxo-2,3-dihydro-benzooxazol-6-yl, 3-methyl-2-oxo-2,3-dihydro-benzooxazol-5-yl, 1-methyl-3-oxo-2,3-dihydro-1H-indazol-6-yl, 2-oxo-1,2,3,4-tetrahydro-quinazolin-6-yl, 1-methyl-2-oxo-1,2,3,4-tetrahydro-quinazolin-6-yl, 1-oxo-1,2,3,4-tetrahydro-isoquinolin-6-yl, 1-methyl-2-oxo-1,2,3,4-tetrahydro-quinazolin-7-yl, and 1-oxo-1,2,3,4-tetrahydro-isoquinolin-7-yl.

The compounds of formula (I)/formula (II) may contain one or more stereogenic or asymmetric centers, such as one or more asymmetric carbon atoms, which are allowed to be present in (R)- as well as (S)-configuration. The compounds of formula (I)/formula (II) may further encompass compounds with one or more double bonds which are allowed to be present in Z- as well as E-configuration and/or compounds with substituents at a ring system which are allowed to be present, relative to each other, in cis- as well as trans-configuration. The compounds of formula (I)/formula (II) may thus be present as mixtures of stereoisomers or preferably as pure stereoisomers. Mixtures of stereoisomers may be separated in a manner known to a person skilled in the art.

In case a particular compound (or generic structure) is designated as (R)- or (S)-enantiomer, such designation is to be understood as referring to the respective compound (or generic structure) in enriched, especially essentially pure, enantiomeric form. Likewise, in case a specific asymmetric center in a compound is designated as being in (R)- or (S)-configuration or as being in a certain relative configuration, such designation is to be understood as referring to the compound that is in enriched, especially essentially pure, form with regard to the respective configuration of said asymmetric center. In analogy, cis- or trans-designations are to be understood as referring to the respective stereoisomer of the respective relative configuration in enriched, especially essentially pure, form. Likewise, in case a particular compound (or generic structure) is designated as Z- or E-stereoisomer (or in case a specific double bond in a compound is designated as being in Z- or E-configuration), such designation is to be understood as referring to the respective compound (or generic structure) in enriched, especially essentially pure, stereoisomeric form (or to the compound that is in enriched, especially essentially pure, form with regard to the respective configuration of the double bond).

The term "enriched", when used in the context of stereoisomers, is to be understood in the context of the present invention to mean that the respective stereoisomer is present in a ratio of at least 70:30, especially of at least 90:10 (i.e., in a purity of at least 70% by weight, especially of at least 90% by weight), with regard to the respective other stereoisomer/the entirety of the respective other stereoisomers.

The term "essentially pure", when used in the context of stereoisomers, is to be understood in the context of the present invention to mean that the respective stereoisomer is present in a purity of at least 95% by weight, especially of at least 99% by weight, with regard to the respective other stereoisomer/the entirety of the respective other stereoisomers.

The present invention also includes isotopically labelled, especially $^2$H (deuterium) labelled compounds of formula (I)/formula (II) according to embodiments 1) to 29), which compounds are identical to the compounds of formula (I)/formula (II) except that one or more atoms have each been replaced by an atom having the same atomic number but an atomic mass different from the atomic mass usually found in nature. Isotopically labelled, especially $^2$H (deuterium) labelled compounds of formula (I)/formula (II) and salts thereof are within the scope of the present invention. Substitution of hydrogen with the heavier isotope $^2$H (deuterium) may lead to greater metabolic stability, resulting e.g. in increased in-vivo half-life or reduced dosage requirements, or may lead to reduced inhibition of cytochrome P450 enzymes, resulting e.g. in an improved safety profile. In one embodiment of the invention, the compounds of formula (I)/formula (II) are not isotopically labelled, or they are labelled only with one or more deuterium atoms. In a sub-embodiment, the compounds of formula (I)/formula (II) are not isotopically labelled at all. Isotopically labelled compounds of formula (I)/formula (II) may be prepared in analogy to the methods described hereinafter, but using the appropriate isotopic variation of suitable reagents or starting materials.

In this patent application, a bond drawn as a dotted line shows the point of attachment of the radical drawn. For example, the radical drawn below

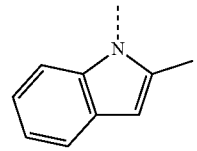

is the 2-methyl-1H-indol-1-yl group.

In some instances, the compounds of formula (I)/formula (II) may contain tautomeric forms. Such tautomeric forms are encompassed in the scope of the present invention. In case tautomeric forms exist of a certain residue, and only one form of such residue is disclosed or defined, the other tautomeric form(s) are understood to be encompassed in such disclosed residue. For example the group 2-oxo-2,3-dihydro-1H-benzo[d]imidazol-5-yl is to be understood as also encompassing its tautomeric forms 2-hydroxy-1H-benzo[d]imidazol-5-yl and 2-hydroxy-3H-benzo[d]imidazol-5-yl. Similarly, 5-oxo-4,5-dihydro-[1,2,4]oxadiazol-3-yl (alternatively named 5-oxo-4H-[1,2,4]oxadiazol-3-yl) encompasses its tautomeric form 5-hydroxy-[1,2,4]oxadiazol-3-yl, and 3-oxo-2,3-dihydro-[1,2,4]oxadiazol-5-yl (alternatively named 3-oxo-2H-[1,2,4]oxadiazol-5-yl) encompasses its tautomeric form 3-hydroxy-[1,2,4]oxadiazol-5-yl.

Where the plural form is used for compounds, salts, pharmaceutical compositions, diseases and the like, this is intended to mean also a single compound, salt, or the like.

Any reference to compounds of formula (I)/formula (II) according to embodiments 1) to 29) is to be understood as referring also to the salts (and especially the pharmaceutically acceptable salts) of such compounds, as appropriate and expedient.

The term "pharmaceutically acceptable salts" refers to salts that retain the desired biological activity of the subject compound and exhibit minimal undesired toxicological effects. Such salts include inorganic or organic acid and/or base addition salts depending on the presence of basic and/or acidic groups in the subject compound. For reference see for example "Handbook of Pharmaceutical Salts. Properties, Selection and Use.", P. Heinrich Stahl, Camille G. Wermuth (Eds.), Wiley-VCH, 2008; and "Pharmaceutical Salts and Co-crystals", Johan Wouters and Luc Quéré (Eds.), RSC Publishing, 2012.

Definitions provided herein are intended to apply uniformly to the compounds of formula (I)/formula (II), as defined in any one of embodiments 1) to 22), and, mutatis mutandis, throughout the description and the claims unless an otherwise expressly set out definition provides a broader or narrower definition. It is well understood that a definition or preferred definition of a term defines and may replace the respective term independently of (and in combination with) any definition or preferred definition of any or all other terms as defined herein. Whenever the group $Ar^1$ or substituents thereof are further defined, such definitions are intended to apply mutatis mutandis also to the groups (Ar-I), (Ar-II), and (Ar-III) and their respective substituents.

Whenever a substituent is denoted as optional, it is understood that such substituent may be absent (i.e. the respective residue is unsubstituted with regard to such optional substituent), in which case all positions having a free valency (to which such optional substituent could have been attached to; such as for example in an aromatic ring the ring carbon atoms and/or the ring nitrogen atoms having a free valency) are substituted with hydrogen where appropriate. Likewise, in case the term "optionally" is used in the context of (ring) heteroatom(s), the term means that either the respective optional heteroatom(s), or the like, are absent (i.e. a certain moiety does not contain heteroatom(s)/is a carbocycle/or the like), or the respective optional heteroatom(s), or the like, are present as explicitly defined.

The term "halogen" means fluorine, chlorine, bromine, or iodine; especially fluorine, chlorine, or bromine; preferably fluorine or chlorine.

The term "alkyl", used alone or in combination, refers to a saturated straight or branched chain hydrocarbon group containing one to six carbon atoms. The term "$(C_{x-y})$alkyl" (x and y each being an integer), refers to an alkyl group as defined before, containing x to y carbon atoms. For example a $(C_{1-6})$alkyl group contains from one to six carbon atoms. Examples of alkyl groups are methyl, ethyl, propyl, isopropyl, butyl, isobutyl, tert.-butyl, 3-methyl-butyl, 2,2-dimethyl-propyl and 3,3-dimethyl-butyl. For avoidance of any doubt, in case a group is referred to as e.g. propyl or butyl, it is meant to be n-propyl, respectively n-butyl. Preferred are methyl and ethyl. Most preferred is methyl. Preferred for substituents of $Ar^1$ being phenyl or 5- or 6-membered heteroaryl are methyl, ethyl, propyl, isobutyl, 1-methyl-propan-1-yl, tert.-butyl, 3-methyl-butyl.

The term "—$(C_{x-y})$alkylene-", used alone or in combination, refers to bivalently bound alkyl group as defined before containing x to y carbon atoms. Preferably, the points of attachment of a —$(C_{1-y})$alkylene group are in 1,1-diyl, in 1,2-diyl, or in 1,3-diyl arrangement. In case a $(C_{0-y})$alkylene group is used in combination with another substituent, the term means that either said substituent is linked through a $(C_{1-y})$alkylene group to the rest of the molecule, or it is directly attached to the rest of the molecule (i.e. a $(C_0)$ alkylene group represents a direct bond linking said substituent to the rest of the molecule). The alkylene group —$C_2He$ refers to —$CH_2$—$CH_2$— if not explicitly indicated otherwise. For the linker $X^1$, examples of $(C_{1-3})$alkylene groups are —$CH_2$—, —$CH(CH_3)$—, —$C(CH_3)_2$—, and —$CH_2$—$CH_2$—, especially —$CH_2$— and —$CH_2$—$CH_2$—. Examples of $(C_{0-3})$alkylene groups as used in the substituents —$(C_{0-3})$alkylene-$COOR^{O2}$ and $(C_{0-3})$alkylene-CO-$OR^{O3}$, respectively, are $(C_0)$alkylene, and methylene, respectively.

The term "alkoxy", used alone or in combination, refers to an alkyl-O— group wherein the alkyl group is as defined before. The term "$(C_{x-y})$alkoxy" (x and y each being an integer) refers to an alkoxy group as defined before containing x to y carbon atoms. For example a $(C_{1-4})$alkoxy group means a group of the formula $(C_{1-4})$alkyl-O— in which the term "$(C_{1-4})$alkyl" has the previously given significance. Examples of alkoxy groups are methoxy, ethoxy, n-propoxy, isopropoxy, n-butoxy, isobutoxy, sec.-butoxy and tert.-butoxy. Preferred are ethoxy and especially methoxy. Preferred for substituents of $Ar^1$ being phenyl or 5- or 6-membered heteroaryl are methoxy, ethoxy, propoxy, butoxy, isobutoxy.

The term "fluoroalkyl", used alone or in combination, refers to an alkyl group as defined before containing one to three carbon atoms in which one or more (and possibly all) hydrogen atoms have been replaced with fluorine. The term "$(C_{x-y})$fluoroalkyl" (x and y each being an integer) refers to a fluoroalkyl group as defined before containing x to y carbon atoms. For example a $(C_{1-3})$fluoroalkyl group contains from one to three carbon atoms in which one to seven hydrogen atoms have been replaced with fluorine. Representative examples of fluoroalkyl groups include trifluoromethyl, 2-fluoroethyl, 2,2-difluoroethyl and 2,2,2-trifluoroethyl. Preferred are $(C_1)$fluoroalkyl groups such as trifluoromethyl. An example of "$(C_{1-3})$fluoroalkyl, wherein said $(C_{1-3})$fluoroalkyl is optionally substituted with hydroxy" is 2,2,2-trifluoro-1-hydroxy-ethyl.

The term "fluoroalkoxy", used alone or in combination, refers to an alkoxy group as defined before containing one to three carbon atoms in which one or more (and possibly all) hydrogen atoms have been replaced with fluorine. The term "$(C_{x-y})$fluoroalkoxy" (x and y each being an integer) refers to a fluoroalkoxy group as defined before containing x to y carbon atoms. For example a $(C_{1-3})$fluoroalkoxy group contains from one to three carbon atoms in which one to seven hydrogen atoms have been replaced with fluorine. Representative examples of fluoroalkoxy groups include trifluoromethoxy, difluoromethoxy, 2-fluoroethoxy, 2,2-difluoroethoxy and 2,2,2-trifluoroethoxy. Preferred are $(C_1)$ fluoroalkoxy groups such as trifluoromethoxy and difluoromethoxy, as well as 2,2,2-trifluoroethoxy.

The term "cycloalkyl", used alone or in combination, refers to a saturated monocyclic hydrocarbon ring containing three to six carbon atoms. The term "$(C_{x-y})$cycloalkyl" (x and y each being an integer), refers to a cycloalkyl group as defined before containing x to y carbon atoms. For example a $(C_{3-6})$cycloalkyl group contains from three to six carbon atoms. Examples of cycloalkyl groups are cyclopropyl, cyclobutyl, cyclopentyl, cyclohexyl, and cycloheptyl. Preferred are cyclopropyl, cyclobutyl, and cyclopentyl; especially cyclopropyl. An example of cycloalkyl groups containing one ring oxygen atom is especially oxetanyl. Examples of $(C_{3-6})$cycloalkyl groups wherein said $(C_{3-6})$ cycloalkyl is optionally mono-substituted with amino are cyclopropyl, 1-amino-cyclopropyl. Examples of $(C_{3-6})$cycloalkyl groups wherein said $(C_{3-6})$cycloalkyl is mono-substituted with —COOH are 1-carboxy-cyclopropyl, 1-carboxy-cyclopentyl.

The term "—$(C_{x-y})$cycloalkylene-", used alone or in combination, refers to bivalently bound cycloalkyl group as defined before containing x to y carbon atoms. Preferably, the points of attachment of any bivalently bound cycloalkyl group are in 1,1-diyl, or in 1,2-diyl arrangement. Examples are cyclopropan-1,1-diyl, cyclopropan-1,2-diyl, and cyclopentan-1,1-diyl; preferred is cyclopropan-1,1-diyl.

Examples of $(C_{3-6})$cycloalkyl-oxy are cyclobutyl-oxy, and cyclopentyl-oxy.

Alkylated amino groups —$N[(C_{1-4})$alkyl$]_2$ as used in groups —$X^1$—CO—$R^{O1}$, wherein $R^{O1}$ represents —O—$CH_2$—CO—$R^{O4}$, wherein $R^{O4}$ represents —$N[(C_{1-4})$ alkyl$]_2$; or wherein $R^{O1}$ represents —O—$CH_2$—$CH_2$—N $[(C_{1-4})$alkyl$]_2$ are such that the two respective $(C_{1-4})$alkyl groups are independently selected. A preferred example of such amino group —N[(C$_{1-4}$)alkyl]$_2$ is —N(CH$_3$)$_2$.

The term "heterocycle", used alone or in combination, and if not explicitly defined in a broader or more narrow way, refers to a saturated monocyclic hydrocarbon ring containing one or two (especially one) ring heteroatoms independently selected from nitrogen, sulfur, and oxygen (especially one nitrogen atom, two nitrogen atoms, one nitrogen atom and one oxygen atom, or one nitrogen atom and one sulfur atom). The term "(C$_{x-y}$)heterocycle" refers to such a heterocycle containing x to y ring atoms. Heterocycles are unsubstituted or substituted as explicitly defined.
Examples of the Fragment:

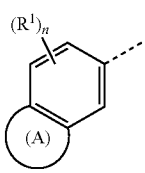

wherein ring (A) represents an aromatic 5- or 6-membered ring which ring (A) is fused to the phenyl group, wherein said ring (A) optionally contains one or two heteroatoms independently selected from nitrogen, oxygen, and sulfur are indolyl, isoindolyl, benzofuranyl, isobenzofuranyl, benzothiophenyl, indazolyl, benzimidazolyl, benzoxazolyl, benzisoxazolyl, benzothiazolyl, benzoisothiazolyl, quinolinyl, isoquinolinyl, cinnolinyl, quinazolinyl, quinoxalinyl, and phthalazinyl; notably benzofuranyl, benzothiophenyl, benzothiazolyl, benzoisothiazolyl, indolyl, indazolyl, naphthyl, quinolinyl, and isoquinolinyl. The above groups are unsubstituted or substituted as explicitly defined.
Examples of the Fragment:

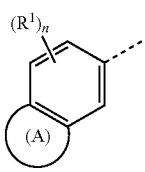

wherein ring (A) represents a non-aromatic 5- to 7-membered ring, which ring (A) is fused to the phenyl group, wherein independently said ring (A) optionally contains one or two heteroatoms independently selected from nitrogen, oxygen, and sulfur are 2,3-dihydro-benzo[b]thiophenyl, benzo[1,3]dioxolyl, 1,3-dihydro-isobenzofuranyl, 2,3-dihydro-benzofuranyl, indanyl, 5,6,7,8-tetrahydro-naphthalenyl, 2,3-dihydro-benzo[1,4]dioxinyl, chromanyl, 3,4-dihydro-2H-benzo[1,4]oxazinyl, 1,2,3,4-tetrahydro-quinolinyl, and 3,4-dihydro-2H-benzo[b][1,4]dioxepinyl. The above groups are unsubstituted or substituted as explicitly defined.

A group composed of a "non-aromatic 5- or 6-membered ring fused to the phenyl group, wherein ring (B) comprises one or two heteroatoms independently selected from nitrogen and oxygen" as used for (Ar-III) refers to phenyl groups which are fused to a (C$_{5-6}$)heterocycle as defined before. Examples are 2,3-dihydro-benzofuranyl, 2,3-dihydro-1H-indolyl, 2,3-dihydro-benzo[1,4]dioxinyl, 2,3-dihydro-1H-indazolyl, 2,3-dihydro-1H-benzo[d]imidazolyl, 2,3-dihydrobenzo[d]isoxazolyl, 2,3-dihydro-isoindolyl, 3-dihydrobenzooxazol-6-yl, 2,3-dihydro-benzooxazol-5-yl, 1,2,3,4-tetrahydro-quinazolin-6-yl, 1,2,3,4-tetrahydro-quinazolin-7-yl, 1,2,3,4-tetrahydro-isoquinolin-6-yl, and 1,2,3,4-tetrahydro-phthalazin-6-yl. The above groups are unsubstituted, mono-, or di-substituted, wherein the substituents are independently selected from oxo, (C$_{1-6}$)alkyl, and —(C$_{0-3}$)alkylene-COOR$^{O3}$ wherein R$^{O3}$ represents hydrogen or (C$_{1-3}$)alkyl (especially methyl); especially substituents are independently selected from oxo, methyl, ethyl, propyl, butyl, isobutyl, or —COOH; wherein the substituents are attached to the fused 5- or 6-membered non-aromatic ring. Oxo substituents are preferably attached to a ring carbon atom which is in alpha position to a ring nitrogen atom. Preferred examples of such groups are 2,3-dihydro-benzofuranyl, 2,3-dihydro-1H-indolyl, 2,3-dihydro-benzo[1,4]dioxinyl; as well as the oxosubstituted heterocyclyl groups 3-oxo-2,3-dihydro-1H-indazolyl, 2-oxo-2,3-dihydro-1H-benzo[d]imidazolyl, 3-oxo-2,3-dihydrobenzo[d]isoxazolyl, 2-oxo-1,3-dihydro-indolyl, 1-oxo-2,3-dihydro-isoindolyl, 2-oxo-2,3-dihydro-benzooxazolyl, 2-oxo-1,2,3,4-tetrahydro-quinazolinyl, 1-oxo-1,2,3,4-tetrahydro-isoquinolinyl, 1,4-dioxo-1,2,3,4-tetrahydro-phthalazinyl; wherein the above groups optionally carry one (further) substituent independently selected from (C$_{1-6}$)alkyl, and —(C$_{0-3}$)alkylene-COOR$^{O3}$ wherein R$^{O3}$ represents hydrogen or (C$_{1-3}$)alkyl (especially methyl). Particular examples are 2-oxo-2,3-dihydro-benzooxazol-6-yl, 3-methyl-2-oxo-2,3-dihydro-benzooxazol-5-yl, 1-methyl-3-oxo-2,3-dihydro-1H-indazol-6-yl, 2-oxo-1,2,3,4-tetrahydro-quinazolin-6-yl, 1-methyl-2-oxo-1,2,3,4-tetrahydro-quinazolin-6-yl, 1-oxo-1,2,3,4-tetrahydro-isoquinolin-6-yl, 1-methyl-2-oxo-1,2,3,4-tetrahydro-quinazolin-7-yl, and 1-oxo-1,2,3,4-tetrahydro-isoquinolin-7-yl.

For avoidance of doubt, certain groups having tautomeric forms which are considered predominantly non-aromatic, such as for example 2-oxo-2,3-dihydro-1H-benzo[d]imidazolyl groups, are defined herein as 8- to 10-membered partially aromatic fused bicyclic heterocyclyl groups, even though their corresponding tautomeric form (2-hydroxy-1H-benzo[d]imidazolyl) could also be considered as a 8- to 10-membered bicyclic heteroaryl group.

The term "aryl", used alone or in combination, means phenyl or naphthyl, especially phenyl. The above-mentioned aryl groups are unsubstituted or substituted as explicitly defined.

Examples of the substituent Ar$^1$ representing phenyl are especially those which are at least mono-substituted in para position with respect to the point of attachment of the rest of the molecule. In addition, such group Ar$^1$ representing phenyl may carry one or two further substituents, especially in one or both meta positions with respect to the point of attachment of the rest of the molecule. The respective substituents of such phenyl groups are as explicitly defined.

The term "heteroaryl", used alone or in combination, means a 5- to 10-membered monocyclic or bicyclic aromatic ring containing one to a maximum of four heteroatoms, each independently selected from oxygen, nitrogen and sulfur. Examples of such heteroaryl groups are 5-membered heteroaryl groups such as furanyl, oxazolyl, isoxazolyl, oxadiazolyl, thiophenyl, thiazolyl, isothiazolyl, thiadiazolyl, pyrrolyl, imidazolyl, pyrazolyl, triazolyl, tetrazolyl; 6-membered heteroaryl groups such as pyridinyl, pyrimidinyl, pyridazinyl, pyrazinyl; and 8- to 10-membered bicyclic heteroaryl groups such as indolyl, isoindolyl, benzofuranyl, isobenzofuranyl, benzothiophenyl, indazolyl, benzimidazolyl, benzoxazolyl, benzisoxazolyl, benzothiazolyl, benzoisothiazolyl, benzotriazolyl, benzoxadiazolyl, benzothiadiazolyl, thienopyridinyl, quinolinyl, isoquinolinyl, naphthyridinyl, cinnolinyl, quinazolinyl, quinoxalinyl, phthalazinyl, pyrrolopyridinyl, pyrazolopyridinyl, pyrazolopyrimidinyl, pyrrolopyrazinyl, imidazopyridinyl, imidazopyrazinyl, and imidazothiazolyl. The above-mentioned heteroaryl groups are unsubstituted or substituted as explicitly defined.

For the substituent $Ar^1$ representing a "5- or 6-membered heteroaryl", the term means the above-mentioned 5- or 6-membered groups such as especially pyridinyl, pyrimidinyl, pyrrolyl, pyrazolyl, isoxazolyl, thiazolyl or thiophenyl. Notably, the term refers to 5-membered groups such as especially thiazolyl or thiophenyl; in particular thiophen-2-yl, thiophen-3-yl, thiazol-2-yl, thiazol-4-yl, thiazol-5-yl. Preferred is thiophenyl, especially thiophen-2-yl; or thiazolyl, especially thiazol-2-yl. The above groups are substituted as explicitly defined. Thiophen-2-yl or thiazol-2-yl are especially di-substituted with one substituent being in position 5, and a second substituent in position 4 (and, for thiophen-2-yl, optionally a halogen substituent in position 3).

For the substituent $Ar^1$ representing a "8- to 10-membered bicyclic heteroaryl" the term means the above-mentioned 8- to 10-membered heteroaryl groups. Notably, the term refers to 9- or 10-membered heteroaryl groups, such as especially indazolyl, benzoimidazolyl, indolyl, benzotriazolyl, benzooxazolyl, quinoxalinyl, isoquinolinyl, quinolinyl, pyrrolopyridinyl, and imidazopyridinyl, as well as benzofuranyl, benzothiophenyl, and benzothiazolyl. The above groups are unsubstituted or substituted as explicitly defined. Particular examples are 1H-indol-2-yl, 1H-indol-3-yl, 1H-indol-4-yl, 1H-indol-5-yl, 1H-indol-6-yl, 1-methyl-1H-indol-5-yl, 1H-indazol-5-yl, 1H-indazol-6-yl, 1-methyl-1H-indazol-6-yl, 3-methyl-1H-indazol-6-yl, 3-methoxy-1H-indazol-6-yl, 6-methoxy-1H-indazol-5-yl, 1H-benzoimidazol-5-yl, 2-methyl-1H-benzoimidazol-5-yl, 2-trifluoromethyl-1H-benzoimidazol-5-yl, 1H-benzotriazol-5-yl, 2-methyl-benzooxazol-5-yl, 2-methyl-benzooxazol-6-yl, quinoxalin-6-yl, isoquinolin-7-yl, quinolin-6-yl, 1H-pyrrolo[2,3-c]pyridin-3-yl, 1H-pyrrolo[2,3-b]pyridin-3-yl, 1H-pyrrolo[2,3-b]pyridin-5-yl, 1-methyl-1H-pyrrolo[2,3-b]pyridin-5-yl, imidazo[1,2-a]pyridin-6-yl, 2-carboxy-1H-indol-5-yl, 3-carboxy-1H-indol-6-yl, 4-carboxy-1H-indol-2-yl, 5-carboxy-1H-indol-2-yl, 6-carboxy-1H-indol-2-yl, 7-carboxy-1H-indol-2-yl, 7-carboxy-1H-indol-4-yl, 7-carboxy-1-methyl-1H-indol-4-yl, 5-(methoxycarbonyl)-1H-indol-2-yl, 6-(methoxycarbonyl)-1H-indol-2-yl), 6-carboxy-benzofuran-2-yl, 3-carboxy-benzofuran-6-yl, 2-carboxy-benzofuran-5-yl, and 2-carboxy-benzofuran-6-yl. Preferred examples are 1H-benzoimidazol-5-yl, 1H-indol-6-yl, 1H-indol-5-yl, 1H-indol-2-yl, 1H-indazol-5-yl, as well as 8- to 10-membered bicyclic heteroaryl which are mono-substituted with —$(C_{0-3})$alkylene-COOR$^{O2}$ such as 3-carboxy-1H-indol-6-yl, 4-carboxy-1H-indol-2-yl, 5-carboxy-1H-indol-2-yl, 6-carboxy-1H-indol-2-yl, 7-carboxy-1H-indol-2-yl, 5-(methoxycarbonyl)-1H-indol-2-yl, 6-(methoxycarbonyl)-1H-indol-2-yl), 6-carboxy-benzofuran-2-yl, 3-carboxy-benzofuran-6-yl, 2-carboxy-benzofuran-5-yl, and 2-carboxy-benzofuran-6-yl, and, in addition, 3-carboxy-1H-indazol-6-yl, and 7-carboxy-1H-indol-4-yl.

For the substituent "—$(CH_2)_p$-HET, wherein p represents the integer 0 or 1, and wherein HET represents a 5- or 6-membered heteroaryl", such 5- or 6-membered heteroaryl is as defined before; notably a nitrogen containing 5-membered heteroaryl such as especially tetrazolyl, or oxazolyl, isoxazolyl, oxadiazolyl, thiazolyl, isothiazolyl, thiadiazolyl, imidazolyl, pyrazolyl, or triazolyl. The above groups are unsubstituted or substituted as explicitly defined. The group —$(CH_2)_p$— is preferably absent, i.e. p represents the integer 0 and the group HET is directly bound to $Ar^1$. Particular examples of —$(CH_2)_p$-HET are especially the —$(CH_2)_0$-HET groups 1H-tetrazol-5-yl, 3-hydroxy-isoxazol-5-yl, 2-hydroxy-[1,3,4]oxadiazol-4-yl; further examples are 3-amino-isoxazol-5-yl, 2-amino-oxazol-5-yl, 5-amino-[1,3,4]thiadiazol-2-yl, 5-methylamino-[1,3,4]thiadiazol-2-yl, 5-methoxy-[1,2,4]oxadiazol-3-yl, 5-amino-[1,2,4]oxadiazol-3-yl, 5-[(2-hydroxy-ethyl)]-amino)-[1,2,4]oxadiazol-3-yl, 5-hydroxymethyl-[1,2,4]oxadiazol-3-yl, 5-(oxetan-3-yl)-[1,2,4]oxadiazol-3-yl, 1H-imidazol-4-yl, 5-methyl-1H-imidazol-4-yl, and 2,5-dimethyl-1H-imidazol-4-yl; as well as 1H-pyrazol-1-yl, 1H-pyrazol-3-yl, 3-methyl-pyrazol-1-yl, 1-methyl-1H-pyrazol-3-yl, 5-methyl-1H-pyrazol-3-yl, 3,5-dimethyl-pyrazol-1-yl, 4-carboxy-1H-pyrazol-3-yl, 1H-imidazol-2-yl, 3-methyl-3H-imidazol-4-yl, 2-methyl-1H-imidazol-4-yl, 1,5-dimethyl-1H-imidazol-2-yl, 1,2-dimethyl-1H-imidazol-4-yl, 1,5-dimethyl-1H-imidazol-4-yl, 2-cyclopropyl-1H-imidazol-4-yl, 2-cyclopropyl-1-methyl-1H-imidazol-4-yl, [1,2,4]oxadiazol-5-yl, 5-methyl-[1,2,4]oxadiazol-3-yl, 3-methyl-[1,2,4]oxadiazol-5-yl, 5-methyl-[1,3,4]oxadiazol-2-yl, isothiazol-5-yl, thiazol-2-yl, thiazol-4-yl, 4-methyl-thiazol-2-yl, 2-methyl-thiazol-4-yl, 2-amino-5-methyl-thiazol-4-yl, 4,5-dimethyl-thiazol-2-yl, 4-carboxy-thiazol-2-yl, 2-carboxy-thiazol-4-yl, 2-hydroxy-thiazol-4-yl, 2-amino-2-oxoethyl)thiazol-4-yl, isoxazol-3-yl, isoxazol-5-yl, 3-methyl-isoxazol-5-yl, 4-methyl-isoxazol-5-yl, 4-carboxy-3-methyl-isoxazol-5-yl, oxazol-5-yl, 2-methyl-oxazol-5-yl, 2-(2-carboxyethyl)-oxazol-5-yl, 2-(2-carboxyethyl)-4-methyl-oxazol-5-yl, 4H-[1,2,4]triazol-3-yl, 1H-[1,2,4]triazol-1-yl, 2-methyl-2H-[1,2,4]triazol-3-yl, pyridin-2-yl, 4-fluoro-pyridin-2-yl, pyrimidin-2-yl, 5-fluoro-pyrimidin-2-yl, 5-methoxy-pyrimidin-2-yl, 4-methoxy-pyrimidin-2-yl, 6-methoxy-pyrimidin-4-yl, 6-dimethylamino-pyrimidin-4-yl, pyrazin-2-yl, 6-methoxy-pyrazin-2-yl, 6-methoxy-pyridazin-3-yl, 3H-imidazol-4-yl, 3H-[1,2,3]triazol-4-yl, oxazol-2-yl, and 4,5-dimethyl-oxazol-2-yl. For avoidance of doubt, certain groups having tautomeric forms which may be considered predominantly aromatic (such as for example 3-hydroxy-isoxazolyl or 2-hydroxy-[1,3,4]oxadiazolyl groups) are defined herein as heteroaryl groups HET, even though their corresponding tautomeric form (3-oxo-2,3-dihydro-2H-isoxazolyl, respectively, 2-oxo-2,3-dihydro-3H-[1,3,4]oxadiazolyl) could also be considered as a non-aromatic group. Likewise, certain groups having tautomeric forms which may be considered predominantly non-aromatic (such as 5-oxo-4,5-dihydro-[1,2,4]oxadiazol-3-yl or 5-thioxo-4,5-dihydro-[1,2,4]oxadiazol-3-yl) as defined for the substituent $HET^1$, are defined herein as not being part of substituted heteroaryl groups as defined for HET, even though their corresponding tautomeric form (5-hydroxy-[1,2,4]oxadiazolyl, respectively, 5-mercapto-[1,2,4]oxadiazolyl), could also be considered as an heteroaryl group. It is understood that the corresponding tautomer is encompassed in the respective scope as defined.

The term "cyano" refers to a group —CN.

The term "oxo" refers to a group =O which is preferably attached to a chain or ring carbon or sulfur atom as for example in a carbonyl group —(CO)—, or a sulfonyl group —$(SO_2)$—.

Examples of "—$X^2$—NR$^{N1}$R$^{N2}$" groups as used for substituents of $Ar^1$ being phenyl or 5- or 6-membered heteroaryl are amino, methylamino, ethylamino, propylamino, aminomethyl, methylamino-methyl, isobutylamino-methyl, cyclopropylamino-methyl, cyclobutylamino-methyl, (2-methoxy-ethyl)amino-methyl, (2,2,2-trifluoro-ethyl)-amino; or —NH—CO—H, —N($C_2H_5$)—CO—H, —NH—CO—

$C_2H_5$, —NH—CO—$CH_2$—$CH_2$—OH, —NH—CO—O—$CH_3$, —N($CH_3$)—CO—O—$CH_3$; or pyrrolidin-1-yl, 2-oxo-pyrrolidin-1-yl, 1,1-dioxo-isothiazolidin-2-yl, morpholin-4-yl, azetidin-1-yl, or piperidin-1-yl; and 2-(dimethylamino)-ethoxy.

Examples of a group "—NH—CO—$NR^{N5}R^{N6}$" as used for substituents of the group $Ar^1$ are ureido (—NH—CO—$NH_2$) and 3-ethylureido (—NH—CO—NH—$C_2H_5$).

Examples of a group "—$(CH_2)_r$CO—$NR^{N3}R^{N4}$ wherein r represents the integer 0 or 1" as used for substituents of the group $Ar^1$ are preferably groups wherein r represents the integer 0 and at least one of $R^{N3}$ and $R^{N4}$ represents hydrogen (or less preferred, methyl). Particular examples of such group —CO—$NR^{N3}R^{N4}$ are —CO—$NH_2$, —CO—NH($CH_3$), —CO—N$(CH_3)_2$, —CO—NH($C_2H_5$), —CO—NH—O-methyl, —CO—NH—O-ethyl, —CO—NH—O-isopropyl, —CO—NH—$C_2H_4$—OH, —CO—NH—O—$C_2H_4$—OH, —CO—NH—$C_2H_4$—$OCH_3$, —CO—NH—$C_2H_4$—N$(CH_3)_2$, and —CO—NH—O-benzyl. Further examples are —CO—NH-isopropyl and —CO—NH—OH, as well as —CO—N$(CH_3)_2$.

Examples of a group "—$X^1$—CO—$R^{O1}$" as used for substituents of the group $Ar^1$ are especially the following groups:

a) $X^1$ represents a direct bond; and $R^{O1}$ represents —OH; (i.e. —$X^1$—CO—$R^{O1}$ represents —COOH); or b) $X^1$ represents a direct bond; and $R^{O1}$ represents —O—$(C_{1-4})$alkyl (especially ethoxy, or methoxy); (i.e. —$X^1$—CO—$R^{O1}$ represents —CO—$(C_{1-4})$alkoxy (especially ethoxycarbonyl, methoxycarbonyl)); or c) $X^1$ represents a direct bond; and $R^{O1}$ represents —NH—$SO_2$—$R^{S3}$; wherein $R^{S3}$ represents $(C_{1-4})$alkyl; $(C_{3-6})$cycloalkyl wherein the $(C_{3-6})$cycloalkyl optionally contains a ring oxygen atom; $(C_{3-6})$cycloalkyl-$(C_{1-3})$alkylene wherein the $(C_{3-6})$cycloalkyl optionally contains a ring oxygen atom; $(C_{1-3})$fluoroalkyl; phenyl; or —$NH_2$; (i.e. —$X^1$—CO—$R^{O1}$ represents —CO—NH—$SO_2$—$R^{S3}$ wherein $R^{S3}$ represents the above mentioned groups; notably methyl, ethyl, isopropyl, cyclopropyl, trifluoromethyl, amino; especially —$X^1$—CO—$R^{O1}$ represents —CO—NH—$SO_2$—$CH_3$, —CO—NH—$SO_2$—C$(CH_3)_2$, —CO—NH—$SO_2$-cyclopropyl, —CO—NH—$SO_2$-ethyl, or —CO—NH—$SO_2$—$NH_2$); or d) $X^1$ represents $(C_{1-3})$alkylene (especially —$CH_2$—, —$CH_2$—$CH_2$—), —O—$(C_{1-3})$alkylene-* (especially —O—$CH_2$—*, —O—CH($CH_3$)—*, —O—C$(CH_3)_2$—*, O—$CH_2$—$CH_2$—*), —NH—$(C_{1-3})$alkylene-* (especially —NH—$CH_2$*, —NH—CH($CH_3$)—*), —S—$CH_2$*, —$CF_2$—, —CH=CH—, or —CH=CH— [in a sub-embodiment $X^1$ represents especially —O—$CH_2$*, —NH—$CH_2$—*, —S—$CH_2$—*, or $(C_{1-3})$alkylene]; wherein the asterisks indicate the bond that is linked to the —CO—$R^{O1}$ group; and $R^{O1}$ represents —OH (i.e. —$X^1$—CO—$R^{O1}$ represents —$X^1$—COOH wherein $X^1$ represents the above mentioned groups; especially —$X^1$—CO—$R^{O1}$ represents —O—$CH_2$—COOH or —NH—$CH_2$—COOH; as well as —$CH_2$—COOH, —$CH_2$—$CH_2$—COOH, —CH=CH—COOH, —CH=CH—OOH, —O—$CH_2$—$CH_2$—OOH, —O—CH($CH_3$)—COOH, or —NH—CH($CH_3$)—COOH); or e) —$X^1$ represents —NH—CO—* or —CO—; wherein the asterisk indicates the bond that is linked to the —CO—$R^{O1}$ group; and $R^{O1}$ represents —OH (i.e. —$X^1$—CO—$R^{O1}$ represents —$X^1$—COOH wherein $X^1$ represents the above mentioned groups; especially —$X^1$—CO—$R^{O1}$ represents —NH—CO—OOH, —CO—COOH); or f) $X^1$ represents $(C_{3-5})$cycloalkylene; and $R^{O1}$ represents —OH; (i.e. —$X^1$—CO—$R^{O1}$ represents $(C_{3-5})$cycloalkyl which is mono-substituted with COOH; especially —$X^1$—CO—$R^{O1}$ represents 1-carboxy-cyclopropan-1-yl or 1-carboxy-cyclopentan-1-yl); or g) $X^1$ represents a direct bond; and $R^{O1}$ represents —O—$CH_2$—CO—$R^{O4}$, wherein $R^{O4}$ represents hydroxy, or $(C_{1-4})$alkoxy, or —N[$(C_{1-4})$alkyl]$_2$; especially —$X^1$—CO—$R^{O1}$ represents —CO—O—$CH_2$—COOH; or wherein each of the groups a), b), c), d), e), f), and g) forms a particular sub-embodiment.

Compounds of Formula (I)/formula (II) containing a group "—$X^1$—CO—$R^{O1}$" wherein $X^1$ represents —CH=CH— may be in E- or Z-configuration. Preferably, such groups are in E-configuration.

Whenever a group $Ar^1$ is substituted with a substituent comprising a carboxylic acid group —COOH (such as in the substituents —$(C_{0-3})$alkylene-COO$R^{O2}$ wherein $R^{O2}$ represents hydrogen; —$(C_{0-3})$alkylene-COO$R^{O3}$ wherein $R^{O3}$ represents hydrogen; or in the substituents —$X^1$—CO—$R^{O1}$ wherein $R^{O1}$ represents —OH, especially in the —$X^1$—CO—$R^{O1}$ groups a), d), e) and f) above) such carboxylic acid group may be present in form of a prodrug group. Such prodrugs are encompassed in the scope of the present invention. In certain instances, compounds comprising such carboxylic acid prodrug groups may as such exhibit biological activity on the EP2 and/or EP4 receptor, whereas in other instances, such compounds comprising such carboxylic acid prodrug groups require (e.g. enzymatic) cleavage of the prodrug to exhibit biological activity on the EP2 and/or EP4 receptor. Prodrugs of the carboxylic acid functional group are well known in the art (see for example J. Rautio (Ed.) Prodrugs and Targeted Delivery: Towards Better ADME Properties, Volume 47, Wiley 2010, ISBN: 978-3-527-32603-7; H. Maag in Stella, V., Borchardt, R., Hageman, M., Oliyai, R., Maag, H., Tilley, J. (Eds.) Prodrugs: Challenges and Rewards, Springer 2007, ISBN 978-0-387-49785-3).

Particular examples of prodrugs, for example suitable for —$X^1$—COOH groups are:

ester groups —$X^1$—CO—O—$P^1$ wherein $P^1$ is for example $(C_{1-4})$alkyl; $(C_{3-6})$cycloalkyl wherein the $(C_{3-6})$cycloalkyl optionally contains a ring oxygen atom; $(C_{3-6})$cycloalkyl-$(C_{1-3})$alkyl wherein the $(C_{3-6})$cycloalkyl optionally contains a ring oxygen atom; $(C_{1-3})$fluoroalkyl; hydroxy-$(C_{2-4})$alkyl; or $(C_{1-4})$alkoxy-$(C_{2-4})$alkyl (especially $P^1$ is $(C_{1-4})$alkyl, in particular methyl or ethyl);

groups —$X^1$—CO—NH—$SO_2$—$R^{S3}$ wherein $R^{S3}$ represents $(C_{1-4})$alkyl, $(C_{3-6})$cycloalkyl wherein the $(C_{3-6})$cycloalkyl optionally contains a ring oxygen atom; $(C_{3-6})$cycloalkyl-$(C_{1-3})$alkyl wherein the $(C_{3-6})$cycloalkyl optionally contains a ring oxygen atom; $(C_{1-3})$fluoroalkyl, —$NH_2$; (especially $R^{S3}$ is $(C_{1-4})$alkyl, $(C_{3-6})$cycloalkyl; in particular methyl);

groups —$X^1$—CO—$R^{O1}$ wherein $R^{O1}$ represents —O—$CH_2$—CO—$R^{O4}$, wherein $R^{O4}$ represents hydroxy, or $(C_{1-4})$alkoxy, or —N[$(C_{1-4})$alkyl]$_2$ (especially —CO—O—$CH_2$—COOH, —CO—O—$CH_2$—CO—N$(CH_3)_2$);

groups —$X^1$—CO—$R^{O1}$ wherein $R^{O1}$ represents —O—$CH_2$—O—CO—$R^{O5}$, wherein $R^{O5}$ represents ($C_{1-4}$)alkyl or ($C_{1-4}$)alkoxy (especially —CO—O—$CH_2$—O—CO—O-ethyl, —CO—O—$CH_2$—O—CO-propyl);

groups —$X^1$—CO—$R^{O1}$ wherein $R^{O1}$ represents —O—$CH_2$—$CH_2$—N[($C_{1-4}$)alkyl]$_2$ (especially —CO—O—$CH_2$—$CH_2$—N($CH_3$)$_2$); and groups —$X^1$—CO—$R^{O1}$ wherein $R^{O1}$ represents 5-methyl-2-oxo-[1,3]dioxol-4-yl)-methyloxy-.

Examples of "hydroxy-($C_{1-4}$)alkyl" groups as used for substituents of the group $Ar^1$ are hydroxymethyl and 1-hydroxy-ethyl.

An example of "dihydroxy-($C_{2-4}$)alkyl" groups as used for substituents of the group $Ar^1$ is 1,2-dihydroxyethyl.

An example of "hydroxy-($C_{2-4}$)alkoxy" groups as used for substituents of the group $Ar^1$ is 2-hydroxy-ethoxy.

An example of "($C_{1-4}$)alkoxy-($C_{2-4}$)alkoxy" groups as used for substituents of the group $Ar^1$ is 2-methoxy-ethoxy.

Examples of a group "—$SO_2$—$R^{S1}$" as used for substituents of the group $Ar^1$ are —$SO_2$—$CH_3$, —$SO_2$—$NH_2$, —$SO_2$—NH—$CH_3$.

Examples of a group "S—$R^{S2}$" as used for substituents of the group $Ar^1$ are methylsulfanyl, ethylsulfanyl, n-propylsulfanyl, isopropylsulfanyl, isobutylsulfanyl), cyclobutylsulfanyl, and (oxetan-3-yl)-sulfanyl.

An example of a "($C_{1-4}$)alkoxy-($C_{2-4}$)alkyl" group is 2-methoxyethyl.

An example of a "hydroxy-($C_{2-4}$)alkoxy" group is 2-hydroxy-ethoxy.

An example of a "hydroxy-($C_{2-4}$)alkyl" group is 2-hydroxy-ethyl.

An example of a "—CO—($C_{1-4}$)alkoxy" group as used for substituents of the group $Ar^1$ is ethoxycarbonyl. Such groups may also be useful as prodrugs of the respective —COOH substituent.

Whenever the word "between" is used to describe a numerical range, it is to be understood that the end points of the indicated range are explicitly included in the range. For example: if a temperature range is described to be between 40° C. and 80° C., this means that the end points 40° C. and 80° C. are included in the range; or if a variable is defined as being an integer between 1 and 4, this means that the variable is the integer 1, 2, 3, or 4.

Unless used regarding temperatures, the term "about" placed before a numerical value "X" refers in the current application to an interval extending from X minus 10% of X to X plus 10% of X, and preferably to an interval extending from X minus 5% of X to X plus 5% of X. In the particular case of temperatures, the term "about" placed before a temperature "Y" refers in the current application to an interval extending from the temperature Y minus 10° C. to Y plus 10° C., and preferably to an interval extending from Y minus 5° C. to Y plus 5° C. Besides, the term "room temperature" as used herein refers to a temperature of about 25° C.

Further embodiments of the invention are presented hereinafter:

9) Another embodiment relates to compounds of formula (II) according to embodiment 8), wherein $R^3$ represents hydrogen.

10) Another embodiment relates to compounds of formula (II) according to embodiment 8), wherein $R^3$ represents methyl.

11) Another embodiment relates to compounds according to any one of embodiments 8) to 10), wherein Ar represents a phenyl group of the structure (Ar-I):

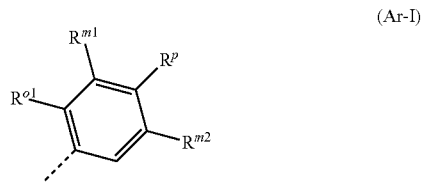

wherein
$R^p$ represents
—$X^1$—CO—$R^{O1}$, wherein
$X^1$ represents a direct bond, ($C_{1-3}$)alkylene (especially —$CH_2$—, —CH($CH_3$)—, —C($CH_3$)$_2$—, —$CH_2$—$CH_2$—), —O—($C_{1-3}$)alkylene-* (especially —O—$CH_2$—*, —O—CH($CH_3$)—*, —O—C($CH_3$)$_2$—*, —O—$CH_2$—$CH_2$—*), —NH—($C_{1-3}$)alkylene-* (especially —NH—$CH_2$*, —NH—CH($CH_3$)—*), —CH=CH—, —NH—CO—*, or ($C_{3-5}$)cycloalkylene; wherein the asterisks indicate the bond that is linked to the —CO—$R^{O1}$ group; and
$R^{O1}$ represents
-OH;
—O—($C_{1-4}$)alkyl (especially ethoxy, methoxy);
—NH—$SO_2$—$R^{S3}$ wherein $R^{S3}$ represents ($C_{1-4}$)alkyl, ($C_{3-6}$)cycloalkyl wherein the ($C_{3-6}$)cycloalkyl optionally contains a ring oxygen atom, ($C_{3-6}$)cycloalkyl-($C_{1-3}$)alkylene wherein the ($C_{3-6}$)cycloalkyl optionally contains a ring oxygen atom, or —$NH_2$;
-O—$CH_2$—CO—$R^{O4}$, wherein $R^{O4}$ represents hydroxy, or ($C_{1-4}$)alkoxy, or —N[($C_{1-4}$)alkyl]$_2$;
-O—$CH_2$—O—CO—$R^{O5}$, wherein $R^{O5}$ represents ($C_{1-4}$)alkyl or ($C_{1-4}$)alkoxy;
-O—$CH_2$—$CH_2$—N[($C_{1-4}$)alkyl]$_2$ (especially —O—$CH_2$—$CH_2$—N($CH_3$)$_2$); or
(5-methyl-2-oxo-[1,3]dioxol-4-yl)-methyloxy-;
[wherein in particular such group —$X^1$—CO—$R^{O1}$ represents —COOH, —CO—O—$CH_3$, —CO—O—$C_2H_5$, —O—$CH_2$—COOH, —O—CH($CH_3$)—COOH, —O—C($CH_3$)$_2$—COOH, —O—$CH_2$—$CH_2$—COOH, —NH—$CH_2$—COOH, —NH—$CH_2$—CO—O—$CH_3$, —NH—CH($CH_3$)—COOH, —CO—NH—$SO_2$—$CH_3$, —CO—NH—$SO_2$—C($CH_3$)$_2$, —CO—NH—$SO_2$-cyclopropyl, —CO—NH—$SO_2$—$C_2H_5$, —CO—NH—$SO_2$—$NH_2$, —CO—O—$CH_2$—COOH, —CO—O—$CH_2$—$CH_2$—N($CH_3$)$_2$, —CO—O—$CH_2$—CO—N($CH_3$)$_2$, —CO—O—$CH_2$—O—CO—O—$C_2H_5$, —CO—O—$CH_2$—O—CO-propyl, (5-methyl-2-oxo-[1,3]dioxol-4-yl)-methyl-O—CO—, —$CH_2$—COOH, —$CH_2$—CO—O—$CH_3$, —$CH_2$—CO—O—$C_2H_5$, —$CH_2$—$CH_2$—COOH, —CH=CH—COOH, —NH—CO—COOH, 1-carboxy-cyclopropan-1-yl];

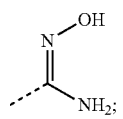

2-hydroxy-3,4-dioxo-cyclobut-1-enyl;
—CO—NR$^{N3}$R$^{N4}$ wherein R$^{N3}$ and R$^{N4}$ independently represent hydrogen, or (C$_{1-4}$)alkyl, (wherein preferably at least one of R$^{N3}$ and R$^{N4}$ represents hydrogen; and wherein particular examples of such group —CO—NR$^{N3}$R$^{N4}$ are —CO—NH$_2$, —CO—NH (CH$_3$), or —CO—NH(C$_2$H$_5$));
NH—CO—NR$^{N5}$R$^{N6}$ wherein R$^{N5}$ and R$^{N6}$ independently represent hydrogen or (C$_{1-4}$)alkyl (wherein preferably at least one of R$^{N5}$ and R$^{N6}$ represents hydrogen; and wherein particular examples of such group —NH—CO—NR$^{N5}$R$^{N6}$ are —NH—CO—NH$_2$, —NH—CO—NH—C$_2$H$_5$);
(CH$_2$)$_q$-HET$^1$, wherein q represents the integer 0, 1 or 2 (especially q is 0, i.e. HET is linked to Ar$^1$ by a direct bond); and wherein HET$^1$ represents 5-oxo-4,5-dihydro-[1,2,4]oxadiazol-3-yl (encompassing its tautomeric form 5-hydroxy-[1,2,4]oxadiazol-3-yl), or 3-oxo-2,3-dihydro-[1,2,4]oxadiazol-5-yl (encompassing its tautomeric form 3-hydroxy-[1,2,4]oxadiazol-5-yl),
—(CH$_2$)$_p$-HET, wherein p represents the integer 0 or 1 (especially p is 0, i.e. HET is linked to Ar$^1$ by a direct bond); and wherein HET represents a 5-membered heteroaryl (especially oxazolyl, isoxazolyl, oxadiazolyl, thiazolyl, isothiazolyl, thiadiazolyl, imidazolyl, pyrazolyl, triazolyl, or tetrazolyl), wherein said 5-membered heteroaryl is unsubstituted, or mono- or di-substituted, wherein the substituents are independently selected from (C$_{1-4}$)alkyl (especially methyl), (C$_{1-4}$)alkoxy (especially methoxy), —COOH, hydroxy, hydroxy-(C$_{1-3}$)alkyl (especially hydroxymethyl), (C$_{3-5}$)cycloalkyl optionally containing one ring oxygen atom (especially cyclopropyl, oxetan-3-yl), or —NR$^{N9}$R$^{N10}$ wherein R$^{N9}$ and R$^{N10}$ independently represent hydrogen, (C$_{1-3}$)alkyl (especially methyl), or hydroxy-(C$_{2-4}$)alkyl (especially 2-hydroxy-ethyl); (especially such group —(CH$_2$)$_p$-HET is 1H-tetrazol-5-yl, 3-hydroxy-isoxazol-5-yl, 2-hydroxy-[1,3,4]oxadiazol-4-yl, 3-amino-isoxazol-5-yl, 2-amino-oxazol-5-yl, 5-amino-[1,3,4]thiadiazol-2-yl, 5-methylamino-[1,3,4]thiadiazol-2-yl, 5-methoxy-[1,2,4]oxadiazol-3-yl, 5-amino-[1,2,4]oxadiazol-3-yl, 5-[(2-hydroxy-ethyl)]-amino)-[1,2,4]oxadiazol-3-yl, 5-hydroxymethyl-[1,2,4]oxadiazol-3-yl, 5-(oxetan-3-yl)-[1,2,4]oxadiazol-3-yl, 1H-imidazol-4-yl, 5-methyl-1H-imidazol-4-yl, 2,5-dimethyl-1H-imidazol-4-yl) [in particular HET is unsubstituted or mono-substituted with hydroxy; especially HET is 1H-tetrazol-5-yl, 3-hydroxy-isoxazol-5-yl, or 2-hydroxy-[1,3,4]oxadiazol-4-yl];
R$^{m1}$ represents
  hydrogen;
  (C$_{1-6}$)alkyl (especially methyl, ethyl, n-propyl, isopropyl, n-butyl, isobutyl);
  (C$_{1-4}$)alkoxy (especially methoxy, ethoxy, n-propoxy, isopropoxy, n-butoxy, isobutoxy);
  (C$_{1-3}$)fluoroalkyl (especially trifluoromethyl);
  (C$_{1-3}$)fluoroalkoxy (especially difluoromethoxy, trifluoromethoxy, 2,2,2-trifluoroethoxy);
  halogen (especially fluoro or chloro);
  (C$_{3-6}$)cycloalkyl (especially cyclopropyl);
  (C$_{3-6}$)cycloalkyl-oxy (especially cyclopropyl-oxy, cyclobutyl-oxy, cyclopentyl-oxy);
  hydroxy;
  hydroxy-(C$_{2-4}$)alkoxy (especially 2-hydroxy-ethoxy);
  —S—R$^{S2}$ wherein R$^{S2}$ represents (C$_{1-4}$)alkyl (especially methyl, ethyl, n-propyl, isopropyl, isobutyl), (C$_{3-6}$)cycloalkyl optionally containing one ring oxygen atom (especially cyclobutyl, oxetan-3-yl);
wherein in a sub-embodiment, R$^{m1}$ especially is different from hydrogen;
R$^{m2}$ represents hydrogen, methyl, fluoro, or chloro; and
R$^{o1}$ represents hydrogen;
or Ar$^1$ represents a 5-membered heteroaryl group of the structure (Ar-I):

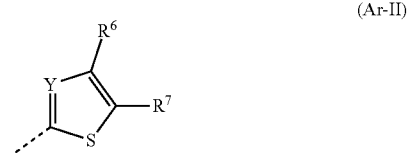

(Ar-II)

wherein
Y represents CH or N;
R$^7$ represents
  —X$^1$—CO—R$^{O1}$, wherein
    X$^1$ represents a direct bond, (C$_{1-3}$)alkylene (especially —CH$_2$—, —CH(CH$_3$)—, —C(CH$_3$)$_2$—, —CH$_2$—CH$_2$—), —O—(C$_{1-3}$)alkylene-* (especially —O—CH$_2$—*, —O—CH(CH$_3$)—*, —O—C(CH$_3$)$_2$—*, —O—CH$_2$—CH$_2$—*), —NH—(C$_{1-3}$)alkylene-* (especially —NH—CH$_2$—*, —NH—CH(CH$_3$)—*), —CH=CH—, —NH—CO—*, or (C$_{3-5}$)cycloalkylene; wherein the asterisks indicate the bond that is linked to the —CO—R$^{O1}$ group; and
    R$^{O1}$ represents
      -OH;
      -O—(C$_{1-4}$)alkyl (especially ethoxy, methoxy);
      —NH—SO$_2$—R$^{S3}$ wherein R$^{S3}$ represents (C$_{1-4}$)alkyl, (C$_{1-6}$)cycloalkyl wherein the (C$_{3-6}$)cycloalkyl optionally contains a ring oxygen atom, (C$_{3-6}$)cycloalkyl-(C$_{1-3}$)alkylene wherein the (C$_{3-6}$)cycloalkyl optionally contains a ring oxygen atom, (C$_{1-3}$)fluoroalkyl, or —NH$_2$;
      [wherein in particular such group —X$^1$—CO—R$^{O1}$ represents —OOH, —CO—O—CH$_3$, —CO—O—C$_2$H$_5$, —O—CH$_2$—COOH, —O—CH(CH$_3$)—COOH, —O—C(CH$_3$)$_2$—COOH, —O—CH$_2$—CH$_2$—COOH, —NH—CH$_2$—COOH, —CO—NH—SO$_2$—CH$_3$, —CO—NH—SO$_2$—C(CH$_3$)$_2$, —CO—NH—SO$_2$-cyclopropyl, —CO—NH—SO$_2$—C$_2$H$_5$, —CO—NH—SO$_2$—NH$_2$, —CH$_2$—COOH, —CH$_2$—CO—O—CH$_3$, CH$_2$—CO—O—C$_2$H$_5$, —CH(CH$_3$)—COOH, —CH$_2$—CH$_2$—COOH, —CH=CH—COOH, —NH—CO—COOH, —NH—CH(CH$_3$)—COOH, —NH—CH$_2$—CO—O—CH$_3$, 1-carboxy-cyclopropan-1-yl];

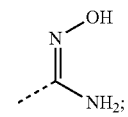

2-hydroxy-3,4-dioxo-cyclobut-1-enyl;
—CO—NR$^{N3}$R$^{N4}$ wherein R$^{N3}$ and R$^{N4}$ independently represent hydrogen, or (C$_{1-4}$)alkyl (wherein preferably at least one of R$^{N3}$ and R$^{N4}$ represents hydrogen; and wherein particular examples of such group —CO—NR$^{N3}$R$^{N4}$ are —CO—NH$_2$, —CO—NH(CH$_3$), or —CO—NH(C$_2$H$_5$);
NH—CO—NR$^{N5}$R$^{N6}$ wherein R$^{N5}$ and R$^{N6}$ independently represent hydrogen or (C$_{1-4}$)alkyl (wherein preferably at least one of R$^{N5}$ and R$^{N6}$ represents hydrogen; and wherein particular examples of such group —NH—CO—NR$^{N5}$R$^{N6}$ are —NH—CO—NH$_2$, —NH—CO—NH—C$_2$H$_5$);
—(CH$_2$)$_q$-HET$^1$, wherein q represents the integer 0, 1 or 2 (especially q is 0, i.e. HET$^1$ is linked to Ar$^1$ by a direct bond); and wherein HET$^1$ represents 5-oxo-4,5-dihydro-[1,2,4]oxadiazol-3-yl (encompassing its tautomeric form 5-hydroxy-[1,2,4]oxadiazol-3-yl), 3-oxo-2,3-dihydro-[1,2,4]oxadiazol-5-yl (encompassing its tautomeric form 3-hydroxy-[1,2,4]oxadiazol-5-yl);
—(CH$_2$)$_p$-HET, wherein p represents the integer 0 or 1 (especially p is 0, i.e. HET is linked to Ar$^1$ by a direct bond); and wherein HET represents a 5-membered heteroaryl (especially oxazolyl, isoxazolyl, oxadiazolyl, thiazolyl, isothiazolyl, thiadiazolyl, imidazolyl, pyrazolyl, triazolyl, or tetrazolyl), wherein said 5-membered heteroaryl is unsubstituted, or mono- or di-substituted, wherein the substituents are independently selected from (C$_{1-4}$)alkyl (especially methyl), (C$_{1-4}$)alkoxy (especially methoxy), —COOH, hydroxy, hydroxy-(C$_{1-3}$)alkyl (especially hydroxymethyl), (C$_{3-5}$)cycloalkyl optionally containing one ring oxygen atom (especially cyclopropyl, oxetan-3-yl), or —NR$^{N9}$R$^{N10}$ wherein R$^{N9}$ and R$^{N10}$ independently represent hydrogen, (C$_{1-3}$)alkyl (especially methyl), or hydroxy-(C$_{2-4}$)alkyl (especially 2-hydroxy-ethyl); (especially such group —(CH$_2$)$_p$-HET is 1H-tetrazol-5-yl, 3-hydroxy-isoxazol-5-yl, 2-hydroxy-[1,3,4]oxadiazol-4-yl, 3-amino-isoxazol-5-yl, 2-amino-oxazol-5-yl, 5-amino-[1,3,4]thiadiazol-2-yl, 5-methylamino-[1,3,4]thiadiazol-2-yl, 5-methoxy-[1,2,4]oxadiazol-3-yl, 5-amino-[1,2,4]oxadiazol-3-yl, 5-[(2-hydroxy-ethyl)]-amino)-[1,2,4]oxadiazol-3-yl, 5-hydroxymethyl-[1,2,4]oxadiazol-3-yl, 5-(oxetan-3-yl)-[1,2,4]oxadiazol-3-yl, 1H-imidazol-4-yl, 5-methyl-1H-imidazol-4-yl, 2,5-dimethyl-1H-imidazol-4-yl) [in particular HET is unsubstituted or mono-substituted with hydroxy; especially HET is 1H-tetrazol-5-yl, 3-hydroxy-isoxazol-5-yl, or 2-hydroxy-[1,3,4]oxadiazol-4-yl];
R$^6$ represents
(C$_{1-6}$)alkyl (especially methyl, ethyl, n-propyl, isopropyl, n-butyl, isobutyl);
(C$_{1-4}$)alkoxy (especially methoxy, ethoxy, n-propoxy, isopropoxy, n-butoxy);
(C$_{1-3}$)fluoroalkyl (especially trifluoromethyl);
(C$_{1-3}$)fluoroalkoxy (especially difluoromethoxy, trifluoromethoxy, 2,2,2-trifluoroethoxy);
halogen (especially fluoro or chloro);
hydroxy;
(C$_{3-6}$)cycloalkyl (especially cyclopropyl);
(C$_{3-6}$)cycloalkyl-oxy (especially cyclopropyl-oxy, cyclobutyl-oxy, cyclopentyl-oxy);
hydroxy-(C$_{2-4}$)alkoxy (especially 2-hydroxy-ethoxy);
—S—R$^{S2}$ wherein R$^{S2}$ represents (C$_{1-4}$)alkyl (especially methyl, ethyl, n-propyl, isopropyl, isobutyl), or (C$_{3-6}$)cycloalkyl optionally containing one ring oxygen atom (especially cyclobutyl, oxetan-3-yl);
or Ar$^1$ represents 3-carboxy-1H-indol-6-yl, 4-carboxy-1H-indol-2-yl, 5-carboxy-1H-indol-2-yl, 6-carboxy-1H-indol-2-yl, 7-carboxy-1H-indol-2-yl, 5-(methoxycarbonyl)-1H-indol-2-yl, 6-(methoxycarbonyl)-1H-indol-2-yl), 6-carboxy-benzofuran-2-yl, 3-carboxy-benzofuran-6-yl, 2-carboxy-benzofuran-5-yl, or 2-carboxy-benzofuran-6-yl;
or Ar$^1$ represents a group of the structure (Ar-III):

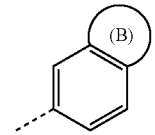

(Ar-III)

wherein ring (B) represents 2-oxo-2,3-dihydro-benzooxazol-6-yl, 3-methyl-2-oxo-2,3-dihydro-benzooxazol-5-yl, 1-methyl-3-oxo-2,3-dihydro-1H-indazol-6-yl, 2-oxo-1,2,3,4-tetrahydro-quinazolin-6-yl, 1-methyl-2-oxo-1,2,3,4-tetrahydro-quinazolin-6-yl, 1-oxo-1,2,3,4-tetrahydro-isoquinolin-6-yl, 1-methyl-2-oxo-1,2,3,4-tetrahydro-quinazolin-7-yl, or 1-oxo-1,2,3,4-tetrahydro-isoquinolin-7-yl;
wherein in a sub-embodiment, Ar$^1$ especially is a phenyl group of the structure (Ar-I) (wherein in particular R$^{m1}$ especially is different from hydrogen), or a 5-membered heteroaryl group of the structure (Ar-II), as defined herein above.

12) Another embodiment relates to compounds according to any one of embodiments 8) to 10), wherein Ar$^1$ represents a phenyl group of the structure (Ar-I):

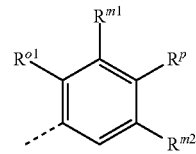

(Ar-I)

wherein
R$^p$ represents
(C$_{4-6}$)cycloalkyl containing a ring oxygen atom, wherein said (C$_{4-6}$)cycloalkyl containing a ring oxygen atom is unsubstituted or mono-substituted with hydroxy (especially 3-hydroxy-oxetan-3-yl);
hydroxy;
—X$^1$—CO—R$^{O1}$, wherein
X$^1$ represents a direct bond, (C$_{1-3}$)alkylene (especially —CH$_2$—, —CH(CH$_3$)—, —C(CH$_3$)$_2$—, —CH$_2$—CH$_2$—), —O—(C$_{1-3}$)alkylene-* (especially —O—CH$_2$—*, —O—CH(CH$_3$)—*, —O—C(CH$_3$)$_2$—*, —O—CH$_2$—CH$_2$—*), —NH—(C$_{1-3}$)alkylene-* (especially —NH—CH$_2$*, —NH—CH(CH$_3$)—*), —S—CH$_2$*, —CF$_2$—, —CH=CH—, ethen-1,1-diyl, or —NH—CO—*; wherein the asterisks indicate the bond that is linked to the —CO—$R^{O1}$ group; and $R^{O1}$ represents

-OH;

-O—$(C_{1-4})$alkyl (especially ethoxy, methoxy);

—NH—$SO_2$—$R^{S3}$ wherein $R^{S3}$ represents $(C_{1-4})$alkyl, $(C_{3-6})$cycloalkyl wherein the $(C_{3-6})$ cycloalkyl optionally contains a ring oxygen atom, $(C_{3-6})$cycloalkyl-$(C_{1-3})$alkylene wherein the $(C_{3-6})$cycloalkyl optionally contains a ring oxygen atom, $(C_{1-3})$fluoroalkyl, or —$NH_2$;

[wherein in particular such group —$X^1$—CO—$R^{O1}$ represents —COOH, —CO—O—$CH_3$, —CO—O—$C_2H_5$, —O—$CH_2$—COOH, —O—CH($CH_3$)—COOH, —O—C($CH_3$)$_2$—COOH, —O—$CH_2$—$CH_2$—COOH, —NH—$CH_2$—COOH, —NH—$CH_2$—CO—O—$CH_3$, —NH—CH($CH_3$)—COOH, —CO—NH—$SO_2$—$CH_3$, —CO—NH—$SO_2$—C($CH_3$)$_2$, —CO—NH—$SO_2$-cyclopropyl, —CO—NH—$SO_2$—$C_2H_5$, —CO—NH—$SO_2$—$NH_2$, —$CH_2$—COOH, —$CH_2$—CO—O—$CH_3$, —$CH_2$—CO—O—$C_2H_5$, —$CH_2$—$CH_2$—COOH, —CH=CH—COOH, —NH—CO—COOH,];

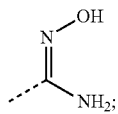

2-hydroxy-3,4-dioxo-cyclobut-1-enyl;

—CO—$NR^{N3}R^{N4}$ wherein $R^{N3}$ and $R^{N4}$ independently represent hydrogen, or $(C_{1-4})$alkyl (wherein preferably at least one of $R^{N3}$ and $R^{N4}$ represents hydrogen; and wherein particular examples of such group —CO—$NR^{N3}R^{N4}$ are —CO—$NH_2$, —CO—NH($CH_3$), or —CO—NH($C_2H_5$),);

$HET^1$, wherein wherein $HET^1$ represents 5-oxo-4,5-dihydro-[1,2,4]oxadiazol-3-yl (encompassing its tautomeric form 5-hydroxy-[1,2,4]oxadiazol-3-yl), or 3-oxo-2,3-dihydro-[1,2,4]oxadiazol-5-yl (encompassing its tautomeric form 3-hydroxy-[1,2,4]oxadiazol-5-yl); or HET, wherein wherein HET represents a 5-membered heteroaryl selected from oxazolyl, isoxazolyl, oxadiazolyl, thiazolyl, isothiazolyl, thiadiazolyl, imidazolyl, pyrazolyl, triazolyl, and tetrazolyl, wherein said 5-membered heteroaryl is unsubstituted, or mono-substituted, wherein the substituent is independently selected from $(C_{1-4})$ alkyl (especially methyl), $(C_{1-4})$alkoxy (especially methoxy), —COOH, hydroxy, hydroxy-$(C_{1-3})$alkyl (especially hydroxymethyl), $(C_{3-5})$cycloalkyl optionally containing one ring oxygen atom (especially cyclopropyl, oxetan-3-yl), or —$NR^{N9}R^{N10}$ wherein $R^{N9}$ and $R^{N10}$ independently represent hydrogen, $(C_{1-3})$alkyl (especially methyl), or hydroxy-$(C_{2-4})$alkyl (especially 2-hydroxy-ethyl); (especially such group HET is 1H-tetrazol-5-yl, 3-hydroxy-isoxazol-5-yl, 2-hydroxy-[1,3,4]oxadiazol-4-yl);

$R^{m1}$ represents hydrogen;

$(C_{1-6})$alkyl (especially methyl, ethyl, n-propyl, isopropyl, n-butyl, isobutyl);

$(C_{1-4})$alkoxy (especially methoxy, ethoxy, n-propoxy, isopropoxy, n-butoxy, isobutoxy);

$(C_{1-3})$fluoroalkyl (especially trifluoromethyl);

$(C_{1-3})$fluoroalkoxy (especially difluoromethoxy, trifluoromethoxy, 2,2,2-trifluoroethoxy);

halogen (especially fluoro or chloro);

$(C_{3-6})$cycloalkyl-oxy (especially cyclopropyl-oxy, cyclobutyl-oxy, cyclopentyl-oxy);

hydroxy;

hydroxy-$(C_{2-4})$alkoxy (especially 2-hydroxy-ethoxy);

—S—$R^{S2}$ wherein $R^{S2}$ represents $(C_{1-4})$alkyl (especially methyl, ethyl, n-propyl, isopropyl, isobutyl), or $(C_{3-6})$cycloalkyl optionally containing one ring oxygen atom (especially cyclobutyl, oxetan-3-yl); wherein in a sub-embodiment, $R^{m1}$ especially is different from hydrogen;

$R^{m2}$ represents hydrogen, methyl, fluoro, or chloro; and $R^{o1}$ represents hydrogen;

or $Ar^1$ represents a 5-membered heteroaryl group of the structure (Ar-II):

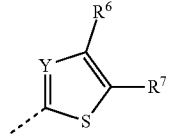

(Ar-II)

wherein

Y represents CH or N;

$R^7$ represents $(C_{4-6})$cycloalkyl containing a ring oxygen atom, wherein said $(C_{4-6})$cycloalkyl containing a ring oxygen atom is unsubstituted or mono-substituted with hydroxy (especially 3-hydroxy-oxetan-3-yl);

—$X^1$—CO—$R^{O1}$, wherein $X^1$ represents a direct bond, $(C_{1-3})$alkylene (especially —$CH_2$—, —CH($CH_3$)—, —C($CH_3$)$_2$—, —$CH_2$—$CH_2$—), —O—$(C_{1-3})$alkylene-* (especially —O—$CH_2$—*, —O—CH($CH_3$)—*, —O—C($CH_3$)$_2$—*, —O—$CH_2$—$CH_2$—*), —NH—$(C_{1-3})$alkylene* (especially —NH—$CH_2$*, —NH—CH($CH_3$)*), —CH=CH—, or —NH—CO—*; wherein the asterisks indicate the bond that is linked to the —CO—$R^{O1}$ group; and $R^{O1}$ represents

-OH;

-O—$(C_{1-4})$alkyl (especially ethoxy, methoxy);

—NH—$SO_2$—$R^{S3}$ wherein $R^{S3}$ represents $(C_{1-4})$alkyl, $(C_{1-6})$cycloalkyl wherein the $(C_{1-6})$ cycloalkyl optionally contains a ring oxygen atom, $(C_{3-6})$cycloalkyl-$(C_{1-3})$alkylene wherein the $(C_{3-6})$cycloalkyl optionally contains a ring oxygen atom, $(C_{1-3})$fluoroalkyl, or —$NH_2$;

[wherein in particular such group —$X^1$—CO—$R^{O1}$ represents —OOH, —CO—O—$CH_3$, —CO—O—$C_2H_5$, —O—$CH_2$—COOH, —O—CH($CH_3$)—OOH, —O—C($CH_3$)$_2$—OOH, —O—$CH_2$—$CH_2$—OOH, —NH—$CH_2$—OOH, —NH—$CH_2$—CO—O—$CH_3$, —NH—CH($CH_3$)—COOH, —CO—NH—$SO_2$—$CH_3$, —CO—NH—SO$_2$—C(CH$_3$)$_2$, —CO—NH—SO$_2$-cyclopropyl, —CO—NH—SO$_2$—C$_2$H$_5$, —CO—NH—SO$_2$—NH$_2$, —CH$_2$—OOH, —CH$_2$—CO—O—CH$_3$, —CH$_2$—CO—O—C$_2$H$_5$, —CH$_2$—CH$_2$—OOH, —CH═CH—OOH, —NH—CO—COOH,];

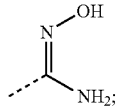

2-hydroxy-3,4-dioxo-cyclobut-1-enyl;
—CO—NR$^{N3}$R$^{N4}$ wherein R$^{N3}$ and R$^{N4}$ independently represent hydrogen, or (C$_{1-4}$)alkyl (wherein preferably at least one of R$^{N3}$ and R$^{N4}$ represents hydrogen; and wherein particular examples of such group —CO—NR$^{N3}$R$^{N4}$ are —CO—NH$_2$, —CO—NH(CH$_3$), —CO—NH(C$_2$H$_5$));

HET$^1$, wherein HET$^1$ represents 5-oxo-4,5-dihydro-[1,2,4]oxadiazol-3-yl (encompassing its tautomeric form 5-hydroxy-[1,2,4]oxadiazol-3-yl), or 3-oxo-2,3-dihydro-[1,2,4]oxadiazol-5-yl (encompassing its tautomeric form 3-hydroxy-[1,2,4]oxadiazol-5-yl;

HET, wherein wherein HET represents a 5-membered heteroaryl selected from oxazolyl, isoxazolyl, oxadiazolyl, thiazolyl, isothiazolyl, thiadiazolyl, imidazolyl, pyrazolyl, triazolyl, and tetrazolyl, wherein said 5-membered heteroaryl is unsubstituted, or mono-substituted, wherein the substituent is independently selected from (C$_{1-4}$) alkyl (especially methyl), (C$_{1-4}$)alkoxy (especially methoxy), —COOH, hydroxy, hydroxy-(C$_{1-3}$)alkyl (especially hydroxymethyl), (C$_{3-5}$)cycloalkyl optionally containing one ring oxygen atom (especially cyclopropyl, oxetan-3-yl), or —NR$^{N9}$R$^{N10}$ wherein R$^{N9}$ and R$^{N10}$ independently represent hydrogen, (C$_{1-3}$)alkyl (especially methyl), or hydroxy-(C$_{2-4}$)alkyl (especially 2-hydroxy-ethyl); (especially such group HET is 1H-tetrazol-5-yl, 3-hydroxy-isoxazol-5-yl, 2-hydroxy-[1,3,4]oxadiazol-4-yl);

R$^6$ represents
(C$_{1-6}$)alkyl (especially methyl, ethyl, n-propyl, isopropyl, n-butyl, isobutyl);
(C$_{1-4}$)alkoxy (especially methoxy, ethoxy, n-propoxy, isopropoxy, n-butoxy);
(C$_{1-3}$)fluoroalkyl (especially trifluoromethyl);
(C$_{1-3}$)fluoroalkoxy (especially difluoromethoxy, trifluoromethoxy, 2,2,2-trifluoroethoxy);
halogen (especially fluoro or chloro);
hydroxy;
(C$_{3-6}$)cycloalkyl-oxy (especially cyclopropyl-oxy, cyclobutyl-oxy, cyclopentyl-oxy);
hydroxy-(C$_{2-4}$)alkoxy (especially 2-hydroxy-ethoxy);
—S—R$^{S2}$ wherein R$^{S2}$ represents (C$_{1-4}$)alkyl (especially methyl, ethyl, n-propyl, isopropyl, isobutyl), or (C$_{3-6}$)cycloalkyl optionally containing one ring oxygen atom (especially cyclobutyl, oxetan-3-yl);

or Ar$^1$ represents 8- to 10-membered bicyclic heteroaryl selected from indazolyl, benzoimidazolyl, indolyl, benzofuranyl, benzooxazolyl, quinoxalinyl, isoquinolinyl, or quinolinyl); wherein said 8- to 10-membered bicyclic heteroaryl independently is mono-substituted with —(C$_{0-3}$)alkylene-COOR$^{O2}$ wherein R$^{O2}$ represents hydrogen or (C$_{1-4}$)alkyl (especially methyl) (wherein especially such group —(C$_{0-3}$)alkylene-COOR$^{O2}$ is —COOH); (in particular such 8- to 10-membered bicyclic heteroaryl is 3-carboxy-1H-indol-6-yl, 4-carboxy-1H-indol-2-yl, 5-carboxy-1H-indol-2-yl, 6-carboxy-1H-indol-2-yl, 7-carboxy-1H-indol-2-yl, 5-(methoxycarbonyl)-1H-indol-2-yl, 6-(methoxycarbonyl)-1H-indol-2-yl, 6-carboxy-benzofuran-2-yl, 3-carboxy-benzofuran-6-yl, 2-carboxy-benzofuran-5-yl, or 2-carboxy-benzofuran-6-yl);

or Ar$^1$ represents a group of the structure (Ar-III):

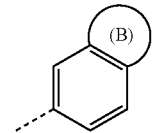

(Ar-III)

which is selected from 2-oxo-2,3-dihydro-benzooxazol-6-yl, 3-methyl-2-oxo-2,3-dihydro-benzooxazol-5-yl, 1-methyl-3-oxo-2,3-dihydro-1H-indazol-6-yl, 2-oxo-1,2,3,4-tetrahydro-quinazolin-6-yl, 1-methyl-2-oxo-1,2,3,4-tetrahydro-quinazolin-6-yl, 1-oxo-1,2,3,4-tetrahydro-isoquinolin-6-yl, 1-methyl-2-oxo-1,2,3,4-tetrahydro-quinazolin-7-yl, and 1-oxo-1,2,3,4-tetrahydro-isoquinolin-7-yl (in particular such group (Ar-III) is 1-methyl-3-oxo-2,3-dihydro-1H-indazol-6-yl);

wherein in a sub-embodiment, Ar$^1$ especially is a phenyl group of the structure (Ar-I) (wherein in particular R$^{m1}$ especially is different from hydrogen), or a 5-membered heteroaryl group of the structure (Ar-II), as defined herein above.

13) Another embodiment relates to compounds according to any one of embodiments 8) to 10), wherein Ar represents a group selected from:

A)

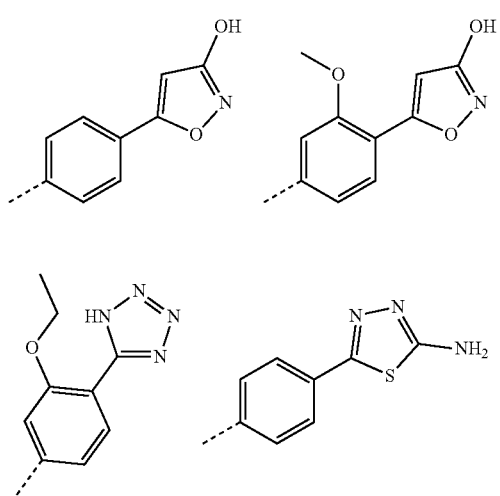

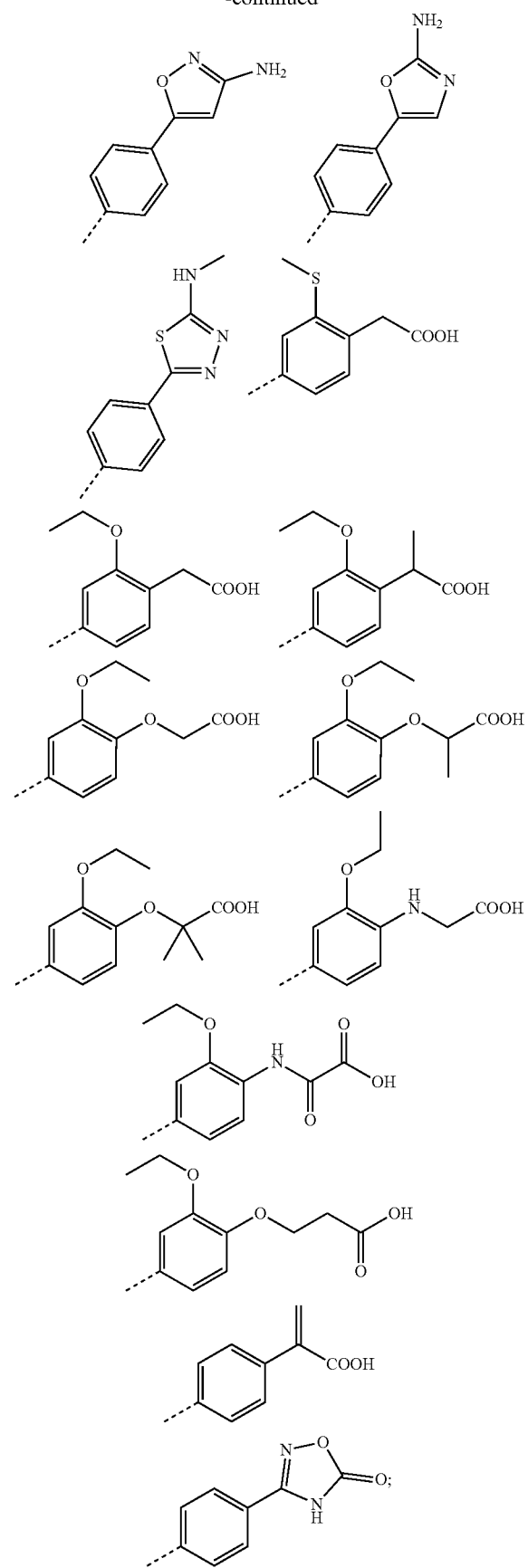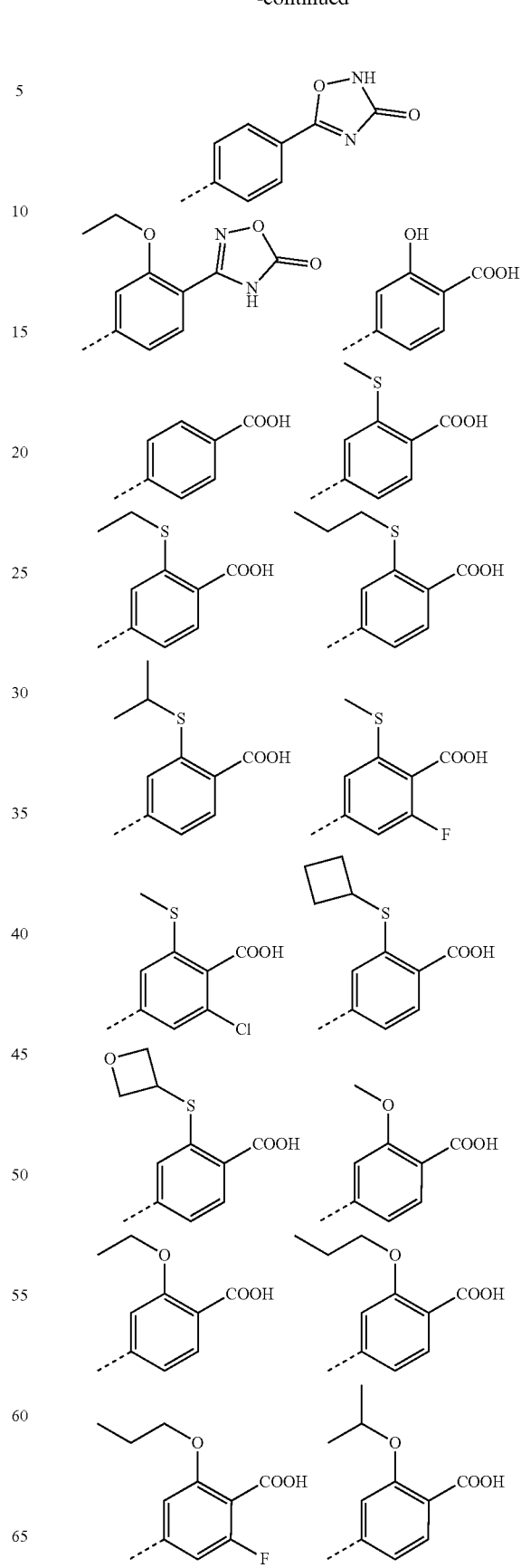

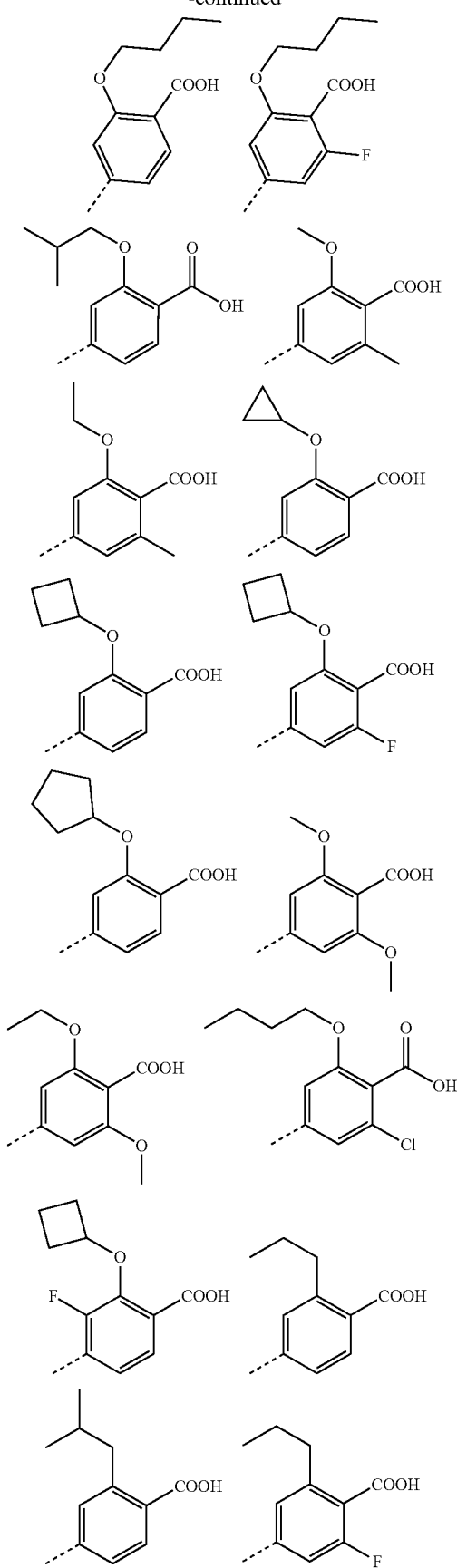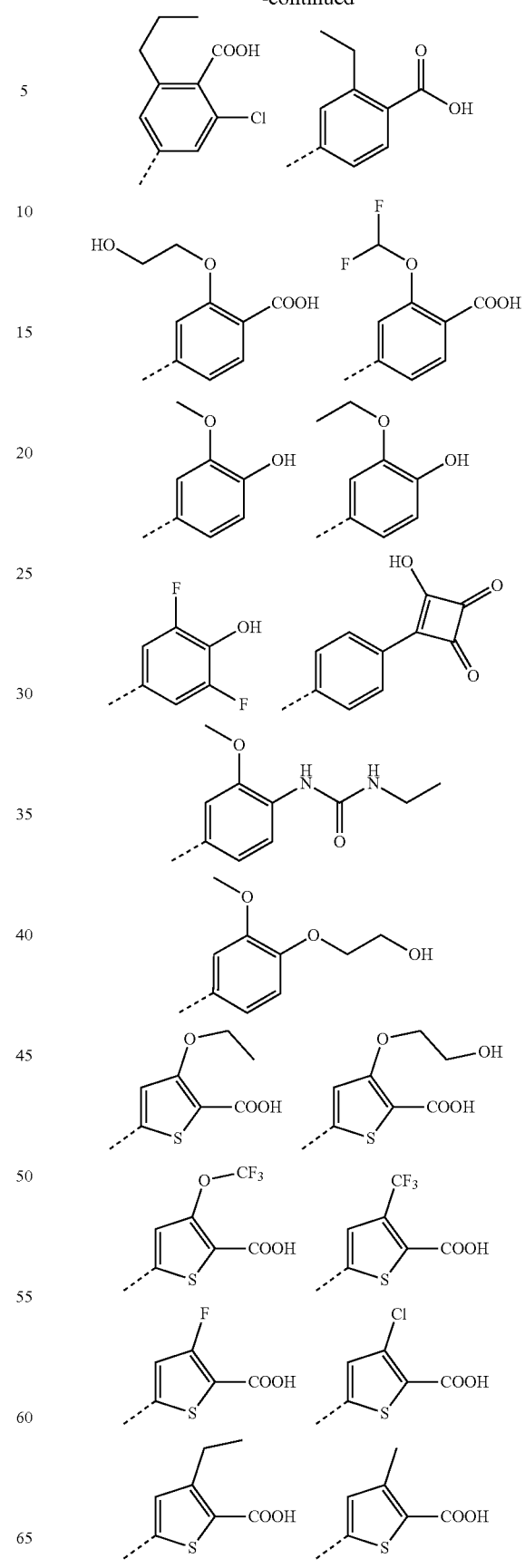

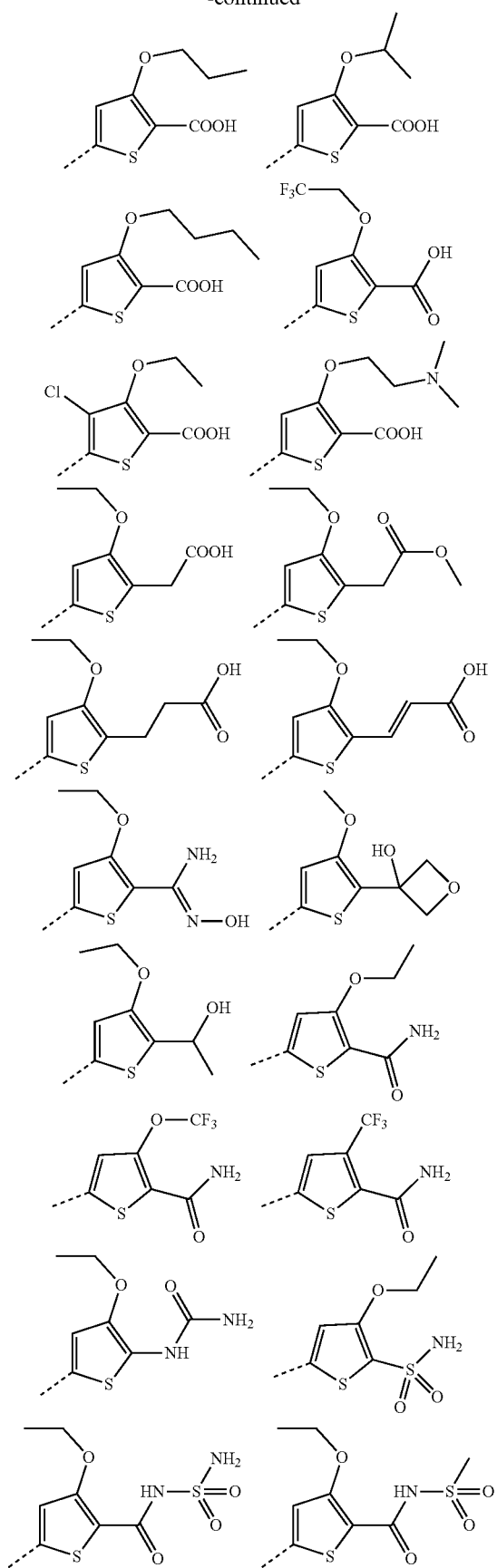
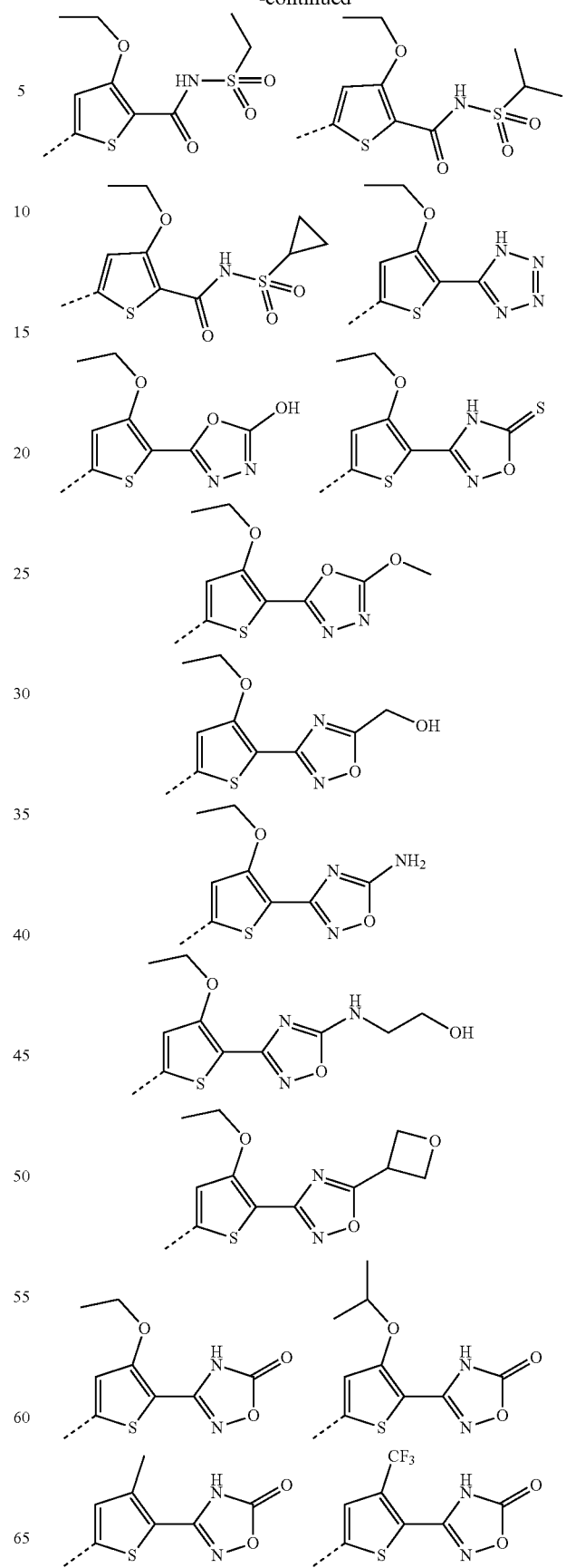

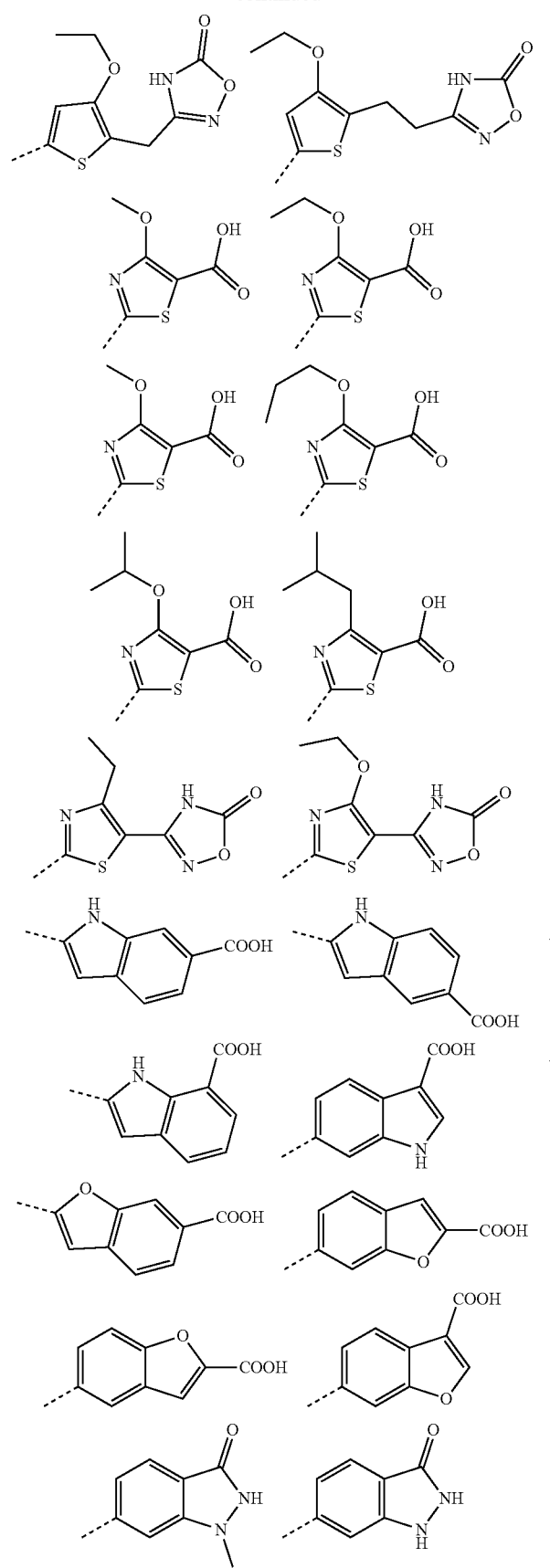
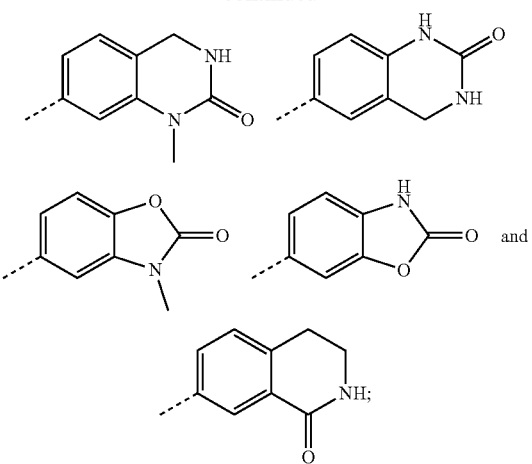
or, in addition, Ar¹ represents a group selected from:
B)
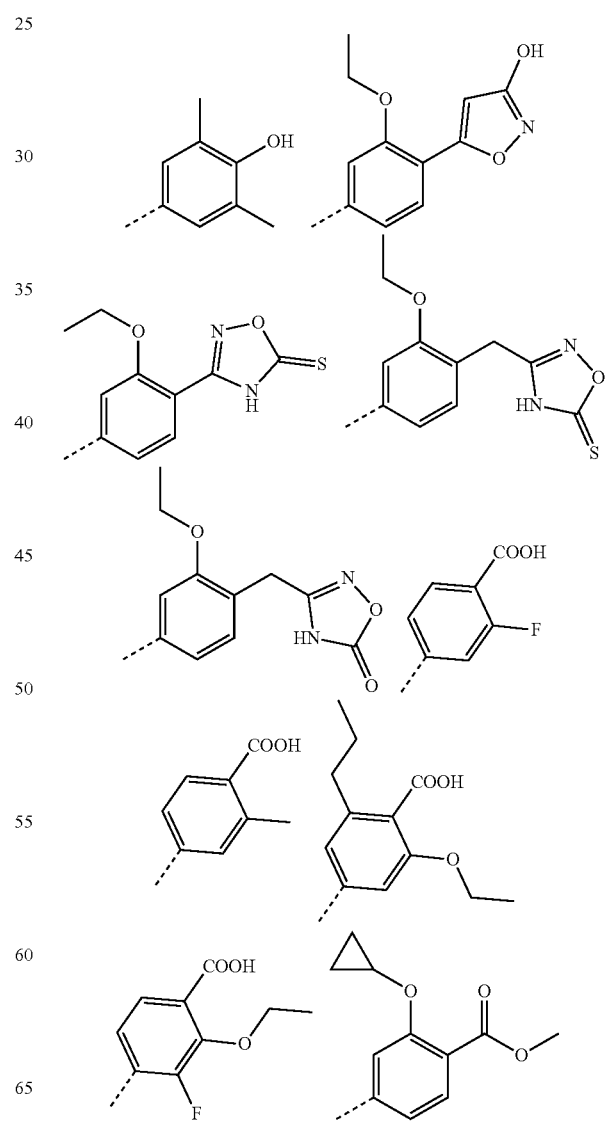

-continued
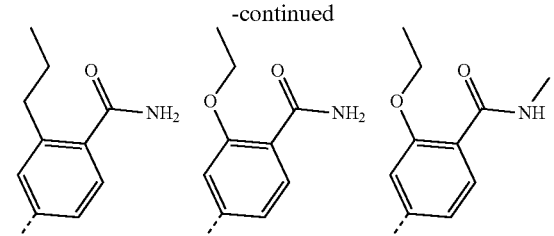
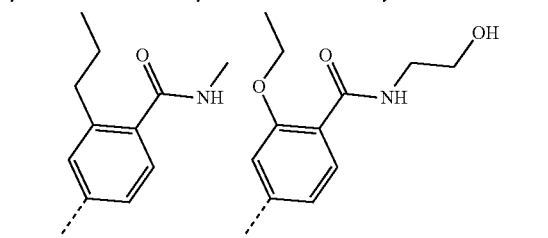
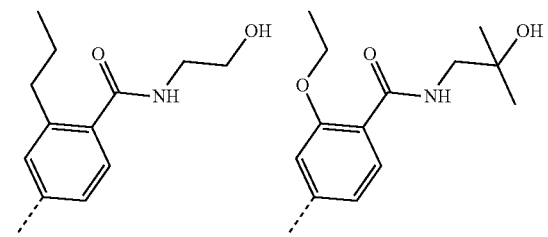
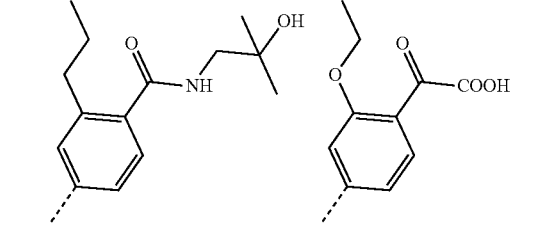
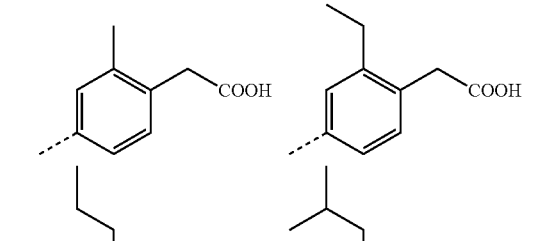
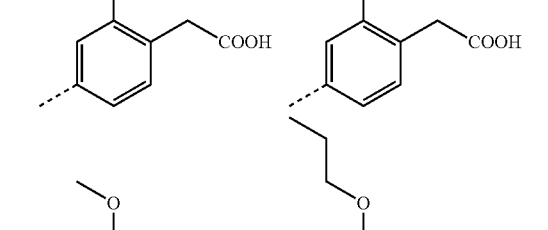
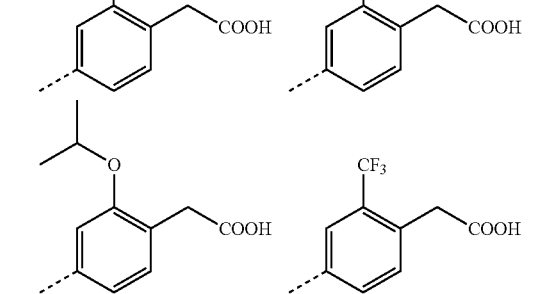
-continued
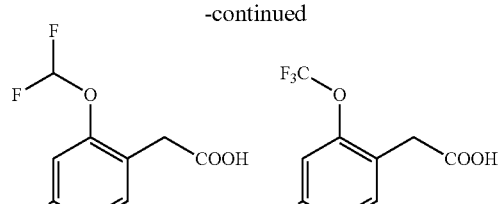
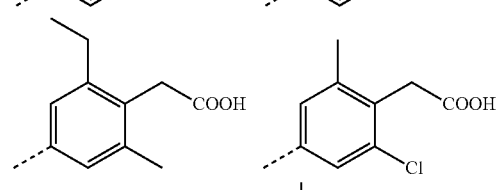
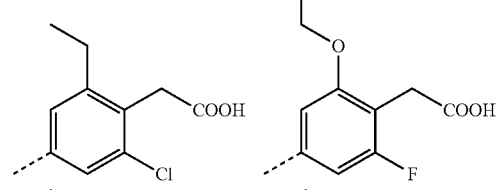
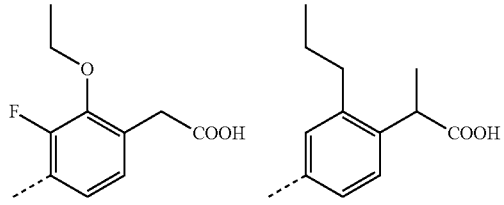
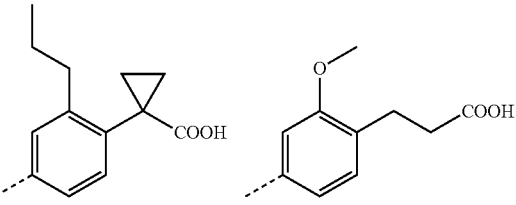
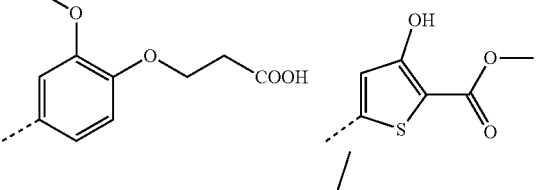
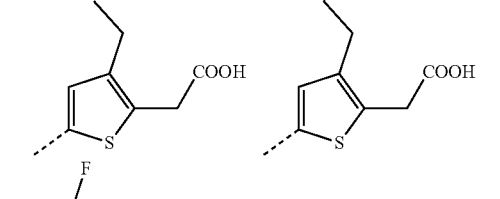
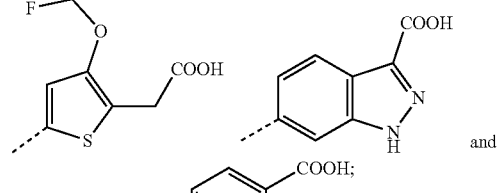
and
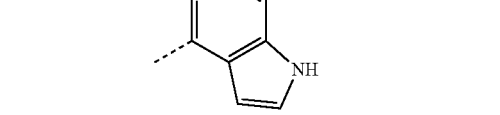

wherein the above groups A) and B) each form a particular sub-embodiment;

wherein in a further sub-embodiment, $Ar^1$ especially is a phenyl group (in particular a di-substituted phenyl group), or a thiophenyl group, or a thiazolyl group, as defined in groups A) and/or B) herein above.

14) Another embodiment relates to compounds according to any one of embodiments 8) to 10), wherein (i) $Ar^1$ represents a phenyl group selected from:

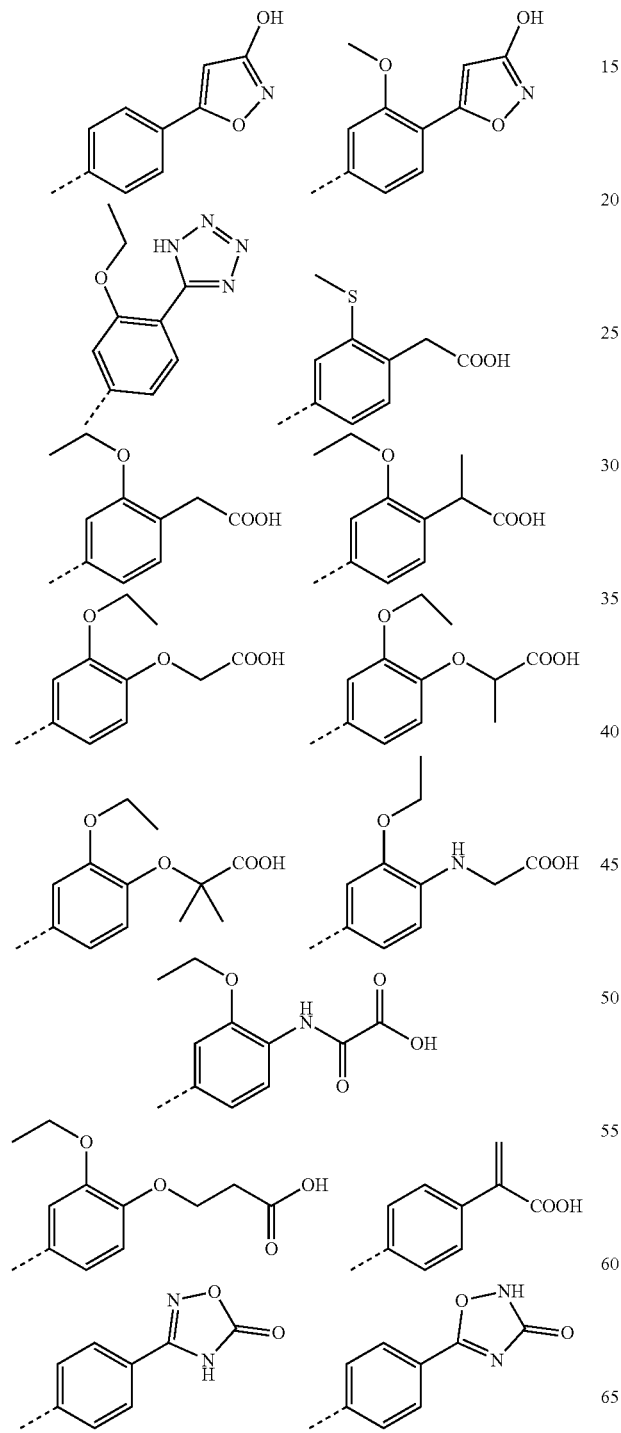

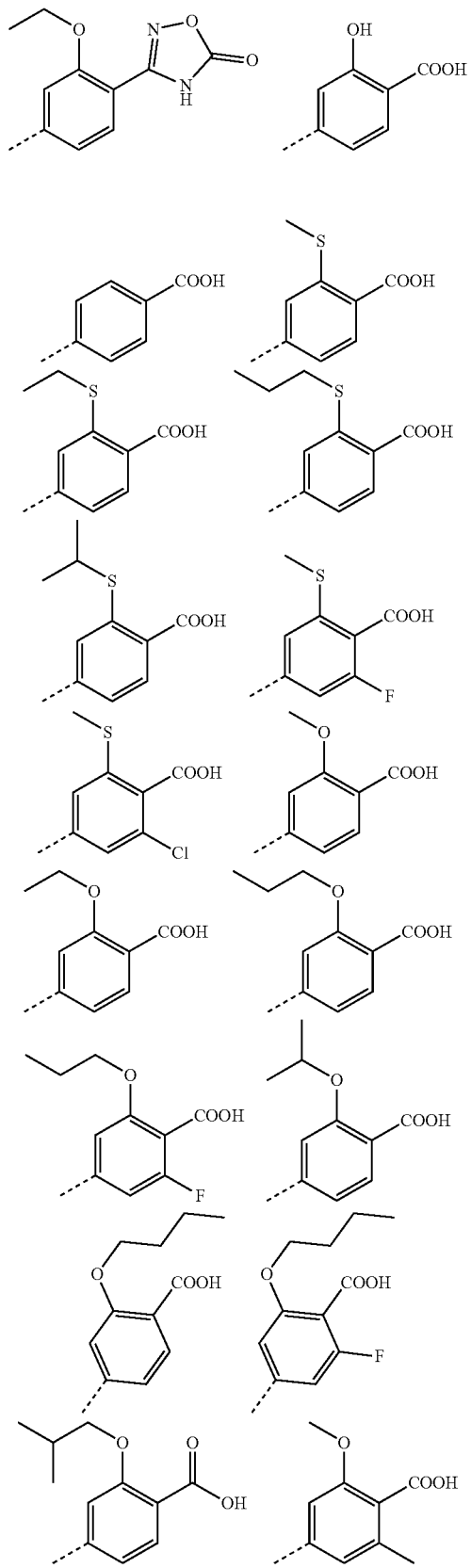

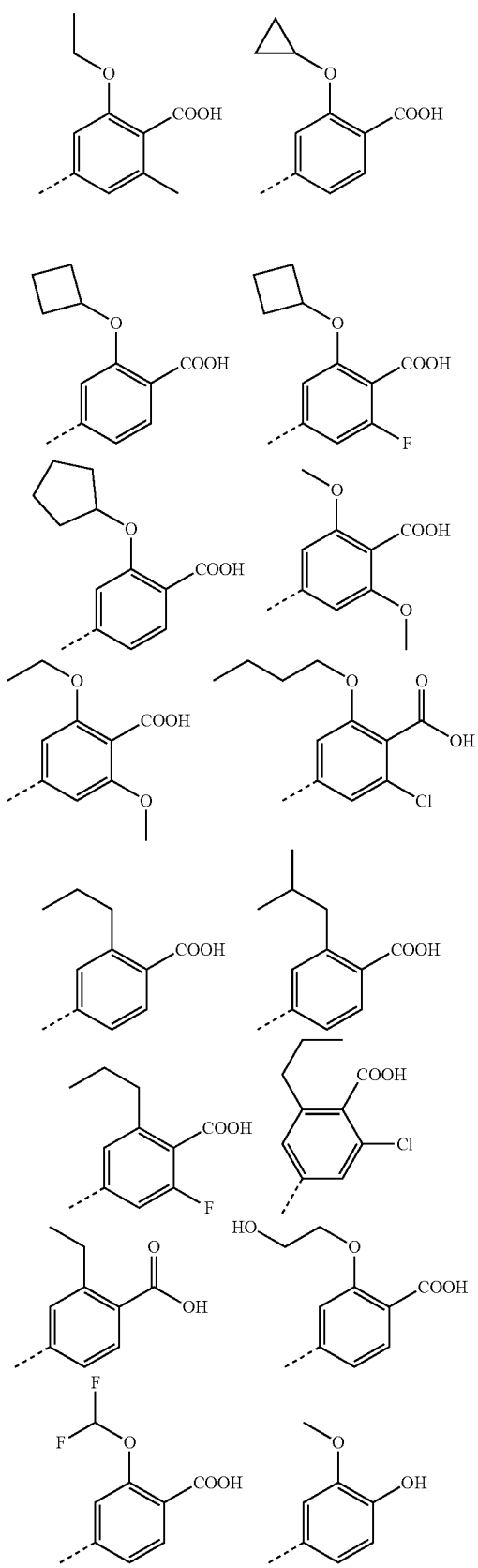
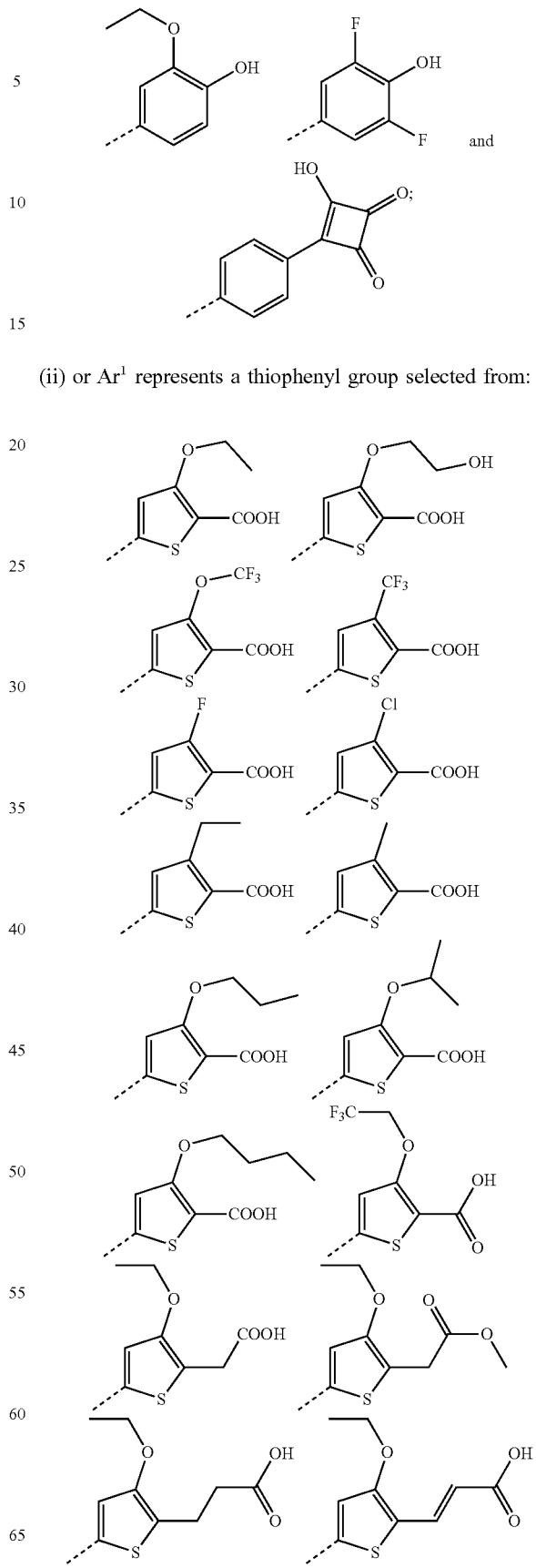
(ii) or Ar¹ represents a thiophenyl group selected from:

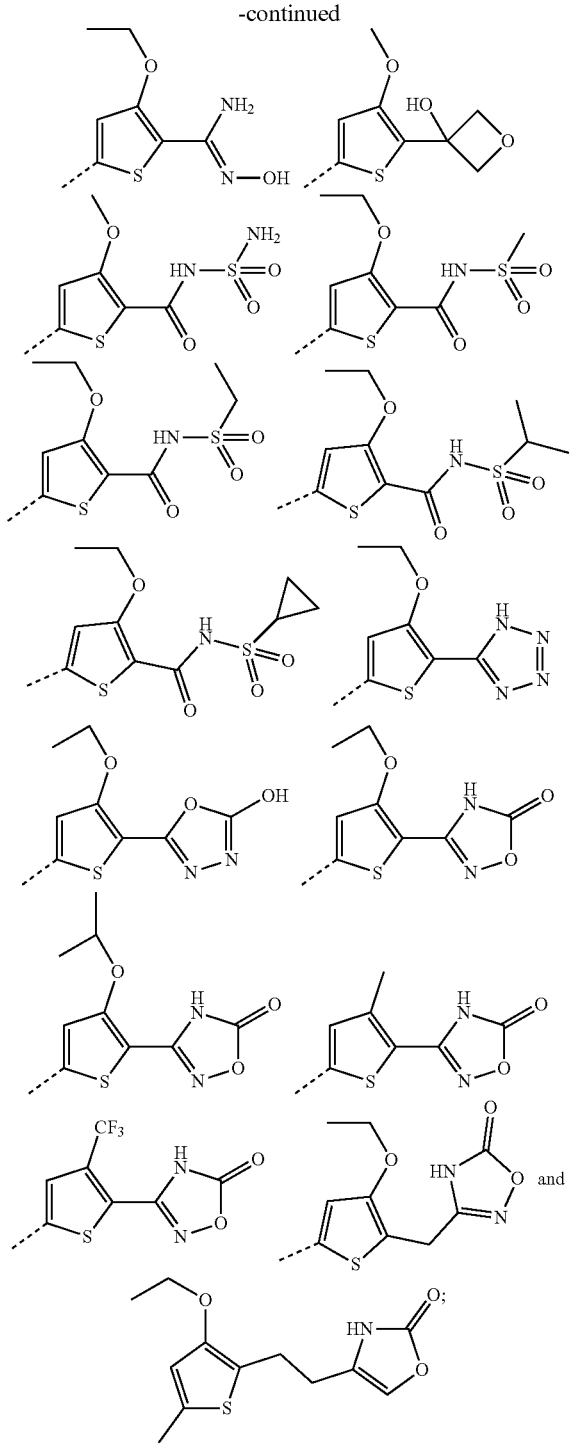
(iii) or Ar[1] represents a thiazolyl group selected from:
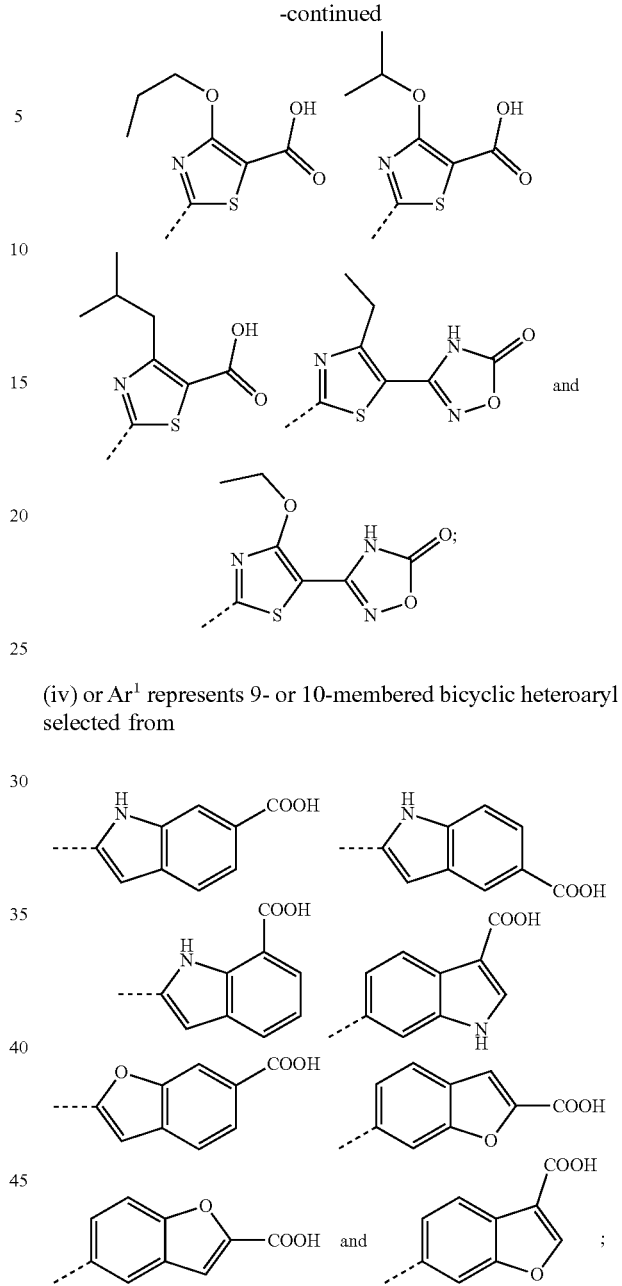
(iv) or Ar[1] represents 9- or 10-membered bicyclic heteroaryl selected from
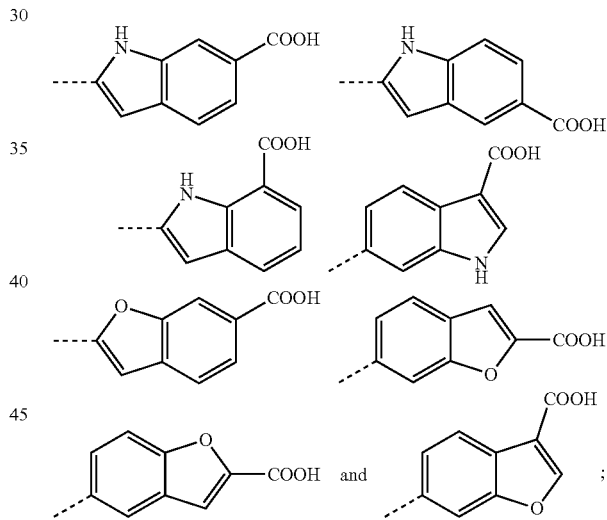
(v) or Ar[1] represents a group selected from:
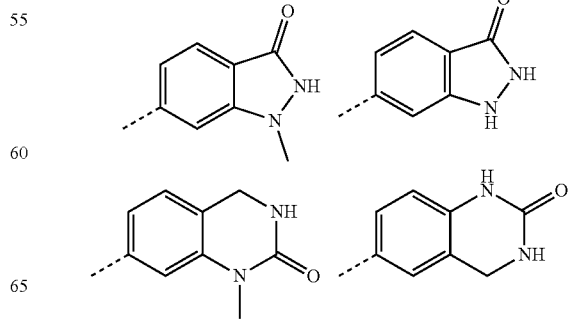

-continued
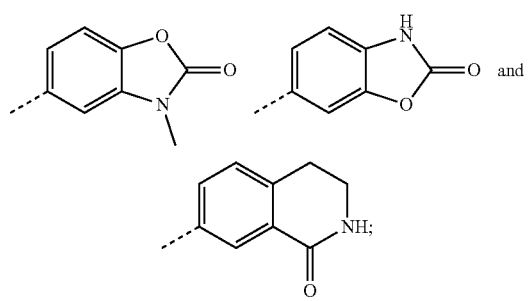
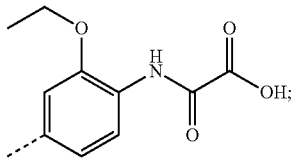 and
wherein in a sub-embodiment, Ar¹ especially is a phenyl group (in particular a di-substituted phenyl group), or a thiophenyl group, or a thiazolyl group, as defined herein above.
15) Another embodiment relates to compounds according to any one of embodiments 8) to 10), wherein
(i) Ar¹ represents a phenyl group selected from:
a)
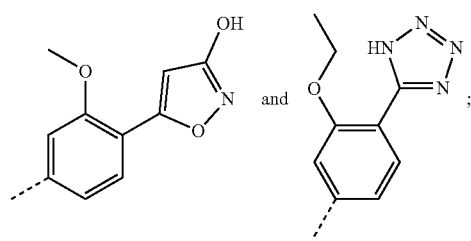
b)
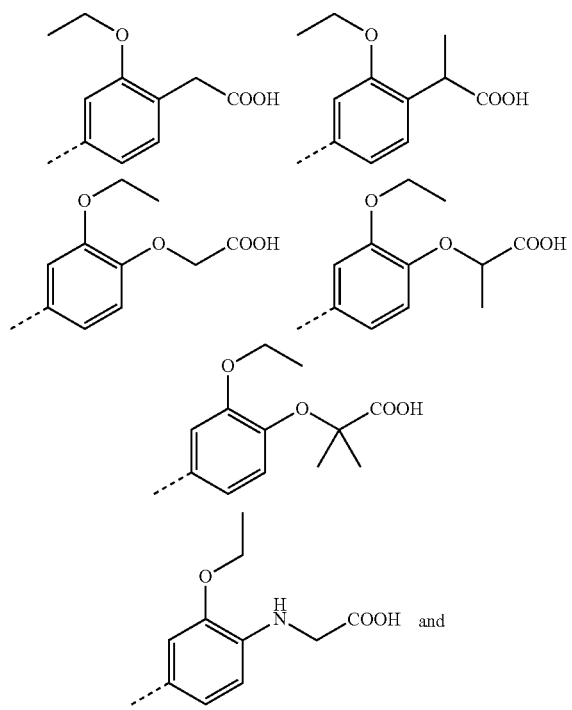
-continued
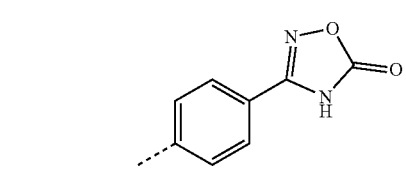
c)
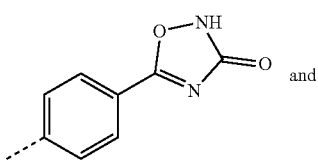
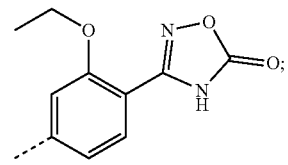 and
d)
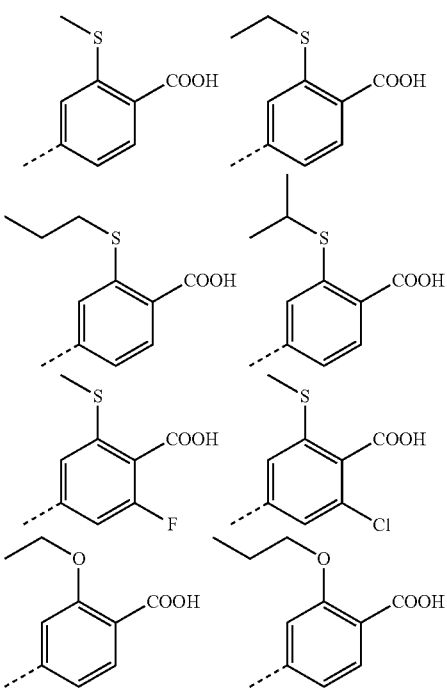

-continued
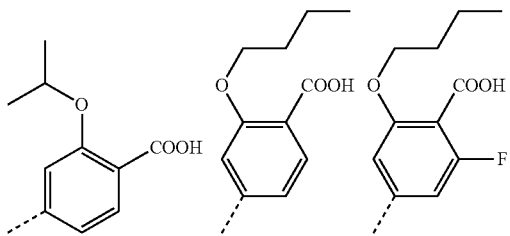
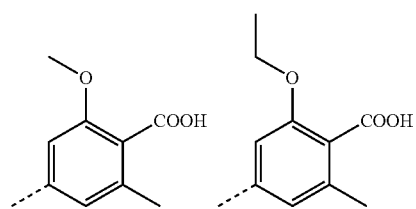
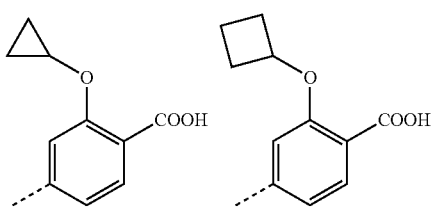
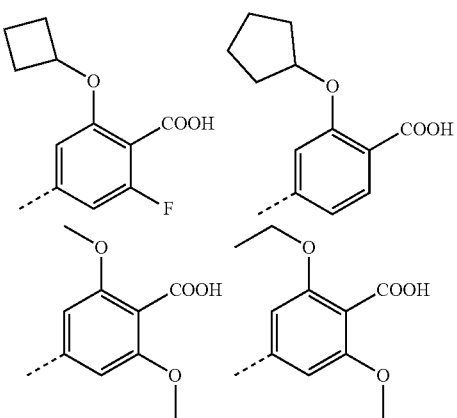
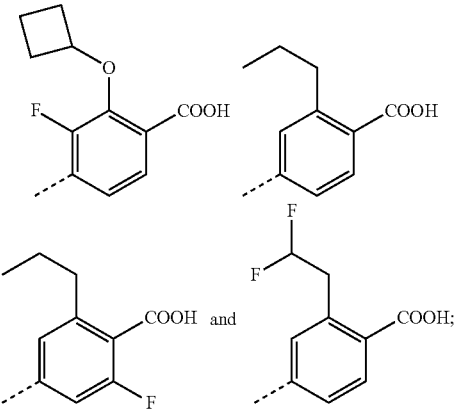
(ii) or Ar¹ represents a thiophenyl group selected from:
a)
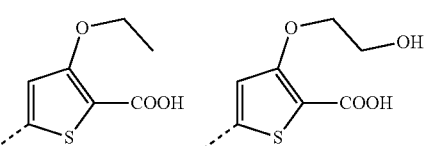
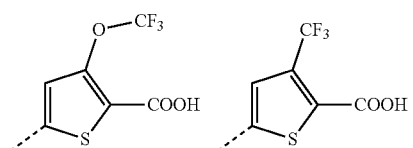
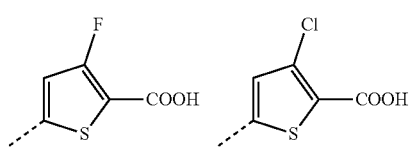
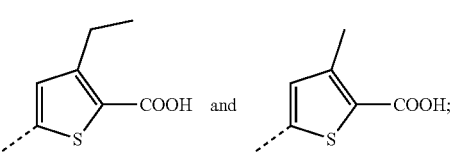
b)
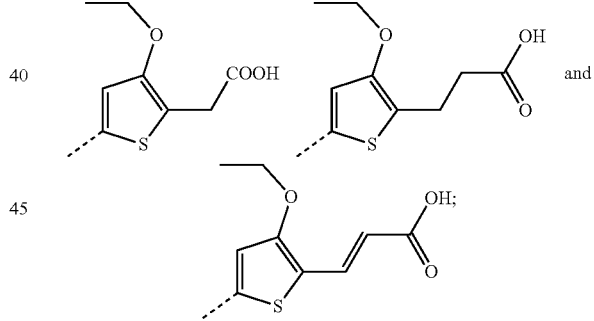
c)
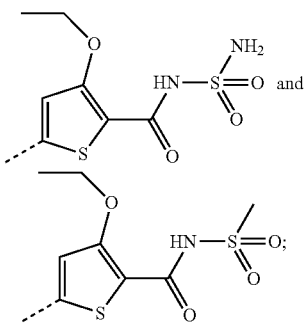

d)
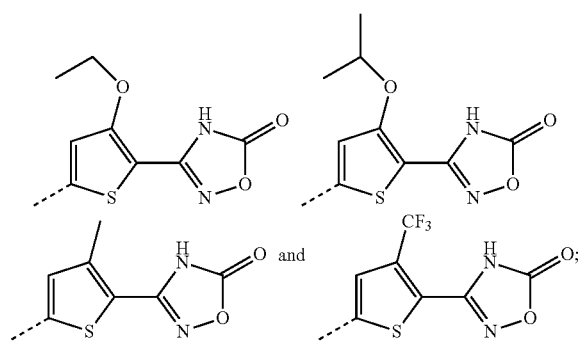
e)
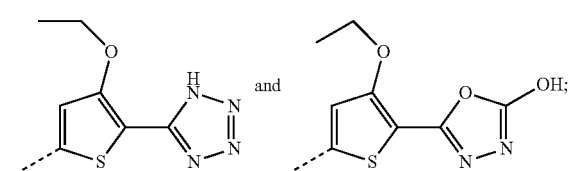
(iii) or Ar¹ represents a thiazolyl group selected from:
a)
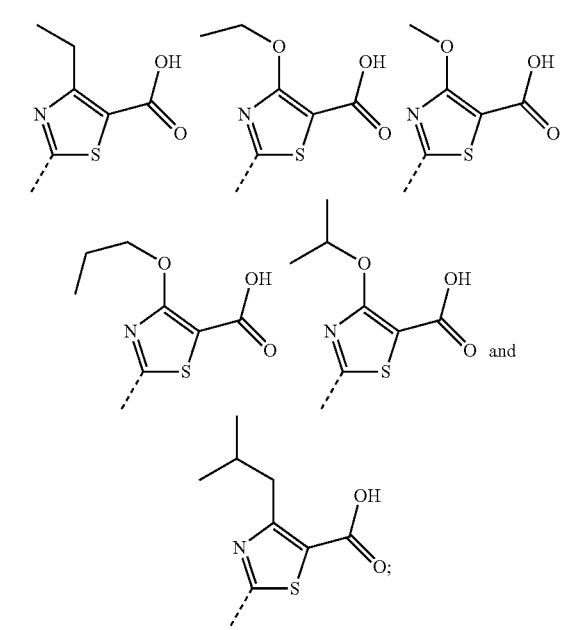
b)
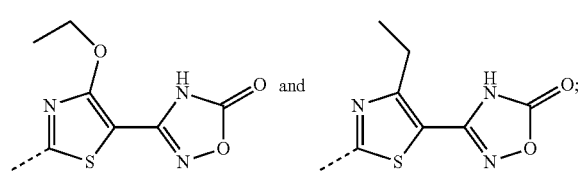
(iv) or Ar¹ represents 9- or 10-membered bicyclic heteroaryl selected from
a)
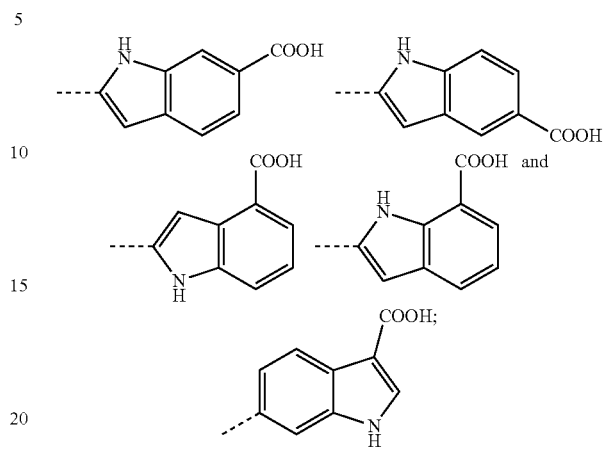
b)
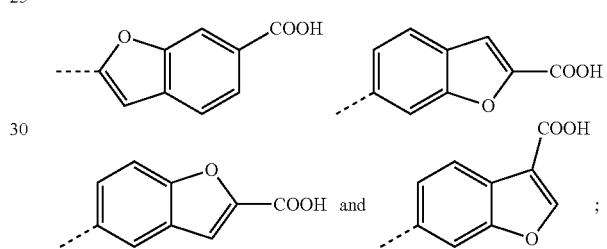
(v) or Ar¹ represents a group selected from:
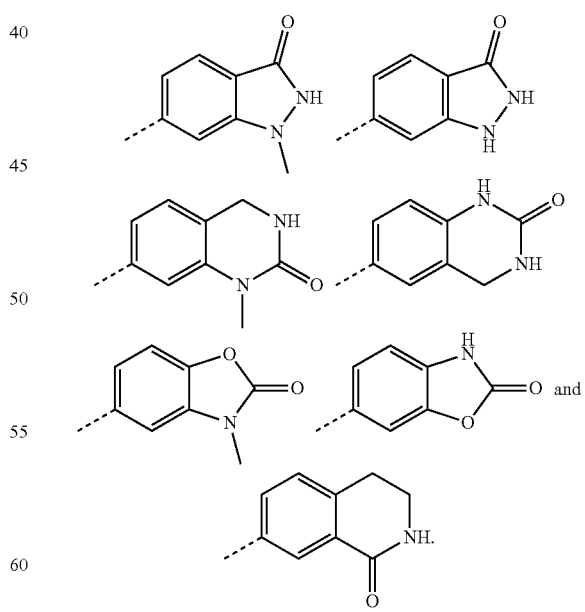
wherein in a sub-embodiment, Ar¹ especially is a phenyl group (in particular a di-substituted phenyl group), or a thiophenyl group, or a thiazolyl group, as defined herein above.

16) Another embodiment relates to compounds according to any one of embodiments 8) to 10), wherein Ar¹ represents a group selected from
A)
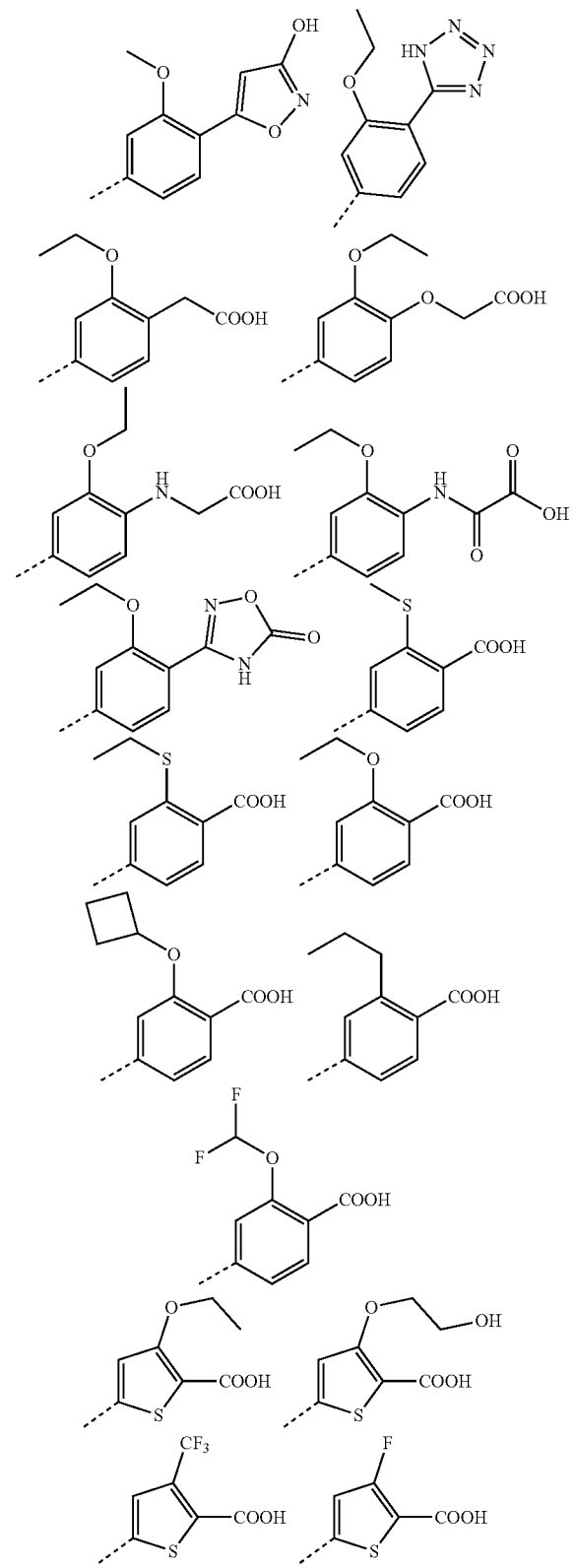
-continued
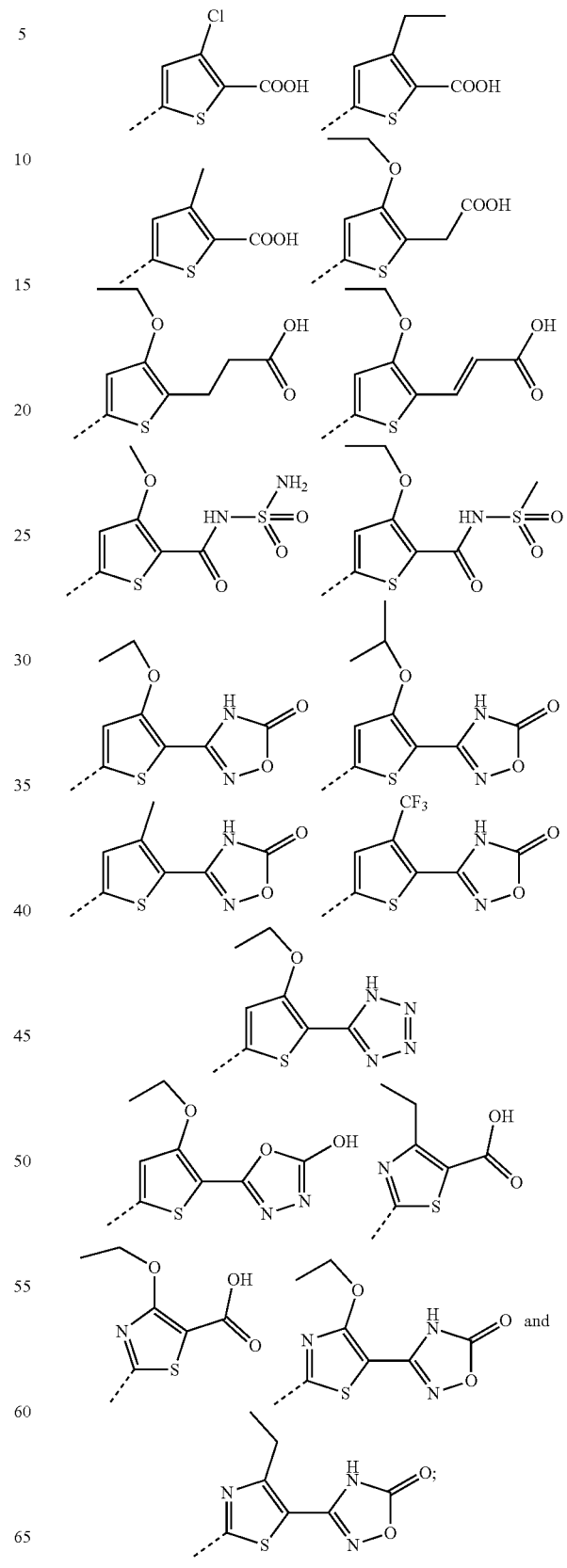

or, in addition, Ar¹ represents a group selected from:
B)

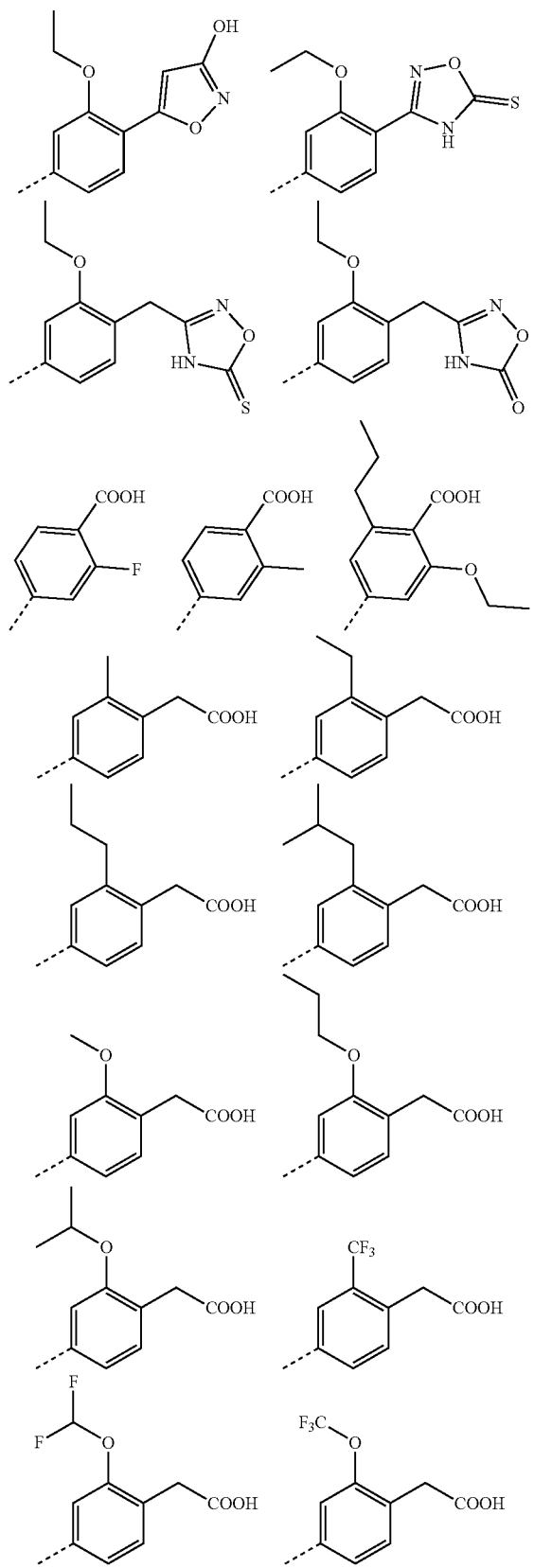

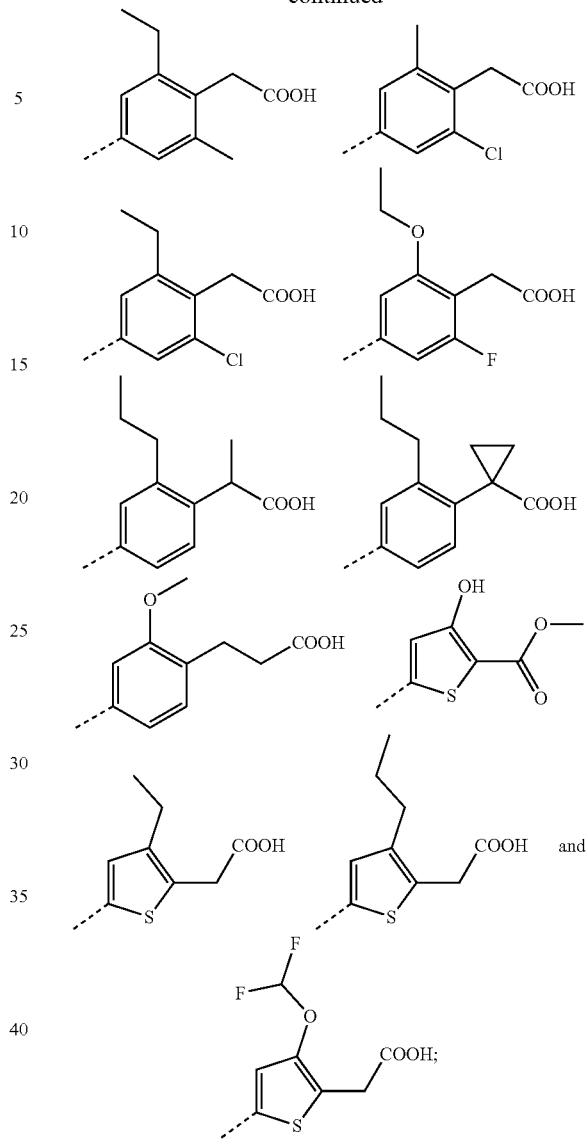

wherein the above groups A) and B) each form a particular sub-embodiment.

17) Another embodiment relates to compounds according to any one of embodiments 8) to 16), wherein in the fragment

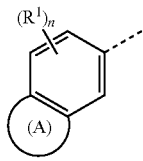

ring (A) represents an aromatic 5- or 6-membered ring fused to the phenyl group, wherein said ring (A) optionally contains one or two heteroatoms independently selected from nitrogen, oxygen, and sulfur (notably such fused group is benzofuranyl, benzothiophenyl, benzothiazolyl, benzoisothiazolyl, indolyl, indazolyl, naphthyl, quinolinyl, isoquinolinyl); wherein said fragment is optionally substituted with $(R^1)_n$; wherein $(R^1)_n$ represents one, two, three, or four optional substituents (i.e. said fragment is unsubstituted, or substituted with one, two, three, or four $R^1$), wherein said substituents $R^1$ are independently selected from $(C_{1-3})$alkyl (especially methyl), $(C_{2-3})$alkenyl (especially vinyl), $(C_{2-3})$alkynyl (especially ethynyl), $(C_{1-3})$alkoxy (especially methoxy, ethoxy, isopropoxy), halogen (especially fluoro, or chloro), $(C_{1-3})$fluoroalkyl (especially trifluoromethyl), $(C_{1-3})$fluoroalkoxy (especially trifluoromethoxy, difluoromethoxy), cyano, or —$NR^{N7}R^{N8}$ wherein $R^{N7}$ and $R^{N8}$ independently represent hydrogen or $(C_{1-4})$alkyl (especially methyl);

or ring (A) represents a non-aromatic 5- to 7-membered ring fused to the phenyl group, wherein said ring (A) optionally contains one or two heteroatoms independently selected from nitrogen, oxygen, and sulfur (notably such fused group is 2,3-dihydro-benzo[b]thiophenyl, benzo[1,3]dioxolyl, 1,3-dihydro-isobenzofuranyl, 2,3-dihydro-benzofuranyl, indanyl, 5,6,7,8-tetrahydronaphthalenyl, 2,3-dihydro-benzo[1,4]dioxinyl, chromanyl, 3,4-dihydro-2H-benzo[1,4]oxazinyl, 1,2,3,4-tetrahydro-quinolinyl, 3,4-dihydro-2H-benzo[b][1,4]dioxepinyl); wherein said fragment is optionally substituted with $(R^1)_n$; wherein $(R^1)_n$ represents one, two, three, or four optional substituents (i.e. said fragment is unsubstituted, or substituted with one, two, three, or four $R^1$), wherein said substituents $R^1$ are independently selected from $(C_{1-3})$alkyl (especially methyl), $(C_{1-3})$alkoxy (especially methoxy, ethoxy, isopropoxy), halogen (especially fluoro, or chloro), —S—$(C_{1-3})$alkyl (especially methylsulfanyl), $(C_{1-3})$fluoroalkyl (especially trifluoromethyl), $(C_{1-3})$fluoroalkoxy (especially trifluoromethoxy, difluoromethoxy), cyano, or oxo.

18) Another embodiment relates to compounds according to any one of embodiments 8) to 16), wherein the fragment

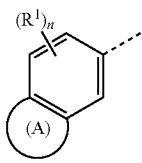

represents
a group selected from benzofuranyl, benzothiophenyl, benzothiazolyl, benzoisothiazolyl, indolyl, indazolyl, naphthyl, quinolinyl, and isoquinolinyl; which group independently is unsubstituted or substituted with $(R^1)_n$; wherein $(R^1)_n$ represents one, two, three, or four substituents, wherein said substituents $R^1$ are independently selected from $(C_{1-3})$alkyl (especially methyl), $(C_{2-3})$alkenyl (especially vinyl), $(C_{2-3})$alkynyl (especially ethynyl), $(C_{1-3})$alkoxy (especially methoxy, ethoxy, isopropoxy), halogen (especially fluoro, or chloro), —S—$(C_{1-3})$alkyl (especially methylsulfanyl), $(C_{1-3})$fluoroalkyl (especially trifluoromethyl), $(C_{1-3})$fluoroalkoxy (especially trifluoromethoxy, difluoromethoxy), cyano, or —$NR^{N7}R^{N8}$ wherein $R^{N7}$ and $R^{N8}$ independently represent hydrogen or $(C_{1-4})$alkyl (especially methyl); [notably said substituents $R^1$ are independently selected from $(C_{1-3})$alkyl (especially methyl), $(C_{2-3})$alkenyl (especially vinyl), $(C_{2-3})$alkynyl (especially ethynyl), $(C_{1-3})$alkoxy (especially methoxy, ethoxy, isopropoxy), halogen (especially fluoro, or chloro), $(C_{1-3})$fluoroalkyl (especially trifluoromethyl), $(C_{1-3})$fluoroalkoxy (especially trifluoromethoxy, difluoromethoxy), cyano, or —$NR^{N7}R^{N8}$ wherein $R^{N7}$ and $R^{N8}$ independently represent hydrogen or $(C_{1-4})$alkyl (especially methyl)]; or a group selected from 2,3-dihydro-benzo[b]thiophenyl, benzo[1,3]dioxolyl, 1,3-dihydro-isobenzofuranyl, 2,3-dihydro-benzofuranyl, indanyl, 5,6,7,8-tetrahydronaphthalenyl, 2,3-dihydro-benzo[1,4]dioxinyl, chromanyl, 3,4-dihydro-2H-benzo[1,4]oxazinyl, 1,2,3,4-tetrahydro-quinolinyl, and 3,4-dihydro-2H-benzo[b][1,4]dioxepinyl; which group independently is unsubstituted, or substituted with $(R^1)_n$; wherein $(R^1)_n$ represents one, two, or three substituents, wherein said substituents $R^1$ are independently selected from $(C_{1-3})$alkyl (especially methyl), $(C_{2-3})$alkenyl (especially vinyl), $(C_{2-3})$alkynyl (especially ethynyl), $(C_{1-3})$alkoxy (especially methoxy, ethoxy, isopropoxy), halogen (especially fluoro, or chloro), —S—$(C_{1-3})$alkyl (especially methylsulfanyl), $(C_{1-3})$fluoroalkyl (especially trifluoromethyl), $(C_{1-3})$fluoroalkoxy (especially trifluoromethoxy, difluoromethoxy), cyano, oxo, or —$NR^{N7}R^{N8}$ wherein $R^{N7}$ and $R^{N8}$ independently represent hydrogen or $(C_{1-4})$alkyl (especially methyl); [notably said substituents $R^1$ are independently selected from $(C_{1-3})$alkyl (especially methyl), $(C_{1-3})$alkoxy (especially methoxy, ethoxy, isopropoxy), halogen (especially fluoro, or chloro), —S—$(C_{1-3})$alkyl (especially methylsulfanyl), $(C_{1-3})$fluoroalkyl (especially trifluoromethyl), $(C_{1-3})$fluoroalkoxy (especially trifluoromethoxy, difluoromethoxy), cyano, or oxo].

19) Another embodiment relates to compounds according to any one of embodiments 8) to 16), wherein the fragment

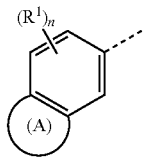

represents a group selected from the following groups a), b), c), and d):
a) benzothiophen-5-yl, benzothiophen-6-yl, 6-methyl-benzothiophen-5-yl, 3-methyl-benzothiophen-5-yl, 4-methyl-benzothiophen-5-yl, 6-methoxy-benzothiophen-5-yl, 5-methoxy-benzothiophen-6-yl, 6-cyano-benzothiophen-5-yl, 3-cyano-benzothiophen-5-yl, 6-ethoxy-benzothiophen-5-yl, 4-fluoro-7-methoxy-2-methyl-benzothiophen-6-yl, benzoisothiazol-5-yl, benzothiazol-5-yl, benzothiazol-6-yl, benzofuran-5-yl, benzofuran-6-yl, 6-fluoro-benzofuran-5-yl, 6-methoxy-benzofuran-5-yl, 5-methoxy-benzofuran-6-yl, 2-fluoro-5-methoxy-benzofuran-6-yl, 6-methoxy-4-methyl-benzofuran-5-yl, 4,5-difluoro-7-methoxy-2-methyl-benzofuran-6-yl, benzooxazol-6-yl, 1H-indol-5-yl, 1H-indol-6-yl, 1-methyl-1H-indol-6-yl, 1-methyl-1H-indol-5-yl, 6-fluoro-1-methyl-1H-indol-5-yl, 1,3-dimethyl-1H-indol-5-yl, 1-ethyl-1H-indol-6-yl, or 5-methoxy-1-methyl-1H-indazol-6-yl;
b) naphthalen-2-yl, 3-chloro-naphthalen-2-yl, 1-chloro-naphthalen-2-yl, 8-fluoro-naphthalen-2-yl, 1-fluoro-naphthalen-2-yl, 3-methyl-naphthalen-2-yl, 1-methyl-naphthalen-2-yl, 1-amino-naphthalen-2-yl, 3-ethynylnaphthalen-2-yl, 1-ethynyl-naphthalen-2-yl, 1-vinyl-naphthalen-2-yl, 1,3-difluoro-naphthalen-2-yl, 3-methoxy-naphthalen-2-yl, 3-cyano-naphthalen-2-yl, 1-cyano-naphthalen-2-yl, 3-methylamino-naphthalen-2-yl, 1-fluoro-3-methoxy-naphthalen-2-yl, 4-chloro-3-methoxy-naphthalen-2-yl, 4-fluoro-3-methoxy-naphthalen-2-yl, 3-ethoxy-naphthalen-2-yl, 3-methoxy-1-methyl-naphthalen-2-yl, 3-cyano-1-fluoro-naphthalen-2-yl, 3-cyano-1-methyl-naphthalen-2-yl, 3-isopropoxy-naphthalen-2-yl, or 3-difluoromethoxy-naphthalen-2-yl;
c) quinolin-6-yl, 6-fluoro-isoquinolin-7-yl, 7-fluoro-isoquinolin-6-yl, 5-fluoro-quinolin-6-yl, 7-methyl-quinolin-6-yl, 8-methyl-quinolin-7-yl, 4-chloro-7-methyl-quinolin-6-yl, 7-chloro-8-methyl-quinolin-6-yl, 5,8-difluoro-quinolin-6-yl, or 7-chloro-8-fluoro-quinolin-6-yl, 5,7-difluoro-quinolin-6-yl; and
d) 2,3-dihydro-benzo[b]thiophen-5-yl, benzo[1,3]dioxol-5-yl, 6-methoxy-benzo[1,3]dioxol-5-yl, 6-cyano-benzo[1,3]dioxol-5-yl, 6-chloro-2,2-difluoro-benzo[1,3]dioxol-5-yl, 6-difluoromethoxy-benzo[1,3]dioxo-5-yl, 1,3-dihydro-isobenzofuran-5-yl, 2,3-dihydro-benzofuran-5-yl, 2,3-dihydro-benzofuran-6-yl, indan-5-yl, 3-methoxy-5,6,7,8-tetrahydro-naphthalen-2-yl, 2,3-dihydro-benzo[1,4]dioxin-6-yl, 8-chloro-2,3-dihydro-benzo[1,4]dioxin-6-yl, 8-fluoro-2,3-dihydro-benzo[1,4]dioxin-6-yl, 8-methyl-2,3-dihydro-benzo[1,4]dioxin-6-yl, 7-methyl-2,3-dihydro-benzo[1,4]dioxin-6-yl, 7-methylsulfanyl-2,3-dihydro-benzo[1,4]dioxin-6-yl, 7-methoxy-2,3-dihydro-benzo[1,4]dioxin-6-yl, 7-cyano-2,3-dihydro-benzo[1,4]dioxin-6-yl, 7-ethoxy-2,3-dihydro-benzo[1,4]dioxin-6-yl, chroman-7-yl, chroman-6-yl, 6-chloro-3,4-dihydro-2H-benzo[1,4]oxazin-7-yl, 7-fluoro-4-methyl-3,4-dihydro-2H-benzo[1,4]oxazin-6-yl, 7-fluoro-1-methyl-1,2,3,4-tetrahydro-quinolin-6-yl, 7-methoxy-1,2,3,4-tetrahydro-quinolin-6-yl, 7-methoxy-1-methyl-2-oxo-1,2,3,4-tetrahydro-quinolin-6-yl, or 8-methoxy-3,4-dihydro-2H-benzo[b][1,4]dioxepin-7-yl;
or said fragment represents a group selected from the following groups e), f) and g):
e) 7-methyl-benzothiophen-5-yl, 7-methyl-benzothiophen-6-yl, 4-fluoro-benzothiophen-5-yl, 7-fluoro-benzothiophen-5-yl, 7-chloro-benzothiophen-5-yl, 3-chloro-benzothiophen-5-yl, 3-chloro-7-fluoro-benzothiophen-5-yl, 7-fluoro-6-methoxy-benzothiophen-5-yl, 7-trifluoromethyl-benzothiophen-5-yl;
f) 3-ethoxy-1-fluoro-naphthalen-2-yl, 3-ethoxy-1-methyl-naphthalen-2-yl; and
g) 7-fluoro-2,3-dihydro-benzo[1,4]dioxin-6-yl, 5-methyl-2,3-dihydro-benzo[1,4]dioxin-6-yl, 7-ethynyl-2,3-dihydro-benzo[1,4]dioxin-6-yl, 5-fluoro-7-methoxy-2,3-dihydro-benzo[1,4]dioxin-6-yl, 7-methoxy-5-methyl-2,3-dihydro-benzo[1,4]dioxin-6-yl, 7-difluoromethoxy-2,3-dihydro-benzo[1,4]dioxin-6-yl;
wherein the above groups a) to d), and, respectively, the above groups e) to g) form a particular sub-embodiment.

20) Another embodiment relates to compounds according to any one of embodiments 8) to 16), wherein the fragment

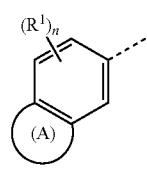

represents
represents a group selected from the following groups a), b), c), and d):
a) benzothiophen-5-yl, 6-methyl-benzothiophen-5-yl, 4-methyl-benzothiophen-5-yl, 6-methoxy-benzothiophen-5-yl, 5-methoxy-benzothiophen-6-yl, 3-cyano-benzothiophen-5-yl, 6-ethoxy-benzothiophen-5-yl, benzothiazol-5-yl, benzofuran-5-yl, 6-fluoro-benzofuran-5-yl, 6-methoxy-benzofuran-5-yl, 5-methoxy-benzofuran-6-yl, 6-methoxy-4-methyl-benzofuran-5-yl, 1H-indol-5-yl, or 1H-indol-6-yl;
b) 1-methyl-naphthalen-2-yl, 1-ethynyl-naphthalen-2-yl, 3-methoxy-naphthalen-2-yl, 1-fluoro-3-methoxy-naphthalen-2-yl, 3-ethoxy-naphthalen-2-yl, 3-methoxy-1-methyl-naphthalen-2-yl, or 3-cyano-1-methyl-naphthalen-2-yl;
c) 7-chloro-8-fluoro-quinolin-6-yl, or 5,7-difluoro-quinolin-6-yl; and
d) 2,3-dihydro-benzo[b]thiophen-5-yl, benzo[1,3]dioxol-5-yl, 6-methoxy-benzo[1,3]dioxol-5-yl, 6-cyano-benzo[1,3]dioxol-5-yl, 6-difluoromethoxy-benzo[1,3]dioxol-5-yl, 7-methyl-2,3-dihydro-benzo[1,4]dioxin-6-yl, 7-methoxy-2,3-dihydro-benzo[1,4]dioxin-6-yl, 7-cyano-2,3-dihydro-benzo[1,4]dioxin-6-yl, 7-ethoxy-2,3-dihydro-benzo[1,4]dioxin-6-yl, or 7-fluoro-4-methyl-3,4-dihydro-2H-benzo[1,4]oxazin-6-yl.
or said fragment represents a group selected from the following groups e) and f):
e) 7-methyl-benzothiophen-6-yl, 4-fluoro-benzothiophen-5-yl, 7-chloro-benzothiophen-5-yl, or 7-fluoro-6-methoxy-benzothiophen-5-yl; and
f) 7-ethynyl-2,3-dihydro-benzo[1,4]dioxin-6-yl, 7-methoxy-5-methyl-2,3-dihydro-benzo[1,4]dioxin-6-yl, or 7-difluoromethoxy-2,3-dihydro-benzo[1,4]dioxin-6-yl;
wherein the above groups a) to d), and, respectively, the above groups e) and f) form a particular sub-embodiment.

21) The invention, thus, relates to compounds of the formula (I) as defined in embodiment 1) for use according to embodiment 1), or to such compounds further limited by the characteristics of any one of embodiments 2) to 20), under consideration of their respective dependencies; to pharmaceutically acceptable salts thereof; and to the use of such compounds according to embodiment 1), and as further described herein below. For avoidance of any doubt, especially the following embodiments relating to the compounds of formula (I) are thus possible and intended and herewith specifically disclosed in individualized form:
1, 2+1, 12+1, 12+2+1, 15+1, 15+2+1, 16+1, 16+2+1, 19+1, 19+2+1, 19+15+1, 19+15+2+1, 19+16+1, 19+16+2+1, 20+1, 20+2+1, 20+15+1, 20+15+2+1, 20+16+1, 20+16+2+1

In the list above the numbers refer to the embodiments according to their numbering provided hereinabove whereas "+" indicates the dependency from another embodiment. The different individualized embodiments are separated by commas. In other words, "20+16+2+1" for example refers to embodiment 20) depending on embodiment 16), depending on embodiment 2), depending on embodiment 1), i.e. embodiment "20+16+2+1" corresponds to the compounds of formula (I) as defined in embodiment 1) for use according to embodiment 1), further limited by all the structural features of the embodiments 2), 16), and 20).

22) The invention, thus, further relates to compounds of the formula (II) as defined in embodiment 8), or to such compounds further limited by the characteristics of any one of embodiments 9) to 20), under consideration of their respective dependencies; to pharmaceutically acceptable salts thereof; and to the use of such compounds as medicaments especially in the prevention/prophylaxis or treatment of diseases which respond to the blockage of the EP2 receptors and/or the EP4 receptors as described herein below. For avoidance of any doubt, especially the following embodiments relating to the compounds of formula (II) are thus possible and intended and herewith specifically disclosed in individualized form:

8, 9+8, 11+8, 11+9+8, 12+8, 12+9+8, 13+8, 13+9+8, 14+8, 14+9+8, 15+8, 15+9+8, 16+8, 16+9+8, 17+8, 17+9+8, 17+11+8, 17+11+9+8, 17+12+8, 17+12+9+8, 17+13+8, 17+13+9+8, 17+14+8, 17+14+9+8, 18+8, 18+9+8, 18+11+8, 18+11+9+8, 18+12+8, 18+12+9+8, 18+13+8, 18+13+9+8, 18+14+8, 18+14+9+8, 19+8, 19+9+8, 19+15+8, 19+15+9+8, 19+16+8, 19+16+9+8, 20+8, 20+9+8, 20+15+8, 20+15+9+8, 20+16+8, 20+16+9+8.

In the list above the numbers refer to the embodiments according to their numbering provided hereinabove whereas "+" indicates the dependency from another embodiment. The different individualized embodiments are separated by commas. In other words, "20+16+9+8" for example refers to embodiment 20) depending on embodiment 16), depending on embodiment 9), depending on embodiment 8), i.e. embodiment "20+16+9+8" corresponds to the compounds of formula (II) according to embodiment 8) further limited by all the features of the embodiments 9), 16), and 20).

23) A third aspect of the invention relates to compounds of the formula (III)

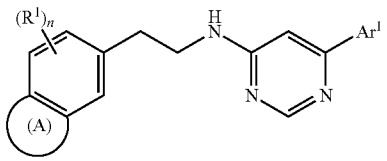

Formula (III)

wherein in compounds of the formula (III) the fragment

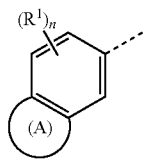

represents a group selected from benzofuranyl, benzothiophenyl, benzothiazolyl, benzoisothiazolyl, indolyl, indazolyl, naphthyl, quinolinyl, and isoquinolinyl; which group independently is unsubstituted or substituted with $(R^1)_n$; wherein $(R^1)_n$ represents one, two, three, or four substituents, wherein said substituents $R^1$ are independently selected from $(C_{1-3})$alkyl (especially methyl), $(C_{2-3})$alkenyl (especially vinyl), $(C_{2-3})$alkynyl (especially ethynyl), $(C_{1-3})$alkoxy (especially methoxy, ethoxy, isopropoxy), halogen (especially fluoro, or chloro), $(C_{1-3})$fluoroalkyl (especially trifluoromethyl), $(C_{1-3})$fluoroalkoxy (especially trifluoromethoxy, difluoromethoxy), cyano, or —$NR^{N7}R^{N8}$ wherein $R^{N7}$ and $R^{N8}$ independently represent hydrogen or $(C_{1-4})$alkyl (especially methyl); or a group selected from 2,3-dihydro-benzo[b]thiophenyl, benzo[1,3]dioxolyl, 1,3-dihydro-isobenzofuranyl, 2,3-dihydro-benzofuranyl, indanyl, 5,6,7,8-tetrahydro-naphthalenyl, 2,3-dihydro-benzo[1,4]dioxinyl, chromanyl, 3,4-dihydro-2H-benzo[1,4]oxazinyl, 1,2,3,4-tetrahydro-quinolinyl, and 3,4-dihydro-2H-benzo[b][1,4]dioxepinyl; which group independently is unsubstituted, or substituted with $(R^1)_n$; wherein $(R^1)_n$ represents one, two, or three substituents, wherein said substituents $R^1$ are independently selected from $(C_{1-3})$alkyl (especially methyl), $(C_{1-3})$alkoxy (especially methoxy, ethoxy, isopropoxy), halogen (especially fluoro, or chloro), —S—$(C_{1-3})$alkyl (especially methylsulfanyl), $(C_{1-3})$fluoroalkyl (especially trifluoromethyl), $(C_{1-3})$fluoroalkoxy (especially trifluoromethoxy, difluoromethoxy), cyano, or oxo;

and $Ar^1$ represents a phenyl group of the structure (Ar-I):

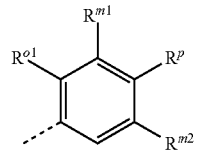

(Ar-I)

wherein $R^P$ represents $X^1$—CO—$R^{O1}$, wherein $X^1$ represents a direct bond, $(C_{1-3})$alkylene (especially —$CH_2$—, —$CH(CH_3)$—, —$C(CH_3)_2$—, —$CH_2$—$CH_2$—), —O—$(C_{1-3})$alkylene-* (especially —O—$CH_2$—*, —O—$CH(CH_3)$—*, —O—$C(CH_3)_2$—*, —O—$CH_2$—$CH_2$—*), —NH—$(C_{1-3})$alkylene* (especially —NH—$CH_2$*, —NH—$CH(CH_3)$—*), —CH=CH—, —NH—CO—*, or $(C_{3-5})$cycloalkylene; wherein the asterisks indicate the bond that is linked to the —CO—$R^{O1}$ group; and $R^{O1}$ represents
-OH;
-O—$(C_{1-4})$alkyl (especially ethoxy, methoxy);
—NH—$SO_2$—$R^{S3}$ wherein $R^{S3}$ represents $(C_{1-4})$alkyl, $(C_{3-6})$cycloalkyl wherein the $(C_{3-6})$cycloalkyl optionally contains a ring oxygen atom, $(C_{3-6})$cycloalkyl-$(C_{1-3})$alkylene wherein the $(C_{3-6})$cycloalkyl optionally contains a ring oxygen atom, $(C_{1-3})$fluoroalkyl, or —$NH_2$;

[wherein in particular such group —$X^1$—CO—$R^{O1}$ represents —COOH, —CO—O—$CH_3$, —CO—O—$C_2H_5$, —O—$CH_2$—COOH, —O—CH($CH_3$)—COOH, —O—C($CH_3$)$_2$—COOH, —O—$CH_2$—$CH_2$—COOH, —NH—$CH_2$—COOH, —NH—$CH_2$—CO—O—$CH_3$, —NH—CH($CH_3$)—COOH, —CO—NH—$SO_2$—$CH_3$, —CO—NH—$SO_2$—C($CH_3$)$_2$, —CO—NH—$SO_2$-cyclopropyl, —CO—NH—$SO_2$—$C_2H_5$, —CO—NH—$SO_2$—$NH_2$, —$CH_2$—COOH, —$CH_2$—CO—O—$CH_3$, —$CH_2$—CO—O—$C_2H_5$, —$CH_2$—$CH_2$—COOH, —CH=CH—COOH, —NH—CO—COOH, 1-carboxy-cyclopropan-1-yl];

$HET^1$, wherein $HET^1$ represents 5-oxo-4,5-dihydro-[1,2,4]oxadiazol-3-yl (encompassing its tautomeric form 5-hydroxy-[1,2,4]oxadiazol-3-yl), or 3-oxo-2,3-dihydro-[1,2,4]oxadiazol-5-yl (encompassing its tautomeric form 3-hydroxy-[1,2,4]oxadiazol-5-yl); or HET, wherein HET represents a 5-membered heteroaryl selected from oxazolyl, isoxazolyl, oxadiazolyl, thiazolyl, isothiazolyl, thiadiazolyl, imidazolyl, pyrazolyl, triazolyl, or tetrazolyl; in particular isoxazolyl, oxadiazolyl and tetrazolyl, wherein said 5-membered heteroaryl is unsubstituted, or mono-substituted with —COOH, hydroxy, hydroxy-$(C_{1-3})$alkyl (especially hydroxymethyl), or —NR$^{N9}$R$^{N10}$ wherein R$^{N9}$ and R$^{N10}$ independently represent hydrogen, $(C_{1-3})$alkyl (especially methyl), or hydroxy-$(C_{2-4})$alkyl (especially 2-hydroxy-ethyl); [in particular HET is unsubstituted or mono-substituted with hydroxy; especially HET is 1H-tetrazol-5-yl, 3-hydroxy-isoxazol-5-yl, or 2-hydroxy-[1,3,4]oxadiazol-4-yl];

R$^{m1}$ represents
- $(C_{1-6})$alkyl (especially methyl, ethyl, n-propyl, isopropyl, n-butyl, isobutyl);
- $(C_{1-4})$alkoxy (especially methoxy, ethoxy, n-propoxy, isopropoxy, n-butoxy, isobutoxy);
- $(C_{1-3})$fluoroalkyl (especially trifluoromethyl);
- $(C_{1-3})$fluoroalkoxy (especially difluoromethoxy, trifluoromethoxy, 2,2,2-trifluoroethoxy);
- halogen (especially fluoro or chloro);
- $(C_{3-6})$cycloalkyl (especially cyclopropyl);
- $(C_{3-6})$cycloalkyl-oxy (especially cyclopropyl-oxy, cyclobutyl-oxy, cyclopentyl-oxy);
- hydroxy-$(C_{2-4})$alkoxy (especially 2-hydroxy-ethoxy); or
- —S—R$^{S2}$ wherein R$^{S2}$ represents $(C_{1-4})$alkyl (especially methyl, ethyl, n-propyl, isopropyl, isobutyl), or $(C_{3-6})$cycloalkyl optionally containing one ring oxygen atom (especially cyclobutyl, oxetan-3-yl);

R$^{m2}$ represents hydrogen, methyl, fluoro, or chloro; and R$^{o1}$ represents hydrogen;

or Ar$^1$ represents a 5-membered heteroaryl group of the structure (Ar-II):

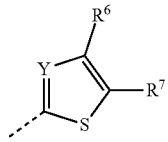

(Ar-II)

wherein
Y represents CH or N;
R$^7$ represents
—X$^1$—CO—R$^{O1}$, wherein
X$^1$ represents a direct bond, $(C_{1-3})$alkylene (especially —CH$_2$—, —CH(CH$_3$)—, —C(CH$_3$)$_2$—, —CH$_2$—CH$_2$—), —O—$(C_{1-3})$alkylene-* (especially —O—CH$_2$—*, —O—CH(CH$_3$)—*, —O—C(CH$_3$)$_2$—*, —O—CH$_2$—CH$_2$—*), —NH—$(C_{1-3})$alkylene* (especially —NH—CH$_2$*, —NH—CH(CH$_3$)—*), —S—CH$_2$*, —CF$_2$—, —CH═CH—, —NH—CO—*, —CO—, or $(C_{3-5})$cycloalkylene; wherein the asterisks indicate the bond that is linked to the —CO—R$^{O1}$ group; and R$^{O1}$ represents
-OH;
-O—$(C_{1-4})$alkyl (especially ethoxy, methoxy);
—NH—SO$_2$—R$^{S3}$ wherein R$^{S3}$ represents $(C_{1-4})$alkyl, $(C_{3-6})$cycloalkyl wherein the $(C_{3-6})$ cycloalkyl optionally contains a ring oxygen atom, $(C_{3-6})$cycloalkyl-$(C_{1-3})$alkylene wherein the $(C_{3-6})$cycloalkyl optionally contains a ring oxygen atom, $(C_{1-3})$fluoroalkyl, or —NH$_2$;
[wherein in particular such group —X$^1$—CO—R$^{O1}$ represents —COOH, —CO—O—CH$_3$, —CO—O—C$_2$H$_5$, —O—CH$_2$—COOH, —O—CH(CH$_3$)—COOH, —O—C(CH$_3$)$_2$—COOH, —O—CH$_2$—CH$_2$—COOH, —NH—CH$_2$—COOH, —NH—CH$_2$—CO—O—CH$_3$, —NH—CH(CH$_3$)—COOH, —CO—NH—SO$_2$—CH$_3$, —CO—NH—SO$_2$—C(CH$_3$)$_2$, —CO—NH—SO$_2$-cyclopropyl, —CO—NH—SO$_2$—C$_2$H$_5$, —CO—NH—SO$_2$—NH$_2$, —CH$_2$—OOH, —CH$_2$—CO—O—CH$_3$, —CH$_2$—CO—O—C$_2$H$_5$, —CH$_2$—CH$_2$—OOH, —CH═CH—OOH, —NH—CO—OOH, 1-carboxy-cyclopropan-1-yl];

HET$^1$, wherein HET$^1$ represents 5-oxo-4,5-dihydro-[1,2,4]oxadiazol-3-yl (encompassing its tautomeric form 5-hydroxy-[1,2,4]oxadiazol-3-yl), or 3-oxo-2,3-dihydro-[1,2,4]oxadiazol-5-yl (encompassing its tautomeric form 3-hydroxy-[1,2,4]oxadiazol-5-yl); or HET, wherein HET represents a 5-membered heteroaryl selected from oxazolyl, isoxazolyl, oxadiazolyl, thiazolyl, isothiazolyl, thiadiazolyl, imidazolyl, pyrazolyl, triazolyl, or tetrazolyl; in particular isoxazolyl, oxadiazolyl and tetrazolyl, wherein said 5-membered heteroaryl is unsubstituted, or mono-substituted with —COOH, hydroxy, hydroxy-$(C_{1-3})$alkyl (especially hydroxymethyl), or —NR$^{N9}$R$^{N10}$ wherein R$^{N9}$ and R$^{N10}$ independently represent hydrogen, $(C_{1-3})$alkyl (especially methyl), or hydroxy-$(C_{2-4})$alkyl (especially 2-hydroxy-ethyl); [in particular HET is unsubstituted or mono-substituted with hydroxy; especially HET is 1H-tetrazol-5-yl, 3-hydroxy-isoxazol-5-yl, or 2-hydroxy-[1,3,4]oxadiazol-4-yl];

R$^6$ represents
- $(C_{1-6})$alkyl (especially methyl, ethyl, n-propyl, isopropyl, n-butyl, isobutyl);
- $(C_{1-4})$alkoxy (especially methoxy, ethoxy, n-propoxy, isopropoxy, n-butoxy);
- $(C_{1-3})$fluoroalkyl (especially trifluoromethyl);
- $(C_{1-3})$fluoroalkoxy (especially difluoromethoxy, trifluoromethoxy, 2,2,2-trifluoroethoxy);
- halogen (especially fluoro or chloro);
- $(C_{3-6})$cycloalkyl (especially cyclopropyl);
- $(C_{3-6})$cycloalkyl-oxy (especially cyclopropyl-oxy, cyclobutyl-oxy, cyclopentyl-oxy);
- hydroxy-$(C_{2-4})$alkoxy (especially 2-hydroxy-ethoxy); or
- —S—R$^{S2}$ wherein R$^{S2}$ represents $(C_{1-4})$alkyl (especially methyl, ethyl, n-propyl, isopropyl, isobutyl), or $(C_{3-6})$cycloalkyl optionally containing one ring oxygen atom (especially cyclobutyl, oxetan-3-yl).

24) Another embodiment relates to compounds of formula (I) as defined in embodiment 1) for use according to embodiment 1) which are selected from the following compounds:

[2-(5,7-Difluoro-quinolin-6-yl)-ethyl]-(6-quinolin-6-yl-py-rimidin-4-yl)-amine;

[2-(1H-Indol-6-yl)-ethyl]-[6-(1H-indol-5-yl)-pyrimidin-4-yl]-amine;

[2-(1H-Indol-6-yl)-ethyl]-[6-(1H-indol-6-yl)-pyrimidin-4-yl]-amine;

5-{6-[2-(1H-Indol-6-yl)-ethylamino]-pyrimidin-4-yl}-thio-phene-2-carboxylic acid amide;

[2-(5,7-Difluoro-quinolin-6-yl)-ethyl]-(6-isoquinolin-6-yl-pyrimidin-4-yl)-amine; and

[2-(5,7-Difluoro-quinolin-6-yl)-ethyl]-[6-(1H-indol-5-yl)-pyrimidin-4-yl]-amine.

25) Another embodiment relates to compounds of formula (II) according to embodiment 8), which are selected from the following compounds:

3-Ethoxy-5-{6-[2-(3-methoxy-1-methyl-naphthalen-2-yl)-ethylamino]-pyrimidin-4-yl}-thiophene-2-carboxylic acid;

5-{6-[2-(3-Cyano-1-methyl-naphthalen-2-yl)-ethylamino]-pyrimidin-4-yl}-3-ethoxy-thiophene-2-carboxylic acid;

3-Ethoxy-5-{6-[2-(1-fluoro-3-methoxy-naphthalen-2-yl)-ethylamino]-pyrimidin-4-yl}-thiophene-2-carboxylic acid;

3-Ethoxy-5-{6-[2-(6-methoxy-benzo[b]thiophen-5-yl)-ethylamino]-pyrimidin-4-yl}-thiophene-2-carboxylic acid;

5-[6-(2-Benzo[b]thiophen-5-yl-ethylamino)-pyrimidin-4-yl]-3-ethoxy-thiophene-2-carboxylic acid;

5-{6-[2-(7-Cyano-2,3-dihydro-benzo[1,4]dioxin-6-yl)-ethylamino]-pyrimidin-4-yl}-3-ethoxy-thiophene-2-carboxylic acid;

3-Ethoxy-5-{6-[2-(1-methyl-naphthalen-2-yl)-ethylamino]-pyrimidin-4-yl}-thiophene-2-carboxylic acid;

3-Ethoxy-5-{6-[2-(6-methoxy-4-methyl-benzofuran-5-yl)-ethylamino]-pyrimidin-4-yl}-thiophene-2-carboxylic acid;

3-Ethoxy-5-{6-[2-(3-methoxy-naphthalen-2-yl)-ethyl-amino]-pyrimidin-4-yl}-thiophene-2-carboxylic acid;

5-[6-(2-Benzo[b]thiophen-6-yl-ethylamino)-pyrimidin-4-yl]-3-ethoxy-thiophene-2-carboxylic acid;

3-Ethoxy-5-{6-[2-(6-methoxy-benzofuran-5-yl)-ethyl-amino]-pyrimidin-4-yl}-thiophene-2-carboxylic acid;

3-Ethoxy-5-{6-[2-(6-fluoro-benzofuran-5-yl)-ethylamino]-pyrimidin-4-yl}-thiophene-2-carboxylic acid;

3-Ethoxy-5-{6-[2-(5-methoxy-benzo[b]thiophen-6-yl)-ethylamino]-pyrimidin-4-yl}-thiophene-2-carboxylic acid;

5-{6-[2-(2,3-Dihydro-benzo[b]thiophen-5-yl)-ethylamino]-pyrimidin-4-yl}-3-ethoxy-thiophene-2-carboxylic acid;

3-Ethoxy-5-{6-[2-(1-ethynyl-naphthalen-2-yl)-ethyl-amino]-pyrimidin-4-yl}-thiophene-2-carboxylic acid;

4-{6-[2-(6-Methoxy-benzo[b]thiophen-5-yl)-ethylamino]-pyrimidin-4-yl}-2-methylsulfanyl-benzoic acid;

3-Ethoxy-5-{6-[2-(4-methyl-benzo[b]thiophen-5-yl)-ethyl-amino]-pyrimidin-4-yl}-thiophene-2-carboxylic acid;

3-Ethoxy-5-{6-[2-(3-ethoxy-naphthalen-2-yl)-ethylamino]-pyrimidin-4-yl}-thiophene-2-carboxylic acid;

3-Ethoxy-5-{6-[2-(1H-indol-6-yl)-ethylamino]-pyrimidin-4-yl}-thiophene-2-carboxylic acid;

2-Cyclobutoxy-4-{6-[2-(1-fluoro-3-methoxy-naphthalen-2-yl)-ethylamino]-pyrimidin-4-yl}-benzoic acid;

3-Ethoxy-5-{6-[2-(7-methoxy-2,3-dihydro-benzo[1,4]di-oxin-6-yl)-ethylamino]-pyrimidin-4-yl}-thiophene-2-car-boxylic acid;

5-{6-[2-(3-Cyano-benzo[b]thiophen-5-yl)-ethylamino]-py-rimidin-4-yl}-3-ethoxy-thiophene-2-carboxylic acid;

4-{6-[2-(1-Methyl-naphthalen-2-yl)-ethylamino]-pyrimi-din-4-yl}-2-propyl-benzoic acid;

4-{6-[2-(1-Fluoro-3-methoxy-naphthalen-2-yl)-ethyl-amino]-pyrimidin-4-yl}-2-methylsulfanyl-benzoic acid;

3-Ethoxy-5-{6-[2-(7-methyl-2,3-dihydro-benzo[1,4]dioxin-6-yl)-ethylamino]-pyrimidin-4-yl}-thiophene-2-carbox-ylic acid;

3-Ethoxy-5-{6-[2-(1H-indol-5-yl)-ethylamino]-pyrimidin-4-yl}-thiophene-2-carboxylic acid;

3-Ethoxy-5-{6-[2-(6-methyl-benzo[b]thiophen-5-yl)-ethyl-amino]-pyrimidin-4-yl}-thiophene-2-carboxylic acid;

3-Ethoxy-5-{6-[2-(8-fluoro-2,3-dihydro-benzo[1,4]dioxin-6-yl)-ethylamino]-pyrimidin-4-yl}-thiophene-2-carbox-ylic acid;

5-[6-(2-Benzo[b]thiophen-5-yl-ethylamino)-pyrimidin-4-yl]-benzofuran-2-carboxylic acid;

3-Ethoxy-5-{6-[2-(7-ethoxy-2,3-dihydro-benzo[1,4]dioxin-6-yl)-ethylamino]-pyrimidin-4-yl}-thiophene-2-carbox-ylic acid;

5-{6-[2-(2,3-Dihydro-benzo[1,4]dioxin-6-yl)-ethylamino]-pyrimidin-4-yl}-3-ethoxy-thiophene-2-carboxylic acid;

3-Ethoxy-5-{6-[2-(1-methyl-1H-indol-6-yl)-ethylamino]-pyrimidin-4-yl}-thiophene-2-carboxylic acid;

5-{6-[2-(5,7-Difluoro-quinolin-6-yl)-ethylamino]-pyrimi-din-4-yl}-3-ethoxy-thiophene-2-carboxylic acid;

5-{6-[2-(3-Difluoromethoxy-naphthalen-2-yl)-ethylamino]-pyrimidin-4-yl}-3-ethoxy-thiophene-2-carboxylic acid;

5-[6-(2-Benzofuran-6-yl-ethylamino)-pyrimidin-4-yl]-3-ethoxy-thiophene-2-carboxylic acid;

3-Ethoxy-5-{6-[2-(3-methyl-benzo[b]thiophen-5-yl)-ethyl-amino]-pyrimidin-4-yl}-thiophene-2-carboxylic acid;

3-(2-Hydroxy-ethoxy)-5-{6-[2-(1-methyl-naphthalen-2-yl)-ethylamino]-pyrimidin-4-yl}-thiophene-2-carboxylic acid;

3-Ethoxy-5-{6-[2-(6-methoxy-benzo[1,3]dioxol-5-yl)-eth-ylamino]-pyrimidin-4-yl}-thiophene-2-carboxylic acid;

5-[6-(2-Benzofuran-5-yl-ethylamino)-pyrimidin-4-yl]-3-ethoxy-thiophene-2-carboxylic acid;

4-{6-[2-(3-Cyano-1-methyl-naphthalen-2-yl)-ethylamino]-pyrimidin-4-yl}-2-methylsulfanyl-benzoic acid;

(2-Ethoxy-4-{6-[2-(6-ethoxy-benzo[b]thiophen-5-yl)-ethyl-amino]-pyrimidin-4-yl}-phenoxy)-acetic acid;

5-[6-(2-Chroman-6-yl-ethylamino)-pyrimidin-4-yl]-3-ethoxy-thiophene-2-carboxylic acid;

3-(3-Ethoxy-5-{6-[2-(1-methyl-naphthalen-2-yl)-ethyl-amino]-pyrimidin-4-yl}-thiophen-2-yl)-propionic acid;

4-{6-[2-(3-Methoxy-1-methyl-naphthalen-2-yl)-ethyl-amino]-pyrimidin-4-yl}-2-methylsulfanyl-benzoic acid;

2-Cyclobutoxy-4-{6-[2-(6-methoxy-benzo[b]thiophen-5-yl)-ethylamino]-pyrimidin-4-yl}-benzoic acid;

5-{6-[2-(6-Cyano-benzo[1,3]dioxol-5-yl)-ethylamino]-py-rimidin-4-yl}-3-ethoxy-thiophene-2-carboxylic acid;

5-{6-[2-(2,3-Dihydro-benzofuran-6-yl)-ethylamino]-py-rimidin-4-yl}-3-ethoxy-thiophene-2-carboxylic acid;

2-Ethoxy-4-{6-[2-(3-methoxy-1-methyl-naphthalen-2-yl)-ethylamino]-pyrimidin-4-yl}-benzoic acid;

2-Fluoro-4-{6-[2-(1-methyl-naphthalen-2-yl)-ethylamino]-pyrimidin-4-yl}-6-propyl-benzoic acid;

4-{6-[2-(6-Cyano-benzo[b]thiophen-5-yl)-ethylamino]-py-rimidin-4-yl}-2-methylsulfanyl-benzoic acid;

2-Cyclobutoxy-4-{6-[2-(3-methoxy-1-methyl-naphthalen-2-yl)-ethylamino]-pyrimidin-4-yl}-benzoic acid;

(2-Ethoxy-4-{6-[2-(6-methoxy-benzo[b]thiophen-5-yl)-eth-ylamino]-pyrimidin-4-yl}-phenoxy)-acetic acid;

6-{6-[2-(7-Methoxy-2,3-dihydro-benzo[1,4]dioxin-6-yl)-ethylamino]-pyrimidin-4-yl}-benzofuran-2-carboxylic acid;

2-Difluoromethoxy-4-{6-[2-(1-methyl-naphthalen-2-yl)-ethylamino]-pyrimidin-4-yl}-benzoic acid;

6-[6-(2-Benzo[b]thiophen-5-yl-ethylamino)-pyrimidin-4-yl]-benzofuran-2-carboxylic acid;
5-{6-[2-(7-Chloro-8-methyl-quinolin-6-yl)-ethylamino]-pyrimidin-4-yl}-3-ethoxy-thiophene-2-carboxylic acid;
5-[6-(2-Benzothiazol-5-yl-ethylamino)-pyrimidin-4-yl]-3-ethoxy-thiophene-2-carboxylic acid;
5-{6-[2-(7-Methoxy-2,3-dihydro-benzo[1,4]dioxin-6-yl)-ethylamino]-pyrimidin-4-yl}-benzofuran-2-carboxylic acid;
5-[6-(2-Benzo[b]thiophen-5-yl-ethylamino)-2-methyl-pyrimidin-4-yl]-3-ethoxy-thiophene-2-carboxylic acid;
4-{6-[2-(7-Cyano-2,3-dihydro-benzo[1,4]dioxin-6-yl)-ethylamino]-pyrimidin-4-yl}-2-methylsulfanyl-benzoic acid;
(2-Ethoxy-4-{6-[2-(7-ethoxy-2,3-dihydro-benzo[1,4]dioxin-6-yl)-ethylamino]-pyrimidin-4-yl}-phenoxy)-acetic acid;
2-Cyclobutoxy-4-{6-[2-(6-methoxy-benzofuran-5-yl)-ethylamino]-pyrimidin-4-yl}-benzoic acid;
2-Ethoxy-4-{6-[2-(1-fluoro-3-methoxy-naphthalen-2-yl)-ethylamino]-pyrimidin-4-yl}-benzoic acid;
(2-Ethoxy-4-{6-[2-(6-methoxy-4-methyl-benzofuran-5-yl)-ethylamino]-pyrimidin-4-yl}-phenoxy)-acetic acid;
(2-Ethoxy-4-{6-[2-(3-ethynyl-naphthalen-2-yl)-ethylamino]-pyrimidin-4-yl}-phenoxy)-acetic acid;
3-Ethoxy-5-{6-[2-(7-fluoro-4-methyl-3,4-dihydro-2H-benzo[1,4]oxazin-6-yl)-ethylamino]-pyrimidin-4-yl}-thiophene-2-carboxylic acid;
2-Ethoxy-4-{6-[2-(3-ethynyl-naphthalen-2-yl)-ethylamino]-pyrimidin-4-yl}-benzoic acid;
2-Ethoxy-4-{6-[2-(6-methoxy-benzo[b]thiophen-5-yl)-ethylamino]-pyrimidin-4-yl}-benzoic acid;
2-Ethylsulfanyl-4-{6-[2-(7-methoxy-2,3-dihydro-benzo[1,4]dioxin-6-yl)-ethylamino]-pyrimidin-4-yl}-benzoic acid;
5-[6-(2-Benzo[1,3]dioxol-5-yl-ethylamino)-pyrimidin-4-yl]-3-ethoxy-thiophene-2-carboxylic acid;
(2-Ethoxy-4-{6-[2-(6-methoxy-benzofuran-5-yl)-ethylamino]-pyrimidin-4-yl}-phenoxy)-acetic acid;
4-{6-[2-(7-Methoxy-2,3-dihydro-benzo[1,4]dioxin-6-yl)-ethylamino]-pyrimidin-4-yl}-2-methylsulfanyl-benzoic acid;
5-{6-[2-(7-Chloro-8-fluoro-quinolin-6-yl)-ethylamino]-pyrimidin-4-yl}-3-ethoxy-thiophene-2-carboxylic acid;
(2-Ethoxy-4-{6-[2-(6-methoxy-benzo[b]thiophen-5-yl)-ethylamino]-pyrimidin-4-yl}-phenyl)-acetic acid;
5-{6-[2-(6-Difluoromethoxy-benzo[1,3]dioxol-5-yl)-ethylamino]-pyrimidin-4-yl}-3-ethoxy-thiophene-2-carboxylic acid;
(2-Ethoxy-4-{6-[2-(7-methoxy-2,3-dihydro-benzo[1,4]dioxin-6-yl)-ethylamino]-pyrimidin-4-yl}-phenoxy)-acetic acid;
2-Cyclobutoxy-4-{6-[2-(5-methoxy-benzofuran-6-yl)-ethylamino]-pyrimidin-4-yl}-benzoic acid;
4-[6-(2-Benzo[b]thiophen-5-yl-ethylamino)-pyrimidin-4-yl]-2-cyclobutoxy-benzoic acid;
2-Ethoxy-4-{6-[2-(6-ethoxy-benzo[b]thiophen-5-yl)-ethylamino]-pyrimidin-4-yl}-benzoic acid;
2-{6-[2-(1-Methyl-naphthalen-2-yl)-ethylamino]-pyrimidin-4-yl}-1H-indole-4-carboxylic acid;
4-{6-[2-(6-Cyano-benzo[b]thiophen-5-yl)-ethylamino]-pyrimidin-4-yl}-2-ethoxy-benzoic acid;
4-[6-(2-Benzo[b]thiophen-5-yl-ethylamino)-pyrimidin-4-yl]-2-methylsulfanyl-benzoic acid;
5-[6-(2-Benzo[d]isothiazol-5-yl-ethylamino)-pyrimidin-4-yl]-3-ethoxy-thiophene-2-carboxylic acid;
4-{6-[2-(7-Ethoxy-2,3-dihydro-benzo[1,4]dioxin-6-yl)-ethylamino]-pyrimidin-4-yl}-2-methylsulfanyl-benzoic acid;
4-{6-[2-(2,3-Dihydro-benzo[b]thiophen-5-yl)-ethylamino]-pyrimidin-4-yl}-2-methylsulfanyl-benzoic acid;
(2-Ethoxy-4-{6-[2-(6-methoxy-benzofuran-5-yl)-ethylamino]-pyrimidin-4-yl}-phenyl)-acetic acid;
(2-Ethoxy-4-{6-[2-(6-fluoro-benzofuran-5-yl)-ethylamino]-pyrimidin-4-yl}-phenoxy)-acetic acid;
5-[6-(2-Benzooxazol-6-yl-ethylamino)-pyrimidin-4-yl]-3-ethoxy-thiophene-2-carboxylic acid;
(3-Ethoxy-5-{6-[2-(1-methyl-naphthalen-2-yl)-ethylamino]-pyrimidin-4-yl}-thiophen-2-yl)-acetic acid;
2-Ethoxy-4-{6-[2-(6-methoxy-benzofuran-5-yl)-ethylamino]-pyrimidin-4-yl}-benzoic acid;
4-{6-[2-(5-Methoxy-benzo[b]thiophen-6-yl)-ethylamino]-pyrimidin-4-yl}-2-methylsulfanyl-benzoic acid;
4-[6-(2-Benzo[b]thiophen-5-yl-ethylamino)-pyrimidin-4-yl]-2-ethoxy-benzoic acid;
(2-Ethoxy-4-{6-[2-(6-methoxy-4-methyl-benzofuran-5-yl)-ethylamino]-pyrimidin-4-yl}-phenyl)-acetic acid;
2-Ethylsulfanyl-4-{6-[2-(6-methoxy-benzofuran-5-yl)-ethylamino]-pyrimidin-4-yl}-benzoic acid;
(2-Ethoxy-4-{6-[2-(5-methoxy-benzofuran-6-yl)-ethylamino]-pyrimidin-4-yl}-phenoxy)-acetic acid;
(2-Ethoxy-4-{6-[2-(3-ethoxy-naphthalen-2-yl)-ethylamino]-pyrimidin-4-yl}-phenoxy)-acetic acid;
5-{6-[2-(1,3-Dihydro-isobenzofuran-5-yl)-ethylamino]-pyrimidin-4-yl}-3-ethoxy-thiophene-2-carboxylic acid;
2-Butoxy-4-{6-[2-(1-methyl-naphthalen-2-yl)-ethylamino]-pyrimidin-4-yl}-benzoic acid;
2-Cyclobutoxy-4-{6-[2-(2,3-dihydro-benzo[b]thiophen-5-yl)-ethylamino]-pyrimidin-4-yl}-benzoic acid;
2-Cyclobutoxy-4-{6-[2-(3-ethoxy-naphthalen-2-yl)-ethylamino]-pyrimidin-4-yl}-benzoic acid;
2-Ethoxy-4-{6-[2-(1-methyl-naphthalen-2-yl)-ethylamino]-pyrimidin-4-yl}-benzoic acid;
5-{6-[2-(4-Chloro-7-methyl-quinolin-6-yl)-ethylamino]-pyrimidin-4-yl}-3-ethoxy-thiophene-2-carboxylic acid;
4-{6-[2-(1-Methyl-naphthalen-2-yl)-ethylamino]-pyrimidin-4-yl}-2-propoxy-benzoic acid;
(2-Ethoxy-4-{6-[2-(7-methyl-2,3-dihydro-benzo[1,4]dioxin-6-yl)-ethylamino]-pyrimidin-4-yl}-phenoxy)-acetic acid;
3-(3-Ethoxy-5-{6-[2-(1H-indol-5-yl)-ethylamino]-pyrimidin-4-yl}-thiophen-2-yl)-[1,2,4]oxadiazol-5(4H)-one [tautomeric form: 3-(5-(6-((2-(1H-indol-5-yl)ethyl)amino)pyrimidin-4-yl)-3-ethoxythiophen-2-yl)-[1,2,4]oxadiazol-5-ol];
3-{5-[6-(2-Benzo[b]thiophen-5-yl-ethylamino)-pyrimidin-4-yl]-3-ethoxy-thiophen-2-yl}-[1,2,4]oxadiazol-5(4H)-one [tautomeric form: 3-(5-(6-((2-(benzo[b]thiophen-5-yl)ethyl)amino)pyrimidin-4-yl)-3-ethoxythiophen-2-yl)-[1,2,4]oxadiazol-5-ol];
3-(3-Ethoxy-5-{6-[2-(7-methyl-2,3-dihydro-benzo[1,4]dioxin-6-yl)-ethylamino]-pyrimidin-4-yl}-thiophen-2-yl)-[1,2,4]oxadiazol-5(4H)-one [tautomeric form: 3-(3-ethoxy-5-(6-((2-(7-methyl-2,3-dihydrobenzo[b][1,4]dioxin-6-yl)ethyl)amino)pyrimidin-4-yl)thiophen-2-yl)-[1,2,4]oxadiazol-5-ol];
3-(3-Ethoxy-5-{6-[2-(6-methoxy-benzo[b]thiophen-5-yl)-ethylamino]-pyrimidin-4-yl}-thiophen-2-yl)-[1,2,4]oxadiazol-5(4H)-one [tautomeric form: 3-(3-ethoxy-5-(6-((2-(6-methoxybenzo[b]thiophen-5-yl)ethyl)amino)pyrimidin-4-yl)thiophen-2-yl)-[1,2,4]oxadiazol-5-ol];

3-(3-Ethoxy-5-{6-[2-(1H-indol-6-yl)-ethylamino]-pyrimidin-4-yl}-thiophen-2-yl)-[1,2,4]oxadiazol-5(4H)-one

[tautomeric form: 3-(5-(6-((2-(1H-indol-6-yl)ethyl)amino)pyrimidin-4-yl)-3-ethoxythiophen-2-yl)-[1,2,4]oxadiazol-5-ol];

3-{5-[6-(2-Benzo[1,3]dioxol-5-yl-ethylamino)-pyrimidin-4-yl]-3-ethoxy-thiophen-2-yl}-[1,2,4]oxadiazol-5(4H)-one

[tautomeric form: 3-(5-(6-((2-(benzo[d][1,3]dioxol-5-yl)ethyl)amino)pyrimidin-4-yl)-3-ethoxythiophen-2-yl)-[1,2,4]oxadiazol-5-ol];

3-(3-Ethoxy-5-{6-[2-(7-fluoro-quinolin-6-yl)-ethylamino]-pyrimidin-4-yl}-thiophen-2-yl)-[1,2,4]oxadiazol-5(4H)-one

[tautomeric form: 3-(3-ethoxy-5-(6-((2-(7-fluoroquinolin-6-yl)ethyl)amino)pyrimidin-4-yl)thiophen-2-yl)-[1,2,4]oxadiazol-5-ol];

{6-[4-Ethoxy-5-(1H-tetrazol-5-yl)-thiophen-2-yl]-pyrimidin-4-yl}-[2-(7-fluoro-quinolin-6-yl)-ethyl]-amine;

4-Ethoxy-2-{6-[2-(1-methyl-naphthalen-2-yl)-ethylamino]-pyrimidin-4-yl}-thiazole-5-carboxylic acid;

3-(4-Ethoxy-2-{6-[2-(1-methyl-naphthalen-2-yl)-ethylamino]-pyrimidin-4-yl}-thiazol-5-yl)-[1,2,4]oxadiazol-5(4H)-one

[tautomeric form: 3-(4-ethoxy-2-(6-((2-(1-methylnaphthalen-2-yl)ethyl)amino)pyrimidin-4-yl)thiazol-5-yl)-[1,2,4]oxadiazol-5-ol];

3-(4-Ethyl-2-{6-[2-(1-methyl-naphthalen-2-yl)-ethylamino]-pyrimidin-4-yl}-thiazol-5-yl)-[1,2,4]oxadiazol-5(4H)-one

[tautomeric form: 3-(4-ethyl-2-(6-((2-(1-methylnaphthalen-2-yl)ethyl)amino)pyrimidin-4-yl)thiazol-5-yl)-[1,2,4]oxadiazol-5-ol];

3-Ethoxy-5-(6-((2-(1-methylnaphthalen-2-yl)ethyl)amino)pyrimidin-4-yl)-N-sulfamoylthiophene-2-carboxamide; and N-(3-Ethoxy-5-{6-[2-(1-methyl-naphthalen-2-yl)-ethylamino]-pyrimidin-4-yl}-thiophene-2-carbonyl)-methanesulfonamide.

26) In addition to the compounds listed in embodiment 25), further compounds of formula (II) according to embodiment 8), are selected from the following compounds:

2-Cyclobutoxy-4-{6-[2-(7-methoxy-2,3-dihydro-benzo[1,4]dioxin-6-yl)-ethylamino]-pyrimidin-4-yl}-benzoic acid;

4-{6-[2-(6-Methyl-benzo[b]thiophen-5-yl)-ethylamino]-pyrimidin-4-yl}-2-methylsulfanyl-benzoic acid;

(2-Ethoxy-4-{6-[2-(7-ethoxy-2,3-dihydro-benzo[1,4]dioxin-6-yl)-ethylamino]-pyrimidin-4-yl}-phenyl)-acetic acid;

4-{6-[2-(6-Methoxy-benzofuran-5-yl)-ethylamino]-pyrimidin-4-yl}-2-methylsulfanyl-benzoic acid;

2-Cyclobutoxy-4-{6-[2-(7-ethoxy-2,3-dihydro-benzo[1,4]dioxin-6-yl)-ethylamino]-pyrimidin-4-yl}-benzoic acid;

6-{6-[2-(7-Methoxy-2,3-dihydro-benzo[1,4]dioxin-6-yl)-ethylamino]-pyrimidin-4-yl}-benzofuran-3-carboxylic acid;

4-{6-[2-(4-Methyl-benzo[b]thiophen-5-yl)-ethylamino]-pyrimidin-4-yl}-2-methylsulfanyl-benzoic acid;

2-Cyclobutoxy-4-{6-[2-(6-methoxy-4-methyl-benzofuran-5-yl)-ethylamino]-pyrimidin-4-yl}-benzoic acid;

4-{6-[2-(3-Cyano-benzo[b]thiophen-5-yl)-ethylamino]-pyrimidin-4-yl}-2-methylsulfanyl-benzoic acid;

2-Cyclobutoxy-4-{6-[2-(6-methoxy-benzo[1,3]dioxol-5-yl)-ethylamino]-pyrimidin-4-yl}-benzoic acid;

2-Ethoxy-4-{6-[2-(6-methoxy-4-methyl-benzofuran-5-yl)-ethylamino]-pyrimidin-4-yl}-benzoic acid;

(4-{6-[2-(6-Methoxy-benzo[b]thiophen-5-yl)-ethylamino]-pyrimidin-4-yl}-2-methylsulfanyl-phenyl)-acetic acid;

2-Ethoxy-4-{6-[2-(6-fluoro-benzofuran-5-yl)-ethylamino]-pyrimidin-4-yl}-benzoic acid;

2-(2-Ethoxy-4-{6-[2-(6-methoxy-benzofuran-5-yl)-ethylamino]-pyrimidin-4-yl}-phenoxy)-propionic acid;

4-{6-[2-(6-Fluoro-benzofuran-5-yl)-ethylamino]-pyrimidin-4-yl}-2-methylsulfanyl-benzoic acid;

4-[6-(2-Benzofuran-5-yl-ethylamino)-pyrimidin-4-yl]-2-methylsulfanyl-benzoic acid;

4-[6-(2-Benzofuran-6-yl-ethylamino)-pyrimidin-4-yl]-2-methylsulfanyl-benzoic acid;

2-Ethoxy-4-{6-[2-(6-methyl-benzo[b]thiophen-5-yl)-ethylamino]-pyrimidin-4-yl}-benzoic acid;

2-Ethoxy-4-{6-[2-(7-ethoxy-2,3-dihydro-benzo[1,4]dioxin-6-yl)-ethylamino]-pyrimidin-4-yl}-benzoic acid;

2-Cyclobutoxy-4-{6-[2-(4-methyl-benzo[b]thiophen-5-yl)-ethylamino]-pyrimidin-4-yl}-benzoic acid;

4-{6-[2-(6-Methoxy-benzo[b]thiophen-5-yl)-ethylamino]-pyrimidin-4-yl}-benzoic acid;

4-{6-[2-(6-Methoxy-benzo[1,3]dioxol-5-yl)-ethylamino]-pyrimidin-4-yl}-2-methylsulfanyl-benzoic acid;

2-Ethoxy-4-{6-[2-(7-methoxy-2,3-dihydro-benzo[1,4]dioxin-6-yl)-ethylamino]-pyrimidin-4-yl}-benzoic acid;

2-Cyclobutoxy-4-{6-[2-(7-methyl-2,3-dihydro-benzo[1,4]dioxin-6-yl)-ethylamino]-pyrimidin-4-yl}-benzoic acid;

2-Ethoxy-4-{6-[2-(4-methyl-benzo[b]thiophen-5-yl)-ethylamino]-pyrimidin-4-yl}-benzoic acid; and 2-Ethoxy-4-{6-[2-(6-methoxy-benzo[1,3]dioxol-5-yl)-ethylamino]-pyrimidin-4-yl}-benzoic acid.

27) In addition to the compounds listed in embodiments 25) and 26), further compounds of formula (II) according to embodiment 8), are selected from the following compounds:

3-Ethoxy-5-{6-[2-(1-fluoro-naphthalen-2-yl)-ethylamino]-pyrimidin-4-yl}-thiophene-2-carboxylic acid;

3-Ethoxy-5-{6-[2-(6-fluoro-1-methyl-1H-indol-5-yl)-ethylamino]-pyrimidin-4-yl}-thiophene-2-carboxylic acid;

5-{6-[2-(4-Chloro-3-methoxy-naphthalen-2-yl)-ethylamino]-pyrimidin-4-yl}-3-ethoxy-thiophene-2-carboxylic acid;

3-Ethoxy-5-{6-[2-(8-methoxy-3,4-dihydro-2H-benzo[b][1,4]dioxepin-7-yl)-ethylamino]-pyrimidin-4-yl}-thiophene-2-carboxylic acid;

3-Ethoxy-5-{6-[2-(8-methyl-quinolin-7-yl)-ethylamino]-pyrimidin-4-yl}-thiophene-2-carboxylic acid;

3-Ethoxy-5-{6-[2-(3-isopropoxy-naphthalen-2-yl)-ethylamino]-pyrimidin-4-yl}-thiophene-2-carboxylic acid;

5-{6-[2-(1-Cyano-naphthalen-2-yl)-ethylamino]-pyrimidin-4-yl}-3-ethoxy-thiophene-2-carboxylic acid;

3-Ethoxy-5-[6-(2-naphthalen-2-yl-ethylamino)-pyrimidin-4-yl]-thiophene-2-carboxylic acid;

(2-Ethoxy-4-{6-[2-(1-fluoro-3-methoxy-naphthalen-2-yl)-ethylamino]-pyrimidin-4-yl}-phenyl)-acetic acid;

3-Ethoxy-5-{6-[2-(3-methyl-naphthalen-2-yl)-ethylamino]-pyrimidin-4-yl}-thiophene-2-carboxylic acid;

3-Ethoxy-5-[6-(2-indan-5-yl-ethylamino)-pyrimidin-4-yl]-thiophene-2-carboxylic acid;

5-{6-[2-(8-Chloro-2,3-dihydro-benzo[1,4]dioxin-6-yl)-ethylamino]-pyrimidin-4-yl}-3-ethoxy-thiophene-2-carboxylic acid;

4-{6-[2-(3-Cyano-1-methyl-naphthalen-2-yl)-ethylamino]-pyrimidin-4-yl}-2-ethoxy-benzoic acid;

5-{6-[2-(4,5-Difluoro-7-methoxy-2-methyl-benzofuran-6-yl)-ethylamino]-pyrimidin-4-yl}-3-ethoxy-thiophene-2-carboxylic acid;

5-[6-(2-Chroman-7-yl-ethylamino)-pyrimidin-4-yl]-3-ethoxy-thiophene-2-carboxylic acid;

3-Ethoxy-5-{6-[2-(3-methoxy-5,6,7,8-tetrahydro-naphthalen-2-yl)-ethylamino]-pyrimidin-4-yl}-thiophene-2-carboxylic acid;
(2-Ethoxy-4-{6-[2-(3-methoxy-1-methyl-naphthalen-2-yl)-ethylamino]-pyrimidin-4-yl}-phenyl)-acetic acid;
5-{6-[2-(3-Chloro-naphthalen-2-yl)-ethylamino]-pyrimidin-4-yl}-3-ethoxy-thiophene-2-carboxylic acid;
3-Ethoxy-5-{6-[2-(1-methyl-1H-indol-5-yl)-ethylamino]-pyrimidin-4-yl}-thiophene-2-carboxylic acid;
3-Ethoxy-5-{6-[2-(8-fluoro-naphthalen-2-yl)-ethylamino]-pyrimidin-4-yl}-thiophene-2-carboxylic acid;
3-Ethoxy-5-{6-[2-(5-fluoro-quinolin-6-yl)-ethylamino]-pyrimidin-4-yl}-thiophene-2-carboxylic acid;
2-Cyclobutoxy-4-{6-[2-(7-methylsulfanyl-2,3-dihydro-benzo[1,4]dioxin-6-yl)-ethylamino]-pyrimidin-4-yl}-benzoic acid;
5-{6-[2-(1-Amino-naphthalen-2-yl)-ethylamino]-pyrimidin-4-yl}-3-ethoxy-thiophene-2-carboxylic acid;
5-{6-[2-(7-Fluoro-1-methyl-1,2,3,4-tetrahydro-quinolin-6-yl)-ethylamino]-pyrimidin-4-yl}-3-trifluoromethyl-thiophene-2-carboxylic acid;
4-{6-[2-(3-Cyano-1-fluoro-naphthalen-2-yl)-ethylamino]-pyrimidin-4-yl}-2-ethoxy-benzoic acid;
3-Ethoxy-5-{6-[2-(1-vinyl-naphthalen-2-yl)-ethylamino]-pyrimidin-4-yl}-thiophene-2-carboxylic acid;
2-Isobutyl-4-{6-[2-(1-methyl-naphthalen-2-yl)-ethylamino]-pyrimidin-4-yl}-benzoic acid;
3-Ethoxy-5-{6-[2-(7-methylsulfanyl-2,3-dihydro-benzo[1,4]dioxin-6-yl)-ethylamino]-pyrimidin-4-yl}-thiophene-2-carboxylic acid;
(4-{6-[2-(6-Cyano-benzo[b]thiophen-5-yl)-ethylamino]-pyrimidin-4-yl}-2-ethoxy-phenyl)-acetic acid;
(4-{6-[2-(3-Cyano-naphthalen-2-yl)-ethylamino]-pyrimidin-4-yl}-2-ethoxy-phenoxy)-acetic acid;
5-{6-[2-(5,8-Difluoro-quinolin-6-yl)-ethylamino]-pyrimidin-4-yl}-3-ethoxy-thiophene-2-carboxylic acid;
(2-Ethoxy-4-{6-[2-(3-isopropoxy-naphthalen-2-yl)-ethylamino]-pyrimidin-4-yl}-phenoxy)-acetic acid;
5-{6-[2-(1-Chloro-naphthalen-2-yl)-ethylamino]-pyrimidin-4-yl}-3-ethoxy-thiophene-2-carboxylic acid;
5-[6-(2-Benzothiazol-6-yl-ethylamino)-pyrimidin-4-yl]-3-ethoxy-thiophene-2-carboxylic acid;
4-{6-[2-(3-Cyano-naphthalen-2-yl)-ethylamino]-pyrimidin-4-yl}-2-ethoxy-benzoic acid;
3-Ethoxy-5-{6-[2-(4-fluoro-7-methoxy-2-methyl-benzo[b]thiophen-6-yl)-ethylamino]-pyrimidin-4-yl}-thiophene-2-carboxylic acid;
3-Ethoxy-5-{6-[2-(8-methyl-2,3-dihydro-benzo[1,4]dioxin-6-yl)-ethylamino]-pyrimidin-4-yl}-thiophene-2-carboxylic acid;
3-Ethoxy-5-{6-[2-(7-fluoro-quinolin-6-yl)-ethylamino]-pyrimidin-4-yl}-thiophene-2-carboxylic acid;
3-Ethoxy-5-{6-[2-(6-fluoro-isoquinolin-7-yl)-ethylamino]-pyrimidin-4-yl}-thiophene-2-carboxylic acid;
(4-{6-[2-(1,3-Difluoro-naphthalen-2-yl)-ethylamino]-pyrimidin-4-yl}-2-ethoxy-phenyl)-acetic acid;
5-{6-[2-(7-Fluoro-isoquinolin-6-yl)-ethylamino]-pyrimidin-4-yl}-3-trifluoromethyl-thiophene-2-carboxylic acid;
4-{6-[2-(7-Cyano-2,3-dihydro-benzo[1,4]dioxin-6-yl)-ethylamino]-pyrimidin-4-yl}-2-cyclobutoxy-benzoic acid;
5-{6-[2-(2,3-Dihydro-benzofuran-5-yl)-ethylamino]-pyrimidin-4-yl}-3-ethoxy-thiophene-2-carboxylic acid;
(4-{6-[2-(1-Fluoro-3-methoxy-naphthalen-2-yl)-ethylamino]-pyrimidin-4-yl}-2-methylsulfanyl-phenyl)-acetic acid;
{4-[6-(2-Benzo[b]thiophen-5-yl-ethylamino)-pyrimidin-4-yl]-2-ethoxy-phenoxy}-acetic acid;
(2-Ethoxy-4-{6-[2-(3-methoxy-naphthalen-2-yl)-ethylamino]-pyrimidin-4-yl}-phenoxy)-acetic acid;
2-Ethoxy-4-{6-[2-(4-fluoro-3-methoxy-naphthalen-2-yl)-ethylamino]-pyrimidin-4-yl}-benzoic acid;
5-{6-[2-(1,3-Difluoro-naphthalen-2-yl)-ethylamino]-pyrimidin-4-yl}-3-ethoxy-thiophene-2-carboxylic acid;
3-{3-Ethoxy-5-[6-(2-quinolin-6-yl-ethylamino)-pyrimidin-4-yl]-thiophen-2-yl}-[1,2,4]oxadiazol-5(4H)-one [tautomeric form: 3-(3-ethoxy-5-(6-((2-(quinolin-6-yl)ethyl)amino)pyrimidin-4-yl)thiophen-2-yl)-[1,2,4]oxadiazol-5-ol]; and
3-{3-Ethoxy-5-[6-(2-naphthalen-2-yl-ethylamino)-pyrimidin-4-yl]-thiophen-2-yl}-[1,2,4]oxadiazol-5(4H)-one [tautomeric form: 3-(3-ethoxy-5-(6-((2-(naphthalen-2-yl)ethyl)amino)pyrimidin-4-yl)thiophen-2-yl)-[1,2,4]oxadiazol-5-ol]. 27) In addition to the compounds listed in embodiments 25) and 26), further compounds of formula (II) according to embodiment 8), are selected from the following compounds:
5-{6-[2-(7-Chloro-benzo[b]thiophen-5-yl)-ethylamino]-pyrimidin-4-yl}-3-ethoxy-thiophene-2-carboxylic acid;
4-{6-[2-(7-Chloro-benzo[b]thiophen-5-yl)-ethylamino]-pyrimidin-4-yl}-2-methylsulfanyl-benzoic acid;
2-Ethoxy-4-{6-[2-(7-fluoro-benzo[b]thiophen-5-yl)-ethylamino]-pyrimidin-4-yl}-benzoic acid;
3-Ethoxy-5-{6-[2-(7-fluoro-benzo[b]thiophen-5-yl)-ethylamino]-pyrimidin-4-yl}-thiophene-2-carboxylic acid;
4-{6-[2-(7-Fluoro-benzo[b]thiophen-5-yl)-ethylamino]-pyrimidin-4-yl}-2-methylsulfanyl-benzoic acid;
2-Ethoxy-4-{6-[2-(4-fluoro-benzo[b]thiophen-5-yl)-ethylamino]-pyrimidin-4-yl}-benzoic acid;
2-Cyclobutoxy-4-{6-[2-(4-fluoro-benzo[b]thiophen-5-yl)-ethylamino]-pyrimidin-4-yl}-benzoic acid;
3-Ethoxy-5-{6-[2-(4-fluoro-benzo[b]thiophen-5-yl)-ethylamino]-pyrimidin-4-yl}-thiophene-2-carboxylic acid;
4-{6-[2-(4-Fluoro-benzo[b]thiophen-5-yl)-ethylamino]-pyrimidin-4-yl}-2-methylsulfanyl-benzoic acid;
(2-Ethoxy-6-fluoro-4-{6-[2-(6-methoxy-benzo[b]thiophen-5-yl)-ethylamino]-pyrimidin-4-yl}-phenyl)-acetic acid;
(2-Ethoxy-6-fluoro-4-{6-[2-(4-methyl-benzo[b]thiophen-5-yl)-ethylamino]-pyrimidin-4-yl}-phenyl)-acetic acid;
3-Ethoxy-5-{6-[2-(7-methyl-benzo[b]thiophen-6-yl)-ethylamino]-pyrimidin-4-yl}-thiophene-2-carboxylic acid;
4-{6-[2-(6-Methoxy-benzo[b]thiophen-5-yl)-ethylamino]-pyrimidin-4-yl}-2-propyl-benzoic acid;
4-{6-[2-(4-Fluoro-benzo[b]thiophen-5-yl)-ethylamino]-pyrimidin-4-yl}-2-propyl-benzoic acid;
4-{6-[2-(7-Methoxy-2,3-dihydro-benzo[1,4]dioxin-6-yl)-ethylamino]-pyrimidin-4-yl}-2-propyl-benzoic acid;
4-{6-[2-(3-Methoxy-1-methyl-naphthalen-2-yl)-ethylamino]-pyrimidin-4-yl}-2-propyl-benzoic acid;
(2-Methoxy-4-{6-[2-(6-methoxy-benzo[b]thiophen-5-yl)-ethylamino]-pyrimidin-4-yl}-phenyl)-acetic acid;
(4-{6-[2-(4-Fluoro-benzo[b]thiophen-5-yl)-ethylamino]-pyrimidin-4-yl}-2-methoxy-phenyl)-acetic acid;
(2-Methoxy-4-{6-[2-(7-methoxy-2,3-dihydro-benzo[1,4]dioxin-6-yl)-ethylamino]-pyrimidin-4-yl}-phenyl)-acetic acid;
(2-Methoxy-4-{6-[2-(3-methoxy-1-methyl-naphthalen-2-yl)-ethylamino]-pyrimidin-4-yl}-phenyl)-acetic acid;
(4-{6-[2-(6-Methoxy-benzo[b]thiophen-5-yl)-ethylamino]-pyrimidin-4-yl}-2-propyl-phenyl)-acetic acid;
(4-{6-[2-(4-Fluoro-benzo[b]thiophen-5-yl)-ethylamino]-pyrimidin-4-yl}-2-propyl-phenyl)-acetic acid;
(4-{6-[2-(7-Methoxy-2,3-dihydro-benzo[1,4]dioxin-6-yl)-ethylamino]-pyrimidin-4-yl}-2-propyl-phenyl)-acetic acid;

(4-{6-[2-(3-Methoxy-1-methyl-naphthalen-2-yl)-ethylamino]-pyrimidin-4-yl}-2-propyl-phenyl)-acetic acid;
4-{6-[2-(7-Fluoro-benzo[b]thiophen-5-yl)-ethylamino]-pyrimidin-4-yl}-2-propyl-benzoic acid;
3-Ethoxy-5-{6-[2-(7-methyl-benzo[b]thiophen-5-yl)-ethylamino]-pyrimidin-4-yl}-thiophene-2-carboxylic acid;
(4-{6-[2-(4-Fluoro-benzo[b]thiophen-5-yl)-ethylamino]-pyrimidin-4-yl}-2-propoxy-phenyl)-acetic acid;
(4-{6-[2-(3-Methoxy-1-methyl-naphthalen-2-yl)-ethylamino]-pyrimidin-4-yl}-2-propoxy-phenyl)-acetic acid;
2-Ethoxy-4-{6-[2-(7-methoxy-5-methyl-2,3-dihydro-benzo[1,4]dioxin-6-yl)-ethylamino]-pyrimidin-4-yl}-benzoic acid;
2-Cyclobutoxy-4-{6-[2-(7-methoxy-5-methyl-2,3-dihydro-benzo[1,4]dioxin-6-yl)-ethylamino]-pyrimidin-4-yl}-benzoic acid;
(4-{6-[2-(7-Methoxy-5-methyl-2,3-dihydro-benzo[1,4]dioxin-6-yl)-ethylamino]-pyrimidin-4-yl}-2-propyl-phenyl)-acetic acid;
(2-Ethoxy-6-fluoro-4-{6-[2-(7-methoxy-5-methyl-2,3-dihydro-benzo[1,4]dioxin-6-yl)-ethylamino]-pyrimidin-4-yl}-phenyl)-acetic acid;
(2-Ethoxy-4-{6-[2-(7-methoxy-5-methyl-2,3-dihydro-benzo[1,4]dioxin-6-yl)-ethylamino]-pyrimidin-4-yl}-phenyl)-acetic acid;
4-{6-[2-(7-Methoxy-5-methyl-2,3-dihydro-benzo[1,4]dioxin-6-yl)-ethylamino]-pyrimidin-4-yl}-2-methylsulfanyl-benzoic acid;
(4-{6-[2-(7-Ethoxy-2,3-dihydro-benzo[1,4]dioxin-6-yl)-ethylamino]-pyrimidin-4-yl}-2-propyl-phenyl)-acetic acid;
(2-Ethoxy-4-{6-[2-(7-ethoxy-2,3-dihydro-benzo[1,4]dioxin-6-yl)-ethylamino]-pyrimidin-4-yl}-6-fluoro-phenyl)-acetic acid;
2-Ethoxy-4-{6-[2-(7-fluoro-6-methoxy-benzo[b]thiophen-5-yl)-ethylamino]-pyrimidin-4-yl}-benzoic acid;
4-{6-[2-(7-Fluoro-6-methoxy-benzo[b]thiophen-5-yl)-ethylamino]-pyrimidin-4-yl}-2-methylsulfanyl-benzoic acid;
(2-Ethoxy-4-{6-[2-(7-fluoro-6-methoxy-benzo[b]thiophen-5-yl)-ethylamino]-pyrimidin-4-yl}-phenyl)-acetic acid;
2-Cyclobutoxy-4-{6-[2-(7-fluoro-6-methoxy-benzo[b]thiophen-5-yl)-ethylamino]-pyrimidin-4-yl}-benzoic acid;
(4-{6-[2-(5-Fluoro-7-methoxy-2,3-dihydro-benzo[1,4]dioxin-6-yl)-ethylamino]-pyrimidin-4-yl}-2-propyl-phenyl)-acetic acid;
(4-{6-[2-(7-Fluoro-6-methoxy-benzo[b]thiophen-5-yl)-ethylamino]-pyrimidin-4-yl}-2-isobutyl-phenyl)-acetic acid;
(2-Isobutyl-4-{6-[2-(7-methoxy-2,3-dihydro-benzo[1,4]dioxin-6-yl)-ethylamino]-pyrimidin-4-yl}-phenyl)-acetic acid;
(4-{6-[2-(7-Ethoxy-2,3-dihydro-benzo[1,4]dioxin-6-yl)-ethylamino]-pyrimidin-4-yl}-2-isobutyl-phenyl)-acetic acid;
4-{6-[2-(4-Fluoro-benzo[b]thiophen-5-yl)-ethylamino]-pyrimidin-4-yl}-2-isobutyl-benzoic acid;
4-{6-[2-(7-Fluoro-6-methoxy-benzo[b]thiophen-5-yl)-ethylamino]-pyrimidin-4-yl}-2-isobutyl-benzoic acid;
4-{6-[2-(7-Ethoxy-2,3-dihydro-benzo[1,4]dioxin-6-yl)-ethylamino]-pyrimidin-4-yl}-2-isobutyl-benzoic acid;
2-Ethoxy-4-{6-[2-(3-ethoxy-1-methyl-naphthalen-2-yl)-ethylamino]-pyrimidin-4-yl}-benzoic acid;
4-{6-[2-(3-Ethoxy-1-methyl-naphthalen-2-yl)-ethylamino]-pyrimidin-4-yl}-2-methylsulfanyl-benzoic acid;
(2-Ethoxy-4-{6-[2-(3-ethoxy-1-methyl-naphthalen-2-yl)-ethylamino]-pyrimidin-4-yl}-phenyl)-acetic acid;
3-(2-Ethoxy-4-{6-[2-(4-fluoro-benzo[b]thiophen-5-yl)-ethylamino]-pyrimidin-4-yl}-phenoxy)-propionic acid;
3-(2-Ethoxy-4-{6-[2-(3-methoxy-1-methyl-naphthalen-2-yl)-ethylamino]-pyrimidin-4-yl}-phenoxy)-propionic acid;
(4-{6-[2-(7-Ethoxy-2,3-dihydro-benzo[1,4]dioxin-6-yl)-ethylamino]-pyrimidin-4-yl}-2-isopropoxy-phenyl)-acetic acid;
(2-Isopropoxy-4-{6-[2-(7-methoxy-5-methyl-2,3-dihydro-benzo[1,4]dioxin-6-yl)-ethylamino]-pyrimidin-4-yl}-phenyl)-acetic acid;
(4-{6-[2-(7-Ethoxy-2,3-dihydro-benzo[1,4]dioxin-6-yl)-ethylamino]-pyrimidin-4-yl}-2-trifluoromethoxy-phenyl)-acetic acid;
(4-{6-[2-(7-Methoxy-5-methyl-2,3-dihydro-benzo[1,4]dioxin-6-yl)-ethylamino]-pyrimidin-4-yl}-2-trifluoromethoxy-phenyl)-acetic acid;
4-{6-[2-(3-Chloro-benzo[b]thiophen-5-yl)-ethylamino]-pyrimidin-4-yl}-2-methylsulfanyl-benzoic acid;
4-{6-[2-(3-Chloro-benzo[b]thiophen-5-yl)-ethylamino]-pyrimidin-4-yl}-2-cyclobutoxy-benzoic acid;
(4-{6-[2-(3-Chloro-benzo[b]thiophen-5-yl)-ethylamino]-pyrimidin-4-yl}-2-ethoxy-phenyl)-acetic acid;
2-Isopropoxy-4-{6-[2-(7-methoxy-5-methyl-2,3-dihydro-benzo[1,4]dioxin-6-yl)-ethylamino]-pyrimidin-4-yl}-benzoic acid;
5-{6-[2-(7-Difluoromethoxy-2,3-dihydro-benzo[1,4]dioxin-6-yl)-ethylamino]-pyrimidin-4-yl}-3-ethoxy-thiophene-2-carboxylic acid;
(2-Methoxy-4-{6-[2-(7-methoxy-5-methyl-2,3-dihydro-benzo[1,4]dioxin-6-yl)-ethylamino]-pyrimidin-4-yl}-phenyl)-acetic acid;
2-Ethoxy-4-{6-[2-(5-fluoro-7-methoxy-2,3-dihydro-benzo[1,4]dioxin-6-yl)-ethylamino]-pyrimidin-4-yl}-benzoic acid;
2-Ethoxy-4-{6-[2-(3-ethoxy-1-fluoro-naphthalen-2-yl)-ethylamino]-pyrimidin-4-yl}-benzoic acid;
3-(4-{6-[2-(4-Fluoro-benzo[b]thiophen-5-yl)-ethylamino]-pyrimidin-4-yl}-2-methoxy-phenoxy)-propionic acid;
2-Ethoxy-4-{6-[2-(7-ethynyl-2,3-dihydro-benzo[1,4]dioxin-6-yl)-ethylamino]-pyrimidin-4-yl}-benzoic acid;
(4-{6-[2-(7-Ethynyl-2,3-dihydro-benzo[1,4]dioxin-6-yl)-ethylamino]-pyrimidin-4-yl}-2-propyl-phenyl)-acetic acid;
(2-Difluoromethoxy-4-{6-[2-(7-methoxy-5-methyl-2,3-dihydro-benzo[1,4]dioxin-6-yl)-ethylamino]-pyrimidin-4-yl}-phenyl)-acetic acid;
(2-Difluoromethoxy-4-{6-[2-(5-fluoro-7-methoxy-2,3-dihydro-benzo[1,4]dioxin-6-yl)-ethylamino]-pyrimidin-4-yl}-phenyl)-acetic acid;
(2-Difluoromethoxy-4-{6-[2-(3-methoxy-1-methyl-naphthalen-2-yl)-ethylamino]-pyrimidin-4-yl}-phenyl)-acetic acid;
(2-Ethyl-4-{6-[2-(7-methoxy-5-methyl-2,3-dihydro-benzo[1,4]dioxin-6-yl)-ethylamino]-pyrimidin-4-yl}-phenyl)-acetic acid;
(2-Ethyl-4-{6-[2-(3-methoxy-1-methyl-naphthalen-2-yl)-ethylamino]-pyrimidin-4-yl}-phenyl)-acetic acid;
2-Ethyl-4-{6-[2-(3-methoxy-1-methyl-naphthalen-2-yl)-ethylamino]-pyrimidin-4-yl}-benzoic acid;
2-Cyclopropoxy-4-{6-[2-(7-ethoxy-2,3-dihydro-benzo[1,4]dioxin-6-yl)-ethylamino]-pyrimidin-4-yl}-benzoic acid;
2-Cyclopropoxy-4-{6-[2-(3-methoxy-1-methyl-naphthalen-2-yl)-ethylamino]-pyrimidin-4-yl}-benzoic acid;
2-Cyclopropoxy-4-{6-[2-(7-fluoro-benzo[b]thiophen-5-yl)-ethylamino]-pyrimidin-4-yl}-benzoic acid;

(4-{6-[2-(7-Methoxy-2,3-dihydro-benzo[1,4]dioxin-6-yl)-ethylamino]-pyrimidin-4-yl}-2-trifluoromethoxy-phenyl)-acetic acid;

3-(2-Ethoxy-4-{6-[2-(7-fluoro-benzo[b]thiophen-5-yl)-ethylamino]-pyrimidin-4-yl}-phenyl)-[1,2,4]oxadiazol-5(4H)-one [tautomeric form: 3-(2-ethoxy-4-{6-[2-(7-fluoro-benzo[b]thiophen-5-yl)-ethylamino]-pyrimidin-4-yl}-phenyl)-[1,2,4]oxadiazol-5-ol];

{6-[3-Ethoxy-4-(1H-tetrazol-5-yl)-phenyl]-pyrimidin-4-yl}-[2-(7-fluoro-benzo[b]thiophen-5-yl)-ethyl]-amine;

4-{6-[2-(7-Fluoro-benzo[b]thiophen-5-yl)-ethylamino]-pyrimidin-4-yl}-2-isobutoxy-benzoic acid;

(3-Ethoxy-5-{6-[2-(7-fluoro-benzo[b]thiophen-5-yl)-ethylamino]-pyrimidin-4-yl}-thiophen-2-yl)-acetic acid;

4-{6-[2-(7-Fluoro-benzo[b]thiophen-5-yl)-ethylamino]-pyrimidin-4-yl}-2-propyl-benzamide;

4-{6-[2-(7-Fluoro-6-methoxy-benzo[b]thiophen-5-yl)-ethylamino]-pyrimidin-4-yl}-2-propyl-benzoic acid;

3-Ethoxy-5-{6-[2-(7-fluoro-6-methoxy-benzo[b]thiophen-5-yl)-ethylamino]-pyrimidin-4-yl}-thiophene-2-carboxyli acid;

(4-{6-[2-(7-Fluoro-6-methoxy-benzo[b]thiophen-5-yl)-ethylamino]-pyrimidin-4-yl}-2-methoxy-phenyl)-acetic acid;

(4-{6-[2-(7-Fluoro-6-methoxy-benzo[b]thiophen-5-yl)-ethylamino]-pyrimidin-4-yl}-2-propyl-phenyl)-acetic acid;

2-(4-{6-[2-(7-Ethoxy-2,3-dihydro-benzo[1,4]dioxin-6-yl)-ethylamino]-pyrimidin-4-yl}-2-propyl-phenyl)-propionic acid;

4-{6-[2-(3-Chloro-benzo[b]thiophen-5-yl)-ethylamino]-pyrimidin-4-yl}-2-ethoxy-benzoic acid;

4-{6-[2-(7-Difluoromethoxy-2,3-dihydro-benzo[1,4]dioxin-6-yl)-ethylamino]-pyrimidin-4-yl}-2-methylsulfanyl-benzoic acid;

(4-{6-[2-(3-Chloro-benzo[b]thiophen-5-yl)-ethylamino]-pyrimidin-4-yl}-2-propyl-phenyl)-acetic acid;

(4-{6-[2-(3-Chloro-benzo[b]thiophen-5-yl)-ethylamino]-pyrimidin-4-yl}-2-trifluoromethoxy-phenyl)-acetic acid;

(4-{6-[2-(3-Methoxy-1-methyl-naphthalen-2-yl)-ethylamino]-pyrimidin-4-yl}-2-trifluoromethoxy-phenyl)-acetic acid;

(4-{6-[2-(7-Ethynyl-2,3-dihydro-benzo[1,4]dioxin-6-yl)-ethylamino]-pyrimidin-4-yl}-2-methoxy-phenyl)-acetic acid;

(4-{6-[2-(5-Methyl-2,3-dihydro-benzo[1,4]dioxin-6-yl)-ethylamino]-pyrimidin-4-yl}-2-propyl-phenyl)-acetic acid;

(2-Difluoromethoxy-4-{6-[2-(7-ethoxy-2,3-dihydro-benzo[1,4]dioxin-6-yl)-ethylamino]-pyrimidin-4-yl}-phenyl)-acetic acid;

2-Ethyl-4-{6-[2-(7-fluoro-benzo[b]thiophen-5-yl)-ethylamino]-pyrimidin-4-yl}-benzoic acid;

2-Cyclopropoxy-4-{6-[2-(7-methoxy-2,3-dihydro-benzo[1,4]dioxin-6-yl)-ethylamino]-pyrimidin-4-yl}-benzoic acid;

2-Cyclopropoxy-4-{6-[2-(1-methyl-naphthalen-2-yl)-ethylamino]-pyrimidin-4-yl}-benzoic acid;

(3-Difluoromethoxy-5-{6-[2-(7-fluoro-benzo[b]thiophen-5-yl)-ethylamino]-pyrimidin-4-yl}-thiophen-2-yl)-acetic acid;

and 3-(2-Ethoxy-4-{6-[2-(1-methyl-naphthalen-2-yl)-ethylamino]-pyrimidin-4-yl}-phenyl)-[1,2,4]oxadiazole-5(4H)-thione

[tautomeric form: 3-(2-ethoxy-4-{6-[2-(1-methyl-naphthalen-2-yl)-ethylamino]-pyrimidin-4-yl}-phenyl)-[1,2,4]oxadiazole-5-thiol].

28) In addition to the compounds listed in embodiments 25), 26) and 27), further compounds of formula (II) according to embodiment 8), are selected from the following compounds:

(4-{6-[2-(6-Methoxy-benzo[b]thiophen-5-yl)-ethylamino]-pyrimidin-4-yl}-2-propoxy-phenyl)-acetic acid;

2-Butoxy-4-{6-[2-(7-fluoro-benzo[b]thiophen-5-yl)-ethylamino]-pyrimidin-4-yl}-benzoic acid;

2-Ethoxy-4-{6-[2-(5-methyl-2,3-dihydro-benzo[1,4]dioxin-6-yl)-ethylamino]-pyrimidin-4-yl}-benzoic acid;

(4-{6-[2-(5-Methyl-2,3-dihydro-benzo[1,4]dioxin-6-yl)-ethylamino]-pyrimidin-4-yl}-2-trifluoromethoxy-phenyl)-acetic acid;

(4-{6-[2-(7-Ethoxy-2,3-dihydro-benzo[1,4]dioxin-6-yl)-ethylamino]-pyrimidin-4-yl}-2-ethyl-phenyl)-acetic acid;

2-Ethyl-4-{6-[2-(5-methyl-2,3-dihydro-benzo[1,4]dioxin-6-yl)-ethylamino]-pyrimidin-4-yl}-benzoic acid;

4-{6-[2-(7-Ethoxy-2,3-dihydro-benzo[1,4]dioxin-6-yl)-ethylamino]-pyrimidin-4-yl}-2-ethyl-benzoic acid;

2-Cyclopropoxy-4-{6-[2-(5-methyl-2,3-dihydro-benzo[1,4]dioxin-6-yl)-ethylamino]-pyrimidin-4-yl}-benzoic acid; and (4-{6-[2-(7-Methyl-2,3-dihydro-benzo[1,4]dioxin-6-yl)-ethylamino]-pyrimidin-4-yl}-2-propyl-phenyl)-acetic acid.

29) In addition to the compounds listed in embodiments 25), 26), 27) and 28), further compounds of formula (II) according to embodiment 8), are selected from the following compounds:

(4-{6-[2-(3-Cyano-1-methyl-naphthalen-2-yl)-ethylamino]-pyrimidin-4-yl}-2-ethoxy-phenyl)-acetic acid;

(2-Ethoxy-4-{6-[2-(7-fluoro-benzo[b]thiophen-5-yl)-ethylamino]-pyrimidin-4-yl}-phenyl)-acetic acid;

(2-Ethoxy-4-{6-[2-(4-fluoro-benzo[b]thiophen-5-yl)-ethylamino]-pyrimidin-4-yl}-phenyl)-acetic acid;

(2-Ethoxy-6-fluoro-4-{6-[2-(3-methoxy-1-methyl-naphthalen-2-yl)-ethylamino]-pyrimidin-4-yl}-phenyl)-acetic acid;

(2-Ethoxy-6-fluoro-4-{6-[2-(4-fluoro-benzo[b]thiophen-5-yl)-ethylamino]-pyrimidin-4-yl}-phenyl)-acetic acid;

(4-{6-[2-(7-Fluoro-benzo[b]thiophen-5-yl)-ethylamino]-pyrimidin-4-yl}-2-propyl-phenyl)-acetic acid;

(4-{6-[2-(4-Fluoro-benzo[b]thiophen-5-yl)-ethylamino]-pyrimidin-4-yl}-2-isobutyl-phenyl)-acetic acid;

4-{6-[2-(7-Fluoro-benzo[b]thiophen-5-yl)-ethylamino]-pyrimidin-4-yl}-2-isobutyl-benzoic acid;

2-Isobutyl-4-{6-[2-(7-methoxy-2,3-dihydro-benzo[1,4]dioxin-6-yl)-ethylamino]-pyrimidin-4-yl}-benzoic acid;

3-(2-Ethoxy-4-{6-[2-(7-fluoro-benzo[b]thiophen-5-yl)-ethylamino]-pyrimidin-4-yl}-phenoxy)-propionic acid;

(4-{6-[2-(4-Fluoro-benzo[b]thiophen-5-yl)-ethylamino]-pyrimidin-4-yl}-2-isopropoxy-phenyl)-acetic acid;

3-(4-{6-[2-(7-Fluoro-benzo[b]thiophen-5-yl)-ethylamino]-pyrimidin-4-yl}-2-methoxy-phenoxy)-propionic acid;

3-Ethyl-5-{6-[2-(7-fluoro-benzo[b]thiophen-5-yl)-ethylamino]-pyrimidin-4-yl}-thiophene-2-carboxylic acid;

2-Ethoxy-4-{6-[2-(7-fluoro-benzo[b]thiophen-5-yl)-ethylamino]-pyrimidin-4-yl}-N-(2-hydroxy-ethyl)-benzamide;

(4-{6-[2-(7-Fluoro-benzo[b]thiophen-5-yl)-ethylamino]-pyrimidin-4-yl}-2-methoxy-phenyl)-acetic acid;

2-{4-[6-(2-Benzo[b]thiophen-5-yl-ethylamino)-pyrimidin-4-yl]-2-propyl-phenyl}-propionic acid;

2-(4-{6-[2-(4-Fluoro-benzo[b]thiophen-5-yl)-ethylamino]-pyrimidin-4-yl}-2-propyl-phenyl)-propionic acid;

3-Ethoxy-5-{6-[2-(7-trifluoromethyl-benzo[b]thiophen-5-yl)-ethylamino]-pyrimidin-4-yl}-thiophene-2-carboxylic acid;

3-(4-(6-((2-(7-Fluorobenzo[b]thiophen-5-yl)ethyl)amino)
pyrimidin-4-yl)phenyl)-[1,2,4]oxadiazol-5(4H)-one
[tautomeric form: 3-(4-{6-[2-(7-fluoro-benzo[b]thiophen-5-
yl)-ethylamino]-pyrimidin-4-yl}-phenyl)-[1,2,4]oxadi-
azol-5-ol];
7-{6-[2-(7-Fluoro-benzo[b]thiophen-5-yl)-ethylamino]-py-
rimidin-4-yl}-1-methyl-3,4-dihydro-1H-quinazolin-2-
one;
4-{6-[2-(7-Fluoro-benzo[b]thiophen-5-yl)-ethylamino]-py-
rimidin-4-yl}-2,6-dimethyl-phenol;
2-Ethylsulfanyl-4-{6-[2-(7-fluoro-benzo[b]thiophen-5-yl)-
ethylamino]-pyrimidin-4-yl}-benzoic acid;
2-Cyclobutoxy-4-{6-[2-(7-fluoro-benzo[b]thiophen-5-yl)-
ethylamino]-pyrimidin-4-yl}-benzoic acid;
3-(3-Ethoxy-5-{6-[2-(7-fluoro-benzo[b]thiophen-5-yl)-eth-
ylamino]-pyrimidin-4-yl}-thiophen-2-yl)-propionic acid;
3-(4-{6-[2-(7-Fluoro-benzo[b]thiophen-5-yl)-ethylamino]-
pyrimidin-4-yl}-phenyl)-4-hydroxy-cyclobut-3-ene-1,2-
dione;
(2-Ethoxy-4-{6-[2-(7-fluoro-benzo[b]thiophen-5-yl)-ethyl-
amino]-pyrimidin-4-yl}-phenyl)-oxo-acetic acid;
2-Cyclopropoxy-4-{6-[2-(7-fluoro-benzo[b]thiophen-5-yl)-
ethylamino]-pyrimidin-4-yl}-benzoic acid methyl ester;
(2-Chloro-6-ethyl-4-{6-[2-(7-fluoro-benzo[b]thiophen-5-
yl)-ethylamino]-pyrimidin-4-yl}-phenyl)-acetic acid;
(2-Ethyl-4-{6-[2-(7-fluoro-benzo[b]thiophen-5-yl)-ethyl-
amino]-pyrimidin-4-yl}-6-methyl-phenyl)-acetic acid;
(3-Ethyl-5-{6-[2-(7-fluoro-benzo[b]thiophen-5-yl)-ethyl-
amino]-pyrimidin-4-yl}-thiophen-2-yl)-acetic acid;
5-(2-Ethoxy-4-{6-[2-(7-fluoro-benzo[b]thiophen-5-yl)-eth-
ylamino]-pyrimidin-4-yl}-phenyl)-isoxazol-3-ol [tauto-
meric form: 5-(2-ethoxy-4-(6-((2-(7-fluorobenzo[b]thio-
phen-5-yl)ethyl)amino)pyrimidin-4-yl)phenyl) isoxazol-
3(2H)-one];
5-(4-{6-[2-(7-Fluoro-benzo[b]thiophen-5-yl)-ethylamino]-
pyrimidin-4-yl}-2-methoxy-phenyl)-isoxazol-3-ol
[tautomeric form: 5-(4-(6-((2-(7-fluorobenzo[b]thiophen-5-
yl)ethyl)amino)pyrimidin-4-yl)-2-methoxyphenyl) isoxa-
zol-3(2H)-one]; and
(5-{6-[2-(7-Fluoro-benzo[b]thiophen-5-yl)-ethylamino]-py-
rimidin-4-yl}-3-propyl-thiophen-2-yl)-acetic acid.

The compounds of formula (I)/formula (II) according to
embodiments 1) to 29) and their pharmaceutically accept-
able salts can be used as medicaments, e.g. in the form of
pharmaceutical compositions for enteral (such especially
oral e.g. in form of a tablet or a capsule) or parenteral
administration (including topical application or inhalation).

The production of the pharmaceutical compositions can
be effected in a manner which will be familiar to any person
skilled in the art (see for example Remington, *The Science
and Practice of Pharmacy,* 21st Edition (2005), Part 5,
"Pharmaceutical Manufacturing" [published by Lippincott
Williams & Wilkins]) by bringing the described compounds
of formula (I)/formula (II) or their pharmaceutically accept-
able salts, optionally in combination with other therapeuti-
cally valuable substances, into a galenical administration
form together with suitable, non-toxic, inert, therapeutically
compatible solid or liquid carrier materials and, if desired,
usual pharmaceutical adjuvants.

The present invention also relates to a method for the
prevention/prophylaxis or treatment of a disease or disorder
mentioned herein comprising administering to a subject a
pharmaceutically active amount of a compound of formula
(I)/formula (II) according to embodiments 1) to 29).

In a preferred embodiment of the invention, the admin-
istered amount is comprised between 1 mg and 2000 mg per
day, particularly between 5 mg and 1000 mg per day, more
particularly between 25 mg and 500 mg per day, especially
between 50 mg and 200 mg per day.

Whenever the word "between" is used to describe a
numerical range, it is to be understood that the end points of
the indicated range are explicitly included in the range. For
example: if a temperature range is described to be between
40° C. and 80° C., this means that the end points 40° C. and
80° C. are included in the range; or if a variable is defined
as being an integer between 1 and 4, this means that the
variable is the integer 1, 2, 3, or 4.

Unless used regarding temperatures, the term "about"
placed before a numerical value "X" refers in the current
application to an interval extending from X minus 10% of X
to X plus 10% of X, and preferably to an interval extending
from X minus 5% of X to X plus 5% of X. In the particular
case of temperatures, the term "about" placed before a
temperature "Y" refers in the current application to an
interval extending from the temperature Y minus 10° C. to
Y plus 10° C., and preferably to an interval extending from
Y minus 5° C. to Y plus 5° C.

For avoidance of any doubt, if compounds are described
as useful for the prevention/prophylaxis or treatment of
certain diseases, such compounds are likewise suitable for
use in the preparation of a medicament for the prevention/
prophylaxis or treatment of said diseases. Likewise, such
compounds are also suitable in a method for the prevention/
prophylaxis or treatment of such diseases, comprising
administering to a subject (mammal, especially human) in
need thereof, an effective amount of such compound.

The compounds of formula (I)/formula (II) according to
embodiments 1) to 29) are useful for the prevention/pro-
phylaxis or treatment of disorders relating to the EP2 and/or
EP4 receptors.

Certain compounds of formula (I)/formula (II) according
to embodiments 1) to 29) exhibit their biological activity as
modulators of the prostaglandin 2 receptors EP2 and/or EP4
in a biological environment, (i.e. in the presence of one or
more enzymes capable of breaking a covalent bond linked to
a carbonyl group such as an amidase, an esterase or any
suitable equivalent thereof capable of removing a prodrug
group from a carboxylic acid group.

Diseases or disorders relating to the EP2 and/or EP4
receptors are especially
cancer (notably melanoma including metastatic mela-
noma; lung cancer including non-small cell lung can-
cer; bladder cancer including urinary bladder cancer,
urothelial cell carcinoma; renal carcinomas including
renal cell carcinoma, metastatic renal cell carcinoma,
metastatic renal clear cell carcinoma; gastro-intestinal
cancers including colorectal cancer, metastatic colorec-
tal cancer, familial adenomatous polyposis (FAP),
oesophageal cancer, gastric cancer, gallbladder cancer,
cholangiocarcinoma, hepatocellular carcinoma, and
pancreatic cancer such as pancreatic adenocarcinoma
or pancreatic ductal carcinoma; endometrial cancer;
ovarian cancer; cervical cancer; neuroblastoma; pros-
tate cancer including castrate-resistant prostate cancer;
brain tumors including brain metastases, malignant
gliomas, glioblastoma multiforme, medulloblastoma,
meningiomas; breast cancer including triple negative
breast carcinoma; oral tumors; nasopharyngeal tumors;
thoracic cancer; head and neck cancer; leukemias
including acute myeloid leukemia, adult T-cell leuke-
mia; carcinomas; adenocarcinomas; thyroid carcinoma
including papillary thyroid carcinoma; choriocarci-
noma; Ewing's sarcoma; osteosarcoma; rhabdomyosar-
coma; Kaposi's sarcoma; lymphoma including Burkitt's lymphoma, Hodgkin's lymphoma, MALT lymphoma; multiple myelomas; and virally induced tumors; especially melanoma; lung cancer; bladder cancer; renal carcinomas; gastro-intestinal cancers; endometrial cancer; ovarian cancer; cervical cancer; and neuroblastoma);

as well as further diseases or disorders relating to the EP2 and/or EP4 receptors such as:
pain (notably inflammatory pain and painful menstruation);
endometriosis;
autosomal dominant polycystic kidney disease;
acute ischemic syndromes in atherosclerotic patients;
pneumonia; and
neurodegenerative diseases including amyotrophic lateral sclerosis, stroke; Parkinson disease, Alzheimer's disease and HIV associated dementia;
and EP2 and/or EP4 antagonists may further be used to control female fertility.

The compounds of formula (I)/formula (II) according to any one of embodiments 1) to 29) are in particular useful as therapeutic agents for the prevention/prophylaxis or treatment of a cancer. They can be used as single therapeutic agents or in combination with one or more chemotherapy agents and/or radiotherapy and/or targeted therapy. Such combined treatment may be effected simultaneously, separately, or over a period of time.

The invention, thus, also relates to pharmaceutical compositions comprising a pharmaceutically acceptable carrier material, and:
a compound of formula (I)/formula (II) according to any one of embodiments 1) to 29);
and one or more cytotoxic chemotherapy agents.

The invention, thus, further relates to a kit comprising
a pharmaceutical composition, said composition comprising a pharmaceutically acceptable carrier material, and:
a compound of formula (I)/formula (II) according to any one of embodiments 1) to 29);
and instructions how to use said pharmaceutical composition for the prevention/prophylaxis or the treatment of a cancer, in combination with chemotherapy and/or radiotherapy and/or targeted therapy.

The terms "radiotherapy" or "radiation therapy" or "radiation oncology", refer to the medical use of ionizing radiation in the prevention/prophylaxis (adjuvant therapy) and/or treatment of cancer; including external and internal radiotherapy.

The term "targeted therapy" refers to the prevention/prophylaxis (adjuvant therapy) and/or treatment of cancer with one or more anti-neoplastic agents such as small molecules or antibodies which act on specific types of cancer cells or stromal cells. Some targeted therapies block the action of certain enzymes, proteins, or other molecules involved in the growth and spread of cancer cells. Other types of targeted therapies help the immune system kill cancer cells (immunotherapies); or inhibit angiogenesis, the growth and formation of new blood vessels in the tumor; or deliver toxic substances directly to cancer cells and kill them. An example of a targeted therapy which is in particular suitable to be combined with the compounds of the present invention is immunotherapy, especially immunotherapy targeting the programmed cell death receptor 1 (PD-1 receptor) or its ligand PD-L1 (Zelenay et al., 2015, Cell 162, 1-14; Yongkui Li et al., Oncoimmunology 2016, 5(2):e1074374).

When used in combination with the compounds of formula (I)/formula (II), the term "targeted therapy" especially refers to agents such as:

a) Epidermal growth factor receptor (EGFR) inhibitors or blocking antibodies (for example Gefitinib, Erlotinib, Afatinib, Icotinib, Lapatinib, Panitumumab, Zalutumumab, Nimotuzumab, Matuzumab and Cetuximab);
b) RAS/RAF/MEK pathway inhibitors (for example Vemurafenib, Sorafenib, Dabrafenib, GDC-0879, PLX-4720, LGX818, RG7304, Trametinib (GSK1120212), Cobimetinib (GDC-0973/XL518), Binimetinib (MEK162, ARRY-162), Selumetinib (AZD6244));
c) Aromatase inhibitors (for example Exemestane, Letrozole, Anastrozole, Vorozole, Formestane, Fadrozole);
d) Angiogenesis inhibitors, especially VEGF signalling inhibitors such as Bevacuzimab (Avastin), Ramucirumab, Sorafenib or Axitinib;
e) Immune Checkpoint inhibitors (for example: anti-PD1 antibodies such as Pembrolizumab (Lambrolizumab, MK-3475), Nivolumab, Pidilizumab (CT-011), AMP-514/MED10680, PDR001, SHR-1210; REGN2810, BGBA317; fusion proteins targeting PD-1 such as AMP-224; small molecule anti-PD1 agents such as for example compounds disclosed in WO2015/033299, WO2015/044900 and WO2015/034820; anti-PD1L antibodies, such as BMS-936559, atezolizumab (MPDL3280A, RG7446), MED14736, avelumab (MSB0010718C), durvalumab (MED14736); anti-PDL2 antibodies, such as AMP224; anti-CTLA-4 antibodies, such as ipilimumab, tremilmumab; anti-Lymphocyte-activation gene 3 (LAG-3) antibodies, such as BMS-986016, IMP701, MK-4280, ImmuFact IMP321; anti T cell immunoglobulin mucin-3 (TIM-3) antibodies, such as MBG453; anti-CD137/4-1BB antibodies, such as BMS-663513/urelumab, PF-05082566; anti T cell immunoreceptor with Ig and ITIM domains (TIGIT) antibodies, such as RG6058 (anti-TIGIT, MTIG7192A);
f) Vaccination approaches (for example dendritic cell vaccination, peptide or protein vaccination (for example with gp100 peptide or MAGE-A3 peptide);
g) Re-introduction of patient derived or allogenic (non-self) cancer cells genetically modified to secrete immunomodulatory factors such as granulocyte monocyte colony stimulating factor (GMCSF) gene-transfected tumor cell vaccine (GVAX) or Fms-related tyrosine kinase 3 (Flt-3) ligand gene-transfected tumor cell vaccine (FVAX), or Toll like receptor enhanced GM-CSF tumor based vaccine (TEGVAX);
h) T-cell based adoptive immunotherapies, including chimeric antigen receptor (CAR) engineered T-cells (for example CTL019);
i) Cytokine or immunocytokine based therapy (for example Interferon alpha, interferon beta, interferon gamma, interleukin 2, interleukin 15);
j) Toll-like receptor (TLR) agonists (for example resiquimod, imiquimod, glucopyranosyl lipid A, CpG oligodesoxynucleotides);
k) Thalidomide analogues (for example Lenalidomide, Pomalidomide);
l) Indoleamin-2,3-Dioxgenase (IDO) and/or Tryptophane-2,3-Dioxygenase (TDO) inhibitors (for example RG6078/NLG919/GDC-0919; Indoximod/1MT (1-methyltryptophan), INCB024360/Epacadostat, PF-06840003 (EOS200271), F001287);
m) Activators of T-cell co-stimulatory receptors (for example anti-OX40/CD134 (Tumor necrosis factor receptor superfamily, member 4, such as RG7888 (MOXR0916), 9B12; MED6469, GSK3174998, MED0562), anti OX40-Ligand/CD252; anti-glucocorticoid-induced TNFR family related gene (GITR) (such as TRX518, MED11873, MK-4166, BMS-986156), anti-CD40 (TNF receptor superfamily member 5) antibodies (such as Dacetuzumab (SGN-40), HCD122, CP-870,893, RG7876, ADC-1013, APX005M, SEA-CD40); anti-CD40-Ligand antibodies (such as BG9588); anti-CD27 antibodies such as Varlilumab);

n) Molecules binding a tumor specific antigen as well as a T-cell surface marker such as bispecific antibodies (for example RG7802 targeting CEA and CD3) or antibody fragments, antibody mimetic proteins such as designed ankyrin repeat proteins (DARPINS), bispecific T-cell engager (BITE, for example AMG103, AMG330);

o) Antibodies or small molecular weight inhibitors targeting colony-stimulating factor-1 receptor (CSF-1R) (for example Emactuzumab (RG7155), Cabiralizumab (FPA-008), PLX3397);

p) Agents targeting immune cell check points on natural killer cells such as antibodies against Killer-cell immunoglobulin-like receptors (KIR) for example Lirilumab (IPH2102/BMS-986015);

q) Agents targeting the Adenosine receptors or the ecto-nucleases CD39 and CD73 that convert ATP to Adenosine, such as MED19447 (anti-CD73 antibody), PBF-509; CPI-444 (Adenosine A2a receptor antagonist).

When used in combination with the compounds of formula (I)/formula (II), immune checkpoint inhibitors such as those listed under d), and especially those targeting the programmed cell death receptor 1 (PD-1 receptor) or its ligand PD-L1, are preferred.

The term "chemotherapy" refers to the treatment of cancer with one or more cytotoxic anti-neoplastic agents ("cytotoxic chemotherapy agents"). Chemotherapy is often used in conjunction with other cancer treatments, such as radiation therapy or surgery. The term especially refers to conventional cytotoxic chemotherapeutic agents which act by killing cells that divide rapidly, one of the main properties of most cancer cells. Chemotherapy may use one drug at a time (single-agent chemotherapy) or several drugs at once (combination chemotherapy or polychemotherapy). Chemotherapy using drugs that convert to cytotoxic activity only upon light exposure is called photochemotherapy or photodynamic therapy.

The term "cytotoxic chemotherapy agent" or "chemotherapy agent" as used herein refers to an active anti-neoplastic agent inducing apoptosis or necrotic cell death. When used in combination with the compounds of formula (I)/formula (II), the term especially refers to conventional cytotoxic chemotherapy agents such as:

a) alkylating agents (for example mechlorethamine, chlorambucil, cyclophosphamide, ifosfamide, streptozocin, carmustine, lomustine, melphalan, dacarbazine, temozolomide, fotemustine, thiotepa or altretamine; especially cyclophosphamide, carmustine, melphalan, dacarbazine, or temozolomide);

b) platinum drugs (especially cisplatin, carboplatin or oxaliplatin);

c) antimetabolite drugs (for example 5-fluorouracil, folic acid/leucovorin, capecitabine, 6-mercaptopurine, methotrexate, gemcitabine, cytarabine, fludarabine or pemetrexed; especially 5-fluorouracil, folic acid/leucovorin, capecitabine, methotrexate, gemcitabine or pemetrexed);

d) anti-tumor antibiotics (for example daunorubicin, doxorubicin, epirubicin, idarubicin, actinomycin-D, bleomycin, mitomycin-C or mitoxantrone; especially doxorubicin);

e) mitotic inhibitors (for example paclitaxel, docetaxel, ixabepilone, vinblastine, vincristine, vinorelbine, vindesine or estramustine; especially paclitaxel, docetaxel, ixabepilone or, vincristine); or f) topoisomerase inhibitors (for example etoposide, teniposide, topotecan, irinotecan, diflomotecan or elomotecan; especially etoposide or irinotecan).

When used in combination with the compounds of formula (I)/formula (II), preferred cytotoxic chemotherapy agents are the above-mentioned alkylating agents (notably fotemustine, cyclophosphamide, ifosfamide, carmustine, dacarbazine and prodrugs thereof such as especially temozolomide or pharmaceutically acceptable salts of these compounds; in particular temozolomide); mitotic inhibitors (notably paclitaxel, docetaxel, ixabepilone; or pharmaceutically acceptable salts of these compounds; in particular paclitaxel); platinum drugs (notably cisplatin, oxaliplatin and carboplatin); as well etoposide and gemcitabine.

Chemotherapy may be given with a curative intent or it may aim to prolong life or to palliate symptoms.

Combined modality chemotherapy is the use of drugs with other cancer treatments, such as radiation therapy or surgery.

Induction chemotherapy is the first line treatment of cancer with a chemotherapeutic drug. This type of chemotherapy is used for curative intent.

Consolidation chemotherapy is the given after remission in order to prolong the overall disease free time and improve overall survival. The drug that is administered is the same as the drug that achieved remission.

Intensification chemotherapy is identical to consolidation chemotherapy but a different drug than the induction chemotherapy is used.

Combination chemotherapy involves treating a patient with a number of different drugs simultaneously. The drugs differ in their mechanism and side effects. The biggest advantage is minimising the chances of resistance developing to any one agent. Also, the drugs can often be used at lower doses, reducing toxicity.

Neoadjuvant chemotherapy is given prior to a local treatment such as surgery, and is designed to shrink the primary tumor. It is also given to cancers with a high risk of micrometastatic disease.

Adjuvant chemotherapy is given after a local treatment (radiotherapy or surgery). It can be used when there is little evidence of cancer present, but there is risk of recurrence. It is also useful in killing any cancerous cells that have spread to other parts of the body. These micrometastases can be treated with adjuvant chemotherapy and can reduce relapse rates caused by these disseminated cells.

Maintenance chemotherapy is a repeated low-dose treatment to prolong remission.

Salvage chemotherapy or palliative chemotherapy is given without curative intent, but simply to decrease tumor load and increase life expectancy. For these regimens, a better toxicity profile is generally expected.

"Simultaneously", when referring to an administration type, means in the present application that the administration type concerned consists in the administration of two or more active ingredients and/or treatments at approximately the same time; wherein it is understood that a simultaneous administration will lead to exposure of the subject to the two or more active ingredients and/or treatments at the same time. When administered simultaneously, said two or more active ingredients may be administered in a fixed dose combination, or in an equivalent non-fixed dose combination (e.g. by using two or more different pharmaceutical compositions to be administered by the same route of administration at approximately the same time), or by a non-fixed dose combination using two or more different routes of administration; wherein said administration leads to essentially simultaneous exposure of the subject to the two or more active ingredients and/or treatments. For example, when used in combination with chemotherapy and/or suitable targeted therapy, the present EP2/EP4 antagonists would possibly be used "simultaneously".

"Fixed dose combination", when referring to an administration type, means in the present application that the administration type concerned consists in the administration of one single pharmaceutical composition comprising the two or more active ingredients.

"Separately", when referring to an administration type, means in the present application that the administration type concerned consists in the administration of two or more active ingredients and/or treatments at different points in time; wherein it is understood that a separate administration will lead to a treatment phase (e.g. at least 1 hour, notably at least 6 hours, especially at least 12 hours) where the subject is exposed to the two or more active ingredients and/or treatments at the same time; but a separate administration may also lead to a treatment phase where for a certain period of time (e.g. at least 12 hours, especially at least one day) the subject is exposed to only one of the two or more active ingredients and/or treatments. Separate administration especially refers to situations wherein at least one of the active ingredients and/or treatments is given with a periodicity substantially different from daily (such as once or twice daily) administration (e.g. wherein one active ingredient and/or treatment is given e.g. once or twice a day, and another is given e.g. every other day, or once a week or at even longer distances). For example, when used in combination with radiotherapy, the present EP2/EP4 antagonists would possibly be used "separately".

By administration "over a period of time" is meant in the present application the subsequent administration of two or more active ingredients and/or treatments at different times. The term in particular refers to an administration method according to which the entire administration of one of the active ingredients and/or treatments is completed before the administration of the other/the others begins. In this way it is possible to administer one of the active ingredients and/or treatments for several months before administering the other active ingredient(s) and/or treatment(s).

Administration "over a period of time" also encompasses situations wherein the compound of formula (I)/formula (II) would be used in a treatment that starts after termination of an initial chemotherapeutic (for example an induction chemotherapy) and/or radiotherapeutic treatment and/or targeted therapy treatment, wherein optionally said treatment would be in combination with a further/an ongoing chemotherapeutic and/or radiotherapeutic treatment and/or targeted therapy treatment (for example in combination with a consolidation chemotherapy, an intensification chemotherapy, an adjuvant chemotherapy, or a maintenance chemotherapy; or radiotherapeutic equivalents thereof); wherein such further/ongoing chemotherapeutic and/or radiotherapeutic treatment and/or targeted therapy treatment would be simultaneously, separately, or over a period of time in the sense of "not given with the same periodicity".

The compounds of formula (I)/formula (II) as defined in embodiments 1) to 29) are also useful in a method of modulating an immune response in a subject having a tumor, comprising the administration of an effective amount of the compound of formula (I)/formula (II) [wherein notably said administration of said effective amount results in the pharmacologically active blockage of the EP2 receptors, or of the EP4 receptors, or of both the EP2 and the EP4 receptors]; wherein said effective amount reactivates the immune system in the tumor of said subject; wherein especially said effective amount:
  counteracts the polarization of tumor-associated macrophages towards tumor-promoting M2 macrophages; and/or
  down-regulates the activation, expansion and/or the effector function of immunosuppressive cells that have accumulated in a tumor (especially of regulatory T cells (Tregs) and/or myeloid derived suppressor cells (MDSC)); and/or
  up-regulates IFN-$\gamma$ and/or TNF-$\alpha$ and/or IL-12 and/or IL-2 expression in immune cells such as natural killer cells, T-cells, dendritic cells and macrophages (leading to the induction of tumor cell apoptosis and/or restrained tumorigenesis); and/or
  directly or indirectly counteracts the suppressed activation, IL-2 responsiveness and expansion of cytotoxic T-cells (thereby decreasing local immunsuppression).

The compounds of formula (I)/formula (II) as defined in embodiments 1) to 29) are also useful in a method of diminishing tumor growth and/or reducing tumor size in a subject having a tumor, comprising the administration of an effective amount of the compound of formula (I)/formula (II) [wherein notably said administration of said effective amount results in the pharmacologically active blockage of the EP2 receptors, or of the EP4 receptors, or of both the EP2 and the EP4 receptors]; wherein said effective amount down-regulates tumor angiogenesis (especially by decreasing endothelial cell motility and/or survival, and/or by decreasing the expression of VEGF (vascular endothelial growth factor)); and/or wherein said effective amount diminishes tumor cell survival and/or induces tumor cell apoptosis (especially via inhibition of P3K/AKT and MAPK signalling).

The compounds of formula (I)/formula (II) as defined in embodiments 1) to 29) are also useful in a method of modulating an immune response in a subject having a tumor, comprising the administration of an effective amount of the compound of formula (I)/formula (II) [wherein notably said administration of said effective amount results in the pharmacologically active blockage of the EP2 receptors, or of the EP4 receptors, or of both the EP2 and the EP4 receptors]; wherein said effective amount reactivates the immune system in the tumor of said subject; wherein said effective amount activates the cytotoxicity and cytokine production of natural killer cells and/or cytotoxic T-cells.

Besides, any preferences and (sub-)embodiments indicated for the compounds of formula (II) (whether for the compounds themselves, salts thereof, compositions containing the compounds or salts thereof, or uses of the compounds or salts thereof, etc.) apply mutatis mutandis to compounds of formula (I).

Preparation of Compounds of Formula (I)/Formula (II):

The compounds of formula (I)/formula (II) can be prepared by well-known literature methods, by the methods given below, by the methods given in the experimental part below or by analogous methods. Optimum reaction conditions may vary with the particular reactants or solvents used, but such conditions can be determined by a person skilled in the art by routine optimisation procedures. In some cases the order of carrying out the following reaction schemes, and/or reaction steps, may be varied to facilitate the reaction or to avoid unwanted reaction products. In the general sequence of reactions outlined below, the generic groups $R^1$, $R^3$, $R^{4a}$, $R^{4b}$, $R^{5a}$, $R^{5b}$ and $Ar^1$ are as defined for formula (I)/formula (II). Other abbreviations used herein are explicitly defined, or are as defined in the experimental section. In some instances the generic groups $R^1$, $R^3$, $R^{4a}$, $R^{4b}$, $R^{5a}$, $R^{5b}$ and $Ar^1$ might be incompatible with the assembly illustrated in the schemes below and so will require the use of protecting groups (PG). The use of protecting groups is well known in the art (see for example "Protective Groups in Organic Synthesis", T. W. Greene, P. G. M. Wuts, Wiley-Interscience, 1999). For the purposes of this discussion, it will be assumed that such protecting groups as necessary are in place. In some cases the final product may be further modified, for example, by manipulation of substituents to give a new final product. These manipulations may include, but are not limited to, reduction, oxidation, alkylation, acylation, hydrolysis and transition-metal catalysed cross-coupling reactions which are commonly known to those skilled in the art. The compounds obtained may also be converted into salts, especially pharmaceutically acceptable salts, in a manner known per se.

Compounds of formula (I)/formula (II) of the present invention can be prepared according to the general sequence of reactions outlined below.

A general synthetic route allowing the preparation of compounds of formula (I)/formula (II) is presented in scheme 1. Thus, precursors A3 can be obtained by nucleophilic aromatic substitutions between primary amines A1 and pyrimidines A2 (wherein X is a chlorine, a bromine or an iodine), in the presence of a base such as TEA, DIPEA or $K_2CO_3$, in a solvent such as isopropanol, butanol, DMF or THF, at RT or at elevated temperatures. Compounds of formula (I) can be produced via Suzuki cross-coupling reactions of the pyrimidine halide derivatives A3 with boronic acids or boronate esters A4. Typical Suzuki cross-coupling reactions may be carried out in the presence of a base such as $K_2CO_3$, $Cs_2CO_3$, $Na_2CO_3$, $K_3PO_4$, or CsF and a catalyst such as $Pd(PPhs)_4$, $Pd(dppf)Cl_2$ or $Pd(OAc)_2$, in a solvent like ethanol, THF, water, or mixtures thereof, typically at elevated temperatures. Boronic acids or boronate esters A4 can be obtained from commercial sources, or synthesized by methods described in the literature, or by methods known by a person skilled in the art. A boronic acid derivative can be formed by the Miyaura borylation reaction, by cross-coupling of bis(pinacolato)diboron with aryl halides or triflates, in the presence of a base such as potassium acetate and a catalyst such as $Pd(dppf)Cl_2$. Alternatively, a boronic acid derivative can be formed by a lithiation/borylation sequence, typically at low temperatures, using butyllithium or lithium diisopropylamide as the base, and tri-isopropylborate or isopropoxyboronic acid pinacol ester, in a solvent such as diethyl ether or THF. In a variant, compounds of formula (I) can be prepared via nucleophilic aromatic substitutions between primary amines A1 and substituted pyrimidine halides A5, wherein X is a chlorine, a bromine or an iodine (scheme 1).

Scheme 1. General preparation of compounds of formula (I); in scheme 1, X represents Cl, Br or I.

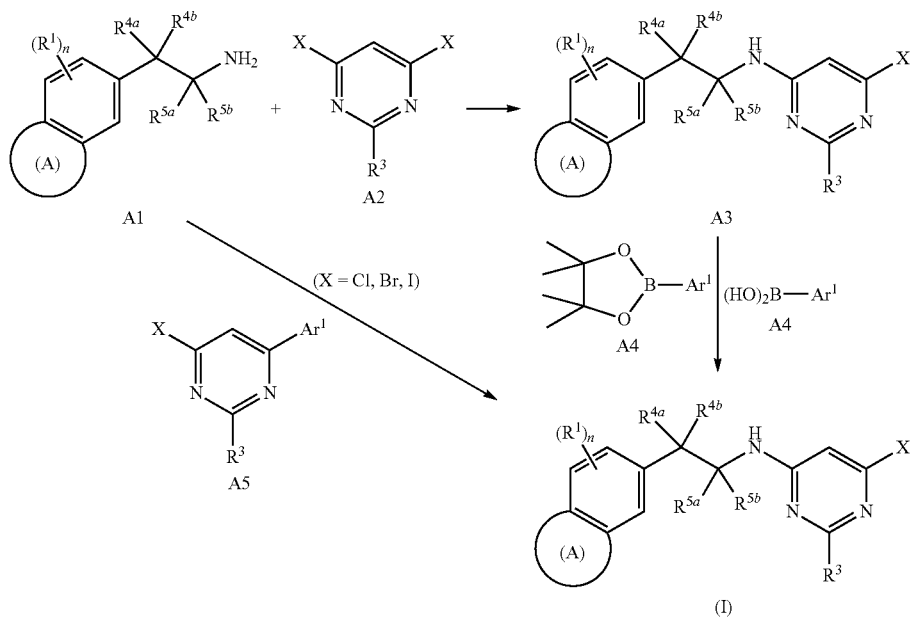

Alternatively, compounds of formula (I) can be synthesized by reacting a compound of formula A1 with a compound of formula A5 wherein X represents OH, in presence of a coupling agent such as (benzotriazol-1-yloxy)-tris(dimethylamino)-phosphonium hexafluorophosphate (BOP), (benzotriazol-1-yl-oxy)-tripyrrolidino-phosphonium hexafluorophosphate (PyBOP) or hexachlorocyclotriphosphazene, in presence of a base such as DBU, DIPEA or TEA in a solvent such as THF, MeCN or DMF, at low temperatures, or at RT or at elevated temperatures.

Preparations of the required primary amines A1 are described in scheme 2. Aminoethylated aromatics or heteroaromatics B3 can be produced via Suzuki-Miyaura cross-coupling reactions of the corresponding aromatic or heteroaromatic electrophiles B1 (bromides, iodides or triflates)

with Boc-protected potassium R-aminoethyltrifluoroborates B2. Such cross-coupling reactions can be performed using described conditions [Pd(dppf)Cl$_2$ or combination of Pd(OAc)$_2$ and RuPhos as the catalytic system, Cs$_2$CO$_3$ as a base, in a mixture of toluene/H$_2$O, at elevated temperatures]. The corresponding primary amines A1 can be obtained after Boc-deprotection of derivatives B3, under acidic conditions, and can be converted into compounds of formula (I) with the synthetic sequences described in scheme 1. In a variant presented in scheme 2, primary amines A1 can be prepared starting from carbonyl precursors B4 and nitro compounds B5 via Henry reaction (butylamine/acetic acid/molecular sieves/90° C.) and subsequent reduction of the produced nitroalkenes B6 (lithium aluminum hydride/THF/80° C.).

reagent. The methoxymethyl group in C3 can be removed under mild acidic conditions to give derivatives C6 that can be converted to the corresponding triflates C7 for subsequent coupling with Boc-protected potassium β-aminoethyltrifluoroborates B2. Boc-deprotection of the resulting products C8 can deliver the corresponding primary amines C9 that can be converted into compounds of formula (I) according to sequences described in scheme 1.

Substituted benzothiophenes corresponding to compounds of formula (I) can be prepared according to the synthetic route described in scheme 4. Ortho-fluorobenzaldehydes or ortho-chlorobenzaldehydes D1 can undergo aromatic nucleophilic substitution by treatment with methyl thioglycolate D2 in the presence of a base (K$_2$CO$_3$/DMF),

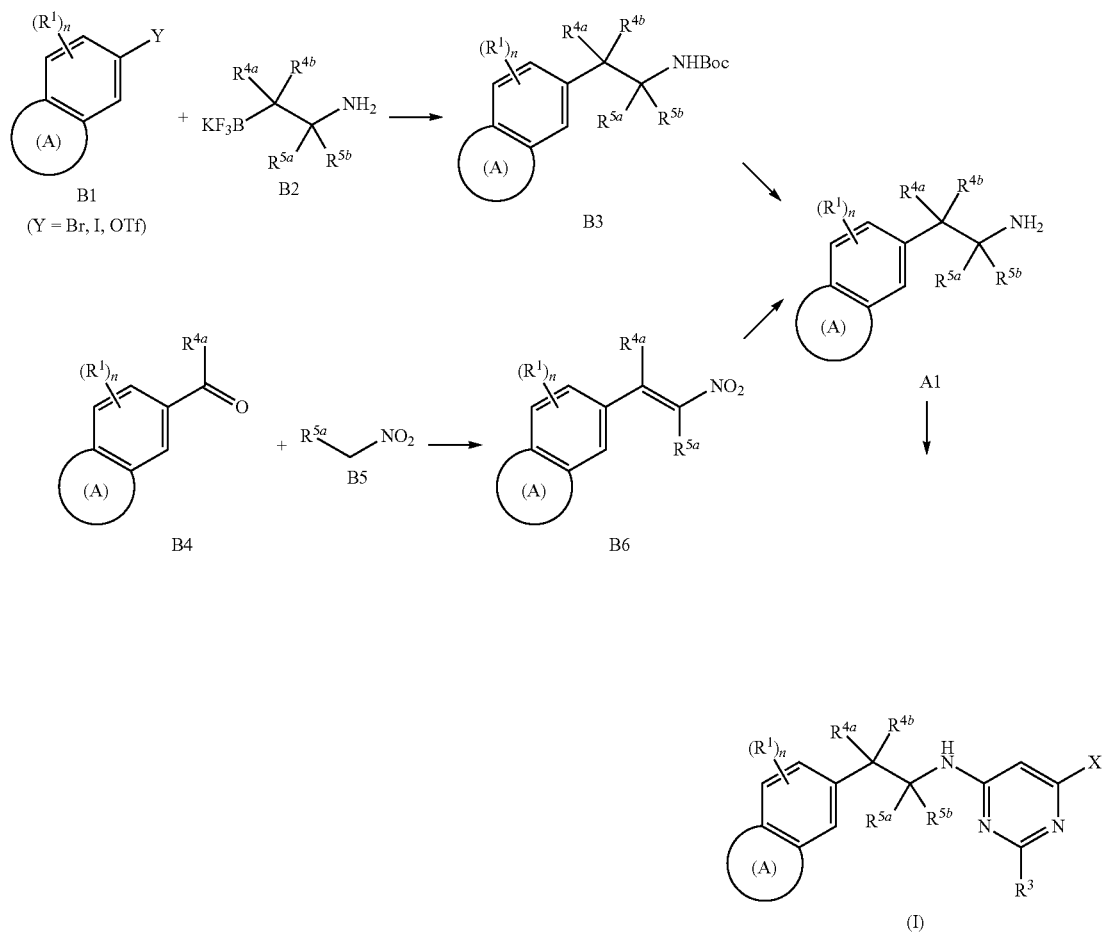

The specific preparation of β-aminoethyl aromatics/heteroaromatics C9 possessing two ortho-substituents (R$^{1a}$ and R$^{1b}$) is described in scheme 3. Derivatives C9 can be synthesized with a directed-metalation based approach by using the methoxymethyl (MOM) moiety as an ortho-directing group. MOM-protected derivatives (C2/C5) can be accessed from the corresponding hydroxy-aromatics/heteroaromatics C1 and C4 (NaH/MeOCH$_2$Cl/DMF) and can be converted regioselectively to the corresponding derivatives C3 via ortho-lithiation (n-BuLi/THF/−78° C.) and subsequent quenching with the appropriate electrophilic and the benzothiophene derivatives D3 can result from a subsequent ring closure at elevated temperatures. Alkaline hydrolysis of the ester functionality in D3 followed by copper-mediated decarboxylation of the resulting benzothiophene-2-carboxylic acids (CuO/DMF/140° C.) can provide derivatives 4. A subsequent Suzuki-Miyaura aminoethylation of bromobenzothiophenes D4 using Boc-protected potassium 3-aminoethyltrifluoroborates B2 can furnish derivatives D5 that can be converted to primary amines D6 after Boc-deprotection under acidic conditions. Finally, target products D7 corresponding to compounds of formula (I) can be obtained with the sequences described in scheme 1.

Scheme 3.
Preparation of substituted β-aminoethyl aromatics/heteroaromatics C9 possessing ortho-substituents $R^{1a}$ and $R^{1b}$; in scheme 3, substituents $R^{1a}$ and $R^{1b}$ are as defined for the substituent R1.
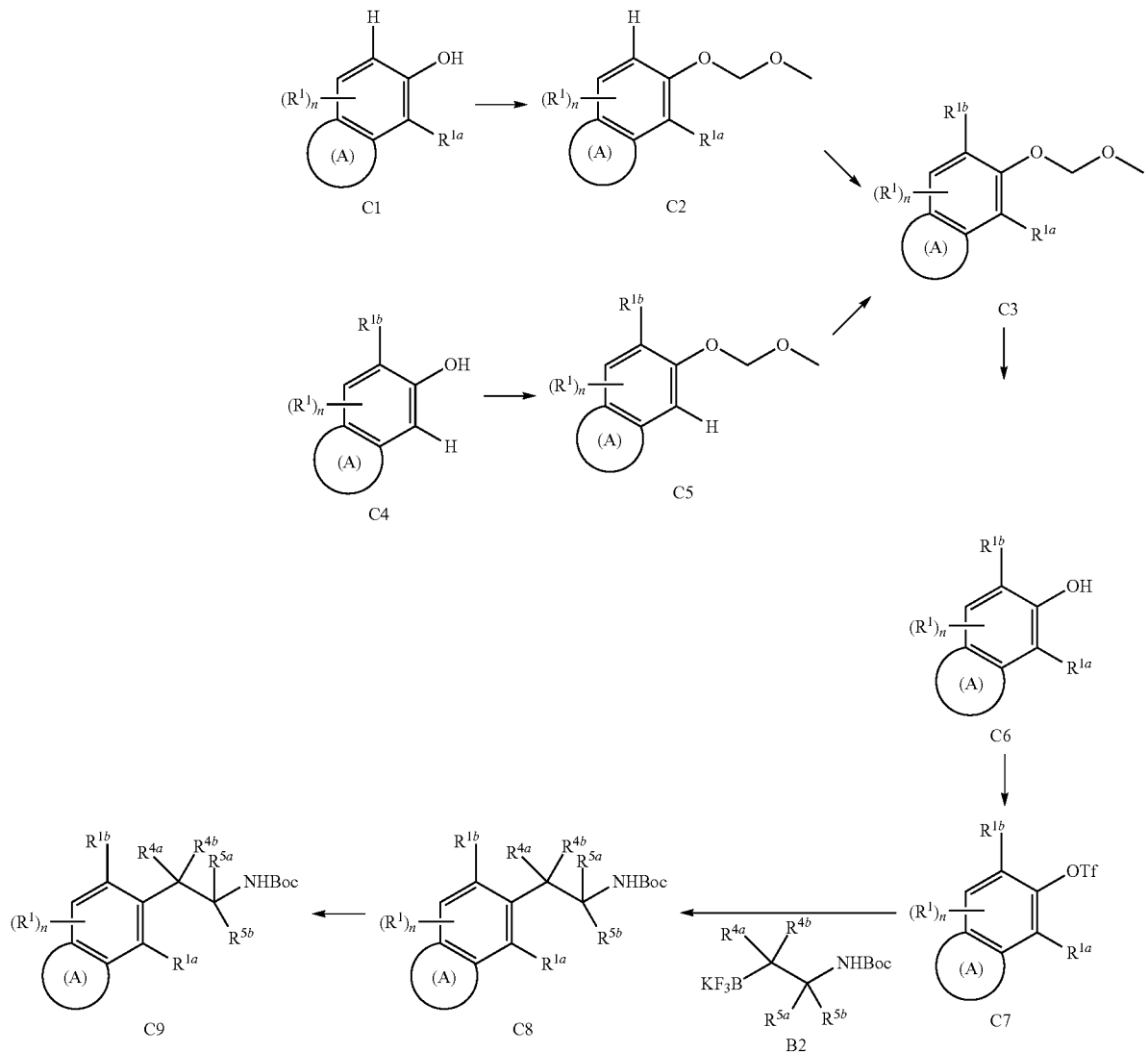
Scheme 4. Preparation of substituted benzothiophenes D7 corresponding to compounds of formula (I); in scheme 4, Z represents F or Cl.
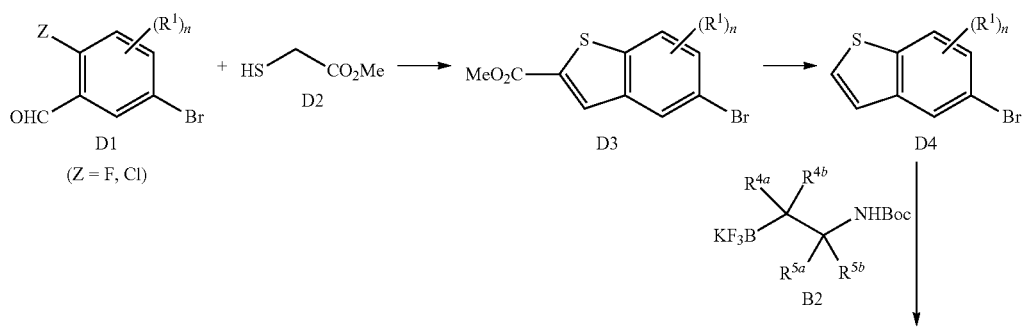

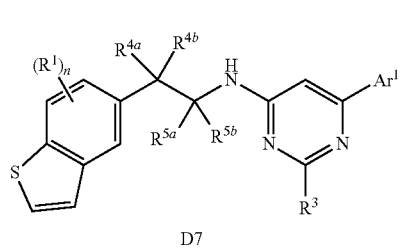
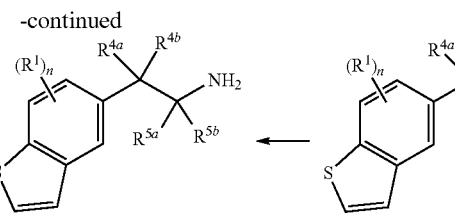

Substituted benzofurans corresponding to compounds of formula (I) can be prepared according to the synthetic route shown in scheme 5. Ortho-hydroxybenzaldehydes E1 can be converted to the corresponding phenoxyacetic acids E3 via O-alkylation with ethyl bromoacetate E2 followed by saponification of the ester functionality. Subsequent heating of the resulting carboxylic acids E3 with sodium acetate in acetic anhydride can deliver the substituted benzofurans E4. Suzuki-Miyaura aminoethylation of bromobenzofurans E4 using Boc-protected potassium β-aminoethyltrifluoroborates B2 can then furnish derivatives E5 that can be converted to primary amines E6 after Boc-deprotection under acidic conditions. Target products E7 corresponding to compounds of formula (I) can be finally obtained from E6 with the preparations described in scheme 1.

LC-MS data (retention time $t_R$ is given in min; molecular weight obtained from the mass spectrum is given in g/mol) using the conditions listed below. In cases where compounds of the present invention appear as a mixture of conformational isomers, particularly visible in their LC-MS spectra, the retention time of the most abundant conformer is given. In some cases compounds are isolated after purification in form of the corresponding ammonium salt (*1), or the respective formic acid salt (*2); such compounds are marked accordingly.

Analytical LC-MS Equipment:
  HPLC pump: Binary gradient pump, Agilent G4220A or equivalent
  Autosampler: Gilson LH215 (with Gilson 845z injector) or equivalent Scheme 5. Preparation of substituted benzofurans E7 corresponding to compounds of formula (I).

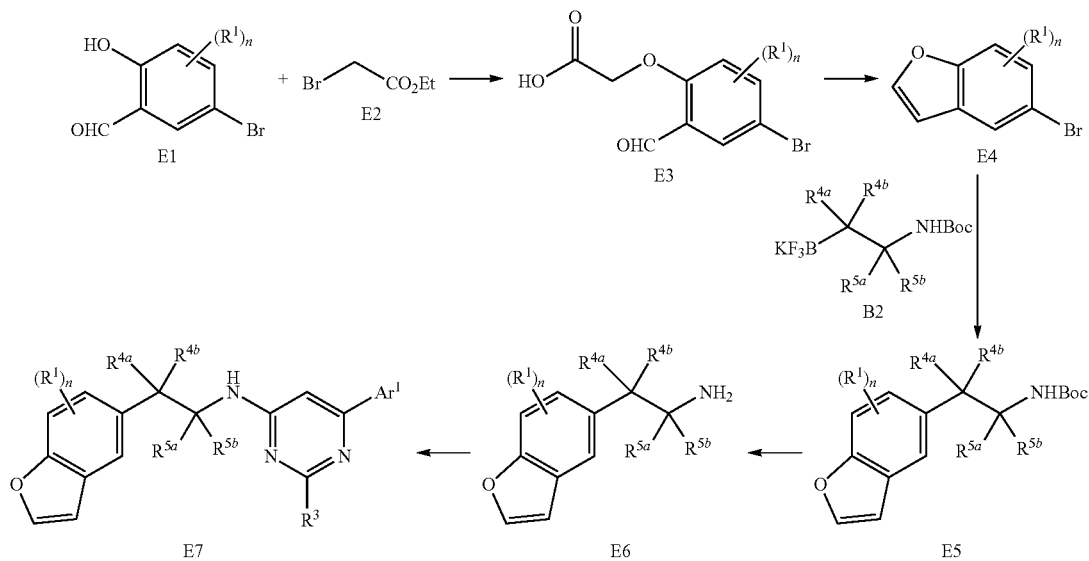

The following examples are provided to illustrate the invention. These examples are illustrative only and should not be construed as limiting the invention in any way.

EXPERIMENTAL PART

I. Chemistry

All temperatures are stated in ° C. Commercially available starting materials were used as received without further purification. Unless otherwise specified, all reactions were carried out in oven-dried glassware under an atmosphere of nitrogen. Compounds were purified by flash column chromatography on silica gel or by preparative HPLC. Compounds described in the invention are characterised by Column compartment: Dionex TCC-3000RS or equivalent
  Degasser: Dionex SRD-3200 or equivalent
  Make-up pump: Dionex HPG-3200SD or equivalent
  DAD detector: Agilent G4212A or equivalent
  MS detector: Single quadrupole mass analyzer, Thermo Finnigan MSQPlus or equivalent
  ELS detector: Sedere SEDEX 90 or equivalent
LC-MS with Acidic Conditions
  Method A: Column: Zorbax SB-aq (3.5 μm, 4.6×50 mm). Conditions: MeCN [eluent A]; water+0.04% TFA [eluent B]. Gradient: 95% B→5% B over 1.5 min (flow: 4.5 mL/min). Detection: UV/Vis+MS.

Method B: Column: Zorbax RRHD SB-aq (1.8 μm, 2.1×50 mm). Conditions: MeCN [eluent A]; water+0.04% TFA [eluent B]. Gradient: 95% B→5% B over 2.0 min (flow: 0.8 mL/min). Detection: UV/Vis+MS.

Method C: Column: Waters XBridge C18 (2.5 μm, 4.6×30 mm). Conditions: MeCN [eluent A]; water+0.04% TFA [eluent B]. Gradient: 95% B→5% B over 1.5 min (flow: 4.5 mL/min). Detection: UV/Vis+MS.

Method D: Waters Acquity Binary, Solvent Manager, MS: Waters SQ Detector, DAD: Acquity UPLC PDA Detector, ELSD: Acquity UPLC ELSD. Column ACQUITY UPLC CSH C18 1.7 um 2.1×50 mm from Waters, thermostated in the Acquity UPLC Column Manager at 60° C. Eluents: A: $H_2O$+0.05% formic acid; B: MeCN+0.045% formic acid. Method: Gradient: 2% B 98% B over 2.0 min. Flow: 1.0 mL/min. Detection: UV 214 nm and ELSD, and MS, $t_R$ is given in min.

LC-MS with Basic Conditions

Method E: Column: Waters BEH $C_{18}$ (3.0×50 mm, 2.5 μm). Eluents: A: Water/$NH_3$ [c($NH_3$)=13 mmol/l], B: MeCN, Method: 5% B to 95% B in 2 min, Flow 1.6 ml/min, Detection UV: 214 nm.

Preparative HPLC Equipment:

Gilson 333/334 HPLC pump equipped with Gilson LH215, Dionex SRD-3200 degasser,

Dionex ISO-3100A make-up pump, Dionex DAD-3000 DAD detector, Single quadrupole mass analyzer MS detector, Thermo Finnigan MSQ Plus, MRA100-000 flow splitter, Polymer Laboratories PL-ELS1000 ELS detector Preparative HPLC with Basic Conditions Column: Waters XBridge (10 μm, 75×30 mm). Conditions: MeCN [eluent A]; water+0.5% $NH_4OH$ (25% aq.) [eluent B]; Gradient see Table 1 (flow: 75 mL/min), the starting percentage of Eluent A (x) is determined depending on the polarity of the compound to purify. Detection: UV/Vis+MS

TABLE 1

| t (min) | 0 | 0.01 | 4.0 | 6.0 | 6.2 | 6.6 |
|---|---|---|---|---|---|---|
| Eluent A (%) | x | x | 95 | 95 | x | x |
| Eluent B (%) | 100-x | 100-x | 5 | 5 | 100-x | 100-x |

Preparative HPLC with Acidic Conditions

Column: Waters Atlantis T3 (10 μm, 75×30 mm). Conditions: MeCN [eluent A]; water+0.5% $HCO_2H$ [eluent B]; Gradient see Table 2 (flow: 75 mL/min), the starting percentage of Eluent A (x) is determined depending on the polarity of the compound to purify. Detection: UV/Vis+MS

TABLE 2

| t (min) | 0 | 0.01 | 4.0 | 6.0 | 6.2 | 6.6 |
|---|---|---|---|---|---|---|
| Eluent A (%) | x | x | 95 | 95 | x | x |
| Eluent B (%) | 100-x | 100-x | 5 | 5 | 100-x | 100-x |

Abbreviations (as Used Hereinbefore or Hereinafter)

AcOH acetic acid
anh. anhydrous
aq. aqueous
atm atmosphere
Boc tert-butoxycarbonyl
BOP (benzotriazol-1-yloxy)-tris(dimethylamino)-phosphonium hexafluorophosphate
BuLi n-butyllithium
d days
DBU 1,8-diazabicyclo[5.4.0]undec-7-ene
DCM dichloromethane
DIBAL/DIBAL-H diisobutylaluminium hydride
DIPEA diisopropyl-ethylamine, Hünig's base
DMAP 4-Dimethylaminopyridine
DMF dimethylformamide
DMSO dimethylsulfoxide
dppf 1,1'-bis(diphenylphosphino)ferrocene
EDC 1-ethyl-3-(3-dimethylaminopropyl)carbodiimide
Et ethyl
$Et_2O$ diethylether
EtOAc ethyl acetate
EtOH ethanol
Ex. example
FC flash chromatography on silica gel
h hour(s)
HATU (1-[Bis(dimethylamino)methylene]-1H-1,2,3-triazolo[4,5-b]pyridinium 3-oxid hexafluorophosphate
hept heptane(s)
HCl hydrochloric acid or hydrogen chloride
HOBT 1-hydroxybenzotriazol
HPLC high performance liquid chromatography
$H_2SO_4$ sulfuric acid
HV high vacuum conditions
$^iBu$ isobutyl
$^iPr$ isopropyl
LAH Lithium aluminium hydride
LC-MS liquid chromatography-mass spectrometry
Lit. Literature
M mol/l
Me methyl
MeCN acetonitrile
MeOH methanol
$MgSO_4$ magnesium sulfate
mL milliliter
min minute(s)
MOM methoxymethyl
MW microwave
$NaHCO_3$ sodium hydrogencarbonate
NaOH sodium hydroxide
NMP N-methyl-2-pyrrolidone
$^iPr$ n-propyl
OAc acetate
$Pd(OAc)_2$ palladium(II) acetate
$Pd_2(dba)_3$ tris(dibenzylideneacetone)dipalladium(0)
$PdCl_2(PPh_3)_2$ bis(triphenylphosphine)palladium(II) dichloride
$Pd(dppf)Cl_2$ [1,1'-bis(diphenylphosphino)ferrocene]dichloropalladium(II)
$Pd(dppf)Cl_2$-DCM [1,1'-bis(diphenylphosphino)-ferrocene]dichloropalladium (II) complex with dichloromethane
$Pd(PPhs)_4$ tetrakis(triphenylphosphine)palladium(0)
Ph phenyl
$PPh_3$ triphenyl phosphine
prep. Preparative
PTFE polytetrafluoroethylene
PyBOP (benzotriazol-1-yl-oxy)-tripyrrolidino-phosphonium hexafluorophosphate
rac racemic
RM reaction mixture RT room temperature
RuPhos 2-dicyclohexylphosphino-2',6'-diisopropoxybiphenyl
s second(s)
sat. saturated (if not indicated otherwise: sat. aq.)
Selectfluor 1-chloromethyl-4-fluoro-1,4-diazoniabicyclo[2.2.2]octane bis(tetrafluoroborate)
tBu tert-butyl=tertiary butyl
TEA triethylamine
Tf trifluoromethanesulfonyl
TFA trifluoroacetic acid
TH F tetrahydrofuran
TLC thin layer chromatography
TMEDA N,N,N',N'-tetramethylethylenediamine
tosyl p-toluene-sulfonyl
$t_R$ retention time
triflate trifluoromethanesulfonate
Xantphos 4,5-bis(diphenylphosphino)-9,9-dimethylxanthene A—Preparation of Precursors and Intermediates A.1. Synthesis of Pyrimidine Halide Derivatives of Formula (A3)

A.1.1. 6-Chloro-N-(2-(3-ethoxynaphthalen-2-yl)ethyl)pyrimidin-4-amine

To a solution of 2-(3-ethoxynaphthalen-2-yl)ethan-1-amine hydrochloride (560 mg, 2.16 mmol) in 2-propanol (22 mL) at RT are added TEA (1.05 mL, 7.54 mmol) and 4,6-dichloropyrimidine (398 mg, 2.67 mmol). The RM is refluxed (90° C.), under nitrogen, for 1.5 h and is then allowed to cool to RT. DCM and water are added and the layers are separated. The aq. layer is extracted twice with DCM and the combined organic layers are then washed with brine, dried over anh. MgSO$_4$, filtered and concentrated under reduced pressure. Purification by FC (from heptane to heptane/EtOAc=1/1) affords 6-chloro-N-(2-(3-ethoxynaphthalen-2-yl)ethyl)pyrimidin-4-amine as an off-white solid (570 mg, 80%). LC-MS A: $t_R$=0.99 min; [M+H]$^+$=328.09.

A.1.1.1. 2-(3-Ethoxynaphthalen-2-yl)ethan-1-amine hydrochloride

To a solution of tert-butyl (2-(3-ethoxynaphthalen-2-yl)ethyl)carbamate (680 mg, 2.16 mmol) in DCM (20 mL) is added 4 M HCl in dioxane (4.30 mL, 17.20 mmol) and the RM is stirred overnight at RT. The RM is then concentrated under reduced pressure affording 2-(3-ethoxynaphthalen-2-yl)ethan-1-amine hydrochloride as a pale yellow solid (560 mg, quantitative). LC-MS A: $t_R$=0.62 min; [M+H]$^+$=216.16.

A.1.1.2. Tert-butyl (2-(3-ethoxynaphthalen-2-yl)ethyl)carbamate

A mixture of 2-bromo-3-ethoxynaphthalene (682 mg, 2.66 mmol), potassium (2-((tert-butoxycarbonyl)amino)ethyl)trifluoroborate (751 mg, 2.99 mmol) and cesium carbonate (2.658 g, 8.15 mmol) in toluene (15 mL) and water (5 mL) is degassed three times. Palladium(II) acetate (30.6 mg, 0.13 mmol) and RuPhos (134 mg, 0.27 mmol) are then added and the mixture is heated to 95° C., under nitrogen, overnight. The RM is allowed to cool to RT. Water is added and the RM is extracted twice with EtOAc. The combined organic layers are then washed with brine, dried over anh. MgSO$_4$, filtered and concentrated under reduced pressure. Purification by FC (from heptane to heptane/EtOAc=1/1) affords tert-butyl (2-(3-ethoxynaphthalen-2-yl)ethyl)carbamate as an off-white solid (680 mg, 81%). LC-MS A: $t_R$=0.99 min: [M+H]$^+$=316.19.

A.1.1.3. 2-Bromo-3-ethoxynaphthalene

A solution of 3-bromonaphthalen-2-ol (600 mg, 2.66 mmol) in anh. DMF (14 mL) is treated at RT with cesium carbonate (868 mg, 2.66 mmol) and iodoethane (0.235 mL, 2.92 mmol) and the RM is stirred at RT, under nitrogen, for 1.25 h. Water is added and the mixture is extracted three times with Et$_2$O. The combined organic layers are then washed twice with water, dried over anh. MgSO$_4$, filtered and concentrated under reduced pressure affording 2-bromo-3-ethoxynaphthalene as a colorless solid (682 mg, quantitative). LC-MS A: $t_R$=0.97 min; no ionization.

A.1.2. 6-Chloro-N-(2-(1-methylnaphthalen-2-yl)ethyl)pyrimidin-4-amine

The title compound is prepared according to the procedure described above in A.1.1. using 2-(1-methylnaphthalen-2-yl)ethan-1-amine hydrochloride. LC-MS A: $t_R$=0.94 min; [M+H]$^+$=298.08.

A.1.2.1. 2-(1-Methylnaphthalen-2-yl)ethan-1-amine hydrochloride

The title compound is prepared according to the procedure described above in A.1.1.1. using tert-butyl (2-(1-methylnaphthalen-2-yl)ethyl)carbamate. LC-MS A: $t_R$=0.58 min; [M+H]$^+$=186.21.

A.1.2.2. Tert-butyl (2-(1-methylnaphthalen-2-yl)ethyl)carbamate

A mixture of 2-bromo-1-methylnaphthalene (1.000 g, 4.52 mmol), potassium (2-((tert-butoxycarbonyl)amino)ethyl)trifluoroborate (1.147 g, 4.56 mmol) and cesium carbonate (4.421 g, 13.56 mmol) in toluene (30 mL) and water (10 mL) is degassed three times. Pd(dppf)Cl$_2$ (185 mg, 0.22 mmol) is then added and the mixture is heated to 95° C., under nitrogen, overnight. The RM is allowed to cool to RT. Water is added and the RM is extracted twice with EtOAc. The combined organic layers are then washed with brine, dried over anh. MgSO$_4$, filtered and concentrated under reduced pressure. Purification by FC (heptane/EtOAc=7/3) affords tert-butyl (2-(1-methylnaphthalen-2-yl)ethyl)carbamate as a pale yellow solid (933 mg, 72%). LC-MS A: $t_R$=0.97 min; no ionization.

A.1.3. 6-Chloro-N-(2-(8-fluoronaphthalen-2-yl)ethyl)pyrimidin-4-amine

The title compound is prepared according to the procedure described above in A.1.1. using 2-(8-fluoronaphthalen-2-yl)ethan-1-amine hydrochloride. LC-MS B: $t_R$=1.03 min; [M+H]$^+$=302.23.

A.1.3.1. 2-(8-Fluoronaphthalen-2-yl)ethan-1-amine hydrochloride

The title compound is prepared according to the procedure described above in A.1.1.1. using tert-butyl (2-(8-fluoronaphthalen-2-yl)ethyl)carbamate. LC-MS B: $t_R$=0.59 min; [M+H]$^+$=190.22.

A.1.3.2. Tert-butyl (2-(8-fluoronaphthalen-2-yl)ethyl)carbamate

The title compound is prepared according to the procedure described above in A.1.1.2. using 8-fluoronaphthalen-2-yl trifluoromethanesulfonate. LC-MS B: $t_R$=1.05 min; no ionization.

A.1.3.3. 8-Fluoronaphthalen-2-yl trifluoromethanesulfonate

A solution of 8-fluoronaphthalen-2-ol (640 mg, 3.87 mmol) and TEA (1.40 mL, 10.04 mmol) in anh. DCM (38 mL) is treated portionwise at RT with 1,1,1-trifluoro-N-phenyl-N-((trifluoromethyl)sulfonyl)methanesulfonamide (1.678 g, 4.65 mmol) and the RM is stirred at RT, under nitrogen, overnight. The RM is then concentrated under reduced pressure. Purification by FC (from heptane to heptane/EtOAc=7/3) affords 8-fluoronaphthalen-2-yl trifluoromethanesulfonate as a yellow oil (1.33 g, quantitative). LC-MS B: $t_R$=1.09 min; no ionization.

A.1.4. 6-Chloro-N-(2-(3-methoxynaphthalen-2-yl)ethyl)pyrimidin-4-amine

The title compound is prepared according to the procedure described above in A.1.1. using 2-(3-methoxynaphthalen-2-yl)ethan-1-amine. LC-MS A: $t_R$=0.94 min; $[M+H]^+$=314.08.

A.1.4.1. 2-(3-Methoxynaphthalen-2-yl)ethan-1-amine

To a solution of 3-methoxy-2-naphthaldehyde (2.00 g, 10.74 mmol) in nitromethane (20 mL) are added successively 4A molecular sieves (100 mg), butylamine (0.126 mL, 1.27 mmol) and acetic acid (0.125 mL, 2.18 mmol). The RM is heated to 90° C., under nitrogen, for 30 min. The RM is then filtered and the filtrate is concentrated under reduced pressure. Purification by FC (heptane/DCM=1/1) affords 2-methoxy-3-(2-nitrovinyl)naphthalene as a yellow solid (1.49 g, 61%). LC-MS A: $t_R$=0.95 min; no ionisation To a cooled (0° C.) solution of 2-methoxy-3-(2-nitrovinyl)naphthalene (1.49 g, 6.49 mmol) in anh. THF (10 mL) is added dropwise a solution of lithium aluminum hydride (2 M in THF, 11.4 mL, 22.8 mmol). The mixture is then heated at reflux (80° C.), under nitrogen, for 15 min. The cooled (0° C.) RM is treated successively with water (0.9 mL), 15% aq. NaOH (0.9 mL), and water (2.6 mL). The resulting heterogeneous mixture is then filtered and the separated solid is washed with Et$_2$O. The layers of the filtrate are separated and the aqueous layer is extracted with Et$_2$O. The combined organic layers are then dried over anh. MgSO$_4$, filtered and concentrated under reduced pressure affording 2-(3-methoxynaphthalen-2-yl)ethan-1-amine as a yellow oil (1.30 g, 99%). LC-MS A: $t_R$=0.58 min; $[M+H]^+$=202.20.

A.1.5. 6-Chloro-N-(2-(naphthalen-2-yl)ethyl)pyrimidin-4-amine

The title compound is prepared according to the procedure described above in A.1.1. using 2-(naphthalen-2-yl)ethan-1-amine. LC-MS A: $t_R$=0.91 min; $[M+H]^+$=283.93.

A.1.5.1. 2-(Naphthalen-2-yl)ethan-1-amine

The title compound is prepared according to the procedure described above in A.1.4.1. using 2-naphthaldehyde. LC-MS A: $t_R$=0.55 min; $[M+H]^+$=172.12.

A.1.6. 6-Chloro-N-(2-(3-methylnaphthalen-2-yl)ethyl)pyrimidin-4-amine

The title compound is prepared according to the procedure described above in A.1.1. using 2-(3-methylnaphthalen-2-yl)ethan-1-amine. LC-MS A: $t_R$=0.95 min; $[M+H]^+$=298.11.

A.1.6.1. 2-(3-Methylnaphthalen-2-yl)ethan-1-amine

The title compound is prepared according to the procedure described above in A.1.4.1. using 3-methyl-2-naphthaldehyde. LC-MS A: $t_R$=0.59 min: $[M+H]^+$=186.28.

A.1.6.2. 3-Methyl-2-naphthaldehyde

To a cooled (−78° C.) solution of 2-bromo-3-methylnaphthalene (733 mg, 3.31 mmol) in anh. THF (44 mL) is added a solution of BuLi (1.6 M in hexanes, 2.10 mL, 3.36 mmol) and the RM is further stirred at −78° C., under nitrogen, for 2 min. A solution of anh. DMF (363 mg, 4.97 mmol) in anh. THF (3 mL) is then added to the previous mixture and stirring at −78° C. is continued for 45 min. The RM is then treated dropwise with sat. aq. NH$_4$Cl (10 mL) and is allowed to warm-up to RT. Water (40 mL) and Et$_2$O (100 mL) are then added and the layers are separated. The aq. layer is further extracted with Et$_2$O and the combined organic layers are dried over anh. MgSO$_4$, filtered and concentrated under reduced pressure. Purification by FC (heptane/DCM=1/1) affords 3-methyl-2-naphthaldehyde as a colorless solid (0.42 g, 74%). LC-MS A: $t_R$=0.87 min; no ionization.

A.1.7. 6-Chloro-N-(2-(1-fluoronaphthalen-2-yl)ethyl)pyrimidin-4-amine

The title compound is prepared according to the procedure described above in A.1.1. using 2-(1-fluoronaphthalen-2-yl)ethan-1-amine hydrochloride. LC-MS A: $t_R$=0.93 min; $[M+H]^+$=302.04.

A.1.7.1. 2-(1-Fluoronaphthalen-2-yl)ethan-1-amine hydrochloride

The title compound is prepared according to the procedure described above in A.1.1.1. using tert-butyl (2-(1-fluoronaphthalen-2-yl)ethyl)carbamate. LC-MS A: $t_R$=0.56 min; $[M+H]^+$=190.16.

A.1.7.2. Tert-butyl (2-(1-fluoronaphthalen-2-yl)ethyl)carbamate

The title compound is prepared according to the procedure described above in A.1.2.2. using 2-bromo-1-fluoronaphthalene. LC-MS A: $t_R$=0.95 min; no ionization.

A.1.8. 6-Chloro-N-(2-(3-(difluoromethoxy)naphthalen-2-yl)ethyl)pyrimidin-4-amine The title compound is prepared according to the procedure described above in A.1.1. using 2-(3-(difluoromethoxy)naphthalen-2-yl)ethan-1-amine hydrochloride. LC-MS A: $t_R$=0.95 min; $[M+H]^+$=350.11.

A.1.8.1. 2-(3-(Difluoromethoxy)naphthalen-2-yl)ethan-1-amine hydrochloride

The title compound is prepared according to the procedure described above in A.1.1.1. using tert-butyl (2-(3-

(difluoromethoxy)naphthalen-2-yl)ethyl)carbamate. LC-MS A: $t_R$=0.63 min; [M+H]$^+$=238.17.

A.1.8.2. Tert-butyl (2-(3-(difluoromethoxy)naphthalen-2-yl)ethyl)carbamate

The title compound is prepared according to the procedure described above in A.1.1.2. using 2-bromo-3-(difluoromethoxy)naphthalene. LC-MS A: $t_R$=0.97 min; no ionization.

A.1.8.3. 2-Bromo-3-(difluoromethoxy)naphthalene

To a cooled (0° C.) solution of 3-bromonaphthalen-2-ol (515 mg, 2.29 mmol) in MeCN (13 mL) and water (13 mL) is added potassium hydroxide (2.56 g, 45.62 mmol). The mixture is stirred at RT for 30 min, and is then cooled to −78° C. Diethyl (bromodifuoromethyl)phosphonate (1.24 g, 4.57 mmol) is added in one portion to the cooled mixture and stirring is then continued at RT overnight. Et$_2$O is added, the layers are separated and the aqueous layer is further extracted with Et$_2$O. The combined organic layers are successively washed with 1 M aq. NaOH, water and brine and are then dried over anh. MgSO$_4$, filtered and concentrated under reduced pressure. Purification by FC (from heptane to heptane/EtOAc=3/7) affords 2-bromo-3-(difluoromethoxy)naphthalene as a pale yellow oil (432 mg, 69%). LC-MS A: $t_R$=0.95 min; no ionization.

A.1.9. 6-Chloro-N-(2-(3-chloronaphthalen-2-yl)ethyl)pyrimidin-4-amine

The title compound is prepared according to the procedure described above in A.1.1. using 2-(3-chloronaphthalen-2-yl)ethan-1-amine. LC-MS A: $t_R$=0.96 min; [M+H]$^+$=317.99.

A.1.9.1. 2-(3-Chloronaphthalen-2-yl)ethan-1-amine

The title compound is prepared according to the procedure described above in A.1.4.1. using 3-chloro-2-naphthaldehyde. LC-MS A: $t_R$=0.60 min; [M+H]$^+$=206.27.

A.1.9.2. 3-Chloro-2-naphthaldehyde

To a cooled (0° C.) suspension of pyridinium chlorochromate (906 mg, 4.20 mmol) in DCM (10 mL) is added a solution of (3-chloronaphthalen-2-yl)methanol (540 mg, 2.80 mmol) in DCM (25 mL). The resulting black suspension is further stirred at 0° C., under nitrogen, for 15 min and then at RT overnight. The RM is then filtered over celite and the filtrate is concentrated under reduced pressure. Purification by FC (DCM) affords 3-chloro-2-naphthaldehyde as a pale yellow solid (504 mg, 94%). LC-MS A: $t_R$=0.89 min; no ionization.

A.1.9.3. (3-Chloronaphthalen-2-yl)methanol

To a cooled (−78° C.) solution of methyl 3-chloro-2-naphthoate (660 mg, 2.99 mmol) in anh. toluene (20 mL) is added dropwise a solution of DIBAL-H (1 M in toluene, 9.0 mL, 9.0 mmol). The mixture is further stirred at −78° C., under nitrogen, for 15 min and is then allowed to warm-up to 0° C. Stirring at 0° C. is continued for 30 min, and the cooled RM is treated successively with water (8 mL) and with 1 N aq. NaOH (16 mL). The mixture is then allowed to warm-up to RT, EtOAc is added and the layers are separated. The aqueous layer is extracted twice with EtOAc. The combined organic layers are washed with brine, dried over anh. MgSO$_4$, filtered and concentrated under reduced pressure affording (3-chloronaphthalen-2-yl)methanol as a pale pink solid (540 mg, 94%). LC-MS A: $t_R$=0.79 min; no ionization.

A.1.9.4. Methyl 3-chloro-2-naphthoate

To a solution of 3-chloro-2-naphthoic acid (770 mg, 3.18 mmol) in anh. DMF (18 mL) at RT are added cesium carbonate (1.457 g, 4.47 mmol) and iodomethane (0.469 mL, 7.46 mmol) and the RM is stirred at RT, under nitrogen, for 30 min. Water and Et$_2$O are added and the layers are separated. The aqueous layer is extracted twice with Et$_2$O and the combined organic layers are washed with brine, dried over anh. MgSO$_4$, filtered and concentrated under reduced pressure. Purification by FC (from heptane to heptane/EtOAc=7/3) affords methyl 3-chloro-2-naphthoate as an orange solid (660 mg, 94%). LC-MS A: $t_R$=0.90 min; [M+H]$^+$=221.20.

A.1.9.5. 3-Chloro-2-naphthoic acid

To a cooled (0° C.) solution of 3-amino-2-naphthoic acid (700 mg, 3.18 mmol) in MeCN (16 mL), water (8 mL) and 12 M aq. HCl (2.15 mL) is added dropwise a solution of sodium nitrite (241 mg, 3.50 mmol) in water (2.5 mL). The RM is further stirred at 0° C. for 1 h and a solution of copper(I) chloride (1.888 g, 19.10 mmol) in 2 M aq. HCl (5 mL) is then added dropwise to the cooled mixture. Stirring at 0° C. is continued for 10 min and the mixture is then heated to 50° C. for 45 min. The resulting RM is then allowed to cool to RT and is poured onto ice/water. The mixture is extracted three times with EtOAc and the combined organic layers are washed with brine, dried over anh. MgSO$_4$, filtered and concentrated under reduced pressure affording 3-chloro-2-naphthoic acid as a brown solid (770 mg, quantitative). LC-MS A: $t_R$=0.77 min; no ionization.

A.1.10. 6-Chloro-N-(2-(3-isopropoxynaphthalen-2-yl)ethyl)pyrimidin-4-amine

The title compound is prepared according to the procedure described above in A.1.1. using 2-(3-isopropoxynaphthalen-2-yl)ethan-1-amine hydrochloride. LC-MS A: $t_R$=1.01 min; [M+H]$^+$=342.16.

A.1.10.1. 2-(3-Isopropoxynaphthalen-2-yl)ethan-1-amine hydrochloride

The title compound is prepared according to the procedure described above in A.1.1.1. using tert-butyl (2-(3-isopropoxynaphthalen-2-yl)ethyl)carbamate. LC-MS A: $t_R$=0.68 min; [M+H]$^+$=230.20.

A.1.10.2. Tert-butyl (2-(3-isopropoxynaphthalen-2-yl)ethyl)carbamate

The title compound is prepared according to the procedure described above in A.1.1.2. using 2-bromo-3-isopropoxynaphthalene. LC-MS A: $t_R$=1.02 min; [M+H]$^+$=330.19.

A.1.10.3. 2-Bromo-3-isopropoxynaphthalene

To a solution of 3-bromonaphthalen-2-ol (600 mg, 2.66 mmol) in anh. DMF (14 mL) at RT are added cesium carbonate (954 mg, 2.93 mmol) and 2-iodopropane (0.292 mL, 2.93 mmol) and the RM is heated to 60° C. for 6 h. The RM is allowed to cool to RT, water and Et$_2$O are added and the layers are separated. The aqueous layer is extracted twice with Et$_2$O and the combined organic layers are washed with brine, dried over anh. MgSO$_4$, filtered and concentrated under reduced pressure affording 2-bromo-3-isopropoxynaphthalene as an orange oil (749 mg, quantitative). LC-MS A: $t_R$=1.00 min; no ionization.

A.1.11. 6-Chloro-N-(2-(3-(methylamino)naphthalen-2-yl)ethyl)pyrimidin-4-amine The title compound is prepared according to the procedure described above in A.1.1. using 3-(2-aminoethyl)-N-methylnaphthalen-2-amine hydrochloride. LC-MS B: $t_R$=0.94 min; [M+H]$^+$=313.18.

A.1.11.1. 3-(2-Aminoethyl)-N-methylnaphthalen-2-amine hydrochloride

The title compound is prepared according to the procedure described above in A.1.1.1. using tert-butyl (2-(3-(methylamino)naphthalen-2-yl)ethyl)carbamate. LC-MS B: $t_R$=0.58 min; [M+H]$^+$=201.17.

A.1.11.2. Tert-butyl (2-(3-(methylamino)naphthalen-2-yl)ethyl)carbamate

The title compound is prepared according to the procedure described above in A.1.1.2. using 3-iodo-N-methylnaphthalen-2-amine. LC-MS B: $t_R$=0.97 min; [M+H]$^+$=301.22.

A.1.11.3. 3-Iodo-N-methylnaphthalen-2-amine

To a solution of 3-iodonaphthalen-2-amine (800 mg, 2.97 mmol) in anh. DMF (4 mL) at RT are added potassium carbonate (616 mg, 4.46 mmol) and iodomethane (0.374 mL, 5.95 mmol) and the RM is stirred at RT for 5.5 h. Water and Et$_2$O are added and the layers are separated. The aqueous layer is extracted twice with Et$_2$O and the combined organic layers are washed with brine, dried over anh. MgSO$_4$, filtered and concentrated under reduced pressure. Purification by FC (from heptane to heptane/EtOAc=7/3) affords 3-iodo-N-methylnaphthalen-2-amine as a yellow oil. LC-MS B: $t_R$=1.04 min; [M+H]$^+$=284.05.

A.1.12. 6-Chloro-N-(2-(1-chloronaphthalen-2-yl)ethyl)pyrimidin-4-amine

The title compound is prepared according to the procedure described above in A.1.1. using 2-(1-chloronaphthalen-2-yl)ethan-1-amine hydrochloride. LC-MS A: $t_R$=0.96 min; [M+H]$^+$=317.99.

A.1.12.1. 2-(1-Chloronaphthalen-2-yl)ethan-1-amine hydrochloride

The title compound is prepared according to the procedure described above in A.1.1.1. using tert-butyl (2-(1-chloronaphthalen-2-yl)ethyl)carbamate. LC-MS A: $t_R$=0.59 min; [M+H]$^+$=206.13.

A.1.12.2. Tert-butyl (2-(1-chloronaphthalen-2-yl)ethyl)carbamate

The title compound is prepared according to the procedure described above in A.1.2.2. using 2-bromo-1-chloronaphthalene. LC-MS A: $t_R$=0.98 min; no ionization.

A.1.13. 6-Chloro-N-(2-(3-((triisopropylsilyl)ethynyl)naphthalen-2-yl)ethyl)pyrimidin-4-amine The title compound is prepared according to the procedure described above in A.1.1. using 2-(3-((triisopropylsilyl)ethynyl)naphthalen-2-yl)ethan-1-amine hydrochloride. LC-MS A: $t_R$=1.20 min; [M+H]$^+$=464.16.

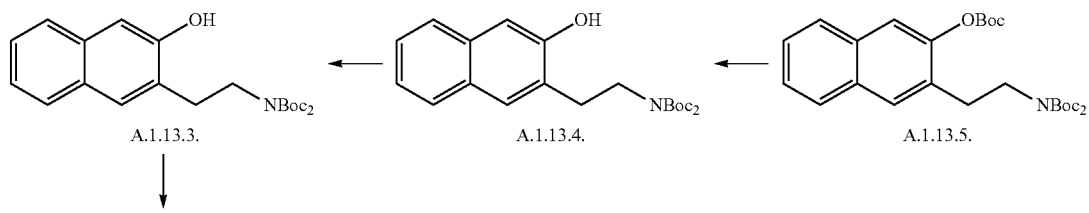

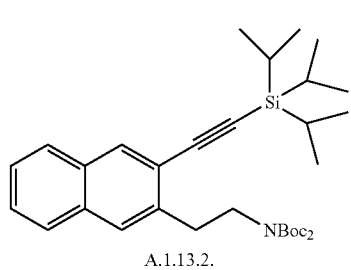 A.1.13.2. → 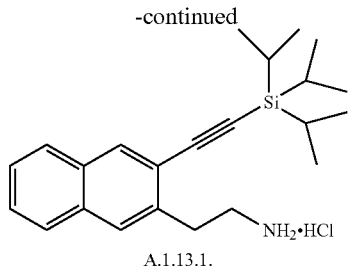 A.1.13.1. → 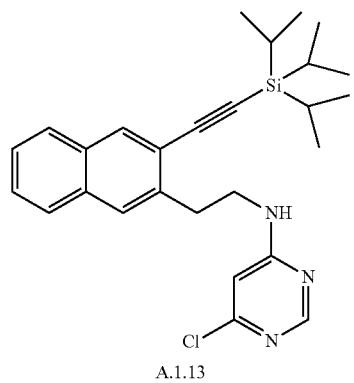 A.1.13

A.1.13.1. 2-(3-((Triisopropylsilyl)ethynyl)naphthalen-2-yl)ethan-1-amine hydrochloride The title compound is prepared according to the procedure described above in A.1.1.1. using the intermediate A.1.13.2. LC-MS A: $t_R$=0.90 min; [M+H]$^+$=352.17.

A.1.13.2. Preparation of the Intermediate A.1.13.2

To a solution of intermediate A.1.13.3. (412 mg, 0.79 mmol) in TEA (7 mL) are added successively copper(I) iodide (21 mg, 0.11 mmol) and PdCl$_2$(PPh$_3$)$_2$ (28 mg, 0.039 mmol). The mixture is then degassed with nitrogen and (triisopropylsilyl)acetylene (0.356 mL, 1.59 mmol) is added. The RM is heated to 50° C., under nitrogen, overnight. The RM is then filtered over celite and the filtrate is concentrated under reduced pressure. Purification by FC (from heptane to heptane/EtOAc=4/1) affords intermediate A.1.13.2. as a brown oil (361 mg, 83%). LC-MS A: $t_R$=1.27 min; no ionization.

A.1.13.3. Preparation of the Intermediate A.1.13.3

A solution of intermediate A.1.13.4. (390 mg, 1.01 mmol) and TEA (0.365 mL, 2.62 mmol) in anh. DCM (10 mL) is treated portionwise at RT with 1,1,1-trifluoro-N-phenyl-N-((trifuoromethyl)sulfonyl)methanesulfonamide (617 mg, 1.71 mmol) and the RM is stirred at RT, under nitrogen, overnight. The RM is then concentrated under reduced pressure. Purification by FC (from heptane to heptane/EtOAc=9/1) affords intermediate A.1.13.3. as a colorless solid (411 mg, 79%). LC-MS A: $t_R$=1.12 min; no ionization.

A.1.13.4. Preparation of the Intermediate A.1.13.4

A suspension of intermediate A.1.13.5. (528 mg, 1.08 mmol) in MeOH (11 mL) is treated at RT with 2.8 M aq. NaOH (3.85 mL, 10.78 mmol) and the RM is heated to 55° C. for 20 min. The RM is then allowed to cool to RT and MeOH is removed under reduced pressure. Sat. aq. NH$_4$Cl is added, the layers are separated and the aqueous layer is extracted three times with DCM. The combined organic layers are washed with brine, dried over anh. MgSO$_4$, filtered and concentrated under reduced pressure affording intermediate A.1.13.4. as an off-white solid (390 mg, 93%). LC-MS A: $t_R$=0.99 min; no ionization.

A.1.13.5. Preparation of the Intermediate A.1.13.5

A solution of intermediate A.1.13.6. (456 mg, 1.18 mmol) in MeCN (12 mL) is treated at RT with di-tert-butyl dicarbonate (337 mg, 1.53 mmol) and 4-(dimethylamino)pyridine (14 mg, 0.11 mmol), and the RM is heated to 60° C. for 1.5 h. A second addition of di-tert-butyl dicarbonate (128 mg, 0.58 mmol) is then performed and heating at 60° C. is continued for 30 min. The RM is allowed to cool to RT, sat. aq. NH$_4$Cl is added, and the layers are separated. The aqueous layer is extracted three times with EtOAc. The combined organic layers are dried over anh. MgSO$_4$, filtered and concentrated under reduced pressure. Purification by FC (from heptane to heptane/EtOAc=1/1) affords intermediate A.1.13.5. as a colorless oil (528 mg, 92%). LC-MS A: $t_R$=1.11 min; no ionization.

A.1.13.6. Tert-butyl (2-(3-((tert-butoxycarbonyl)oxy)naphthalen-2-yl)ethyl)carbamate The title compound is prepared according to the procedure described above in A.1.1.2. using 3-bromonaphthalen-2-yl tert-butyl carbonate. LC-MS A: $t_R$=1.01 min: [M+H]$^+$=388.30.

A.1.13.7. 3-Bromonaphthalen-2-yl tert-butyl carbonate

A solution of 3-bromonaphthalen-2-ol (410 mg, 1.82 mmol) in MeCN (18 mL) is treated at RT with di-tert-butyl dicarbonate (521 mg, 2.37 mmol) and 4-(dimethylamino)pyridine (22 mg, 0.18 mmol). The RM is then heated to 50° C. for 45 min. The RM is allowed to cool to RT, sat. aq. NH$_4$Cl is added, and the layers are separated. The aqueous layer is extracted three times with EtOAc. The combined organic layers are dried over anh. MgSO$_4$, filtered and concentrated under reduced pressure. Purification by FC (from heptane to heptane/EtOAc=1/1) affords 3-bromonaphthalen-2-yl tert-butyl carbonate as a colorless solid (643 mg, quantitative). LC-MS A: $t_R$=1.00 min; no ionization.

A.1.14. 3-(2-((6-Chloropyrimidin-4-yl)amino)ethyl)-2-naphthonitrile

The title compound is prepared according to the procedure described above in A.1.1. using 3-(2-aminoethyl)-2-naphthonitrile hydrochloride. LC-MS A: $t_R$=0.89 min; [M+H]$^+$=309.06.

115

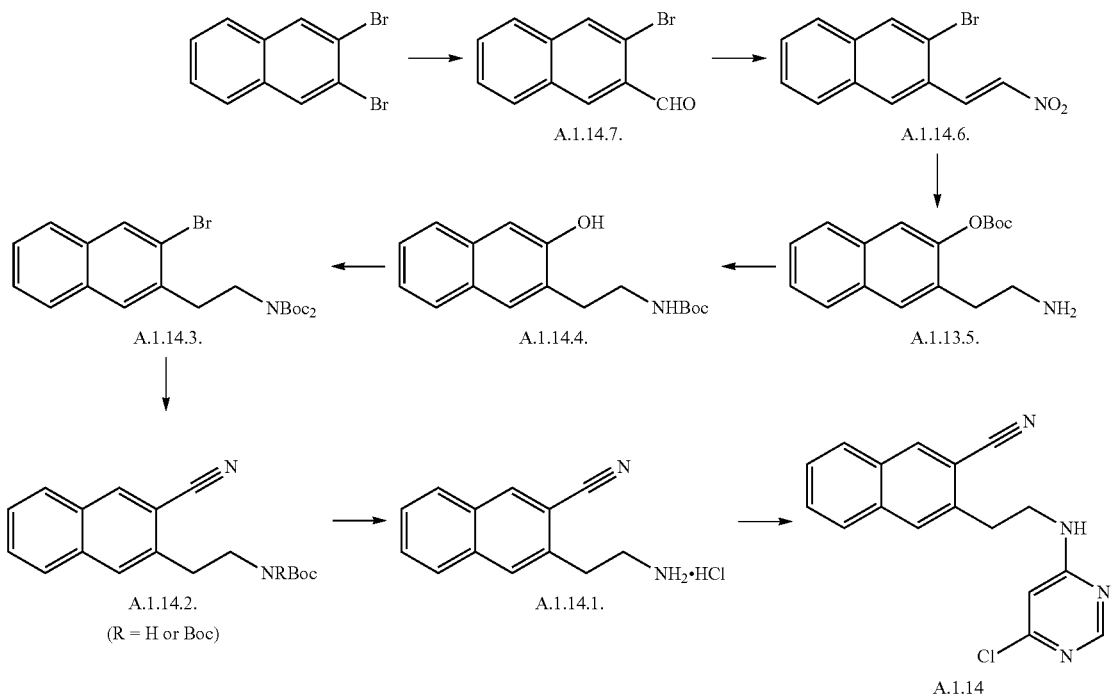

A.1.14.1. 3-(2-Aminoethyl)-2-naphthonitrile hydrochloride

The title compound is prepared according to the procedure described above in A.1.1.1. using intermediate A.1.14.2. (with R=H, Boc). LC-MS A: $t_R$=0.56 min; [M+H]$^+$=197.22.

A.1.14.2. Preparation of Intermediate A.1.14.2

To a solution of intermediate A.1.14.3. (500 mg, 1.11 mmol) in anh. DMF (6 mL) are added successively zinc cyanide (160 mg, 1.33 mmol), Pd$_2$(dba)$_3$ (52 mg, 0.055 mmol), Xantphos (66 mg, 0.11 mmol) and TMEDA (33 μL, 0.22 mmol). The RM is heated to 140° C. for 20 min. The RM is allowed to cool to RT and is then filtered over celite. Water and Et$_2$O are added, the layers are separated and the aqueous layer is extracted twice with Et$_2$O. The combined organic layers are dried over anh. MgSO$_4$, filtered and concentrated under reduced pressure. Purification by FC (from heptane to heptane/EtOAc=85/15) affords intermediate A.1.14.2. (R=Boc) as a pale yellow solid (211 mg, 48%). LC-MS A: $t_R$=1.05 min; no ionisation. Intermediate A.1.14.2. (R=H) is also isolated as a colorless solid (81 mg). LC-MS A: $t_R$=0.92 min; no ionization.

A.1.14.3. Preparation of the Intermediate A.1.14.3

A solution of tert-butyl (2-(3-bromonaphthalen-2-yl)ethyl)carbamate (1.52 g, 4.34 mmol) in MeCN (20 mL) is treated at RT with di-tert-butyl dicarbonate (1.24 g, 5.64 mmol) and 4-(dimethylamino)pyridine (54 mg, 0.43 mmol). The RM is then heated to 50° C. for 15 h. The RM is allowed to cool to RT, sat. aq. NH$_4$Cl is added, and the layers are separated. The aqueous layer is extracted three times with EtOAc. The combined organic layers are dried over anh. MgSO$_4$, filtered and concentrated under reduced pressure.

116

Purification by FC (from heptane to heptane/EtOAc=1/1) affords intermediate A.1.14.3. as an orange oil (1.64 g, 84%). LC-MS A: $t_R$=1.11 min; no ionization.

A.1.14.4. Tert-butyl (2-(3-bromonaphthalen-2-yl)ethyl)carbamate

A cooled (0° C.) solution of 2-(3-bromonaphthalen-2-yl)ethan-1-amine (1.85 g, 7.41 mmol) and DIPEA (2.54 mL, 14.80 mmol) in DCM (25 mL) is treated with a solution of di-tert-butyl dicarbonate (1.94 g, 8.89 mmol) in DCM (10 mL). The RM is further stirred at 0° C. for 15 min and then at RT for 15 h. Water is added and the layers are separated. The organic layer is then washed with brine, dried over anh. MgSO$_4$, filtered and concentrated under reduced pressure. Purification by FC (from heptane to heptane/EtOAc=3/2) affords tert-butyl (2-(3-bromonaphthalen-2-yl)ethyl)carbamate as an orange solid (1.72 g, 66%). LC-MS A: $t_R$=0.99 min; no ionization.

A.1.14.5. 2-(3-Bromonaphthalen-2-yl)ethan-1-amine

95% H$_2$SO$_4$ (0.47 mL) is added dropwise to a cooled (−10° C.) solution of LAH (2 M in THF, 17.20 mL, 34.40 mmol) and the mixture is stirred at −10° C. for 20 min. A solution of 2-bromo-3-(2-nitrovinyl)naphthalene (2.14 g, 7.69 mmol) in anh. THF (25 mL) is then added dropwise and stirring is continued at −10° C. for 25 min and then at RT for 30 min. The RM is cooled to 0° C. and treated successively with 2-propanol (17 mL) and with 2.8 M aq. NaOH (3.4 mL). The resulting suspension is then filtered and the filtrate is concentrated under reduced pressure affording 2-(3-bromonaphthalen-2-yl)ethan-1-amine as a brown gel (1.73 g, 90%). LC-MS A: $t_R$=0.61 min; [M+H]$^+$=250.11.

A.1.14.6. 2-Bromo-3-(2-nitrovinyl)naphthalene

To a solution of 3-bromo-2-naphthaldehyde (1.95 g, 6.91 mmol) in nitromethane (14 mL) are added successively 4A molecular sieves (266 mg), butylamine (81 μL, 0.81 mmol) and acetic acid (80 μL, 1.41 mmol). The RM is heated to 90° C. for 20 min. The RM is then filtered and the filtrate is concentrated under reduced pressure affording 2-bromo-3-(2-nitrovinyl)naphthalene as a yellow solid (2.14 g, quantitative). LC-MS A: $t_R$=0.98 min: no ionization.

A.1.14.7. 3-Bromo-2-naphthaldehyde

To a cooled (−20° C.) solution of 2,3-dibromonaphthalene (3.12 g, 10.70 mmol) in anh. THF (45 mL) is added dropwise a solution of isopropylmagnesium chloride lithium chloride complex (1.3 M in THF, 12.40 mL, 16.12 mmol) and the RM is further stirred at −20° C., under nitrogen, for 30 min. Anh. DMF (4.12 mL, 53.57 mmol) is then added dropwise and stirring at −20° C. is continued for 30 min. The RM is successively treated with water (35 mL) and 12 M aq. HCl (4.7 mL) and is allowed to warm-up to RT. Et$_2$O is added, the layers are separated, and the aq. layer is extracted twice with Et$_2$O. The combined organic layers are then washed with brine, dried over anh. MgSO$_4$, filtered and concentrated under reduced pressure. Purification by FC (from heptane to heptane/EtOAc=9/1) affords 3-bromo-2-naphthaldehyde as a pale yellow solid (1.50 g, 60%). LC-MS A: $t_R$=0.90 min; no ionization.

A.1.15. 6-Chloro-N-(2-(1-((triisopropylsilyl)ethynyl)naphthalen-2-yl)ethyl)pyrimidin-4-amine The title compound is prepared according to the procedure described above in A.1.1. using 2-(1-((triisopropylsilyl)ethynyl)naphthalen-2-yl)ethan-1-amine hydrochloride. LC-MS A: $t_R$=1.21 min; [M+H]$^+$=464.16.

A.1.15.1. 2-(1-((Triisopropylsilyl)ethynyl)naphthalen-2-yl)ethan-1-amine hydrochloride The title compound is prepared according to the procedure described above in A.1.1.1. using tert-butyl (2-(1-((triisopropylsilyl)ethynyl)naphthalen-2-yl)ethyl)carbamate. LC-MS A: $t_R$=0.88 min; [M+H]$^+$=352.16.

A.1.15.2. Tert-butyl (2-(1-((triisopropylsilyl)ethynyl)naphthalen-2-yl)ethyl)carbamate The title compound is prepared according to the procedure described above in A.1.13.2. using tert-butyl (2-(1-iodonaphthalen-2-yl)ethyl)carbamate. LC-MS A: $t_R$=1.20 min; [M+H]$^+$=452.23.

A.1.15.3. Tert-butyl (2-(1-iodonaphthalen-2-yl)ethyl)carbamate

To a mixture of tert-butyl (2-(1-bromonaphthalen-2-yl)ethyl)carbamate (500 mg, 1.43 mmol) and trans-N,N'-dimethylcyclohexane-1,2-diamine (22 μL, 0.14 mmol) in dioxane (2 mL) at RT are added copper(I) iodide (14 mg, 0.07 mmol) and sodium iodide (432 mg, 2.86 mmol). The RM is refluxed (110° C.) for 3 days. The RM is then allowed to cool to RT, water and DCM are added, and the layers are separated. The aqueous layer is extracted twice with DCM and the combined organic layers are dried over anh. MgSO$_4$, filtered and concentrated under reduced pressure. Purification by FC (from heptane to heptane/EtOAc=4/1) affords tert-butyl (2-(1-iodonaphthalen-2-yl)ethyl)carbamate as a yellow solid (330 mg, 58%). LC-MS A: $t_R$=1.00 min; no ionization.

A.1.15.4. Tert-butyl (2-(1-bromonaphthalen-2-yl)ethyl)carbamate

The title compound is prepared according to the procedure described above in A.1.14.4. using 2-(1-bromonaphthalen-2-yl)ethan-1-amine. LC-MS A: $t_R$=0.99 min; no ionization.

A.1.15.5. 2-(1-Bromonaphthalen-2-yl)ethan-1-amine

The title compound is prepared according to the procedure described above in A.1.14.5. using 1-bromo-2-(2-nitrovinyl)naphthalene. LC-MS A: $t_R$=0.60 min: [M+H]$^+$=250.14.

A.1.15.6. 1-Bromo-2-(2-nitrovinyl)naphthalene

The title compound is prepared according to the procedure described above in A.1.14.6. using 1-bromo-2-naphthaldehyde. LC-MS A: $t_R$=0.98 min; no ionization.

A.1.16. 2-(2-((6-Chloropyrimidin-4-yl)amino)ethyl)-1-naphthonitrile

The title compound is prepared according to the procedure described above in A.1.1. using 2-(2-aminoethyl)-1-naphthonitrile hydrochloride. LC-MS A: $t_R$=0.89 min; [M+H]$^+$=309.06.

A.1.16.1. 2-(2-Aminoethyl)-1-naphthonitrile hydrochloride

The title compound is prepared according to the procedure described above in A.1.1.1. using tert-butyl (2-(1-cyanonaphthalen-2-yl)ethyl)carbamate. LC-MS A: $t_R$=0.56 min; [M+H]$^+$=197.20.

A.1.16.2. Tert-butyl (2-(1-cyanonaphthalen-2-yl)ethyl)carbamate

The title compound is synthesized according to the procedure described above in A.1.14.2. using tert-butyl (2-(1-bromonaphthalen-2-yl)ethyl)carbamate (preparation described in A.1.15.4.). LC-MS A: $t_R$=0.92 min; no ionization.

A.1.17. N-(2-(1-Aminonaphthalen-2-yl)ethyl)-6-chloropyrimidin-4-amine

The title compound is prepared according to the procedure described above in A.1.1. using 2-(2-aminoethyl)naphthalen-1-amine hydrochloride. LC-MS A: $t_R$=0.81 min; [M+H]$^+$=299.08.

A.1.17.1. 2-(2-Aminoethyl)naphthalen-1-amine hydrochloride

The title compound is prepared according to the procedure described above in A.1.1.1. using tert-butyl (2-(1-aminonaphthalen-2-yl)ethyl)carbamate. LC-MS A: $t_R$=0.49 min; [M+H]$^+$=187.29.

A.1.17.2. Tert-butyl (2-(1-aminonaphthalen-2-yl)ethyl)carbamate

The title compound is synthesized according to the procedure described above in A.1.1.2. using 2-bromonaphthalen-1-amine. LC-MS A: $t_R$=0.84 min; [M+H]$^+$=287.18.

A.1.18. 6-Chloro-N-(2-(1-vinylnaphthalen-2-yl) ethyl)pyrimidin-4-amine

The title compound is prepared according to the procedure described above in A.1.1. using 2-(1-vinylnaphthalen-2-yl)ethan-1-amine hydrochloride. LC-MS A: $t_R$=0.97 min; [M+H]$^+$=310.09.

A.1.18.1. 2-(1-Vinylnaphthalen-2-yl)ethan-1-amine hydrochloride

The title compound is prepared according to the procedure described above in A.1.1.1. using tert-butyl (2-(1-vinylnaphthalen-2-yl)ethyl)carbamate. LC-MS A: $t_R$=0.62 min; [M+H]$^+$=198.22.

A.1.18.2. Tert-butyl (2-(1-vinylnaphthalen-2-yl)ethyl)carbamate

A suspension of tert-butyl (2-(1-bromonaphthalen-2-yl) ethyl)carbamate (800 mg, 2.28 mmol; preparation described in A.1.15.4.), 2,4,6-trivinyl-1,3,5,2,4,6-trioxatriborinane pyridine complex (289 mg, 1.14 mmol) and 2 M aq. K$_2$CO (2.28 mL, 4.56 mmol) in dioxane (22 mL) is degassed with nitrogen. Pd(PPhs)$_4$ (135 mg, 0.11 mmol) is added and the mixture is degassed again with nitrogen. The RM is then heated to 90° C., under nitrogen, overnight. The RM is allowed to cool to RT, diluted with DCM and sat. aq. NaHCO$_3$ is added. The layers are separated and the aqueous layer is extracted twice with DCM. The combined organic layers are then washed with brine, dried over anh. MgSO$_4$, filtered and concentrated under reduced pressure. Purification by FC (from heptane to heptane/EtOAc=4/1) affords tert-butyl (2-(1-vinylnaphthalen-2-yl)ethyl)carbamate as a yellow oil (582 mg, 86%). LC-MS A: $t_R$=0.99 min; no ionization.

A.1.19. 6-Chloro-N-(2-(3-methoxy-1-methylnaphthalen-2-yl)ethyl)pyrimidin-4-amine The title compound is prepared according to the procedure described above in A.1.1. using 2-(3-methoxy-1-methylnaphthalen-2-yl)ethan-1-amine hydrochloride. LC-MS B: $t_R$=1.09 min; [M+H]$^+$=328.17.

A.1.19.1. 2-(3-Methoxy-1-methylnaphthalen-2-yl)ethan-1-amine hydrochloride

The title compound is prepared according to the procedure described above in A.1.1.1. using tert-butyl (2-(3-methoxy-1-methylnaphthalen-2-yl)ethyl)carbamate. LC-MS B: $t_R$=0.65 min; [M+H]$^+$=216.30.

A.1.19.2. Tert-butyl (2-(3-methoxy-1-methylnaphthalen-2-yl)ethyl)carbamate

The title compound is prepared according to the procedure described above in A.1.1.2. using 3-methoxy-1-methylnaphthalen-2-yl trifluoromethanesulfonate. LC-MS B: $t_R$=1.10 min; [M+H]$^+$=316.26.

A.1.19.3. 3-Methoxy-1-methylnaphthalen-2-yl trifluoromethanesulfonate

A solution of 3-methoxy-1-methylnaphthalen-2-ol (802 mg, 4.26 mmol) and TEA (1.54 mL, 11.10 mmol) in anh. DCM (42 mL) is treated portionwise at RT with 1,1,1-trifluoro-N-phenyl-N-((trifluoromethyl)sulfonyl)methanesulfonamide (2.587 g, 7.24 mmol) and the RM is stirred at RT, under nitrogen, overnight. The RM is then concentrated under reduced pressure. Purification by FC (from heptane to heptane/EtOAc=1/1) affords 3-methoxy-1-methylnaphthalen-2-yl trifluoromethanesulfonate as a colorless oil (1.09 g, 80%). LC-MS B: $t_R$=1.13 min; no ionization.

A.1.19.4. 3-Methoxy-1-methylnaphthalen-2-ol

A mixture of 3-methoxy-2-(methoxymethoxy)-1-methylnaphthalene (1.127 g, 4.85 mmol) in MeOH (9 mL) and DCM (9 mL) is treated with 12 M aq. HCl (0.80 mL; 9.60 mmol) and the resulting suspension is stirred at RT overnight. Water and DCM are added and the layers are separated. The aqueous layer is extracted twice with DCM and the combined organic layers are washed with brine, dried over MgSO$_4$, filtered and concentrated under reduced pressure. Purification by FC (from heptane to heptane/EtOAc=3/7) affords 3-methoxy-1-methylnaphthalen-2-ol as a colorless solid (802 mg, 88%). LC-MS B: $t_R$=0.91 min; no ionization.

A.1.19.5. 3-Methoxy-2-(methoxymethoxy)-1-methylnaphthalene

A mixture of 1-bromo-3-methoxy-2-(methoxymethoxy) naphthalene (1.50 g, 5.05 mmol) and Cs$_2$CO$_3$ (4.984 g, 15.10 mmol) in DMF (20 mL) is degassed with nitrogen. Pd(PPhs)$_4$ (583 mg, 0.50 mmol) and 2,4,6-trimethyl-1,3,5, 2,4,6-trioxatriborinane (659 mg, 5.25 mmol) are then added and the mixture is degassed again with nitrogen. The RM is then heated to 90° C., under nitrogen, overnight. The RM is allowed to cool to RT, and diluted with Et$_2$O and water. The layers are separated and the aqueous layer is extracted twice with Et$_2$O. The combined organic layers are then washed with brine, dried over anh. MgSO$_4$, filtered and concentrated under reduced pressure. Purification by FC (from heptane to heptane/EtOAc=7/3) affords 3-methoxy-2-(methoxymethoxy)-1-methylnaphthalene as a colorless oil (950 mg, 81%). LC-MS B: $t_R$=0.99 min; [M+H]$^+$=233.31.

A.1.19.6. 1-Bromo-3-methoxy-2-(methoxymethoxy)naphthalene

A cooled (0° C.) solution of 1-bromo-3-methoxynaphthalen-2-ol (3.00 g, 11.30 mmol) in anh. DMF (50 mL) is treated portionwise with sodium hydride (60% dispersion in mineral oil, 540 mg, 13.50 mmol) and the mixture is stirred at RT, under nitrogen, for 15 min. To the resulting cooled (0° C.) mixture is then added chloromethyl methyl ether (1.71 mL, 22.50 mmol) and stirring at RT is continued for 1.5 h. Water and Et$_2$O are added and the layers are separated. The organic layer is successively washed with water and brine, dried over anh. MgSO$_4$, filtered and concentrated under reduced pressure. Purification by FC (from heptane to heptane/EtOAc=1/1) affords 1-bromo-3-methoxy-2-(methoxymethoxy)naphthalene as a colorless oil (3.29 g, 98%). LC-MS B: $t_R$=1.03 min; no ionization.

A.1.20. 6-Chloro-N-(2-(1-fluoro-3-methoxynaphthalen-2-yl)ethyl)pyrimidin-4-amine The title compound is prepared according to the procedure described above in A.1.1. using 2-(1-fluoro-3- methoxynaphthalen-2-yl)ethan-1-amine hydrochloride. LC-MS B: $t_R$=1.07 min; $[M+H]^+$=332.16.

A.1.20.1. 2-(1-Fluoro-3-methoxynaphthalen-2-yl)ethan-1-amine hydrochloride

The title compound is prepared according to the procedure described above in A.1.1.1. using tert-butyl (2-(1-fluoro-3-methoxynaphthalen-2-yl)ethyl)carbamate. LC-MS B: $t_R$=0.64 min; $[M+H]^+$=220.28.

A.1.20.2. Tert-butyl (2-(1-fluoro-3-methoxynaphthalen-2-yl)ethyl)carbamate

The title compound is prepared according to the procedure described above in A.1.1.2. using 1-fluoro-3-methoxynaphthalen-2-yl trifluoromethanesulfonate. LC-MS B: $t_R$=1.09 min; $[M+H]^+$=320.18.

A.1.20.3. 1-Fluoro-3-methoxynaphthalen-2-yl trifluoromethanesulfonate

A solution of 1-fluoro-3-methoxynaphthalen-2-ol (740 mg, 3.85 mmol) and TEA (1.40 mL, 10.00 mmol) in anh. DCM (38 mL) is treated portionwise at RT with 1,1,1-trifluoro-N-phenyl-N-((trifluoromethyl)sulfonyl)methanesulfonamide (1.667 g, 4.62 mmol) and the RM is stirred at RT, under nitrogen, overnight. The RM is then concentrated under reduced pressure. Purification by FC (from heptane to heptane/EtOAc=1/1) affords 1-fluoro-3-methoxynaphthalen-2-yl trifluoromethanesulfonate as a colorless oil (1.02 g, 82%). LC-MS B: $t_R$=1.13 min; no ionization.

A.1.20.4. 1-Fluoro-3-methoxynaphthalen-2-ol

The title compound is prepared according to the procedure described above in A.1.19.4. using 1-fluoro-3-methoxy-2-(methoxymethoxy)naphthalene. LC-MS B: $t_R$=0.84 min; no ionization.

A.1.20.5. 1-Fluoro-3-methoxy-2-(methoxymethoxy)naphthalene

To a cooled (−78° C.) solution of 1-bromo-3-methoxy-2-(methoxymethoxy)naphthalene (1.78 g, 5.99 mmol) in anh. Et$_2$O (60 mL) is added dropwise a solution of BuLi (1.6 M in hexanes, 11.30 mL, 18.08 mmol) and the RM is allowed to warm-up to 0° C. and is then further stirred at 0° C., under nitrogen, for 1 h. A solution of N-fluoro-N-(phenylsulfonyl)benzenesulfonamide (5.842 g, 18.00 mmol) in anh. THF (60 mL) is added dropwise to the previous mixture and stirring is then continued at RT for 1 h. The cooled (0° C.) RM is then treated dropwise with water and is allowed to warm-up to RT. EtOAc is added and the layers are separated. The aqueous layer is extracted twice with EtOAc and the combined organic layers are washed with brine, dried over anh. MgSO$_4$, filtered and concentrated under reduced pressure. Purification by FC (from heptane to heptane/EtOAc=1/1) affords 1-fluoro-3-methoxy-2-(methoxymethoxy)naphthalene as a yellow solid (1.23 g, 87%). LC-MS B: $t_R$=0.96 min; $[M+H]^+$=237.11.

A.1.20.6. 1-Bromo-3-methoxy-2-(methoxymethoxy)naphthalene

The title compound is prepared according to the procedure described above in A.1.19.6. using 1-bromo-3-methoxynaphthalen-2-ol. LC-MS B: $t_R$=1.03 min; no ionization.

A.1.21. 3-(2-((6-Chloropyrimidin-4-yl)amino)ethyl)-4-methyl-2-naphthonitrile The title compound is prepared according to the procedure described above in A.1.1. using 3-(2-aminoethyl)-4-methyl-2-naphthonitrile hydrochloride. LC-MS B: $t_R$=1.03 min; $[M+H]^+$=323.12.

A.1.21.1. 3-(2-Aminoethyl)-4-methyl-2-naphthonitrile hydrochloride

The title compound is prepared according to the procedure described above in A.1.1.1. using tert-butyl (2-(3-cyano-1-methylnaphthalen-2-yl)ethyl)carbamate. LC-MS B: $t_R$=0.61 min; $[M+H]^+$=211.28.

A.1.21.2. Tert-butyl (2-(3-cyano-1-methylnaphthalen-2-yl)ethyl)carbamate

The title compound is prepared according to the procedure described above in A.1.1.2. using 3-cyano-1-methylnaphthalen-2-yl trifluoromethanesulfonate. LC-MS B: $t_R$=1.06 min; $[M+H]^+$=311.28.

A.1.21.3. 3-Cyano-1-methylnaphthalen-2-yl trifluoromethanesulfonate

The title compound is prepared according to the procedure described above in A.1.20.3. using 3-hydroxy-4-methyl-2-naphthonitrile. LC-MS B: $t_R$=1.10 min; no ionization.

A.1.21.4. 3-Hydroxy-4-methyl-2-naphthonitrile

To a solution of 3-bromo-1-methylnaphthalen-2-ol (2.28 g, 9.62 mmol) in anh. DMF (60 mL) are added successively zinc cyanide (1.383 g, 11.50 mmol), Pd$_2$(dba)$_3$ (454 mg, 0.48 mmol), Xantphos (574 mg, 0.96 mmol) and TMEDA (291 µL, 1.92 mmol). The RM is heated to 140° C. for 20 min. The RM is allowed to cool to RT and is then filtered over celite. Water and Et$_2$O are added, the layers are separated and the aqueous layer is extracted twice with Et$_2$O. The combined organic layers are washed with brine, dried over anh. MgSO$_4$, filtered and concentrated under reduced pressure. Purification by FC (from heptane to heptane/EtOAc=1/1) affords 3-hydroxy-4-methyl-2-naphthonitrile as a yellow solid (1.54 g, 87%). LC-MS B: $t_R$=0.87 min: no ionization.

A.1.21.5. 3-Bromo-2-(methoxymethoxy)-1-methylnaphthalene

To a cooled (0° C.) solution of 2-(methoxymethoxy)-1-methylnaphthalene (3.06 g, 15.10 mmol) in anh. Et$_2$O (168 mL) is added dropwise a solution of BuLi (1.6 M in hexanes, 18.90 mL, 30.24 mmol) and the RM is allowed to warm-up to RT and is then further stirred at RT, under nitrogen, for 2 h. Commercially available 1,2-dibromoethane (5.27 mL, 60.50 mmol) is added dropwise to the previous mixture and stirring is then continued at RT for 1.5 h. The cooled (0° C.) RM is then treated dropwise with sat. aq. NH$_4$Cl and is allowed to warm-up to RT. EtOAc is added and the layers are separated. The aqueous layer is extracted twice with EtOAc and the combined organic layers are washed with brine, dried over anh. MgSO$_4$, filtered and concentrated under reduced pressure. Purification by FC (from heptane to heptane/EtOAc=1/1) affords 3-bromo-2-(methoxymethoxy)-1-methylnaphthalene as a yellow oil (3.36 g, 79%). LC-MS B: $t_R$=1.05 min; [M+H]$^+$=281.03.

A.1.21.6. 2-(Methoxymethoxy)-1-methylnaphthalene

The title compound is prepared according to the procedure described above in A.1.19.6. using 1-methylnaphthalen-2-ol. LC-MS B: $t_R$=0.99 min; [M+H]$^+$=203.18.

A.1.22. 3-(2-((6-Chloropyrimidin-4-yl)amino)ethyl)-4-fluoro-2-naphthonitrile The title compound is prepared according to the procedure described above in A.1.1. using 3-(2-aminoethyl)-4-fluoro-2-naphthonitrile hydrochloride. LC-MS B: $t_R$=0.99 min; [M+H]$^+$=327.09.

A.1.22.1. 3-(2-Aminoethyl)-4-fluoro-2-naphthonitrile hydrochloride

The title compound is prepared according to the procedure described above in A.1.1.1. using tert-butyl (2-(3-cyano-1-fluoronaphthalen-2-yl)ethyl)carbamate. LC-MS B: $t_R$=0.58 min; [M+H]$^+$=215.27.

A.1.22.2. Tert-butyl (2-(3-cyano-1-fluoronaphthalen-2-yl)ethyl)carbamate

The title compound is prepared according to the procedure described above in A.1.1.2. using 3-cyano-1-fluoronaphthalen-2-yl trifluoromethanesulfonate. LC-MS B: $t_R$=1.04 min; [M+H]$^+$=315.22.

A.1.22.3. 3-Cyano-1-fluoronaphthalen-2-yl trifluoromethanesulfonate

The title compound is prepared according to the procedure described above in A.1.19.3. using 4-fluoro-3-hydroxy-2-naphthonitrile. LC-MS B: $t_R$=1.09 min; no ionization.

A.1.22.4. 4-Fluoro-3-hydroxy-2-naphthonitrile

To a solution of 4-fluoro-3-(methoxymethoxy)-2-naphthaldehyde (1.15 g, 4.91 mmol) in anh. pyridine (1.66 mL, 20.50 mmol) is added hydroxylamine hydrochloride (383 mg, 5.45 mmol) and the mixture is stirred at RT for 1 h. The RM is heated to 80° C., and acetic anhydride (0.89 mL, 9.42 mmol) is then added dropwise. After completion of the addition, the mixture is heated to 100° C. for 20 min. The RM is then allowed to cool to RT, diluted with EtOAc and washed successively with 1 M aq. HCl and sat. aq. NaHCO$_3$. The organic layer is dried over anh. MgSO$_4$, filtered and concentrated under reduced pressure. Purification by FC (from heptane to EtOAc) affords 4-fluoro-3-hydroxy-2-naphthonitrile as a pale yellow solid (630 mg, 69%). LC-MS B: $t_R$=0.84 min: no ionization.

A.1.22.5. 4-Fluoro-3-(methoxymethoxy)-2-naphthaldehyde

To a cooled (−78° C.) solution of 1-fluoro-2-(methoxymethoxy)naphthalene (2.533 g, 12.30 mmol) in anh. THF (100 mL) is added dropwise a solution of BuLi (1.6 M in hexanes, 19.20 mL, 30.72 mmol) and the RM is further stirred at −78° C., under nitrogen, for 1 h. Anh. DMF (1.90 mL, 24.60 mmol) is then added dropwise to the previous mixture, and stirring at −78° C. is continued for 15 min. The cooled RM is then treated dropwise with sat. aq. NH$_4$Cl and is allowed to warm-up to RT. EtOAc is added, the layers are separated, and the aqueous layer is extracted twice with EtOAc. The combined organic layers are washed with brine, dried over anh. MgSO$_4$, filtered and concentrated under reduced pressure affording 4-fluoro-3-(methoxymethoxy)-2-naphthaldehyde as a yellow oil (2.90 g, quantitative). LC-MS B: $t_R$=0.95 min; [M+H]$^+$=235.27.

A.1.22.6. 1-Fluoro-2-(methoxymethoxy)naphthalene

The title compound is prepared according to the procedure described above in A.1.19.6. using 1-fluoronaphthalen-2-ol. LC-MS B: $t_R$=0.97 min; [M+H]$^+$=207.25.

A.1.23. 6-Chloro-N-(2-(1,3-difluoronaphthalen-2-yl)ethyl)pyrimidin-4-amine

The title compound is prepared according to the procedure described above in A.1.1. using 2-(1,3-difluoronaphthalen-2-yl)ethan-1-amine hydrochloride. LC-MS B: $t_R$=1.06 min; [M+H]$^+$=320.13.

A.1.23.1. 2-(1,3-Difluoronaphthalen-2-yl)ethan-1-amine hydrochloride

The title compound is prepared according to the procedure described above in A.1.1.1. using tert-butyl (2-(1,3-difluoronaphthalen-2-yl)ethyl)carbamate. LC-MS B: $t_R$=0.60 min; [M+H]$^+$=208.26.

A.1.23.2. Tert-butyl (2-(1,3-difluoronaphthalen-2-yl)ethyl)carbamate

The title compound is prepared according to the procedure described above in A.1.1.2. using 1,3-difluoronaphthalen-2-yl trifluoromethanesulfonate. LC-MS B: $t_R$=1.08 min; no ionization.

A.1.23.3. 1,3-Difluoronaphthalen-2-yl trifluoromethanesulfonate

The title compound is prepared according to the procedure described above in A.1.20.3. using 1,3-difluoronaphthalen-2-ol. LC-MS B: $t_R$=1.12 min; no ionization.

A.1.23.4. 1,3-Difluoronaphthalen-2-ol

The title compound is prepared according to the procedure described above in A.1.19.4. using 1,3-difluoro-2-(methoxymethoxy)naphthalene. LC-MS B: $t_R$=0.85 min; no ionization.

A.1.23.5. 1,3-Difluoro-2-(methoxymethoxy)naphthalene

To a cooled (−78° C.) solution of 1-fluoro-2-(methoxymethoxy)naphthalene (1.50 g, 7.27 mmol; preparation described in A.1.22.6.) in anh. THF (35 mL) is added dropwise a solution of BuLi (1.6 M in hexanes, 9.06 mL, 14.49 mmol) and the mixture is further stirred at −78° C., under nitrogen, for 1 h. A solution of N-fluoro-N-(phenylsulfonyl)benzenesulfonamide (5.202 g, 16.00 mmol) in anh. THF (10 mL) is added dropwise to the previous mixture and stirring is then continued at 0° C. for 15 min. The RM is treated dropwise with sat. aq. NH$_4$Cl and is then allowed to warm-up to RT. EtOAc is added and the layers are separated. The aqueous layer is extracted twice with EtOAc and the combined organic layers are washed with brine, dried over anh. MgSO$_4$, filtered and concentrated under reduced pressure. Purification by FC (from heptane to heptane/EtOAc=7/3) affords 1,3-difluoro-2-(methoxymethoxy)naphthalene as a yellow oil (1.30 g, 80%). LC-MS B: $t_R$=1.00 min; no ionization.

A.1.24. 6-Chloro-N-(2-(4-chloro-3-methoxynaphthalen-2-yl)ethyl)pyrimidin-4-amine A solution of 1-chloro-3-(2-((6-chloropyrimidin-4-yl)amino)ethyl)naphthalen-2-ol (100 mg, 0.29 mmol) in anh. DMF (3 mL) is treated at RT with cesium carbonate (117 mg, 0.35 mmol) and iodomethane (38 µL, 0.61 mmol) and the RM is stirred at RT, under nitrogen, for 3 h. Water is added and the mixture is extracted three times with Et$_2$O. The combined organic layers are then washed twice with water, dried over anh. MgSO$_4$, filtered and concentrated under reduced pressure affording 6-chloro-N-(2-(4-chloro-3-methoxynaphthalen-2-yl)ethyl)pyrimidin-4-amine as an off-white solid (98 mg, 94%). LC-MS B: $t_R$=1.08 min; [M+H]$^+$=348.13.

A.1.24.1. 1-Chloro-3-(2-((6-chloropyrimidin-4-yl)amino)ethyl)naphthalen-2-ol A mixture of 6-chloro-N-(2-(4-chloro-3-(methoxymethoxy)naphthalen-2-yl)ethyl)pyrimidin-4-amine (390 mg, 1.03 mmol) in MeOH (2 mL) and DCM (2 mL) is treated with 12 M aq. HCl (0.17 mL; 2.04 mmol) and the resulting suspension is stirred at RT overnight. Water and DCM are then added, and the resulting precipitate is filtered. The isolated solid is further dried under high vacuum affording 1-chloro-3-(2-((6-chloropyrimidin-4-yl)amino)ethyl)naphthalen-2-ol as a colorless solid (304 mg, 88%). LC-MS B: $t_R$=0.99 min; [M+H]$^+$=334.12.

A.1.24.2. 6-Chloro-N-(2-(4-chloro-3-(methoxymethoxy)naphthalen-2-yl)ethyl)pyrimidin-4-amine The title compound is prepared according to the procedure described above in A.1.1. using 2-(4-chloro-3-(methoxymethoxy)naphthalen-2-yl)ethan-1-amine. LC-MS B: $t_R$=1.08 min; [M+H]$^+$=378.17.

A.1.24.3. 2-(4-Chloro-3-(methoxymethoxy)naphthalen-2-yl)ethan-1-amine

95% H$_2$SO$_4$ (88 µL) is added dropwise to a cooled (−10° C.) solution of LAH (2 M in THF, 2.51 mL, 5.02 mmol) and the mixture is stirred at −10° C. for 20 min. A solution of 1-chloro-2-(methoxymethoxy)-3-(2-nitrovinyl)naphthalene (420 mg, 1.43 mmol) in anh. THF (10 mL) is then added dropwise and stirring is continued at −10° C. for 30 min, and then at 0° C. for 1 h. The RM is treated successively with 2-propanol (23 mL) and with 2.8 M aq. NaOH (0.6 mL), and is then allowed to warm-up to RT. The resulting suspension is filtered and the filtrate is concentrated under reduced pressure affording 2-(4-chloro-3-(methoxymethoxy)naphthalen-2-yl)ethan-1-amine as an orange oil (384 mg, quantitative). LC-MS B: $t_R$=0.68 min; [M+H]$^+$=266.25.

A.1.24.4. 1-Chloro-2-(methoxymethoxy)-3-(2-nitrovinyl)naphthalene

To a solution of 4-chloro-3-(methoxymethoxy)-2-naphthaldehyde (910 mg, 3.63 mmol) in nitromethane (7 mL) are added successively molecular sieves (4A, 95 mg), butylamine (42 µL, 0.42 mmol) and acetic acid (42 µL, 0.74 mmol). The RM is heated to 90° C. for 25 min. The RM is then filtered and the filtrate is concentrated under reduced pressure. Purification by FC (from heptane to EtOAc) affords 1-chloro-2-(methoxymethoxy)-3-(2-nitrovinyl)naphthalene as an orange solid (420 mg, 39%). LC-MS B: $t_R$=1.08 min; no ionization.

A.1.24.5. 4-Chloro-3-(methoxymethoxy)-2-naphthaldehyde

To a cooled (−78° C.) solution of 1-chloro-2-(methoxymethoxy)naphthalene (810 mg, 3.64 mmol) in anh. THF (30 mL) is added dropwise a solution of BuLi (1.6 M in hexanes, 5.70 mL, 9.12 mmol) and the RM is further stirred at −78° C., under nitrogen, for 1 h. Anh. DMF (0.563 mL, 7.28 mmol) is then added dropwise to the previous mixture, and stirring at −78° C. is continued for 15 min. The cooled RM is then treated dropwise with sat. aq. NH$_4$Cl and is allowed to warm-up to RT. EtOAc is added, the layers are separated, and the aqueous layer is extracted twice with EtOAc. The combined organic layers are washed with brine, dried over anh. MgSO$_4$, filtered and concentrated under reduced pressure affording 4-chloro-3-(methoxymethoxy)-2-naphthaldehyde as a pale yellow solid (910 mg, 99%). LC-MS B: $t_R$=0.99 min; [M+H]$^+$=251.24.

A.1.24.6. 1-Chloro-2-(methoxymethoxy)naphthalene

The title compound is prepared according to the procedure described above in A.1.19.6. using 1-chloronaphthalen-2-ol. LC-MS B: $t_R$=1.01 min; [M+H]$^+$=223.18.

A.1.25. 6-Chloro-N-(2-(4-fluoro-3-methoxynaphthalen-2-yl)ethyl)pyrimidin-4-amine A solution of 3-(2-((6-chloropyrimidin-4-yl)amino)ethyl)-1-fluoronaphthalen-2-ol (149 mg, 0.46 mmol) in anh. DMF (6 mL) is treated at RT with cesium carbonate (183 mg, 0.56 mmol) and iodomethane (59 µL, 0.93 mmol) and the RM is stirred at RT, under nitrogen, for 1.5 h. Water is added and the mixture is extracted three times with Et$_2$O. The combined organic layers are then washed twice with water, dried over anh. MgSO$_4$, filtered and concentrated under reduced pressure. Purification by FC (from heptane to heptane/EtOAc=1/1) affords 6-chloro-N-(2-(4-fluoro-3-methoxynaphthalen-2-yl)ethyl)pyrimidin-4-amine as a colorless solid (89 mg, 57%). LC-MS B: $t_R$=1.06 min; [M+H]$^+$=332.20.

A.1.25.1. 3-(2-((6-Chloropyrimidin-4-yl)amino)ethyl)-1-fluoronaphthalen-2-ol The title compound is prepared according to the procedure described above in A.1.19.4. using 6-chloro-N-(2-(4-fluoro-3-(methoxymethoxy)naphthalen-2-yl)ethyl)pyrimidin-4-amine. LC-MS B: $t_R$=0.95 min; [M+H]$^+$=318.16.

A.1.25.2. 6-Chloro-N-(2-(4-fluoro-3-(methoxymethoxy)naphthalen-2-yl)ethyl)pyrimidin-4-amine The title compound is prepared according to the procedure described above in A.1.1. using 2-(4-fluoro-3-(methoxymethoxy)naphthalen-2-yl)ethan-1-amine. LC-MS B: $t_R$=1.05 min; [M+H]$^+$=362.20.

A.1.25.3. 2-(4-Fluoro-3-(methoxymethoxy)naphthalen-2-yl)ethan-1-amine

The title compound is prepared according to the procedure described above in A.1.24.3. using 1-fluoro-2-(methoxymethoxy)-3-(2-nitrovinyl)naphthalene. LC-MS B: $t_R$=0.65 min: [M+H]$^+$=250.31.

A.1.25.4. 1-Fluoro-2-(methoxymethoxy)-3-(2-nitrovinyl)naphthalene

The title compound is prepared according to the procedure described above in A.1.24.4. using 4-fluoro-3-(methoxymethoxy)-2-naphthaldehyde (preparation described in A.1.22.5.). LC-MS B: $t_R$=1.06 min; [M+H]$^+$=278.40.

A.1.26. N-(2-(Benzo[b]thiophen-5-yl)ethyl)-6-chloropyrimidin-4-amine

The title compound is prepared according to the procedure described above in A.1.1. using 2-(benzo[b]thiophen-5-yl)ethan-1-amine hydrochloride. LC-MS B: $t_R$=1.01 min; [M+H]$^+$=289.95.

A.1.26.1. 2-(Benzo[b]thiophen-5-yl)ethan-1-amine hydrochloride

The title compound is prepared according to the procedure described above in A.1.1.1. using tert-butyl (2-(benzo[b]thiophen-5-yl)ethyl)carbamate. LC-MS B: $t_R$=0.56 min; [M+H]$^+$=178.12.

A.1.26.2. Tert-butyl (2-(benzo[b]thiophen-5-yl)ethyl)carbamate

The title compound is synthesized according to the procedure described above in A.1.1.2. using 5-bromobenzo[b]thiophene. LC-MS B: $t_R$=1.03 min; [M+H]$^+$=278.03.

A.1.27. N-(2-(Benzo[b]thiophen-6-yl)ethyl)-6-chloropyrimidin-4-amine

The title compound is prepared according to the procedure described above in A.1.1. using 2-(benzo[b]thiophen-6-yl)ethan-1-amine. LC-MS A: $t_R$=0.90 min; [M+H]$^+$=290.05.

A.1.27.1. 2-(Benzo[b]thiophen-6-yl)ethan-1-amine

The title compound is prepared according to the procedure described above in A.1.4.1. using benzo[b]thiophene-6-carbaldehyde. LC-MS A: $t_R$=0.52 min; [M+H]$^+$=178.27.

A.1.28. N-(2-(Benzo[b]thiophen-5-yl)ethyl)-6-chloro-2-methylpyrimidin-4-amine The title compound is prepared according to the procedure described above in A.1.1. using 2-(benzo[b]thiophen-5-yl)ethan-1-amine hydrochloride (preparation described in A.1.26.1.) and 4,6-dichloro-2-methylpyrimidine. LC-MS B: $t_R$=0.94 min; [M+H]$^+$=303.99.

A.1.29. 6-Chloro-N-(2-(3-methylbenzo[b]thiophen-5-yl)ethyl)pyrimidin-4-amine The title compound is prepared according to the procedure described above in A.1.1. using 2-(3-methylbenzo[b]thiophen-5-yl)ethan-1-amine hydrochloride. LC-MS B: $t_R$=1.03 min; [M+H]$^+$=304.04.

A.1.29.1. 2-(3-Methylbenzo[b]thiophen-5-yl)ethan-1-amine hydrochloride

The title compound is prepared according to the procedure described above in A.1.1.1. using tert-butyl (2-(3-methylbenzo[b]thiophen-5-yl)ethyl)carbamate. LC-MS B: $t_R$=0.58 min; [M+H]$^+$=192.18.

A.1.29.2. Tert-butyl (2-(3-methylbenzo[b]thiophen-5-yl)ethyl)carbamate

The title compound is synthesized according to the procedure described above in A.1.1.2. using 5-bromo-3-methylbenzo[b]thiophene. LC-MS B: $t_R$=1.06 min: no ionization.

A.1.30. 5-(2-((6-Chloropyrimidin-4-yl)amino)ethyl)benzo[b]thiophene-3-carbonitrile The title compound is prepared according to the procedure described above in A.1.1. using 5-(2-aminoethyl)benzo[b]thiophene-3-carbonitrile hydrochloride. LC-MS B: $t_R$=0.96 min; [M+H]$^+$=315.01.

A.1.30.1. 5-(2-Aminoethyl)benzo[b]thiophene-3-carbonitrile hydrochloride

The title compound is prepared according to the procedure described above in A.1.1.1. using tert-butyl (2-(3-cyanobenzo[b]thiophen-5-yl)ethyl)carbamate. LC-MS B: $t_R$=0.55 min; [M+H]$^+$=203.04.

A.1.30.2. Tert-butyl (2-(3-cyanobenzo[b]thiophen-5-yl)ethyl)carbamate

The title compound is synthesized according to the procedure described above in A.1.1.2. using 5-bromobenzo[b]thiophene-3-carbonitrile. LC-MS B: $t_R$=0.99 min; [M+H]$^+$=303.08.

A.1.30.3. 5-Bromobenzo[b]thiophene-3-carbonitrile

A well-stirred suspension of 5-bromobenzo[b]thiophene-3-carbaldehyde (1.00 g, 4.02 mmol) and sodium azide (392 mg, 6.03 mmol) in anh. MeCN (4 mL) is treated at RT with a solution of trifluoromethanesulfonic acid (1.09 mL, 12.10 mmol) in anh. MeCN (10 mL). The RM is further stirred at RT, under nitrogen, for 0.5 h. Water is then added and the mixture is filtered. The collected solid is washed with water and is then dissolved in EtOAc. The organic layer is dried over anh. MgSO$_4$, filtered and concentrated under reduced pressure. Purification by FC (from heptane to heptane/EtOAc=1/1) affords 5-bromobenzo[b]thiophene-3-carbonitrile as a red solid (694 mg, 72%). LC-MS B: $t_R$=0.97 min; no ionization.

A.1.31. 6-Chloro-N-(2-(6-methoxybenzo[b]thiophen-5-yl)ethyl)pyrimidin-4-amine The title compound is prepared according to the procedure described above in A.1.1. using 2-(6-methoxybenzo[b]thiophen-5-yl)ethan-1-amine hydrochloride. LC-MS B: $t_R$=1.04 min; [M+H]$^+$=320.09.

A.1.31.1. 2-(6-Methoxybenzo[b]thiophen-5-yl)ethan-1-amine hydrochloride

The title compound is prepared according to the procedure described above in A.1.1.1. using tert-butyl (2-(6-methoxybenzo[b]thiophen-5-yl)ethyl)carbamate. LC-MS B: $t_R$=0.58 min; [M+H]$^+$=208.19.

A.1.31.2. Tert-butyl (2-(6-methoxybenzo[b]thiophen-5-yl)ethyl)carbamate

The title compound is synthesized according to the procedure described above in A.1.1.2. using 5-bromo-6-methoxybenzo[b]thiophene. LC-MS B: $t_R$=1.04 min; [M+H]$^+$=308.12.

A.1.31.3. 5-Bromo-6-methoxybenzo[b]thiophene

A mixture of 5-bromo-6-methoxybenzo[b]thiophene-2-carboxylic acid (2.260 g, 7.87 mmol) and copper(I) oxide (4.393 g, 30.70 mmol) in DMF (42 mL) is heated to 140° C. for 21 h. The RM is allowed to cool to RT and is filtered over celite to remove copper salts that are washed with Et$_2$O. Water and Et$_2$O are added to the filtrate and the layers are separated. The aqueous layer is extracted twice with Et$_2$O and the combined organic layers are washed with brine, dried over anh. MgSO$_4$, filtered and concentrated under reduced pressure. Purification by FC (from heptane to heptane/EtOAc=1/1) affords 5-bromo-6-methoxybenzo[b]thiophene as a pale orange solid (1.580 g, 87%). LC-MS B: $t_R$=0.99 min: no ionization.

A.1.31.4. 5-Bromo-6-methoxybenzo[b]thiophene-2-carboxylic acid

A mixture of methyl 5-bromo-6-methoxybenzo[b]thiophene-2-carboxylate (2.970 g, 9.86 mmol) in THF (80 mL), MeOH (9 mL) and water (27 mL) is treated portionwise with lithium hydroxide (709 mg, 29.60 mmol). The RM is stirred at RT overnight. The RM is then acidified by addition of 2 M aq. HCl and the organic solvents are removed under reduced pressure. The resulting suspension is filtered and the separated solid is then washed with water and dried under high vacuum to give 5-bromo-6-methoxybenzo[b]thiophene-2-carboxylic acid as a colorless solid (2.260 g, 80%). LC-MS B: $t_R$=0.87 min; no ionization.

A.1.31.5. Methyl 5-bromo-6-methoxybenzo[b]thiophene-2-carboxylate

To a cooled (0° C.) mixture of 5-bromo-2-fluoro-4-methoxybenzaldehyde (2.500 g, 10.50 mmol) and potassium carbonate (2.224 g, 15.80 mmol) in DMF (15 mL) is added dropwise methyl 2-mercaptoacetate (0.99 mL, 10.50 mmol). The RM is stirred at RT for 1 h, and then heated to 60° C. overnight. The RM is allowed to cool to RT and water is added. The resulting suspension is filtered and the separated solid is then washed with water and dried under high vacuum to give methyl 5-bromo-6-methoxybenzo[b]thiophene-2-carboxylate as a yellow solid (2.970 g, 94%). LC-MS B: $t_R$=1.06 min; no ionization.

A.1.32. 6-Chloro-N-(2-(6-ethoxybenzo[b]thiophen-5-yl)ethyl)pyrimidin-4-amine The title compound is prepared according to the procedure described above in A.1.1. using 2-(6-ethoxybenzo[b]thiophen-5-yl)ethan-1-amine hydrochloride. LC-MS B: $t_R$=1.07 min; [M+H]$^+$=334.07.

A.1.32.1. 2-(6-Ethoxybenzo[b]thiophen-5-yl)ethan-1-amine hydrochloride

The title compound is prepared according to the procedure described above in A.1.1.1. using tert-butyl (2-(6-ethoxybenzo[b]thiophen-5-yl)ethyl)carbamate. LC-MS B: $t_R$=0.65 min; [M+H]$^+$=222.10.

A.1.32.2. Tert-butyl (2-(6-ethoxybenzo[b]thiophen-5-yl)ethyl)carbamate

The title compound is synthesized according to the procedure described above in A.1.1.2. using 5-bromo-6-ethoxybenzo[b]thiophene. LC-MS B: $t_R$=1.08 min; [M+H]$^+$=322.02.

A.1.32.3. 5-Bromo-6-ethoxybenzo[b]thiophene

To a solution of 5-bromobenzo[b]thiophen-6-ol (190 mg, 0.82 mmol) in anh. DMF (8 mL) at RT are added cesium carbonate (270 mg, 0.82 mmol) and iodoethane (73 µL, 0.91 mmol) and the RM is stirred at RT, under nitrogen, for 1 h. Water and Et$_2$O are added and the layers are separated. The aqueous layer is extracted twice with Et$_2$O and the combined organic layers are washed with brine, dried over anh. MgSO$_4$, filtered and concentrated under reduced pressure affording 5-bromo-6-ethoxybenzo[b]thiophene as a yellow oil (241 mg, quantitative). LC-MS B: $t_R$=1.05 min; no ionization.

A.1.32.4. 5-Bromobenzo[b]thiophen-6-ol

To a cooled (−78° C.) solution of 5-bromo-6-methoxybenzo[b]thiophene (710 mg, 2.92 mmol; preparation described in A.1.31.3.) in anh. DCM (10 mL) is added dropwise a solution of boron tribromide (1 M in DCM, 5.84 mL, 5.84 mmol) and the RM is stirred at RT, under nitrogen, overnight. The RM is then poured onto ice-water and the layers are separated. The aqueous layer is extracted twice with DCM and the combined organic layers are washed with brine, dried over anh. MgSO$_4$, filtered and concentrated under reduced pressure. Purification by FC (from heptane to heptane/EtOAc=7/3) affords 5-bromobenzo[b]thiophen-6-ol as a pale orange solid (190 mg, 28%). LC-MS B: $t_R$=0.86 min; no ionization.

A.1.33. 5-(2-((6-Chloropyrimidin-4-yl)amino)ethyl)benzo[b]thiophene-6-carbonitrile The title compound is prepared according to the procedure described above in A.1.1. using 5-(2-aminoethyl)benzo[b]thiophene-6-carbonitrile hydrochloride. LC-MS B: $t_R$=0.94 min; [M+H]$^+$=315.03.

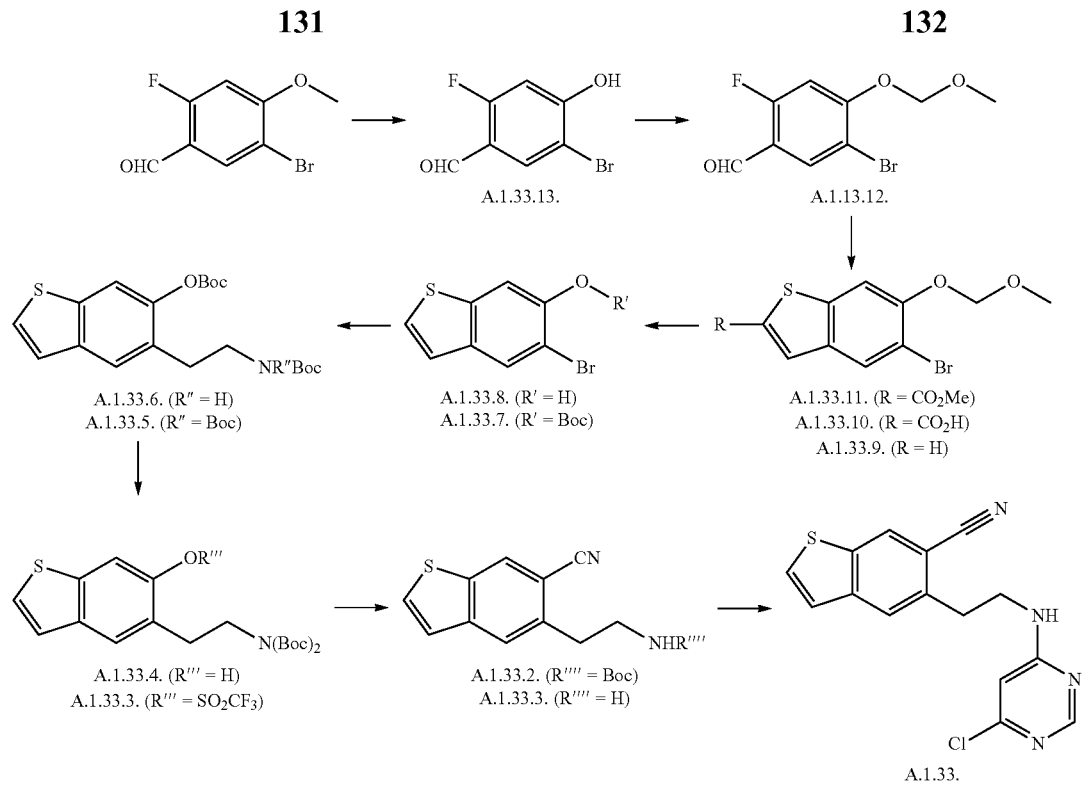

A.1.33.1. 5-(2-Aminoethyl)benzo[b]thiophene-6-carbonitrile hydrochloride

The title compound is prepared according to the procedure described above in A.1.1.1. using tert-butyl (2-(6-cyanobenzo[b]thiophen-5-yl)ethyl)carbamate. LC-MS B: $t_R$=0.54 min; [M+H]$^+$=203.15.

A.1.33.2. Tert-butyl (2-(6-cyanobenzo[b]thiophen-5-yl)ethyl)carbamate

The title compound is prepared according to the procedure described above in A.1.14.2. using intermediate A.1.33.3. LC-MS B: $t_R$=1.00 min; [M+H]$^+$=303.07.

A.1.33.3. Preparation of Intermediate A.1.33.3

The title compound is prepared according to the procedure described above in A.1.13.3. using intermediate A.1.33.4. LC-MS B: $t_R$=1.26 min: no ionization

A.1.33.4. Preparation of Intermediate A.1.33.4

The title compound is prepared according to the procedure described above in A.1.13.4. using intermediate A.1.33.5. LC-MS B: $t_R$=1.10 min; [M+H]$^+$=394.16

A.1.33.5. Preparation of Intermediate A.1.33.5

The title compound is prepared according to the procedure described above in A.1.13.5. using tert-butyl (2-(6-((tert-butoxycarbonyl)oxy)benzo[b]thiophen-5-yl)ethyl)carbamate. LC-MS B: $t_R$=1.24 min; no ionization.

A.1.33.6. Tert-butyl (2-(6-((tert-butoxycarbonyl)oxy)benzo[b]thiophen-5-yl)ethyl)carbamate The title compound is prepared according to the procedure described above in A.1.1.2. using 5-bromobenzo[b]thiophen-6-yl tert-butyl carbonate. LC-MS B: $t_R$=1.12 min; [M+H]$^+$=394.17.

A.1.33.7. 5-Bromobenzo[b]thiophen-6-yl tert-butyl carbonate

The title compound is prepared according to the procedure described above in A.1.13.7. using 5-bromobenzo[b]thiophen-6-ol. LC-MS B: $t_R$=1.09 min; no ionization.

A.1.33.8. 5-Bromobenzo[b]thiophen-6-ol

A mixture of 5-bromo-6-(methoxymethoxy)benzo[b]thiophene (1.55 g, 5.67 mmol) in MeOH (11 mL) and DCM (11 mL) is treated with 12 M aq. HCl (0.94 mL; 11.28 mmol) and the resulting suspension is stirred at RT overnight. The RM is then concentrated under reduced pressure and the residue is further dried under high vacuum affording 5-bromobenzo[b]thiophen-6-ol as a yellow solid. LC-MS B: $t_R$=0.85 min; no ionization.

A.1.33.9. 5-Bromo-6-(methoxymethoxy)benzo[b]thiophene

A mixture of 5-bromo-6-(methoxymethoxy)benzo[b]thiophene-2-carboxylic acid (2.30 g, 7.25 mmol) and copper(I) oxide (259 mg, 1.81 mmol) in DMF (36 mL) is heated to 140° C. for 15 h. The RM is allowed to cool to RT and is filtered over celite to remove copper salts that are washed with Et$_2$O. Water and Et$_2$O are added to the filtrate and the layers are separated. The aqueous layer is extracted twice with Et$_2$O and the combined organic layers are washed with brine, dried over anh. MgSO$_4$, filtered and concentrated under reduced pressure. Purification by FC (from heptane to heptane/EtOAc=4/1) affords 5-bromo-6-(methoxymethoxy) benzo[b]thiophene as a yellow oil (1.550 g, 78%). LC-MS B: $t_R$=1.02 min; no ionization.

A.1.33.10. 5-Bromo-6-(methoxymethoxy)benzo[b] thiophene-2-carboxylic acid

A mixture of methyl 5-bromo-6-(methoxymethoxy)benzo [b]thiophene-2-carboxylate (2.380 g, 7.19 mmol) in THF (85 mL), MeOH (17 mL) and water (17 mL) is treated portionwise with lithium hydroxide (516 mg, 21.60 mmol). The RM is stirred at RT for 3 h. The organic solvents are then removed under reduced pressure and the aqueous layer is acidified by addition of 1 M aq. HCl. The resulting suspension is filtered and the separated solid is then washed with water and dried under high vacuum to give 5-bromo-6-(methoxymethoxy)benzo[b]thiophene-2-carboxylic acid as a colorless solid (2.30 g, quantitative). LC-MS B: $t_R$=0.88 min: no ionization.

A.1.33.11. Methyl 5-bromo-6-(methoxymethoxy) benzo[b]thiophene-2-carboxylate

The title compound is prepared according to the procedure described above in A.1.31.5. using 5-bromo-2-fluoro-4-(methoxymethoxy)benzaldehyde and methyl 2-mercaptoacetate. LC-MS B: $t_R$=1.04 min; no ionization.

A.1.33.12. 5-Bromo-2-fluoro-4-(methoxymethoxy)benzaldehyde

A cooled (0° C.) solution of 5-bromo-2-fluoro-4-hydroxybenzaldehyde (1.90 g, 8.68 mmol) in anh. DMF (40 mL) is treated portionwise with sodium hydride (60% dispersion in mineral oil, 347 mg, 8.68 mmol) and the mixture is stirred at RT, under nitrogen, for 15 min. To the resulting cooled (0° C.) mixture is then added chloromethyl methyl ether (1.32 mL, 17.40 mmol) and stirring at RT is continued overnight. Water and Et$_2$O are added and the layers are separated. The organic layer is successively washed with water and brine, dried over anh. MgSO$_4$, filtered and concentrated under reduced pressure to give 5-bromo-2-fluoro-4-(methoxymethoxy)benzaldehyde as a pale yellow solid (2.33 g, quantitative). LC-MS B: $t_R$=0.90 min; no ionization.

A.1.33.13. 5-Bromo-2-fluoro-4-hydroxybenzaldehyde

A mixture of 5-bromo-2-fluoro-4-methoxybenzaldehyde (3.311 g, 13.90 mmol) and lithium chloride (2.385 g, 55.70 mmol) in anh. DMF (60 mL) is heated to 140° C. overnight. The RM is allowed to cool to RT, poured onto ice-water and is then acidified by addition of 12 M aq. HCl. The resulting solution is extracted three times with EtOAc and the combined organic layers are washed with brine, dried over anh. MgSO$_4$, filtered and concentrated under reduced pressure. Purification by FC (from heptane to heptane/EtOAc=7/3) affords 5-bromo-2-fluoro-4-hydroxybenzaldehyde as a pale yellow solid (1.90 g, 62%). LC-MS B: $t_R$=0.76 min; no ionization.

A.1.34. N-(2-(Benzofuran-6-yl)ethyl)-6-chloropyrimidin-4-amine

The title compound is prepared according to the procedure described above in A.1.1. using 2-(benzofuran-6-yl) ethan-1-amine hydrochloride. LC-MS A: $t_R$=0.87 min; [M+H]$^+$=273.99.

A.1.34.1. 2-(Benzofuran-6-yl)ethan-1-amine hydrochloride

The title compound is prepared according to the procedure described above in A.1.1.1. using tert-butyl (2-(benzofuran-6-yl)ethyl)carbamate. LC-MS A: $t_R$=0.48 min; [M+H]$^+$=162.14.

A.1.34.2. Tert-butyl (2-(benzofuran-6-yl)ethyl)carbamate

The title compound is prepared according to the procedure described above in A.1.2.2. using 6-bromobenzofuran. LC-MS A: $t_R$=0.89 min; no ionization.

A.1.35. N-(2-(Benzofuran-5-yl)ethyl)-6-chloropyrimidin-4-amine

The title compound is prepared according to the procedure described above in A.1.1. using 2-(benzofuran-5-yl) ethan-1-amine. LC-MS A: $t_R$=0.86 min: [M+H]$^+$=273.96.

A.1.35.1. 2-(Benzofuran-5-yl)ethan-1-amine

To a solution of benzofuran-5-carbaldehyde (600 mg, 4.02 mmol) in nitromethane (4 mL) are added successively 4A molecular sieves (47 mg), butylamine (47 μL, 0.47 mmol) and acetic acid (47 μL, 0.82 mmol). The RM is heated to 90° C., under nitrogen, for 1 h. The RM is then filtered and the filtrate is concentrated under reduced pressure. Purification by FC (from heptane/DCM=4/1 to heptane/DCM=2/3) affords 5-(2-nitrovinyl)benzofuran as a pale yellow solid (451 mg, 59%). LC-MS A: $t_R$=0.86 min; no ionisation To a cooled (0° C.) solution of 5-(2-nitrovinyl)benzofuran (451 mg, 2.39 mmol) in anh. THF (19 mL) is added dropwise a solution of lithium aluminum hydride (2 M in THF, 4.17 mL, 8.34 mmol). The mixture is then stirred at RT, under nitrogen, overnight. The cooled (0° C.) RM is treated successively with water (0.3 mL), 15% aq. NaOH (0.3 mL), and water (1 mL). The resulting heterogeneous mixture is then filtered and the separated solid is washed with Et$_2$O. The layers of the filtrate are separated and the aqueous layer is extracted with Et$_2$O. The combined organic layers are then dried over anh. MgSO$_4$, filtered and concentrated under reduced pressure. Purification by FC (from DCM to DCM/MeOH/25% aq. NH$_4$OH=10/1/0.2) affords 2-(benzofuran-5-yl)ethan-1-amine as a pale yellow oil (182 mg, 47%). LC-MS A: $t_R$=0.49 min; [M+H]$^+$=162.09.

A.1.36. 6-Chloro-N-(2-(6-methoxybenzofuran-5-yl) ethyl)pyrimidin-4-amine

The title compound is prepared according to the procedure described above in A.1.1. using 2-(6-methoxybenzofuran-5-yl)ethan-1-amine hydrochloride. LC-MS A: $t_R$=0.89 min; [M+H]$^+$=304.07.

A.1.36.1. 2-(6-Methoxybenzofuran-5-yl)ethan-1-amine hydrochloride

The title compound is prepared according to the procedure described above in A.1.1.1. using tert-butyl (2-(6-methoxybenzofuran-5-yl)ethyl)carbamate. LC-MS A: $t_R$=0.54 min; [M+H]$^+$=192.24.

A.1.36.2. Tert-butyl (2-(6-methoxybenzofuran-5-yl)ethyl)carbamate

The title compound is prepared according to the procedure described above in A.1.1.2. using 5-bromo-6-methoxybenzofuran. LC-MS A: $t_R$=0.91 min; [M+H]$^+$=292.16.

A.1.36.3. 5-Bromo-6-methoxybenzofuran

To a solution of 5-bromo-2-hydroxy-4-methoxybenzaldehyde (5.00 g, 20.60 mmol) in anh. DMF (40 mL) at RT are added successively ethyl 2-bromoacetate (2.44 mL, 21.56 mmol), potassium carbonate (2.98 g, 21.56 mmol) and potassium iodide (171 mg, 1.03 mmol). The RM is heated to 80° C., under nitrogen, for 80 min. The RM is then allowed to cool to RT. Water is added and the resulting precipitate is filtered and washed with water. The obtained solid is then dissolved in EtOAc and this solution is dried over anh. MgSO$_4$, filtered and concentrated under reduced pressure giving ethyl 2-(4-bromo-2-formyl-5-methoxyphenoxy)acetate as a colorless solid (6.68 g, quantitative). LC-MS A: $t_R$=0.86 min; [M+H]$^+$=316.95.

To a solution of ethyl 2-(4-bromo-2-formyl-5-methoxyphenoxy)acetate (6.68 g, 20.60 mmol) in EtOH (27 mL) at RT is added 1 M aq. NaOH (27.40 mL, 27.40 mmol) and the RM is heated to 50° C., under nitrogen, for 20 min. The RM is then allowed to cool to RT and is treated with 1 M aq. HCl (27.40 mL). EtOH is removed under reduced pressure and the residual aqueous mixture is extracted twice with DCM. The combined organic layers are washed with brine, dried over anh. MgSO$_4$, filtered and concentrated under reduced pressure affording 2-(4-bromo-2-formyl-5-methoxyphenoxy)acetic acid as a pale yellow solid (6.01 g, 100%). LC-MS A: $t_R$=0.71 min; [M+H]$^+$=288.99.

A mixture of 2-(4-bromo-2-formyl-5-methoxyphenoxy) acetic acid (1.50 g, 5.19 mmol) in acetic anhydride (6.13 mL, 64.84 mmol) at RT is treated with sodium acetate (1.27 g, 15.48 mmol) and is then heated at reflux (150° C.), under nitrogen, for 15 h. The RM is allowed to cool to RT, diluted with toluene (20 mL) and treated with 1 M aq. NaOH (40 mL). After stirring at RT for 1 h, the RM is diluted with water and extracted twice with EtOAc. The combined organic layers are washed with brine, dried over anh. MgSO$_4$, filtered and concentrated under reduced pressure. Purification by FC (from heptane to heptane/EtOAc=9/1) affords 5-bromo-6-methoxybenzofuran as a colorless oil (0.74 g, 63%). LC-MS A: $t_R$=0.87 min; no ionization.

A.1.37. 6-Chloro-N-(2-(6-fluorobenzofuran-5-yl)ethyl)pyrimidin-4-amine

The title compound is prepared according to the procedure described above in A.1.1. using 2-(6-fluorobenzofuran-5-yl)ethan-1-amine hydrochloride. LC-MS A: $t_R$=0.88 min; [M+H]$^+$=292.07.

A.1.37.1. 2-(6-Fluorobenzofuran-5-yl)ethan-1-amine hydrochloride

The title compound is prepared according to the procedure described above in A.1.1.1. using tert-butyl (2-(6-fluorobenzofuran-5-yl)ethyl)carbamate. LC-MS A: $t_R$=0.51 min; [M+H]$^+$=180.27.

A.1.37.2. Tert-butyl (2-(6-fluorobenzofuran-5-yl)ethyl)carbamate

The title compound is prepared according to the procedure described above in A.1.1.2. using 5-bromo-6-fluorobenzofuran. LC-MS A: $t_R$=0.91 min; no ionization.

A.1.37.3. 5-Bromo-6-fluorobenzofuran

The title compound is prepared according to the procedure described above in A.1.36.3. using 5-bromo-4-fluoro-2-hydroxybenzaldehyde. LC-MS A: $t_R$=0.88 min; no ionization.

A.1.38. 6-Chloro-N-(2-(5-methoxybenzofuran-6-yl)ethyl)pyrimidin-4-amine

The title compound is prepared according to the procedure described above in A.1.1. using 2-(5-methoxybenzofuran-6-yl)ethan-1-amine hydrochloride. LC-MS A: $t_R$=0.89 min; [M+H]$^+$=304.06.

A.1.38.1. 2-(5-Methoxybenzofuran-6-yl)ethan-1-amine hydrochloride

The title compound is prepared according to the procedure described above in A.1.1.1. using tert-butyl (2-(5-methoxybenzofuran-6-yl)ethyl)carbamate. LC-MS A: $t_R$=0.53 min: [M+H]$^+$=192.22.

A.1.38.2. Tert-butyl (2-(5-methoxybenzofuran-6-yl)ethyl)carbamate

The title compound is prepared according to the procedure described above in A.1.2.2. using 6-bromo-5-methoxybenzofuran. LC-MS A: $t_R$=0.91 min; no ionization.

A.1.38.3. 6-Bromo-5-methoxybenzofuran and 6-bromo-5-methoxybenzofuran-2-carboxylic acid To a solution of 4-bromo-2-hydroxy-5-methoxybenzaldehyde (3.00 g, 12.60 mmol) in anh. DMF (25 mL) at RT are added successively ethyl 2-bromoacetate (1.50 mL, 13.20 mmol), potassium carbonate (1.828 g, 13.20 mmol) and potassium iodide (105 mg, 0.63 mmol). The RM is heated to 80° C., under nitrogen, for 30 min. The RM is then allowed to cool to RT. Water is added and the resulting precipitate is filtered and washed with water. The obtained solid is then dissolved in EtOAc and this solution is dried over anh. MgSO$_4$, filtered and concentrated under reduced pressure giving ethyl 2-(5-bromo-2-formyl-4-methoxyphenoxy)acetate as a colorless solid (4.027 g, 100%). LC-MS A: $t_R$=0.87 min; [M+H]$^+$=316.95

To a solution of ethyl 2-(5-bromo-2-formyl-4-methoxyphenoxy)acetate (4.027 g, 12.60 mmol) in EtOH (16 mL) at RT is added 1 M aq. NaOH (16.5 mL, 16.5 mmol) and the RM is heated to 50° C., under nitrogen, for 30 min. The RM is then allowed to cool to RT and is treated with 1 M aq. HCl (16.5 mL). EtOH is removed under reduced pressure and the residual aqueous mixture is extracted twice with DCM. The combined organic layers are washed with brine, dried over anh. MgSO$_4$, filtered and concentrated under reduced pressure affording 2-(5-bromo-2-formyl-4-methoxyphenoxy) acetic acid as a yellow solid (3.447 g, 94%). LC-MS A: $t_R$=0.70 min; [M+H]$^+$=288.98.

A mixture of 2-(5-bromo-2-formyl-4-methoxyphenoxy) acetic acid (3.447 g, 11.90 mmol) in acetic anhydride (14.1 mL, 149.0 mmol) at RT is treated with sodium acetate (2.935 g, 35.80 mmol) and is then heated at reflux (150° C.), under nitrogen, for 15 h. The RM is allowed to cool to RT, diluted with toluene (50 mL) and treated with 1 M aq. NaOH (100 mL). After stirring at RT for 1 h, the RM is further diluted with water and EtOAc. A subsequent filtration affords 6-bromo-5-methoxybenzofuran-2-carboxylic acid as a grey solid that is further dried under high vacuum (2.09 g). LC-MS A: $t_R$=0.75 min; no ionization. The layers of the filtrate are then separated and the aqueous layer is extracted twice with EtOAc. The combined organic layers are washed with brine, dried over anh. MgSO$_4$, filtered and concentrated under reduced pressure. Purification by FC (from heptane to heptane/EtOAc=9/1) affords 6-bromo-5-methoxybenzofuran as a colorless solid (838 mg, 31%). LC-MS A: $t_R$=0.87 min; no ionization.

A.1.39. 6-Chloro-N-(2-(2-fluoro-5-methoxybenzofuran-6-yl)ethyl)pyrimidin-4-amine The title compound is prepared according to the procedure described above in A.1.1. using 2-(2-fluoro-5-methoxybenzofuran-6-yl)ethan-1-amine hydrochloride. LC-MS A: $t_R$=0.92 min; [M+H]$^+$=322.04.

A.1.39.1. 2-(2-Fluoro-5-methoxybenzofuran-6-yl)ethan-1-amine hydrochloride

The title compound is prepared according to the procedure described above in A.1.1.1. using tert-butyl (2-(2-fluoro-5-methoxybenzofuran-6-yl)ethyl)carbamate. LC-MS A: $t_R$=0.57 min: [M+H]$^+$=210.13.

A.1.39.2. Tert-butyl (2-(2-fluoro-5-methoxybenzofuran-6-yl)ethyl)carbamate

The title compound is prepared according to the procedure described above in A.1.1.2. using 6-bromo-2-fluoro-5-methoxybenzofuran. LC-MS A: $t_R$=0.95 min; [M+H]$^+$=310.09.

A.1.39.3. 6-Bromo-2-fluoro-5-methoxybenzofuran

A well-stirred mixture of 6-bromo-5-methoxybenzofuran-2-carboxylic acid (1.60 g, 5.90 mmol, preparation described in A.1.38.3.), 1-chloromethyl-4-fluoro-1,4-diazoniabicyclo[2.2.2]octane bis(tetrafluoroborate) (3.30 g, 8.85 mmol) and sodium hydrogencarbonate (1.438 g, 17.10 mmol) in EtOAc (18 mL) and water (18 mL) is heated to 50° C. for 3 h. A second addition of Selectfluor (3.30 g, 8.85 mmol) is then performed and the RM is further stirred at 50° C. for 2.5 h. The RM is allowed to cool to RT, diluted with EtOAc and treated with 1 M aq. NaOH. After filtration over celite and separation of the layers, the organic layer is washed with brine, dried over anh. MgSO$_4$, filtered and concentrated under reduced pressure. Purification by FC (from heptane to heptane/EtOAc=9/1) affords 6-bromo-2-fluoro-5-methoxybenzofuran as a yellow oil (240 mg, 17%). LC-MS A: $t_R$=0.91 min; no ionization.

A.1.40. 6-Chloro-N-(2-(6-methoxy-4-methylbenzofuran-5-yl)ethyl)pyrimidin-4-amine The title compound is prepared according to the procedure described above in A.1.1. using 2-(6-methoxy-4-methylbenzofuran-5-yl)ethan-1-amine hydrochloride. LC-MS B: $t_R$=1.04 min; [M+H]$^+$=318.06.

A.1.40.1. 2-(6-Methoxy-4-methylbenzofuran-5-yl)ethan-1-amine hydrochloride

The title compound is prepared according to the procedure described above in A.1.1.1. using tert-butyl (2-(6-methoxy-4-methylbenzofuran-5-yl)ethyl)carbamate. LC-MS B: $t_R$=0.59 min; [M+H]$^+$=206.13.

A.1.40.2. Tert-butyl (2-(6-methoxy-4-methylbenzofuran-5-yl)ethyl)carbamate

The title compound is prepared according to the procedure described above in A.1.1.2. using 5-bromo-6-methoxy-4-methylbenzofuran. LC-MS B: $t_R$=1.06 min; [M+H]$^+$=305.98.

A.1.40.3. 5-Bromo-6-methoxy-4-methylbenzofuran

The title compound is prepared according to the procedure described above in A.1.36.3. using 3-bromo-6-hydroxy-4-methoxy-2-methylbenzaldehyde. LC-MS B: $t_R$=1.02 min; no ionization.

A.1.40.4. 3-Bromo-6-hydroxy-4-methoxy-2-methylbenzaldehyde

A solution of 2-hydroxy-4-methoxy-6-methylbenzaldehyde (3.90 g, 23.50 mmol) in anh. MeCN (75 mL) is treated with p-toluenesulfonic acid monohydrate (228 mg, 1.18 mmol) and the mixture is stirred at RT for 15 min. N-bromosuccinimide (4.18 g, 23.50 mmol) is then added portionwise and the RM is stirred at RT for 15 h. Et$_2$O and 10% aq. sodium thiosulfate are added to the RM and the layers are separated. The organic layer is successively washed with 10% aq. sodium thiosulfate and water, dried over anh. MgSO$_4$, filtered and concentrated under reduced pressure. Purification by FC (from heptane to heptane/EtOAc=9/1) affords 3-bromo-6-hydroxy-4-methoxy-2-methylbenzaldehyde as a colorless solid (4.10 g, 71%). LC-MS B: $t_R$=0.93 min: [M+H]$^+$=245.07.

A.1.40.5. 2-Hydroxy-4-methoxy-6-methylbenzaldehyde

A solution of 2,4-dihydroxy-6-methylbenzaldehyde (4.01 g, 25.80 mmol) in anh. acetone (180 mL) is treated with potassium carbonate (3.57 g, 25.80 mmol) and iodomethane (24.2 mL, 387.0 mmol), and the RM is stirred at RT for 15 h. Water and EtOAc are added and the layers are separated. The aqueous layer is further extracted with EtOAc and the combined organic layers are then washed with brine, dried over anh. MgSO$_4$, filtered and concentrated under reduced pressure. Purification by FC (heptane/EtOAc=9/1) affords 2-hydroxy-4-methoxy-6-methylbenzaldehyde as a colorless solid (3.90 g, 91%). LC-MS B: $t_R$=0.86 min; [M+H]$^+$=167.03.

A.1.41. N-(2-(1H-Indol-6-yl)ethyl)-6-chloropyrimidin-4-amine

The title compound is prepared according to the procedure described above in A.1.1. using 2-(1H-indol-6-yl)ethan-1-amine. LC-MS A: $t_R$=0.81 min; [M+H]$^+$=273.09.

A.1.41.1. 2-(1H-Indol-6-yl)ethan-1-amine

The title compound is prepared according to the procedure described above in A.1.4.1. using 1H-indole-6-carbaldehyde. LC-MS A: $t_R$=0.46 min; [M+H]$^+$=161.19.

A.1.42. N-(2-(1H-Indol-5-yl)ethyl)-6-chloropyrimidin-4-amine

The title compound is prepared according to the procedure described above in A.1.1. using 2-(1H-indol-5-yl)ethan-1-amine. LC-MS A: $t_R$=0.81 min; [M+H]$^+$=273.05.

A.1.42.1. 2-(1H-Indol-5-yl)ethan-1-amine

The title compound is prepared according to the procedure described above in A.1.4.1. using 1H-indole-5-carbaldehyde. LC-MS A: $t_R$=0.40 min; [M+H]$^+$=161.46.

A.1.43. 6-Chloro-N-(2-(1-methyl-1H-indol-6-yl)ethyl)pyrimidin-4-amine

The title compound is prepared according to the procedure described above in A.1.1. using 2-(1-methyl-1H-indol-6-yl)ethan-1-amine. LC-MS A: $t_R$=0.87 min; [M+H]$^+$=287.08.

A.1.43.1. 2-(1-Methyl-1H-indol-6-yl)ethan-1-amine

The title compound is prepared according to the procedure described above in A.1.4.1. using 1-methyl-1H-indole-6-carbaldehyde. LC-MS A: $t_R$=0.51 min; [M+H]$^+$=175.35.

A.1.44. 6-Chloro-N-(2-(1-methyl-1H-indol-5-yl)ethyl)pyrimidin-4-amine

The title compound is prepared according to the procedure described above in A.1.1. using 2-(1-methyl-1H-indol-5-yl)ethan-1-amine. LC-MS A: $t_R$=0.88 min; [M+H]$^+$=287.14.

A.1.44.1. 2-(1-Methyl-1H-indol-5-yl)ethan-1-amine

The title compound is prepared according to the procedure described above in A.1.4.1. using 1-methyl-1H-indole-5-carbaldehyde. LC-MS A: $t_R$=0.51 min: [M+H]$^+$=175.36.

A.1.45. 6-Chloro-N-(2-(1-ethyl-1H-indol-6-yl)ethyl)pyrimidin-4-amine

The title compound is prepared according to the procedure described above in A.1.1. using 2-(1-ethyl-1H-indol-6-yl)ethan-1-amine. LC-MS A: $t_R$=0.91 min; [M+H]$^+$=301.10.

A.1.45.1. 2-(1-Ethyl-1H-indol-6-yl)ethan-1-amine

The title compound is prepared according to the procedure described above in A.1.4.1. using 1-ethyl-1H-indole-6-carbaldehyde. LC-MS A: $t_R$=0.55 min; [M+H]$^+$=189.27.

A.1.46. 6-Chloro-N-(2-(1,3-dimethyl-1H-indol-5-yl)ethyl)pyrimidin-4-amine

The title compound is prepared according to the procedure described above in A.1.1. using 2-(1,3-dimethyl-1H-indol-5-yl)ethan-1-amine. LC-MS A: $t_R$=0.92 min; [M+H]$^+$=301.08.

A.1.46.1. 2-(1,3-Dimethyl-1H-indol-5-yl)ethan-1-amine

The title compound is prepared according to the procedure described above in A.1.4.1. using 1,3-dimethyl-1H-indole-5-carbaldehyde. LC-MS A: $t_R$=0.55 min; [M+H]$^+$=189.20.

A.1.46.2. 1,3-Dimethyl-1H-indole-5-carbaldehyde

To a cooled (−78° C.) solution of 5-bromo-1,3-dimethyl-1H-indole (1.31 g, 5.85 mmol) in anh. THF (60 mL) is added a solution of BuLi (2.5 M in hexanes, 2.45 mL, 6.12 mmol) and the RM is further stirred at −78° C., under nitrogen, for 4 min. Anh. DMF (641 mg, 8.77 mmol) is then added to the previous mixture and stirring at −50° C. is continued for 20 min. The RM is treated with sat. aq. NH$_4$Cl and is allowed to warm-up to RT. Water and Et$_2$O are then added and the layers are separated. The aq. layer is further extracted with Et$_2$O and the combined organic layers are dried over anh. MgSO$_4$, filtered and concentrated under reduced pressure. Purification by FC (heptane/EtOAc=4/1) affords 1,3-dimethyl-1H-indole-5-carbaldehyde as a yellow oil (0.56 g, 55%). LC-MS A: $t_R$=0.81 min; [M+H]$^+$=174.27.

A.1.46.3. 5-Bromo-1,3-dimethyl-1H-indole

To a solution of 5-bromo-3-methyl-1H-indole (2.00 g, 9.52 mmol) in anh. DMF (15 mL) is added portionwise sodium hydride (60% dispersion in mineral oil, 419 mg, 10.47 mmol) and the RM is further stirred at RT, under nitrogen, for 30 min. Iodomethane (1.2 mL, 19.27 mmol) is then added dropwise to the previous mixture and stirring at RT is continued for 1.5 h. The cooled (0° C.) RM is treated with water and is allowed to warm-up to RT. The RM is then extracted three times with Et$_2$O and the combined organic layers are washed with water, dried over anh. MgSO$_4$, filtered and concentrated under reduced pressure. Purification by FC (heptane/DCM=1/1) affords 5-bromo-1,3-dimethyl-1H-indole as a pale yellow oil (1.86 g, 87%). LC-MS A: $t_R$=0.94 min; [M+H]$^+$=224.07.

A.1.47. 6-chloro-N-(2-(6-fluoro-1-methyl-1H-indol-5-yl)ethyl)pyrimidin-4-amine The title compound is prepared according to the procedure described above in A.1.1. using 2-(6-fluoro-1-methyl-1H-indol-5-yl)ethan-1-amine hydrochloride. LC-MS A: $t_R$=0.90 min: [M+H]$^+$=305.01.

A.1.47.1. 2-(6-Fluoro-1-methyl-1H-indol-5-yl)ethan-1-amine hydrochloride

The title compound is prepared according to the procedure described above in A.1.1.1. using tert-butyl (2-(6- fluoro-1-methyl-1H-indol-5-yl)ethyl)carbamate. LC-MS A: $t_R$=0.52 min; [M+H]⁺=193.21.

A.1.47.2. Tert-butyl (2-(6-fluoro-1-methyl-1H-indol-5-yl)ethyl)carbamate

The title compound is prepared according to the procedure described above in A.1.1.2. using 5-bromo-6-fluoro-1-methyl-1H-indole. LC-MS A: $t_R$=0.92 min; [M+H]⁺=293.15.

A.1.47.3. 5-Bromo-6-fluoro-1-methyl-1H-indole

The title compound is prepared according to the procedure described above in A.1.46.3. using 5-bromo-6-fluoro-1H-indole. LC-MS A: $t_R$=0.91 min; [M+H]⁺=227.93.

A.1.48. N-(2-(Benzo[d]thiazol-6-yl)ethyl)-6-chloropyrimidin-4-amine

The title compound is prepared according to the procedure described above in A.1.1. using 2-(benzo[d]thiazol-6-yl)ethan-1-amine hydrochloride. LC-MS A: $t_R$=0.79 min; [M+H]⁺=291.01.

A.1.48.1. 2-(Benzo[d]thiazol-6-yl)ethan-1-amine hydrochloride

The title compound is prepared according to the procedure described above in A.1.1.1. using tert-butyl (2-(benzo[d]thiazol-6-yl)ethyl)carbamate. LC-MS A: $t_R$=0.43 min; [M+H]⁺=179.24.

A.1.48.2. Tert-butyl (2-(benzo[d]thiazol-6-yl)ethyl)carbamate

The title compound is prepared according to the procedure described above in A.1.2.2. using 6-bromobenzo[d]thiazole. LC-MS A: $t_R$=0.83 min; [M+H]⁺=279.16.

A.1.49. N-(2-(Benzo[d]thiazol-5-yl)ethyl)-6-chloropyrimidin-4-amine

The title compound is prepared according to the procedure described above in A.1.1. using 2-(benzo[d]thiazol-5-yl)ethan-1-amine hydrochloride. LC-MS B: $t_R$=0.85 min; [M+H]⁺=290.97.

A.1.49.1. 2-(Benzo[d]thiazol-5-yl)ethan-1-amine hydrochloride

The title compound is prepared according to the procedure described above in A.1.1.1. using tert-butyl (2-(benzo[d]thiazol-5-yl)ethyl)carbamate. LC-MS B: $t_R$=0.44 min; [M+H]⁺=179.22.

A.1.49.2. Tert-butyl (2-(benzo[d]thiazol-5-yl)ethyl)carbamate

The title compound is prepared according to the procedure described above in A.1.2.2. using 5-bromobenzo[d]thiazole. LC-MS B: $t_R$=0.89 min; [M+H]⁺=279.08.

A.1.50. N-(2-(Benzo[d]oxazol-6-yl)ethyl)-6-chloropyrimidin-4-amine

The title compound is prepared according to the procedure described above in A.1.1. using 2-(benzo[d]oxazol-6-yl)ethan-1-amine hydrochloride. LC-MS A: $t_R$=0.76 min; [M+H]⁺=275.06.

A.1.50.1. 2-(Benzo[d]oxazol-6-yl)ethan-1-amine hydrochloride

The title compound is prepared according to the procedure described above in A.1.1.1. using tert-butyl (2-(benzo[d]oxazol-6-yl)ethyl)carbamate. LC-MS A: $t_R$=0.39 min: [M+H]⁺=163.51.

A.1.50.2. Tert-butyl (2-(benzo[d]oxazol-6-yl)ethyl)carbamate

The title compound is prepared according to the procedure described above in A.1.2.2. using 6-bromobenzo[d]oxazole. LC-MS A: $t_R$=0.81 min; [M+H]⁺=263.19.

A.1.51. N-(2-(Benzo[d]isothiazol-5-yl)ethyl)-6-chloropyrimidin-4-amine

The title compound is prepared according to the procedure described above in A.1.1. using 2-(benzo[d]isothiazol-5-yl)ethan-1-amine hydrochloride. LC-MS B: $t_R$=0.89 min; [M+H]⁺=290.96.

A.1.51.1. 2-(Benzo[d]isothiazol-5-yl)ethan-1-amine hydrochloride

The title compound is prepared according to the procedure described above in A.1.1.1. using tert-butyl (2-(benzo[d]isothiazol-5-yl)ethyl)carbamate. LC-MS B: $t_R$=0.46 min; [M+H]⁺=179.21.

A.1.51.2. Tert-butyl (2-(benzo[d]isothiazol-5-yl)ethyl)carbamate

The title compound is prepared according to the procedure described above in A.1.2.2. using 5-bromobenzo[d]isothiazole. LC-MS B: $t_R$=0.93 min; [M+H]⁺=279.08.

A.1.52. 6-Chloro-N-(2-(5-methoxy-1-methyl-1H-indazol-6-yl)ethyl)pyrimidin-4-amine The title compound is prepared according to the procedure described above in A.1.1. using 2-(5-methoxy-1-methyl-1H-indazol-6-yl)ethan-1-amine hydrochloride. LC-MS A: $t_R$=0.83 min; [M+H]⁺=318.03.

A.1.52.1. 2-(5-Methoxy-1-methyl-1H-indazol-6-yl)ethan-1-amine hydrochloride

The title compound is prepared according to the procedure described above in A.1.1.1. using tert-butyl (2-(5-methoxy-1-methyl-1H-indazol-6-yl)ethyl)carbamate. LC-MS A: $t_R$=0.49 min; [M+H]⁺=206.16.

A.1.52.2. Tert-butyl (2-(5-methoxy-1-methyl-1H-indazol-6-yl)ethyl)carbamate

The title compound is prepared according to the procedure described above in A.1.1.2. using 6-bromo-5-methoxy-1-methyl-1H-indazole. LC-MS A: $t_R$=0.86 min; [M+H]⁺=306.02.

A.1.52.3.
6-Bromo-5-methoxy-1-methyl-1H-indazole

To a solution of 6-bromo-1-methyl-1H-indazol-5-ol (1.00 g, 4.27 mmol) in anh. DMF (21 mL) at RT are added cesium carbonate (1.67 g, 5.13 mmol) and iodomethane (0.537 mL, 8.54 mmol) and the RM is stirred at RT, under nitrogen, for 45 min. Water and DCM are added and the layers are separated. The aqueous layer is extracted twice with DCM and the combined organic layers are washed with brine, dried over anh. MgSO$_4$, filtered and concentrated under reduced pressure affording 6-bromo-5-methoxy-1-methyl-1H-indazole as a pink solid (1.00 g, 98%). LC-MS A: $t_R$=0.81 min; [M+H]$^+$=241.04.

A.1.53. 6-Chloro-N-(2-(5-fluoroquinolin-6-yl)ethyl)pyrimidin-4-amine

The title compound is prepared according to the procedure described above in A.1.1. using 2-(5-fluoroquinolin-6-yl)ethan-1-amine hydrochloride. LC-MS A: $t_R$=0.67 min; [M+H]$^+$=303.02.

A.1.53.1. 2-(5-Fluoroquinolin-6-yl)ethan-1-amine hydrochloride

The title compound is prepared according to the procedure described above in A.1.1.1. using tert-butyl (2-(5-fluoroquinolin-6-yl)ethyl)carbamate. LC-MS A: $t_R$=0.35 min: [M+H]$^+$=191.23.

A.1.53.2. Tert-butyl (2-(5-fluoroquinolin-6-yl)ethyl)carbamate

The title compound is prepared according to the procedure described above in A.1.1.2. using 6-bromo-5-fluoroquinoline. LC-MS A: $t_R$=0.71 min; [M+H]$^+$=291.10.

A.1.54. 6-Chloro-N-(2-(7-fluoroquinolin-6-yl)ethyl)pyrimidin-4-amine

The title compound is prepared according to the procedure described above in A.1.1. using 2-(7-fluoroquinolin-6-yl)ethan-1-amine hydrochloride. LC-MS A: $t_R$=0.60 min; [M+H]$^+$=303.02.

A.1.54.1. 2-(7-Fluoroquinolin-6-yl)ethan-1-amine hydrochloride

The title compound is prepared according to the procedure described above in A.1.1.1. using tert-butyl (2-(7-fluoroquinolin-6-yl)ethyl)carbamate. LC-MS A: $t_R$=0.28 min; [M+H]$^+$=191.22.

A.1.54.2. Tert-butyl (2-(7-fluoroquinolin-6-yl)ethyl)carbamate

The title compound is prepared according to the procedure described above in A.1.1.2. using 6-bromo-7-fluoroquinoline. LC-MS A: $t_R$=0.64 min; [M+H]$^+$=291.10.

A.1.55. 6-Chloro-N-(2-(5,7-difluoroquinolin-6-yl)ethyl)pyrimidin-4-amine

The title compound is prepared according to the procedure described above in A.1.1. using 2-(5,7-difluoroquinolin-6-yl)ethan-1-amine hydrochloride. LC-MS A: $t_R$=0.78 min; [M+H]$^+$=321.01.

A.1.55.1. 2-(5,7-Difluoroquinolin-6-yl)ethan-1-amine hydrochloride

The title compound is prepared according to the procedure described above in A.1.1.1. using tert-butyl (2-(5,7-difluoroquinolin-6-yl)ethyl)carbamate. LC-MS A: $t_R$=0.43 min; [M+H]$^+$=209.11.

A.1.55.2. Tert-butyl (2-(5,7-difluoroquinolin-6-yl)ethyl)carbamate

The title compound is prepared according to the procedure described above in A.1.1.2. using 6-bromo-5,7-difluoroquinoline. LC-MS A: $t_R$=0.82 min; [M+H]$^+$=309.08.

A.1.56. 6-Chloro-N-(2-(5,8-difluoroquinolin-6-yl)ethyl)pyrimidin-4-amine

The title compound is prepared according to the procedure described above in A.1.1. using 2-(5,8-difluoroquinolin-6-yl)ethan-1-amine hydrochloride. LC-MS A: $t_R$=0.80 min; [M+H]$^+$=321.02.

A.1.56.1. 2-(5,8-Difluoroquinolin-6-yl)ethan-1-amine hydrochloride

The title compound is prepared according to the procedure described above in A.1.1.1. using tert-butyl (2-(5,8-difluoroquinolin-6-yl)ethyl)carbamate. LC-MS A: $t_R$=0.45 min; [M+H]$^+$=209.13.

A.1.56.2. Tert-butyl (2-(5,8-difluoroquinolin-6-yl)ethyl)carbamate

The title compound is prepared according to the procedure described above in A.1.1.2. using 6-bromo-5,8-difluoroquinoline. LC-MS A: $t_R$=0.84 min; [M+H]$^+$=309.11.

A.1.57. 6-Chloro-N-(2-(7-methylquinolin-6-yl)ethyl)pyrimidin-4-amine

The title compound is prepared according to the procedure described above in A.1.1. using 2-(7-methylquinolin-6-yl)ethan-1-amine hydrochloride. LC-MS A: $t_R$=0.57 min: [M+H]$^+$=299.04.

A.1.57.1. 2-(7-Methylquinolin-6-yl)ethan-1-amine hydrochloride

The title compound is prepared according to the procedure described above in A.1.1.1. using tert-butyl (2-(7-methylquinolin-6-yl)ethyl)carbamate. LC-MS A: $t_R$=0.26 min; [M+H]$^+$=187.19.

A.1.57.2. Tert-butyl (2-(7-methylquinolin-6-yl)ethyl)carbamate

The title compound is prepared according to the procedure described above in A.1.1.2. using 6-bromo-7-methylquinoline. LC-MS A: $t_R$=0.59 min; [M+H]$^+$=287.16.

A.1.58. 6-Chloro-N-(2-(4-chloro-7-methylquinolin-6-yl)ethyl)pyrimidin-4-amine The title compound is prepared according to the procedure described above in A.1.1. using 2-(4-chloro-7-methylquinolin-6-yl)ethan-1-amine hydrochloride. LC-MS A: $t_R$=0.74 min; $[M+H]^+$=332.99.

A.1.58.1. 2-(4-Chloro-7-methylquinolin-6-yl)ethan-1-amine hydrochloride

The title compound is prepared according to the procedure described above in A.1.1.1. using tert-butyl (2-(4-chloro-7-methylquinolin-6-yl)ethyl)carbamate. LC-MS A: $t_R$=0.43 min; $[M+H]^+$=221.04.

A.1.58.2. Tert-butyl (2-(4-chloro-7-methylquinolin-6-yl)ethyl)carbamate

The title compound is prepared according to the procedure described above in A.1.1.2. using 6-bromo-4-chloro-7-methylquinoline. LC-MS A: $t_R$=0.78 min; $[M+H]^+$=321.05.

A.1.59. 6-Chloro-N-(2-(7-chloro-8-methylquinolin-6-yl)ethyl)pyrimidin-4-amine The title compound is prepared according to the procedure described above in A.1.1. using 2-(7-chloro-8-methylquinolin-6-yl)ethan-1-amine hydrochloride. LC-MS A: $t_R$=0.76 min; $[M+H]^+$=333.01.

A.1.59.1. 2-(7-Chloro-8-methylquinolin-6-yl)ethan-1-amine hydrochloride

The title compound is prepared according to the procedure described above in A.1.1.1. using tert-butyl (2-(7-chloro-8-methylquinolin-6-yl)ethyl)carbamate. LC-MS A: $t_R$=0.44 min; $[M+H]^+$=221.06.

A.1.59.2. Tert-butyl (2-(7-chloro-8-methylquinolin-6-yl)ethyl)carbamate

The title compound is prepared according to the procedure described above in A.1.1.2. using 6-bromo-7-chloro-8-methylquinoline. LC-MS A: $t_R$=0.79 min; $[M+H]^+$=321.05.

A.1.60. 6-Chloro-N-(2-(7-chloro-8-fluoroquinolin-6-yl)ethyl)pyrimidin-4-amine The title compound is prepared according to the procedure described above in A.1.1. using 2-(7-chloro-8-fluoroquinolin-6-yl)ethan-1-amine hydrochloride. LC-MS A: $t_R$=0.82 min; $[M+H]^+$=336.96.

A.1.60.1. 2-(7-Chloro-8-fluoroquinolin-6-yl)ethan-1-amine hydrochloride

The title compound is prepared according to the procedure described above in A.1.1.1. using tert-butyl (2-(7-chloro-8-fluoroquinolin-6-yl)ethyl)carbamate. LC-MS A: $t_R$=0.49 min; $[M+H]^+$=225.13.

A.1.60.2. Tert-butyl (2-(7-chloro-8-fluoroquinolin-6-yl)ethyl)carbamate

The title compound is prepared according to the procedure described above in A.1.1.2. using 6-bromo-7-chloro-8-fluoroquinoline. LC-MS A: $t_R$=0.86 min; $[M+H]^+$=325.08.

A.1.61. 6-Chloro-N-(2-(7-fluoroisoquinolin-6-yl)ethyl)pyrimidin-4-amine

The title compound is prepared according to the procedure described above in A.1.1. using 2-(7-fluoroisoquinolin-6-yl)ethan-1-amine hydrochloride. LC-MS A: $t_R$=0.56 min; $[M+H]^+$=303.03.

A.1.61.1. 2-(7-Fluoroisoquinolin-6-yl)ethan-1-amine hydrochloride

The title compound is prepared according to the procedure described above in A.1.1.1. using tert-butyl (2-(7-fluoroisoquinolin-6-yl)ethyl)carbamate. LC-MS A: $t_R$=0.23 min; $[M+H]^+$=191.22.

A.1.61.2. Tert-butyl (2-(7-fluoroisoquinolin-6-yl)ethyl)carbamate

The title compound is prepared according to the procedure described above in A.1.1.2. using 6-bromo-7-fluoroisoquinoline. LC-MS A: $t_R$=0.60 min; $[M+H]^+$=291.15.

A.1.62. 6-Chloro-N-(2-(6-fluoroisoquinolin-7-yl)ethyl)pyrimidin-4-amine

The title compound is prepared according to the procedure described above in A.1.1. using 2-(6-fluoroisoquinolin-7-yl)ethan-1-amine hydrochloride. LC-MS A: $t_R$=0.55 min; $[M+H]^+$=303.04.

A.1.62.1. 2-(6-Fluoroisoquinolin-7-yl)ethan-1-amine hydrochloride

The title compound is prepared according to the procedure described above in A.1.1.1. using tert-butyl (2-(6-fluoroisoquinolin-7-yl)ethyl)carbamate. LC-MS A: $t_R$=0.21 min; $[M+H]^+$=191.18.

A.1.62.2. Tert-butyl (2-(6-fluoroisoquinolin-7-yl)ethyl)carbamate

The title compound is prepared according to the procedure described above in A.1.1.2. using 7-bromo-6-fluoroisoquinoline. LC-MS A: $t_R$=0.60 min; $[M+H]^+$=291.12.

A.1.63. 6-Chloro-N-(2-(8-methylquinolin-7-yl)ethyl)pyrimidin-4-amine

The title compound is prepared according to the procedure described above in A.1.1. using 2-(8-methylquinolin-7-yl)ethan-1-amine hydrochloride. LC-MS A: $t_R$=0.57 min; $[M+H]^+$=299.08.

A.1.63.1. 2-(8-Methylquinolin-7-yl)ethan-1-amine hydrochloride

The title compound is prepared according to the procedure described above in A.1.1.1. using tert-butyl (2-(8-methylquinolin-7-yl)ethyl)carbamate. LC-MS A: $t_R$=0.28 min; $[M+H]^+$=187.27.

A.1.63.2. Tert-butyl (2-(8-methylquinolin-7-yl)ethyl)carbamate

The title compound is prepared according to the procedure described above in A.1.1.2. using 7-bromo-8-methylquinoline. LC-MS A: $t_R$=0.60 min; $[M+H]^+$=287.17.

A.1.64. 6-Chloro-N-(2-(4,5-difluoro-7-methoxy-2-methylbenzofuran-6-yl)ethyl)pyrimidin-4-amine The title compound is prepared according to the procedure described above in A.1.1. using 2-(4,5-difluoro-7-methoxy-2-methylbenzofuran-6-yl)ethan-1-amine. LC-MS A: $t_R$=0.98 min; [M+H]$^+$=353.95.

A.1.64.1. 2-(4,5-Difluoro-7-methoxy-2-methylbenzofuran-6-yl)ethan-1-amine

The title compound is prepared according to the procedure described above in A.1.4.1. using 4,5-difluoro-7-methoxy-2-methylbenzofuran-6-carbaldehyde. LC-MS A: $t_R$=0.63 min: [M+H]$^+$=242.02.

A.1.64.2. 4,5-Difluoro-7-methoxy-2-methylbenzofuran-6-carbaldehyde

To a cooled (0° C.) solution of 4,5-difluoro-7-methoxy-2-methylbenzofuran (1.482 g, 7.48 mmol) in anh. DCM (15 mL) is added dropwise tin(IV) chloride (1.75 mL, 15.00 mmol) and the mixture is further stirred at 0° C., under nitrogen, for 15 min. Dichloromethyl methyl ether (0.828 mL, 8.97 mmol) is then added and the mixture is stirred at RT, under nitrogen, for 3 h. This formylation led to the formation of target 4,5-difluoro-7-methoxy-2-methylbenzofuran-6-carbaldehyde and isomeric 4,5-difluoro-7-methoxy-2-methylbenzofuran-3-carbaldehyde. The resulting RM is then poured onto ice-water (50 mL) and 1 M aq. HCl (20 mL) is added. The layers are separated and the aq. layer is extracted twice with DCM. The combined organic layers are dried over anh. MgSO$_4$, filtered and concentrated under reduced pressure. Purification by FC (from heptane/DCM=7/3 to heptane/DCM=3/7) affords 4,5-difluoro-7-methoxy-2-methylbenzofuran-6-carbaldehyde as a colorless solid. LC-MS A: $t_R$=0.87 min; [M+H]$^+$=227.06.

A.1.64.3. 4,5-Difluoro-7-methoxy-2-methylbenzofuran

To a solution of 2,3-difluoro-6-hydroxy-5-methoxybenzaldehyde (5.35 g, 28.40 mmol) in anh. DMF (25 mL) at RT are added successively ethyl 2-bromopropanoate (3.69 mL, 28.40 mmol), potassium carbonate (4.127 g, 29.90 mmol) and potassium iodide (236 mg, 1.42 mmol). The RM is heated to 80° C., under nitrogen, for 1 h. The RM is then allowed to cool to RT. Water and Et$_2$O are added and the layers are separated. The aq. layer is extracted twice with Et$_2$O and the combined organic layers are washed with water, dried over anh. MgSO$_4$, filtered and concentrated under reduced pressure giving ethyl 2-(3,4-difluoro-2-formyl-6-methoxyphenoxy)propanoate as a yellow solid (5.66 g, 69%). LC-MS A: $t_R$=0.88 min; [M+H]$^+$=289.13

To a solution of ethyl 2-(3,4-difluoro-2-formyl-6-methoxyphenoxy)propanoate (5.66 g, 17.30 mmol) in MeOH (90 mL) and water (23 mL) at RT is added 1 M aq. NaOH (19.0 mL, 19.0 mmol) and the RM is heated to 50° C., under nitrogen, for 3 h. The RM is then allowed to cool to RT and is treated with 1 M aq. HCl (19.0 mL). MeOH is removed under reduced pressure and the residual aqueous mixture is extracted twice with DCM. The combined organic layers are washed with water, dried over anh. MgSO$_4$, filtered and concentrated under reduced pressure affording 2-(3,4-difluoro-2-formyl-6-methoxyphenoxy)propanoic acid as a yellow solid (6.05 g, quantitative). LC-MS A: $t_R$=0.72 min; [M+H]$^+$=261.12.

A mixture of 2-(3,4-difluoro-2-formyl-6-methoxyphenoxy)propanoic acid (6.05 g, 17.30 mmol) in acetic anhydride (19.80 mL, 209.00 mmol) at RT is treated with sodium acetate (4.12 g, 50.20 mmol) and is then heated at reflux (150° C.), under nitrogen, for 16 h. The RM is allowed to cool to RT, diluted with toluene (35 mL) and treated with 1 M aq. NaOH (60 mL). After stirring at RT for 1 h, the RM is diluted with water and extracted twice with EtOAc. The combined organic layers are washed successively with water and brine, dried over anh. MgSO$_4$, filtered and concentrated under reduced pressure. Purification by FC (from heptane to heptane/EtOAc=8/2) affords 4,5-difluoro-7-methoxy-2-methylbenzofuran as a colorless oil (1.482 g, 43%). LC-MS A: $t_R$=0.91 min: no ionization.

A.1.64.4. 2,3-Difluoro-6-hydroxy-5-methoxybenzaldehyde

To a cooled (−78° C.) solution of 2,3-difluoro-5,6-dimethoxybenzaldehyde (4.72 g, 21.70 mmol) in anh. DCM (50 mL) is added dropwise a solution of boron trichloride (1 M in DCM, 23.90 mL, 23.90 mmol) and the RM is stirred at RT, under nitrogen, for 15 h. The RM is then cooled to 0° C., treated dropwise with water (40 mL), and is further stirred at RT for 1.5 h. Water and DCM are added and the layers are separated. The aqueous layer is extracted twice with DCM and the combined organic layers are washed with brine, dried over anh. MgSO$_4$, filtered and concentrated under reduced pressure affording 2,3-difluoro-6-hydroxy-5-methoxybenzaldehyde as a yellow solid (4.38 g, quantitative). LC-MS A: $t_R$=0.74 min; no ionization.

A.1.64.5. 2,3-Difluoro-5,6-dimethoxybenzaldehyde

To a cooled (−78° C.) solution of 1,2-difluoro-4,5-dimethoxybenzene (4.00 g, 23.00 mmol) in anh. THF (80 mL) is added a solution of BuLi (2.5 M in hexanes, 10.10 mL, 25.25 mmol) and the RM is further stirred at −78° C., under nitrogen, for 1 h. Anh. DMF (2.67 mL, 34.50 mmol) is then added to the previous mixture and stirring at −78° C. is continued for 1 h. The RM is then treated dropwise with sat. aq. NH$_4$Cl (50 mL) and is allowed to warm-up to RT. Water (50 mL) and EtOAc (100 mL) are then added and the layers are separated. The aq. layer is further extracted with EtOAc (100 mL) and the combined organic layers are washed with water, dried over anh. MgSO$_4$, filtered and concentrated under reduced pressure affording 2,3-difluoro-5,6-dimethoxybenzaldehyde as a yellow solid (4.72 g, quantitative). LC-MS A: $t_R$=0.77 min; [M+H]+=203.08.

A.1.65. 6-Chloro-N-(2-(4-fluoro-7-methoxy-2-methylbenzo[b]thiophen-6-yl)ethyl)pyrimidin-4-amine The title compound is prepared according to the procedure described above in A.1.1. using 2-(4-fluoro-7-methoxy-2-methylbenzo[b]thiophen-6-yl)ethan-1-amine. LC-MS A: $t_R$=0.98 min; [M+H]$^+$=352.07.

A.1.65.1. 2-(4-Fluoro-7-methoxy-2-methylbenzo[b]thiophen-6-yl)ethan-1-amine The title compound is prepared according to the procedure described above in A.1.4.1. using 4-fluoro-7-methoxy-2-methylbenzo[b]thiophene-6-carbaldehyde. LC-MS A: $t_R$=0.63 min; [M+H]$^+$=240.12.

A.1.65.2. 4-Fluoro-7-methoxy-2-methylbenzo[b]thiophene-6-carbaldehyde

To a cooled (0° C.) solution of 4-fluoro-7-methoxy-2-methylbenzo[b]thiophene (3.75 g, 19.10 mmol) in anh. DCM (45 mL) is added dropwise tin(IV) chloride (4.47 mL, 38.20 mmol) and the mixture is further stirred at 0° C., under nitrogen, for 15 min. Dichloromethyl methyl ether (2.12 mL, 22.90 mmol) is then added and the mixture is stirred at RT, under nitrogen, for 1 h. This formylation led to the formation of target 4-fluoro-7-methoxy-2-methylbenzo[b]thiophene-6-carbaldehyde and isomeric 4-fluoro-7-methoxy-2-methylbenzo[b]thiophene-3-carbaldehyde (1:1 ratio). The resulting RM is then poured onto ice-water (200 mL) and 1 M aq. HCl (50 mL) is added. The layers are separated and the aq. layer is extracted twice with DCM. The combined organic layers are dried over anh. MgSO$_4$, filtered and concentrated under reduced pressure. Purification by FC (from heptane/DCM=4/1 to heptane/DCM=3/7) affords 4-fluoro-7-methoxy-2-methylbenzo[b]thiophene-6-carbaldehyde as a pale yellow solid. LC-MS A: $t_R$=0.91 min: [M+H]$^+$=225.11.

A.1.65.3. 4-Fluoro-7-methoxy-2-methylbenzo[b]thiophene

To a solution of 5-fluoro-2-methoxybenzenethiol (4.77 g, 30.20 mmol) in anh. acetone (50 mL) are added successively potassium carbonate (5.472 g, 39.20 mmol) and 2,3-dichloroprop-1-ene (2.84 mL, 30.20 mmol). The RM is heated at reflux (60° C.), under nitrogen, for 2 h. The RM is then allowed to cool to RT and is concentrated under reduced pressure. EtOAc (100 mL) and water (100 mL) are added and the layers are separated. The aq. layer is extracted twice with EtOAc and the combined organic layers are washed with brine, dried over anh. MgSO$_4$, filtered and concentrated under reduced pressure giving (2-chloroallyl)(5-fluoro-2-methoxyphenyl)sulfane as a pale yellow oil (8.00 g, quantitative). LC-MS A: $t_R$=0.93 min; no ionization A solution of the crude (2-chloroallyl)(5-fluoro-2-methoxyphenyl)sulfane obtained above (8.00 g, 30.20 mmol) in N,N-diethylaniline (90 mL) is heated to 185° C., under nitrogen, for 48 h. The resulting RM is then allowed to cool to RT, diluted with EtOAc (300 mL) and washed with 1 M aq. HCl (4×150 mL). The organic layer is then dried over anh. MgSO$_4$, filtered and concentrated under reduced pressure. Purification by FC (from heptane/EtOAc=19/1 to heptane/EtOAc=1/1) affords 4-fluoro-7-methoxy-2-methylbenzo[b]thiophene as a yellow oil (3.75 g, 63%). LC-MS A: $t_R$=0.94 min; no ionization.

A.1.66. 6-Chloro-N-(2-(chroman-7-yl)ethyl)pyrimidin-4-amine

The title compound is prepared according to the procedure described above in A.1.1. using 2-(chroman-7-yl)ethan-1-amine hydrochloride. LC-MS A: $t_R$=0.87 min; [M+H]$^+$=290.01.

A.1.66.1. 2-(Chroman-7-yl)ethan-1-amine hydrochloride

The title compound is prepared according to the procedure described above in A.1.1.1. using tert-butyl (2-(chroman-7-yl)ethyl)carbamate. LC-MS A: $t_R$=0.50 min; [M+H]$^+$=178.31.

A.1.66.2. Tert-butyl (2-(chroman-7-yl)ethyl)carbamate

The title compound is prepared according to the procedure described above in A.1.1.2. using 7-bromochromane. LC-MS A: $t_R$=0.90 min; no ionization.

A.1.67. 6-Chloro-N-(2-(8-methoxy-3,4-dihydro-2H-benzo[b][1,4]dioxepin-7-yl)ethyl)pyrimidin-4-amine The title compound is prepared according to the procedure described above in A.1.1. using 2-(8-methoxy-3,4-dihydro-2H-benzo[b][1,4]dioxepin-7-yl)ethan-1-amine. LC-MS A: $t_R$=0.85 min; [M+H]$^+$=336.13.

A.1.67.1. 2-(8-Methoxy-3,4-dihydro-2H-benzo[b][1,4]dioxepin-7-yl)ethan-1-amine The title compound is prepared according to the procedure described above in A.1.4.1. using 8-methoxy-3,4-dihydro-2H-benzo[b][1,4]dioxepine-7-carbaldehyde. LC-MS A: $t_R$=0.49 min; [M+H]$^+$=223.97.

A.1.68. 6-Chloro-N-(2-(2,3-dihydrobenzo[b][1,4]dioxin-6-yl)ethyl)pyrimidin-4-amine The title compound is prepared according to the procedure described above in A.1.1. using 2-(2,3-dihydrobenzo[b][1,4]dioxin-6-yl)ethan-1-amine. LC-MS C: $t_R$=0.68 min: [M+H]$^+$=292.11.

A.1.68.1. 2-(2,3-Dihydrobenzo[b][1,4]dioxin-6-yl)ethan-1-amine

The title compound is prepared according to the procedure described above in A.1.4.1. using 2,3-dihydrobenzo[b][1,4]dioxine-6-carbaldehyde. LC-MS C: $t_R$=0.35 min; [M+H]$^+$=180.29.

A.1.69. 6-Chloro-N-(2-(7-methoxy-2,3-dihydrobenzo[b][1,4]dioxin-6-yl)ethyl)pyrimidin-4-amine The title compound is prepared according to the procedure described above in A.1.1. using 2-(7-methoxy-2,3-dihydrobenzo[b][1,4]dioxin-6-yl)ethan-1-amine. LC-MS B: $t_R$=0.92 min; [M+H]$^+$=321.97.

A.1.69.1. 2-(7-Methoxy-2,3-dihydrobenzo[b][1,4]dioxin-6-yl)ethan-1-amine

The title compound is prepared according to the procedure described above in A.1.4.1. using 7-methoxy-2,3-dihydrobenzo[b][1,4]dioxine-6-carbaldehyde. LC-MS B: $t_R$=0.50 min; [M+H]$^+$=210.32.

A.1.70. 6-Chloro-N-(2-(7-ethoxy-2,3-dihydrobenzo[b][1,4]dioxin-6-yl)ethyl)pyrimidin-4-amine The title compound is prepared according to the procedure described above in A.1.1. using 2-(7-ethoxy-2,3-dihydrobenzo[b][1,4]dioxin-6-yl)ethan-1-amine. LC-MS B: $t_R$=0.97 min; [M+H]$^+$=336.10.

A.1.70.1. 2-(7-Ethoxy-2,3-dihydrobenzo[b][1,4]dioxin-6-yl)ethan-1-amine

The title compound is prepared according to the procedure described above in A.1.4.1. using 7-ethoxy-2,3-dihydrobenzo[b][1,4]dioxine-6-carbaldehyde. LC-MS B: $t_R$=0.54 min; [M+H]$^+$=223.94.

A.1.70.2. 7-Ethoxy-2,3-dihydrobenzo[b][1,4]dioxine-6-carbaldehyde

A solution of 7-hydroxy-2,3-dihydrobenzo[b][1,4]dioxine-6-carbaldehyde (730 mg, 4.05 mmol) in anh. DMF (20 mL) is treated at RT with cesium carbonate (1.584 g, 4.86 mmol) and iodoethane (0.358 mL, 4.46 mmol) and the RM is stirred at RT, under nitrogen, for 15 h. Water is added and the mixture is extracted three times with Et$_2$O. The combined organic layers are then washed twice with water, dried over anh. MgSO$_4$, filtered and concentrated under reduced pressure. Purification by FC (heptane/EtOAc=4/1) affords 7-ethoxy-2,3-dihydrobenzo[b][1,4]dioxine-6-carbaldehyde as a yellow solid (800 mg, 95%). LC-MS B: $t_R$=0.86 min; [M+H]$^+$=209.19.

A.1.70.3. 7-Hydroxy-2,3-dihydrobenzo[b][1,4]dioxine-6-carbaldehyde

A suspension of aluminum chloride (2.372 g, 17.60 mmol) in anh. DCM (25 mL) is treated at RT with a solution of 7-methoxy-2,3-dihydrobenzo[b][1,4]dioxine-6-carbaldehyde (1.000 g, 4.89 mmol) in anh. DCM (20 mL) and the RM is stirred at RT, under nitrogen, for 2 h. 1 M aq. HCl is then added and the layers are separated. The aqueous layer is extracted twice with DCM and the combined organic layers are then dried over anh. MgSO$_4$, filtered and concentrated under reduced pressure affording 7-hydroxy-2,3-dihydrobenzo[b][1,4]dioxine-6-carbaldehyde as a beige solid (730 mg, 83%). LC-MS B: $t_R$=0.74 min; [M+H]$^+$=181.25.

A.1.71. 6-Chloro-N-(2-(7-methyl-2,3-dihydrobenzo[b][1,4]dioxin-6-yl)ethyl)pyrimidin-4-amine The title compound is prepared according to the procedure described above in A.1.1. using 2-(7-methyl-2,3-dihydrobenzo[b][1,4]dioxin-6-yl)ethan-1-amine. LC-MS A: $t_R$=0.85 min: [M+H]$^+$=305.95.

A.1.71.1. 2-(7-Methyl-2,3-dihydrobenzo[b][1,4]dioxin-6-yl)ethan-1-amine

The title compound is prepared according to the procedure described above in A.1.4.1. using 7-methyl-2,3-dihydrobenzo[b][1,4]dioxine-6-carbaldehyde. LC-MS A: $t_R$=0.50 min; [M+H]$^+$=194.22.

A.1.72. 6-Chloro-N-(2-(7-(methylthio)-2,3-dihydrobenzo[b][1,4]dioxin-6-yl)ethyl)pyrimidin-4-amine The title compound is prepared according to the procedure described above in A.1.1. using 2-(7-(methylthio)-2,3-dihydrobenzo[b][1,4]dioxin-6-yl)ethan-1-amine. LC-MS A: $t_R$=0.88 min; [M+H]$^+$=337.97.

A.1.72.1. 2-(7-(Methylthio)-2,3-dihydrobenzo[b][1,4]dioxin-6-yl)ethan-1-amine The title compound is prepared according to the procedure described above in A.1.4.1. using 7-(methylthio)-2,3-dihydrobenzo[b][1,4]dioxine-6-carbaldehyde. LC-MS A: $t_R$=0.52 min; [M+H]$^+$=226.01.

A.1.73. 6-Chloro-N-(2-(8-chloro-2,3-dihydrobenzo[b][1,4]dioxin-6-yl)ethyl)pyrimidin-4-amine The title compound is prepared according to the procedure described above in A.1.1. using 2-(8-chloro-2,3-dihydrobenzo[b][1,4]dioxin-6-yl)ethan-1-amine. LC-MS B: $t_R$=0.97 min; [M+H]$^+$=326.04.

A.1.73.1. 2-(8-Chloro-2,3-dihydrobenzo[b][1,4]dioxin-6-yl)ethan-1-amine

The title compound is prepared according to the procedure described above in A.1.4.1. using 8-chloro-2,3-dihydrobenzo[b][1,4]dioxine-6-carbaldehyde. LC-MS B: $t_R$=0.51 min; [M+H]$^+$=214.13.

A.1.74. 6-Chloro-N-(2-(8-methyl-2,3-dihydrobenzo[b][1,4]dioxin-6-yl)ethyl)pyrimidin-4-amine The title compound is prepared according to the procedure described above in A.1.1. using 2-(8-methyl-2,3-dihydrobenzo[b][1,4]dioxin-6-yl)ethan-1-amine. LC-MS B: $t_R$=0.94 min; [M+H]$^+$=306.00.

A.1.74.1. 2-(8-Methyl-2,3-dihydrobenzo[b][1,4]dioxin-6-yl)ethan-1-amine

The title compound is prepared according to the procedure described above in A.1.4.1. using 8-methyl-2,3-dihydrobenzo[b][1,4]dioxine-6-carbaldehyde. LC-MS B: $t_R$=0.50 min; [M+H]$^+$=194.27.

A.1.74.2. 8-Methyl-2,3-dihydrobenzo[b][1,4]dioxine-6-carbaldehyde

A mixture of 8-bromo-2,3-dihydrobenzo[b][1,4]dioxine-6-carbaldehyde (2.00 g, 7.82 mmol) and Cs$_2$CO$_3$ (7.718 g, 23.50 mmol) in DMF (18 mL) is degassed with nitrogen. Pd(PPhs)$_4$ (903 mg, 0.78 mmol) and 2,4,6-trimethyl-1,3,5,2,4,6-trioxatriborinane (1.021 g, 8.13 mmol) are then added and the mixture is degassed again with nitrogen. The RM is then heated to 90° C., under nitrogen, overnight. The RM is allowed to cool to RT, and diluted with Et$_2$O and water. The layers are separated and the aqueous layer is extracted twice with Et$_2$O. The combined organic layers are then washed with brine, dried over anh. MgSO$_4$, filtered and concentrated under reduced pressure. Purification by FC (from heptane to heptane/EtOAc=7/3) affords 8-methyl-2,3-dihydrobenzo[b][1,4]dioxine-6-carbaldehyde as a colorless oil (1.120 g, 80%). LC-MS B: $t_R$=0.81 min; [M+H]$^+$=179.25.

A.1.75. 6-Chloro-N-(2-(8-fluoro-2,3-dihydrobenzo[b][1,4]dioxin-6-yl)ethyl)pyrimidin-4-amine The title compound is prepared according to the procedure described above in A.1.1. using 2-(8-fluoro-2,3-dihydrobenzo[b][1,4]dioxin-6-yl)ethan-1-amine hydrochloride. LC-MS B: $t_R$=0.91 min: [M+H]$^+$=310.10.

A.1.75.1. 2-(8-Fluoro-2,3-dihydrobenzo[b][1,4]dioxin-6-yl)ethan-1-amine hydrochloride The title compound is prepared according to the procedure described above in A.1.1.1. using tert-butyl (2-(8- fluoro-2,3-dihydrobenzo[b][1,4]dioxin-6-yl)ethyl)carbamate. LC-MS B: $t_R$=0.49 min; [M+H]$^+$=198.13.

A.1.75.2. Tert-butyl (2-(8-fluoro-2,3-dihydrobenzo[b][1,4]dioxin-6-yl)ethyl)carbamate The title compound is prepared according to the procedure described above in A.1.1.2. using 7-bromo-5-fluoro-2,3-dihydrobenzo[b][1,4]dioxine. LC-MS B: $t_R$=0.97 min; no ionization.

A.1.75.3. 7-Bromo-5-fluoro-2,3-dihydrobenzo[b][1,4]dioxine

To a solution of 5-bromo-3-fluorobenzene-1,2-diol (500 mg, 2.29 mmol) in anh. DMF (7 mL) at RT are added potassium carbonate (634 mg, 4.59 mmol) and 1,2-dibromoethane (0.242 mL, 2.75 mmol) and the RM is heated to 100° C. for 2 h. The RM is then allowed to cool to RT, water and Et$_2$O are added and the layers are separated. The aqueous layer is extracted twice with Et$_2$O and the combined organic layers are washed with water, dried over anh. MgSO$_4$, filtered and concentrated under reduced pressure affording 7-bromo-5-fluoro-2,3-dihydrobenzo[b][1,4]dioxine as a colorless solid (323 mg, 61%). LC-MS B: $t_R$=0.96 min; no ionization.

A.1.76. 7-(2-(((6-Chloropyrimidin-4-yl)amino)ethyl)-2,3-dihydrobenzo[b][1,4]dioxine-6-carbonitrile Tert-butyl (6-chloropyrimidin-4-yl)(2-(7-cyano-2,3-dihydrobenzo[b][1,4]dioxin-6-yl)ethyl)carbamate (900 mg, 2.16 mmol) is treated with 4 M HCl in dioxane (10 mL, 40.00 mmol) and the RM is stirred at RT for 5 h. The RM is then concentrated under reduced pressure and the residue is partitioned between DCM and sat. aq. NaHCO$_3$. The aqueous layer is extracted with DCM and the combined organic layers are dried over anh. MgSO$_4$, filtered and concentrated under reduced pressure. Purification by FC (from heptane to EtOAc) affords 7-(2-((6-chloropyrimidin-4-yl)amino)ethyl)-2,3-dihydrobenzo[b][1,4]dioxine-6-carbonitrile as a yellow solid (630 mg, 92%). LC-MS B: $t_R$=0.88 min; [M+H]$^+$=317.08.

A.1.76.1. Tert-butyl (6-chloropyrimidin-4-yl)(2-(7-cyano-2,3-dihydrobenzo[b][1,4]dioxin-6-yl)ethyl)carbamate A cooled (15° C.) solution of tert-butyl (2-(7-cyano-2,3-dihydrobenzo[b][1,4]dioxin-6-yl)ethyl)carbamate (690 mg, 2.27 mmol) in anh. dioxane (22 mL) is treated portionwise with sodium hydride (60% dispersion in mineral oil, 363 mg, 9.07 mmol) and the mixture is stirred at RT, under nitrogen, for 15 min. To the resulting cooled (15° C.) mixture is then added 4,6-dichloropyrimidine (844 mg, 5.67 mmol) and heating at 90° C. is continued for 6 h. Water and EtOAc are added and the layers are separated. The organic layer is washed with brine, dried over anh. MgSO$_4$, filtered and concentrated under reduced pressure. Purification by FC (from heptane to heptane/EtOAc=1/1) affords tert-butyl (6-chloropyrimidin-4-yl)(2-(7-cyano-2,3-dihydrobenzo[b][1,4]dioxin-6-yl)ethyl)carbamate as a yellow solid (900 mg, 95%). LC-MS B: $t_R$=1.15 min; [M+H]$^+$=417.04.

A.1.76.2. Tert-butyl (2-(7-cyano-2,3-dihydrobenzo[b][1,4]dioxin-6-yl)ethyl)carbamate The title compound is prepared according to the procedure described above in A.1.1.2. using 7-bromo-2,3-dihydrobenzo[b][1,4]dioxine-6-carbonitrile. LC-MS B: $t_R$=0.92 min; [M+H]$^+$=305.11.

A.1.76.3. 7-Bromo-2,3-dihydrobenzo[b][1,4]dioxine-6-carbonitrile

A well-stirred suspension of 7-bromo-2,3-dihydrobenzo[b][1,4]dioxine-6-carbaldehyde (1.00 g, 4.11 mmol) and sodium azide (401 mg, 6.17 mmol) in anh. MeCN (10 mL) is treated at RT with a solution of trifluoromethanesulfonic acid (1.11 mL, 12.30 mmol) in anh. MeCN (5 mL). The RM is further stirred at RT, under nitrogen, for 0.5 h. Water is then added and the mixture is filtered. The collected solid is washed with water and is then dissolved in EtOAc. The organic layer is dried over anh. MgSO$_4$, filtered and concentrated under reduced pressure affording 7-bromo-2,3-dihydrobenzo[b][1,4]dioxine-6-carbonitrile as a pale yellow solid (920 mg, 93%). LC-MS B: $t_R$=0.89 min; no ionization.

A.1.77. 6-Chloro-N-(2-(chroman-6-yl)ethyl)pyrimidin-4-amine

The title compound is prepared according to the procedure described above in A.1.1. using 2-(chroman-6-yl)ethan-1-amine hydrochloride. LC-MS B: $t_R$=0.94 min; [M+H]$^+$=289.90.

A.1.77.1. 2-(Chroman-6-yl)ethan-1-amine hydrochloride

The title compound is prepared according to the procedure described above in A.1.1.1. using tert-butyl (2-(chroman-6-yl)ethyl)carbamate. LC-MS B: $t_R$=0.49 min; [M+H]$^+$=178.26.

A.1.77.2. Tert-butyl (2-(chroman-6-yl)ethyl)carbamate

The title compound is prepared according to the procedure described above in A.1.1.2. using 6-bromochromane. LC-MS B: $t_R$=0.98 min; [M+H]$^+$=278.16.

A.1.78. 6-Chloro-N-(2-(3-methoxy-5,6,7,8-tetrahydronaphthalen-2-yl)ethyl)pyrimidin-4-amine The title compound is prepared according to the procedure described above in A.1.1. using 2-(3-methoxy-5,6,7,8-tetrahydronaphthalen-2-yl)ethan-1-amine. LC-MS A: $t_R$=0.98 min; [M+H]$^+$=318.06.

A.1.78.1. 2-(3-Methoxy-5,6,7,8-tetrahydronaphthalen-2-yl)ethan-1-amine

The title compound is prepared according to the procedure described above in A.1.4.1. using 3-methoxy-5,6,7,8-tetrahydronaphthalene-2-carbaldehyde. LC-MS A: $t_R$=0.63 min; [M+H]$^+$=206.18.

A.1.79. 6-Chloro-N-(2-(7-methoxy-1,2,3,4-tetrahydroquinolin-6-yl)ethyl)pyrimidin-4-amine The title compound is prepared according to the procedure described above in A.1.1. using 2-(7-methoxy-1,2,3,4-tetrahydroquinolin-6-yl)ethan-1-amine hydrochloride. LC-MS B: $t_R$=0.61 min; [M+H]$^+$=319.09.

A.1.79.1. 2-(7-Methoxy-1,2,3,4-tetrahydroquinolin-6-yl)ethan-1-amine hydrochloride The title compound is prepared according to the procedure described above in A.1.1.1. using tert-butyl (2-(7-methoxy-1,2,3,4-tetrahydroquinolin-6-yl)ethyl)carbamate. LC-MS B: $t_R$=0.32 min: [M+H]$^+$=207.42.

A.1.79.2. Tert-butyl (2-(7-methoxy-1,2,3,4-tetrahydroquinolin-6-yl)ethyl)carbamate The title compound is prepared according to the procedure described above in A.1.1.2. using 6-bromo-7-methoxy-1,2,3,4-tetrahydroquinoline. LC-MS B: $t_R$=0.64 min; [M+H]$^+$=307.15.

A.1.80. N-(2-(Benzo[d][1,3]dioxol-5-yl)ethyl)-6-chloropyrimidin-4-amine

The title compound is prepared according to the procedure described above in A.1.1. using 2-(benzo[d][1,3]dioxol-5-yl)ethan-1-amine. LC-MS B: $t_R$=0.90 min; [M+H]$^+$=278.19.

A.1.80.1. 2-(Benzo[d][1,3]dioxol-5-yl)ethan-1-amine

The title compound is prepared according to the procedure described above in A.1.4.1. using benzo[d][1,3]dioxole-5-carbaldehyde. LC-MS B: $t_R$=0.43 min; [M+H]$^+$=166.13.

A.1.81. 6-Chloro-N-(2-(6-methoxybenzo[d][1,3]dioxol-5-yl)ethyl)pyrimidin-4-amine The title compound is prepared according to the procedure described above in A.1.1. using 2-(6-methoxybenzo[d][1,3]dioxol-5-yl)ethan-1-amine. LC-MS B: $t_R$=0.93 min; [M+H]$^+$=308.15.

A.1.81.1. 2-(6-Methoxybenzo[d][1,3]dioxol-5-yl)ethan-1-amine

The title compound is prepared according to the procedure described above in A.1.4.1. using 6-methoxybenzo[d][1,3]dioxole-5-carbaldehyde. LC-MS B: $t_R$=0.49 min; [M+H]$^+$=196.29.

A.1.82. 6-Chloro-N-(2-(6-(difluoromethoxy)benzo[d][1,3]dioxol-5-yl)ethyl)pyrimidin-4-amine The title compound is prepared according to the procedure described above in A.1.1. using 2-(6-(difluoromethoxy)benzo[d][1,3]dioxol-5-yl)ethan-1-amine. LC-MS A: $t_R$=0.87 min; [M+H]$^+$=343.95.

A.1.82.1. 2-(6-(Difluoromethoxy)benzo[d][1,3]dioxol-5-yl)ethan-1-amine

The title compound is prepared according to the procedure described above in A.1.4.1. using 6-(difluoromethoxy)benzo[d][1,3]dioxole-5-carbaldehyde. LC-MS A: $t_R$=0.52 min; [M+H]$^+$=232.04.

A.1.83. 6-(2-((6-Chloropyrimidin-4-yl)amino)ethyl)benzo[d][1,3]dioxole-5-carbonitrile The title compound is prepared according to the procedure described above in A.1.76. using tert-butyl (6-chloropyrimidin-4-yl)(2-(6-cyanobenzo[d][1,3]dioxol-5-yl)ethyl)carbamate. LC-MS A: $t_R$=0.79 min; [M+H]$^+$=303.02.

A.1.83.1. Tert-butyl (6-chloropyrimidin-4-yl)(2-(6-cyanobenzo[d][1,3]dioxol-5-yl)ethyl)carbamate The title compound is prepared according to the procedure described above in A.1.76.1. using tert-butyl (2-(6-cyanobenzo[d][1,3]dioxo-5-yl)ethyl)carbamate. LC-MS A: $t_R$=1.01 min; [M+H]$^+$=403.02.

A.1.83.2. Tert-butyl (2-(6-cyanobenzo[d][1,3]dioxol-5-yl)ethyl)carbamate

The title compound is prepared according to the procedure described above in A.1.2.2. using 6-bromobenzo[d][1,3]dioxole-5-carbonitrile. LC-MS A: $t_R$=0.84 min: [M+H]$^+$=291.08.

A.1.84. 6-Chloro-N-(2-(2,3-dihydrobenzo[b]thiophen-5-yl)ethyl)pyrimidin-4-amine The title compound is prepared according to the procedure described above in A.1.1. using 2-(2,3-dihydrobenzo[b]thiophen-5-yl)ethan-1-amine hydrochloride. LC-MS B: $t_R$=0.98 min; [M+H]$^+$=291.98.

A.1.84.1. 2-(2,3-Dihydrobenzo[b]thiophen-5-yl)ethan-1-amine hydrochloride

The title compound is prepared according to the procedure described above in A.1.1.1. using tert-butyl (2-(2,3-dihydrobenzo[b]thiophen-5-yl)ethyl)carbamate. LC-MS B: $t_R$=0.54 min; [M+H]$^+$=180.12.

A.1.84.2. Tert-butyl (2-(2,3-dihydrobenzo[b]thiophen-5-yl)ethyl)carbamate

The title compound is prepared according to the procedure described above in A.1.1.2. using 5-bromo-2,3-dihydrobenzo[b]thiophene. LC-MS B: $t_R$=1.01 min; [M+H]$^+$=280.14.

A.1.85. 6-Chloro-N-(2-(2,3-dihydro-1H-inden-5-yl)ethyl)pyrimidin-4-amine

The title compound is prepared according to the procedure described above in A.1.1. using 2-(2,3-dihydro-1H-inden-5-yl)ethan-1-amine hydrochloride. LC-MS B: $t_R$=1.04 min; [M+H]$^+$=274.03.

A.1.85.1. 2-(2,3-Dihydro-1H-inden-5-yl)ethan-1-amine hydrochloride

The title compound is prepared according to the procedure described above in A.1.1.1. using tert-butyl (2-(2,3-dihydro-1H-inden-5-yl)ethyl)carbamate. LC-MS B: $t_R$=0.45 min; no ionization.

A.1.85.2. Tert-butyl (2-(2,3-dihydro-1H-inden-5-yl)ethyl)carbamate

The title compound is prepared according to the procedure described above in A.1.1.2. using 5-bromo-2,3-dihydro-1H-indene. LC-MS B: $t_R$=1.09 min; [M+H]$^+$=262.13.

A.1.86. 6-Chloro-N-(2-(2,3-dihydrobenzofuran-6-yl)ethyl)pyrimidin-4-amine

The title compound is prepared according to the procedure described above in A.1.1. using 2-(2,3-dihydrobenzofuran-6-yl)ethan-1-amine hydrochloride. LC-MS B: $t_R$=0.92 min; [M+H]$^+$=276.28.

A.1.86.1. 2-(2,3-Dihydrobenzofuran-6-yl)ethan-1-amine hydrochloride

The title compound is prepared according to the procedure described above in A.1.1.1. using tert-butyl (2-(2,3-dihydrobenzofuran-6-yl)ethyl)carbamate. LC-MS B: $t_R$=0.45 min; [M+H]$^+$=164.07.

A.1.86.2. Tert-butyl (2-(2,3-dihydrobenzofuran-6-yl)ethyl)carbamate

The title compound is prepared according to the procedure described above in A.1.1.2. using 6-bromo-2,3-dihydrobenzofuran. LC-MS B: $t_R$=0.99 min; [M+H]$^+$=264.10.

A.1.87. 6-Chloro-N-(2-(2,3-dihydrobenzofuran-5-yl)ethyl)pyrimidin-4-amine

The title compound is prepared according to the procedure described above in A.1.1. using 2-(2,3-dihydrobenzofuran-5-yl)ethan-1-amine hydrochloride. LC-MS B: $t_R$=0.89 min; [M+H]$^+$=276.06.

A.1.87.1. 2-(2,3-Dihydrobenzofuran-5-yl)ethan-1-amine hydrochloride

The title compound is prepared according to the procedure described above in A.1.1.1. using tert-butyl (2-(2,3-dihydrobenzofuran-5-yl)ethyl)carbamate. LC-MS B: $t_R$=0.46 min; [M+H]$^+$=164.08.

A.1.87.2. Tert-butyl (2-(2,3-dihydrobenzofuran-5-yl)ethyl)carbamate

The title compound is prepared according to the procedure described above in A.1.1.2. using 5-bromo-2,3-dihydrobenzofuran. LC-MS B: $t_R$=0.95 min; no ionization.

A.1.88. 6-Chloro-N-(2-(1,3-dihydroisobenzofuran-5-yl)ethyl)pyrimidin-4-amine The title compound is prepared according to the procedure described above in A.1.1. using 2-(1,3-dihydroisobenzofuran-5-yl)ethan-1-amine hydrochloride. LC-MS B: $t_R$=0.85 min; [M+H]$^+$=276.01.

A.1.88.1. 2-(1,3-Dihydroisobenzofuran-5-yl)ethan-1-amine hydrochloride

The title compound is prepared according to the procedure described above in A.1.1.1. using tert-butyl (2-(1,3-dihydroisobenzofuran-5-yl)ethyl)carbamate. LC-MS B: $t_R$=0.41 min; [M+H]$^+$=164.08.

A.1.88.2. Tert-butyl (2-(1,3-dihydroisobenzofuran-5-yl)ethyl)carbamate

The title compound is prepared according to the procedure described above in A.1.1.2. using 5-bromo-1,3-dihydroisobenzofuran. LC-MS B: $t_R$=0.89 min; no ionization.

A.1.89. 6-Chloro-N-(2-(6-chloro-2,2-difluorobenzo[d][1,3]dioxol-5-yl)ethyl)pyrimidin-4-amine The title compound is prepared according to the procedure described above in A.1.1. using 2-(6-chloro-2,2-difluorobenzo[d][1,3]dioxol-5-yl)ethan-1-amine hydrochloride. LC-MS A: $t_R$=0.95 min; [M+H]$^+$=347.99.

A.1.89.1. 2-(6-Chloro-2,2-difluorobenzo[d][1,3]dioxol-5-yl)ethan-1-amine hydrochloride The title compound is prepared according to the procedure described above in A.1.1.1. using tert-butyl (2-(6-chloro-2,2-difluorobenzo[d][1,3]dioxol-5-yl)ethyl)carbamate. LC-MS A: $t_R$=0.59 min; [M+H]$^+$=236.00.

A.1.89.2. Tert-butyl (2-(6-chloro-2,2-difluorobenzo[d][1,3]dioxol-5-yl)ethyl)carbamate The title compound is prepared according to the procedure described above in A.1.1.2. using 5-bromo-6-chloro-2,2-difluorobenzo[d][1,3]dioxole. LC-MS A: $t_R$=0.98 min; no ionization.

A.1.90. 6-Chloro-N-(2-(6-chloro-3,4-dihydro-2H-benzo[b][1,4]oxazin-7-yl)ethyl)pyrimidin-4-amine The title compound is prepared according to the procedure described above in A.1.1. using 2-(6-chloro-3,4-dihydro-2H-benzo[b][1,4]oxazin-7-yl)ethan-1-amine hydrochloride. LC-MS A: $t_R$=0.82 min; [M+H]$^+$=324.97.

A.1.90.1. 2-(6-Chloro-3,4-dihydro-2H-benzo[b][1,4]oxazin-7-yl)ethan-1-amine hydrochloride The title compound is prepared according to the procedure described above in A.1.1.1. using tert-butyl (2-(6-chloro-3,4-dihydro-2H-benzo[b][1,4]oxazin-7-yl)ethyl)carbamate. LC-MS A: $t_R$=0.45 min; [M+H]$^+$=213.12.

A.1.90.2. Tert-butyl (2-(6-chloro-3,4-dihydro-2H-benzo[b][1,4]oxazin-7-yl)ethyl)carbamate The title compound is prepared according to the procedure described above in A.1.1.2. using 7-bromo-6-chloro-3,4-dihydro-2H-benzo[b][1,4]oxazine. LC-MS A: $t_R$=0.85 min; [M+H]$^+$=313.05.

A.1.91. 6-Chloro-N-(2-(7-fluoro-4-methyl-3,4-dihydro-2H-benzo[b][1,4]oxazin-6-yl)ethyl)pyrimidin-4-amine The title compound is prepared according to the procedure described above in A.1.1. using 2-(7-fluoro-4-methyl-3,4-dihydro-2H-benzo[b][1,4]oxazin-6-yl)ethan-1-amine hydrochloride. LC-MS A: $t_R$=0.85 min; $[M+H]^+$=323.04.

A.1.91.1. 2-(7-Fluoro-4-methyl-3,4-dihydro-2H-benzo[b][1,4]oxazin-6-yl)ethan-1-amine hydrochloride The title compound is prepared according to the procedure described above in A.1.1.1. using tert-butyl (2-(7-fluoro-4-methyl-3,4-dihydro-2H-benzo[b][1,4]oxazin-6-yl)ethyl)carbamate. LC-MS A: $t_R$=0.49 min; $[M+H]^+$=211.15.

A.1.91.2. tert-Butyl (2-(7-fluoro-4-methyl-3,4-dihydro-2H-benzo[b][1,4]oxazin-6-yl)ethyl)carbamate The title compound is prepared according to the procedure described above in A.1.1.2. using 6-bromo-7-fluoro-4-methyl-3,4-dihydro-2H-benzo[b][1,4]oxazine. LC-MS A: $t_R$=0.89 min; $[M+H]^+$=311.16.

A.1.91.3. 6-Bromo-7-fluoro-4-methyl-3,4-dihydro-2H-benzo[b][1,4]oxazine

To a cooled (0° C.) suspension of sodium hydride (60% dispersion in mineral oil, 194 mg, 4.84 mmol)) in anh. DMF (15 mL) is added a solution of 6-bromo-7-fluoro-3,4-dihydro-2H-benzo[b][1,4]oxazine (1.00 g, 3.72 mmol) in anh. DMF (10 mL). The mixture is stirred at 0° C. for 15 min., and iodomethane (0.937 mL, 14.90 mmol) is then added. The RM is stirred at 0° C. for 15 min., and then at RT overnight. Water and Et$_2$O are added and the layers are separated. The aqueous layer is extracted twice with Et$_2$O and the combined organic layers are washed with water, dried over anh. MgSO$_4$, filtered and concentrated under reduced pressure. Purification by FC (heptane/DCM=1/1) affords 6-bromo-7-fluoro-4-methyl-3,4-dihydro-2H-benzo[b][1,4]oxazine as a yellow oil (311 mg, 34%). LC-MS A: $t_R$=0.89 min; no ionization.

A.1.92. 6-(2-((6-Chloropyrimidin-4-yl)amino)ethyl)-7-methoxy-1-methyl-3,4-dihydroquinolin-2(1H)-one The title compound is prepared according to the procedure described above in A.1.1. using 6-(2-aminoethyl)-7-methoxy-1-methyl-3,4-dihydroquinolin-2(1H)-one hydrochloride. LC-MS A: $t_R$=0.81 min; $[M+H]^+$=346.94.

A.1.92.1. 6-(2-Aminoethyl)-7-methoxy-1-methyl-3,4-dihydroquinolin-2(1H)-one hydrochloride The title compound is prepared according to the procedure described above in A.1.1.1. using tert-butyl (2-(7-methoxy-1-methyl-2-oxo-1,2,3,4-tetrahydroquinolin-6-yl)ethyl)carbamate. LC-MS A: $t_R$=0.47 min; $[M+H]^+$=235.11.

A.1.92.2. Tert-butyl (2-(7-methoxy-1-methyl-2-oxo-1,2,3,4-tetrahydroquinolin-6-yl)ethyl)carbamate The title compound is prepared according to the procedure described above in A.1.1.2. using 6-bromo-7-methoxy-1-methyl-3,4-dihydroquinolin-2(1H)-one. LC-MS A: $t_R$=0.84 min; $[M+H]^+$=335.10.

A.1.93. 6-Chloro-N-(2-(7-fluoro-1-methyl-1,2,3,4-tetrahydroquinolin-6-yl)ethyl)pyrimidin-4-amine The title compound is prepared according to the procedure described above in A.1.1. using 2-(7-fluoro-1-methyl-1,2,3,4-tetrahydroquinolin-6-yl)ethan-1-amine hydrochloride.

A.1.93.1. 2-(7-Fluoro-1-methyl-1,2,3,4-tetrahydroquinolin-6-yl)ethan-1-amine hydrochloride The title compound is prepared according to the procedure described above in A.1.1.1. using tert-butyl (2-(7-fluoro-1-methyl-1,2,3,4-tetrahydroquinolin-6-yl)ethyl)carbamate. LC-MS A: $t_R$=0.52 min; $[M+H]^+$=209.26.

A.1.93.2. Tert-butyl (2-(7-fluoro-1-methyl-1,2,3,4-tetrahydroquinolin-6-yl)ethyl)carbamate The title compound is prepared according to the procedure described above in A.1.1.2. using 6-bromo-7-fluoro-1-methyl-1,2,3,4-tetrahydroquinoline. LC-MS A: $t_R$=0.89 min; $[M+H]^+$=309.19.

A.1.93.3. 6-Bromo-7-fluoro-1-methyl-1,2,3,4-tetrahydroquinoline

The title compound is prepared according to the procedure described above in A.1.91.3. using 6-bromo-7-fluoro-1,2,3,4-tetrahydroquinoline.

A.1.94. 6-Chloro-N-(2-(6-methylbenzo[b]thiophen-5-yl)ethyl)pyrimidin-4-amine The title compound is prepared according to the procedure described above in A.1.1. using 2-(6-methylbenzo[b]thiophen-5-yl)ethan-1-amine hydrochloride. LC-MS B: $t_R$=1.02 min; $[M+H]^+$=304.11.

A.1.94.1. 2-(6-Methylbenzo[b]thiophen-5-yl)ethan-1-amine hydrochloride

The title compound is prepared according to the procedure described above in A.1.1.1. using tert-butyl (2-(6-methylbenzo[b]thiophen-5-yl)ethyl)carbamate. LC-MS B: $t_R$=0.58 min; $[M+H]^+$=192.18.

A.1.94.2. Tert-butyl (2-(6-methylbenzo[b]thiophen-5-yl)ethyl)carbamate

The title compound is prepared according to the procedure described above in A.1.1.2. using 5-bromo-6-methylbenzo[b]thiophene. LC-MS B: $t_R$=1.06 min; no ionization.

A.1.94.3. 5-Bromo-6-methylbenzo[b]thiophene

The title compound is prepared according to the procedure described above in A.1.31.3. using 5-bromo-6-methylbenzo[b]thiophene-2-carboxylic acid. LC-MS B: $t_R$=1.04 min; no ionization.

A.1.94.4. 5-Bromo-6-methylbenzo[b]thiophene-2-carboxylic acid

The title compound is prepared according to the procedure described above in A.1.31.4. using methyl 5-bromo-6-methylbenzo[b]thiophene-2-carboxylate. LC-MS B: $t_R$=0.93 min; no ionization.

A.1.94.5. Methyl 5-bromo-6-methylbenzo[b]thiophene-2-carboxylate

The title compound is prepared according to the procedure described above in A.1.31.5. using 5-bromo-2-fluoro-4-methylbenzaldehyde. LC-MS B: $t_R$=1.08 min; no ionization.

A.1.95. 6-Chloro-N-(2-(4-methylbenzo[b]thiophen-5-yl)ethyl)pyrimidin-4-amine The title compound is prepared according to the procedure described above in A.1.1. using 2-(4-methylbenzo[b]thiophen-5-yl)ethan-1-amine hydrochloride. LC-MS B: $t_R$=1.01 min; [M+H]$^+$=304.11.

A.1.95.1. 2-(4-Methylbenzo[b]thiophen-5-yl)ethan-1-amine hydrochloride

The title compound is prepared according to the procedure described above in A.1.1.1. using tert-butyl (2-(4-methylbenzo[b]thiophen-5-yl)ethyl)carbamate. LC-MS B: $t_R$=0.59 min; [M+H]$^+$=192.29.

A.1.95.2. Tert-butyl (2-(4-methylbenzo[b]thiophen-5-yl)ethyl)carbamate

The title compound is prepared according to the procedure described above in A.1.1.2. using 4-methylbenzo[b]thiophen-5-yl trifluoromethanesulfonate. LC-MS B: $t_R$=1.05 min; no ionization.

A.1.95.3. 4-Methylbenzo[b]thiophen-5-yl trifluoromethanesulfonate

The title compound is prepared according to the procedure described above in A.1.20.3. using 4-methylbenzo[b]thiophen-5-ol. LC-MS B: $t_R$=1.09 min; no ionization.

A.1.95.4. 4-Methylbenzo[b]thiophen-5-ol

The title compound is prepared according to the procedure described above in A.1.19.4. using 5-(methoxymethoxy)-4-methylbenzo[b]thiophene. LC-MS B: $t_R$=0.82 min; no ionization.

A.1.95.5. 5-(Methoxymethoxy)-4-methylbenzo[b]thiophene

The title compound is prepared according to the procedure described above in A.1.19.5. using 4-bromo-5-(methoxymethoxy)benzo[b]thiophene. LC-MS B: $t_R$=0.97 min; [M+H]$^+$=209.19.

A.1.95.6. 4-Bromo-5-(methoxymethoxy)benzo[b]thiophene

The title compound is prepared according to the procedure described above in A.1.19.6. using 4-bromobenzo[b]thiophen-5-ol. LC-MS B: $t_R$=1.00 min; no ionization.

A.1.95.7. 4-Bromobenzo[b]thiophen-5-ol

A cooled (0° C.) solution of benzo[b]thiophen-5-ol (3.00 g, 19.40 mmol) and diisopropylamine (0.272 mL, 1.94 mmol) in anh. DCM (60 mL) is treated dropwise with a solution of N-bromosuccinimide (3.621 g, 20.30 mmol) in anh. DCM (135 mL). The RM is further stirred at 0° C. for 2 h. Water is added and the layers are separated. The organic layer is then washed successively with sat. aq. NaHCO$_3$ and with brine, dried over anh. MgSO$_4$, filtered and concentrated under reduced pressure. Purification by FC (from heptane to heptane/EtOAc=1/1) affords 4-bromobenzo[b]thiophen-5-ol as an orange solid (3.13 g, 71%). LC-MS B: $t_R$=0.86 min; no ionization.

A.1.96. 6-Chloro-N-(2-(5-methoxybenzo[b]thiophen-6-yl)ethyl)pyrimidin-4-amine The title compound is prepared according to the procedure described above in A.1.1. using 2-(5-methoxybenzo[b]thiophen-6-yl)ethan-1-amine hydrochloride. LC-MS B: $t_R$=1.03 min; [M+H]$^+$=320.13.

A.1.96.1. 2-(5-Methoxybenzo[b]thiophen-6-yl)ethan-1-amine hydrochloride

The title compound is prepared according to the procedure described above in A.1.1.1. using tert-butyl (2-(5-methoxybenzo[b]thiophen-6-yl)ethyl)carbamate. LC-MS B: $t_R$=0.57 min; [M+H]$^+$=208.15.

A.1.96.2. Tert-butyl (2-(5-methoxybenzo[b]thiophen-6-yl)ethyl)carbamate

The title compound is prepared according to the procedure described above in A.1.1.2. using 6-bromo-5-methoxybenzo[b]thiophene. LC-MS B: $t_R$=1.04 min; [M+H]$^+$=308.20.

A.1.96.3. 6-Bromo-5-methoxybenzo[b]thiophene

The title compound is prepared according to the procedure described above in A.1.31.3. using 6-bromo-5-methoxybenzo[b]thiophene-2-carboxylic acid. LC-MS B: $t_R$=0.98 min; no ionization.

A.1.96.4. 6-Bromo-5-methoxybenzo[b]thiophene-2-carboxylic acid

The title compound is prepared according to the procedure described above in A.1.31.4. using methyl 6-bromo-5-methoxybenzo[b]thiophene-2-carboxylate. LC-MS B: $t_R$=0.87 min; no ionization.

A.1.96.5. Methyl 6-bromo-5-methoxybenzo[b]thiophene-2-carboxylate

The title compound is prepared according to the procedure described above in A.1.31.5. using 4-bromo-2-fluoro-5-methoxybenzaldehyde. LC-MS B: $t_R$=1.03 min; no ionization.

A.1.97. 6-Chloro-N-(2-(3-ethoxy-1-fluoronaphthalen-2-yl)ethyl)pyrimidin-4-amine The title compound is prepared according to the procedure described above in A.1.1. using 2-(3-ethoxy-1-fluoronaphthalen-2-yl)ethan-1-amine hydrochloride. LC-MS B: $t_R$=1.12 min; [M+H]$^+$=346.19.

A.1.97.1. 2-(3-Ethoxy-1-fluoronaphthalen-2-yl)ethan-1-amine hydrochloride

The title compound is prepared according to the procedure described above in A.1.1.1. using tert-butyl (2-(3-ethoxy-1-fluoronaphthalen-2-yl)ethyl)carbamate. LC-MS B: $t_R$=0.71 min; [M+H]$^+$=234.26.

A.1.97.2. Tert-butyl (2-(3-ethoxy-1-fluoronaphthalen-2-yl)ethyl)carbamate

The title compound is prepared according to the procedure described above in A.1.1.2. using 3-ethoxy-1-fluoronaphthalen-2-yl trifluoromethanesulfonate. LC-MS B: $t_R$=1.13 min; [M+H]$^+$=334.23.

A.1.97.3. 3-Ethoxy-1-fluoronaphthalen-2-yl trifluoromethanesulfonate

The title compound is prepared according to the procedure described above in A.1.3.3. using 3-ethoxy-1-fluoronaphthalen-2-ol. LC-MS B: $t_R$=1.13 min; no ionization.

A.1.97.4. 3-Ethoxy-1-fluoronaphthalen-2-ol

The title compound is prepared according to the procedure described above in A.1.19.4. using 3-ethoxy-1-fluoro-2-(methoxymethoxy)naphthalene. LC-MS B: $t_R$=0.91 min; no ionization.

A.1.97.5. 3-Ethoxy-1-fluoro-2-(methoxymethoxy)naphthalene

The title compound is prepared according to the procedure described above in A.1.20.5. using 1-bromo-3-ethoxy-2-(methoxymethoxy)naphthalene. LC-MS B: $t_R$=1.01 min; [M+H]$^+$=251.23.

A.1.97.6. 1-Bromo-3-ethoxy-2-(methoxymethoxy)naphthalene

The title compound is prepared according to the procedure described above in A.1.21.5. using 2-ethoxy-3-(methoxymethoxy)naphthalene. LC-MS B: $t_R$=1.07 min; no ionization. $^1$H NMR (400 MHz, d6-DMSO) δ: 8.02-8.05 (m, 1H), 7.85-7.87 (m, 1H), 7.49-7.51 (m, 3H), 5.25 (s, 2H), 4.21 (q, J=6.9 Hz, 2H), 3.60 (s, 3H), 1.44 (t, J=6.9 Hz, 3H).

A.1.97.7. 2-Ethoxy-3-(methoxymethoxy)naphthalene

The title compound is prepared according to the procedure described above in A.1.19.6. using 2-hydroxy-3-ethoxynaphthalene. LC-MS B: $t_R$=0.96 min; [M+H]$^+$=233.37

A.1.98. 6-chloro-N-(2-(3-ethoxy-1-methylnaphthalen-2-yl)ethyl)pyrimidin-4-amine The title compound is prepared according to the procedure described above in A.1.1. using 2-(3-ethoxy-1-methylnaphthalen-2-yl)ethan-1-amine hydrochloride. LC-MS B: $t_R$=1.10 min; [M+H]$^+$=342.31.

A.1.98.1. 2-(3-Ethoxy-1-methylnaphthalen-2-yl)ethan-1-amine hydrochloride

The title compound is prepared according to the procedure described above in A.1.1.1. using tert-butyl (2-(3-ethoxy-1-methylnaphthalen-2-yl)ethyl)carbamate. LC-MS B: $t_R$=0.72 min; [M+H]$^+$=230.42.

A.1.98.2. Tert-butyl (2-(3-ethoxy-1-methylnaphthalen-2-yl)ethyl)carbamate

The title compound is prepared according to the procedure described above in A.1.1.2. using 3-ethoxy-1-methylnaphthalen-2-yl trifluoromethanesulfonate. LC-MS B: $t_R$=1.14 min; [M+H]$^+$=330.31.

A.1.98.3. 3-Ethoxy-1-methylnaphthalen-2-yl trifluoromethanesulfonate

The title compound is prepared according to the procedure described above in A.1.3.3. using 3-ethoxy-1-methylnaphthalen-2-ol. LC-MS B: $t_R$=1.16 min; [M+H]$^+$=335.07.

A.1.98.4. 3-Ethoxy-1-methylnaphthalen-2-ol

The title compound is prepared according to the procedure described above in A.1.19.4. using 3-ethoxy-1-methyl-2-(methoxymethoxy)naphthalene. LC-MS B: $t_R$=0.97 min; [M+H]$^+$=202.3.

A.1.98.5. 3-Ethoxy-1-methyl-2-(methoxymethoxy)naphthalene

The title compound is prepared according to the procedure described above in A.1.20.5. using 1-bromo-3-ethoxy-2-(methoxymethoxy)naphthalene (A.1.97.6.). LC-MS B: $t_R$=1.07 min; [M+H]$^+$=247.34.

A.1.99. 6-Chloro-N-(2-(7-fluorobenzo[b]thiophen-5-yl)ethyl)pyrimidin-4-amine To a solution of 2-(7-fluorobenzo[b]thiophen-5-yl)ethan-1-amine hydrochloride (3.970 g, 17.10 mmol) in 2-propanol (170 mL) at RT are added TEA (8.35 mL, 60.00 mmol) and 4,6-dichloropyrimidine (3.063 g, 20.60 mmol). The mixture is refluxed (90° C.), under nitrogen, for 1.5 h and a second addition of 4,6-dichloropyrimidine (2.547 g, 17.10 mmol) is then performed. The RM is further refluxed (90° C.), under nitrogen, for 4 h and is allowed to cool to RT. The solvent is partially removed under reduced pressure, DCM and water are added and the layers are separated. The aq. layer is extracted twice with DCM and the combined organic layers are then washed with brine, dried over anh. MgSO$_4$, filtered and concentrated under reduced pressure. Purification by FC (from heptane/EtOAc=7/3 to EtOAc) affords 6-chloro-N-(2-(7-fluorobenzo[b]thiophen-5-yl)ethyl)pyrimidin-4-amine as a yellow solid (4.96 g, 94%). LC-MS B: $t_R$=0.99 min; [M+H]$^+$=308.12.

A.1.99.1. 2-(7-Fluorobenzo[b]thiophen-5-yl)ethan-1-amine hydrochloride

To a solution of tert-butyl (2-(7-fluorobenzo[b]thiophen-5-yl)ethyl)carbamate (12.090 g, 40.00 mmol) in DCM (100 mL) is added 4 M HCl in dioxane (100.0 mL, 400.0 mmol) and the mixture is stirred at RT for 2 h. The RM is then concentrated under reduced pressure affording 2-(7-fluorobenzo[b]thiophen-5-yl)ethan-1-amine hydrochloride as a colorless solid that is further dried under high vacuum (5.030 g, 54%). LC-MS B: $t_R$=0.60 min; [M+H]$^+$=196.19.

A.1.99.2. Tert-butyl (2-(7-fluorobenzo[b]thiophen-5-yl)ethyl)carbamate

A mixture of 5-bromo-7-fluorobenzo[b]thiophene (10.222 g, 44.20 mmol), potassium (2-((tert-butoxycarbonyl)amino)ethyl)trifluoroborate (12.861 g, 48.70 mmol) and cesium carbonate (43.237 g, 133.00 mmol) in toluene (120 mL) and water (40 mL) is degassed three times with nitrogen. Palladium(II) acetate (497 mg, 2.21 mmol) and RuPhos (2.173 g, 4.42 mmol) are then added and the mixture is heated to 95° C., under nitrogen, overnight. The RM is allowed to cool to RT, water is added and the mixture is extracted twice with EtOAc. The combined organic layers are then washed with brine, dried over anh. MgSO$_4$, filtered and concentrated under reduced pressure. Purification by FC (from heptane to heptane/EtOAc=7/3) affords tert-butyl (2-(7-fluorobenzo[b]thiophen-5-yl)ethyl)carbamate as a light yellow solid (12.09 g, 93%). LC-MS B: $t_R$=1.04 min; no ionization.

A.1.99.3. 5-Bromo-7-fluorobenzo[b]thiophene

A mixture of crude 5-bromo-7-fluorobenzo[b]thiophene-2-carboxylic acid (19.350 g, 64.50 mmol) and copper(I) oxide (5.033 g, 35.20 mmol) in DMF (200 mL) is heated to 140° C., under nitrogen, overnight. The RM is allowed to cool to RT and is filtered over celite to remove copper salts that are washed with Et$_2$O. Water and Et$_2$O are added to the filtrate and the layers are separated. The aqueous layer is extracted twice with Et$_2$O and the combined organic layers are washed with brine, dried over anh. MgSO$_4$, filtered and concentrated under reduced pressure. Purification by FC (from heptane to heptane/EtOAc=4/1) affords 5-bromo-7-fluorobenzo[b]thiophene as a colorless solid (11.985 g, 80%). LC-MS B: $t_R$=1.02 min; no ionization.

A.1.99.4. 5-Bromo-7-fluorobenzo[b]thiophene-2-carboxylic acid

A mixture of crude methyl 5-bromo-7-fluorobenzo[b]thiophene-2-carboxylate (24.140 g, 64.50 mmol) in THF (180 mL), MeOH (23 mL) and water (58 mL) is treated portionwise with lithium hydroxide (5.998 g, 250.00 mmol). The resulting mixture is stirred at RT for 1 h. The cooled (0° C.) RM is then acidified by addition of 2 M aq. HCl and the organic solvents are removed under reduced pressure. The resulting suspension is filtered and the obtained solid is washed with water and dried under high vacuum to give crude 5-bromo-7-fluorobenzo[b]thiophene-2-carboxylic acid as a colorless solid (19.350 g, quantitative). LC-MS B: $t_R$=0.91 min; no ionization.

A.1.99.5. Methyl 5-bromo-7-fluorobenzo[b]thiophene-2-carboxylate

To a cooled (0° C.) mixture of 5-bromo-2,3-difluorobenzaldehyde (15.000 g, 64.50 mmol) and potassium carbonate (13.640 g, 96.70 mmol) in DMF (150 mL) is added dropwise methyl 2-mercaptoacetate (7.28 mL, 77.40 mmol) and the resulting mixture is stirred at RT for 1 h. The RM is then treated with water and stirred at RT for 15 min. The resulting suspension is filtered and the obtained solid is washed with water and dried under high vacuum to give crude methyl 5-bromo-7-fluorobenzo[b]thiophene-2-carboxylate as a colorless solid (24.140 g, quantitative). LC-MS B: $t_R$=1.06 min; no ionization.

A.1.100. 6-Chloro-N-(2-(7-chlorobenzo[b]thiophen-5-yl)ethyl)pyrimidin-4-amine To a solution of 2-(7-chlorobenzo[b]thiophen-5-yl)ethan-1-amine hydrochloride (468 mg, 1.81 mmol) in 2-propanol (20 mL) at RT are added TEA (0.88 mL, 6.34 mmol) and 4,6-dichloropyrimidine (324 mg, 2.17 mmol). The mixture is refluxed (90° C.), under nitrogen, for 1.5 h. The RM is allowed to cool to RT, DCM and water are added and the layers are separated. The aq. layer is extracted twice with DCM and the combined organic layers are washed with brine, dried over anh. MgSO$_4$, filtered and concentrated under reduced pressure. Purification by FC (from heptane to heptane/EtOAc=1/1) affords 6-chloro-N-(2-(7-chlorobenzo[b]thiophen-5-yl)ethyl)pyrimidin-4-amine as a colorless solid. LC-MS B: $t_R$=1.04 min; [M+H]$^+$=324.05.

A.1.100.1. 2-(7-Chlorobenzo[b]thiophen-5-yl)ethan-1-amine hydrochloride

To a solution of tert-butyl (2-(7-chlorobenzo[b]thiophen-5-yl)ethyl)carbamate (568 mg, 1.77 mmol) in DCM (20 mL) is added 4 M HCl in dioxane (4.5 mL, 18.0 mmol) and the mixture is stirred at RT overnight. The RM is then concentrated under reduced pressure to afford 2-(7-chlorobenzo[b]thiophen-5-yl)ethan-1-amine hydrochloride as a colorless solid (468 mg, quantitative). LC-MS B: $t_R$=0.62 min; [M+H]$^+$=212.10.

A.1.100.2. Tert-butyl(2-(7-chlorobenzo[b]thiophen-5-yl)ethyl)carbamate

A mixture of 5-bromo-7-chlorobenzo[b]thiophene (672 mg, 2.52 mmol), potassium (2-((tert-butoxycarbonyl)amino)ethyl)trifluoroborate (734 mg, 2.78 mmol) and cesium carbonate (2.468 g, 7.57 mmol) in toluene (20 mL) and water (7 mL) is degassed three times with nitrogen. Palladium(II) acetate (28.4 mg, 0.12 mmol) and RuPhos (124 mg, 0.25 mmol) are added and the resulting mixture is heated to 95° C., under nitrogen, overnight. The RM is allowed to cool to RT, water is added and the mixture is extracted twice with EtOAc. The combined organic layers are then washed with brine, dried over anh. MgSO$_4$, filtered and concentrated under reduced pressure. Purification by FC (from heptane to heptane/EtOAc=4/1) affords tert-butyl (2-(7-chlorobenzo[b]thiophen-5-yl)ethyl)carbamate as a yellow solid (568 mg, 72%). LC-MS B: $t_R$=1.06 min; no ionization.

A.1.100.3. 5-Bromo-7-chlorobenzo[b]thiophene

A mixture of 5-bromo-7-chlorobenzo[b]thiophene-2-carboxylic acid (1.004 g, 3.41 mmol) and copper(I) oxide (1.903 g, 13.30 mmol) in DMF (17 mL) is heated to 140° C., under nitrogen, overnight. The RM is allowed to cool to RT and is filtered over celite to remove copper salts that are washed with Et$_2$O. Water and Et$_2$O are added to the filtrate and the layers are separated. The aqueous layer is extracted twice with Et$_2$O and the combined organic layers are washed with brine, dried over anh. MgSO$_4$, filtered and concentrated under reduced pressure. Purification by FC (from heptane to heptane/EtOAc=1/1) affords 5-bromo-7-chlorobenzo[b] thiophene as a colorless solid (672 mg, 80%). LC-MS B: $t_R$=1.05 min; no ionization.

A.1.100.4. 5-Bromo-7-chlorobenzo[b]thiophene-2-carboxylic acid

A mixture of methyl 5-bromo-7-chlorobenzo[b]thiophene-2-carboxylate (1.137 g, 3.61 mmol) in THF (30 mL), MeOH (4 mL) and water (10 mL) is treated portionwise with lithium hydroxide (259 mg, 10.80 mmol). The resulting mixture is stirred at RT for 1 h. The cooled (0° C.) RM is then acidified by addition of 2 M aq. HCl and the organic solvents are removed under reduced pressure. The resulting suspension is filtered and the obtained solid is washed with water and dried under high vacuum to give 5-bromo-7-chlorobenzo[b]thiophene-2-carboxylic acid as a beige solid (1.003 g, 95%). LC-MS B: $t_R$=0.95 min; no ionization.

A.1.100.5. Methyl 5-bromo-7-chlorobenzo[b]thiophene-2-carboxylate

To a cooled (0° C.) mixture of 5-bromo-3-chloro-2-fluorobenzaldehyde (1.000 g, 4.13 mmol) and potassium carbonate (873 mg, 6.19 mmol) in DMF (10 mL) is added dropwise methyl 2-mercaptoacetate (0.466 mL, 4.95 mmol) and the resulting mixture is stirred at RT for 1.5 h, and then at 60° C. for 1 h. The RM is treated with water and stirred at RT for 15 min. The resulting suspension is filtered and the obtained solid is washed with water and dried under high vacuum to give methyl 5-bromo-7-chlorobenzo[b]thiophene-2-carboxylate as a colorless solid (1.137 g, 90%). LC-MS B: $t_R$=1.11 min; no ionization.

A.1.101. 6-Chloro-N-(2-(7-methylbenzo[b]thiophen-5-yl)ethyl)pyrimidin-4-amine To a solution of 2-(7-methylbenzo[b]thiophen-5-yl)ethan-1-amine hydrochloride (1.985 g, 8.72 mmol) in 2-propanol (40 mL) at RT are added TEA (4.25 mL, 30.50 mmol) and 4,6-dichloropyrimidine (1.558 g, 10.50 mmol).

The mixture is refluxed (90° C.), under nitrogen, for 2.5 h. The RM is allowed to cool to RT, DCM and water are added and the layers are separated. The aq. layer is extracted twice with DCM and the combined organic layers are washed with brine, dried over anh. MgSO$_4$, filtered and concentrated under reduced pressure. Purification by FC (from heptane to heptane/EtOAc=1/1) affords 6-chloro-N-(2-(7-methylbenzo[b]thiophen-5-yl)ethyl)pyrimidin-4-amine as a colorless solid (2.379 g, 90%). LC-MS B: $t_R$=1.02 min; [M+H]$^+$=304.15.

A.1.101.1. 2-(7-Methylbenzo[b]thiophen-5-yl)ethan-1-amine hydrochloride

To a solution of tert-butyl (2-(7-methylbenzo[b]thiophen-5-yl)ethyl)carbamate (2.882 g, 9.89 mmol) in DCM (25 mL) is added 4 M HCl in dioxane (25.0 mL, 100.0 mmol) and the mixture is stirred at RT for 1 h. The RM is then cooled in an ice bath for 15 min and the obtained solid is filtered off and further dried under high vacuum to afford 2-(7-methylbenzo[b]thiophen-5-yl)ethan-1-amine hydrochloride as a colorless solid (1.985 g, 88%). LC-MS B: $t_R$=0.60 min; [M+H]$^+$=192.30.

A.1.101.2. Tert-butyl(2-(7-methylbenzo[b]thiophen-5-yl)ethyl)carbamate

A mixture of 5-bromo-7-methylbenzo[b]thiophene (2.360 g, 9.91 mmol), potassium (2-((tert-butoxycarbonyl)amino) ethyl)trifluoroborate (2.882 g, 10.90 mmol) and cesium carbonate (9.689 g, 29.70 mmol) in toluene (24 mL) and water (12 mL) is degassed three times with nitrogen. Palladium(II) acetate (111 mg, 0.49 mmol) and RuPhos (487 mg, 0.99 mmol) are then added and the mixture is heated to 95° C., under nitrogen, overnight. The RM is allowed to cool to RT, water is added and the mixture is extracted twice with EtOAc. The combined organic layers are washed with brine, dried over anh. MgSO$_4$, filtered and concentrated under reduced pressure. Purification by FC (from heptane to heptane/EtOAc=7/3) affords tert-butyl (2-(7-methylbenzo[b] thiophen-5-yl)ethyl)carbamate as a yellow solid (2.882 g, 99%). LC-MS B: $t_R$=1.05 min; no ionization.

A.1.101.3. 5-Bromo-7-methylbenzo[b]thiophene

A mixture of 5-bromo-7-methylbenzo[b]thiophene-2-carboxylic acid (3.440 g, 12.70 mmol) and copper(I) oxide (1.812 g, 12.70 mmol) in DMF (40 mL) is heated to 140° C., under nitrogen, overnight. The RM is allowed to cool to RT and is filtered over celite to remove copper salts that are washed with Et$_2$O. Water and Et$_2$O are added to the filtrate and the layers are separated. The aqueous layer is extracted twice with Et$_2$O and the combined organic layers are washed with brine, dried over anh. MgSO$_4$, filtered and concentrated under reduced pressure. Purification by FC (from heptane to heptane/EtOAc=1/1) affords 5-bromo-7-methylbenzo[b] thiophene as a clear oil (2.361 g, 82%). LC-MS B: $t_R$=1.04 min; no ionization.

A.1.101.4. 5-Bromo-7-methylbenzo[b]thiophene-2-carboxylic acid

A mixture of methyl 5-bromo-7-methylbenzo[b]thiophene-2-carboxylate (4.000 g, 13.50 mmol) in THF (60 mL), MeOH (8 mL) and water (20 mL) is treated portionwise with lithium hydroxide (1.002 g, 41.80 mmol). The resulting mixture is stirred at RT for 1 h. The cooled (0° C.) RM is then acidified by addition of 2 M aq. HCl and the organic solvents are removed under reduced pressure. The resulting suspension is filtered and the obtained solid is washed with water and dried under high vacuum to give crude 5-bromo-7-methylbenzo[b]thiophene-2-carboxylic acid as an off-white solid (3.442 g, 94%). LC-MS B: $t_R$=0.93 min; no ionization.

A.1.101.5. Methyl 5-bromo-7-methylbenzo[b]thiophene-2-carboxylate

To a cooled (0° C.) suspension of 5-bromo-2-fluoro-3-methylbenzaldehyde (3.000 g, 13.50 mmol) and potassium carbonate (2.865 g, 20.30 mmol) in DMF (25 mL) is added dropwise methyl 2-mercaptoacetate (1.53 mL, 16.30 mmol) and the mixture is stirred at RT for 1 h, and then at 60° C. for 3 h. The RM is treated with water and stirred at RT for 15 min. The resulting suspension is filtered and the obtained solid is washed with water and dried under high vacuum to give crude methyl 5-bromo-7-methylbenzo[b]thiophene-2-carboxylate as an off-white solid (4.000 g, quantitative). LC-MS B: $t_R$=1.08 min; no ionization.

A.1.102. 6-Chloro-N-(2-(7-fluoro-6-methoxybenzo[b]thiophen-5-yl)ethyl)pyrimidin-4-amine To a solution of 2-(7-fluoro-6-methoxybenzo[b]thiophen-5-yl)ethan-1-amine hydrochloride (0.986 g, 3.77 mmol) in 2-propanol (20 mL) at RT are added TEA (1.84 mL, 13.20 mmol) and 4,6-dichloropyrimidine (0.673 g, 4.52 mmol). The resulting mixture is refluxed (90° C.), under nitrogen, for 1.5 h. The RM is allowed to cool to RT, DCM and water are added and the layers are separated. The aq. layer is extracted twice with DCM and the combined organic layers are washed with brine, dried over anh. MgSO$_4$, filtered and concentrated under reduced pressure. Purification by FC (from heptane to heptane/EtOAc=1/1) affords 6-chloro-N-(2-(7-fluoro-6-methoxybenzo[b]thiophen-5-yl)ethyl)pyrimidin-4-amine as an off-white solid (1.141 g, 90%). LC-MS B: $t_R$=1.03 min; [M+H]$^+$=337.98.

A.1.102.1. 2-(7-Fluoro-6-methoxybenzo[b]thiophen-5-yl)ethan-1-amine hydrochloride To a solution of tert-butyl (2-(7-fluoro-6-methoxybenzo[b]thiophen-5-yl)ethyl)carbamate (1.398 g, 4.28 mmol) in DCM (11 mL) is added 4 M HCl in dioxane (11.0 mL, 44.0 mmol) and the mixture is stirred at RT for 1 h. The RM is then concentrated to dryness under reduced pressure affording 2-(7-fluoro-6-methoxybenzo[b]thiophen-5-yl)ethan-1-amine hydrochloride as a light yellow solid (0.986 g, 88%). LC-MS B: $t_R$=0.64 min; [M+H]$^+$=226.21.

A.1.102.2. Tert-butyl (2-(7-fluoro-6-methoxybenzo[b]thiophen-5-yl)ethyl)carbamate A mixture of 5-bromo-7-fluoro-6-methoxybenzo[b]thiophene (1.413 g, 5.41 mmol), potassium (2-((tert-butoxycarbonyl)amino)ethyl)trifluoroborate (1.573 g, 5.95 mmol) and cesium carbonate (5.289 g, 16.20 mmol) in toluene (24 mL) and water (12 mL) is degassed three times with nitrogen. Palladium(II) acetate (60.8 mg, 0.27 mmol) and RuPhos (266 mg, 0.54 mmol) are added and the resulting mixture is heated to 95° C., under nitrogen, overnight. The RM is allowed to cool to RT, water is added and the mixture is extracted twice with EtOAc. The combined organic layers are then washed with brine, dried over anh. MgSO$_4$, filtered and concentrated under reduced pressure. Purification by FC (from heptane to heptane/EtOAc=7/3) affords tert-butyl (2-(7-fluoro-6-methoxybenzo[b]thiophen-5-yl)ethyl)carbamate as a light yellow solid (1.398 g, 79%). LC-MS B: $t_R$=1.06 min; [M+H]$^+$=326.19.

A.1.102.3. 5-Bromo-7-fluoro-6-methoxybenzo[b]thiophene

A mixture of crude 5-bromo-7-fluoro-6-methoxybenzo[b]thiophene-2-carboxylic acid (4.082 g, 12.70 mmol) and copper(I) oxide (1.915 g, 13.40 mmol) in DMF (40 mL) is heated to 140° C., under nitrogen, overnight. The RM is allowed to cool to RT and is filtered over celite to remove copper salts that are washed with Et$_2$O. Water and Et$_2$O are added to the filtrate and the layers are separated. The aqueous layer is extracted twice with Et$_2$O and the combined organic layers are washed with brine, dried over anh. MgSO$_4$, filtered and concentrated under reduced pressure. Purification by FC (from heptane to heptane/EtOAc=3/1) affords 5-bromo-7-fluoro-6-methoxybenzo[b]thiophene as a yellow solid (1.413 g, 42%). LC-MS B: $t_R$=1.03 min; no ionization.

A.1.102.4. 5-Bromo-7-fluoro-6-methoxybenzo[b]thiophene-2-carboxylic acid

A mixture of methyl 5-bromo-7-fluoro-6-methoxybenzo[b]thiophene-2-carboxylate (4.066 g, 12.70 mmol) in THF (60 mL), MeOH (8 mL) and water (20 mL) is treated portionwise with lithium hydroxide (0.915 g, 38.20 mmol). The resulting mixture is stirred at RT for 1 h. The cooled (0° C.) RM is then acidified by addition of 2 M aq. HCl and the organic solvents are removed under reduced pressure. The obtained suspension is filtered and the separated solid is washed with water and dried under high vacuum to give crude 5-bromo-7-fluoro-6-methoxybenzo[b]thiophene-2-carboxylic acid as an off-white solid (4.082 g, quantitative). LC-MS B: $t_R$=0.92 min; no ionization.

A.1.102.5. Methyl 5-bromo-7-fluoro-6-methoxybenzo[b]thiophene-2-carboxylate

To a cooled (0° C.) suspension of 5-bromo-2,3-difluoro-4-methoxybenzaldehyde (3.635 g, 13.70 mmol) and potassium carbonate (2.904 g, 20.60 mmol) in DMF (30 mL) is added dropwise methyl 2-mercaptoacetate (1.55 mL, 16.50 mmol) and the mixture is stirred at RT for 1 h, and then heated to 60° C. for 1.5 h. The RM is allowed to cool to RT, water is added and the resulting suspension is stirred at RT for 15 min. After filtration, the obtained solid is washed with water and dried under high vacuum to give methyl 5-bromo-7-fluoro-6-methoxybenzo[b]thiophene-2-carboxylate as a colorless solid (4.066 g, 93%). LC-MS B: $t_R$=1.08 min; no ionization.

A.1.102.6. 5-Bromo-2,3-difluoro-4-methoxybenzaldehyde

To a solution of 5-bromo-2,3-difluoro-4-hydroxybenzaldehyde (4.700 g, 19.10 mmol) in anh. DMF (50 mL) at RT are added cesium carbonate (7.475 g, 22.90 mmol) and iodomethane (2.40 mL, 38.20 mmol) and the resulting mixture is stirred at RT, under nitrogen, overnight. Water and Et$_2$O are added and the layers are separated. The aqueous layer is extracted twice with Et$_2$O and the combined organic layers are washed with brine, dried over anh. MgSO$_4$, filtered and concentrated under reduced pressure. Purification by FC (from heptane to heptane/EtOAc=1/1) affords 5-bromo-2,3-difluoro-4-methoxybenzaldehyde as an off-white solid (3.635 g, 76%). LC-MS B: $t_R$=0.92 min; no ionization.

A.1.102.7. 5-Bromo-2,3-difluoro-4-hydroxybenzaldehyde

A cooled (0° C.) solution of 2,3-difluoro-4-hydroxybenzaldehyde (4.600 g, 27.90 mmol) and diisopropylamine (0.391 mL, 2.79 mmol) in anh. DCM (20 mL) is treated dropwise with a solution of N-bromosuccinimide (5.220 g, 29.30 mmol) in anh. DCM (130 mL). The resulting mixture is further stirred at 0° C., under nitrogen, for 1 h. Water is added and the layers are separated. The aqueous layer is extracted twice with DCM and the combined organic layers are washed with brine, dried over anh. MgSO$_4$, filtered and concentrated under reduced pressure. Purification by FC (from heptane to heptane/EtOAc=1/1) affords 5-bromo-2,3-difluoro-4-hydroxybenzaldehyde as a beige solid (4.575 g, 69%). LC-MS B: $t_R$=0.77 min: no ionization.

A.1.103. 6-Chloro-N-(2-(3-chlorobenzo[b]thiophen-5-yl)ethyl)pyrimidin-4-amine To a solution of 2-(3-chlorobenzo[b]thiophen-5-yl)ethan-1-amine hydrochloride (0.537 g, 1.94 mmol) in 2-propanol (15 mL) at RT are added TEA (0.947 mL, 6.80 mmol) and 4,6-dichloropyrimidine (0.347 g, 2.33 mmol) and the mixture is refluxed (90° C.), under nitrogen, for 2 h. The RM is allowed to cool to RT, DCM and water are added and the layers are separated. The aq. layer is extracted twice with DCM and the combined organic layers are then washed with brine, dried over anh. MgSO$_4$, filtered and concentrated under reduced pressure. Purification by FC (from heptane to heptane/EtOAc=1/1) affords 6-chloro-N-(2-(3-chlorobenzo [b]thiophen-5-yl)ethyl)pyrimidin-4-amine as a light yellow solid (0.574 g, 91%). LC-MS B: $t_R$=1.04 min; [M+H]$^+$=324.03.

A.1.103.1. 2-(3-Chlorobenzo[b]thiophen-5-yl)ethan-1-amine hydrochloride

To a solution of tert-butyl (2-(3-chlorobenzo[b]thiophen-5-yl)ethyl)carbamate (943 mg, 2.57 mmol) in DCM (15 mL) is added 4 M HCl in dioxane (6.5 mL, 26.0 mmol) and the mixture is stirred at RT for 2 h. The RM is then cooled in an ice bath for 15 min and the obtained solid is filtered off and further dried under high vacuum to afford 2-(3-chlorobenzo [b]thiophen-5-yl)ethan-1-amine hydrochloride as a light orange solid (537 mg, 84%). LC-MS B: $t_R$=0.63 min; [M+H]$^+$=212.16.

A.1.103.2. Tert-butyl(2-(3-chlorobenzo[b]thiophen-5-yl)ethyl)carbamate

A mixture of 5-bromo-3-chlorobenzo[b]thiophene (1.275 g, 3.78 mmol), potassium (2-((tert-butoxycarbonyl)amino) ethyl)trifluoroborate (0.957 g, 3.81 mmol) and cesium carbonate (3.690 g, 11.30 mmol) in toluene (24 mL) and water (12 mL) is degassed three times with nitrogen. Palladium(II) acetate (42.4 mg, 0.18 mmol) and RuPhos (185 mg, 0.37 mmol) are then added and the mixture is heated to 95° C., under nitrogen, overnight. The RM is allowed to cool to RT, water is added and the mixture is extracted twice with EtOAc. The combined organic layers are then washed with brine, dried over anh. MgSO$_4$, filtered and concentrated under reduced pressure. Purification by FC (from heptane to heptane/EtOAc=7/3) affords tert-butyl (2-(3-chlorobenzo[b] thiophen-5-yl)ethyl)carbamate as a light yellow solid (0.943 g, 80%). LC-MS B: $t_R$=1.06 min; no ionization.

A.1.103.3. 5-Bromo-3-chlorobenzo[b]thiophene

A mixture of 5-bromo-3-chlorobenzo[b]thiophene-2-carboxylic acid (1.529 g, 3.89 mmol) and copper(I) oxide (0.278 g, 1.95 mmol) in DMF (35 mL) is heated to 140° C., under nitrogen, overnight. The RM is allowed to cool to RT and is filtered over celite to remove copper salts that are washed with Et$_2$O. Water and Et$_2$O are added to the filtrate and the layers are separated. The aqueous layer is extracted twice with Et$_2$O and the combined organic layers are washed with brine, dried over anh. MgSO$_4$, filtered and concentrated under reduced pressure. Purification by FC (from heptane to heptane/EtOAc=4/1) affords 5-bromo-3-chlorobenzo[b] thiophene as a colorless solid (1.275 g, 96%). LC-MS B: $t_R$=1.06 min; no ionization.

A.1.103.4. 5-Bromo-3-chlorobenzo[b]thiophene-2-carboxylic acid

A solution of methyl 5-bromo-3-chlorobenzo[b]thiophene-2-carboxylate (1.604 g, 4.56 mmol) in THF (44 mL), MeOH (5 mL) and water (15 mL) is treated portionwise with lithium hydroxide (0.334 g, 13.70 mmol) and the mixture is stirred at RT for 1 h. The cooled (0° C.) RM is then acidified by addition of 2 M aq. HCl and the organic solvents are removed under reduced pressure. The resulting suspension is filtered and the obtained solid is washed with water and dried under high vacuum to give crude 5-bromo-3-chlorobenzo[b]thiophene-2-carboxylic acid as a light yellow solid (1.529 g, 82%). LC-MS B: $t_R$=0.93 min; no ionization.

A.1.103.5. Methyl 5-bromo-3-chlorobenzo[b]thiophene-2-carboxylate

To a solution of methyl 3-amino-5-bromobenzo[b]thiophene-2-carboxylate (4.000 g, 13.30 mmol) in anh. MeCN (70 mL) is added copper(II) chloride (1.841 g, 13.30 mmol) and the mixture is heated to 45° C., under nitrogen. A solution of tert-butyl nitrite (1.74 mL, 14.60 mmol) in anh. MeCN (2 mL) is then added dropwise and the resulting mixture is heated at 45° C., under nitrogen, for 1 h. The RM is then allowed to cool to RT and is concentrated to dryness under reduced pressure. DCM is added, solids are removed by filtration and the filtrate is concentrated to dryness under reduced pressure. Purification by FC (from heptane to heptane/EtOAc=3/1) affords methyl 5-bromo-3-chlorobenzo[b] thiophene-2-carboxylate as a yellow solid (1.604 g, 40%). LC-MS B: $t_R$=1.09 min; no ionization.

A.1.104. 6-Chloro-N-(2-(4-fluorobenzo[b]thiophen-5-yl)ethyl)pyrimidin-4-amine To a solution of 2-(4-fluorobenzo[b]thiophen-5-yl)ethan-1-amine hydrochloride (1.109 g, 4.79 mmol) in 2-propanol (24 mL) at RT are added TEA (1.67 mL, 12.00 mmol) and 4,6-dichloropyrimidine (0.856 g, 5.74 mmol) and the mixture is refluxed (90° C.), under nitrogen, for 1 h. The RM is then allowed to cool to RT, DCM and water are added and the layers are separated. The aq. layer is extracted twice with DCM and the combined organic layers are washed with brine, dried over anh. MgSO$_4$, filtered and concentrated under reduced pressure. Purification by FC (from heptane to EtOAc) affords 6-chloro-N-(2-(4-fluorobenzo[b]thiophen-5-yl)ethyl)pyrimidin-4-amine as a colorless solid (1.269 g, 86%). LC-MS B: $t_R$=1.00 min; [M+H]$^+$=308.13.

A.1.104.1. 2-(4-Fluorobenzo[b]thiophen-5-yl)ethan-1-amine hydrochloride

To a solution of tert-butyl (2-(4-fluorobenzo[b]thiophen-5-yl)ethyl)carbamate (1.620 g, 5.48 mmol) in DCM (27 mL) is added 4 M HCl in dioxane (8.2 mL, 32.8 mmol) and the mixture is stirred at RT overnight. The RM is then filtered to afford 2-(4-fluorobenzo[b]thiophen-5-yl)ethan-1-amine hydrochloride as a colorless solid that was further dried under high vacuum (1.109 g, 87%). LC-MS B: $t_R$=0.57 min; [M+H]$^+$=196.07.

A.1.104.2. Tert-butyl (2-(4-fluorobenzo[b]thiophen-5-yl)ethyl)carbamate

A mixture of 4-fluorobenzo[b]thiophen-5-yl trifluoromethanesulfonate (2.160 g, 7.19 mmol), potassium (2-((tert-butoxycarbonyl)amino)ethyl)trifluoroborate (1.987 g, 7.91 mmol) and cesium carbonate (7.032 g, 21.60 mmol) in toluene (34 mL) and water (8.5 mL) is degassed three times with nitrogen. Palladium(II) acetate (80.8 mg, 0.36 mmol) and RuPhos (353 mg, 0.71 mmol) are then added and the mixture is heated to 95° C., under nitrogen, overnight. The RM is allowed to cool to RT, water is added and the mixture is extracted twice with EtOAc. The combined organic layers are washed with brine, dried over anh. MgSO$_4$, filtered and concentrated under reduced pressure. Purification by FC (from heptane to heptane/EtOAc=1/1) affords tert-butyl (2-(4-fluorobenzo[b]thiophen-5-yl)ethyl)carbamate as a yellow oil (1.620 g, 76%). LC-MS B: $t_R$=1.02 min; no ionization.

A.1.104.3. 4-Fluorobenzo[b]thiophen-5-yl trifluoromethanesulfonate

A solution of 4-fluorobenzo[b]thiophen-5-ol (1.230 g, 7.31 mmol) and TEA (2.65 mL, 19.00 mmol) in anh. DCM (38 mL) is treated portionwise at RT with 1,1,1-trifluoro-N-phenyl-N-((trifluoromethyl)sulfonyl)methanesulfonamide (3.167 g, 8.78 mmol) and the mixture is stirred at RT, under nitrogen, overnight. The RM is then concentrated to dryness under reduced pressure. Purification by FC (from heptane to heptane/EtOAc=1/1) affords 4-fluorobenzo[b]thiophen-5-yl trifluoromethanesulfonate as a yellow solid (2.160 g, 98%). LC-MS B: $t_R$=1.10 min; no ionization.

A.1.104.4. 4-Fluorobenzo[b]thiophen-5-ol

A mixture of 4-fluoro-5-(methoxymethoxy)benzo[b]thiophene (2.050 g, 9.84 mmol) in MeOH (22 mL) and DCM (22 mL) is treated with 12 M aq. HCl (1.64 mL; 19.68 mmol) and the resulting suspension is stirred at RT overnight. Water and DCM are added and the layers are separated. The aqueous layer is extracted twice with DCM and the combined organic layers are washed with brine, dried over anh. MgSO$_4$, filtered and concentrated under reduced pressure. Purification by FC (from heptane to heptane/EtOAc=3/2) affords 4-fluorobenzo[b]thiophen-5-ol as an orange oil (1.230 g, 74%). LC-MS B: $t_R$=0.77 min; no ionization.

A.1.104.5. 4-Fluoro-5-(methoxymethoxy)benzo[b]thiophene

To a cooled (−78° C.) solution of 4-bromo-5-(methoxymethoxy)benzo[b]thiophene (2.730 g, 9.99 mmol; preparation described in A.1.95.6.) in anh. Et$_2$O (100 mL) is added dropwise a solution of BuLi (1.6 M in hexanes, 6.20 mL, 9.92 mmol) and the mixture is further stirred at −78° C., under nitrogen, for 10 min. A solution of N-fluoro-N-(phenylsulfonyl)benzenesulfonamide (3.249 g, 9.99 mmol) in anh. THF (100 mL) is added dropwise to the previous mixture and stirring is continued at −78° C., under nitrogen, for 25 min. The cooled (0° C.) RM is then treated dropwise with water and is allowed to warm-up to RT. EtOAc is added and the layers are separated. The aqueous layer is extracted twice with EtOAc and the combined organic layers are washed with brine, dried over anh. MgSO$_4$, filtered and concentrated under reduced pressure. Purification by FC (from heptane to heptane/EtOAc=1/1) affords 4-fluoro-5-(methoxymethoxy)benzo[b]thiophene as a yellow oil (1.906 g, 90%). LC-MS B: $t_R$=0.93 min; no ionization.

A.1.105. 6-Chloro-N-(2-(7-methylbenzo[b]thiophen-6-yl)ethyl)pyrimidin-4-amine To a solution of 2-(7-methylbenzo[b]thiophen-6-yl)ethan-1-amine hydrochloride (0.448 g, 1.97 mmol) in 2-propanol (10 mL) at RT are added TEA (0.685 mL, 4.92 mmol) and 4,6-dichloropyrimidine (0.352 g, 2.36 mmol) and the resulting mixture is refluxed (90° C.), under nitrogen, for 4 h. The RM is allowed to cool to RT, DCM and water are added and the layers are separated. The aq. layer is extracted twice with DCM and the combined organic layers are washed with brine, dried over anh. MgSO$_4$, filtered and concentrated under reduced pressure. Purification by FC (from heptane to EtOAc) affords 6-chloro-N-(2-(7-methylbenzo[b]thiophen-6-yl)ethyl)pyrimidin-4-amine as a colorless solid (0.302 g, 51%). LC-MS B: $t_R$=1.02 min; [M+H]$^+$=304.21.

A.1.105.1. 2-(7-Methylbenzo[b]thiophen-6-yl)ethan-1-amine hydrochloride

To a solution of tert-butyl (2-(7-methylbenzo[b]thiophen-6-yl)ethyl)carbamate (0.362 g, 1.24 mmol) in DCM (12 mL) is added 4 M HCl in dioxane (1.86 mL, 7.44 mmol) and the mixture is stirred at RT for 2 h. The RM is then concentrated under reduced pressure affording 2-(7-methylbenzo[b]thiophen-6-yl)ethan-1-amine hydrochloride as a colorless solid that is further dried under high vacuum (0.254 g, 90%). LC-MS B: $t_R$=0.59 min; [M+H]$^+$=192.19.

A.1.105.2. Tert-butyl(2-(7-methylbenzo[b]thiophen-6-yl)ethyl)carbamate

A mixture of 6-bromo-7-methylbenzo[b]thiophene (0.338 g, 1.49 mmol), potassium (2-((tert-butoxycarbonyl)amino)ethyl)trifluoroborate (0.411 g, 1.64 mmol) and cesium carbonate (1.456 g, 4.47 mmol) in toluene (8 mL) and water (2 mL) is degassed three times with nitrogen. Palladium(II) acetate (16.7 mg, 0.074 mmol) and RuPhos (73.2 mg, 0.14 mmol) are then added and the mixture is heated to 95° C., under nitrogen, overnight. The RM is allowed to cool to RT, water is added and the mixture is extracted twice with EtOAc. The combined organic layers are then washed with brine, dried over anh. MgSO$_4$, filtered and concentrated under reduced pressure. Purification by FC (from heptane to heptane/EtOAc=1/1) affords tert-butyl (2-(7-methylbenzo[b]thiophen-6-yl)ethyl)carbamate as a yellow oil (0.362 g, 83%). LC-MS B: $t_R$=1.05 min; no ionization.

A.1.105.3. 6-Bromo-7-methylbenzo[b]thiophene

A mixture of 6-bromo-7-methylbenzo[b]thiophene-2-carboxylic acid (0.492 g, 1.81 mmol) and copper(I) oxide (64.9 mg, 0.45 mmol) in DMF (9 mL) is heated to 140° C., under nitrogen, overnight. The RM is allowed to cool to RT and is filtered over celite to remove copper salts that are washed with Et$_2$O. Water and Et$_2$O are added to the filtrate and the layers are separated. The aqueous layer is extracted twice with Et$_2$O and the combined organic layers are washed with brine, dried over anh. MgSO$_4$, filtered and concentrated under reduced pressure. Purification by FC (from heptane to heptane/EtOAc=9/1) affords 6-bromo-7-methylbenzo[b]thiophene as a yellow oil (0.338 g, 82%). LC-MS B: $t_R$=1.04 min; no ionization.

A.1.105.4. 6-Bromo-7-methylbenzo[b]thiophene-2-carboxylic acid

A mixture of methyl 6-bromo-7-methylbenzo[b]thiophene-2-carboxylate (0.538 g, 1.83 mmol) in THF (15 mL), MeOH (1.5 mL) and water (5 mL) is treated portionwise with lithium hydroxide (0.131 g, 5.49 mmol) and the resulting mixture is stirred at RT for 45 min. The cooled (0° C.) RM is then acidified by addition of 2 M aq. HCl and the organic solvents are removed under reduced pressure. The resulting suspension is filtered and the obtained solid is washed with water and dried under high vacuum to give 6-bromo-7-methylbenzo[b]thiophene-2-carboxylic acid as a colorless solid (0.492 g, 99%). LC-MS B: $t_R$=0.92 min; no ionization.

A.1.105.5. Methyl 6-bromo-7-methylbenzo[b]thiophene-2-carboxylate

To a cooled (0° C.) mixture of 4-bromo-2-fluoro-3-methylbenzaldehyde (1.638 g, 7.40 mmol) and potassium carbonate (1.565 g, 11.10 mmol) in DMF (20 mL) is added dropwise methyl 2-mercaptoacetate (0.835 mL, 8.88 mmol) and the resulting mixture is stirred at RT, under nitrogen, for 1 h. Water and EtOAc are added and the layers are separated. The aqueous layer is extracted twice with EtOAc and the combined organic layers are washed with brine, dried over anh. MgSO$_4$, filtered and concentrated under reduced pressure. Purification by FC (from heptane to heptane/EtOAc=4/1) affords methyl 6-bromo-7-methylbenzo[b]thiophene-2-carboxylate as a colorless solid (0.538 g, 26%). LC-MS B: $t_R$=1.08 min; no ionization.

A.1.105.6. 4-Bromo-2-fluoro-3-methylbenzaldehyde

To a cooled (0° C.) suspension of pyridinium chlorochromate (2.509 g, 11.60 mmol) in anh. DCM (30 mL) is added a solution of (4-bromo-2-fluoro-3-methylphenyl)methanol (1.700 g, 7.76 mmol) in anh. DCM (25 mL) and the resulting mixture is stirred at 0° C., under nitrogen, for 15 min, and then at RT for 4 h. The RM is filtered over celite washing with DCM, and the filtrate is concentrated under reduced pressure. Purification by FC (DCM) affords 4-bromo-2-fluoro-3-methylbenzaldehyde as a colorless solid (1.638 g, 97%). LC-MS B: $t_R$=0.92 min; no ionization.

A.1.105.7. (4-Bromo-2-fluoro-3-methylphenyl)methanol

To a cooled (−78° C.) solution of methyl 4-bromo-2-fluoro-3-methylbenzoate (2.000 g, 7.85 mmol) in anh. toluene (55 mL) is added dropwise a solution of diisobutylaluminum hydride (1 M in toluene, 23.6 mL, 23.6 mmol). The resulting mixture is further stirred at −78° C., under nitrogen, for 45 min, and then at 0° C. for 30 min. The cooled RM is treated successively with water (22 mL) and with 2.8 N aq. NaOH (0.5 mL), and stirring is continued at RT for 1 h. EtOAc and water are added, the layers are separated and the aqueous layer is extracted twice with EtOAc. The combined organic layers are dried over anh. MgSO$_4$, filtered and concentrated under reduced pressure affording (4-bromo-2-fluoro-3-methylphenyl)methanol as a colorless solid that is further dried under high vacuum (1.700 g, 99%). LC-MS B: $t_R$=0.81 min; no ionization.

A.1.106. 6-Chloro-N-(2-(7-(difluoromethoxy)-2,3-dihydrobenzo[b][1,4]dioxin-6-yl)ethyl)pyrimidin-4-amine To a solution of 2-(7-(difluoromethoxy)-2,3-dihydrobenzo[b][1,4]dioxin-6-yl)ethan-1-amine hydrochloride (1.000 g, 3.55 mmol) in 2-propanol (20 mL) at RT are added TEA (1.24 mL, 8.88 mmol) and 4,6-dichloropyrimidine (0.635 g, 4.26 mmol) and the resulting mixture is refluxed (95° C.), under nitrogen, for 2.5 h. The RM is allowed to cool to RT, DCM and water are added and the layers are separated. The aq. layer is extracted twice with DCM and the combined organic layers are washed with brine, dried over anh. MgSO$_4$, filtered and concentrated under reduced pressure. Purification by FC (from heptane to EtOAc) affords 6-chloro-N-(2-(7-(difluoromethoxy)-2,3-dihydrobenzo[b][1,4]dioxin-6-yl)ethyl)pyrimidin-4-amine as a colorless solid (1.290 g, quantitative). LC-MS B: $t_R$=0.95 min; [M+H]$^+$=358.07.

A.1.106.1. 2-(7-(Difluoromethoxy)-2,3-dihydrobenzo[b][1,4]dioxin-6-yl)ethan-1-amine hydrochloride To a solution of tert-butyl (2-(7-(difluoromethoxy)-2,3-dihydrobenzo[b][1,4]dioxin-6-yl)ethyl)carbamate (1.970 g, 5.70 mmol) in DCM (25 mL) is added 4 M HCl in dioxane (8.55 mL, 34.20 mmol) and the mixture is stirred at RT for 1.5 h. The RM is concentrated under reduced pressure affording 2-(7-(difluoromethoxy)-2,3-dihydrobenzo[b][1,4]dioxin-6-yl)ethan-1-amine hydrochloride as a colorless solid that is further dried under high vacuum (1.480 g, 92%). LC-MS B: $t_R$=0.54 min; [M+H]$^+$=246.10.

A.1.106.2. Tert-butyl (2-(7-(difluoromethoxy)-2,3-dihydrobenzo[b][1,4]dioxin-6-yl)ethyl)carbamate A mixture of 6-bromo-7-(difluoromethoxy)-2,3-dihydrobenzo[b][1,4]dioxine (1.900 g, 6.76 mmol), potassium (2-((tert-butoxycarbonyl)amino)ethyl)trifluoroborate (1.867 g, 7.44 mmol) and cesium carbonate (6.608 g, 20.30 mmol) in toluene (45 mL) and water (15 mL) is degassed three times with nitrogen. Palladium(II) acetate (76 mg, 0.33 mmol) and RuPhos (332 mg, 0.67 mmol) are then added and the mixture is heated to 95° C., under nitrogen, overnight. The RM is allowed to cool to RT, water is added and the mixture is extracted twice with EtOAc. The combined organic layers are washed with brine, dried over anh. MgSO$_4$, filtered and concentrated under reduced pressure. Purification by FC (from heptane to heptane/EtOAc=1/1) affords tert-butyl (2-(7-(difluoromethoxy)-2,3-dihydrobenzo[b][1,4]dioxin-6-yl)ethyl)carbamate as a pale yellow solid (1.970 g, 84%). LC-MS B: $t_R$=0.99 min; no ionization.

A.1.106.3. 6-Bromo-7-(difluoromethoxy)-2,3-dihydrobenzo[b][1,4]dioxine

To a cooled (0° C.) solution of 7-bromo-2,3-dihydrobenzo[b][1,4]dioxin-6-ol (1.850 g, 8.01 mmol) in MeCN (45 mL) and water (45 mL) is added potassium hydroxide (8.986 g, 160.00 mmol), and the mixture is stirred at RT for 30 min. The resulting mixture is cooled to −30° C., treated with diethyl (bromodifluoromethyl)phosphonate (2.9 mL, 16.00 mmol) in one portion and stirred at RT for 75 min. The RM is diluted with Et$_2$O, the layers are separated and the aqueous layer is extracted twice with Et$_2$O. The combined organic layers are successively washed with 1 M aq. NaOH, water and brine and are then dried over anh. MgSO$_4$, filtered and concentrated under reduced pressure. Purification by FC (from heptane to heptane/EtOAc=3/7) affords 6-bromo-7-(difluoromethoxy)-2,3-dihydrobenzo[b][1,4]dioxine as a colorless solid (1.900 g, 84%). LC-MS B: $t_R$=0.96 min; no ionization.

A.1.106.4. 7-Bromo-2,3-dihydrobenzo[b][1,4]dioxin-6-ol

To a solution of 2,3-dihydrobenzo[b][1,4]dioxin-6-ol (5.000 g, 31.20 mmol) in anh. DMF (50 mL) at RT is added portionwise N-bromosuccinimide (5.557 g, 31.22 mmol)

and the mixture is stirred at RT, under nitrogen, for 2 h. A second addition of N-bromosuccinimide (1.111 g, 6.24 mmol) is performed and the resulting mixture is further stirred at RT, under nitrogen, for 30 min. The RM is treated with water and is extracted three times with Et$_2$O/EtOAc. The combined organic layers are washed with water and brine, dried over anh. MgSO$_4$, filtered and concentrated under reduced pressure. Purification by FC (from heptane to heptane/EtOAc=3/2) affords 7-bromo-2,3-dihydrobenzo[b][1,4]dioxin-6-ol as a red oil (4.120 g, 57%). LC-MS B: $t_R$=0.75 min; no ionization.

A.1.107. 6-Chloro-N-(2-(7-((triisopropylsilyl)ethynyl)-2,3-dihydrobenzo[b][1,4]dioxin-6-yl)ethyl)pyrimidin-4-amine To a solution of 2-(7-((triisopropylsilyl)ethynyl)-2,3-dihydrobenzo[b][1,4]dioxin-6-yl)ethan-1-amine (0.770 g, 2.14 mmol) in 2-propanol (21 mL) at RT are added TEA (0.745 mL, 5.35 mmol) and 4,6-dichloropyrimidine (0.383 g, 2.57 mmol) and the resulting mixture is refluxed (90° C.), under nitrogen, for 2 h. The RM is allowed to cool to RT, DCM and water are added and the layers are separated. The aq. layer is extracted twice with DCM and the combined organic layers are washed with brine, dried over anh. MgSO$_4$, filtered and concentrated under reduced pressure. Purification by FC (from heptane to EtOAc) affords 6-chloro-N-(2-(7-((triisopropylsilyl)ethynyl)-2,3-dihydrobenzo[b][1,4]dioxin-6-yl)ethyl)pyrimidin-4-amine as a pale yellow oil (0.723 g, 72%). LC-MS B: $t_R$=1.29 min; [M+H]$^+$=472.21.

A.1.107.1. 2-(7-((Triisopropylsilyl)ethynyl)-2,3-dihydrobenzo[b][1,4]dioxin-6-yl)ethan-1-amine To a solution of tert-butyl (2-(7-((triisopropylsilyl)ethynyl)-2,3-dihydrobenzo[b][1,4]dioxin-6-yl)ethyl)carbamate (0.870 g, 1.89 mmol) in MeOH (9.5 mL) is added chlorotrimethylsilane (1.21 mL, 9.46 mmol) and the mixture is stirred at RT for 4.5 h. The RM is treated carefully with aq. sat. NaHCO$_3$ and the resulting mixture is extracted three times with DCM. The combined organic layers are dried over anh. MgSO$_4$, filtered and concentrated under reduced pressure to afford 2-(7-((triisopropylsilyl)ethynyl)-2,3-dihydrobenzo[b][1,4]dioxin-6-yl)ethan-1-amine as an orange oil (0.679 g, 99%). LC-MS B: $t_R$=0.92 min; [M+H]$^+$=360.20.

A.1.107.2. Tert-butyl (2-(7-((triisopropylsilyl)ethynyl)-2,3-dihydrobenzo[b][1,4]dioxin-6-yl)ethyl)carbamate To a solution of tert-butyl (2-(7-iodo-2,3-dihydrobenzo[b][1,4]dioxin-6-yl)ethyl)carbamate (1.340 g, 3.31 mmol) in TEA (22 mL) are added successively copper(I) iodide (88 mg, 0.46 mmol) and PdCl$_2$(PPh$_3$)$_2$ (117 mg, 0.16 mmol), and the resulting mixture is degassed with nitrogen. (Triisopropylsilyl)acetylene (1.48 mL, 6.61 mmol) is then added and the mixture is heated to 50° C., under nitrogen, for 2 h. The RM is filtered over celite and the filtrate is concentrated under reduced pressure. Purification by FC (from heptane to heptane/EtOAc=4/1) affords tert-butyl (2-(7-((triisopropylsilyl)ethynyl)-2,3-dihydrobenzo[b][1,4]dioxin-6-yl)ethyl)carbamate as a yellow oil (1.060 g, 70%). LC-MS B: $t_R$=1.30 min; [M+H]$^+$=460.28.

A.1.107.3. Tert-butyl (2-(7-iodo-2,3-dihydrobenzo[b][1,4]dioxin-6-yl)ethyl)carbamate A solution of tert-butyl (2-(2,3-dihydrobenzo[b][1,4]dioxin-6-yl)ethyl)carbamate (0.950 g, 3.40 mmol) in MeCN (9 mL) and water (9 mL) is treated with N-iodosuccinimide (3.222 g, 13.60 mmol) and the mixture is stirred at RT for 2 h. The RM is treated with aq. sat. sodium thiosulfate and extracted three times with EtOAc. The combined organic layers are washed with brine, dried over anh. MgSO$_4$, filtered and concentrated under reduced pressure. Purification by FC (from heptane to heptane/EtOAc=3/7) affords tert-butyl (2-(7-iodo-2,3-dihydrobenzo[b][1,4]dioxin-6-yl)ethyl)carbamate as an off-white solid (1.340 g, quantitative). LC-MS B: $t_R$=1.01 min; [M+H]$^+$=406.05.

A.1.107.4. Tert-butyl (2-(2,3-dihydrobenzo[b][1,4]dioxin-6-yl)ethyl)carbamate A mixture of 6-bromo-2,3-dihydrobenzo[b][1,4]dioxine (1.081 g, 4.87 mmol), potassium (2-((tert-butoxycarbonyl)amino)ethyl)trifluoroborate (1.417 g, 5.36 mmol) and cesium carbonate (4.764 g, 14.60 mmol) in toluene (33 mL) and water (11 mL) is degassed three times with nitrogen. Palladium(II) acetate (54.8 mg, 0.244 mmol) and RuPhos (239 mg, 0.48 mmol) are added and the mixture is heated to 90° C., under nitrogen, for 4 h. The RM is allowed to cool to RT, water is added and the mixture is extracted three times with EtOAc. The combined organic layers are washed with brine, dried over anh. MgSO$_4$, filtered and concentrated under reduced pressure. Purification by FC (from heptane to heptane/EtOAc=1/1) affords tert-butyl (2-(2,3-dihydrobenzo[b][1,4]dioxin-6-yl)ethyl)carbamate as a pale yellow solid (1.230 g, 90%). LC-MS B: $t_R$=0.91 min; no ionization.

A.1.108. 6-Chloro-N-(2-(7-methoxy-5-methyl-2,3-dihydrobenzo[b][1,4]dioxin-6-yl)ethyl)pyrimidin-4-amine To a solution of 2-(7-methoxy-5-methyl-2,3-dihydrobenzo[b][1,4]dioxin-6-yl)ethan-1-amine hydrochloride (0.300 g, 1.16 mmol) in 2-propanol (20 mL) at RT are added TEA (0.40 mL, 2.89 mmol) and 4,6-dichloropyrimidine (0.206 g, 1.39 mmol) and the mixture is refluxed (95° C.), under nitrogen, for 2 h. The RM is then allowed to cool to RT, DCM and water are added, and the layers are separated. The aq. layer is extracted twice with DCM and the combined organic layers are washed with brine, dried over anh. MgSO$_4$, filtered and concentrated under reduced pressure. Purification by FC (from heptane to EtOAc) affords 6-chloro-N-(2-(7-methoxy-5-methyl-2,3-dihydrobenzo[b][1,4]dioxin-6-yl)ethyl)pyrimidin-4-amine as a colorless solid (0.343 g, 88%). LC-MS B: $t_R$=0.98 min; [M+H]$^+$=336.14.

A.1.108.1. 2-(7-Methoxy-5-methyl-2,3-dihydrobenzo[b][1,4]dioxin-6-yl)ethan-1-amine hydrochloride To a solution of tert-butyl (2-(7-methoxy-5-methyl-2,3-dihydrobenzo[b][1,4]dioxin-6-yl)ethyl)carbamate (1.520 g, 4.70 mmol) in DCM (25 mL) is added 4 M HCl in dioxane (7.0 mL, 28.0 mmol) and the mixture is stirred at RT overnight. The RM is concentrated under reduced pressure and the obtained solid is triturated in DCM. The solid is filtered, washed with DCM and dried under high vacuum to afford 2-(7-methoxy-5-methyl-2,3-dihydrobenzo[b][1,4]dioxin-6-yl)ethan-1-amine hydrochloride as a colorless solid (0.625 g, 51%). LC-MS B: $t_R$=0.57 min; [M+H]$^+$=224.26.

A.1.108.2. Tert-butyl (2-(7-methoxy-5-methyl-2,3-dihydrobenzo[b][1,4]dioxin-6-yl)ethyl)carbamate A mixture of 7-methoxy-5-methyl-2,3-dihydrobenzo[b][1,4]dioxin-6-yl trifluoromethanesulfonate (1.600 g, 4.87 mmol), potassium (2-((tert-butoxycarbonyl)amino)ethyl)trifluoroborate (1.417 g, 5.36 mmol) and cesium carbonate (4.764 g, 14.60 mmol) in toluene (33 mL) and water (11 mL) is degassed three times with nitrogen. Palladium(II) acetate (54.8 mg, 0.24 mmol) and RuPhos (239 mg, 0.48 mmol) are added and the mixture is heated to 95° C., under nitrogen, overnight. The RM is allowed to cool to RT, water is added and the mixture is extracted three times with EtOAc. The combined organic layers are washed with brine, dried over anh. $MgSO_4$, filtered and concentrated under reduced pressure. Purification by FC (from heptane to heptane/EtOAc=1/1) affords tert-butyl (2-(7-methoxy-5-methyl-2,3-dihydrobenzo[b][1,4]dioxin-6-yl)ethyl)carbamate as a colorless solid (1.520 g, 96%). LC-MS B: $t_R$=1.01 min; $[M+H]^+$=324.22.

A.1.108.3. 7-Methoxy-5-methyl-2,3-dihydrobenzo[b][1,4]dioxin-6-yl trifluoromethanesulfonate A solution of 7-methoxy-5-methyl-2,3-dihydrobenzo[b][1,4]dioxin-6-ol (1.140 g, 5.81 mmol) and TEA (2.11 mL, 15.10 mmol) in anh. DCM (54 mL) is treated portionwise at RT with 1,1,1-trifluoro-N-phenyl-N-((trifluoromethyl)sulfonyl)methanesulfonamide (2.516 g, 6.97 mmol) and the mixture is stirred at RT, under nitrogen, overnight. The RM is concentrated to dryness under reduced pressure and subsequent purification by FC (from heptane to heptane/EtOAc=1/1) affords 7-methoxy-5-methyl-2,3-dihydrobenzo[b][1,4]dioxin-6-yl trifluoromethanesulfonate as a colorless oil (1.600 g, 84%). LC-MS B: $t_R$=1.07 min; no ionization.

A.1.108.4. 7-Methoxy-5-methyl-2,3-dihydrobenzo[b][1,4]dioxin-6-ol

A mixture of 7-methoxy-6-(methoxymethoxy)-5-methyl-2,3-dihydrobenzo[b][1,4]dioxine (1.423 g, 5.92 mmol) in MeOH (13 mL) and DCM (13 mL) is treated with 12 M aq. HCl (1.0 mL; 12.0 mmol) and the resulting suspension is stirred at RT overnight. Water and DCM are added and the layers are separated. The aqueous layer is extracted twice with DCM and the combined organic layers are washed with brine, dried over anh. $MgSO_4$, filtered and concentrated under reduced pressure. Purification by FC (from heptane to EtOAc) affords 7-methoxy-5-methyl-2,3-dihydrobenzo[b][1,4]dioxin-6-ol as a colorless solid (1.140 g, 98%). LC-MS B: $t_R$=0.74 min; no ionization.

A.1.108.5. 7-Methoxy-6-(methoxymethoxy)-5-methyl-2,3-dihydrobenzo[b][1,4]dioxine A mixture of 5-bromo-7-methoxy-6-(methoxymethoxy)-2,3-dihydrobenzo[b][1,4]dioxine (0.909 g, 2.98 mmol) and $Cs_2CO_3$ (2.941 g, 8.94 mmol) in DMF (13 mL) is degassed with nitrogen. $Pd(PPh_3)_4$ (344 mg, 0.29 mmol) and 2,4,6-trimethyl-1,3,5,2,4,6-trioxatriborinane (393 mg, 3.10 mmol) are added and the mixture is degassed again with nitrogen. The resulting mixture is then heated to 90° C., under nitrogen, overnight. The RM is allowed to cool to RT and diluted with $Et_2O$ and water. The layers are separated and the aqueous layer is extracted twice with $Et_2O$. The combined organic layers are washed with brine, dried over anh. $MgSO_4$, filtered and concentrated under reduced pressure. Purification by FC (from heptane to heptane/EtOAc=1/1) affords 7-methoxy-6-(methoxymethoxy)-5-methyl-2,3-dihydrobenzo[b][1,4]dioxine as a colorless oil (0.599 g, 84%). LC-MS B: $t_R$=0.84 min; $[M+H]^+$=241.16.

A.1.108.6. 5-Bromo-7-methoxy-6-(methoxymethoxy)-2,3-dihydrobenzo[b][1,4]dioxine A cooled (0° C.) solution of 5-bromo-7-methoxy-2,3-dihydrobenzo[b][1,4]dioxin-6-ol (2.516 g, 9.64 mmol) in anh. DMF (24 mL) is treated portionwise with sodium hydride (60% dispersion in mineral oil, 501 mg, 12.50 mmol) and the mixture is stirred at RT, under nitrogen, for 15 min. The cooled (0° C.) mixture is treated with chloromethyl methyl ether (1.46 mL, 19.30 mmol) and is then stirred at RT, under nitrogen, overnight. Water and $Et_2O$ are added and the layers are separated. The organic layer is washed twice with water, dried over anh. $MgSO_4$, filtered and concentrated under reduced pressure. Purification by FC (from heptane to heptane/EtOAc=1/1) affords 5-bromo-7-methoxy-6-(methoxymethoxy)-2,3-dihydrobenzo[b][1,4]dioxine as a colorless oil (2.360 g, 80%). LC-MS B: $t_R$=0.87 min; no ionization.

A.1.108.7. 5-Bromo-7-methoxy-2,3-dihydrobenzo[b][1,4]dioxin-6-ol

A cooled (0° C.) solution of 7-methoxy-2,3-dihydrobenzo[b][1,4]dioxin-6-ol (2.790 g, 15.30 mmol) in anh. DCM (20 mL) is treated with a solution of N-bromosuccinimide (2.998 g, 16.80 mmol) in anh. DCM (80 mL), and the mixture is stirred at 0° C., under nitrogen, for 5 min. Water is added and the layers are separated. The aqueous layer is extracted twice with DCM and the combined organic layers are washed with brine, dried over anh. $MgSO_4$, filtered and concentrated under reduced pressure. Purification by FC (from heptane to heptane/EtOAc=1/1) affords 5-bromo-7-methoxy-2,3-dihydrobenzo[b][1,4]dioxin-6-ol as a pale orange solid (2.353 g, 59%). LC-MS B: $t_R$=0.75 min; no ionization.

A.1.108.8. 7-Methoxy-2,3-dihydrobenzo[b][1,4]dioxin-6-ol

To a cooled (0° C.) solution of 7-methoxy-2,3-dihydrobenzo[b][1,4]dioxine-6-carbaldehyde (5.000 g, 25.70 mmol) in anh. DCM (100 mL) is added 3-chloroperbenzoic acid (11.541 g, 51.50 mmol) and the resulting mixture is stirred at RT, under nitrogen, overnight. The RM is filtered over celite washing with DCM, and the filtrate is concentrated to dryness under reduced pressure. MeOH and 4N aq. NaOH (56 mL) are added, and the resulting mixture is stirred at RT for 1.5 h. MeOH is removed under reduced pressure and the residue is diluted with aq. sat. $NH_4Cl$ and extracted three times with EtOAc. The combined organic layers are washed with brine, dried over anh. $MgSO_4$, filtered and concentrated under reduced pressure. Purification by FC (from heptane to EtOAc) affords 7-methoxy-2,3-dihydrobenzo[b][1,4]dioxin-6-ol as a yellow oil (3.030 g, 65%). LC-MS B: $t_R$=0.61 min; no ionization.

A.1.109. 6-Chloro-N-(2-(5-fluoro-7-methoxy-2,3-dihydrobenzo[b][1,4]dioxin-6-yl)ethyl)pyrimidin-4-amine To a solution of 2-(5-fluoro-7-methoxy-2,3-dihydrobenzo[b][1,4]dioxin-6-yl)ethan-1-amine hydrochloride (0.120 g, 0.44 mmol) in 2-propanol (10 mL) at RT are added TEA (0.158 mL, 1.14 mmol) and 4,6-dichloropyrimidine (81.4 mg, 0.54 mmol) and the mixture is refluxed (90° C.), under nitrogen, for 3 h. The RM is allowed to cool to RT, DCM and water are added, and the layers are separated. The aq. layer is extracted twice with DCM and the combined organic layers are washed with brine, dried over anh. MgSO$_4$, filtered and concentrated under reduced pressure. Purification by FC (from heptane to EtOAc) affords 6-chloro-N-(2-(5-fluoro-7-methoxy-2,3-dihydrobenzo[b][1,4]dioxin-6-yl)ethyl)pyrimidin-4-amine as a colorless solid (0.124 g, 81%). LC-MS B: $t_R$=0.94 min; [M+H]$^+$=340.13.

A.1.109.1. 2-(5-Fluoro-7-methoxy-2,3-dihydrobenzo[b][1,4]dioxin-6-yl)ethan-1-amine hydrochloride To a solution of tert-butyl (2-(5-fluoro-7-methoxy-2,3-dihydrobenzo[b][1,4]dioxin-6-yl)ethyl)carbamate (0.145 g, 0.44 mmol) in DCM (10 mL) is added 4 M HCl in dioxane (0.665 mL, 2.66 mmol) and the mixture is stirred at RT overnight. The RM is concentrated to dryness under reduced pressure and the obtained solid is dried under high vacuum to afford 2-(5-fluoro-7-methoxy-2,3-dihydrobenzo[b][1,4]dioxin-6-yl)ethan-1-amine hydrochloride as a colorless solid (0.120 g, quantitative). LC-MS B: $t_R$=0.54 min; [M+H]$^+$=228.23.

A.1.109.2. Tert-butyl (2-(5-fluoro-7-methoxy-2,3-dihydrobenzo[b][1,4]dioxin-6-yl)ethyl)carbamate A mixture of 5-fluoro-7-methoxy-2,3-dihydrobenzo[b][1,4]dioxin-6-yl trifluoromethanesulfonate (0.173 g, 0.52 mmol), potassium (2-((tert-butoxycarbonyl)amino)ethyl)trifluoroborate (0.152 g, 0.57 mmol) and cesium carbonate (0.510 g, 1.56 mmol) in toluene (3.5 mL) and water (1.2 mL) is degassed three times with nitrogen. Palladium(II) acetate (6 mg, 0.026 mmol) and RuPhos (25.6 mg, 0.052 mmol) are added and the mixture is heated to 95° C., under nitrogen, overnight. The RM is allowed to cool to RT, water is added and the mixture is extracted three times with EtOAc. The combined organic layers are washed with brine, dried over anh. MgSO$_4$, filtered and concentrated under reduced pressure. Purification by FC (from heptane to heptane/EtOAc=1/1) affords tert-butyl (2-(5-fluoro-7-methoxy-2,3-dihydrobenzo[b][1,4]dioxin-6-yl)ethyl)carbamate as a pale yellow solid (0.145 g, 85%). LC-MS B: $t_R$=0.98 min; no ionization.

A.1.109.3. 5-Fluoro-7-methoxy-2,3-dihydrobenzo[b][1,4]dioxin-6-yl trifluoromethanesulfonate A solution of 5-fluoro-7-methoxy-2,3-dihydrobenzo[b][1,4]dioxin-6-ol (0.121 g, 0.60 mmol) and TEA (0.219 mL, 1.57 mmol) in anh. DCM (10 mL) is treated portionwise at RT with 1,1,1-trifluoro-N-phenyl-N-((trifluoromethyl)sulfonyl)methanesulfonamide (0.262 g, 0.72 mmol) and the mixture is stirred at RT, under nitrogen, overnight. The RM is concentrated to dryness under reduced pressure and subsequent purification by FC (from heptane to heptane/EtOAc=1/1) affords 5-fluoro-7-methoxy-2,3-dihydrobenzo[b][1,4]dioxin-6-yl trifluoromethanesulfonate as a colorless oil (0.173 g, 86%). LC-MS B: $t_R$=1.03 min; no ionization.

A.1.109.4. 5-Fluoro-7-methoxy-2,3-dihydrobenzo[b][1,4]dioxin-6-ol

A mixture of 5-fluoro-7-methoxy-6-(methoxymethoxy)-2,3-dihydrobenzo[b][1,4]dioxine (0.257 g, 1.05 mmol) in MeOH (2.5 mL) and DCM (2.5 mL) is treated with 12 M aq. HCl (0.176 mL; 2.11 mmol) and the resulting suspension is stirred at RT overnight. Water and DCM are added and the layers are separated. The aqueous layer is extracted twice with DCM and the combined organic layers are washed with brine, dried over anh. MgSO$_4$, filtered and concentrated under reduced pressure. Purification by FC (from heptane to heptane/EtOAc=3/2) affords 5-fluoro-7-methoxy-2,3-dihydrobenzo[b][1,4]dioxin-6-ol as a colorless solid (0.121 g, 57%). LC-MS B: $t_R$=0.66 min; no ionization.

A.1.109.5. 5-Fluoro-7-methoxy-6-(methoxymethoxy)-2,3-dihydrobenzo[b][1,4]dioxine To a cooled (−78° C.) solution of 5-bromo-7-methoxy-6-(methoxymethoxy)-2,3-dihydrobenzo[b][1,4]dioxine (0.498 g, 1.82 mmol) in anh. Et$_2$O (18 mL) is added dropwise a solution of BuLi (1.6 M in hexanes, 1.14 mL, 1.82 mmol) and the mixture is further stirred at −78° C., under nitrogen, for 10 min. A solution of N-fluoro-N-(phenylsulfonyl)benzenesulfonamide (0.592 g, 1.82 mmol) in anh. THF (18 mL) is then added dropwise and the resulting mixture is stirred at −78° C. for 25 min. The RM is treated dropwise with water and is allowed to warm-up to RT. EtOAc is added and the layers are separated. The aqueous layer is extracted twice with EtOAc and the combined organic layers are washed with brine, dried over anh. MgSO$_4$, filtered and concentrated under reduced pressure. Purification by FC (from heptane to heptane/EtOAc=1/1) affords 5-fluoro-7-methoxy-6-(methoxymethoxy)-2,3-dihydrobenzo[b][1,4]dioxine as a pale yellow oil (0.257 g, 58%). LC-MS B: $t_R$=0.84 min; [M+H]$^+$=245.25.

A.1.110. 6-Chloro-N-(2-(7-(trifluoromethyl)benzo[b]thiophen-5-yl)ethyl)pyrimidin-4-amine To a solution of 2-(7-(trifluoromethyl)benzo[b]thiophen-5-yl)ethan-1-amine hydrochloride (0.965 g, 3.43 mmol) in 2-propanol (20 mL) at RT are added TEA (1.67 mL, 12.00 mmol) and 4,6-dichloropyrimidine (0.612 g, 4.11 mmol) and the mixture is refluxed (90° C.), under nitrogen, for 2 h. The RM is allowed to cool to RT, DCM and water are added and the layers are separated. The aq. layer is extracted twice with DCM and the combined organic layers are washed with brine, dried over anh. MgSO$_4$, filtered and concentrated under reduced pressure. Purification by FC (from heptane to heptane/EtOAc=1/1) affords 6-chloro-N-(2-(7-(trifluoromethyl)benzo[b]thiophen-5-yl)ethyl)pyrimidin-4-amine as a colorless solid (1.019 g, 83%). LC-MS B: $t_R$=1.06 min; [M+H]$^+$=358.07.

A.1.110.1. 2-(7-(Trifluoromethyl)benzo[b]thiophen-5-yl)ethan-1-amine hydrochloride To a solution of tert-butyl (2-(7-(trifluoromethyl)benzo[b]thiophen-5-yl)ethyl)carbamate (1.686 g, 4.86 mmol) in DCM (15 mL) is added 4 M HCl in dioxane (12.2 mL, 48.8 mmol) and the mixture is stirred at RT for 2 h. The RM is then cooled in an ice bath for 15 min and the obtained solid is filtered off and further dried under high vacuum to afford 2-(7-(trifluoromethyl)benzo[b]thiophen-5-yl)ethan-1-amine hydrochloride as a colorless solid (0.965 g, 71%). LC-MS B: $t_R$=0.69 min; [M+H]$^+$=246.20.

A.1.110.2. Tert-butyl (2-(7-(trifluoromethyl)benzo[b]thiophen-5-yl)ethyl)carbamate A mixture of 5-bromo-7-(trifluoromethyl)benzo[b]thiophene (1.690 g, 5.51 mmol), potassium (2-((tert-butoxycarbonyl)amino)ethyl)trifluoroborate (1.601 g, 6.06 mmol) and cesium carbonate (5.383 g, 16.50 mmol) in toluene (24 mL) and water (12 mL) is degassed three times with nitrogen. Palladium(II) acetate (62 mg, 0.27 mmol) and RuPhos (0.271 g, 0.55 mmol) are then added and the mixture is heated to 95° C., under nitrogen, overnight. The RM is allowed to cool to RT, water is added and the mixture is extracted twice with EtOAc. The combined organic layers are washed with brine, dried over anh. MgSO$_4$, filtered and concentrated under reduced pressure. Purification by FC (from heptane to heptane/EtOAc=7/3) affords tert-butyl (2-(7-(trifluoromethyl)benzo[b]thiophen-5-yl)ethyl)carbamate as a light yellow solid (1.686 g, 89%). LC-MS B: $t_R$=1.09 min; no ionization.

A.1.110.3. 5-Bromo-7-(trifluoromethyl)benzo[b]thiophene

A mixture of 5-bromo-7-(trifluoromethyl)benzo[b]thiophene-2-carboxylic acid (2.658 g, 8.12 mmol) and copper(I) oxide (1.162 g, 8.12 mmol) in DMF (30 mL) is heated to 140° C. under nitrogen, overnight. The RM is allowed to cool to RT and is filtered over celite to remove copper salts that are washed with Et$_2$O. Water and Et$_2$O are added to the filtrate and the layers are separated. The aqueous layer is extracted twice with Et$_2$O and the combined organic layers are washed with brine, dried over anh. MgSO$_4$, filtered and concentrated under reduced pressure. Purification by FC (from heptane to heptane/EtOAc=7/3) affords 5-bromo-7-(trifluoromethyl)benzo[b]thiophene as a clear oil (1.690 g, 74%). LC-MS B: $t_R$=1.09 min; no ionization.

A.1.110.4. 5-Bromo-7-(trifluoromethyl)benzo[b]thiophene-2-carboxylic acid

A mixture of methyl 5-bromo-7-(trifluoromethyl)benzo[b]thiophene-2-carboxylate (2.930 g, 8.64 mmol) in THF (45 mL), MeOH (6 mL) and water (15 mL) is treated portionwise with lithium hydroxide (0.621 g, 25.90 mmol). The resulting mixture is stirred at RT for 1 h. The cooled (0° C.) RM is then acidified by addition of 2 M aq. HCl and the organic solvents are removed under reduced pressure. The resulting suspension is filtered and the obtained solid is washed with water and dried under high vacuum to give 5-bromo-7-(trifluoromethyl)benzo[b]thiophene-2-carboxylic acid as a colorless solid (2.658 g, 95%). LC-MS B: $t_R$=0.98 min; no ionization.

A.1.110.5. Methyl 5-bromo-7-(trifluoromethyl)benzo[b]thiophene-2-carboxylate To a cooled (0° C.) mixture of 5-bromo-2-fluoro-3-(trifluoromethyl)benzaldehyde (3.000 g, 10.80 mmol) and potassium carbonate (2.295 g, 16.30 mmol) in DMF (25 mL) is added dropwise methyl 2-mercaptoacetate (1.23 mL, 13.00 mmol) and the resulting mixture is stirred at RT for 2 h, and then at 60° C. for 1.5 h. The RM is treated with water and stirred at RT for 15 min. The resulting suspension is filtered and the obtained solid is washed with water and dried under high vacuum to give methyl 5-bromo-7-(trifluoromethyl)benzo[b]thiophene-2-carboxylate as an off-white solid (2.930 g, 80%). LC-MS B: $t_R$=1.13 min; no ionization.

A.1.111. 6-Chloro-N-(2-(3-chloro-7-fluorobenzo[b]thiophen-5-yl)ethyl)pyrimidin-4-amine To a solution of 2-(3-chloro-7-fluorobenzo[b]thiophen-5-yl)ethan-1-amine hydrochloride (0.548 g, 2.05 mmol) in 2-propanol (15 mL) at RT are added TEA (1.00 mL, 7.18 mmol) and 4,6-dichloropyrimidine (0.367 g, 2.46 mmol) and the mixture is refluxed (90° C.), under nitrogen, for 2 h. The RM is allowed to cool to RT, DCM and water are added and the layers are separated. The aq. layer is extracted twice with DCM and the combined organic layers are washed with brine, dried over anh. MgSO$_4$, filtered and concentrated under reduced pressure. Purification by FC (from heptane to heptane/EtOAc=1/1) affords 6-chloro-N-(2-(3-chloro-7-fluorobenzo[b]thiophen-5-yl)ethyl)pyrimidin-4-amine as a colorless solid (0.649 g, 92%). LC-MS B: $t_R$=1.04 min; [M+H]$^+$=341.99.

A.1.111.1. 2-(3-Chloro-7-fluorobenzo[b]thiophen-5-yl)ethan-1-amine hydrochloride To a solution of tert-butyl (2-(3-chloro-7-fluorobenzo[b]thiophen-5-yl)ethyl)carbamate (0.690 g, 2.08 mmol) in DCM (10 mL) is added 4 M HCl in dioxane (5.2 mL, 20.8 mmol) and the mixture is stirred at RT overnight. The RM is concentrated under reduced pressure to afford 2-(3-chloro-7-fluorobenzo[b]thiophen-5-yl)ethan-1-amine hydrochloride as a colorless solid (0.548 g, 99%). LC-MS B: $t_R$=0.64 min; [M+H]$^+$=230.13.

A.1.111.2. Tert-butyl (2-(3-chloro-7-fluorobenzo[b]thiophen-5-yl)ethyl)carbamate A mixture of 5-bromo-3-chloro-7-fluorobenzo[b]thiophene (1.928 g, 7.26 mmol), potassium (2-((tert-butoxycarbonyl)amino)ethyl)trifluoroborate (2.111 g, 7.99 mmol) and cesium carbonate (7.097 g, 21.80 mmol) in toluene (45 mL) and water (15 mL) is degassed three times with nitrogen. Palladium(II) acetate (82 mg, 0.36 mmol) and RuPhos (0.357 g, 0.72 mmol) are then added and the mixture is heated to 95° C., under nitrogen, overnight. The RM is allowed to cool to RT, water is added and the mixture is extracted three times with EtOAc. The combined organic layers are washed with brine, dried over anh. MgSO$_4$, filtered and concentrated under reduced pressure. Purification by FC (from heptane to heptane/EtOAc=9/1) affords tert-butyl (2-(3-chloro-7-fluorobenzo[b]thiophen-5-yl)ethyl)carbamate as a yellow solid (0.690 g, 29%). LC-MS B: $t_R$=1.06 min; no ionization.

A.1.111.3. 5-Bromo-3-chloro-7-fluorobenzo[b]thiophene

A mixture of 5-bromo-3-chloro-7-fluorobenzo[b]thiophene-2-carboxylic acid (3.632 g, 11.70 mmol) and copper (I) oxide (0.839 g, 5.87 mmol) in DMF (70 mL) is heated to 140° C., under nitrogen, overnight. The RM is allowed to cool to RT and is filtered over celite to remove copper salts that are washed with Et$_2$O. Water and Et$_2$O are added to the filtrate and the layers are separated. The aqueous layer is extracted twice with Et$_2$O and the combined organic layers are washed with brine, dried over anh. MgSO$_4$, filtered and concentrated under reduced pressure. Purification by FC (from heptane to heptane/EtOAc=9/1) affords 5-bromo-3-chloro-7-fluorobenzo[b]thiophene as a colorless solid (2.228 g, 72%). LC-MS B: $t_R$=1.06 min; no ionization.

A.1.111.4. 5-Bromo-3-chloro-7-fluorobenzo[b]thiophene-2-carboxylic acid

A mixture of methyl 5-bromo-3-chloro-7-fluorobenzo[b]thiophene-2-carboxylate (3.813 g, 11.80 mmol) in THF (44 mL), MeOH (5 mL) and water (15 mL) is treated portionwise with lithium hydroxide (0.864 g, 35.40 mmol). The resulting mixture is stirred at RT for 1 h. The cooled (0° C.) RM is then acidified by addition of 2 M aq. HCl and the organic solvents are removed under reduced pressure. The resulting suspension is filtered and the obtained solid is washed with water and dried under high vacuum to give 5-bromo-3-chloro-7-fluorobenzo[b]thiophene-2-carboxylic acid as a light yellow solid (3.632 g, 99%). LC-MS B: $t_R$=0.93 min; no ionization.

A.1.111.5. Methyl 5-bromo-3-chloro-7-fluorobenzo[b]thiophene-2-carboxylate

To a solution of methyl 3-amino-5-bromo-7-fluorobenzo[b]thiophene-2-carboxylate (5.291 g, 17.40 mmol) in anh. MeCN (60 mL) is added copper(II) chloride (2.411 g, 17.40 mmol) and the mixture is heated to 45° C., under nitrogen. A solution of tert-butyl nitrite (2.27 mL, 19.10 mmol) in anh. MeCN (15 mL) is then added dropwise and the resulting mixture is heated at 45° C. under nitrogen, for 1.5 h. The RM is allowed to cool to RT and is concentrated to dryness under reduced pressure. DCM is added, solids are removed by filtration and the filtrate is concentrated to dryness under reduced pressure. Purification by FC (from heptane to heptane/EtOAc=7/3) affords methyl 5-bromo-3-chloro-7-fluorobenzo[b]thiophene-2-carboxylate as a light yellow solid (3.671 g, 65%). LC-MS B: $t_R$=1.09 min; no ionization.

A.1.111.6. Methyl 3-amino-5-bromo-7-fluorobenzo[b]thiophene-2-carboxylate

To a cooled (0° C.) mixture of 5-bromo-2,3-difluorobenzonitrile (4.010 g, 17.70 mmol) and potassium carbonate (4.930 g, 35.30 mmol) in DMF (40 mL) is added dropwise a solution of methyl 2-mercaptoacetate (1.66 mL, 17.70 mmol) in DMF (10 mL) and the resulting mixture is stirred at 0° C. for 1 h. The RM is treated with water and stirred at RT for 15 min. The resulting suspension is filtered and the obtained solid is washed with water and dried under high vacuum to give methyl 3-amino-5-bromo-7-fluorobenzo[b]thiophene-2-carboxylate as an off-white solid (5.489 g, quantitative). LC-MS B: $t_R$=1.04 min; [M+H]$^+$=304.01.

A.1.112. 6-Chloro-N-(2-(5-methyl-2,3-dihydrobenzo[b][1,4]dioxin-6-yl)ethyl)pyrimidin-4-amine To a solution of 2-(5-methyl-2,3-dihydrobenzo[b][1,4]dioxin-6-yl)ethan-1-amine (1.774 g, 7.17 mmol) in 2-propanol (25 mL) at RT are added TEA (1.57 mL, 11.20 mmol) and 4,6-dichloropyrimidine (0.574 g, 3.86 mmol) and the mixture is refluxed (90° C.), under nitrogen, for 1.5 h. The RM is allowed to cool to RT, DCM and water are added and the layers are separated. The aq. layer is extracted twice with DCM and the combined organic layers are washed with brine, dried over anh. MgSO$_4$, filtered and concentrated under reduced pressure. Purification by FC (from heptane to heptane/EtOAc=7/3) affords 6-chloro-N-(2-(5-methyl-2,3-dihydrobenzo[b][1,4]dioxin-6-yl)ethyl)pyrimidin-4-amine as a yellow solid (1.080 g, 49%). LC-MS B: $t_R$=0.92 min; [M+H]$^+$=305.94.

A.1.112.1. 2-(5-Methyl-2,3-dihydrobenzo[b][1,4]dioxin-6-yl)ethan-1-amine

To a solution of 5-methyl-2,3-dihydrobenzo[b][1,4]dioxine-6-carbaldehyde (1.387 g, 7.72 mmol) in nitromethane (15 mL) are added successively 4A molecular sieves (180 mg), butylamine (0.091 mL, 0.91 mmol) and acetic acid (0.090 mL, 1.58 mmol) and the resulting mixture is heated to 90° C., under nitrogen, for 30 min. The RM is filtered and the filtrate is concentrated under reduced pressure affording crude (E)-5-methyl-6-(2-nitrovinyl)-2,3-dihydrobenzo[b][1,4]dioxine as an orange solid (1.978 g, quantitative). LC-MS B: $t_R$=0.95 min; no ionisation To a cooled (0° C.) solution of crude (E)-5-methyl-6-(2-nitrovinyl)-2,3-dihydrobenzo[b][1,4]dioxine (1.978 g, 7.72 mmol) in anh. THF (15 mL) is added dropwise a solution of lithium aluminum hydride (2 M in THF, 12.5 mL, 25.0 mmol) and the mixture is heated at reflux (70° C.), under nitrogen, for 15 min. The cooled (0° C.) RM is treated successively with water, 15% aq. NaOH, and water and is further stirred at 0° C. for 1 h. The resulting heterogeneous mixture is filtered and the separated solids are washed with Et$_2$O. The layers of the filtrate are separated and the aqueous layer is extracted with Et$_2$O. The combined organic layers are dried over anh. MgSO$_4$, filtered and concentrated under reduced pressure to afford crude 2-(5-methyl-2,3-dihydrobenzo[b][1,4]dioxin-6-yl)ethan-1-amine as an amber oil (1.774 g, quantitative). LC-MS B: $t_R$=0.51 min; [M+H]$^+$=194.28.

A.1.112.2. 5-Methyl-2,3-dihydrobenzo[b][1,4]dioxine-6-carbaldehyde

To a cooled (0° C.) suspension of pyridinium chlorochromate (3.051 g, 14.20 mmol) in DCM (30 mL) is added a solution of (5-methyl-2,3-dihydrobenzo[b][1,4]dioxin-6-yl)methanol (1.723 g, 9.44 mmol) in DCM (25 mL). The resulting suspension is further stirred at 0° C., under nitrogen, for 15 min and then at RT for 1 h. The RM is filtered over celite and the filtrate is concentrated under reduced pressure. Purification by FC (from heptane to heptane/EtOAc=1/1) affords 5-methyl-2,3-dihydrobenzo[b][1,4]dioxine-6-carbaldehyde as an off-white solid (1.387 g, 83%). LC-MS B: $t_R$=0.81 min; [M+H]$^+$=179.32.

A.1.112.3. (5-Methyl-2,3-dihydrobenzo[b][1,4]dioxin-6-yl)methanol

To a cooled (−78° C.) solution of methyl 5-methyl-2,3-dihydrobenzo[b][1,4]dioxine-6-carboxylate (2.054 g, 9.78 mmol) in anh. toluene (55 mL) is added dropwise a solution of diisobutylaluminum hydride (1 M in toluene, 29.6 mL, 29.6 mmol). The mixture is further stirred at −78° C., under nitrogen, for 30 min and is then allowed to warm-up to 0° C. Stirring at 0° C. is continued for 45 min, and the cooled RM is treated successively with water (22 mL) and with 2.8 N aq. NaOH (0.5 mL). The mixture is allowed to warm-up to RT and is further stirred for 1 h. The resulting mixture is filtered over celite, EtOAc and water are added and the layers are separated. The aqueous layer is extracted twice with EtOAc and the combined organic layers are dried over anh. MgSO$_4$, filtered and concentrated under reduced pressure to afford (5-methyl-2,3-dihydrobenzo[b][1,4]dioxin-6-yl)methanol as a colorless oil (1.723 g, 97%). LC-MS B: $t_R$=0.65 min; no ionization.

A.1.112.4. Methyl 5-methyl-2,3-dihydrobenzo[b][1,4]dioxine-6-carboxylate

To a solution of 5-methyl-2,3-dihydrobenzo[b][1,4]dioxine-6-carboxylic acid (2.000 g, 9.78 mmol) in anh. DMF (20 mL) at RT are added cesium carbonate (6.376 g, 19.60 mmol) and iodomethane (1.23 mL, 19.60 mmol) and the mixture is stirred at RT for 1 h. Water and Et$_2$O are added and the layers are separated. The aqueous layer is extracted twice with Et$_2$O and the combined organic layers are washed with brine, dried over anh. MgSO$_4$, filtered and concentrated under reduced pressure. Purification by FC (from heptane to heptane/EtOAc=1/1) affords methyl 5-methyl-2,3-dihydrobenzo[b][1,4]dioxine-6-carboxylate as a colorless solid (2.054 g, quantitative). LC-MS B: $t_R$=0.89 min; [M+H]$^+$=209.20.

A.1.113. 6-Chloro-N-(2-(7-fluoro-2,3-dihydrobenzo[b][1,4]dioxin-6-yl)ethyl)pyrimidin-4-amine To a solution of 2-(7-fluoro-2,3-dihydrobenzo[b][1,4]dioxin-6-yl)ethan-1-amine hydrochloride (0.206 g, 0.88 mmol) in 2-propanol (10 mL) at RT are added TEA (0.43 mL, 3.09 mmol) and 4,6-dichloropyrimidine (0.158 g, 1.06 mmol) and the mixture is refluxed (90° C.), under nitrogen, for 2 h. The RM is allowed to cool to RT, DCM and water are added, and the layers are separated. The aq. layer is extracted twice with DCM and the combined organic layers are washed with brine, dried over anh. MgSO$_4$, filtered and concentrated under reduced pressure. Purification by FC (from heptane to EtOAc) affords 6-chloro-N-(2-(7-fluoro-2,3-dihydrobenzo[b][1,4]dioxin-6-yl)ethyl)pyrimidin-4-amine as a colorless solid (0.224 g, 82%). LC-MS B: $t_R$=0.90 min; [M+H]$^+$=310.18.

A.1.113.1. 2-(7-Fluoro-2,3-dihydrobenzo[b][1,4]dioxin-6-yl)ethan-1-amine hydrochloride To a solution of tert-butyl (2-(7-fluoro-2,3-dihydrobenzo[b][1,4]dioxin-6-yl)ethyl)carbamate (0.321 g, 1.08 mmol) in DCM (10 mL) is added 4 M HCl in dioxane (1.62 mL, 6.48 mmol) and the mixture is stirred at RT overnight. The RM is concentrated to dryness under reduced pressure and the obtained solid is dried under high vacuum to afford 2-(7-fluoro-2,3-dihydrobenzo[b][1,4]dioxin-6-yl)ethan-1-amine hydrochloride as a colorless solid (0.206 g, 82%). LC-MS B: $t_R$=0.48 min; [M+H]$^+$=198.20.

A.1.113.2. Tert-butyl (2-(7-fluoro-2,3-dihydrobenzo[b][1,4]dioxin-6-yl)ethyl)carbamate A mixture of 7-fluoro-2,3-dihydrobenzo[b][1,4]dioxin-6-yl trifluoromethanesulfonate (0.358 g, 1.18 mmol), potassium (2-((tert-butoxycarbonyl)amino)ethyl)trifluoroborate (0.327 g, 1.30 mmol) and cesium carbonate (1.157 g, 3.55 mmol) in toluene (9 mL) and water (3 mL) is degassed three times with nitrogen. Palladium(II) acetate (13 mg, 0.059 mmol) and RuPhos (58 mg, 0.118 mmol) are added and the mixture is heated to 95° C., under nitrogen, overnight. The RM is allowed to cool to RT, water is added and the mixture is extracted three times with EtOAc. The combined organic layers are washed with brine, dried over anh. MgSO$_4$, filtered and concentrated under reduced pressure. Purification by FC (from heptane to heptane/EtOAc=3/7) affords tert-butyl (2-(7-fluoro-2,3-dihydrobenzo[b][1,4]dioxin-6-yl)ethyl)carbamate as a pale yellow oil (0.321 g, 91%). LC-MS B: $t_R$=0.94 min; no ionization.

A.1.113.3. 7-Fluoro-2,3-dihydrobenzo[b][1,4]dioxin-6-yl trifluoromethanesulfonate A solution of 7-fluoro-2,3-dihydrobenzo[b][1,4]dioxin-6-ol (0.242 g, 1.42 mmol) and TEA (0.516 mL, 3.70 mmol) in anh. DCM (15 mL) is treated portionwise at RT with 1,1,1-trifluoro-N-phenyl-N-((trifluoromethyl)sulfonyl)methanesulfonamide (0.617 g, 1.71 mmol) and the mixture is stirred at RT, under nitrogen, overnight. The RM is concentrated to dryness under reduced pressure and a subsequent purification by FC (from heptane to heptane/EtOAc=7/3) affords 7-fluoro-2,3-dihydrobenzo[b][1,4]dioxin-6-yl trifluoromethanesulfonate as a colorless oil (0.357 g, 83%). LC-MS B: $t_R$=1.01 min; no ionization.

A.1.113.4. 7-Fluoro-2,3-dihydrobenzo[b][1,4]dioxin-6-ol

A mixture of 6-fluoro-7-(methoxymethoxy)-2,3-dihydrobenzo[b][1,4]dioxine (0.524 g, 2.45 mmol) in MeOH (5 mL) and DCM (5 mL) is treated with 12 M aq. HCl (0.407 mL; 4.88 mmol) and the resulting suspension is stirred at RT overnight. Water and DCM are added and the layers are separated. The aqueous layer is extracted twice with DCM and the combined organic layers are washed with brine, dried over anh. MgSO$_4$, filtered and concentrated under reduced pressure. Purification by FC (from heptane to heptane/EtOAc=3/2) affords 7-fluoro-2,3-dihydrobenzo[b][1,4]dioxin-6-ol as a colorless solid (0.325 g, 78%). LC-MS B: $t_R$=0.63 min: no ionization.

A.1.113.5. 6-Fluoro-7-(methoxymethoxy)-2,3-dihydrobenzo[b][1,4]dioxine

To a cooled (−78° C.) solution of 6-bromo-7-(methoxymethoxy)-2,3-dihydrobenzo[b][1,4]dioxine (0.500 g, 1.82 mmol) in anh. THF (15 mL) is added dropwise a solution of BuLi (1.6 M in hexanes, 1.14 mL, 1.82 mmol) and the mixture is further stirred at −78° C., under nitrogen, for 1 min. A solution of N-fluoro-N-(phenylsulfonyl)benzenesulfonamide (0.650 g, 2.00 mmol) in anh. THF (10 mL) is then added dropwise and the resulting mixture is stirred at −78° C. for 10 min. The RM is treated dropwise with water and is allowed to warm-up to RT. EtOAc is added and the layers are separated. The aqueous layer is extracted twice with EtOAc and the combined organic layers are washed with brine, dried over anh. MgSO$_4$, filtered and concentrated under reduced pressure. Purification by FC (from heptane to heptane/EtOAc=3/7) affords 6-fluoro-7-(methoxymethoxy)-2,3-dihydrobenzo[b][1,4]dioxine as a yellow oil (0.229 g, 59%). LC-MS B: $t_R$=0.83 min; [M+H]$^+$=215.12.

A.1.113.6. 6-Bromo-7-(methoxymethoxy)-2,3-dihydrobenzo[b][1,4]dioxine

A cooled (0° C.) solution of 7-bromo-2,3-dihydrobenzo[b][1,4]dioxin-6-ol (6.260 g, 27.10 mmol, preparation described in A.1.106.4.) in anh. DMF (72 mL) is treated portionwise with sodium hydride (60% dispersion in mineral oil, 1.300 g, 32.50 mmol) and the mixture is stirred at RT, under nitrogen, for 15 min. The cooled (0° C.) mixture is treated with chloromethyl methyl ether (4.12 mL, 54.20 mmol) and is stirred at RT, under nitrogen, for 1.5 h. Water and Et$_2$O are added and the layers are separated. The organic layer is washed twice with water, dried over anh. MgSO$_4$, filtered and concentrated under reduced pressure. Purification by FC (from heptane to heptane/EtOAc=1/1) affords 6-bromo-7-(methoxymethoxy)-2,3-dihydrobenzo[b][1,4]dioxine as a colorless oil (7.140 g, 96%). LC-MS B: $t_R$=0.90 min; [M+H]$^+$=275.01.

A.2. Synthesis of boronic acid derivatives of formula (A4)

A.2.1. Methyl 2-(2-(methylthio)-4-(4,4,5,5-tetramethyl-1,3,2-dioxaborolan-2-yl)phenyl)acetate To a solution of methyl 2-(4-bromo-2-(methylthio)phenyl)acetate (1.45 g, 5.27 mmol) in anh. DMF (12 mL) are added at RT 4,4,4',4',5,5,5',5'-octamethyl-2,2'-bi(1,3,2-dioxaborolane) (1.352 g, 5.27 mmol), potassium acetate (2.069 g, 21.10 mmol) and Pd(dppf)Cl$_2$ (428 mg, 0.58 mmol). The RM is heated to 90° C., under nitrogen, for 17 h. The RM is then allowed to cool to RT and is filtered through a pad of celite, washing with EtOAc. The filtrate is washed with water and the aqueous layer is extracted twice with EtOAc. The combined organic layers are then washed with brine, dried over MgSO$_4$, filtered and concentrated under reduced pressure. Purification by FC (from heptane to EtOAc) affords methyl 2-(2-(methylthio)-4-(4,4,5,5-tetramethyl-1,3,2-dioxaborolan-2-yl)phenyl)acetate as a pale yellow solid (664 mg, 39%). LC-MS B: $t_R$=1.04 min; [M+H]$^+$=323.16.

A.2.1.1. Methyl 2-(4-bromo-2-(methylthio)phenyl)acetate

To a solution of 2-(4-bromo-2-(methylthio)phenyl)acetic acid (1.86 g, 7.12 mmol) in anh. DMF (17 mL) at RT are added cesium carbonate (2.901 g, 8.90 mmol) and iodomethane (0.667 mL, 10.70 mmol) and the RM is stirred at RT, under nitrogen, for 1 h. Water and Et$_2$O are added and the layers are separated. The aqueous layer is extracted twice with Et$_2$O and the combined organic layers are washed with brine, dried over anh. MgSO$_4$, filtered and concentrated under reduced pressure. Purification by FC (from heptane to heptane/EtOAc=1/1) affords methyl 2-(4-bromo-2-(methylthio)phenyl)acetate as a yellow oil (1.45 g, 74%). LC-MS B: $t_R$=0.97 min; no ionization.

A.2.1.2. 2-(4-Bromo-2-(methylthio)phenyl)acetic acid

A mixture of 2-(4-bromo-2-(methylthio)phenyl)acetonitrile (1.76 g, 7.27 mmol), water (7 mL), 95% sulfuric acid (7.8 mL) and acetic acid (5.4 mL) is heated to 110° C., under nitrogen, for 4.5 h. The RM is then allowed to cool to RT and is poured onto ice/water. The mixture is extracted twice with DCM and the combined organic layers are washed with brine, dried over anh. MgSO$_4$, filtered and concentrated under reduced pressure affording 2-(4-bromo-2-(methylthio)phenyl)acetic acid as a yellow solid (1.86 g, 98%). LC-MS B: $t_R$=0.82 min; [M+H]$^+$=260.70.

A.2.1.3. 2-(4-Bromo-2-(methylthio)phenyl)acetonitrile

A solution of (5-bromo-2-(chloromethyl)phenyl)(methyl)sulfane (2.45 g, 9.74 mmol) in MeCN (26 mL) and water (3.4 mL) is treated with sodium cyanide (646 mg, 12.70 mmol) and the RM is heated to 80° C., under nitrogen, for 16 h. Additional sodium cyanide (238 mg, 4.85 mmol) is then added and the mixture is heated to 80° C. for 4 h. The RM is then allowed to cool to RT and is diluted with water. Acetonitrile is removed under reduced pressure and the RM is extracted twice with DCM. The combined organic layers are dried over anh. MgSO$_4$, filtered and concentrated under reduced pressure. Purification by FC (from heptane to heptane/EtOAc=1/1) affords 2-(4-bromo-2-(methylthio)phenyl)acetonitrile as a pale yellow solid (1.76 g, 75%). LC-MS B: $t_R$=0.95 min; [M+H]$^+$=241.81.

A.2.1.4. (5-Bromo-2-(chloromethyl)phenyl)(methyl)sulfane

A cooled (0° C.) mixture of (4-bromo-2-(methylthio)phenyl)methanol (2.31 g, 9.91 mmol) and zinc chloride (33.8 mg, 0.248 mmol) in anh. DCM (20 mL) is treated dropwise with thionyl chloride (1.45 mL, 19.80 mmol) and the RM is stirred at 0° C. for 3 h, and then at RT for 15 h. The RM is concentrated under reduced pressure affording (5-bromo-2-(chloromethyl)phenyl)(methyl)sulfane as a yellow oil (2.45 g, 98%). LC-MS B: $t_R$=1.04 min; no ionization.

A.2.1.5. (4-Bromo-2-(methylthio)phenyl)methanol

To a cooled (−78° C.) solution of methyl 4-bromo-2-(methylthio)benzoate (2.87 g, 11.00 mmol) in anh. THF (30 mL) is added dropwise a solution of diisobutylaluminum hydride (1 M in toluene, 33.0 mL, 33.0 mmol). The mixture is further stirred at −78° C., under nitrogen, for 15 min and is then allowed to warm-up to 0° C. Stirring at 0° C. is continued for 15 min, and the cooled RM is treated successively with water (31 mL) and with 2.8 N aq. NaOH (22 mL). The mixture is then allowed to warm-up to RT, EtOAc is added and the layers are separated. The aqueous layer is extracted twice with EtOAc. The combined organic layers are dried over anh. MgSO$_4$, filtered and concentrated under reduced pressure. Purification by FC (from heptane to heptane/EtOAc=1/1) affords (4-bromo-2-(methylthio)phenyl)methanol as a colorless solid (2.31 g, 90%). LC-MS B: $t_R$=0.83 min; [M+H]$^+$=232.99.

A.2.1.6. Methyl 4-bromo-2-(methylthio)benzoate

To a solution of 4-bromo-2-mercaptobenzoic acid (3.00 g, 12.20 mmol) in anh. DMF (20 mL) at RT is added cesium carbonate (11.952 g, 36.70 mmol) and the mixture is stirred at RT for 15 min. The cooled (0° C.) mixture is then treated with iodomethane (1.92 mL, 30.60 mmol) and the RM is stirred at RT for 16 h. Water and Et$_2$O are added and the layers are separated. The aqueous layer is extracted twice with Et$_2$O and the combined organic layers are washed with brine, dried over anh. MgSO$_4$, filtered and concentrated under reduced pressure affording methyl 4-bromo-2-(methylthio)benzoate as a pale orange solid (2.87 g, 90%). LC-MS B: $t_R$=0.96 min; [M+H]$^+$=261.06.

A.2.2. Methyl 6-(4,4,5,5-tetramethyl-1,3,2-dioxaborolan-2-yl)benzofuran-2-carboxylate To a solution of methyl 6-bromobenzofuran-2-carboxylate (528 mg, 1.97 mmol) in anh. DMF (10 mL) are added at RT 4,4,4',4',5,5,5',5'-octamethyl-2,2'-bi(1,3,2-dioxaborolane) (505 mg, 1.97 mmol), potassium acetate (773 mg, 7.87 mmol) and Pd(dppf)Cl$_2$ (160 mg, 0.21 mmol). The RM is heated to 95° C., under nitrogen, for 17 h. The RM is then allowed to cool to RT and is filtered through a pad of celite, washing with Et$_2$O. The filtrate is washed with water and the aqueous layer is extracted twice with Et$_2$O. The combined organic layers are then washed with brine, dried over MgSO$_4$, filtered and concentrated under reduced pressure. Purification by FC (from heptane to heptane/EtOAc=7/3) affords methyl 6-(4,4,5,5-tetramethyl-1,3,2-dioxaborolan-2- yl)benzofuran-2-carboxylate as a colorless solid (286 mg, 48%). LC-MS B: $t_R$=1.06 min; [M+H]⁺=303.19.

A.2.3. Methyl 5-(4,4,5,5-tetramethyl-1,3,2-dioxaborolan-2-yl)benzofuran-2-carboxylate To a solution of methyl 5-bromobenzofuran-2-carboxylate (510 mg, 1.96 mmol) in anh. DMF (10 mL) are added at RT 4,4,4',4',5,5,5',5'-octamethyl-2,2'-bi(1,3,2-dioxaborolane) (503 mg, 1.96 mmol), potassium acetate (769 mg, 7.84 mmol) and Pd(dppf)Cl₂ (159 mg, 0.21 mmol). The RM is heated to 95° C., under nitrogen, for 17 h. The RM is then allowed to cool to RT and is filtered through a pad of celite, washing with Et₂O. The filtrate is washed with water and the aqueous layer is extracted twice with Et₂O. The combined organic layers are then washed with brine, dried over MgSO₄, filtered and concentrated under reduced pressure. Purification by FC (from heptane to heptane/EtOAc=7/3) affords methyl 5-(4,4,5,5-tetramethyl-1,3,2-dioxaborolan-2-yl)benzofuran-2-carboxylate as a pale yellow oil (298 mg, 50%). LC-MS B: $t_R$=1.06 min; [M+H]⁺=303.16.

A.2.4. Ethyl 6-(4,4,5,5-tetramethyl-1,3,2-dioxaborolan-2-yl)benzofuran-3-carboxylate To a solution of ethyl 6-bromobenzofuran-3-carboxylate (430 mg, 1.60 mmol) in anh. DMF (10 mL) are added at RT 4,4,4',4',5,5,5',5'-octamethyl-2,2'-bi(1,3,2-dioxaborolane) (410 mg, 1.60 mmol), potassium acetate (627 mg, 6.39 mmol) and Pd(dppf)Cl₂ (130 mg, 0.17 mmol). The RM is heated to 95° C., under nitrogen, for 17 h. The RM is then allowed to cool to RT and is filtered through a pad of celite, washing with Et₂O. The filtrate is washed with water and the aqueous layer is extracted twice with Et₂O. The combined organic layers are then washed with brine, dried over MgSO₄, filtered and concentrated under reduced pressure. Purification by FC (from heptane to heptane/EtOAc=7/3) affords ethyl 6-(4,4,5,5-tetramethyl-1,3,2-dioxaborolan-2-yl)benzofuran-3-carboxylate as a colorless solid (238 mg, 47%). LC-MS B: $t_R$=1.12 min; [M+H]⁺=317.23.

A.2.5. Methyl 6-(4,4,5,5-tetramethyl-1,3,2-dioxaborolan-2-yl)-1H-indole-3-carboxylate To a solution of methyl 6-bromo-1H-indole-3-carboxylate (500 mg, 1.97 mmol) in anh. DMF (10 mL) are added at RT 4,4,4',4',5,5,5',5'-octamethyl-2,2'-bi(1,3,2-dioxaborolane) (505 mg, 1.97 mmol), potassium acetate (773 mg, 7.87 mmol) and Pd(dppf)Cl₂ (160 mg, 0.21 mmol). The RM is heated to 95° C., under nitrogen, for 17 h. The RM is then allowed to cool to RT and is filtered through a pad of celite, washing with Et₂O. The filtrate is washed with water and the aqueous layer is extracted twice with Et₂O. The combined organic layers are then washed with brine, dried over MgSO₄, filtered and concentrated under reduced pressure. Purification by FC (from heptane to heptane/EtOAc=7/3) affords methyl 6-(4,4,5,5-tetramethyl-1,3,2-dioxaborolan-2-yl)-1H-indole-3-carboxylate as a colorless solid (186 mg, 31%). LC-MS B: $t_R$=0.96 min; [M+H]⁺=302.25.

A.2.6. Ethyl 2-(4-(4,4,5,5-tetramethyl-1,3,2-dioxaborolan-2-yl)phenyl)acrylate To a solution of ethyl 2-(4-bromophenyl)acrylate (500 mg, 1.86 mmol) in anh. DMF (10 mL) are added at RT 4,4,4',4',5,5,5',5'-octamethyl-2,2'-bi(1,3,2-dioxaborolane) (478 mg, 1.86 mmol), potassium acetate (731 mg, 7.45 mmol) and Pd(dppf)Cl₂ (151 mg, 0.20 mmol). The RM is heated to 95° C., under nitrogen, for 16 h. The RM is then allowed to cool to RT and is filtered through a pad of celite, washing with Et₂O. The filtrate is washed with water and the aqueous layer is extracted twice with Et₂O. The combined organic layers are then washed with brine, dried over MgSO₄, filtered and concentrated under reduced pressure. Purification by FC (heptane/EtOAc=7/3) affords ethyl 2-(4-(4,4,5,5-tetramethyl-1,3,2-dioxaborolan-2-yl)phenyl)acrylate as a colorless oil (128 mg, 23%). LC-MS B: $t_R$=1.08 min; [M+H]⁺=303.21.

A.2.7. Ethyl 2-(2-ethoxy-4-(4,4,5,5-tetramethyl-1,3,2-dioxaborolan-2-yl)phenyl)propanoate To a solution of ethyl 2-(4-bromo-2-ethoxyphenyl)propanoate (359 mg, 1.19 mmol) in anh. DMF (5 mL) are added at RT 4,4,4',4',5,5,5',5'-octamethyl-2,2'-bi(1,3,2-dioxaborolane) (306 mg, 1.19 mmol), potassium acetate (468 mg, 4.77 mmol) and Pd(dppf)Cl₂ (97 mg, 0.13 mmol). The RM is heated to 95° C., under nitrogen, for 17 h. The RM is then allowed to cool to RT and is filtered through a pad of celite, washing with Et₂O. The filtrate is washed with water and the aqueous layer is extracted twice with Et₂O. The combined organic layers are then washed with brine, dried over MgSO₄, filtered and concentrated under reduced pressure. Purification by FC (from heptane to heptane/EtOAc=7/3) affords ethyl 2-(2-ethoxy-4-(4,4,5,5-tetramethyl-1,3,2-dioxaborolan-2-yl)phenyl)propanoate as a colorless oil (249 mg, 60%). LC-MS B: $t_R$=1.13 min; [M+H]⁺=349.30.

A.2.7.1. Ethyl 2-(4-bromo-2-ethoxyphenyl)propanoate

To a cooled (−78° C.) solution of lithium diisopropylamide (1.0 M in THF/hexanes, 7.80 mL, 7.80 mmol) in anh. THF (15 mL) is added dropwise a solution of ethyl 2-(4-bromo-2-ethoxyphenyl)acetate (2.01 g, 7.76 mmol) in anh. THF (5 mL), and the RM is further stirred at −78° C., under nitrogen, for 30 min. Iodomethane (0.745 mL, 10.10 mmol) is then added to the previous mixture and stirring is continued at −78° C. for 10 min, and then at 0° C. for 30 min. The RM is then treated dropwise with sat. aq. NH₄Cl and is allowed to warm-up to RT. Water and EtOAc are added and the layers are separated. The aq. layer is further extracted with EtOAc and the combined organic layers are dried over anh. MgSO₄, filtered and concentrated under reduced pressure. Purification by FC (heptane/EtOAc=4/1) affords ethyl 2-(4-bromo-2-ethoxyphenyl)propanoate as a colorless solid. LC-MS B: $t_R$=1.06 min; [M+H]⁺=301.09.

A.2.7.2. Ethyl 2-(4-bromo-2-ethoxyphenyl)acetate

To a solution of 2-(4-bromo-2-hydroxyphenyl)acetic acid (2.00 g, 8.66 mmol) in anh. DMF (35 mL) at RT are added cesium carbonate (5.641 g, 17.30 mmol) and iodoethane (2.44 mL, 30.30 mmol) and the RM is stirred at RT, under nitrogen, for 16 h. Water and Et₂O are added and the layers are separated. The aqueous layer is extracted twice with Et₂O and the combined organic layers are washed with brine, dried over anh. MgSO₄, filtered and concentrated under reduced pressure. Purification by FC (heptane/

EtOAc=7/3) affords ethyl 2-(4-bromo-2-ethoxyphenyl)acetate as a pale yellow oil (2.01 g, 81%). LC-MS B: $t_R$=1.03 min; [M+H]+=287.14.

A.2.8. 2-(2-Ethoxy-4-(4,4,5,5-tetramethyl-1,3,2-dioxaborolan-2-yl)phenyl)acetic acid Following the procedure described for the synthesis of A.2.7., using 2-(4-bromo-2-ethoxyphenyl)acetic acid, the title compound is obtained as a beige solid. LC-MS B: $t_R$=0.91 min; [M+H]$^+$=307.27.

A.2.8.1. 2-(4-Bromo-2-ethoxyphenyl)acetic acid

Ethyl 2-(4-bromo-2-ethoxyphenyl)acetate (4538 mg, 16.6 mmol) is dissolved in ethanol (30 mL), NaOH 10% (27.7 mL, 73.1 mmol) is added and the mixture is stirred overnight at RT. The mixture is treated by dropwise addition of HCl 37% (6.37 mL, 76.3 mmol), extracted with 60 mL DCM then twice with 30 mL of EtOAc, dried over MgSO$_4$ and evaporated under vacuum, affording the title compound as a pale yellow solid (2.5 g, 99%). LC-MS B: $t_R$=0.84 min; no ionization

A.2.8.2. Ethyl 2-(4-bromo-2-ethoxyphenyl)acetate

Following the procedure described for A.2.7.2., using 4-bromo-2-hydroxyphenylacetic acid and iodoethane, the title compound is obtained as a clear oil. LC-MS B: $t_R$=1.03 min; [M+H]$^+$=287.18.

A.2.9. 5-(4,4,5,5-Tetramethyl-1,3,2-dioxaborolan-2-yl)-3-(trifluoromethyl)thiophene-2-carboxylic acid Lithium diisopropylamide solution (2.0 M in TH/hexanes, 2.53 mL, 5.05 mmol) is added dropwise to a solution of 3-(trifluoromethyl)thiophene-2-carboxylic acid (330 mg, 1.68 mmol) in THE (7 mL) at −78° C. The RM is stirred for 30 min at −78° C. then at 0° C. for 10 min. Back at −78° C., a solution of 2-isopropoxy-4,4,5,5-tetramethyl-1,3,2-dioxaborolane (0.771 mL, 3.7 mmol) in THE (15 mL) is added dropwise and the RM is slowly allowed to warm to RT overnight. HCl 0.5N (20 mL) is added and the mixture is extracted with EtOAc. The combined organic layers are washed with brine, dried over MgSO$_4$ and the solvent is removed. The crude product is purified by FC (DCM/MeOH 1:0 to 19:1) to afford the title compound as a light orange solid (443 mg, 82%). LC-MS A: $t_R$=0.59 min; no ionization.

A.2.9.1. 3-(Trifluoromethyl)thiophene-2-carboxylic acid

To a −78° C. solution of 3-(trifluoromethyl)thiophene (0.4 mL, 3.68 mmol) in dry THE (10 mL) is added dropwise a solution of BuLi (1.38M in hexane, 2.93 mL, 4.05 mmol) and the RM is stirred for 30 min. The RM is then poured over an excess of freshly crushed dry ice carbon dioxide. Once the RM is back at RT, HCl 1N is added until pH<3 and the mixture is extracted with DCM (3×). The organic layer is dried over MgSO$_4$ and concentrated under vacuum, affording the title compound as a pale yellow solid (0.72 g, quantitative). LC-MS A: $t_R$=0.69 min; no ionization.

A.2.10. 3-Ethoxy-5-(4,4,5,5-tetramethyl-1,3,2-dioxaborolan-2-yl)thiophene-2-carboxylic acid The title compound is prepared according to the synthesis of A.2.9. using 3-ethoxythiophene-2-carboxylic acid. LC-MS A: $t_R$=0.48 min; [M+H]$^+$=217.07 (boronic acid, from hydrolysis of the pinacol ester on the LC-MS-column).

A.2.11. 5-(2-Ethoxy-4-(4,4,5,5-tetramethyl-1,3,2-dioxaborolan-2-yl)phenyl)-1H-tetrazole A mixture of 2-ethoxy-4-(4,4,5,5-tetramethyl-1,3,2-dioxaborolan-2-yl)benzonitrile (500 mg, 1.83 mmol), azidotributyltin(IV) (0.768 mL, 2.75 mmol), and dry toluene (4 mL) is heated at 180° C. for 1 h in a sealed MW vial under MW irradiation. The mixture is cooled to RT, treated with HCl 0.1N and extracted with EtOAc. The organic layer is dried over MgSO$_4$ and concentrated under vacuum. The residue is purified via FC, eluting with a gradient from Heptane:EtOAc 100:0 to 10:90. This affords the title compound as a white solid (135 mg, 23%). LC-MS B: $t_R$=0.94 min; [M+H]$^+$=317.26.

A.2.11.1. 2-Ethoxy-4-(4,4,5,5-tetramethyl-1,3,2-dioxaborolan-2-yl)benzonitrile A solution of 2-hydroxy-4-(4,4,5,5-tetramethyl-1,3,2-dioxaborolan-2-yl)benzonitrile (1.50 g, 6.12 mmol), K$_2$CO (1.69 g, 12.2 mmol) in DMF (4 mL) and iodoethane (0.596 mL, 7.34 mmol) is heated at 120° C. for 30 min. The RM is cooled down to RT, partitioned between DCM and 1N NaHCO$_3$. The aqueous layer is re-extracted with DCM, the combined organics are dried (MgSO$_4$), and concentrated under reduced pressure. This affords the title compound as a beige solid (1.31 g, 78%). LC-MS B: $t_R$=1.06 min; [M+CH3CN+H]$^+$=315.26.

A.2.12. 2-(Difluoromethoxy)-4-(4,4,5,5-tetramethyl-1,3,2-dioxaborolan-2-yl)benzoic acid To a solution of 4-bromo-2-(difluoromethoxy)benzoic acid (1.00 g, 3.56 mmol) in DMF (20 mL) are added at RT bis(pinacolato)diboron (1.355 g, 5.34 mmol), KOAc (1.047 g, 10.7 mmol) and Pd(dppf)Cl$_2$ (208 mg, 0.285 mmol). The RM is stirred at 100° C. for 17 h, then cooled to RT and filtered through a pad of celite, washing with EtOAC. The filtrate is washed with water and the aqueous layer is extrated (×2) with EtOAc. Organic layers are combined, washed with brine, dried over MgSO$_4$, filtered and concentrated under reduced pressure. The residue is purified by FC eluting with DCM to afford the title compound as an orange solid (846 mg, 76%). LC-MS A: $t_R$=0.37 min; [M+H]$^+$=313.11.

Following the procedure described for the synthesis of A.2.12. described above, the following boronic acid derivatives are synthesized, starting from the corresponding halides (see table 3).

TABLE 3

Boronic acid derivatives A.2.13.-A.2.16.

| No. | Compound | $t_R$ [min] (LC-MS) | MS Data m/z [M + H]$^+$ |
|---|---|---|---|
| A.2.13. | 2-Cyclobutoxy-5-(4,4,5,5-tetramethyl-1,3,2-dioxaborolan-2-yl)benzoic acid | 0.91 (A) | 319.11 |
| A.2.14. | Methyl 2-(methylthio)-4-(4,4,5,5-tetramethyl-1,3,2-dioxaborolan-2-yl)benzoate | 0.96 (A) | 309.18 |
| A.2.15. | 5-(4-(4,4,5,5-Tetramethyl-1,3,2-dioxaborolan-2-yl)phenyl)-[1,2,4-]oxadiazol-3-ol | 0.82 (B) | 290.10 |
| A.2.16. | 1-Methyl-6-(4,4,5,5-tetramethyl-1,3,2-dioxaborolan-2-yl)-1,2-dihydro-3H-indazol-3-one | 0.77 (A) | 275.27 |

A.2.17. 2-Fluoro-6-propyl-4-(4,4,5,5-tetramethyl-1,3,2-dioxaborolan-2-yl)benzoic acid The title compound is prepared according to the procedure described for A.2.12. starting with 4-bromo-2-fluoro-6-propylbenzoic acid. LC-MS E: $t_R$=0.48 min; [M−H]$^+$=307.11.

A.2.17.1. 4-Bromo-2-fluoro-6-propylbenzoic acid

To a solution of 4-bromo-2,6-difluorobenzoic acid (5.00 g, 21.1 mmol) in THF (50 mL) at 0° C. is added dropwise over 30 min n-propylmagnesium bromide (2M in THF, 21.6 mL, 43.2 mmol). The RM is allowed to reach RT and stirred for 17 h, then quenched carefully at 0° C. with MeOH (10 mL). After stirring for 5 min, the solvent is removed under reduced pressure. The residue is partitioned between EtOAc and 2N HCl. The aqueous phase is re-extracted with EtOAc (2×). The combined org. phases are washed with water, brine, dried over MgSO$_4$, filtered and concentrated. The residue is purified by FC (heptane/EtOAc 100:0 to 70:30) to afford the title compound as a white solid (4.45 g, 81%). LC-MS A: $t_R$=0.84 min; no ionization.

A.2.18. 2-(2-Ethoxy-4-(4,4,5,5-tetramethyl-1,3,2-dioxaborolan-2-yl)phenoxy)acetic acid A solution of ethyl 2-(2-ethoxy-4-(4,4,5,5-tetramethyl-1,3,2-dioxaborolan-2-yl)phenoxy)acetate (1.285 g, 3.82 mmol) in EtOH (15 mL) is treated with NaOH 10% (7.64 mL, 19.1 mmol) and the RM is stirred at 50° C. for 30 min. The RM is cooled to RT and diluted with EtOAc. HCl 2N (15 mL) is added to reach acidic pH (<1). The aqueous layer is extracted twice with EtOAc. The resulting organic phase is dried over MgSO$_4$ and concentrated, affording the title compound as an orange paste (1.10 g, 90%). LC-MS A: $t_R$=0.80 min; [M+H]$^+$=323.12.

A.2.18.1. Ethyl 2-(2-ethoxy-4-(4,4,5,5-tetramethyl-1,3,2-dioxaborolan-2-yl)phenoxy)acetate A solution of 2-ethoxy-4-(4,4,5,5-tetramethyl-1,3,2-dioxaborolan-2-yl)phenol (3.47 g, 12.5 mmol) in anhydrous DMF (50 mL) is treated successively with cesium carbonate (6.10 g, 18.7 mmol) and ethyl bromoacetate (1.48 mL, 13.1 mmol). The RM is stirred at RT for 1 h. Water is added, and the mixture is extracted with Et$_2$O (×3). The combined organic layers are then washed successively with water (×2) and brine, dried over MgSO$_4$, filtered, and concentrated under reduced pressure to afford the pure product as a colorless oil (1.46 g, 77%). LC-MS A: $t_R$=0.94 min; [M+H]$^+$=351.18.

A.2.19. (2-Ethoxy-4-(4,4,5,5-tetramethyl-1,3,2-dioxaborolan-2-yl)phenyl)glycine To a solution of methyl (2-ethoxy-4-(4,4,5,5-tetramethyl-1,3,2-dioxaborolan-2-yl)phenyl)glycinate (207 mg, 0.61 mmol) in THF/H2O (4:1) (5 mL) is added LiOH·H2O (51 mg, 1.21 mmol) and the RM is stirred at RT for 2 h. The mixture is treated with HCl 1N (1 mL) and extracted with EtOAc, dried over MgSO$_4$ and concentrated, affording the title compound as a brown oil (0.151 g, 78%). LC-MS A: $t_R$=0.82 min; [M+H]$^+$=322.07.

A.2.19.1. Methyl (2-ethoxy-4-(4,4,5,5-tetramethyl-1,3,2-dioxaborolan-2-yl)phenyl)glycinate The title compound is prepared according to the procedure described for A.2.12., starting with methyl (4-bromo-2-ethoxyphenyl)glycinate. LC-MS A: $t_R$=0.93 min; [M+H]$^+$=336.28.

A.2.19.2. Methyl (4-bromo-2-ethoxyphenyl)glycinate

To a solution of 4-bromo-2-ethoxyaniline (0.60 g, 2.64 mmol) in DMF (2.5 mL) is added DiPEA (0.673 mL, 3.96 mmol) followed by methyl bromoacetate (0.275 mL, 2.9 mmol). The mixture is stirred at 90° C. for 1 h in the microwave apparatus. The DMF is evaporated under high vacuum and the residue is purified by FC, eluting with Hept/EtOAc 1:0 to 17:3 affording the title compound as a dark red oil (0.71 g, 94%). LC-MS A: $t_R$=0.89 min; [M+H]$^+$=288.08.

A.2.20. 3-(2-Ethoxy-4-(4,4,5,5-tetramethyl-1,3,2-dioxaborolan-2-yl)phenyl)-[1,2,4]oxadiazol-5(4H)-one The title compound is prepared according to the procedure described for A.2.12., starting with 3-(4-bromo-2-ethoxyphenyl)-[1,2,4]oxadiazol-5(4H)-one. LC-MS A: $t_R$=0.89 min; [M+H]$^+$=333.06.

A.2.20.1. 3-(4-Bromo-2-ethoxyphenyl)-[1,2,4]oxadiazol-5(4H)-one

A solution of 4-bromo-2-ethoxy-N'-hydroxybenzimidamide (1.395 g, 5.38 mmol), 1,1'-carbonyldiimidazole (1.31 g, 8.08 mmol) and 1,8-diazabicyclo[5.4.0]undec-7-ene (1.23 mL, 8.08 mmol) in dioxane (20 mL) is stirred at 90° C. for 4 h30 min. Once at RT, the product precipitated upon addition of HCl 1M. Dioxane is partially evaporated via N2 stream prior to filtering off the solid under vacuum, washing with water. The title compound is obtained as a white solid (1.375 g, 90%). LC-MS A: $t_R$=0.81 min, [M+MeCN]$^+$=325.89.

A.2.20.2. 4-Bromo-2-ethoxy-N'-hydroxybenzimidamide

A suspension of 4-bromo-2-ethoxybenzonitrile (1.50 g, 6.5 mmol), hydroxylamine hydrochloride (913 mg, 13 mmol) and NaHCO$_3$ (1.365 g, 16.3 mmol) in water (1.32 mL) and EtOH (26.6 mL) is stirred in a sealed tube at 90° C. for 3 h. Once at RT, the product precipitated from the rxn mix upon addition of water. The solid is filtered off under high vacuum, washing with water and some Et$_2$O. A first crop of pure title compound (947 mg) is thus obtained as white solid. The filtrate is extracted with EtOAc. The organic layer is then washed twice with brine, dried over MgSO$_4$, filtered and concentrated. The residue is purified by FC (hept/EtOAc 5:5) to yield another crop of the pure title compound as a white solid (448 mg), merged with the first batch from precipitation. The title compound is obtained as a white solid (1.395 g, 83%). LC-MS A: $t_R$=0.53 min, [M+H]$^+$=259.03.

A.2.21. 3-(2-Ethoxy-4-(4,4,5,5-tetramethyl-1,3,2-dioxaborolan-2-yl)phenoxy)propanoic acid The title compound is prepared according to the procedure described for A.2.12., starting with 3-(4-bromo-2-ethoxyphenoxy)propanoic acid. LC-MS B: $t_R$=0.89 min; [M+H]$^+$=337.32.

A.2.21.1. 3-(4-Bromo-2-ethoxyphenoxy)propanoic acid

A MW vial is charged with 4-bromo-2-ethoxyphenol (1300 mg, 5.98 mmol), H2O (5 mL), NaOH 32% (1.332 mL, 14.38 mmol) and 3-chloropropionic acid (674 mg, 6.08 mmol). It is sealed and irradiated at 120° C., for 40 min at high energy level. The RM is diluted in water and pH is decreased to pH9 with HCl 2N then is extracted twice with EtOAc. The basic aqueous layer is then acidified to pH2 and extracted twice with EtOAc, the combined organic extracts are washed with water, brine, dried over MgSO$_4$, filtered and evaporated to dryness, yielding the title compound as a a white powder (0.448 g, 56%). LC-MS B: $t_R$=0.89 min; [M+H]$^+$=289.10.

A.2.22. Methyl (E)-3-(3-ethoxy-5-(4,4,5,5-tetramethyl-1,3,2-dioxaborolan-2-yl)thiophen-2-yl)acrylate The title compound is prepared according to the procedure described for A.2.9. starting with methyl (E)-3-(3-ethoxythiophen-2-yl)acrylate. LC-MS A: $t_R$=1.02 min; [M+H]$^+$=339.14.

A.2.22.1. Methyl (E)-3-(3-ethoxythiophen-2-yl)acrylate

A suspension of 3-ethoxythiophene-2-carbaldehyde (2.90 g, 18.6 mmol), methyl bromoacetate (3.07 mL, 33.4 mmol), and triphenylphosphine (7.305 g, 27.8 mmol) in aq saturated NaHCO$_3$ (100 mL) is stirred at RT for 5 h. THE (30 mL) is added and the RM is stirred overnight at RT. It is then extracted twice with DCM. The combined organic layers are dried over MgSO$_4$, filtered, and concentrated under vacuum. The crude is purified by FC (Hept/EtOAc 9:1) to afford the title compound as a dark orange oil (2.9 g, 100%). LC-MS A: $t_R$=0.69 min; [M+MeCN]$^+$=198.26.

A.2.23. 3-(3-Ethoxy-5-(4,4,5,5-tetramethyl-1,3,2-dioxaborolan-2-yl)thiophen-2-yl)propanoic acid To a solution of methyl (E)-3-(3-ethoxy-5-(4,4,5,5-tetramethyl-1,3,2-dioxaborolan-2-yl)thiophen-2-yl)acrylate [A.2.22.] (250 mg, 0.786 mmol) in MeOH (15 mL) is added Pd/C 5% wet (50 mg). Then the vessel is inertized with N$_2$ and flushed with H$_2$. The mixture is placed in a autoclave and it is stirred overnight at RT under 4 Bar of H$_2$, then for 1d at 50° C. under 4 bar of H$_2$. After filtration on whatman filter, NaOH 10% (1.18 mL, 11.8 mmol) is added and the RM is stirred for 1 h at RT. It is then treated with HCl 2N until pH<1 and extracted twice with EtOAc. The organic layer is dried over MgSO$_4$ and concentrated, to afford the title compound as a dark yellow oil (287 mg, 74%). LC-MS A: $t_R$=0.86 min; [M+H]$^+$=327.09.

A.2.24. Methyl 2-(3-ethoxy-5-(4,4,5,5-tetramethyl-1,3,2-dioxaborolan-2-yl)thiophen-2-yl)acetate A suspension of methyl 2-(3-ethoxythiophen-2-yl)acetate (815 mg, 4.07 mmol), bis(pinacolato)diboron (633 mg, 2.44 mmol), (1,5-cyclooctadiene)(methoxy)iridium(I) dimer (28.9 mg, 0.0437 mmol) and 4,4'-di-tert-butyl-2,2'-dipyridyl (26.8 mg, 0.0999 mmol) in THE (19.3 mL) is degassed with a nitrogen stream for 15 min and then stirred at 80° C. overnight. The RM is concentrated under reduced pressure and the residue is purified by FC (Hept to Hept/EtOAc 9:1) to afford the title compound as a colourless oil which crystallized upon standing (908 mg, 68%). LC-MS B: $t_R$=1.03 min, [M+H]$^+$=327.14.

A.2.24.1. Methyl 2-(3-ethoxythiophen-2-yl)acetate

Silver benzoate (1800 mg, 7.78 mmol) is added portionwise to a solution of 2-diazo-1-(3-ethoxythiophen-2-yl)ethan-1-one (2025 mg, 10.3 mmol) and TEA (4.31 mL, 31 mmol) in MeOH (52.7 mL) and the RM is stirred at RT for 2 h. It is then diluted with EtOAc and filtered over celite. The filtrate is washed twice with sat. aq. NaHCO$_3$ and once with brine. The organic layer is dried over MgSO$_4$, filtered and concentrated. The residue is purified by FC (Hept to Hept/EtOAc 95:5) to yield the title compound as a light yellow oil (817 mg, 40%). LC-MS B: $t_R$=0.86 min, [M+H]$^+$=201.14.

A.2.24.2. 2-Diazo-1-(3-ethoxythiophen-2-yl)ethan-1-one

A solution of 3-ethoxythiophene-2-carboxylicacid (2500 mg, 14.1 mmol) in DCM (120 mL) is treated with thionyl chloride (1.56 mL, 21.1 mmol), dropwise. The RM is stirred at RT overnight, it is then concentrated in vacuo, and the residue is dissolved in MeCN (80 mL). TEA (2.2 mL, 15.8 mmol) is added dropwise and the solution is cooled down to 0° C. (Trimethylsilyl)diazomethane (2M solution, 15 mL, 30 mmol) is added dropwise and the RM is stirred at RT for 2d. It is then carefully quenched by dropwise addition of AcOH, until no more bubbling is observed. The RM is then concentrated and the residue is partitioned between EtOAc and water. The organic layer is then washed with sat. aq.

A.2.25. Ethyl 2-((2-ethoxy-4-(4,4,5,5-tetramethyl-1,3,2-dioxaborolan-2-yl)phenyl)amino)-2-oxoacetate The title compound is prepared according to the procedure described for A.2.12., starting with ethyl 2-((4-bromo-2-ethoxyphenyl)amino)-2-oxoacetate. LC-MS A: $t_R$=0.98 min; $[M+H]^+$=364.21.

A.2.25.1. Ethyl 2-((4-bromo-2-ethoxyphenyl)amino)-2-oxoacetate

To a solution of 4-bromo-2-ethoxyaniline (1.10 g, 4.84 mmol) in DCM (35 mL) is added TEA (0.748 mL, 5.32 mmol) at RT. The RM is cooled to 0° C. and ethyl oxalyl chloride (0.61 mL, 5.32 mmol) is added dropwise. The RM is stirred for 30 min at 0° C. then allowed to warm to RT and stirred for 30 min. The RM is partitioned between EtOAc and sat. aq. NaHCO$_3$. The two layers are separated and the organic layers washed with water, brine then dried over MgSO$_4$, filtered and solvent removed under vacuo, affording the title compound as a brown solid (1.52 g, 99%). LC-MS A: $t_R$=0.92 min; $[M+MeCN]^+$=316.04.

A.2.26. 2-Butoxy-6-fluoro-4-(4,4,5,5-tetramethyl-1,3,2-dioxaborolan-2-yl)benzoic acid The title compound is prepared according to the procedure described for A.2.12., starting with 4-bromo-2-butoxy-6-fluorobenzoic acid. LC-MS A: $t_R$=0.92 min; $[M+H]^+$=339.21.

A.2.26.1. 4-Bromo-2-butoxy-6-fluorobenzoic acid

Methyl 4-bromo-2-butoxy-6-fluorobenzoate (1246 mg, 3.94 mmol) is dissolved in EtOH (15 mL). NaOH 32% (1.82 mL, 19.7 mmol) is added and the RM is heated up to 60° C. for 1 h. it is then cooled to RT and diluted with EtOAc. HCl 2N (10 mL) is added to reach acidic pH (<2). The aq. layer is extracted twice with EtOAc. The resulting organic phase is dried over MgSO$_4$ and concentrated, affording the title compound as a white solid. LC-MS E: $t_R$=0.52 min; $[M-H]^+$=290.89.

A.2.26.2. Methyl 4-bromo-2-butoxy-6-fluorobenzoate

To a solution of methyl 4-bromo-2-fluoro-6-hydroxybenzoate (1.00 g, 4.02 mmol) in DMF (10 mL), is added Cs$_2$CO$_3$ (2.62 g, 8.03 mmol) followed by 1-iodobutane (0.685 mL, 6.02 mmol). The RM is stirred at 120° C. for 2 h under MW irradiation. The RM is concentrated under reduced pressure, the residue is partitioned between DCM and water. The aqueous layer is re-extracted with DCM, the combined organics are dried (MgSO$_4$), and concentrated under reduced pressure. Purification by FC (Hept/EtOAc 1:0 to 19:1) affords the title compound as a colourless oil (1.24 g, 99%). LC-MS A: $t_R$=0.98 min; $[M+H]^+$=306.84.

A.2.27. Methyl 2-(2-hydroxyethoxy)-4-(4,4,5,5-tetramethyl-1,3,2-dioxaborolan-2-yl)benzoate The title compound is prepared according to the procedure described for A.2.12., starting with methyl 4-bromo-2-(2-hydroxyethoxy)benzoate. LC-MS B: $t_R$=0.89 min; $[M+H]^+$=323.26.

A.2.27.1. Methyl 4-bromo-2-(2-hydroxyethoxy)benzoate

NaH (101 mg, 4.2 mmol) is added portionwise to a 0° C. solution of methyl 4-bromo-2-hydroxybenzoate (500 mg, 2.1 mmol) in DMF (5 mL). The RM is stirred for a few minutes at 0° C., then 2-bromoethanol (0.235 mL, 3.15 mmol) is added and the RM is stirred at 90° C. for 2 h45, then cooled to RT. Water is added to the RM and it is extracted twice with EtOAc. The combined organic layers are washed with brine, dried over MgSO$_4$, filtered and concentrated under reduced pressure. The residue is purified by FC (heptane/EtOAc, 1:0 to 6:4), affording the title compound as a colorless oil (358 mg, 62%). LC-MS B: $t_R$=0.77 min; $[M+H]^+$=275.14.

A.2.28. 7-(4,4,5,5-Tetramethyl-1,3,2-dioxaborolan-2-yl)-2,3-dihydro-5H-thieno[3,2-e][1,4]dioxepin-5-one The title compound is prepared according to the procedure described for A.2.24., starting with 2,3-dihydro-5H-thieno[3,2-e][1,4]dioxepin-5-one. LC-MS B: $t_R$=0.51 min; $[M+H]^+$=215.41 (mass from boronic acid from pinacol ester cleavage during LC-MS analysis).

A.2.28.1. 2,3-Dihydro-5H-thieno[3,2-e][1,4]dioxepin-5-one

A MW vial is charged with K$_2$CO (623 mg, 4.5 mmol), methyl 3-hydroxythiophene-2-carboxylate (250 mg, 1.5 mmol) and DMF (5 mL). The RM is stirred for a few minutes then 2-bromoethanol (0.146 mL, 1.95 mmol) is added, the vial is capped and heated at 100° C. for 2 h under MW irradiation. 2-Bromoethanol (0.0319 mL, 0.45 mmol) is added and the RM is stirred at 90° C. overnight, under thermal conditions. Once at RT, water is added and the RM is extracted thrice with EtOAc. The combined organic layers are dried over MgSO$_4$, filtered and concentrated under reduced pressure, affording the crude title compound as a brownish solid (338 mg, quantitative). LC-MS B: $t_R$=0.61 min; $[M+H]^+$=170.94.

A.2.29. Methyl 2-(2-ethoxy-4-(4,4,5,5-tetramethyl-1,3,2-dioxaborolan-2-yl)phenoxy) propanoate To a solution of 2-ethoxy-4-(4,4,5,5-tetramethyl-1,3,2-dioxaborolan-2-yl)phenol (390 mg, 1.48 mmol) in DMF (15 mL) at RT is added K$_2$CO (427 mg, 3.03 mmol). The RM is stirred 15 min at 60° C. then methyl 2-bromopropionate (0.2 mL, 1.77 mmol) is added and the RM is stirred overnight at 60° C. The RM is cooled to RT, concentrated in vacuo, and the residue is partitioned between EtOAc and water. The organic layer is washed once more with water, then brine, dried over MgSO$_4$, filtered and evaporated to dryness, affording the title compound as a pale yellow oil which crystallizes upon standing (447 mg, 86%). LC-MS B: $t_R$=1.04 min; $[M+H]^+$=351.08.

A.2.30. 3-(3-Methoxy-5-(4,4,5,5-tetramethyl-1,3,2-dioxaborolan-2-yl)thiophen-2-yl)oxetan-3-ol The title compound is prepared according to the procedure described for A.2.9., starting with 3-(3-methoxythiophen-2-yl)oxetan-3-ol. LC-MS A: $t_R$=0.78 min; $[M-H_2O]^+$=295.12.

A.2.30.1. 3-(3-Methoxythiophen-2-yl)oxetan-3-ol

To a stirred solution of 3-methoxythiophene (1.00 g, 8.58 mmol) and N,N,N',N'-tetramethylethylenediamine (1.55 mL, 10.3 mmol) in Et$_2$O (30 mL) is added BuLi (1.6M in Hexane, 6.4 mL, 10.3 mmol) dropwise at 0° C. The RM is stirred at RT for 30 min, then 3-oxetanone (0.761 mL, 12.9 mmol) is added dropwise and the RM is stirred at RT for 35 min, then diluted with water, the aqueous layer is extracted three times with EtOAc and the combined organic layers are dried over MgSO$_4$, filtered and concentrated under reduced pressure. The residue is purified by FC (Hept to Hept/EtOAc 8:2) to give the title compound as a light-yellow oil (1.123 g, 70%). LC-MS A: $t_R$=0.53 min; [M−H$_2$O]$^+$=169.04.

A.2.31. 3-Ethoxy-4-(4-(4,4,5,5-tetramethyl-1,3,2-dioxaborolan-2-yl)phenyl)cyclobut-3-ene-1,2-dione 3-Ethoxy-4-(tributylstannyl)cyclobut-3-ene-1,2-dione (335 mg, 0.807 mmol) and 4-iodophenylboronic acid, pinacol ester (298 mg, 0.904 mmol) are dissolved in DMF (4 mL) with N$_2$ bubbling for 5 min. Trans-Benzyl(chloro)bis(triphenylphosphine)palladium(II) (36.7 mg, 0.0484 mmol) and CuI (15.4 mg, 0.0807 mmol) are added and the RM is stirred at RT for 3 h., then filtered over a microglass filter, concentrated under vacuum and purified by FC (Hept:EtOAc 100:0 to 80:20) to obtain the title compound as a yellow solid (127 mg, 48%). LC-MS A: $t_R$=0.97 min; [M+MeCN]$^+$=370.07.

A.2.32. 2,6-Dimethoxy-4-(4,4,5,5-tetramethyl-1,3,2-dioxaborolan-2-yl)benzoic acid The title compound is prepared according to the procedure described for A.2.12., starting with 4-bromo-2,6-dimethoxybenzoic acid. LC-MS B: $t_R$=0.84 min; [M+H]$^+$=309.10.

A.2.33. Methyl 2-ethoxy-6-methoxy-4-(4,4,5,5-tetramethyl-1,3,2-dioxaborolan-2-yl)benzoate The title compound is prepared according to the procedure described for A.2.12., starting with methyl 4-bromo-2-ethoxy-6-methoxybenzoate. LC-MS B: $t_R$=1.04 min; [M+H]$^+$=337.18.

A.2.33.1. Methyl 4-bromo-2-ethoxy-6-methoxybenzoate

To 4-bromo-2-ethoxy-6-methoxybenzoic acid (3080 mg, 11.2 mmol) in DMF (30 mL) is added portionise Cs$_2$CO$_3$ (4742 mg, 14.6 mmol), followed by methyl iodide (0.836 mL, 13.4 mmol), dropwise. The RM is stirred at RT for 2 h, then water is added and the mixture is extracted with Et$_2$O. The organic layer is successively washed with water and brine, dried over MgSO$_4$ and concentrated under reduced pressure. The residue is purified by FC (Hept/EtOAc from 1:0 to 1:1) to afford the product as a white solid (2.87 g, 89%). LC-MS B: $t_R$=0.96 min; [M+H]$^+$=288.99.

A.2.33.2. 4-Bromo-2-ethoxy-6-methoxybenzoic acid

4-Bromo-2-ethoxy-6-methoxybenzaldehyde (2950 mg, 11.4 mmol) is suspended in t-BuOH (48 mL) and a solution of sodium chlorite (2574 mg, 22.8 mmol) and sodium phosphate monobasic monohydrate (7935 mg, 56.9 mmol) in water (24 mL) is added dropwise. After complete addition, 2-methyl-2-butene (10.2 mL, 91.1 mmol) is added. The RM is stirred at RT for 30 min then concentrated under reduced pressure. The residue is suspended in water, acidified with 1N aq HCl and extracted 3 time with Et$_2$O. The combined extracts are washed with 1N aq NaOH (3 times). The combined aqueous layers are acidified with 6N aq HCl and extracted 3 times with EtOAc. The organic extracts are dried over MgSO$_4$, filtered and concentrated under reduced pressure, to provide the title compound as a pale yellow solid (3.08 g, 98%). LC-MS B: $t_R$=0.79 min; [M+H]$^+$=274.91.

A.2.33.3. 4-Bromo-2-ethoxy-6-methoxybenzaldehyde

To a solution of 4-bromo-2-hydroxy-6-methoxybenzaldehyde (2880 mg, 12.5 mmol) in DMF (30 mL) is added cesium carbonate (4874 mg, 15 mmol), followed by iodoethane (1.1 mL, 13.7 mmol). The RM is stirred at RT overnight. Water is added and the aqueous layer is extracted with Et$_2$O (3×). The combined organic layers are washed with water, dried over MgSO$_4$, concentrated. Purification by FC (Hept/EtOAc from 1:0 to 1:1) affords the title compound as a white solid (2.95 g, 91%). LC-MS B: $t_R$=0.90 min; [M+H]$^+$=258.95.

A.2.34. Ethyl 2-(2-ethoxy-4-(4,4,5,5-tetramethyl-1,3,2-dioxaborolan-2-yl)phenoxy)-2-methylpropanoate The title compound is prepared according to the procedure described for A.2.12., starting with ethyl 2-(4-bromo-2-ethoxyphenoxy)-2-methylpropanoate. LC-MS B: $t_R$=1.13 min; [M+H]$^+$=379.22.

A.2.34.1. Ethyl 2-(4-bromo-2-ethoxyphenoxy)-2-methylpropanoate

The title compound is prepared according to the procedure described for A.2.18.1., using 4-bromo-2-ethoxyphenol and ethyl 2-bromoisobutyrate. LC-MS B: $t_R$=1.09 min: [M+H]$^+$=331.09.

A.2.35. Methyl 2-(2-ethoxy-6-fluoro-4-(4,4,5,5-tetramethyl-1,3,2-dioxaborolan-2-yl)phenyl)acetate To a solution of methyl 2-(4-bromo-2-ethoxy-6-fluorophenyl)acetate (1.370 g, 4.71 mmol) in anh. DMF (12 mL) are added at RT 4,4,4',4',5,5,5',5'-octamethyl-2,2'-bi(1,3,2-dioxaborolane) (1.207 g, 4.71 mmol), potassium acetate (1.847 g, 18.80 mmol) and Pd(dppf)Cl$_2$ (383 mg, 0.51 mmol). The RM is heated to 90° C., under nitrogen, overnight. The RM is then allowed to cool to RT and is filtered through a pad of celite, washing with EtOAc. The filtrate is washed with water and the aqueous layer is extracted twice with EtOAc. The combined organic layers are then washed with brine, dried over MgSO$_4$, filtered and concentrated under reduced pressure. Purification by FC (from heptane to heptane/EtOAc=1/1) affords methyl 2-(2-ethoxy-6-fluoro-4-(4,4,5,5-tetramethyl-1,3,2-dioxaborolan-2-yl)phenyl)acetate as a colorless solid (0.970 g, 61%). LC-MS B: $t_R$=1.09 min; [M+H]$^+$=339.21.

A.2.35.1. Methyl 2-(4-bromo-2-ethoxy-6-fluorophenyl)acetate

To a solution of 2-(4-bromo-2-ethoxy-6-fluorophenyl)acetic acid (1.440 g, 5.20 mmol) in anh. DMF (15 mL) at RT are added cesium carbonate (2.117 g, 6.50 mmol) and iodomethane (0.48 mL, 7.80 mmol) and the RM is stirred at RT, under nitrogen, for 15 min. Water and Et$_2$O are added and the layers are separated. The aqueous layer is extracted twice with Et$_2$O and the combined organic layers are washed with brine, dried over anh. MgSO$_4$, filtered and concentrated under reduced pressure. Purification by FC (from heptane to heptane/EtOAc=1/1) affords methyl 2-(4-bromo-2-ethoxy-6-fluorophenyl)acetate as a colorless oil (1.370 g, 91%). LC-MS B: $t_R$=1.01 min; [M+H]$^+$=290.99.

A.2.35.2. 2-(4-Bromo-2-ethoxy-6-fluorophenyl)acetic acid

A mixture of 2-(4-bromo-2-ethoxy-6-fluorophenyl)acetonitrile (1.440 g, 5.58 mmol), water (5 mL), 95% sulfuric acid (6 mL) and acetic acid (7 mL) is heated to 110° C., under nitrogen, for 3 h. The RM is then allowed to cool to RT and is poured onto ice/water. The mixture is extracted twice with DCM and the combined organic layers are washed with brine, dried over anh. MgSO$_4$, filtered and concentrated under reduced pressure affording crude 2-(4-bromo-2-ethoxy-6-fluorophenyl)acetic acid as a colorless solid (1.440 g, 93%). LC-MS B: $t_R$=0.88 min; no ionization.

A.2.35.3. 2-(4-Bromo-2-ethoxy-6-fluorophenyl)acetonitrile

A solution of 5-bromo-2-(chloromethyl)-1-ethoxy-3-fluorobenzene (2.860 g, 10.10 mmol) in MeCN (27 mL) and water (3.5 mL) is treated with sodium cyanide (669 mg, 13.10 mmol) and the RM is heated to 80° C., under nitrogen, overnight. The RM is then allowed to cool to RT and is diluted with water. Acetonitrile is removed under reduced pressure and the mixture is extracted twice with DCM. The combined organic layers are dried over anh. MgSO$_4$, filtered and concentrated under reduced pressure. Purification by FC (from heptane to heptane/EtOAc=1/1) affords 2-(4-bromo-2-ethoxy-6-fluorophenyl)acetonitrile as a colorless solid (1.440 g, 55%). LC-MS B: $t_R$=0.97 min; no ionization.

A.2.35.4. 5-Bromo-2-(chloromethyl)-1-ethoxy-3-fluorobenzene

A cooled (0° C.) mixture of (4-bromo-2-ethoxy-6-fluorophenyl)methanol (2.180 g, 8.75 mmol) and zinc chloride (29.8 mg, 0.219 mmol) in anh. DCM (17 mL) is treated dropwise with thionyl chloride (1.28 mL, 17.50 mmol) and the RM is stirred at 0° C. for 2 h. The RM is concentrated under reduced pressure affording crude 5-bromo-2-(chloromethyl)-1-ethoxy-3-fluorobenzene as a pale pink oil (2.330 g, 99%). LC-MS B: $t_R$=1.07 min; no ionization.

A.2.35.5. (4-Bromo-2-ethoxy-6-fluorophenyl)methanol

To a cooled (−78° C.) solution of methyl 4-bromo-2-ethoxy-6-fluorobenzoate (3.150 g, 11.40 mmol) in anh. THF (30 mL) is added dropwise a solution of diisobutylaluminum hydride (1 M in toluene, 34.1 mL, 34.1 mmol). The mixture is further stirred at −78° C., under nitrogen, for 15 min and is then allowed to warm-up to 0° C. Stirring at 0° C. is continued for 45 min, and the cooled RM is then treated successively with water (35 mL) and 2.8 N aq. NaOH (25 mL). The mixture is allowed to warm-up to RT and is further stirred for 30 min. The resulting mixture is filtered over celite, washing with THF. EtOAc and water are added and the layers are separated. The aqueous layer is extracted twice with EtOAc and the combined organic layers are dried over anh. MgSO$_4$, filtered and concentrated under reduced pressure. Purification by FC (from heptane to EtOAc) affords (4-bromo-2-ethoxy-6-fluorophenyl)methanol as a colorless solid (2.680 g, 95%). LC-MS B: $t_R$=0.84 min; no ionization.

A.2.35.6. Methyl 4-bromo-2-ethoxy-6-fluorobenzoate

To a solution of methyl 4-bromo-2-fluoro-6-hydroxybenzoate (2.930 g, 11.20 mmol) in anh. DMF (14 mL) at RT are added successively cesium carbonate (3.642 g, 11.20 mmol) and iodoethane (0.90 mL, 11.20 mmol) and the RM is stirred at RT for 30 min. Additional cesium carbonate (3.729 g, 11.40 mmol) and iodoethane (0.92 mL, 11.40 mmol) are then added and the RM is stirred at RT for 20 min. Water and Et$_2$O are added and the layers are separated. The aqueous layer is extracted twice with Et$_2$O and the combined organic layers are washed with brine, dried over anh. MgSO$_4$, filtered and concentrated under reduced pressure. Purification by FC (from heptane to heptane/EtOAc=1/1) affords methyl 4-bromo-2-ethoxy-6-fluorobenzoate as a yellow oil (3.150 g, quantitative). LC-MS B: $t_R$=0.97 min; [M+H]$^+$=277.08.

A.2.36. Isopropyl 2-(2-isopropoxy-4-(4,4,5,5-tetramethyl-1,3,2-dioxaborolan-2-yl)phenyl)acetate Bis(pinacolato)diboron (1618 mg, 6.31 mmol) followed by potassium acetate (2477 mg, 25.2 mmol) are added to a RT solution of isopropyl 2-(4-bromo-2-isopropoxyphenyl)acetate (2046 mg, 6.31 mmol) in DMF (25 mL). The RM is purged with N$_2$ and dichloro(1,1'-bis(diphenylphosphino)ferrocene) palladium (II) (513 mg, 0.694 mmol) is added. The RM is heated at 95° C. overnight, then cooled to RT, filtered over a pad of celite and rinsed with Et$_2$O. Water and Et$_2$O are added, and the two layers are separated. The aqueous layer is extracted with Et$_2$O (3×). The combined organic layers are washed with water (2×), brine, dried over MgSO$_4$, filtered and evaporated in vacuum. The residue is purified by FC (Hept:EtOAc 100:0 to 70:30) to afford the title compound as a light green oil (1.604 g, 70%). LC-MS B: $t_R$=1.14 min; [M+H]$^+$=363.25.

A.2.36.1. Isopropyl 2-(4-bromo-2-isopropoxyphenyl)acetate

To 4-bromo-2-hydroxyphenylacetic acid (2000 mg, 8.22 mmol) in DMF (25 mL) is added cesium carbonate (5359 mg, 16.4 mmol) and 2-bromopropane (2.73 mL, 28.8 mmol) at 0° C. The RM is warmed up to RT and stirred for 1 h, then heated to 45° C. and stirred for 24 h. Water is added and the resulting mixture is extracted with Et$_2$O (3×). Organic layers are mixed and washed with additional water (2×), brine, then dried over a phase separator and concentrated under vacuum. The residue is purified by FC (Hept:EtOAc 100:0 to 75:25) to yield the title compound as a light green oil (2.046 g, 79%). LC-MS B: $t_R$=1.10 min; [M+H]$^+$=315.11.

A.2.37. Methyl 2-(2-isobutyl-4-(4,4,5,5-tetramethyl-1,3,2-dioxaborolan-2-yl)phenyl)acetate To a solution of methyl 2-(4-bromo-2-isobutylphenyl)acetate (2.271 g, 7.13 mmol) in anh. DMF (25 mL) are added at RT 4,4,4',4',5,5,5',5'-octamethyl-2,2'-bi(1,3,2-dioxaborolane) (1.828 g, 7.13 mmol), potassium acetate (2.798 g, 28.50 mmol) and Pd(dppf)Cl$_2$ (579 mg, 0.78 mmol). The RM is heated to 95° C., under nitrogen, for 16 h. The RM is then allowed to cool to RT and is filtered through a pad of celite, washing with EtOAc. The filtrate is washed with water and the aqueous layer is extracted twice with EtOAc. The combined organic layers are then washed with brine, dried over MgSO$_4$, filtered and concentrated under reduced pressure. Purification by FC (from heptane to heptane/EtOAc=1/1) affords methyl 2-(2-isobutyl-4-(4,4,5,5-tetramethyl-1,3,2-dioxaborolan-2-yl)phenyl)acetate as a yellow oil (1.822 g, 77%). LC-MS B: $t_R$=1.13 min; [M+H]$^+$=333.24.

A.2.37.1. Methyl 2-(4-bromo-2-isobutylphenyl)acetate

To a solution of 2-(4-bromo-2-isobutylphenyl)acetic acid (2.457 g, 8.64 mmol) in anh. DMF (30 mL) at RT are added cesium carbonate (5.633 g, 17.30 mmol) and iodomethane (1.09 mL, 17.30 mmol) and the RM is stirred at RT, under nitrogen, for 1 h. Water and Et$_2$O are added and the layers are separated. The aqueous layer is extracted twice with Et$_2$O and the combined organic layers are washed with brine, dried over anh. MgSO$_4$, filtered and concentrated under reduced pressure. Purification by FC (from heptane to heptane/EtOAc=1/1) affords methyl 2-(4-bromo-2-isobutylphenyl)acetate as a clear oil (2.271 g, 92%). LC-MS B: $t_R$=1.06 min; no ionization.

A.2.37.2. 2-(4-Bromo-2-isobutylphenyl)acetic acid

A mixture of 2-(4-bromo-2-isobutylphenyl)acetonitrile (2.162 g, 8.41 mmol), water (8 mL), 95% sulfuric acid (9 mL) and acetic acid (6 mL) is heated to 110° C., under nitrogen, overnight. The RM is then allowed to cool to RT and is poured onto ice/water. The mixture is extracted twice with DCM and the combined organic layers are washed with brine, dried over anh. MgSO$_4$, filtered and concentrated under reduced pressure affording crude 2-(4-bromo-2-isobutylphenyl)acetic acid as an amber oil (2.457 g, quantitative). LC-MS B: $t_R$=0.96 min; no ionization.

A.2.37.3. 2-(4-Bromo-2-isobutylphenyl)acetonitrile

A solution of 4-bromo-1-(chloromethyl)-2-isobutylbenzene (2.381 g, 9.00 mmol) in MeCN (24 mL) and water (3 mL) is treated with sodium cyanide (597 mg, 11.70 mmol) and the RM is heated to 80° C., under nitrogen, overnight. The RM is then allowed to cool to RT and is diluted with water. Acetonitrile is removed under reduced pressure and the RM is extracted twice with DCM. The combined organic layers are dried over anh. MgSO$_4$, filtered and concentrated under reduced pressure. Purification by FC (from heptane to heptane/EtOAc=1/1) affords 2-(4-bromo-2-isobutylphenyl)acetonitrile as a clear oil (2.162 g, 95%). LC-MS B: $t_R$=1.05 min; no ionization.

A.2.37.4. 4-Bromo-1-(chloromethyl)-2-isobutylbenzene

A cooled (0° C.) mixture of (4-bromo-2-isobutylphenyl)methanol (2.192 g, 8.83 mmol) and zinc chloride (30.1 mg, 0.221 mmol) in anh. DCM (20 mL) is treated dropwise with thionyl chloride (1.29 mL, 17.70 mmol) and the RM is stirred at 0° C. for 4 h. The RM is concentrated under reduced pressure affording crude 4-bromo-1-(chloromethyl)-2-isobutylbenzene as a light pink oil (2.381 g, quantitative). LC-MS B: $t_R$=1.13 min; no ionization.

A.2.37.5. (4-Bromo-2-isobutylphenyl)methanol

To a cooled (−78° C.) solution of methyl 4-bromo-2-isobutylbenzoate (2.712 g, 9.71 mmol) in anh. THF (60 mL) is added dropwise a solution of diisobutylaluminum hydride (1 M in toluene, 29.1 mL, 29.1 mmol). The mixture is further stirred at −78° C., under nitrogen, for 15 min and is then allowed to warm-up to 0° C. Stirring at 0° C. is continued for 30 min, and the cooled RM is treated successively with water (1 mL), 2.8 N aq. NaOH (1 mL) and water (3 mL). The mixture is then allowed to warm-up to RT and is further stirred for 30 min. The resulting mixture is filtered over celite, washing with THF and the filtrate is concentrated to dryness under reduced pressure. EtOAc and water are added and the layers are separated. The aqueous layer is extracted twice with EtOAc and the combined organic layers are dried over anh. MgSO$_4$, filtered and concentrated under reduced pressure. Purification by FC (from heptane to heptane/EtOAc=1/1) affords (4-bromo-2-isobutylphenyl)methanol (2.192 g, 93%). LC-MS B: $t_R$=0.96 min; no ionization.

A.2.37.6. Methyl 4-bromo-2-isobutylbenzoate

To a solution of 4-bromo-2-isobutylbenzoic acid (4.254 g, 14.30 mmol) in anh. DMF (50 mL) at RT are added successively cesium carbonate (9.304 g, 28.60 mmol) and iodomethane (1.80 mL, 28.60 mmol) and the RM is stirred at RT for 1 h. Water and Et$_2$O are added and the layers are separated. The aqueous layer is extracted twice with Et$_2$O and the combined organic layers are washed with brine, dried over anh. MgSO$_4$, filtered and concentrated under reduced pressure. Purification by FC (from heptane to heptane/EtOAc=7/3) affords methyl 4-bromo-2-isobutylbenzoate as a light yellow oil (3.462 g, 89%). LC-MS B: $t_R$=1.11 min; no ionization.

A.2.37.7. 4-Bromo-2-isobutylbenzoic acid

To a cooled (0° C.) solution of 4-bromo-2-fluorobenzoic acid (5.000 g, 22.40 mmol) in anh. THF (40 mL) is added dropwise a solution of isobutylmagnesium bromide (2.0 M in Et$_2$O, 33.5 mL, 67.0 mmol) and the RM is further stirred at RT, under nitrogen, overnight. MeOH (10 mL) is then added dropwise to the cooled (0° C.) reaction mixture that is further stirred at 0° C. for 5 min. The resulting mixture is then concentrated to dryness under reduced pressure and the residue is partitioned between EtOAc and 2 M aq. HCl. The layers are separated, and the aq. layer is extracted twice with EtOAc. The combined organic layers are then washed with brine, dried over anh. MgSO$_4$, filtered and concentrated under reduced pressure. Purification by FC (from heptane to heptane/EtOAc=7/3) affords 4-bromo-2-isobutylbenzoic acid as a light yellow solid (4.254 g, 74%). LC-MS B: $t_R$=0.97 min; no ionization.

A.2.38. Methyl 2-(4-(4,4,5,5-tetramethyl-1,3,2-dioxaborolan-2-yl)-2-(trifluoromethoxy)phenyl)acetate To a solution of methyl 2-(4-bromo-2-(trifluoromethoxy)phenyl)acetate (1.896 g, 5.58 mmol) in anh. DMF (25 mL) are added at RT 4,4,4',4',5,5,5',5'-octamethyl-2,2'-bi(1,3,2-dioxaborolane) (1.432 g, 5.58 mmol), potassium acetate (2.192 g, 22.30 mmol) and Pd(dppf)Cl$_2$ (454 mg, 0.61 mmol). The RM is heated to 95° C., under nitrogen, overnight. The RM is then allowed to cool to RT and is filtered through a pad of celite, washing with Et$_2$O. The filtrate is washed with water and the aqueous layer is extracted twice with Et$_2$O. The combined organic layers are then washed with brine, dried over MgSO$_4$, filtered and concentrated under reduced pressure. Purification by FC (from heptane to heptane/EtOAc=7/3) affords methyl 2-(4-(4,4,5,5-tetramethyl-1,3,2-dioxaborolan-2-yl)-2-(trifluoromethoxy)phenyl)acetate as a green oil (1.574 g, 78%). LC-MS B: $t_R$=1.09 min; [M+H]$^+$=361.13.

A.2.38.1. Methyl 2-(4-bromo-2-(trifluoromethoxy)phenyl)acetate

To a solution of 2-(4-bromo-2-(trifluoromethoxy)phenyl)acetic acid (2.000 g, 6.56 mmol) in anh. DMF (30 mL) at RT are added cesium carbonate (4.277 g, 13.10 mmol) and iodomethane (0.82 mL, 13.10 mmol) and the RM is stirred at RT, under nitrogen, for 1 h. Water and Et$_2$O are added and the layers are separated. The aqueous layer is extracted twice with Et$_2$O and the combined organic layers are washed with brine, dried over anh. MgSO$_4$, filtered and concentrated under reduced pressure. Purification by FC (from heptane to heptane/EtOAc=1/1) affords methyl 2-(4-bromo-2-(trifluoromethoxy)phenyl)acetate as a clear oil (1.896 g, 92%). LC-MS B: $t_R$=1.01 min; no ionization.

A.2.39. Methyl 2-(2-(difluoromethoxy)-4-(4,4,5,5-tetramethyl-1,3,2-dioxaborolan-2-yl)phenyl)acetate To a solution of methyl 2-(4-bromo-2-(difluoromethoxy)phenyl)acetate (800 mg, 2.71 mmol) in anh. DMF (20 mL) are added at RT 4,4,4',4',5,5,5',5'-octamethyl-2,2'-bi(1,3,2-dioxaborolane) (695 mg, 2.71 mmol), potassium acetate (1.064 g, 10.80 mmol) and Pd(dppf)Cl$_2$ (220 mg, 0.29 mmol). The RM is heated to 90° C., under nitrogen, overnight. The RM is then allowed to cool to RT and is filtered through a pad of celite, washing with EtOAc. The filtrate is washed with water and the aqueous layer is extracted twice with EtOAc. The combined organic layers are then washed with brine, dried over MgSO$_4$, filtered and concentrated under reduced pressure. Purification by FC (from heptane to heptane/EtOAc=1/1) affords methyl 2-(2-(difluoromethoxy)-4-(4,4,5,5-tetramethyl-1,3,2-dioxaborolan-2-yl)phenyl)acetate as a yellow oil (367 mg, 40%). LC-MS B: $t_R$=1.03 min; no ionization.

A.2.39.1. Methyl 2-(4-bromo-2-(difluoromethoxy)phenyl)acetate

To a solution of 2-(4-bromo-2-(difluoromethoxy)phenyl)acetic acid (3.560 g, 12.70 mmol) in anh. DMF (20 mL) at RT are added cesium carbonate (6.191 g, 19.00 mmol) and iodomethane (0.95 mL, 15.20 mmol) and the RM is stirred at RT, under nitrogen, for 1 h. Water and Et$_2$O are added and the layers are separated. The aqueous layer is extracted twice with Et$_2$O and the combined organic layers are washed with brine, dried over anh. MgSO$_4$, filtered and concentrated under reduced pressure. Purification by FC (from heptane to heptane/EtOAc=1/1) affords methyl 2-(4-bromo-2-(difluoromethoxy)phenyl)acetate as a colorless oil (2.390 g, 64%). LC-MS B: $t_R$=0.94 min; no ionization.

A.2.39.2. 2-(4-Bromo-2-(difluoromethoxy)phenyl)acetic acid

To a mixture of 2-(4-bromo-2-(difluoromethoxy)phenyl)acetonitrile (3.460 g, 13.20 mmol) in EtOH (100 mL) and water (100 mL) at RT is added potassium hydroxide (2.222 g, 39.60 mmol) and the RM is heated at reflux, under nitrogen, overnight. The RM is then allowed to cool to RT and ethanol is removed under reduced pressure. The resulting mixture is treated with 1 M aq. HCl and is extracted twice with DCM. The combined organic layers are washed with brine, dried over anh. MgSO$_4$, filtered and concentrated under reduced pressure affording crude 2-(4-bromo-2-(difluoromethoxy)phenyl)acetic acid as an off-white solid (3.560 g, 96%). LC-MS B: $t_R$=0.82 min; no ionization.

A.2.39.3. 2-(4-Bromo-2-(difluoromethoxy)phenyl)acetonitrile

A solution of 4-bromo-1-(chloromethyl)-2-(difluoromethoxy)benzene (3.890 g, 14.30 mmol) in MeCN (38 mL) and water (5 mL) is treated with sodium cyanide (913 mg, 18.60 mmol) and the RM is heated to 85° C., under nitrogen, for 3 h. The RM is then allowed to cool to RT and is diluted with water. Acetonitrile is removed under reduced pressure and the mixture is extracted twice with DCM. The combined organic layers are dried over anh. MgSO$_4$, filtered and concentrated under reduced pressure. Purification by FC (from heptane to EtOAc) affords 2-(4-bromo-2-(difluoromethoxy)phenyl)acetonitrile as a pale yellow solid (3.560 g, 95%). LC-MS B: $t_R$=0.92 min; no ionization.

A.2.39.4. 4-Bromo-1-(chloromethyl)-2-(difluoromethoxy)benzene

A cooled (0° C.) mixture of (4-bromo-2-(difluoromethoxy)phenyl)methanol (3.580 g, 14.10 mmol) and zinc chloride (48.2 mg, 0.354 mmol) in anh. DCM (28 mL) is treated dropwise with thionyl chloride (2.06 mL, 28.30 mmol) and the RM is stirred at 0° C. for 3.5 h. The RM is concentrated under reduced pressure affording crude 4-bromo-1-(chloromethyl)-2-(difluoromethoxy)benzene as a colorless oil (3.890 g, quantitative). LC-MS B: $t_R$=1.00 min; no ionization.

A.2.39.5. (4-Bromo-2-(difluoromethoxy)phenyl)

To a cooled (0° C.) solution of 4-bromo-2-(difluoromethoxy)benzaldehyde (3.820 g, 15.20 mmol) in anh. MeOH (75 mL) is added portionwise sodium borohydride (1.727 g, 45.70 mmol) and the mixture is further stirred at 0° C., under nitrogen, for 1 h. Methanol is then removed under reduced pressure. DCM and water are added and the layers are separated. The aqueous layer is extracted twice with DCM and the combined organic layers are dried over anh. MgSO$_4$, filtered and concentrated under reduced pressure. Purification by FC (from heptane to heptane/EtOAc=1/1) affords (4-bromo-2-(difluoromethoxy)phenyl)methanol as a colorless oil (3.890 g, quantitative). LC-MS B: $t_R$=0.81 min; no ionization.

A.2.39.6. 4-Bromo-2-(difluoromethoxy)benzaldehyde

To a cooled (0° C.) solution of 4-bromo-2-hydroxybenzaldehyde (5.000 g, 24.40 mmol) in MeCN (135 mL) and water (135 mL) is added potassium hydroxide (27.355 g, 488.00 mmol). The mixture is stirred at RT for 30 min, and is then cooled to −30° C. Diethyl (bromodifluoromethyl)phosphonate (13.283 g, 48.80 mmol) is added in one portion to the cooled mixture and stirring is then continued at RT for 2 h. Et$_2$O is added, the layers are separated and the aqueous layer is further extracted with Et$_2$O. The combined organic layers are successively washed with 1 M aq. NaOH, water and brine and are then dried over anh. MgSO$_4$, filtered and concentrated under reduced pressure. Purification by FC (from heptane to heptane/EtOAc=7/3) affords 4-bromo-2-(difluoromethoxy)benzaldehyde as a pale yellow solid (3.820 g, 62%). LC-MS B: t$_R$=0.92 min; no ionization.

A.2.40. Methyl 2-(2-propyl-4-(4,4,5,5-tetramethyl-1,3,2-dioxaborolan-2-yl)phenyl)acetate To a solution of methyl 2-(4-bromo-2-propylphenyl)acetate (2.380 g, 8.78 mmol) in anh. DMF (20 mL) are added at RT 4,4,4',4',5,5,5',5'-octamethyl-2,2'-bi(1,3,2-dioxaborolane) (2.251 g, 8.78 mmol), potassium acetate (3.446 g, 35.10 mmol) and Pd(dppf)Cl$_2$ (714 mg, 0.96 mmol). The RM is heated to 90° C., under nitrogen, for 16 h. The RM is then allowed to cool to RT and is filtered through a pad of celite, washing with EtOAc. The filtrate is washed with water and the aqueous layer is extracted twice with EtOAc. The combined organic layers are then washed with brine, dried over MgSO$_4$, filtered and concentrated under reduced pressure. Purification by FC (from heptane to heptane/EtOAc=1/1) affords methyl 2-(2-propyl-4-(4,4,5,5-tetramethyl-1,3,2-dioxaborolan-2-yl)phenyl)acetate as a colorless oil (2.230 g, 80%). LC-MS B: t$_R$=1.10 min; [M+H]$^+$=319.31.

A.2.40.1. Methyl 2-(4-bromo-2-propylphenyl)acetate

To a solution of 2-(4-bromo-2-propylphenyl)acetic acid (2.770 g, 10.80 mmol) in anh. DMF (20 mL) at RT are added cesium carbonate (5.265 g, 16.20 mmol) and iodomethane (1.02 mL, 16.20 mmol) and the RM is stirred at RT, under nitrogen, for 1 h. Water and Et$_2$O are added and the layers are separated. The aqueous layer is extracted twice with Et$_2$O and the combined organic layers are washed with brine, dried over anh. MgSO$_4$, filtered and concentrated under reduced pressure. Purification by FC (from heptane to heptane/EtOAc=1/1) affords methyl 2-(4-bromo-2-propylphenyl)acetate as a yellow oil (2.380 g, 81%). LC-MS B: t$_R$=1.04 min; no ionization.

A.2.40.2. 2-(4-Bromo-2-propylphenyl)acetic acid

A mixture of 2-(4-bromo-2-propylphenyl)acetonitrile (2.570 g, 10.80 mmol), water (10 mL), 95% sulfuric acid (11.5 mL) and acetic acid (8 mL) is heated to 110° C., under nitrogen, for 3 h. The RM is then allowed to cool to RT and is poured onto ice/water. The mixture is extracted twice with DCM and the combined organic layers are washed with brine, dried over anh. MgSO$_4$, filtered and concentrated under reduced pressure affording crude 2-(4-bromo-2-propylphenyl)acetic acid as a pale grey solid (3.390 g, quantitative). LC-MS B: t$_R$=0.91 min; no ionization.

A.2.40.3. 2-(4-Bromo-2-propylphenyl)acetonitrile

A solution of 4-bromo-1-(chloromethyl)-2-propylbenzene (2.980 g, 12.00 mmol) in MeCN (32 mL) and water (3.9 mL) is treated with sodium cyanide (767 mg, 15.60 mmol) and the RM is heated to 80° C., under nitrogen, overnight. The RM is then allowed to cool to RT and is diluted with water. Acetonitrile is removed under reduced pressure and the RM is extracted twice with DCM. The combined organic layers are dried over anh. MgSO$_4$, filtered and concentrated under reduced pressure. Purification by FC (from heptane to EtOAc) affords 2-(4-bromo-2-propylphenyl)acetonitrile as a pale yellow oil (2.570 g, 90%). LC-MS B: t$_R$=1.02 min; no ionization.

A.2.40.4. 4-Bromo-1-(chloromethyl)-2-propylbenzene

A cooled (0° C.) mixture of (4-bromo-2-propylphenyl)methanol (2.650 g, 11.60 mmol) and zinc chloride (39.4 mg, 0.289 mmol) in anh. DCM (23 mL) is treated dropwise with thionyl chloride (1.69 mL, 23.10 mmol) and the RM is stirred at 0° C. for 3 h, and then at RT overnight. The RM is concentrated under reduced pressure affording crude 4-bromo-1-(chloromethyl)-2-propylbenzene as a grey oil (2.98 g, quantitative). LC-MS B: t$_R$=1.10 min; no ionization.

A.2.40.5. (4-Bromo-2-propylphenyl)methanol

To a cooled (−78° C.) solution of methyl 4-bromo-2-propylbenzoate (3.300 g, 12.80 mmol) in anh. THE (60 mL) is added dropwise a solution of diisobutylaluminum hydride (1 M in toluene, 38.5 mL, 38.5 mmol). The mixture is further stirred at −78° C., under nitrogen, for 15 min and is then allowed to warm-up to 0° C. Stirring at 0° C. is continued for 45 min, and the cooled RM is treated successively with water (1.5 mL), 2.8 N aq. NaOH (1.5 mL) and water (4 mL). The mixture is then allowed to warm-up to RT and stirring was continued for 30 min. The resulting mixture was filtered over celite washing with THE and the filtrate was concentrated to dryness under reduced pressure. Purification by FC (from heptane to heptane/EtOAc=1/1) affords (4-bromo-2-propylphenyl)methanol as a colorless oil (2.650 g, 90%). LC-MS B: t$_R$=0.91 min; no ionization.

A.2.40.6. Methyl 4-bromo-2-propylbenzoate

To a solution of 4-bromo-2-propylbenzoic acid (3.590 g, 14.80 mmol) in anh. DMF (30 mL) at RT are added successively cesium carbonate (9.623 g, 29.50 mmol) and iodomethane (1.86 mL, 29.50 mmol) and the RM is stirred at RT for 16 h. Water and Et$_2$O are added and the layers are separated. The aqueous layer is extracted twice with Et$_2$O and the combined organic layers are washed with brine, dried over anh. MgSO$_4$, filtered and concentrated under reduced pressure. Purification by FC (from heptane to heptane/EtOAc=1/1) affords methyl 4-bromo-2-propylbenzoate as a colorless oil (3.300 g, 87%). LC-MS B: t$_R$=1.05 min; no ionization.

A.2.40.7. 4-Bromo-2-propylbenzoic acid

To a cooled (0° C.) solution of 4-bromo-2-fluorobenzoic acid (5.000 g, 22.40 mmol) in anh. THE (40 mL) is added dropwise a solution of propylmagnesium bromide (2.0 M in THF, 33.50 mL, 67.00 mmol) and the RM is further stirred at RT, under nitrogen, overnight. MeOH (10 mL) is then added dropwise to the cooled (0° C.) reaction mixture that is further stirred at 0° C. for 5 min. The resulting mixture is then concentrated to dryness under reduced pressure and the residue is partitioned between EtOAc and 2 M aq. HCl. The layers are separated, and the aq. layer is extracted twice with EtOAc. The combined organic layers are then washed with brine, dried over anh. MgSO$_4$, filtered and concentrated under reduced pressure. Purification by FC (from heptane to heptane/EtOAc=3/2) affords 4-bromo-2-propylbenzoic acid as a colorless solid (3.590 g, 66%). LC-MS B: $t_R$=0.93 min; no ionization.

A.2.41. Methyl 2-(2-ethyl-4-(4,4,5,5-tetramethyl-1,3,2-dioxaborolan-2-yl)phenyl)acetate To a solution of methyl 2-(4-bromo-2-ethylphenyl)acetate (900 mg, 3.24 mmol) in anh. DMF (15 mL) are added at RT 4,4,4',4,5,5,5',5'-octamethyl-2,2'-bi(1,3,2-dioxaborolane) (832 mg, 3.24 mmol), potassium acetate (1.274 g, 13.00 mmol) and Pd(dppf)Cl$_2$ (264 mg, 0.35 mmol). The RM is heated to 90° C., under nitrogen, overnight. The RM is then allowed to cool to RT and is filtered through a pad of celite, washing with EtOAc. The filtrate is washed with water and the aqueous layer is extracted twice with EtOAc. The combined organic layers are then washed with brine, dried over MgSO$_4$, filtered and concentrated under reduced pressure. Purification by FC (from heptane to heptane/EtOAc=4/1) affords methyl 2-(2-ethyl-4-(4,4,5,5-tetramethyl-1,3,2-dioxaborolan-2-yl)phenyl)acetate as a light yellow oil (708 mg, 72%). LC-MS B: $t_R$=1.05 min; [M+H]$^+$=305.22.

A.2.41.1. Methyl 2-(4-bromo-2-ethylphenyl)acetate

To a solution of 2-(4-bromo-2-ethylphenyl)acetic acid (2.118 g, 8.05 mmol) in anh. DMF (20 mL) at RT are added cesium carbonate (5.246 g, 16.10 mmol) and iodomethane (1.01 mL, 16.10 mmol) and the RM is stirred at RT, under nitrogen, for 1 h. Water and Et$_2$O are added and the layers are separated. The aqueous layer is extracted twice with Et$_2$O and the combined organic layers are washed with brine, dried over anh. MgSO$_4$, filtered and concentrated under reduced pressure. Purification by FC (from heptane to heptane/EtOAc=7/3) affords methyl 2-(4-bromo-2-ethylphenyl)acetate as a light yellow oil (2.043 g, 99%). LC-MS B: $t_R$=0.99 min; no ionization.

A.2.41.2. 2-(4-Bromo-2-ethylphenyl)acetic acid

A mixture of 2-(4-bromo-2-ethylphenyl)acetonitrile (1.859 g, 7.99 mmol), water (7.5 mL), 95% sulfuric acid (8.3 mL) and acetic acid (5.8 mL) is heated to 110° C., under nitrogen, for 4 h. The RM is then allowed to cool to RT and is poured onto ice/water. The mixture is extracted twice with DCM and the combined organic layers are washed with brine, dried over anh. MgSO$_4$, filtered and concentrated under reduced pressure affording crude 2-(4-bromo-2-ethylphenyl)acetic acid as an amber solid (2.118 g, quantitative). LC-MS B: $t_R$=0.85 min; no ionization.

A.2.41.3. 2-(4-Bromo-2-ethylphenyl)acetonitrile

A solution of 4-bromo-1-(chloromethyl)-2-ethylbenzene (2.050 g, 8.34 mmol) in MeCN (24 mL) and water (3 mL) is treated with sodium cyanide (553 mg, 10.80 mmol) and the RM is heated to 80° C., under nitrogen, overnight. The RM is then allowed to cool to RT and is diluted with water. Acetonitrile is removed under reduced pressure and the RM is extracted twice with DCM. The combined organic layers are dried over anh. MgSO$_4$, filtered and concentrated under reduced pressure. Purification by FC (from heptane to heptane/EtOAc=7/3) affords 2-(4-bromo-2-ethylphenyl)acetonitrile as a colorless solid (1.859 g, 99%). LC-MS B: $t_R$=0.95 min: no ionization.

A.2.41.4. 4-Bromo-1-(chloromethyl)-2-ethylbenzene

A cooled (0° C.) mixture of (4-bromo-2-ethylphenyl)methanol (1.854 g, 8.30 mmol) and zinc chloride (28.3 mg, 0.208 mmol) in anh. DCM (20 mL) is treated dropwise with thionyl chloride (1.21 mL, 16.60 mmol) and the RM is stirred at 0° C. for 2 h. The RM is concentrated under reduced pressure affording crude 4-bromo-1-(chloromethyl)-2-ethylbenzene as a light purple oil (2.050 g, quantitative). LC-MS B: $t_R$=1.04 min; no ionization.

A.2.41.5. (4-Bromo-2-ethylphenyl)methanol

To a cooled (−78° C.) solution of methyl 4-bromo-2-ethylbenzoate (2.219 g, 9.01 mmol) in anh. THF (60 mL) is added dropwise a solution of diisobutylaluminum hydride (1 M in toluene, 27.0 mL, 27.0 mmol). The mixture is further stirred at −78° C., under nitrogen, for 15 min and is then allowed to warm-up to 0° C. Stirring at 0° C. is continued for 45 min, and the cooled RM is treated successively with water (1 mL), 2.8 N aq. NaOH (1 mL) and water (3 mL). The mixture is then allowed to warm-up to RT and is further stirred for 30 min. The resulting mixture is filtered over celite, washing with THF and the filtrate is concentrated to dryness under reduced pressure. EtOAc and water are added and the layers are separated. The aqueous layer is extracted twice with EtOAc and the combined organic layers are dried over anh. MgSO$_4$, filtered and concentrated under reduced pressure. Purification by FC (from heptane to heptane/EtOAc=1/1) affords (4-bromo-2-ethylphenyl)methanol (1.854 g, 96%). LC-MS B: $t_R$=0.84 min; no ionization.

A.2.41.6. Methyl 4-bromo-2-ethylbenzoate

To a solution of 4-bromo-2-ethylbenzoic acid (3.003 g, 12.80 mmol) in anh. DMF (30 mL) at RT are added cesium carbonate (8.355 g, 25.60 mmol) and iodomethane (1.61 mL, 25.60 mmol) and the RM is stirred at RT for 1 h. Water and Et$_2$O are added and the layers are separated. The aqueous layer is extracted twice with Et$_2$O and the combined organic layers are washed with brine, dried over anh. MgSO$_4$, filtered and concentrated under reduced pressure. Purification by FC (from heptane to heptane/EtOAc=7/3) affords methyl 4-bromo-2-ethylbenzoate as a clear oil (2.735 g, 88%). LC-MS B: $t_R$=1.02 min; no ionization.

A.2.41.7. 4-Bromo-2-ethylbenzoic acid

To a cooled (0° C.) solution of 4-bromo-2-fluorobenzoic acid (5.000 g, 22.40 mmol) in anh. THF (40 mL) is added dropwise a solution of ethylmagnesium bromide (1.0 M in THF, 67.1 mL, 67.1 mmol) and the RM is further stirred at RT, under nitrogen, for 3 h. MeOH (15 mL) is then added dropwise to the cooled (0° C.) reaction mixture that is further stirred at 0° C. for 5 min. The resulting mixture is then concentrated to dryness under reduced pressure and the residue is partitioned between EtOAc and 2 M aq. HCl. The layers are separated, and the aq. layer is extracted twice with EtOAc. The combined organic layers are then washed with brine, dried over anh. MgSO$_4$, filtered and concentrated under reduced pressure. Purification by FC (from heptane to heptane/EtOAc=7/3) affords 4-bromo-2-ethylbenzoic acid as a colorless solid (3.003 g, 59%). LC-MS B: $t_R$=0.87 min: no ionization.

A.2.42. 2-(2-Propoxy-4-(4,4,5,5-tetramethyl-1,3,2-dioxaborolan-2-yl)phenyl)acetic acid To a solution of propyl 2-(2-propoxy-4-(4,4,5,5-tetramethyl-1,3,2-dioxaborolan-2-yl)phenyl)acetate (308 mg, 0.85 mmol) in EtOH (9 mL) is added NaOH (10% aq. Solution, 3.4 mL) and the mixture is stirred at RT for 2 h. EtOH is removed in vacuo. pH of the resulting basic aqueous layer is adjusted to pH=3-4 using HCl 1N and extracted twice with EtOAc. The combined organic layers are washed with water, brine, dried over MgSO$_4$, filtered and solvent is removed in vacuo, yielding the title compound as a white powder (0.238 g, 87%). LC-MS A: t$_R$=0.88 min; [M+H]$^+$=321.08.

A.2.42.1. Propyl 2-(2-propoxy-4-(4,4,5,5-tetramethyl-1,3,2-dioxaborolan-2-yl)phenyl)acetate The title compound is prepared according to the procedure described for A.2.12., starting with propyl 2-(4-bromo-2-propoxyphenyl)acetate. LC-MS A: t$_R$=1.04 min; [M+H]$^+$=363.12.

A.2.42.2. Propyl 2-(4-bromo-2-propoxyphenyl)acetate

To a solution of 4-bromo-2-hydroxyphenylacetic acid (1.50 g, 6.37 mmol,) in DMF (50 mL) is added 1-iodopropane (1.38 mL, 14 mmol, 2.2 eq) and Cs$_2$CO$_3$ (6.23 g, 19.1 mmol). The RM is stirred at 100° C. over night, then cooled to RT. Water is added, and the DMF is removed under reduced pressure. The residue is partitioned between EtOAc and water. The aqueous layer is re-extracted twice with EtOAc. The combined organic extracts are washed with brine, dried (MgSO$_4$) and concentrated in vacuo. The residue is purified by FC (Hept:EtOAc 100:0 to 90:10), affording the title compound as a colourless oil (0.775 g, 39%). LC-MS A: t$_R$=1.00 min; [M+H]$^+$=315.07.

A.2.43. Methyl 3-ethyl-5-(4,4,5,5-tetramethyl-1,3,2-dioxaborolan-2-yl)thiophene-2-carboxylate To a solution of lithium diisopropylamide (2.0 M in THF/heptane/ethylbenzene, 10 mL, 9.6 mmol) in THF (20 mL) at −78° C. is added dropwise a solution of methyl 3-ethylthiophene-2-carboxylate (1123 mg, 6.4 mmol) in THF (15 mL). The RM is stirred for 10 min at −78° C. then a solution of 2-isopropoxy-4,4,5,5-tetramethyl-1,3,2-dioxaborolane (2 mL, 9.6 mmol) in THF (25 mL) is added dropwise, the RM is stirred for 20 min at −78° C. then it is allowed to warm to RT and stirred for 1.5 h. HCl 2N (25 mL, 51.2 mmol) is added to the RM at 0° C., and it is stirred for 5 min. The mixture is extracted with EtOAc (3 times). The combined organic layers are washed with brine, dried over MgSO$_4$ and concentrated to dryness, to afford the title compound as an orange oil, crystallizing upon standing (2.00 g, quant.).; LC-MS B: t$_R$=1.10 min; [M+H]$^+$=297.27.

A.2.44. Rac-methyl 2-(2-propyl-4-(4,4,5,5-tetramethyl-1,3,2-dioxaborolan-2-yl)phenyl)propanoate The title compound is prepared according to the procedure described for A.2.12., starting with rac-methyl 2-(4-bromo-2-propylphenyl)propanoate. LC-MS B: t$_R$=1.14 min; [M+H]$^+$=333.25.

A.2.44.1. Rac-methyl 2-(4-bromo-2-propylphenyl)propanoate

To a solution of 2-(4-bromo-2-propylphenyl)acetic acid (A.2.40.2., 2150 mg, 8.36 mmol) in anhydrous DMF (10 mL) is added Cs$_2$CO (5449 mg, 16.7 mmol) followed by iodomethane (1.05 mL, 16.7 mmol). The RM is stirred at RT overnight. Water is added and the mixture is extracted with Et$_2$O (3×). Organic layers are mixed and washed with water (2×), then dried over MgSO$_4$, filtered and concentrated to dryness. Purification by FC (Hept/EtOAc from 1:0 to 1:1) afforded the title compound as a pale yellow oil (1.60 g, 76%). LC-MS B: t$_R$=1.04 min; no ionization.

A.2.45. 3-(2-Methoxy-4-(4,4,5,5-tetramethyl-1,3,2-dioxaborolan-2-yl)phenoxy)propanoic acid The title compound is prepared according to the procedure described for A.2.12., starting with 3-(4-bromo-2-methoxyphenoxy)propanoic acid. LC-MS B: t$_R$=0.85 min; [M+H]$^+$=323.16.

A.2.45.1. 3-(4-Bromo-2-methoxyphenoxy)propanoic acid

To a suspension of NaH (60% in oil, 1431 mg, 35.8 mmol) in DMF (10 mL) is added dropwise 4-bromo-2-methoxyphenol (2850 mg, 13.8 mmol) in DMF (10 mL). After 30 min, 3-bromopropionic acid (2525 mg, 16.5 mmol) in DMF (8 mL) is added dropwise, and the RM is stirred at RT overnight. 2M aq HCl is added carefully and the resulting mixture is extracted with EtOAc (3×). Organic layers are mixed and washed with water (2×), then dried over phase separator and concentrated to dryness. Purification by FC (Hept/EtOAc from 1:0 to 1:1) afforded the title compound as a white solid (1.29 g, 34%). LC-MS B: t$_R$=0.78 min; no ionization.

A.2.46. 1-(2-Propyl-4-(4,4,5,5-tetramethyl-1,3,2-dioxaborolan-2-yl)phenyl)cyclopropane-1-carboxylic acid The title compound is prepared according to the procedure described for A.2.12., starting with 1-(4-bromo-2-propylphenyl)cyclopropane-1-carboxylic acid. LC-MS B: t$_R$=1.02 min; [M+MeCN]$^+$=372.47.

A.2.46.1. 1-(4-Bromo-2-propylphenyl)cyclopropane-1-carboxylic acid

In a flask containing 1-(4-bromo-2-propylphenyl)cyclopropane-1-carbonitrile (465 mg, 1.69 mmol) and equipped with a condenser, are added successively H$_2$O (1.6 mL), AcOH (1.2 mL) and H$_2$SO$_4$ (1.8 mL). The RM is stirred at 110° C. for 3 d, then cooled to RT. The RM is poured into ice water and the mixture is extracted with DCM (3×). The combined organic layers are washed with NaOH 1N. The basic aqueous layer is extracted once more with EtOAc. The aqueous layer is acidified till pH2-3 by addition of 2N HCl. This acidic aqueous layer is then extracted twice with EtOAc. These organic layers (acidic extraction) are combined, washed with water, brine, dried over MgSO$_4$, filtered and concentrated under reduced pressure, affording the title compound as a white solid (283 mg, 65%). LC-MS B: t$_R$=0.96 min; no ionization. $^1$H NMR (400 MHz, d$_6$-DMSO) δ: 12.13-12.49 (m, 1H), 7.36-7.41 (m, 1H), 7.23-7.33 (m, 1H), 7.13-7.22 (m, 1H), 2.59-2.67 (m, 2H), 1.61 (m, 2H), 1.43-1.56 (m, 2H), 1.06-1.15 (m, 2H), 0.81-0.98 (m, 3H).

A.2.46.2. 1-(4-Bromo-2-propylphenyl)cyclopropane-1-carbonitrile

To a solution of 2-(4-bromo-2-propylphenyl)acetonitrile (A.3.42.3., 1180 mg, 4.81 mmol) in toluene (25 mL) are added at RT under argon 1,2-dibromoethane (1.26 mL, 14.4 mmol), benzyltriethylammonium chloride (89.4 mg, 0.385 mmol) and NaOH (1346 mg, 33.6 mmol). The RM is stirred over 2 nights at 110° C., it is then cooled to RT and 1,2-dibromoethane (1.26 mL, 14.4 mmol), benzyltriethylammonium chloride (89.4 mg, 0.385 mmol) and NaOH (1346 mg, 33.6 mmol) are added and the RM is stirred overnight at 110° C. Once at RT, the RM is quenched with water and concentrated in vacuo. The residue is partitioned between EtOAc and water. The aqueous is extracted once more with EtOAc. The combined organic layers are washed with water, brine, dried over MgSO$_4$, filtered and concentrated in vacuo. The residue is purified by FC (Hept:EtOAc, 100:0 to 95:5), affording the title compound as a yellow oil (468 mg 37%). LC-MS B: $t_R$=1.06 min; [M+H]$^+$=263.92.

A.2.47. Methyl 3-hydroxy-5-(4,4,5,5-tetramethyl-1,3,2-dioxaborolan-2-yl)thiophene-2-carboxylate To a solution of methyl 3-hydroxythiophene-2-carboxylate (815 mg, 5.15 mmol) in THF (36 mL) cooled at −78° C., lithium diisopropylamide (2.0 M in TH/hexanes, 7.75 mL, 15.5 mmol) is added dropwise. The RM is stirred 10 min at −78° C. then a solution of 2-isopropoxy-4,4,5,5-tetramethyl-1,3,2-dioxaborolane (2.36 mL, 11.3 mmol) in THF (12 mL) is added dropwise and the RM is kept stirring 15 min at −78° C. then is allowed to warm to RT over 2 h. HCl 1M (42 mL, 41.2 mmol) is added to the RM and it is extracted with EtOAc (3*40 mL). The combined organic layers are washed with brine, dried over MgSO$_4$ and the solvent is removed in vacuo yielding the title compound as a brown oil which crytallizes upon standing (1.7 g, quant.). LC-MS B: $t_R$=0.86 min; no ionization.

A.2.48. 2-(2-Ethoxy-4-(4,4,5,5-tetramethyl-1,3,2-dioxaborolan-2-yl)phenoxy)acetic acid A solution of ethyl 2-(2-ethoxy-4-(4,4,5,5-tetramethyl-1,3,2-dioxaborolan-2-yl)phenoxy)acetate (1.285 g, 3.82 mmol) in EtOH (15 mL) is treated with NaOH 10% (7.64 mL, 19.1 mmol) and the RM is stirred at 50° C. for 30 min. The RM is cooled to RT and diluted with EtOAc. HCl 2N (15 mL) is added to reach acidic pH (<1). The aqueous layer is extracted twice with EtOAc. The resulting organic phase is dried over MgSO$_4$ and concentrated, affording the title compound as an orange paste (1.11 g, 90%). LC-MS A: $t_R$=0.80 min; [M+H]$^+$=323.12.

A.2.48.1. Ethyl 2-(2-ethoxy-4-(4,4,5,5-tetramethyl-1,3,2-dioxaborolan-2-yl)phenoxy)acetate A solution of 2-ethoxy-4-(4,4,5,5-tetramethyl-1,3,2-dioxaborolan-2-yl)phenol (3.47 g, 12.5 mmol) in anhydrous DMF (50 mL) is treated successively with Cs$_2$CO$_3$ (6.10 g, 18.7 mmol) and ethyl bromoacetate (1.48 mL, 13.1 mmol). The RM is stirred at RT for 1 h. Water is added, and the mixture is extracted with Et2O (×3). The combined organic layers are then washed successively with water (×2) and brine, dried over MgSO$_4$, filtered, and concentrated to dryness under reduced pressure to afford the pure product as a colorless oil (1.46 g, 77%). LC-MS A: $t_R$=0.94 min; [M+H]$^+$=351.18.

A.2.49. 5-(4-(4,4,5,5-Tetramethyl-1,3,2-dioxaborolan-2-yl)phenyl)-[1,2,4]oxadiazol-3-ol (The title compound is prepared according to the procedure described for A.2.12., starting with 5-(4-bromophenyl)-2,3-dihydro-[1,2,4]oxadiazol-3-one. LC-MS A: $t_R$=0.82 min; [M+MeCN]$^+$=330.07.

A.2.50. Methyl 4-(4,4,5,5-tetramethyl-1,3,2-dioxaborolan-2-yl)-1H-indole-7-carboxylate The title compound is prepared according to the procedure described for A.2.12., starting with methyl 4-bromo-1H-indole-7-carboxylate. LC-MS A: $t_R$=0.95 min; [M+H]$^+$=302.23.

A.2.51. 3-(3-Ethoxy-5-(4,4,5,5-tetramethyl-1,3,2-dioxaborolan-2-yl)thiophen-2-yl)propanoic acid To a solution of methyl (E)-3-(3-ethoxy-5-(4,4,5,5-tetramethyl-1,3,2-dioxaborolan-2-yl)thiophen-2-yl)acrylate (250 mg, 0.786 mmol) in MeOH (15 mL) is added Pd/C 5% wet (50 mg). Then the vessel is inertized with N$_2$ and flushed with H$_2$. The mixture is placed in a autoclave and it is stirred overnight at RT under 4 bar of H$_2$, then for 1d at 50° C. under 4 bar of H$_2$. After filtration on whatman filter, NaOH 10% (1.18 mL, 11.8 mmol) is added and the RM is stirred for 1 h at RT. It is then treated with HCl 2N until pH<1 and extracted twice with EtOAc. The organic layer is dried over MgSO$_4$ and concentrated, to afford the title compound as a dark yellow oil (287 mg, 74%). LC-MS A: $t_R$=0.86 min; [M+H]$^+$=327.09.

A.2.51.1. Methyl (E)-3-(3-ethoxy-5-(4,4,5,5-tetramethyl-1,3,2-dioxaborolan-2-yl)thiophen-2-yl)acrylate The title compound is prepared according to the procedure described for A.2.47., starting with methyl (E)-3-(3-ethoxythiophen-2-yl)acrylate. LC-MS A: $t_R$=1.02 min; [M+H]$^+$=339.14.

A.2.51.2. Methyl (E)-3-(3-ethoxythiophen-2-yl)acrylate

A suspension of 3-ethoxythiophene-2-carbaldehyde (2.90 g, 18.6 mmol), methyl bromoacetate (3.07 mL, 33.4 mmol), and triphenylphosphine (7.305 g, 27.8 mmol) in aq saturated NaHCO$_3$ (100 mL) is stirred at RT for 5 h. THF (30 mL) is added and the RM is stirred overnight at RT. It is then extracted twice with DCM. The combined organic layers are dried over MgSO$_4$, filtered, and concentrated under vacuum. The crude is purified by FC (Hept/EtOAc 9:1) to afford the title compound as a dark orange oil (2.9 g, 100%). LC-MS A: $t_R$=0.69 min; [M+MeCN]$^+$=198.26.

A.2.52. 2-Ethoxy-6-propyl-4-(4,4,5,5-tetramethyl-1,3,2-dioxaborolan-2-yl)benzoic acid The title compound is prepared according to the procedure described for A.2.12., starting with 4-bromo-2-ethoxy-6-propylbenzoic acid. LC-MS A: $t_R$=0.90 min; [M+H]$^+$=335.11.

A.2.52.1. 4-Bromo-2-ethoxy-6-propylbenzoic acid

To 4-bromo-2-fluoro-6-propylbenzoic acid (3430 mg, 13.9 mmol) in DMF (20 mL) is added sodium hydride (60% in oil, 1222 mg, 30.5 mmol) portionwise. When the vigorous gas evolution slowed, dry ethanol (0.891 mL, 15.3 mmol) in 5 mL of DMF is added and the RM is heated at 100° C. for 1 h. Once cooled, the mixture is poured into water, pH adjusted to 3 and then extracted 3 times with EtOAc. The combined org. phases are washed with water, brine, dried over MgSO$_4$, filtered and concentrated. The residue is purified by FC (heptane/ethyl acetate from 100:0 to 80:20),

A.2.53. 5-(2-Methoxy-4-(4,4,5,5-tetramethyl-1,3,2-dioxaborolan-2-yl)phenyl) isoxazol-3-ol Butyllithium (1.6M in hexane, 1.1 mL, 1.76 mmol) is added dropwise, at −78° C. under nitrogen, to a stirred solution of 5-(4-bromo-2-methoxyphenyl) isoxazol-3-ol (158 mg, 0.585 mmol) in dry THE (4 mL). The RM is stirred at −78° C. for 25 min, then isopropoxyboronic acid, pinacol ester (0.418 mL, 2.05 mmol) is added dropwise and the RM is stirred at −78° C. for 45 min then at RT for 40 min. The RM is quenched with sat. aq. NH$_4$Cl and extracted with EtOAc. The organic layer is washed twice with brine, dried over MgSO$_4$, filtered and concentrated. The residue is purified by FC (Hept:EtOAc 9:1 to 8:2) to afford the expected product as a white solid (42 mg, 23%). LC-MS A: $t_R$=0.86 min, [M+H]$^+$=318.14.

A.2.53.1. 5-(4-Bromo-2-methoxyphenyl) isoxazol-3-ol

HCl conc. (6.8 mL) is added dropwise at RT to a stirred suspension of 3-(4-bromo-2-methoxyphenyl)-3-oxo-N-((tetrahydro-2H-pyran-2-yl)oxy)propanamide (284 mg, 0.763 mmol) in MeOH (1.7 mL). The RM is stirred at RT for 30 min. Water (4 mL) is added and the precipitate is filtered off, washing with 1.2 mL water to afford the expected product as a white solid (169 mg, 82%) LC-MS A: $t_R$=0.79 min, [M+H]$^+$=271.99.

A.2.53.2. 3-(4-Bromo-2-methoxyphenyl)-3-oxo-N-((tetrahydro-2H-pyran-2-yl)oxy)propanamide To a solution of ethyl 3-(4-bromo-2-methoxyphenyl)-3-oxopropanoate (971 mg, 1.33 mmol) in NMP (15.7 mL) are sequentially added 0-(tetrahydro-2H-pyran-2-yl)hydroxylamine (512 mg, 4.19 mmol) and DMAP (433 mg, 3.55 mmol) at RT. The RM is heated to 115° C. and stirred overnight, then cooled to RT. The mixture is partitioned between 40 mL HCl 0.5M (pH 2) and 40 mL EtOAc. The organic layer is washed three times with 40 mL NaCl sat. The aqueous layer is reextracted with 40 mL EtOAc. The organic layers are combined, dried over MgSO$_4$, filtered and concentrated. The residue is purified by FC (Hept:EtOAc), affording the title compound as a white solid (301 mg, 25%). LC-MS A: $t_R$=0.76 min, [M+H]$^+$=373.98.

A.2.53.3. Ethyl 3-(4-bromo-2-methoxyphenyl)-3-oxopropanoate 1-(4-bromo-2-methoxyphenyl)ethanone (1.00 g, 4.37 mmol) is dissolved in diethyl carbonate (5.6 mL, 46.2 mmol). NaH (66% suspension in oil, 384 mg, 9.6 mmol) is added carefully. The RM is stirred overnight at RT. Water is added carefully and the mixture is extracted two times with EtOAc. The organic layers are washed with water, brine, dried over MgSO$_4$, filtered and concentrated. The residue is purified by FC (Hept-EtOAc, affording the title compound as a light yellow oil (933 mg, 71%). LC-MS A: $t_R$=0.87 min, [M+H]$^+$=303.01.

A.2.54. Ethyl 2-(2-ethoxy-4-(4,4,5,5-tetramethyl-1,3,2-dioxaborolan-2-yl)phenyl)-2-oxoacetate The title compound is prepared according to the procedure described for A.2.12., starting with ethyl 2-(4-bromo-2-ethoxyphenyl)-2-oxoacetate. LC-MS A: $t_R$=0.98 min: [M+H]$^+$=349.19.

A.2.54.1. Ethyl 2-(4-bromo-2-ethoxyphenyl)-2-oxoacetate

To a solution of 2-(4-bromo-2-hydroxyphenyl)-2-oxoacetic acid (1.00 g, 3.88 mmol) and K$_2$CO (1.605 g,) in DMF (10 mL) is added iodethane (0.799 mL, 9.69 mmol) and the RM is stirred at 50° C. for 2 d. K$_2$CO$_3$ (1.605 g, 11.6 mmol) and iodethane (0.799 mL, 9.69 mmol) are added and the RM is stirred at 60° C. for 20 h. The RM is filtered, rinsed with DCM and concentrated under reduced. The residue is purified by FC (Hept/EtOAc 1:0 to 4:1) to afford the title compound as a beige solid (0.921 g, 79%). LC-MS A: $t_R$=0.92 min; [M+H]$^+$=303.03.

A.2.55. 1-Methyl-7-(4,4,5,5-tetramethyl-1,3,2-dioxaborolan-2-yl)-3,4-dihydroquinazolin-2(1H)-one The title compound is prepared according to the procedure described for A.2.12., starting with 7-bromo-1-methyl-3,4-dihydroquinazolin-2(1H)-one. LC-MS A: $t_R$=0.80 min; [M+H]$^+$=289.18.

A.2.56. Ethyl 6-(4,4,5,5-tetramethyl-1,3,2-dioxaborolan-2-yl)benzofuran-3-carboxylate To a solution of ethyl 6-bromobenzofuran-3-carboxylate (1.850 g, 6.87 mmol) in anh. DMF (20 mL) are added at RT 4,4,4',4',5,5,5',5'-octamethyl-2,2'-bi(1,3,2-dioxaborolane) (1.763 g, 6.87 mmol), potassium acetate (2.699 g, 27.50 mmol) and Pd(dppf)Cl$_2$ (559 mg, 0.75 mmol). The RM is heated to 95° C., under nitrogen, overnight. The RM is then allowed to cool to RT and is filtered through a pad of celite, washing with Et$_2$O. The filtrate is washed with water and the aqueous layer is extracted twice with Et$_2$O. The combined organic layers are then washed with brine, dried over MgSO$_4$, filtered and concentrated under reduced pressure. Purification by FC (from heptane to heptane/EtOAc=7/3) affords ethyl 6-(4,4,5,5-tetramethyl-1,3,2-dioxaborolan-2-yl)benzofuran-3-carboxylate as a light yellow solid (1.528 g, 70%). LC-MS B: $t_R$=1.11 min; [M+H]$^+$=317.23.

A.2.57. 3-Ethoxy-4-(4-(4,4,5,5-tetramethyl-1,3,2-dioxaborolan-2-yl)phenyl)cyclobut-3-ene-1,2-dione 3-Ethoxy-4-(tributylstannyl)cyclobut-3-ene-1,2-dione (335 mg, 0.807 mmol) and 4-iodophenylboronic acid, pinacol ester (298 mg, 0.904 mmol) are dissolved in DMF (4 mL) with N$_2$ bubbling for 5 min. Trans-benzyl(chloro)bis(triphenylphosphine)palladium(II) (36.7 mg, 0.0484 mmol) and CuI (15.4 mg, 0.0807 mmol) are added and the RM is stirred at RT for 3 h., then filtered over a microglass filter, concentrated under vacuum and purified by FC (Hept.: EtOAc 100:0 to 80:20) to obtain the title compound as a yellow solid (127 mg, 48%). LC-MS A: $t_R$=0.97 min; [M+MeCN]$^+$=370.07.

A.2.58. 5-(2-ethoxy-4-(4,4,5,5-tetramethyl-1,3,2-dioxaborolan-2-yl)phenyl) isoxazol-3-ol Butyllithium solution 2.5M (2 mL, 5.03 mmol) is added dropwise, at −78° C. under nitrogen, to a stirred solution of 5-(4-bromo-2-ethoxyphenyl) isoxazol-3-ol (286 mg, 1.01 mmol) and 2-isopropoxy-4,4,5,5-tetramethyl-1,3,2-dioxaborolane (0.733 mL, 3.52 mmol) in dry THF (15 mL). The RM is stirred at −78° C. for 15 min then water is added at −78° C. and mixture is left stirring at RT for 40 min. A saturated solution of $NH_4Cl$ is added and the aqueous phase is extracted with EtOAc. The organic layer is washed twice with brine, then it is dried over $MgSO_4$, filtered and concentrated. The crude residue is purified by FC (Hept to Hept/EtOAc 1:1), to afford the title compound as a white solid (390 mg, quant.). LC-MS B: $t_R$=0.98 min; $[M+H]^+$=332.34 & $[M+H+MeCN]^+$=373.55

A.2.58.1. 5-(4-bromo-2-ethoxyphenyl) isoxazol-3-ol

To a solution of ethyl 3-(4-bromo-2-ethoxyphenyl)propiolate (1017 mg, 3.42 mmol) in EtOH (30 mL), Hydroxylamine hydrochloride (721 mg, 10.3 mmol) is added followed by dropwise addition of NaOH 10% (6.85 mL, 18.8 mmol); the RM is stirred overnight at RT. The solvent is distilled off under reduced pressure, the residue obtained is suspended in water, and the suspension is adjusted to pH 2-3 with a 2N aqueous HCl solution. The resultant solid is filtered off to afford the title compound as a white solid (380 mg, 39%). LC-MS B: $t_R$=0.91 min; $[M+H]^+$=284.17/286.25.

A.2.58.2. Ethyl 3-(4-bromo-2-ethoxyphenyl)propiolate

A $CO_{2\,(gas)}$ inlet is set up in the reaction apparatus and $CO_2$ is bubbled continuously into a stirred solution of ((4-bromo-2-ethoxyphenyl)ethynyl)trimethylsilane (1950 mg, 6.56 mmol) in DMSO (20 mL). Cesium fluoride (1220 mg, 7.87 mmol) is added and the RM is stirred at RT for 2 h. $CO_2$ bubbling is stopped and iodoethane (0.639 mL, 7.87 mmol) is added dropwise. The RM is further stirred at RT for 3 h and then poured into water. The aqueous phase is extracted twice with EtOAc and the combined organic layers are washed back with water and finally brine. The organic phase is dried over $MgSO_4$ and concentrated to dryness. Purification by FC (Hept:EtOAc 100:0 to 85:15) yields the tile compound as an orange oil (1.017 g, 52%). LC-MS B: $t_R$=1.08 min; $[M+H]^+$=297.20/299.23.

A.2.58.3. ((4-Bromo-2-ethoxyphenyl)ethynyl)trimethylsilane

To a solution of 4-bromo-2-ethoxy-1-iodobenzene (2120 mg, 6.48 mmol) in THF (20 mL) are added TEA (2.71 mL, 19.5 mmol), ethynyltrimethylsilane (1.12 mL, 7.78 mmol) and copper iodide (61.7 mg, 0.324 mmol). The RM is degassed and put under argon 3 times. Then trans-dichlorobis(triphenylphosphine)palladium(II) (91 mg, 0.13 mmol) is added and the RM is degassed a last time, put under argon and stirred at 70° C. for 16 h. The mixture is cooled to RT and partitioned between EtOAc and water. The organic layer is washed with brine, dried over $Na_2SO_4$, filtered and the solvent is evaporated. The resulting residue is purified by FC (Hept:EtOAc 100:0 to 90:10) to yield the title compound as an orange oil (1.95 g, 100%). LC-MS B: $t_R$=1.18 min; no ionization; $^1$H NMR (400 MHz, d6-DMSO) δ: 7.31 (d, J=8.2 Hz, 1H), 7.24 (d, J=1.6 Hz, 1H), 7.10 (dd, $J_1$=1.7 Hz, $J_2$=8.1 Hz, 1H), 4.09 (q, J=7.0 Hz, 2H), 1.33 (t, J=6.8 Hz, 3H), 0.22 (s, 9H).

A.2.59. 3-(4-(4,4,5,5-Tetramethyl-1,3,2-dioxaborolan-2-yl)phenyl)-[1,2,4]oxadiazol-5(4H)-one The title compound is prepared according to the procedure described for A.2.12., starting with 3-(4-bromophenyl)-[1,2,4]oxadiazol-5(4H)-one. LC-MS B: $t_R$=0.90 min: $[M+MeCN]^+$=330.12.

A.2.60. Methyl 2-(2-chloro-6-ethyl-4-(4,4,5,5-tetramethyl-1,3,2-dioxaborolan-2-yl)phenyl)acetate To a solution of methyl 2-(4-bromo-2-chloro-6-ethylphenyl)acetate (254 mg, 0.87 mmol) in anh. DMF (10 mL) are added at RT 4,4,4',4,5,5,5',5'-octamethyl-2,2'-bi(1,3,2-dioxaborolane) (223 mg, 0.87 mmol), potassium acetate (342 mg, 3.48 mmol) and $Pd(dppf)Cl_2$ (70 mg, 0.095 mmol). The RM is heated to 90° C., under nitrogen, for 5.5 h. The RM is then allowed to cool to RT and is filtered through a pad of celite, washing with EtOAc. The filtrate is washed with water and the aqueous layer is extracted twice with EtOAc. The combined organic layers are then washed with brine, dried over $MgSO_4$, filtered and concentrated under reduced pressure. Purification by FC (from heptane to heptane/EtOAc=1/1) affords methyl 2-(2-chloro-6-ethyl-4-(4,4,5,5-tetramethyl-1,3,2-dioxaborolan-2-yl)phenyl)acetate as a pale yellow oil (126 mg, 43%). LC-MS B: $t_R$=1.14 min; $[M+H]^+$=339.35.

A.2.60.1. Methyl 2-(4-bromo-2-chloro-6-ethylphenyl)acetate

To a solution of 2-(4-bromo-2-chloro-6-ethylphenyl)acetic acid (259 mg, 0.93 mmol) in anh. DMF (9 mL) at RT are added cesium carbonate (456 mg, 1.40 mmol) and iodomethane (70 μL, 1.12 mmol) and the RM is stirred at RT, under nitrogen, for 30 min. Water and $Et_2O$ are added and the layers are separated. The aqueous layer is extracted twice with $Et_2O$ and the combined organic layers are washed with brine, dried over anh. $MgSO_4$, filtered and concentrated under reduced pressure. Purification by FC (from heptane to heptane/EtOAc=1/1) affords methyl 2-(4-bromo-2-chloro-6-ethylphenyl)acetate as a pale yellow solid (254 mg, 93%). LC-MS B: $t_R$=1.03 min; no ionization.

A.2.60.2. 2-(4-Bromo-2-chloro-6-ethylphenyl)acetic acid

A mixture of 2-(4-bromo-2-chloro-6-ethylphenyl)acetonitrile (511 mg, 1.98 mmol), potassium hydroxide (333 mg, 5.93 mmol) in EtOH (15 mL) and water (15 mL) is heated to 110° C., under nitrogen, for 24 h. The RM is then allowed to cool to RT and is concentrated under reduced pressure. 1 M aq. HCl and DCM are successively added, the layers are then separated and the aqueous layer is extracted twice with DCM. The combined organic layers are washed with brine, dried over anh. $MgSO_4$, filtered and concentrated under reduced pressure affording crude 2-(4-bromo-2-chloro-6-ethylphenyl)acetic acid as an off-white solid (259 mg). LC-MS B: $t_R$=0.90 min; no ionization.

A.2.60.3. 2-(4-Bromo-2-chloro-6-ethylphenyl)acetonitrile

A solution of 5-bromo-1-chloro-2-(chloromethyl)-3-ethylbenzene (740 mg, 2.76 mmol) in MeCN (14 mL) and water (2 mL) is treated with sodium cyanide (176 mg, 3.59 mmol) and the RM is heated to 80° C., under nitrogen, overnight. The RM is then allowed to cool to RT and is diluted with water. Acetonitrile is removed under reduced pressure and the mixture is extracted twice with DCM. The combined organic layers are dried over anh. MgSO$_4$, filtered and concentrated under reduced pressure. Purification by FC (from heptane to heptane/EtOAc=1/1) affords 2-(4-bromo-2-chloro-6-ethylphenyl)acetonitrile as a colorless oil (511 mg, 72%). LC-MS B: t$_R$=0.99 min: no ionization.

A.2.60.4. 5-Bromo-1-chloro-2-(chloromethyl)-3-ethylbenzene

A cooled (0° C.) mixture of (4-bromo-2-chloro-6-ethylphenyl)methanol (645 mg, 2.58 mmol) and zinc chloride (9 mg, 0.064 mmol) in anh. DCM (10 mL) is treated dropwise with thionyl chloride (0.37 mL, 5.17 mmol) and the RM is stirred at 0° C. for 3 h, and then at RT overnight. The RM is concentrated under reduced pressure affording crude 5-bromo-1-chloro-2-(chloromethyl)-3-ethylbenzene as a grey oil (740 mg, quantitative). LC-MS B: t$_R$=1.09 min; no ionization.

A.2.60.5. (4-Bromo-2-chloro-6-ethylphenyl)methanol

To a cooled (−78° C.) solution of methyl 4-bromo-2-chloro-6-ethylbenzoate (2.115 g, 7.62 mmol) in anh. THE (50 mL) is added dropwise a solution of diisobutylaluminum hydride (1 M in toluene, 45.7 mL, 45.7 mmol). The mixture is further stirred at −78° C., under nitrogen, for 15 min and is then allowed to warm-up to 0° C. Stirring at 0° C. is continued for 45 min, and the cooled RM is treated successively with water (2 mL), 2.8 N aq. NaOH (2 mL) and water (5 mL). The mixture is then allowed to warm-up to RT and is further stirred for 30 min. The resulting mixture is filtered over celite, washing with THE and the filtrate is concentrated to dryness under reduced pressure. EtOAc and water are added and the layers are separated. The aqueous layer is extracted twice with EtOAc and the combined organic layers are dried over anh. MgSO$_4$, filtered and concentrated under reduced pressure. Purification by FC (from heptane to heptane/EtOAc=1/1) affords pure (4-bromo-2-chloro-6-ethylphenyl)methanol (645 mg, 34%). LC-MS B: t$_R$=0.89 min; no ionization.

A.2.60.6. Methyl 4-bromo-2-chloro-6-ethylbenzoate

To a solution of 4-bromo-2-chloro-6-ethylbenzoic acid (2.660 g, 10.10 mmol) in anh. DMF (20 mL) at RT are added cesium carbonate (4.933 g, 15.10 mmol) and iodomethane (0.76 mL, 12.10 mmol) and the RM is stirred at RT for 1.5 h. Water and Et$_2$O are added and the layers are separated. The aqueous layer is extracted twice with Et$_2$O and the combined organic layers are washed with brine, dried over anh. MgSO$_4$, filtered and concentrated under reduced pressure. Purification by FC (from heptane to heptane/EtOAc=1/1) affords methyl 4-bromo-2-chloro-6-ethylbenzoate as a colorless oil (1.930 g, 69%). LC-MS B: t$_R$=1.03 min; no ionization.

A.2.60.7. 4-Bromo-2-chloro-6-ethylbenzoic acid

To a cooled (0° C.) solution of 4-bromo-2-chloro-6-fluorobenzoic acid (4.530 g, 17.00 mmol) in anh. THE (40 mL) is added dropwise a solution of ethylmagnesium bromide (1.0 M in THF, 67.9 mL, 67.9 mmol) and the RM is further stirred at RT, under nitrogen, for 50 min. MeOH (20 mL) is then added dropwise to the cooled (0° C.) reaction mixture that is further stirred at 0° C. for 5 min. The resulting mixture is then concentrated to dryness under reduced pressure and the residue is partitioned between EtOAc and 2 M aq. HCl. The layers are separated, and the aq. layer is extracted twice with EtOAc. The combined organic layers are then washed with brine, dried over anh. MgSO$_4$, filtered and concentrated under reduced pressure. Purification by FC (from heptane to heptane/EtOAc=1/1) affords 4-bromo-2-chloro-6-ethylbenzoic acid as a colorless solid (2.660 g, 59%). LC-MS B: t$_R$=0.86 min: no ionization.

A.2.61. Methyl 2-(2-ethyl-6-methyl-4-(4,4,5,5-tetramethyl-1,3,2-dioxaborolan-2-yl)phenyl)acetate To a solution of methyl 2-(4-bromo-2-ethyl-6-methylphenyl)acetate (1.176 g, 4.34 mmol) in anh. DMF (15 mL) are added at RT 4,4,4',4',5,5,5',5'-octamethyl-2,2'-bi(1,3,2-dioxaborolane) (1.112 g, 4.34 mmol), potassium acetate (1.703 g, 17.30 mmol) and Pd(dppf)Cl$_2$ (353 mg, 0.47 mmol). The RM is heated to 90° C., under nitrogen, for 16 h. The RM is then allowed to cool to RT and is filtered through a pad of celite, washing with EtOAc. The filtrate is washed with water and the aqueous layer is extracted twice with EtOAc. The combined organic layers are then washed with brine, dried over MgSO$_4$, filtered and concentrated under reduced pressure. Purification by FC (from heptane to heptane/EtOAc=7/3) affords methyl 2-(2-ethyl-6-methyl-4-(4,4,5,5-tetramethyl-1,3,2-dioxaborolan-2-yl)phenyl)acetate as a light green oil (895 mg, 65%). LC-MS B: t$_R$=1.08 min; [M+H]$^+$=319.28.

A.2.61.1. Methyl 2-(4-bromo-2-ethyl-6-methylphenyl)acetate

To a solution of 2-(4-bromo-2-ethyl-6-methylphenyl)acetic acid (2.993 g, 11.60 mmol) in anh. DMF (20 mL) at RT are added cesium carbonate (7.585 g, 23.30 mmol) and iodomethane (1.46 mL, 23.30 mmol) and the RM is stirred at RT, under nitrogen, for 5 h. Water and Et$_2$O are added and the layers are separated. The aqueous layer is extracted twice with Et$_2$O and the combined organic layers are washed with brine, dried over anh. MgSO$_4$, filtered and concentrated under reduced pressure. Purification by FC (from heptane to heptane/EtOAc=7/3) affords methyl 2-(4-bromo-2-ethyl-6-methylphenyl)acetate as a yellow oil (1.176 g, 37%). LC-MS B: t$_R$=1.03 min; no ionization.

A.2.61.2. 2-(4-Bromo-2-ethyl-6-methylphenyl)acetic acid

A mixture of 2-(4-bromo-2-ethyl-6-methylphenyl)acetonitrile (2.477 g, 10.40 mmol), water (10 mL), 95% sulfuric acid (11 mL) and acetic acid (7.5 mL) is heated to 110° C., under nitrogen, for 1.5 h. The RM is then allowed to cool to RT and is poured onto ice/water. The mixture is extracted twice with DCM and the combined organic layers are washed with brine, dried over anh. MgSO$_4$, filtered and concentrated under reduced pressure affording crude 2-(4-bromo-2-ethyl-6-methylphenyl)acetic acid as an off-white solid (2.993 g, quantitative). LC-MS B: t$_R$=0.81 min; no ionization.

A.2.61.3. 2-(4-Bromo-2-ethyl-6-methylphenyl)acetonitrile

A solution of 5-bromo-2-(chloromethyl)-1-ethyl-3-methylbenzene (2.849 g, 11.50 mmol) in MeCN (30 mL) and water (3.7 mL) is treated with sodium cyanide (764 mg, 15.00 mmol) and the RM is heated to 80° C., under nitrogen, for 1 h. The RM is then allowed to cool to RT and is diluted with water. Acetonitrile is removed under reduced pressure and the RM is extracted twice with DCM. The combined organic layers are dried over anh. MgSO$_4$, filtered and concentrated under reduced pressure. Purification by FC (from heptane to heptane/EtOAc=7/3) affords 2-(4-bromo-2-ethyl-6-methylphenyl)acetonitrile as a clear oil (2.477 g, 90%). LC-MS B: $t_R$=0.99 min; no ionization.

A.2.61.4. 5-Bromo-2-(chloromethyl)-1-ethyl-3-methylbenzene

A cooled (0° C.) mixture of (4-bromo-2-ethyl-6-methylphenyl)methanol (2.525 g, 11.00 mmol) and zinc chloride (37.6 mg, 0.276 mmol) in anh. DCM (30 mL) is treated dropwise with thionyl chloride (1.61 mL, 22.00 mmol) and the RM is stirred at 0° C. for 1 h. The RM is concentrated under reduced pressure affording crude 5-bromo-2-(chloromethyl)-1-ethyl-3-methylbenzene as a light brown oil (2.849 g, quantitative). LC-MS B: $t_R$=1.08 min; no ionization.

A.2.61.5. (4-Bromo-2-ethyl-6-methylphenyl)methanol

To a cooled (−78° C.) solution of methyl 4-bromo-2-ethyl-6-methylbenzoate (3.355 g, 13.00 mmol) in anh. THF (60 mL) is added dropwise a solution of diisobutylaluminum hydride (1 M in toluene, 39.0 mL, 39.0 mmol). The mixture is further stirred at −78° C., under nitrogen, for 15 min and is then allowed to warm-up to 0° C. Stirring at 0° C. is continued for 1 h, and the cooled RM is treated successively with water (1 mL), 2.8 N aq. NaOH (1 mL) and water (3 mL). The mixture is then allowed to warm-up to RT and is further stirred for 30 min. The resulting mixture is filtered over celite, washing with THF and the filtrate is concentrated to dryness under reduced pressure. EtOAc and water are added and the layers are separated. The aqueous layer is extracted twice with EtOAc and the combined organic layers are dried over anh. MgSO$_4$, filtered and concentrated under reduced pressure. Purification by FC (from heptane to heptane/EtOAc=1/1) affords (4-bromo-2-ethyl-6-methylphenyl)methanol (2.525 g, 84%). LC-MS B: $t_R$=0.87 min; no ionization.

A.2.61.6. Methyl 4-bromo-2-ethyl-6-methylbenzoate

To a solution of 4-bromo-2-ethyl-6-methylbenzoic acid (3.465 g, 14.30 mmol) in anh. DMF (35 mL) at RT are added cesium carbonate (9.288 g, 28.50 mmol) and iodomethane (1.79 mL, 28.50 mmol) and the RM is stirred at RT for 1 h. Water and Et$_2$O are added and the layers are separated. The aqueous layer is extracted twice with Et$_2$O and the combined organic layers are washed with brine, dried over anh. MgSO$_4$, filtered and concentrated under reduced pressure. Purification by FC (from heptane to heptane/EtOAc=3/1) affords methyl 4-bromo-2-ethyl-6-methylbenzoate as a clear oil (3.355 g, 92%). LC-MS B: $t_R$=1.02 min; no ionization.

A.2.61.7. 4-Bromo-2-ethyl-6-methylbenzoic acid

To a cooled (0° C.) solution of 4-bromo-2-fluoro-6-methylbenzoic acid (4.000 g, 16.30 mmol) in anh. THF (40 mL) is added dropwise a solution of ethylmagnesium bromide (1.0 M in THF, 49.0 mL, 49.0 mmol) and the RM is further stirred at RT, under nitrogen, overnight. MeOH (15 mL) is then added dropwise to the cooled (0° C.) reaction mixture that is further stirred at 0° C. for 5 min. The resulting mixture is then concentrated to dryness under reduced pressure and the residue is partitioned between EtOAc and 2 M aq. HCl. The layers are separated, and the aq. layer is extracted twice with EtOAc. The combined organic layers are then washed with brine, dried over anh. MgSO$_4$, filtered and concentrated under reduced pressure. Purification by FC (from heptane to heptane/EtOAc=3/1) affords 4-bromo-2-ethyl-6-methylbenzoic acid as a colorless solid (3.465 g, 87%). LC-MS B: $t_R$=0.86 min; no ionization.

A.2.62. Methyl 2-(3-ethyl-5-(4,4,5,5-tetramethyl-1,3,2-dioxaborolan-2-yl)thiophen-2-yl)acetate A mixture of methyl 2-(3-ethylthiophen-2-yl)acetate (1.340 g, 7.27 mmol), 4,4,4',4',5,5,5',5'-octamethyl-2,2'-bi (1,3,2-dioxaborolane) (1.119 g, 4.36 mmol), bis(1,5-cyclooctadiene)diiridium(I) dichloride (50.4 mg, 0.0727 mmol) and 4,4'-di-tert-butyl-2,2'-bipyridine (47.8 mg, 0.175 mmol) in THF (35 mL) is degassed with a nitrogen stream and then stirred at 80° C., under nitrogen, overnight. The RM is concentrated under reduced pressure and the residue is purified by FC (from heptane to heptane/EtOAc=4/1) to afford methyl 2-(3-ethyl-5-(4,4,5,5-tetramethyl-1,3,2-dioxaborolan-2-yl)thiophen-2-yl)acetate as a pale yellow oil (1.781 g, 79%). LC-MS B: $t_R$=1.04 min; [M+H]$^+$=311.22.

A.2.62.1. Methyl 2-(3-ethylthiophen-2-yl)acetate

To a solution of 2-(3-ethylthiophen-2-yl)acetic acid (1.248 g, 7.33 mmol) in anh. DMF (20 mL) at RT are added cesium carbonate (3.581 g, 11.00 mmol) and iodomethane (0.55 mL, 8.79 mmol) and the RM is stirred at RT, under nitrogen, for 40 min. Water and Et$_2$O are added and the layers are separated. The aqueous layer is extracted twice with Et$_2$O and the combined organic layers are washed with brine, dried over anh. MgSO$_4$, filtered and concentrated under reduced pressure. Purification by FC (from heptane to heptane/EtOAc=1/1) affords methyl 2-(3-ethylthiophen-2-yl)acetate as a yellow oil (1.340 g, 99%). LC-MS B: $t_R$=0.87 min; [M+H]$^+$=185.19.

A.2.62.2. 2-(3-Ethylthiophen-2-yl)acetic acid

To a mixture of 2-(3-ethylthiophen-2-yl)acetonitrile (1.150 g, 7.60 mmol) in EtOH (6 mL) and water (6 mL) at RT is added potassium hydroxide (1.280 g, 22.80 mmol) and the RM is heated at reflux, under nitrogen, for 75 min. The RM is then allowed to cool to RT and ethanol is removed under reduced pressure. The resulting mixture is treated with 1 M aq. HCl and is extracted twice with DCM. The combined organic layers are dried over anh. MgSO$_4$, filtered and concentrated under reduced pressure affording crude 2-(3-ethylthiophen-2-yl)acetic acid as a yellow oil (1.247 g, 96%). LC-MS B: $t_R$=0.72 min; [M+H]$^+$=170.94.

A.2.62.3. 2-(3-Ethylthiophen-2-yl)acetonitrile

A solution of 2-(chloromethyl)-3-ethylthiophene (506 mg, 3.15 mmol) in anhydrous DMSO (20 mL) is treated with sodium cyanide (617 mg, 12.60 mmol) and the RM is heated to 80° C., under nitrogen, for 40 min. The RM is then allowed to cool to RT and is diluted with water. The resulting mixture is extracted three times with EtOAc and the combined organic layers are washed with brine, dried over anh. MgSO$_4$, filtered and concentrated under reduced pressure. Purification by FC (from heptane to heptane/EtOAc=1/1) affords 2-(3-ethylthiophen-2-yl)acetonitrile as a yellow oil (360 mg, 76%). LC-MS B: t$_R$=0.83 min; no ionization.

A.2.62.4. 2-(Chloromethyl)-3-ethylthiophene

To a cooled (0° C.) solution of (3-ethylthiophen-2-yl) methanol (500 mg, 3.52 mmol) in anh. DCM (18 mL) are added successively triethylamine (0.63 mL, 4.57 mmol) and 4-dimethylaminopyridine (43 mg, 0.35 mmol). Methanesulfonyl chloride (0.32 mL, 4.22 mmol) is then added dropwise and the resulting mixture is stirred at RT, under nitrogen, for 1 h. The RM is then diluted with water, the layers are separated and the aqueous layer is extracted twice with DCM. The combined organic layers are dried over anh. MgSO$_4$, filtered and concentrated under reduced pressure affording crude 2-(chloromethyl)-3-ethylthiophene as a yellow oil (505 mg, 90%). LC-MS B: t$_R$=0.86 min: no ionization.

A.2.62.5. (3-Ethylthiophen-2-yl)methanol

To a cooled (−78° C.) solution of methyl 3-ethylthiophene-2-carboxylate (2.270 g, 13.30 mmol) in anh. THF (80 mL) is added dropwise a solution of diisobutylaluminum hydride (1 M in toluene, 40.0 mL, 40.0 mmol). The mixture is further stirred at −78° C., under nitrogen, for 10 min and is then allowed to warm-up to 0° C. Stirring at 0° C. is continued for 30 min, and the cooled RM is then treated successively with water (1.5 mL), 15% aq. NaOH (1.5 mL) and water (4 mL). The mixture is allowed to warm-up to RT and is further stirred for 1 h. The resulting mixture is filtered over celite, washing with THF. EtOAc and water are added and the layers are separated. The aqueous layer is extracted twice with EtOAc and the combined organic layers are dried over anh. MgSO$_4$, filtered and concentrated under reduced pressure. Purification by FC (from heptane to heptane/EtOAc=1/1) affords (3-ethylthiophen-2-yl)methanol as a colorless oil (2.030 g, quantitative). LC-MS B: t$_R$=0.66 min; no ionization.

A.2.62.6. Methyl 3-ethylthiophene-2-carboxylate

To a solution of 3-ethylthiophene-2-carboxylic acid (3.130 g, 19.00 mmol) in anh. DMF (20 mL) at RT are added successively cesium carbonate (9.303 g, 28.60 mmol) and iodomethane (1.44 mL, 22.80 mmol) and the RM is stirred at RT for 1.5 h. Water and Et$_2$O are added and the layers are separated. The aqueous layer is extracted twice with Et$_2$O and the combined organic layers are washed with brine, dried over anh. MgSO$_4$, filtered and concentrated under reduced pressure affording methyl 3-ethylthiophene-2-carboxylate as a yellow oil (3.340 g, quantitative). LC-MS B: t$_R$=0.89 min; [M+H]$^+$=171.04.

A.2.63. Methyl 2-(2-chloro-6-methyl-4-(4,4,5,5-tetramethyl-1,3,2-dioxaborolan-2-yl)phenyl)acetate To a solution of methyl 2-(4-bromo-2-chloro-6-methylphenyl)acetate (2.614 g, 9.42 mmol) in anh. DMF (25 mL) are added at RT 4,4,4',4',5,5,5',5'-octamethyl-2,2'-bi(1,3,2-dioxaborolane) (2.416 g, 9.42 mmol), potassium acetate (3.697 g, 37.70 mmol) and Pd(dppf)Cl$_2$ (766 mg, 1.04 mmol). The RM is heated to 90° C., under nitrogen, overnight. The RM is then allowed to cool to RT and is filtered through a pad of celite, washing with EtOAc. The filtrate is washed with water and the aqueous layer is extracted twice with EtOAc. The combined organic layers are then washed with brine, dried over MgSO$_4$, filtered and concentrated under reduced pressure. Purification by FC (from heptane to heptane/EtOAc=7/3) affords methyl 2-(2-chloro-6-methyl-4-(4,4,5,5-tetramethyl-1,3,2-dioxaborolan-2-yl)phenyl)acetate as a light green oil (1.939 g, 63%). LC-MS B: t$_R$=1.08 min; [M+H]$^+$=325.19.

A.2.63.1. Methyl 2-(4-bromo-2-chloro-6-methylphenyl)acetate

To a solution of 2-(4-bromo-2-chloro-6-methylphenyl) acetic acid (2.648 g, 10.00 mmol) in anh. DMF (25 mL) at RT are added cesium carbonate (6.548 g, 20.10 mmol) and iodomethane (1.26 mL, 20.10 mmol) and the RM is stirred at RT, under nitrogen, for 1 h. Water and Et$_2$O are added and the layers are separated. The aqueous layer is extracted twice with Et$_2$O and the combined organic layers are washed with brine, dried over anh. MgSO$_4$, filtered and concentrated under reduced pressure. Purification by FC (from heptane to heptane/EtOAc=7/3) affords methyl 2-(4-bromo-2-chloro-6-methylphenyl)acetate as a clear oil (2.614 g, 94%). LC-MS B: t$_R$=1.00 min: no ionization.

A.2.63.2. 2-(4-Bromo-2-chloro-6-methylphenyl)acetic acid

A mixture of 2-(4-bromo-2-chloro-6-methylphenyl)acetonitrile (2.504 g, 10.20 mmol), water (9 mL), 95% sulfuric acid (11 mL) and acetic acid (7 mL) is heated to 110° C., under nitrogen, for 4 h. The RM is then allowed to cool to RT and is poured onto ice/water. The mixture is extracted twice with DCM and the combined organic layers are washed with brine, dried over anh. MgSO$_4$, filtered and concentrated under reduced pressure affording crude 2-(4-bromo-2-chloro-6-methylphenyl)acetic acid as an off-white solid (2.648 g, 98%). LC-MS B: t$_R$=0.86 min; no ionization.

A.2.63.3. 2-(4-Bromo-2-chloro-6-methylphenyl)acetonitrile

A solution of 5-bromo-1-chloro-2-(chloromethyl)-3-methylbenzene (2.752 g, 10.80 mmol) in MeCN (30 mL) and water (4 mL) is treated with sodium cyanide (719 mg, 14.10 mmol) and the RM is heated to 80° C., under nitrogen, for 1 h. The RM is then allowed to cool to RT and is diluted with water. Acetonitrile is removed under reduced pressure and the mixture is extracted twice with DCM. The combined organic layers are dried over anh. MgSO$_4$, filtered and concentrated under reduced pressure. Purification by FC (from heptane to heptane/EtOAc=7/3) affords 2-(4-bromo-2-chloro-6-methylphenyl)acetonitrile as a colorless solid (2.504 g, 94%). LC-MS B: t$_R$=0.96 min; no ionization.

A.2.63.4. 5-Bromo-1-chloro-2-(chloromethyl)-3-methylbenzene

A cooled (0° C.) mixture of (4-bromo-2-chloro-6-methylphenyl)methanol (2.529 g, 10.70 mmol) and zinc chloride (36.6 mg, 0.268 mmol) in anh. DCM (30 mL) is treated dropwise with thionyl chloride (1.57 mL, 21.50 mmol) and the RM is stirred at 0° C. for 4 h. The RM is concentrated under reduced pressure affording crude 5-bromo-1-chloro- 2-(chloromethyl)-3-methylbenzene as a dark pink solid (2.752 g, quantitative). LC-MS B: $t_R$=1.05 min; no ionization.

A.2.63.5. (4-Bromo-2-chloro-6-methylphenyl)methanol

To a cooled (−78° C.) solution of methyl 4-bromo-2-chloro-6-methylbenzoate (3.450 g, 12.60 mmol) in anh. THF (60 mL) is added dropwise a solution of diisobutyl-aluminum hydride (1 M in toluene, 38.0 mL, 38.0 mmol). The mixture is further stirred at −78° C., under nitrogen, for 30 min and is then allowed to warm-up to RT. Stirring at RT is continued for 1.5 h, and the cooled RM is then treated successively with water (1 mL), 2.8 N aq. NaOH (1 mL) and water (3 mL). The mixture is allowed to warm-up to RT and is further stirred for 30 min. The resulting mixture is filtered over celite, washing with THF and the filtrate is concentrated to dryness under reduced pressure. EtOAc and water are added and the layers are separated. The aqueous layer is extracted twice with EtOAc and the combined organic layers are dried over anh. MgSO$_4$, filtered and concentrated under reduced pressure. Purification by FC (from heptane to heptane/EtOAc=1/1) affords pure (4-bromo-2-chloro-6-methylphenyl)methanol (2.529 g, 85%). LC-MS B: $t_R$=0.90 min; no ionization.

A.2.63.6. Methyl 4-bromo-2-chloro-6-methylbenzoate

To a solution of 4-bromo-2-chloro-6-methylbenzoic acid (3.500 g, 13.30 mmol) in anh. DMF (35 mL) at RT are added successively cesium carbonate (8.685 g, 26.70 mmol) and iodomethane (1.68 mL, 26.70 mmol) and the RM is stirred at RT for 1 h. Water and Et$_2$O are added and the layers are separated. The aqueous layer is extracted twice with Et$_2$O and the combined organic layers are washed with brine, dried over anh. MgSO$_4$, filtered and concentrated under reduced pressure. Purification by FC (from heptane to heptane/EtOAc=7/3) affords methyl 4-bromo-2-chloro-6-methylbenzoate as a dark orange oil (3.450 g, 98%). LC-MS B: $t_R$=0.99 min; no ionization.

A.2.64. Methyl 1-ethyl-4-(4,4,5,5-tetramethyl-1,3,2-dioxaborolan-2-yl)-1H-pyrrole-2-carboxylate To a solution of methyl 4-bromo-1-ethyl-1H-pyrrole-2-carboxylate (1.567 g, 6.75 mmol) in anh. DMF (15 mL) are added at RT 4,4,4',4',5,5,5',5'-octamethyl-2,2'-bi(1,3,2-dioxaborolane) (1.715 g, 6.75 mmol), potassium acetate (2.651 g, 27.00 mmol) and Pd(dppf)Cl$_2$ (494 mg, 0.67 mmol). The RM is heated to 90° C., under nitrogen, overnight. The RM is then allowed to cool to RT and is filtered through a pad of celite, washing with EtOAc. The filtrate is washed with water and the aqueous layer is extracted twice with EtOAc. The combined organic layers are then washed with brine, dried over MgSO$_4$, filtered and concentrated under reduced pressure. Purification by FC (from heptane to heptane/EtOAc=3/1) affords methyl 1-ethyl-4-(4,4,5,5-tetramethyl-1,3,2-dioxaborolan-2-yl)-1H-pyrrole-2-carboxylate as a light yellow oil (841 mg, 45%). LC-MS B: $t_R$=0.96 min; [M+H]$^+$=280.24.

A.2.64.1. Methyl 4-bromo-1-ethyl-1H-pyrrole-2-carboxylate

To a solution of methyl 4-bromo-1H-pyrrole-2-carboxylate (1.500 g, 7.21 mmol) in anh. DMF (15 mL) at RT are added potassium carbonate (1.494 g, 10.80 mmol) and iodoethane (1.43 mL, 8.65 mmol) and the RM is stirred at RT, under nitrogen, for 2.5 h. Water and Et$_2$O are added and the layers are separated. The aqueous layer is extracted twice with Et$_2$O and the combined organic layers are washed with brine, dried over anh. MgSO$_4$, filtered and concentrated under reduced pressure. Purification by FC (from heptane to heptane/EtOAc=7/3) affords methyl 4-bromo-1-ethyl-1H-pyrrole-2-carboxylate as a clear oil (1.567 g, 94%). LC-MS B: $t_R$=0.94 min; no ionization.

A.2.65. Methyl 1-propyl-4-(4,4,5,5-tetramethyl-1,3,2-dioxaborolan-2-yl)-1H-pyrrole-2-carboxylate To a solution of methyl 4-bromo-1-propyl-1H-pyrrole-2-carboxylate (1.721 g, 6.99 mmol) in anh. DMF (15 mL) are added at RT 4,4,4',4',5,5,5',5'-octamethyl-2,2'-bi(1,3,2-dioxaborolane) (1.776 g, 6.99 mmol), potassium acetate (2.745 g, 28.00 mmol) and Pd(dppf)Cl$_2$ (512 mg, 0.69 mmol). The RM is heated to 90° C., under nitrogen, overnight. The RM is then allowed to cool to RT and is filtered through a pad of celite, washing with EtOAc. The filtrate is washed with water and the aqueous layer is extracted twice with EtOAc. The combined organic layers are then washed with brine, dried over MgSO$_4$, filtered and concentrated under reduced pressure. Purification by FC (from heptane to heptane/EtOAc=3/1) affords methyl 1-propyl-4-(4,4,5,5-tetramethyl-1,3,2-dioxaborolan-2-yl)-1H-pyrrole-2-carboxylate as a yellow oil (1.036 g, 51%). LC-MS B: $t_R$=1.02 min; [M+H]$^+$=294.33.

A.2.65.1. Methyl 4-bromo-1-propyl-1H-pyrrole-2-carboxylate

To a solution of methyl 4-bromo-1H-pyrrole-2-carboxylate (1.500 g, 7.21 mmol) in anh. DMF (15 mL) at RT are added potassium carbonate (1.494 g, 10.80 mmol) and 1-iodopropane (0.84 mL, 8.65 mmol) and the RM is stirred at RT, under nitrogen, overnight. Water and Et$_2$O are added and the layers are separated. The aqueous layer is extracted twice with Et$_2$O and the combined organic layers are washed with brine, dried over anh. MgSO$_4$, filtered and concentrated under reduced pressure. Purification by FC (from heptane to heptane/EtOAc=7/3) affords methyl 4-bromo-1-propyl-1H-pyrrole-2-carboxylate as a clear oil (1.721 g, 97%). LC-MS B: $t_R$=0.99 min; no ionization.

A.2.66. 2-Ethoxy-3-fluoro-4-(4,4,5,5-tetramethyl-1,3,2-dioxaborolan-2-yl)benzoic acid Ethyl 2-ethoxy-3-fluoro-4-(4,4,5,5-tetramethyl-1,3,2-dioxaborolan-2-yl)benzoate (960 mg, 2.38 mmol) is dissolved in MeOH/THF (1:1) (10 mL). Then NaOH 10% (4.77 mL, 11.9 mmol) is added and the RM is stirred at RT for 4 h. It is treated with HCl 2N (~10 mL) to reach acidic pH (<2) and extracted with EtOAc. The resulting organic phase is dried over MgSO$_4$ and concentrated, yielding the title compound as a yellow solid (0.735 g, 81%). LC-MS B: $t_R$=0.91 min; [M+H]$^+$=311.26.

A.2.66.1. Ethyl 2-ethoxy-3-fluoro-4-(4,4,5,5-tetramethyl-1,3,2-dioxaborolan-2-yl)benzoate The title compound is prepared according to the procedure described for A.2.12., starting with ethyl 4-bromo-2-ethoxy-3-fluorobenzoate. LC-MS B: $t_R$=1.10 min; [M+H]$^+$=339.26.

A.2.66.2. Ethyl 4-bromo-2-ethoxy-3-fluorobenzoate

To a solution for 4-bromo-3-fluoro-2-hydroxybenzoic acid (750 mg, 3.1 mmol) and $K_2CO$ (1070 mg, 7.74 mmol) in DMF (6 mL), is added ethyl iodide (0.508 mL, 6.35 mmol). The reaction is stirred for 2.5 d at RT, then it is partitioned between DCM and brine. The aqueous layer is re-extracted with DCM, the combined organics are washed with brine then dried ($MgSO_4$), and concentrated under reduced pressure to afford the title compound as a dark orange oil. LC-MS B: $t_R$=1.03 min; $[M+H]^+$=291.01.

A.2.67. Methyl 3-(2-methoxy-4-(4,4,5,5-tetramethyl-1,3,2-dioxaborolan-2-yl)phenyl)propanoate To a solution of methyl 3-(4-bromo-2-methoxyphenyl)propanoate (0.899 g, 3.26 mmol) in anh. DMF (10 mL) are added at RT 4,4,4',4',5,5,5',5'-octamethyl-2,2'-bi(1,3,2-dioxaborolane) (0.835 g, 3.26 mmol), potassium acetate (1.278 g, 13.00 mmol) and $Pd(dppf)Cl_2$ (265 mg, 0.35 mmol). The mixture is heated to 90° C., under nitrogen, overnight. The RM is allowed to cool to RT and is filtered through a pad of celite, washing with EtOAc. The filtrate is washed with water and the aqueous layer is extracted twice with EtOAc. The combined organic layers are washed with brine, dried over $MgSO_4$, filtered and concentrated under reduced pressure. Purification by FC (from heptane to heptane/EtOAc=4/1) affords methyl 3-(2-methoxy-4-(4,4,5,5-tetramethyl-1,3,2-dioxaborolan-2-yl)phenyl)propanoate as a light yellow oil (0.752 g, 72%). LC-MS B: $t_R$=1.02 min; $[M+H]^+$=321.22.

A.2.67.1. Methyl 3-(4-bromo-2-methoxyphenyl)propanoate

To a solution of 3-(4-bromo-2-methoxyphenyl)propanoic acid (1.000 g, 3.86 mmol) in anh. DMF (10 mL) at RT are added cesium carbonate (2.515 g, 7.72 mmol) and iodomethane (0.485 mL, 7.72 mmol) and the mixture is stirred at RT, under nitrogen, for 1 h. Water and $Et_2O$ are added and the layers are separated. The aqueous layer is extracted twice with $Et_2O$ and the combined organic layers are washed with brine, dried over anh. $MgSO_4$, filtered and concentrated under reduced pressure. Purification by FC (from heptane to heptane/EtOAc=7/3) affords methyl 3-(4-bromo-2-methoxyphenyl)propanoate as a clear oil (0.899 g, 85%). LC-MS B: $t_R$=0.96 min; no ionization.

A.2.68. Methyl 5-(4,4,5,5-tetramethyl-1,3,2-dioxaborolan-2-yl)-2,3-dihydrobenzofuran-2-carboxylate To a solution of methyl 5-bromo-2,3-dihydrobenzofuran-2-carboxylate (1.513 g, 5.86 mmol) in anh. DMF (20 mL) are added at RT 4,4,4',4',5,5,5',5'-octamethyl-2,2'-bi(1,3,2-dioxaborolane) (1.504 g, 5.86 mmol), potassium acetate (2.301 g, 23.40 mmol) and $Pd(dppf)Cl_2$ (477 mg, 0.64 mmol). The mixture is heated to 90° C., under nitrogen, overnight. The RM is allowed to cool to RT and is filtered through a pad of celite, washing with $Et_2O$. The filtrate is washed with water and the aqueous layer is extracted twice with $Et_2O$. The combined organic layers are washed with brine, dried over $MgSO_4$, filtered and concentrated under reduced pressure. Purification by FC (from heptane to heptane/EtOAc=7/3) affords methyl 5-(4,4,5,5-tetramethyl-1,3,2-dioxaborolan-2-yl)-2,3-dihydrobenzofuran-2-carboxylate as a light yellow oil (1.168 g, 66%). LC-MS B: $t_R$=0.98 min; $[M+H]^+$=305.22.

A.2.68.1. Methyl 5-bromo-2,3-dihydrobenzofuran-2-carboxylate

To a solution of 5-bromo-2,3-dihydrobenzofuran-2-carboxylic acid (1.500 g, 5.86 mmol) in anh. DMF (20 mL) at RT are added cesium carbonate (2.388 g, 7.33 mmol) and iodomethane (0.547 mL, 8.79 mmol) and the mixture is stirred at RT, under nitrogen, overnight. Water and $Et_2O$ are added and the layers are separated. The aqueous layer is extracted twice with $Et_2O$ and the combined organic layers are washed with brine, dried over anh. $MgSO_4$, filtered and concentrated under reduced pressure to afford methyl 5-bromo-2,3-dihydrobenzofuran-2-carboxylate as a yellow oil (1.513 g, quantitative). LC-MS B: $t_R$=0.90 min; no ionization.

A.2.69. Methyl 2-(3-propyl-5-(4,4,5,5-tetramethyl-1,3,2-dioxaborolan-2-yl)thiophen-2-yl)acetate A mixture of methyl 2-(3-propylthiophen-2-yl)acetate (0.600 g, 3.03 mmol), 4,4,4',4',5,5,5',5'-octamethyl-2,2'-bi(1,3,2-dioxaborolane) (0.470 g, 1.82 mmol), (1,5-cyclooctadiene)(methoxy)iridium(I) dimer (21.5 mg, 0.0325 mmol) and 4,4'-di-tert-butyl-2,2'-bipyridine (20 mg, 0.074 mmol) in THF (15 mL) is degassed with a nitrogen stream and stirred at 80° C., under nitrogen, overnight. The RM is concentrated under reduced pressure and the residue is purified by FC (from heptane to heptane/EtOAc=7/3) to afford methyl 2-(3-propyl-5-(4,4,5,5-tetramethyl-1,3,2-dioxaborolan-2-yl)thiophen-2-yl)acetate as a clear oil (0.671 g, 68%). LC-MS B: $t_R$=1.07 min; $[M+H]^+$=325.24.

A.2.69.1. Methyl 2-(3-propylthiophen-2-yl)acetate

A mixture of methyl 2-(3-bromothiophen-2-yl)acetate (1.655 g, 7.04 mmol), potassium n-propyltrifluorborate (1.223 g, 7.74 mmol) and cesium carbonate (6.881 g, 21.10 mmol) in toluene (24 mL) and water (12 mL) is degassed three times with nitrogen. Palladium(II) acetate (79 mg, 0.35 mmol) and RuPhos (0.346 g, 0.70 mmol) are then added and the mixture is heated to 95° C., under nitrogen, overnight. The RM is allowed to cool to RT, water is added and the mixture is extracted three times with EtOAc. The combined organic layers are washed with brine, dried over anh. $MgSO_4$, filtered and concentrated under reduced pressure. Purification by FC (from heptane to heptane/EtOAc=7/3) affords methyl 2-(3-propylthiophen-2-yl)acetate as a yellow oil (1.336 g, 96%). LC-MS B: $t_R$=0.94 min; $[M+H]^+$=199.26.

A.2.69.2. Methyl 2-(3-bromothiophen-2-yl)acetate

To a solution of 2-(3-bromothiophen-2-yl)acetic acid (2.000 g, 9.05 mmol) in anh. DMF (20 mL) at RT are added cesium carbonate (5.895 g, 18.10 mmol) and iodomethane (1.14 mL, 18.10 mmol) and the mixture is stirred at RT, under nitrogen, for 1 h. Water and $Et_2O$ are added and the layers are separated. The aqueous layer is extracted twice with $Et_2O$ and the combined organic layers are washed with brine, dried over anh. $MgSO_4$, filtered and concentrated under reduced pressure. Purification by FC (from heptane to heptane/EtOAc=7/3) affords methyl 2-(3-bromothiophen-2-yl)acetate as a yellow oil (2.183 g, quantitative). LC-MS B: $t_R$=0.86 min; no ionization.

A.2.70. Methyl 2-(4-(4,4,5,5-tetramethyl-1,3,2-dioxaborolan-2-yl)-2-(trifluoromethyl)phenyl)acetate To a solution of methyl 2-(4-bromo-2-(trifluoromethyl)phenyl)acetate (2.556 g, 8.60 mmol) in anh. DMF (30 mL)

are added at RT 4,4,4',4',5,5,5',5'-octamethyl-2,2'-bi(1,3,2-dioxaborolane) (2.207 g, 8.60 mmol), potassium acetate (3.378 g, 34.40 mmol) and Pd(dppf)Cl$_2$ (0.700 g, 0.94 mmol). The mixture is heated to 90° C., under nitrogen, overnight. The RM is allowed to cool to RT and is filtered through a pad of celite, washing with EtOAc. The filtrate is washed with water and the aqueous layer is extracted twice with EtOAc. The combined organic layers are washed with brine, dried over MgSO$_4$, filtered and concentrated under reduced pressure. Purification by FC (from heptane to heptane/EtOAc=3/1) affords methyl 2-(4-(4,4,5,5-tetramethyl-1,3,2-dioxaborolan-2-yl)-2-(trifluoromethyl)phenyl)acetate as a yellow oil (2.256 g, 76%). LC-MS B: t$_R$=1.07 min; no ionization.

A.2.70.1. Methyl 2-(4-bromo-2-(trifluoromethyl)phenyl)acetate

To a solution of 2-(4-bromo-2-(trifluoromethyl)phenyl)acetic acid (2.694 g, 9.52 mmol) in anh. DMF (25 mL) at RT are added cesium carbonate (6.202 g, 19.00 mmol) and iodomethane (1.20 mL, 19.00 mmol) and the mixture is stirred at RT, under nitrogen, for 1 h. Water and Et$_2$O are added and the layers are separated. The aqueous layer is extracted twice with Et$_2$O and the combined organic layers are washed with brine, dried over anh. MgSO$_4$, filtered and concentrated under reduced pressure. Purification by FC (from heptane to heptane/EtOAc=7/3) affords methyl 2-(4-bromo-2-(trifluoromethyl)phenyl)acetate as a light yellow oil (2.556 g, 90%). LC-MS B: t$_R$=0.98 min; no ionization.

A.2.70.2. 2-(4-Bromo-2-(trifluoromethyl)phenyl)acetic acid

A mixture of 2-(4-bromo-2-(trifluoromethyl)phenyl)acetonitrile (2.385 g, 9.03 mmol), water (8.5 mL), 95% sulfuric acid (9.5 mL) and acetic acid (6.5 mL) is heated to 110° C., under nitrogen, overnight. The RM is allowed to cool to RT and is poured onto ice/water. The mixture is extracted three times with DCM and the combined organic layers are washed with brine, dried over anh. MgSO$_4$, filtered and concentrated under reduced pressure affording crude 2-(4-bromo-2-(trifluoromethyl)phenyl)acetic acid as a light yellow solid (2.694 g, quantitative). LC-MS B: t$_R$=0.85 min: no ionization.

A.2.70.3. 2-(4-Bromo-2-(trifluoromethyl)phenyl)acetonitrile

A solution of 4-bromo-1-(chloromethyl)-2-(trifluoromethyl)benzene (2.707 g, 9.81 mmol) in MeCN (32 mL) and water (4 mL) is treated with sodium cyanide (0.651 g, 12.80 mmol) and the mixture is heated to 80° C., under nitrogen, overnight. The RM is allowed to cool to RT and is diluted with water. Acetonitrile is removed under reduced pressure and the mixture is extracted twice with DCM. The combined organic layers are dried over anh. MgSO$_4$, filtered and concentrated under reduced pressure. Purification by FC (from heptane to heptane/EtOAc=7/3) affords 2-(4-bromo-2-(trifluoromethyl)phenyl)acetonitrile as a light yellow solid (2.385 g, 92%). LC-MS B: t$_R$=0.95 min; no ionization.

A.2.70.4. 4-Bromo-1-(chloromethyl)-2-(trifluoromethyl)benzene

A cooled (0° C.) mixture of (4-bromo-2-(trifluoromethyl)phenyl)methanol (2.500 g, 9.62 mmol) and zinc chloride (32.8 mg, 0.24 mmol) in anh. DCM (25 mL) is treated dropwise with thionyl chloride (1.40 mL, 19.20 mmol) and the mixture is stirred at 0° C. for 4 h, and then at RT overnight. The RM is concentrated under reduced pressure affording crude 4-bromo-1-(chloromethyl)-2-(trifluoromethyl)benzene as a light yellow oil (2.707 g, quantitative). LC-MS B: t$_R$=1.03 min; no ionization.

A.2.71. Methyl 2-(2-ethoxy-3-fluoro-4-(4,4,5,5-tetramethyl-1,3,2-dioxaborolan-2-yl)phenyl)acetate To a solution of methyl 2-(4-bromo-2-ethoxy-3-fluorophenyl)acetate (1.939 g, 6.66 mmol) in anh. DMF (20 mL) are added at RT 4,4,4',4',5,5,5',5'-octamethyl-2,2'-bi(1,3,2-dioxaborolane) (1.708 g, 6.66 mmol), potassium acetate (2.615 g, 26.60 mmol) and Pd(dppf)Cl$_2$ (0.542 g, 0.73 mmol). The mixture is heated to 90° C., under nitrogen, overnight. The RM is allowed to cool to RT and is filtered through a pad of celite, washing with EtOAc. The filtrate is washed with water and the aqueous layer is extracted twice with EtOAc. The combined organic layers are washed with brine, dried over anh. MgSO$_4$, filtered and concentrated under reduced pressure. Purification by FC (from heptane to heptane/EtOAc=7/3) affords methyl 2-(2-ethoxy-3-fluoro-4-(4,4,5,5-tetramethyl-1,3,2-dioxaborolan-2-yl)phenyl)acetate as a dark green oil (1.254 g, 56%). LC-MS B: t$_R$=1.05 min; [M+H]$^+$=339.23.

A.2.71.1. Methyl 2-(4-bromo-2-ethoxy-3-fluorophenyl)acetate

To a solution of 2-(4-bromo-2-ethoxy-3-fluorophenyl)acetic acid (2.186 g, 7.28 mmol) in anh. DMF (20 mL) at RT are added cesium carbonate (3.213 g, 9.86 mmol) and iodomethane (0.738 mL, 11.80 mmol) and the mixture is stirred at RT, under nitrogen, for 15 min. Water and Et$_2$O are added and the layers are separated. The aqueous layer is extracted twice with Et$_2$O and the combined organic layers are washed with brine, dried over anh. MgSO$_4$, filtered and concentrated under reduced pressure. Purification by FC (from heptane to heptane/EtOAc=7/3) affords methyl 2-(4-bromo-2-ethoxy-3-fluorophenyl)acetate as a clear oil (1.939 g, 91%). LC-MS B: t$_R$=0.99 min; [M+H]$^+$=291.10.

A.2.71.2. 2-(4-Bromo-2-ethoxy-3-fluorophenyl)acetic acid

A mixture of 2-(4-bromo-2-ethoxy-3-fluorophenyl)acetonitrile (1.879 g, 7.28 mmol), water (7 mL), 95% sulfuric acid (8 mL) and acetic acid (9 mL) is heated to 110° C. under nitrogen, for 1.5 h. The RM is then allowed to cool to RT and is poured onto ice/water. The mixture is extracted twice with DCM and the combined organic layers are washed with brine, dried over anh. MgSO$_4$, filtered and concentrated under reduced pressure affording 2-(4-bromo-2-ethoxy-3-fluorophenyl)acetic acid as an off-white solid (2.186 g, quantitative). LC-MS B: t$_R$=0.85 min; no ionization.

A.2.71.3. 2-(4-Bromo-2-ethoxy-3-fluorophenyl)acetonitrile

A solution of 1-bromo-4-(chloromethyl)-3-ethoxy-2-fluorobenzene (2.124 g, 7.94 mmol) in MeCN (24 mL) and water (3 mL) is treated with sodium cyanide (0.527 g, 10.30 mmol) and the mixture is heated to 80° C., under nitrogen, overnight. The RM is allowed to cool to RT and is diluted with water. Acetonitrile is removed under reduced pressure and the mixture is extracted twice with DCM. The combined organic layers are washed with brine, dried over anh. MgSO$_4$, filtered and concentrated under reduced pressure. Purification by FC (from heptane to heptane/EtOAc=7/3) affords 2-(4-bromo-2-ethoxy-3-fluorophenyl)acetonitrile as a colorless solid (1.879 g, 92%). LC-MS B: $t_R$=0.97 min; no ionization.

A.2.71.4. 1-Bromo-4-(chloromethyl)-3-ethoxy-2-fluorobenzene

A cooled (0° C.) mixture of (4-bromo-2-ethoxy-3-fluorophenyl)methanol (1.947 g, 7.82 mmol) and zinc chloride (26.6 mg, 0.19 mmol) in anh. DCM (25 mL) is treated dropwise with thionyl chloride (1.14 mL, 15.60 mmol) and the mixture is stirred at 0° C. for 2 h. The RM is concentrated under reduced pressure affording 1-bromo-4-(chloromethyl)-3-ethoxy-2-fluorobenzene as a clear oil (2.124 g, quantitative). LC-MS B: $t_R$=1.06 min; no ionization.

A.2.71.5. (4-Bromo-2-ethoxy-3-fluorophenyl)methanol

To a cooled (−78° C.) solution of ethyl 4-bromo-2-ethoxy-3-fluorobenzoate (2.920 g, 10.00 mmol) in anh. THF (30 mL) is added dropwise a solution of diisobutylaluminum hydride (1 M in toluene, 30.1 mL, 30.1 mmol) and the mixture is further stirred at −78° C., under nitrogen, for 45 min. The RM is then allowed to warm-up to 0° C. and is treated successively with water and with 2.8 N aq. NaOH. EtOAc is added, the layers are separated and the aqueous layer is extracted twice with EtOAc. The combined organic layers are dried over anh. MgSO$_4$, filtered and concentrated under reduced pressure. Purification by FC (from heptane to heptane/EtOAc=7/3) affords (4-bromo-2-ethoxy-3-fluorophenyl)methanol as a colorless solid (1.947 g, 78%). LC-MS B: $t_R$=0.85 min; no ionization.

A.2.71.6. Ethyl 4-bromo-2-ethoxy-3-fluorobenzoate

To a solution of 4-bromo-3-fluoro-2-hydroxybenzoic acid (3.000 g, 12.80 mmol) in anh. DMF (25 mL) at RT are added potassium carbonate (3.529 g, 25.50 mmol) and iodoethane (2.05 mL, 25.50 mmol) and the mixture is stirred at 80° C., under nitrogen, overnight. Water and Et$_2$O are added and the layers are separated. The aqueous layer is extracted twice with Et$_2$O and the combined organic layers are washed with brine, dried over anh. MgSO$_4$, filtered and concentrated under reduced pressure. Purification by FC (from heptane to heptane/EtOAc=3/1) affords ethyl 4-bromo-2-ethoxy-3-fluorobenzoate as a yellow oil (2.920 g, 79%). LC-MS B: $t_R$=1.04 min: [M+H]$^+$=291.09.

A.2.72. Methyl 2-(3-(difluoromethoxy)-5-(4,4,5,5-tetramethyl-1,3,2-dioxaborolan-2-yl)thiophen-2-yl)acetate A mixture of methyl 2-(3-(difluoromethoxy)thiophen-2-yl)acetate (0.365 g, 1.64 mmol), 4,4,4',4',5,5,5',5'-octamethyl-2,2'-bi(1,3,2-dioxaborolane) (0.253 g, 0.98 mmol), (1,5-cyclooctadiene)(methoxy)iridium(I) dimer (11 mg, 0.0164 mmol) and 4,4'-di-tert-butyl-2,2'-bipyridine (11 mg, 0.039 mmol) in THF (8 mL) is degassed with a nitrogen stream and stirred at 80° C., under nitrogen, overnight. The RM is concentrated under reduced pressure and the residue is purified by FC (from heptane to heptane/EtOAc=4/1) to afford methyl 2-(3-(difluoromethoxy)-5-(4,4,5,5-tetramethyl-1,3,2-dioxaborolan-2-yl)thiophen-2-yl)acetate as a yellow oil (0.473 g, 83%). LC-MS B: $t_R$=1.02 min; [M+H]$^+$=349.15.

A.2.72.1. Methyl 2-(3-(difluoromethoxy)thiophen-2-yl)acetate

To a solution of 2-(3-(difluoromethoxy)thiophen-2-yl) acetic acid (0.401 g, 1.93 mmol) in anh. DMF (8 mL) at RT are added cesium carbonate (0.941 g, 2.89 mmol) and iodomethane (0.145 mL, 2.31 mmol) and the mixture is stirred at RT, under nitrogen, for 30 min. Water and Et$_2$O are added and the layers are separated. The aqueous layer is extracted twice with Et$_2$O and the combined organic layers are washed with brine, dried over anh. MgSO$_4$, filtered and concentrated under reduced pressure. Purification by FC (from heptane to heptane/EtOAc=4/1) affords methyl 2-(3-(difluoromethoxy)thiophen-2-yl)acetate as a pale yellow oil (0.364 g, 85%). LC-MS B: $t_R$=0.83 min; no ionization.

A.2.72.2. 2-(3-(Difluoromethoxy)thiophen-2-yl)acetic acid

A mixture of 2-(3-(difluoromethoxy)thiophen-2-yl)acetonitrile (0.306 g, 1.62 mmol), potassium hydroxide (0.272 g, 4.85 mmol) in EtOH (3 mL) and water (3 mL) is heated to 110° C., under nitrogen, for 2.5 h. The RM is allowed to cool to RT and is concentrated under reduced pressure. 1 M aq. HCl and DCM are successively added, the layers are separated and the aqueous layer is extracted twice with DCM. The combined organic layers are washed with brine, dried over anh. MgSO$_4$, filtered and concentrated under reduced pressure affording 2-(3-(difluoromethoxy)thiophen-2-yl)acetic acid as an orange oil (0.296 g, 88%). LC-MS B: $t_R$=0.68 min; no ionization.

A.2.72.3. 2-(3-(Difluoromethoxy)thiophen-2-yl)acetonitrile

A solution of 2-(chloromethyl)-3-(difluoromethoxy)thiophene (0.426 g, 2.14 mmol) in anhydrous DMSO (10.5 mL) is treated with sodium cyanide (0.217 g, 4.29 mmol) and the mixture is heated to 80° C., under nitrogen, for 75 min. The RM is allowed to cool to RT and is diluted with water. The resulting mixture is extracted three times with Et$_2$O and the combined organic layers are washed with brine, dried over anh. MgSO$_4$, filtered and concentrated under reduced pressure. Purification by FC (from heptane to heptane/EtOAc=4/1) affords 2-(3-(difluoromethoxy)thiophen-2-yl)acetonitrile as a pale yellow oil (0.306 g, 75%). LC-MS B: $t_R$=0.78 min; no ionization.

A.2.72.4. 2-(Chloromethyl)-3-(difluoromethoxy)thiophene

A cooled (0° C.) mixture of (3-(difluoromethoxy)thiophen-2-yl)methanol (0.360 g, 2.00 mmol) and zinc chloride (7 mg, 0.049 mmol) in anh. DCM (20 mL) is treated dropwise with thionyl chloride (0.291 mL, 3.99 mmol) and the mixture is stirred at RT for 3 h. The mixture is cooled to 0° C., treated dropwise with thionyl chloride (0.291 mL, 3.99 mmol) and further stirred at RT for 1 h. The RM is concentrated under reduced pressure to afford 2-(chloromethyl)-3-(difluoromethoxy)thiophene as a black oil (0.328 g, 83%). LC-MS B: $t_R$=0.82 min; no ionization.

A.2.72.5. (3-(Difluoromethoxy)thiophen-2-yl)methanol

To a cooled (−78° C.) solution of methyl 3-(difluoromethoxy)thiophene-2-carboxylate (1.450 g, 6.97 mmol) in anh. THF (50 mL) is added dropwise a solution of diisobutylaluminum hydride (1 M in THF, 21.0 mL, 21.0 mmol). The mixture is further stirred at −78° C., under nitrogen, for 20 min and is then allowed to warm-up to 0° C. Stirring at 0° C. is continued for 20 min, and the RM is treated successively with water (1 mL), 2.8 N aq. NaOH (1 mL) and water (2 mL). The mixture is then allowed to warm-up to RT and stirred for 1 h. The resulting mixture was filtered over celite washing with THF and the filtrate was concentrated to dryness under reduced pressure. Purification by FC (from heptane to heptane/EtOAc=1/1) affords (3-(difluoromethoxy)thiophen-2-yl)methanol as a pale yellow oil (1.075 g, 86%). LC-MS B: $t_R$=0.63 min; no ionization.

A.2.72.6. Methyl 3-(difluoromethoxy)thiophene-2-carboxylate

To a solution of 3-(difluoromethoxy)thiophene-2-carboxylic acid (0.500 g, 2.45 mmol) in anh. DMF (4 mL) at RT are added successively cesium carbonate (1.196 g, 3.67 mmol) and iodomethane (0.185 mL, 2.94 mmol) and the mixture is stirred at RT for 40 min. Water and Et$_2$O are added and the layers are separated. The aqueous layer is extracted twice with Et$_2$O and the combined organic layers are washed with brine, dried over anh. MgSO$_4$, filtered and concentrated under reduced pressure. Purification by FC (from heptane to heptane/EtOAc=1/1) affords methyl 3-(difluoromethoxy)thiophene-2-carboxylate as a colorless oil (0.495 g, 97%). LC-MS B: $t_R$=0.81 min; no ionization.

A.2.73. Methyl 2-cyclopropoxy-4-(4,4,5,5-tetramethyl-1,3,2-dioxaborolan-2-yl)benzoate To a solution of methyl 4-bromo-2-cyclopropoxybenzoate (0.991 g, 3.65 mmol) in anh. 1,4-dioxane (20 mL) are added at RT 4,4,4',4',5,5,5',5'-octamethyl-2,2'-bi(1,3,2-dioxaborolane) (0.936 g, 3.65 mmol), potassium acetate (1.432 g, 14.60 mmol) and Pd(dppf)Cl$_2$ (297 mg, 0.40 mmol). The mixture is heated to 95° C., under nitrogen, overnight. The RM is allowed to cool to RT and is filtered through a pad of celite, washing with EtOAc. The filtrate is washed with water and the aqueous layer is extracted twice with EtOAc. The combined organic layers are dried over MgSO$_4$, filtered and concentrated under reduced pressure. Purification by FC (from heptane to heptane/EtOAc=7/3) affords methyl 2-cyclopropoxy-4-(4,4,5,5-tetramethyl-1,3,2-dioxaborolan-2-yl)benzoate as an amber oil (1.004 g, 87%). LC-MS B: $t_R$=1.03 min; [M+H]$^+$=319.25.

A.2.73.1. Methyl 4-bromo-2-cyclopropoxybenzoate

A cooled (0° C.) solution of diethylzinc (1 M in hexanes, 14.5 mL, 14.5 mmol) in anh. DCM (10 mL) is treated dropwise with trifluoroacetic acid (0.767 mL, 9.92 mmol) and the mixture is stirred at 0° C., under nitrogen, for 10 min. Diiodomethane (2.38 mL, 29.00 mmol) is added dropwise to the cooled mixture and stirring at 0° C. is continued for 10 min. A solution of methyl 4-bromo-2-(vinyloxy)benzoate (0.981 g, 3.82 mmol) in anh. DCM (15 mL) is added dropwise and the resulting mixture is further stirred at 0° C. for 30 min, and then at RT overnight. The RM is treated with aq. sat. NH$_4$Cl and the layers are separated. The aqueous layer is extracted twice with DCM and the combined organic layers are washed with brine, dried over anh. MgSO$_4$, filtered and concentrated under reduced pressure. Purification by FC (from heptane to heptane/EtOAc=4/1) affords methyl 4-bromo-2-cyclopropoxybenzoate as a clear oil (0.991 g, 96%). LC-MS B: $t_R$=0.95 min; [M+H]$^+$=271.11.

A.2.73.2. Methyl 4-bromo-2-(vinyloxy)benzoate

To a cooled (0° C.) solution of 4-bromo-2-(vinyloxy)benzoic acid (1.161 g, 4.78 mmol) in anh. DMF (20 mL) are added cesium carbonate (2.023 g, 6.21 mmol) and iodomethane (0.452 mL, 7.17 mmol) and the mixture is stirred at 0° C., under nitrogen, for 15 min and then at RT for 1 h. Water and EtOAc are added and the layers are separated. The aqueous layer is extracted twice with EtOAc and the combined organic layers are washed with brine, dried over anh. MgSO$_4$, filtered and concentrated under reduced pressure. Purification by FC (from heptane to heptane/EtOAc=7/3) affords methyl 4-bromo-2-(vinyloxy)benzoate as a yellow oil (1.181 g, 96%). LC-MS B: $t_R$=0.93 min; [M+H]$^+$=256.99.

A.2.73.3. 4-Bromo-2-(vinyloxy)benzoic acid

A cooled (0° C.) solution of methyl 4-bromo-2-(2-chloroethoxy)benzoate (5.440 g, 18.50 mmol) in anh. THF (50 mL) is treated portionwise with potassium tert-butoxide (2.485 g, 22.10 mmol) and the resulting solution is stirred at 0° C., under nitrogen, for 45 min and then at RT for 30 min. Additional potassium tert-butoxide (1.037 g, 9.241 mmol) is then added portionwise to the cooled (0° C.) mixture and stirring at RT is continued for 4 h. Water and EtOAc are added and the layers are separated. The aqueous layer is acidified with 1M aq. HCl and extracted three times with EtOAc. The combined organic layers are washed with brine, dried over anh. MgSO$_4$, filtered and concentrated under reduced pressure. Purification by FC (from heptane to heptane/EtOAc=3/1) affords 4-bromo-2-(vinyloxy)benzoic acid as a light orange solid (1.161 g, 26%). LC-MS B: $t_R$=0.79 min; no ionization.

A.2.73.4. Methyl 4-bromo-2-(2-chloroethoxy)benzoate

To a solution of methyl 4-bromo-2-hydroxybenzoate (5.000 g, 21.00 mmol) in anh. DMF (30 mL) at RT are added cesium carbonate (10.363 g, 31.50 mmol) and 2-chloroethyl p-toluenesulfonate (4.71 mL, 25.20 mmol) and the mixture is heated to 65° C., under nitrogen, for 2 h. The RM is allowed to cool to RT, water and Et$_2$O are added, and the layers are separated. The aqueous layer is extracted three times with Et$_2$O and the combined organic layers are washed with brine, dried over anh. MgSO$_4$, filtered and concentrated under reduced pressure. Purification by FC (from heptane to heptane/EtOAc=4/1) affords methyl 4-bromo-2-(2-chloroethoxy)benzoate as a colorless solid (5.840 g, 95%). LC-MS B: $t_R$=0.96 min; [M+H]$^+$=293.10.

B—Preparation of Examples

General Procedure A: Suzuki Coupling with Pd(PPh$_3$)$_4$

A mixture of the respective pyrimidine halide derivative (A3) (0.15 mmol), the respective boronic acid derivative (A4) (0.18 mmol), and K$_2$CO$_3$ 2M (0.3 mL, 0.6 mmol) in ethanol (3 mL) is purged with argon, Pd(PPh$_3$)$_4$ (0.0075 mmol) is added, and the RM is heated at 90° C. overnight. Alternatively, the reaction can be performed in a MW apparatus, at 120° C. for 15-30 min. The RM is filtered through a 0.45 um Glass MicroFiber filter, washed with EtOH/MeCN and DMF. The filtrate is purified either by preparative HPLC or FC. Alternatively, it is diluted with water, if needed the pH is adjusted, and extracted with EtOAc (3×). The combined organic extracts are dried (MgSO$_4$) and concentrated under reduced pressure. The residue is purified by preparative HPLC or by FC.

General Procedure B: Suzuki Coupling with Pd(PPh$_3$)$_4$ Followed by Ester Hydrolysis A mixture of the respective pyrimidine halide derivative (A3) (0.15 mmol), the respective boronic acid derivative (A4) (0.18 mmol), and K$_2$CO$_3$ 2M (0.3 mL, 0.6 mmol) in EtOH (3 mL) is purged with argon, Pd(PPh$_3$)$_4$ (0.0075 mmol) is added, and the RM is heated at 90° C. overnight. Alternatively, the reaction can be performed in a MW apparatus, at 120° C. for 15-30 min. NaOH (32% solution, 0.5 mL) is added, and the RM is stirred at RT for 2-20 h or at 90° C. for 0. 5-20 h. It is then filtered through a 0.45 um Glass MicroFiber filter, washed with EtOH and water. The filtrate is either purified directly by preparative HPLC or diluted with 1N HCl, and extracted 3× with EtOAc. The combined organic extracts are dried (MgSO$_4$) and concentrated under reduced pressure. The residue is purified by preparative HPLC or by FC.

General Procedure C: Suzuki Coupling with PdCl$_2$(Dppf) Followed by Ester Hydrolysis A mixture of the respective pyrimidine halide derivative (A3) (0.15 mmol), the respective boronic acid derivative (A4) (0.18-0.3 mmol), and Cs$_2$CO$_3$ (0.75 mmol) in THF (4 mL) and water (0.5 mL) is purged with argon, Pd(dppf)Cl$_2$-DCM (0.015 mmol) is added, and the RM is heated at 80° C. overnight. NaOH (32% solution, 0.5 mL) is added, and the RM is stirred at 80° C. for 2 h. It is then filtered through a 0.45 um Glass MicroFiber filter, washed with EtOH and water. The filtrate is either purified directly by preparative HPLC or diluted with 1N HCl, and extracted 3× with EtOAc. The combined organic extracts are dried (MgSO$_4$) and concentrated under reduced pressure. The residue is purified by preparative HPLC or by FC.

General Procedure D: Phosphonium-Mediated SNAr

To a solution of 6-hydroxy-pyrimidine derivative (0.1 mmol) in DMF (1 mL) and TEA (0.4 mmol) is added PyBOP (0.16 mmol). The solution is stirred at RT for 15 min-1 h, then the respective aryl-ethylamine (0.125 mmol) is added and the RM is stirred at 80° C. overnight. The RM is cooled to RT and treated with a few drops of water and purified by preparative HPLC. Alternatively, the RM is diluted with EtOAc and washed twice with brine. The organic layer is dried over MgSO$_4$, filtered and concentrated. The residue is purified by preparative HPLC or by FC if needed. Alternatively, a solution of 6-hydroxy-pyrimidine derivative (0.1 mmol) in DMF (1 mL) is treated with DBU (0.15 mmol) and BOP (0.13 mmol). The solution is stirred at RT for 15 min-1 h, then the respective aryl-ethylamine (0.125 mmol) is added, and the RM is stirred at 80° C. for 2-20 h. The RM is cooled to RT and treated with a few drops of water and purified by preparative HPLC. Or the RM is diluted with EtOAc and washed twice with brine. The organic layer is dried over MgSO$_4$, filtered and concentrated. The residue is purified by preparative HPLC or by FC if needed.

Compounds of Examples 1-337 listed in Table 4 below are prepared by applying either one of the above-mentioned procedures A, B or C to the pyrimidine halide derivatives A.1.1-A.1.96. coupled with commercially available boronic acid derivatives or with boronic acid derivatives A.2.1.-A.2.34.

TABLE 4

Examples 1-337

| Ex. | Compound | $t_R$ [min] (LC-MS) | MS Data m/z [M + H]$^+$ |
|---|---|---|---|
| 1 | 3-Ethoxy-5-{6-[2-(3-methoxy-1-methyl-naphthalen-2-yl)-ethylamino]-pyrimidin-4-yl}-thiophene-2-carboxylic acid (*1) | 1.1 (D) | 464.3 |
| 2 | 5-{6-[2-(3-Cyano-1-methyl-naphthalen-2-yl)-ethylamino]-pyrimidin-4-yl}-3-ethoxy-thiophene-2-carboxylic acid (*1) | 1.1 (D) | 459.2 |
| 3 | 3-Ethoxy-5-{6-[2-(1-fluoro-3-methoxy-naphthalen-2-yl)-ethylamino]-pyrimidin-4-yl}-thiophene-2-carboxylic acid | 1.1 (D) | 468 |
| 4 | 3-Ethoxy-5-{6-[2-(6-methoxy-benzo[b]thiophen-5-yl)-ethylamino]-pyrimidin-4-yl}-thiophene-2-carboxylic acid (*1) | 1.1 (D) | 456.2 |
| 5 | 5-[6-(2-Benzo[b]thiophen-5-yl-ethylamino)-pyrimidin-4-yl]-3-ethoxy-thiophene-2-carboxylic acid | 1.0 (D) | 426.1 |
| 6 | 5-{6-[2-(7-Cyano-2,3-dihydro-benzo[1,4]dioxin-6-yl)-ethylamino]-pyrimidin-4-yl}-3-ethoxy-thiophene-2-carboxylic acid (*1) | 0.9 (D) | 453.4 |
| 7 | 3-Ethoxy-5-{6-[2-(1-methyl-naphthalen-2-yl)-ethylamino]-pyrimidin-4-yl}-thiophene-2-carboxylic acid | 1.1 (D) | 434 |
| 8 | 3-Ethoxy-5-{6-[2-(6-methoxy-4-methyl-benzofuran-5-yl)-ethylamino]-pyrimidin-4-yl}-thiophene-2-carboxylic acid | 1.0 (D) | 454.4 |
| 9 | 3-Ethoxy-5-{6-[2-(3-methoxy-naphthalen-2-yl)-ethylamino]-pyrimidin-4-yl}-thiophene-2-carboxylic acid | 1.1 (D) | 450.1 |
| 10 | 5-[6-(2-Benzo[b]thiophen-6-yl-ethylamino)-pyrimidin-4-yl]-3-ethoxy-thiophene-2-carboxylic acid | 1.0 (D) | 426.4 |
| 11 | 3-Ethoxy-5-{6-[2-(1-fluoro-naphthalen-2-yl)-ethylamino]-pyrimidin-4-yl}-thiophene-2-carboxylic acid | 1.1 (D) | 438.4 |
| 12 | 3-Ethoxy-5-{6-[2-(6-methoxy-benzofuran-5-yl)-ethylamino]-pyrimidin-4-yl}-thiophene-2-carboxylic acid | 1.0 (D) | 440.4 |

TABLE 4-continued

Examples 1-337

| Ex. | Compound | $t_R$ [min] (LC-MS) | MS Data m/z [M + H]$^+$ |
|---|---|---|---|
| 13 | 3-Ethoxy-5-{6-[2-(6-fluoro-benzofuran-5-yl)-ethylamino]-pyrimidin-4-yl}-thiophene-2-carboxylic acid | 1.0 (D) | 428.2 |
| 14 | 3-Ethoxy-5-{6-[2-(5-methoxy-benzo[b]thiophen-6-yl)-ethylamino]-pyrimidin-4-yl}-thiophene-2-carboxylic acid | 1.1 (D) | 456.1 |
| 15 | 5-{6-[2-(2,3-Dihydro-benzo[b]thiophen-5-yl)-ethylamino]-pyrimidin-4-yl}-3-ethoxy-thiophene-2-carboxylic acid (*1) | 1.0 (D) | 428.2 |
| 16 | 3-Ethoxy-5-{6-[2-(6-fluoro-1-methyl-1H-indol-5-yl)-ethylamino]-pyrimidin-4-yl}-thiophene-2-carboxylic acid (*1) | 1.0 (D) | 441.3 |
| 17 | 3-Ethoxy-5-{6-[2-(1-ethynyl-naphthalen-2-yl)-ethylamino]-pyrimidin-4-yl}-thiophene-2-carboxylic acid (*1) | 1.1 (D) | 444.3 |
| 18 | 4-{6-[2-(6-Methoxy-benzo[b]thiophen-5-yl)-ethylamino]-pyrimidin-4-yl}-2-methylsulfanyl-benzoic acid | 0.9 (D) | 452.2 |
| 19 | 5-{6-[2-(4-Chloro-3-methoxy-naphthalen-2-yl)-ethylamino]-pyrimidin-4-yl}-3-ethoxy-thiophene-2-carboxylic acid (*1) | 1.2 (D) | 484.4 |
| 20 | 3-Ethoxy-5-{6-[2-(4-methyl-benzo[b]thiophen-5-yl)-ethylamino]-pyrimidin-4-yl}-thiophene-2-carboxylic acid (*1) | 1.1 (D) | 440.1 |
| 21 | 3-Ethoxy-5-{6-[2-(8-methoxy-3,4-dihydro-2H-benzo[b][1,4]dioxepin-7-yl)-ethylamino]-pyrimidin-4-yl}-thiophene-2-carboxylic acid | 0.9 (D) | 472.1 |
| 22 | 3-Ethoxy-5-{6-[2-(8-methyl-quinolin-7-yl)-ethylamino]-pyrimidin-4-yl}-thiophene-2-carboxylic acid (*1) | 0.7 (D) | 435 |
| 23 | 3-Ethoxy-5-{6-[2-(3-ethoxy-naphthalen-2-yl)-ethylamino]-pyrimidin-4-yl}-thiophene-2-carboxylic acid (*1) | 1.2 (D) | 464.2 |
| 24 | 3-Ethoxy-5-{6-[2-(1H-indol-6-yl)-ethylamino]-pyrimidin-4-yl}-thiophene-2-carboxylic acid | 0.9 (D) | 409.2 |
| 25 | 2-Cyclobutoxy-4-{6-[2-(1-fluoro-3-methoxy-naphthalen-2-yl)-ethylamino]-pyrimidin-4-yl}-benzoic acid (*1) | 1.1 (D) | 488.3 |
| 26 | 3-Ethoxy-5-{6-[2-(7-methoxy-2,3-dihydro-benzo[1,4]dioxin-6-yl)-ethylamino]-pyrimidin-4-yl}-thiophene-2-carboxylic acid (*1) | 0.9 (D) | 458.1 |
| 27 | 5-{6-[2-(3-Cyano-benzo[b]thiophen-5-yl)-ethylamino]-pyrimidin-4-yl}-3-ethoxy-thiophene-2-carboxylic acid (*1) | 1.0 (D) | 451.2 |
| 28 | 4-{6-[2-(1-Methyl-naphthalen-2-yl)-ethylamino]-pyrimidin-4-yl}-2-propyl-benzoic acid | 1.0 (D) | 426 |
| 29 | 4-{6-[2-(1-Fluoro-3-methoxy-naphthalen-2-yl)-ethylamino]-pyrimidin-4-yl}-2-methylsulfanyl-benzoic acid (*1) | 1.0 (D) | 464.1 |
| 30 | 3-Ethoxy-5-{6-[2-(7-methyl-2,3-dihydro-benzo[1,4]dioxin-6-yl)-ethylamino]-pyrimidin-4-yl}-thiophene-2-carboxylic acid | 0.9 (D) | 442.3 |
| 31 | 3-Ethoxy-5-{6-[2-(3-isopropoxy-naphthalen-2-yl)-ethylamino]-pyrimidin-4-yl}-thiophene-2-carboxylic acid (*1) | 1.2 (D) | 478.3 |
| 32 | 3-Ethoxy-5-{6-[2-(1H-indol-5-yl)-ethylamino]-pyrimidin-4-yl}-thiophene-2-carboxylic acid | 0.9 (D) | 409 |
| 33 | 5-{6-[2-(1-Cyano-naphthalen-2-yl)-ethylamino]-pyrimidin-4-yl}-3-ethoxy-thiophene-2-carboxylic acid (*1) | 1.0 (D) | 445.1 |
| 34 | 3-Ethoxy-5-{6-[2-(6-methyl-benzo[b]thiophen-5-yl)-ethylamino]-pyrimidin-4-yl}-thiophene-2-carboxylic acid | 1.1 (D) | 439.9 |
| 35 | 3-Ethoxy-5-{6-[2-(8-fluoro-2,3-dihydro-benzo[1,4]dioxin-6-yl)-ethylamino]-pyrimidin-4-yl}-thiophene-2-carboxylic acid (*1) | 0.9 (D) | 446.2 |
| 36 | 3-Ethoxy-5-[6-(2-naphthalen-2-yl-ethylamino)-pyrimidin-4-yl]-thiophene-2-carboxylic acid | 1.1 (D) | 420.1 |
| 37 | (2-Ethoxy-4-{6-[2-(1-fluoro-3-methoxy-naphthalen-2-yl)-ethylamino]-pyrimidin-4-yl}-phenyl)-acetic acid (*1) | 0.9 (D) | 476 |
| 38 | 5-[6-(2-Benzo[b]thiophen-5-yl-ethylamino)-pyrimidin-4-yl]-benzofuran-2-carboxylic acid | 0.8 (D) | 416.2 |
| 39 | 3-Ethoxy-5-{6-[2-(7-ethoxy-2,3-dihydro-benzo[1,4]dioxin-6-yl)-ethylamino]-pyrimidin-4-yl}-thiophene-2-carboxylic acid | 1.0 (D) | 472 |
| 40 | 3-Ethoxy-5-{6-[2-(3-methyl-naphthalen-2-yl)-ethylamino]-pyrimidin-4-yl}-thiophene-2-carboxylic acid | 1.1 (D) | 434.3 |
| 41 | 5-{6-[2-(2,3-Dihydro-benzo[1,4]dioxin-6-yl)-ethylamino]-pyrimidin-4-yl}-3-ethoxy-thiophene-2-carboxylic acid | 0.9 (D) | 428.4 |
| 42 | 3-Ethoxy-5-{6-[2-(1-methyl-1H-indol-6-yl)-ethylamino]-pyrimidin-4-yl}-thiophene-2-carboxylic acid | 1.0 (D) | 423 |
| 43 | 5-{6-[2-(5,7-Difluoro-quinolin-6-yl)-ethylamino]-pyrimidin-4-yl}-3-ethoxy-thiophene-2-carboxylic acid (*1) | 0.9 (D) | 457.2 |
| 44 | 3-Ethoxy-5-[6-(2-indan-5-yl-ethylamino)-pyrimidin-4-yl]-thiophene-2-carboxylic acid | 1.1 (D) | 410.1 |
| 45 | 5-{6-[2-(3-Difluoromethoxy-naphthalen-2-yl)-ethylamino]-pyrimidin-4-yl}-3-ethoxy-thiophene-2-carboxylic acid (*1) | 1.1 (D) | 486.3 |
| 46 | 5-[6-(2-Benzofuran-6-yl-ethylamino)-pyrimidin-4-yl]-3-ethoxy-thiophene-2-carboxylic acid (*1) | 1.0 (D) | 410 |
| 47 | 3-Ethoxy-5-{6-[2-(3-methyl-benzo[b]thiophen-5-yl)-ethylamino]-pyrimidin-4-yl}-thiophene-2-carboxylic acid | 1.1 (D) | 440.1 |
| 48 | 3-(2-Hydroxy-ethoxy)-5-{6-[2-(1-methyl-naphthalen-2-yl)-ethylamino]-pyrimidin-4-yl}-thiophene-2-carboxylic acid (*1) | 1.0 (D) | 450.1 |
| 49 | 3-Ethoxy-5-{6-[2-(6-methoxy-benzo[1,3]dioxol-5-yl)-ethylamino]-pyrimidin-4-yl}-thiophene-2-carboxylic acid | 0.9 (D) | 444.2 |

TABLE 4-continued

Examples 1-337

| Ex. | Compound | t$_R$ [min] (LC-MS) | MS Data m/z [M + H]$^+$ |
|---|---|---|---|
| 50 | 5-[6-(2-Benzofuran-5-yl-ethylamino)-pyrimidin-4-yl]-3-ethoxy-thiophene-2-carboxylic acid (*1) | 1.0 (D) | 410.1 |
| 51 | 5-{6-[2-(8-Chloro-2,3-dihydro-benzo[1,4]dioxin-6-yl)-ethylamino]-pyrimidin-4-yl}-3-ethoxy-thiophene-2-carboxylic acid | 1.0 (D) | 462.1 |
| 52 | 4-{6-[2-(3-Cyano-1-methyl-naphthalen-2-yl)-ethylamino]-pyrimidin-4-yl}-2-methylsulfanyl-benzoic acid (*1) | 0.9 (D) | 455.1 |
| 53 | (2-Ethoxy-4-{6-[2-(6-ethoxy-benzo[b]thiophen-5-yl)-ethylamino]-pyrimidin-4-yl}-phenoxy)-acetic acid (*1) | 0.9 (D) | 494 |
| 54 | 4-{6-[2-(3-Cyano-1-methyl-naphthalen-2-yl)-ethylamino]-pyrimidin-4-yl}-2-ethoxy-benzoic acid (*1) | 0.9 (D) | 453 |
| 55 | 5-{6-[2-(4,5-Difluoro-7-methoxy-2-methyl-benzofuran-6-yl)-ethylamino]-pyrimidin-4-yl}-3-ethoxy-thiophene-2-carboxylic acid | 1.1 (D) | 490.4 |
| 56 | 5-[6-(2-Chroman-6-yl-ethylamino)-pyrimidin-4-yl]-3-ethoxy-thiophene-2-carboxylic acid | 1.0 (D) | 426.3 |
| 57 | 3-(3-Ethoxy-5-{6-[2-(1-methyl-naphthalen-2-yl)-ethylamino]-pyrimidin-4-yl}-thiophen-2-yl)-propionic acid | 1.0 (D) | 462 |
| 58 | 5-[6-(2-Chroman-7-yl-ethylamino)-pyrimidin-4-yl]-3-ethoxy-thiophene-2-carboxylic acid | 1.0 (D) | 426.2 |
| 59 | 4-{6-[2-(3-Methoxy-1-methyl-naphthalen-2-yl)-ethylamino]-pyrimidin-4-yl}-2-methylsulfanyl-benzoic acid (*1) | 1.0 (D) | 460.3 |
| 60 | 3-Ethoxy-5-{6-[2-(3-methoxy-5,6,7,8-tetrahydro-naphthalen-2-yl)-ethylamino]-pyrimidin-4-yl}-thiophene-2-carboxylic acid | 1.2 (D) | 454.1 |
| 61 | (2-Ethoxy-4-{6-[2-(3-methoxy-1-methyl-naphthalen-2-yl)-ethylamino]-pyrimidin-4-yl}-phenyl)-acetic acid (*1) | 0.9 (D) | 472.4 |
| 62 | 5-{6-[2-(3-Chloro-naphthalen-2-yl)-ethylamino]-pyrimidin-4-yl}-3-ethoxy-thiophene-2-carboxylic acid | 1.2 (D) | 454.2 |
| 63 | 2-Cyclobutoxy-4-{6-[2-(6-methoxy-benzo[b]thiophen-5-yl)-ethylamino]-pyrimidin-4-yl}-benzoic acid (*1) | 1.0 (D) | 476.4 |
| 64 | 5-{6-[2-(6-Cyano-benzo[1,3]dioxol-5-yl)-ethylamino]-pyrimidin-4-yl}-3-ethoxy-thiophene-2-carboxylic acid (*1) | 0.9 (D) | 439.2 |
| 65 | 3-Ethoxy-5-{6-[2-(1-methyl-1H-indol-5-yl)-ethylamino]-pyrimidin-4-yl}-thiophene-2-carboxylic acid | 1.0 (D) | 423.3 |
| 66 | 3-Ethoxy-5-{6-[2-(8-fluoro-naphthalen-2-yl)-ethylamino]-pyrimidin-4-yl}-thiophene-2-carboxylic acid (*1) | 1.1 (D) | 438.3 |
| 67 | 5-{6-[2-(2,3-Dihydro-benzofuran-6-yl)-ethylamino]-pyrimidin-4-yl}-3-ethoxy-thiophene-2-carboxylic acid | 0.9 (D) | 412.3 |
| 68 | 2-Ethoxy-4-{6-[2-(3-methoxy-1-methyl-naphthalen-2-yl)-ethylamino]-pyrimidin-4-yl}-benzoic acid (*1) | 1.0 (D) | 457.2002 |
| 69 | 3-Ethoxy-5-{6-[2-(5-fluoro-quinolin-6-yl)-ethylamino]-pyrimidin-4-yl}-thiophene-2-carboxylic acid (*1) | 0.8 (D) | 439.1 |
| 70 | 2-Cyclobutoxy-4-{6-[2-(7-methylsulfanyl-2,3-dihydro-benzo[1,4]dioxin-6-yl)-ethylamino]-pyrimidin-4-yl}-benzoic acid | 0.9 (D) | 494.3 |
| 71 | 5-{6-[2-(1-Amino-naphthalen-2-yl)-ethylamino]-pyrimidin-4-yl}-3-ethoxy-thiophene-2-carboxylic acid | 0.9 (D) | 435.1 |
| 72 | 5-{6-[2-(7-Fluoro-1-methyl-1,2,3,4-tetrahydro-quinolin-6-yl)-ethylamino]-pyrimidin-4-yl}-3-trifluoromethyl-thiophene-2-carboxylic acid | 1.3 (D) | 481.4 |
| 73 | 4-{6-[2-(3-Cyano-1-fluoro-naphthalen-2-yl)-ethylamino]-pyrimidin-4-yl}-2-ethoxy-benzoic acid (*1) | 0.9 (D) | 457.3 |
| 74 | 2-Fluoro-4-{6-[2-(1-methyl-naphthalen-2-yl)-ethylamino]-pyrimidin-4-yl}-6-propyl-benzoic acid | 1.1 (D) | 444.2 |
| 75 | 3-Ethoxy-5-{6-[2-(1-vinyl-naphthalen-2-yl)-ethylamino]-pyrimidin-4-yl}-thiophene-2-carboxylic acid (*1) | 1.2 (D) | 446.2 |
| 76 | 2-Isobutyl-4-{6-[2-(1-methyl-naphthalen-2-yl)-ethylamino]-pyrimidin-4-yl}-benzoic acid | 1.1 (D) | 440.4 |
| 77 | 4-{6-[2-(6-Cyano-benzo[b]thiophen-5-yl)-ethylamino]-pyrimidin-4-yl}-2-methylsulfanyl-benzoic acid (*1) | 0.8 (D) | 447.2 |
| 78 | 3-Ethoxy-5-{6-[2-(7-methylsulfanyl-2,3-dihydro-benzo[1,4]dioxin-6-yl)-ethylamino]-pyrimidin-4-yl}-thiophene-2-carboxylic acid | 1.0 (D) | 474 |
| 79 | 2-Cyclobutoxy-4-{6-[2-(3-methoxy-1-methyl-naphthalen-2-yl)-ethylamino]-pyrimidin-4-yl}-benzoic acid (*1) | 1.1 (D) | 484.2 |
| 80 | (2-Ethoxy-4-{6-[2-(6-methoxy-benzo[b]thiophen-5-yl)-ethylamino]-pyrimidin-4-yl}-phenoxy)-acetic acid (*1) | 0.8 (D) | 480 |
| 81 | 6-{6-[2-(7-Methoxy-2,3-dihydro-benzo[1,4]dioxin-6-yl)-ethylamino]-pyrimidin-4-yl}-benzofuran-2-carboxylic acid | 0.7 (D) | 448.2 |
| 82 | (4-{6-[2-(6-Cyano-benzo[b]thiophen-5-yl)-ethylamino]-pyrimidin-4-yl}-2-ethoxy-phenyl)-acetic acid (*1) | 0.8 (D) | 459.3 |
| 83 | 2-Difluoromethoxy-4-{6-[2-(1-methyl-naphthalen-2-yl)-ethylamino]-pyrimidin-4-yl}-benzoic acid | 1.0 (D) | 450 |
| 84 | (4-{6-[2-(3-Cyano-naphthalen-2-yl)-ethylamino]-pyrimidin-4-yl}-2-ethoxy-phenoxy)-acetic acid (*1) | 0.8 (D) | 469.3 |
| 85 | 6-[6-(2-Benzo[b]thiophen-5-yl-ethylamino)-pyrimidin-4-yl]-benzofuran-2-carboxylic acid | 0.76 (B) | 416.16 |
| 86 | 5-{6-[2-(5,8-Difluoro-quinolin-6-yl)-ethylamino]-pyrimidin-4-yl}-3-ethoxy-thiophene-2-carboxylic acid (*1) | 0.9 (D) | 457.2 |

TABLE 4-continued

Examples 1-337

| Ex. | Compound | $t_R$ [min] (LC-MS) | MS Data m/z $[M + H]^+$ |
|---|---|---|---|
| 87 | 5-{6-[2-(7-Chloro-8-methyl-quinolin-6-yl)-ethylamino]-pyrimidin-4-yl}-3-ethoxy-thiophene-2-carboxylic acid (*1) | 1.0 (D) | 469.4 |
| 88 | 5-[6-(2-Benzothiazol-5-yl-ethylamino)-pyrimidin-4-yl]-3-ethoxy-thiophene-2-carboxylic acid (*1) | 0.8 (D) | 427.4 |
| 89 | (2-Ethoxy-4-{6-[2-(3-isopropoxy-naphthalen-2-yl)-ethylamino]-pyrimidin-4-yl}-phenoxy)-acetic acid (*1) | 0.9 (D) | 502.4 |
| 90 | 5-{6-[2-(1-Chloro-naphthalen-2-yl)-ethylamino]-pyrimidin-4-yl}-3-ethoxy-thiophene-2-carboxylic acid | 1.2 (D) | 454.2 |
| 91 | 5-[6-(2-Benzothiazol-6-yl-ethylamino)-pyrimidin-4-yl]-3-ethoxy-thiophene-2-carboxylic acid (*1) | 0.8 (D) | 426.08 |
| 92 | 4-{6-[2-(3-Cyano-naphthalen-2-yl)-ethylamino]-pyrimidin-4-yl}-2-ethoxy-benzoic acid (*1) | 0.9 (D) | 439.1 |
| 93 | 5-{6-[2-(7-Methoxy-2,3-dihydro-benzo[1,4]dioxin-6-yl)-ethylamino]-pyrimidin-4-yl}-benzofuran-2-carboxylic acid | 0.7 (D) | 448 |
| 94 | 3-Ethoxy-5-{6-[2-(4-fluoro-7-methoxy-2-methyl-benzo[b]thiophen-6-yl)-ethylamino]-pyrimidin-4-yl}-thiophene-2-carboxylic acid (*1) | 0.85 (A) | 487.98 |
| 95 | 3-Ethoxy-5-{6-[2-(8-methyl-2,3-dihydro-benzo[1,4]dioxin-6-yl)-ethylamino]-pyrimidin-4-yl}-thiophene-2-carboxylic acid (*1) | 1.0 (D) | 442.3 |
| 96 | 5-[6-(2-Benzo[b]thiophen-5-yl-ethylamino)-2-methyl-pyrimidin-4-yl]-3-ethoxy-thiophene-2-carboxylic acid (*1) | 0.9 (D) | 440.3 |
| 97 | 4-{6-[2-(7-Cyano-2,3-dihydro-benzo[1,4]dioxin-6-yl)-ethylamino]-pyrimidin-4-yl}-2-methylsulfanyl-benzoic acid (*1) | 0.7 (D) | 449 |
| 98 | 3-Ethoxy-5-{6-[2-(7-fluoro-quinolin-6-yl)-ethylamino]-pyrimidin-4-yl}-thiophene-2-carboxylic acid (*1) | 0.8 (D) | 439.1 |
| 99 | (2-Ethoxy-4-{6-[2-(7-ethoxy-2,3-dihydro-benzo[1,4]dioxin-6-yl)-ethylamino]-pyrimidin-4-yl}-phenoxy)-acetic acid | 0.7 (D) | 496 |
| 100 | 2-Cyclobutoxy-4-{6-[2-(6-methoxy-benzofuran-5-yl)-ethylamino]-pyrimidin-4-yl}-benzoic acid | 0.9 (D) | 460.3 |
| 101 | 2-Ethoxy-4-{6-[2-(1-fluoro-3-methoxy-naphthalen-2-yl)-ethylamino]-pyrimidin-4-yl}-benzoic acid | 1.0 (D) | 461.1751 |
| 102 | (2-Ethoxy-4-{6-[2-(6-methoxy-4-methyl-benzofuran-5-yl)-ethylamino]-pyrimidin-4-yl}-phenoxy)-acetic acid | 0.9 (D) | 478.3 |
| 103 | (2-Ethoxy-4-{6-[2-(3-ethynyl-naphthalen-2-yl)-ethylamino]-pyrimidin-4-yl}-phenoxy)-acetic acid | 0.8 (D) | 468.3 |
| 104 | 3-Ethoxy-5-{6-[2-(7-fluoro-4-methyl-3,4-dihydro-2H-benzo[1,4]oxazin-6-yl)-ethylamino]-pyrimidin-4-yl}-thiophene-2-carboxylic acid | 1.0 (D) | 459.1 |
| 105 | 2-Ethoxy-4-{6-[2-(3-ethynyl-naphthalen-2-yl)-ethylamino]-pyrimidin-4-yl}-benzoic acid | 1.0 (D) | 438 |
| 106 | 3-Ethoxy-5-{6-[2-(6-fluoro-isoquinolin-7-yl)-ethylamino]-pyrimidin-4-yl}-thiophene-2-carboxylic acid (*1) | 0.6 (D) | 439.2 |
| 107 | (4-{6-[2-(1,3-Difluoro-naphthalen-2-yl)-ethylamino]-pyrimidin-4-yl}-2-ethoxy-phenyl)-acetic acid (*1) | 0.9 (D) | 464.3 |
| 108 | 5-{6-[2-(7-Fluoro-isoquinolin-6-yl)-ethylamino]-pyrimidin-4-yl}-3-trifluoromethyl-thiophene-2-carboxylic acid (*1) | 0.9 (D) | 463.1 |
| 109 | 2-Ethoxy-4-{6-[2-(6-methoxy-benzo[b]thiophen-5-yl)-ethylamino]-pyrimidin-4-yl}-benzoic acid (*1) | 0.9 (D) | 450.1 |
| 110 | 2-Ethylsulfanyl-4-{6-[2-(7-methoxy-2,3-dihydro-benzo[1,4]dioxin-6-yl)-ethylamino]-pyrimidin-4-yl}-benzoic acid | 0.8 (D) | 468.1 |
| 111 | 5-[6-(2-Benzo[1,3]dioxol-5-yl-ethylamino)-pyrimidin-4-yl]-3-ethoxy-thiophene-2-carboxylic acid | 0.9 (D) | 414.2 |
| 112 | (2-Ethoxy-4-{6-[2-(6-methoxy-benzofuran-5-yl)-ethylamino]-pyrimidin-4-yl}-phenoxy)-acetic acid | 0.7 (D) | 464.1 |
| 113 | 4-{6-[2-(7-Cyano-2,3-dihydro-benzo[1,4]dioxin-6-yl)-ethylamino]-pyrimidin-4-yl}-2-cyclobutoxy-benzoic acid (*1) | 0.8 (D) | 473.3 |
| 114 | 5-{6-[2-(2,3-Dihydro-benzofuran-5-yl)-ethylamino]-pyrimidin-4-yl}-3-ethoxy-thiophene-2-carboxylic acid (*1) | 0.9 (D) | 412.1 |
| 115 | (4-{6-[2-(1-Fluoro-3-methoxy-naphthalen-2-yl)-ethylamino]-pyrimidin-4-yl}-2-methylsulfanyl-phenyl)-acetic acid (*1) | 0.9 (D) | 478.3 |
| 116 | 4-{6-[2-(7-Methoxy-2,3-dihydro-benzo[1,4]dioxin-6-yl)-ethylamino]-pyrimidin-4-yl}-2-methylsulfanyl-benzoic acid | 0.8 (D) | 453.9 |
| 117 | 5-{6-[2-(7-Chloro-8-fluoro-quinolin-6-yl)-ethylamino]-pyrimidin-4-yl}-3-ethoxy-thiophene-2-carboxylic acid (*1) | 0.9 (D) | 473.1 |
| 118 | (2-Ethoxy-4-{6-[2-(6-methoxy-benzo[b]thiophen-5-yl)-ethylamino]-pyrimidin-4-yl}-phenyl)-acetic acid (*1) | 0.8 (D) | 464.3 |
| 119 | 5-{6-[2-(6-Difluoromethoxy-benzo[1,3]dioxol-5-yl)-ethylamino]-pyrimidin-4-yl}-3-ethoxy-thiophene-2-carboxylic acid | 1.0 (D) | 480.2 |
| 120 | (2-Ethoxy-4-{6-[2-(7-methoxy-2,3-dihydro-benzo[1,4]dioxin-6-yl)-ethylamino]-pyrimidin-4-yl}-phenoxy)-acetic acid (*1) | 1.1 (D) | 482.3 |
| 121 | {4-[6-(2-Benzo[b]thiophen-5-yl-ethylamino)-pyrimidin-4-yl]-2-ethoxy-phenoxyl-acetic acid | 0.8 (D) | 450.3 |
| 122 | (2-Ethoxy-4-{6-[2-(3-methoxy-naphthalen-2-yl)-ethylamino]-pyrimidin-4-yl}-phenoxy)-acetic acid | 0.8 (D) | 474.1 |
| 123 | [2-(5,7-Difluoro-quinolin-6-yl)-ethyl]-(6-quinolin-6-yl-pyrimidin-4-yl)-amine | 0.7 (D) | 414.1 |

TABLE 4-continued

Examples 1-337

| Ex. | Compound | $t_R$ [min] (LC-MS) | MS Data m/z [M + H]$^+$ |
|---|---|---|---|
| 124 | 2-Cyclobutoxy-4-{6-[2-(5-methoxy-benzofuran-6-yl)-ethylamino]-pyrimidin-4-yl}-benzoic acid | 0.9 (D) | 460.1 |
| 125 | 4-[6-(2-Benzo[b]thiophen-5-yl-ethylamino)-pyrimidin-4-yl]-2-cyclobutoxy-benzoic acid | 1.0 (D) | 446 |
| 126 | 2-Ethoxy-4-{6-[2-(6-ethoxy-benzo[b]thiophen-5-yl)-ethylamino]-pyrimidin-4-yl}-benzoic acid (*1) | 1.0 (D) | 464.3 |
| 127 | 2-{6-[2-(1-Methyl-naphthalen-2-yl)-ethylamino]-pyrimidin-4-yl}-1H-indole-4-carboxylic acid | 1.0 (D) | 423.3 |
| 128 | 4-{6-[2-(6-Cyano-benzo[b]thiophen-5-yl)-ethylamino]-pyrimidin-4-yl}-2-ethoxy-benzoic acid (*1) | 0.8 (D) | 445.2 |
| 129 | (4-{6-[2-(3-Difluoromethoxy-naphthalen-2-yl)-ethylamino]-pyrimidin-4-yl}-2-ethoxy-phenoxy)-acetic acid (*1) | 0.8 (D) | 510.3 |
| 130 | (E)-3-(3-Ethoxy-5-{6-[2-(1-methyl-naphthalen-2-yl)-ethylamino]-pyrimidin-4-yl}-thiophen-2-yl)-acrylic acid | 1.2 (D) | 460.3 |
| 131 | 2-Cyclobutoxy-4-{6-[2-(1-ethynyl-naphthalen-2-yl)-ethylamino]-pyrimidin-4-yl}-benzoic acid (*1) | 1.1 (D) | 464.4 |
| 132 | 4-[6-(2-Benzo[b]thiophen-5-yl-ethylamino)-pyrimidin-4-yl]-2-methylsulfanyl-benzoic acid | 0.9 (D) | 422.1 |
| 133 | 5-{6-[2-(1,3-Dimethyl-1H-indol-5-yl)-ethylamino]-pyrimidin-4-yl}-3-ethoxy-thiophene-2-carboxylic acid | 1.0 (D) | 437.3 |
| 134 | 3-(2-Ethoxy-4-{6-[2-(1-methyl-naphthalen-2-yl)-ethylamino]-pyrimidin-4-yl}-phenoxy)-propionic acid (*1) | 0.8 (D) | 472.4 |
| 135 | 5-[6-(2-Benzo[d]isothiazol-5-yl-ethylamino)-pyrimidin-4-yl]-3-ethoxy-thiophene-2-carboxylic acid (*1) | 0.9 (D) | 427.2 |
| 136 | (2-Ethoxy-4-{6-[2-(1-fluoro-naphthalen-2-yl)-ethylamino]-pyrimidin-4-yl}-phenoxy)-acetic acid | 0.8 (D) | 462.4 |
| 137 | 4-{6-[2-(7-Ethoxy-2,3-dihydro-benzo[1,4]dioxin-6-yl)-ethylamino]-pyrimidin-4-yl}-2-methylsulfanyl-benzoic acid | 0.8 (D) | 468.3 |
| 138 | 4-{6-[2-(2,3-Dihydro-benzo[b]thiophen-5-yl)-ethylamino]-pyrimidin-4-yl}-2-methylsulfanyl-benzoic acid (*1) | 0.9 (D) | 424.2 |
| 139 | (2-Ethoxy-4-{6-[2-(6-methoxy-benzofuran-5-yl)-ethylamino]-pyrimidin-4-yl}-phenyl)-acetic acid | 0.8 (D) | 448 |
| 140 | (2-Ethoxy-4-{6-[2-(1-ethynyl-naphthalen-2-yl)-ethylamino]-pyrimidin-4-yl}-phenoxy)-acetic acid (*1) | 0.8 (D) | 467.1 |
| 141 | 2-Ethoxy-4-{6-[2-(1-ethynyl-naphthalen-2-yl)-ethylamino]-pyrimidin-4-yl}-benzoic acid (*1) | 1.0 (D) | 438.1 |
| 142 | (2-Ethoxy-4-{6-[2-(6-fluoro-benzofuran-5-yl)-ethylamino]-pyrimidin-4-yl}-phenoxy)-acetic acid | 0.7 (D) | 452.3 |
| 143 | (2-Ethoxy-4-{6-[2-(3-methoxy-5,6,7,8-tetrahydro-naphthalen-2-yl)-ethylamino]-pyrimidin-4-yl}-phenoxy)-acetic acid | 0.9 (D) | 478.4 |
| 144 | {4-[6-(2-Benzo[b]thiophen-6-yl-ethylamino)-pyrimidin-4-yl]-2-ethoxy-phenoxyl-acetic acid | 0.8 (D) | 450.3 |
| 145 | (2-Ethoxy-4-{6-[2-(7-methylsulfanyl-2,3-dihydro-benzo[1,4]dioxin-6-yl)-ethylamino]-pyrimidin-4-yl}-phenoxy)-acetic acid | 0.7 (D) | 498.3 |
| 146 | 5-[6-(2-Benzooxazol-6-yl-ethylamino)-pyrimidin-4-yl]-3-ethoxy-thiophene-2-carboxylic acid (*1) | 0.8 (D) | 411.2 |
| 147 | 4-[6-(2-Benzo[b]thiophen-6-yl-ethylamino)-pyrimidin-4-yl]-2-cyclobutoxy-benzoic acid | 1.0 (D) | 446.3 |
| 148 | (3-Ethoxy-5-{6-[2-(1-methyl-naphthalen-2-yl)-ethylamino]-pyrimidin-4-yl}-thiophen-2-yl)-acetic acid (*1) | 1.0 (D) | 448 |
| 149 | 5-{6-[2-(6-Chloro-3,4-dihydro-2H-benzo[1,4]oxazin-7-yl)-ethylamino]-pyrimidin-4-yl}-3-ethoxy-thiophene-2-carboxylic acid (*1) | 0.9 (D) | 460.1 |
| 150 | 2-Butoxy-6-fluoro-4-{6-[2-(1-methyl-naphthalen-2-yl)-ethylamino]-pyrimidin-4-yl}-benzoic acid | 1.2 (D) | 474.1 |
| 151 | 2-Ethoxy-4-{6-[2-(6-methoxy-benzofuran-5-yl)-ethylamino]-pyrimidin-4-yl}-benzoic acid | 0.8 (D) | 434.3 |
| 152 | 4-{6-[2-(5-Methoxy-benzo[b]thiophen-6-yl)-ethylamino]-pyrimidin-4-yl}-2-methylsulfanyl-benzoic acid | 0.9 (D) | 452.2 |
| 153 | 4-{6-[2-(5,7-Difluoro-quinolin-6-yl)-ethylamino]-pyrimidin-4-yl}-2-ethylsulfanyl-benzoic acid | 0.8 (D) | 467 |
| 154 | {4-[6-(2-Chroman-7-yl-ethylamino)-pyrimidin-4-yl]-2-ethoxy-phenoxyl-acetic acid | 0.7 (D) | 450.1 |
| 155 | 4-[6-(2-Benzo[b]thiophen-5-yl-ethylamino)-pyrimidin-4-yl]-2-ethoxy-benzoic acid | 0.9 (D) | 420.1 |
| 156 | {6-[3-Ethoxy-4-(1H-tetrazol-5-yl)-phenyl]-pyrimidin-4-yl}-[2-(1-methyl-naphthalen-2-yl)-ethyl]-amine | 1.0 (D) | 452.3 |
| 157 | (2-Ethoxy-4-{6-[2-(6-methoxy-4-methyl-benzofuran-5-yl)-ethylamino]-pyrimidin-4-yl}-phenyl)-acetic acid | 0.8 (D) | 462.4 |
| 158 | 2-Ethylsulfanyl-4-{6-[2-(6-methoxy-benzofuran-5-yl)-ethylamino]-pyrimidin-4-yl}-benzoic acid | 0.9 (D) | 450.3 |
| 159 | (2-Ethoxy-4-{6-[2-(5-methoxy-benzofuran-6-yl)-ethylamino]-pyrimidin-4-yl}-phenoxy)-acetic acid | 0.7 (D) | 464.1 |
| 160 | (2-Ethoxy-4-{6-[2-(3-ethoxy-naphthalen-2-yl)-ethylamino]-pyrimidin-4-yl}-phenoxy)-acetic acid (*1) | 0.9 (D) | 488.4 |
| 161 | 2-{4-[6-(2-Benzo[b]thiophen-5-yl-ethylamino)-pyrimidin-4-yl]-2-ethoxy-phenyl}-propionic acid | 0.8 (D) | 448.3 |

TABLE 4-continued

Examples 1-337

| Ex. | Compound | $t_R$ [min] (LC-MS) | MS Data m/z [M + H]$^+$ |
|---|---|---|---|
| 162 | 2-Ethoxy-4-{6-[2-(3-methoxy-naphthalen-2-yl)-ethylamino]-pyrimidin-4-yl}-benzoic acid | 0.9 (D) | 444.1 |
| 163 | (4-{6-[2-(3-Methoxy-1-methyl-naphthalen-2-yl)-ethylamino]-pyrimidin-4-yl}-2-methylsulfanyl-phenyl)-acetic acid (*1) | 0.9 (D) | 474.3 |
| 164 | 5-{6-[2-(1,3-Dihydro-isobenzofuran-5-yl)-ethylamino]-pyrimidin-4-yl}-3-ethoxy-thiophene-2-carboxylic acid (*1) | 1.2 (D) | 412.3 |
| 165 | 5-{6-[2-(6-Chloro-2,2-difluoro-benzo[1,3]dioxol-5-yl)-ethylamino]-pyrimidin-4-yl}-3-ethoxy-thiophene-2-carboxylic acid (*1) | 1.1 (D) | 484 |
| 166 | (2-Ethoxy-4-{6-[2-(1-methyl-naphthalen-2-yl)-ethylamino]-pyrimidin-4-yl}-phenoxy)-acetic acid | 0.8 (D) | 458.4 |
| 167 | 4-[6-(2-Benzo[b]thiophen-6-yl-ethylamino)-pyrimidin-4-yl]-2-ethoxy-benzoic acid | 0.9 (D) | 420.3 |
| 168 | 2-Cyclobutoxy-4-{6-[2-(1-methyl-naphthalen-2-yl)-ethylamino]-pyrimidin-4-yl}-benzoic acid | 1.1 (D) | 454.4 |
| 169 | 2-Butoxy-4-{6-[2-(1-methyl-naphthalen-2-yl)-ethylamino]-pyrimidin-4-yl}-benzoic acid | 1.1 (D) | 456.4 |
| 170 | 2-Cyclobutoxy-4-{6-[2-(2,3-dihydro-benzo[b]thiophen-5-yl)-ethylamino]-pyrimidin-4-yl}-benzoic acid (*1) | 1.0 (D) | 448.3 |
| 171 | 2-Cyclobutoxy-4-{6-[2-(3-ethoxy-naphthalen-2-yl)-ethylamino]-pyrimidin-4-yl}-benzoic acid (*1) | 1.1 (D) | 484.4 |
| 172 | 2-Ethoxy-4-{6-[2-(1-methyl-naphthalen-2-yl)-ethylamino]-pyrimidin-4-yl}-benzoic acid | 1.0 (D) | 428 |
| 173 | 3-Ethoxy-5-{6-[2-(7-methoxy-1,2,3,4-tetrahydro-quinolin-6-yl)-ethylamino]-pyrimidin-4-yl}-thiophene-2-carboxylic acid (*1) | 0.7 (D) | 454.1 |
| 174 | 2-Ethoxy-4-{6-[2-(4-fluoro-3-methoxy-naphthalen-2-yl)-ethylamino]-pyrimidin-4-yl}-benzoic acid (*1) | 1.0 (D) | 462.3 |
| 175 | (2-Ethoxy-4-{6-[2-(7-methoxy-2,3-dihydro-benzo[1,4]dioxin-6-yl)-ethylamino]-pyrimidin-4-yl}-phenyl)-acetic acid | 0.7 (D) | 466.3 |
| 176 | 4-[6-(2-Benzo[b]thiophen-6-yl-ethylamino)-pyrimidin-4-yl]-2-methylsulfanyl-benzoic acid | 0.9 (D) | 422.2 |
| 177 | 3-Ethoxy-5-{6-[2-(7-methyl-quinolin-6-yl)-ethylamino]-pyrimidin-4-yl}-thiophene-2-carboxylic acid (*1) | 0.6 (D) | 435.3 |
| 178 | 5-{6-[2-(4-Chloro-7-methyl-quinolin-6-yl)-ethylamino]-pyrimidin-4-yl}-3-ethoxy-thiophene-2-carboxylic acid (*1) | 0.9 (D) | 469.1 |
| 179 | (4-{6-[2-(7-Chloro-8-methyl-quinolin-6-yl)-ethylamino]-pyrimidin-4-yl}-2-ethoxy-phenoxy)-acetic acid (*1) | 0.7 (D) | 493.1 |
| 180 | 2-Cyclobutoxy-4-{6-[2-(3-difluoromethoxy-naphthalen-2-yl)-ethylamino]-pyrimidin-4-yl}-benzoic acid (*1) | 1.1 (D) | 506.3 |
| 181 | (4-{6-[2-(2,3-Dihydro-benzo[b]thiophen-5-yl)-ethylamino]-pyrimidin-4-yl}-2-ethoxy-phenyl)-acetic acid (*1) | 0.8 (D) | 436.3 |
| 182 | 2-Cyclobutoxy-4-{6-[2-(1-fluoro-naphthalen-2-yl)-ethylamino]-pyrimidin-4-yl}-benzoic acid | 1.1 (D) | 458.3 |
| 183 | 4-{6-[2-(1-Methyl-naphthalen-2-yl)-ethylamino]-pyrimidin-4-yl}-2-propoxy-benzoic acid | 1.0 (D) | 442.2 |
| 184 | (2-Ethoxy-4-{6-[2-(7-methyl-2,3-dihydro-benzo[1,4]dioxin-6-yl)-ethylamino]-pyrimidin-4-yl}-phenoxy)-acetic acid | 0.7 (D) | 466.3 |
| 185 | 4-[6-(2-Indan-5-yl-ethylamino)-pyrimidin-4-yl]-2-methylsulfanyl-benzoic acid | 0.9 (D) | 406.3 |
| 186 | 4-{6-[2-(4-Chloro-3-methoxy-naphthalen-2-yl)-ethylamino]-pyrimidin-4-yl}-2-methylsulfanyl-benzoic acid (*1) | 1.0 (D) | 480.1 |
| 187 | 2-Cyclobutoxy-4-{6-[2-(7-methoxy-2,3-dihydro-benzo[1,4]dioxin-6-yl)-ethylamino]-pyrimidin-4-yl}-benzoic acid (*1) | 0.9 (D) | 478.2 |
| 188 | 2-Ethoxy-4-{6-[2-(3-ethoxy-naphthalen-2-yl)-ethylamino]-pyrimidin-4-yl}-benzoic acid (*1) | 1.0 (D) | 458.4 |
| 189 | {4-[6-(2-Benzo[b]thiophen-5-yl-ethylamino)-pyrimidin-4-yl]-2-ethoxy-phenyl}-acetic acid | 0.8 (D) | 434.1 |
| 190 | 4-{6-[2-(6-Methyl-benzo[b]thiophen-5-yl)-ethylamino]-pyrimidin-4-yl}-2-methylsulfanyl-benzoic acid | 0.9 (D) | 436.3 |
| 191 | (4-{6-[2-(5,7-Difluoro-quinolin-6-yl)-ethylamino]-pyrimidin-4-yl}-2-ethoxy-phenoxy)-acetic acid (*1) | 0.7 (D) | 481.3 |
| 192 | (2-Ethoxy-4-{6-[2-(7-ethoxy-2,3-dihydro-benzo[1,4]dioxin-6-yl)-ethylamino]-pyrimidin-4-yl}-phenyl)-acetic acid | 0.8 (D) | 480.4 |
| 193 | 4-{6-[2-(6-Methoxy-benzofuran-5-yl)-ethylamino]-pyrimidin-4-yl}-2-methylsulfanyl-benzoic acid | 0.8 (D) | 436.3 |
| 194 | (2-Ethoxy-4-{6-[2-(1H-indol-6-yl)-ethylamino]-pyrimidin-4-yl}-phenoxy)-acetic acid | 0.7 (D) | 433.2 |
| 195 | (2-Ethoxy-4-{6-[2-(6-fluoro-benzofuran-5-yl)-ethylamino]-pyrimidin-4-yl}-phenyl)-acetic acid | 0.8 (D) | 436.3 |
| 196 | 2-Cyclobutoxy-4-{6-[2-(7-ethoxy-2,3-dihydro-benzo[1,4]dioxin-6-yl)-ethylamino]-pyrimidin-4-yl}-benzoic acid | 0.9 (D) | 492.4 |
| 197 | (4-{6-[2-(7-Methoxy-2,3-dihydro-benzo[1,4]dioxin-6-yl)-ethylamino]-pyrimidin-4-yl}-2-methylsulfanyl-phenyl)-acetic acid (*1) | 0.7 (D) | 468.3 |
| 198 | {4-[6-(2-Benzofuran-5-yl-ethylamino)-pyrimidin-4-yl]-2-ethoxy-phenoxy}-acetic acid (*1) | 0.7 (D) | 434.1 |
| 199 | 6-{6-[2-(7-Methoxy-2,3-dihydro-benzo[1,4]dioxin-6-yl)-ethylamino]-pyrimidin-4-yl}-benzofuran-3-carboxylic acid | 0.74 (B) | 448.16 |

TABLE 4-continued

Examples 1-337

| Ex. | Compound | $t_R$ [min] (LC-MS) | MS Data m/z [M + H]$^+$ |
|---|---|---|---|
| 200 | 2-Cyclobutoxy-4-{6-[2-(6-fluoro-benzofuran-5-yl)-ethylamino]-pyrimidin-4-yl}-benzoic acid | 1.0 (D) | 448 |
| 201 | 2-(2-Ethoxy-4-{6-[2-(7-methoxy-2,3-dihydro-benzo[1,4]dioxin-6-yl)-ethylamino]-pyrimidin-4-yl}-phenoxy)-propionic acid | 0.7 (D) | 496.4 |
| 202 | 2-{4-[6-(2-Benzo[b]thiophen-5-yl-ethylamino)-pyrimidin-4-yl]-2-ethoxy-phenoxyl-propionic acid | 0.8 (D) | 464 |
| 203 | 4-{6-[2-(7-Cyano-2,3-dihydro-benzo[1,4]dioxin-6-yl)-ethylamino]-pyrimidin-4-yl}-2-ethoxy-benzoic acid (*1) | 0.7 (D) | 447 |
| 204 | 4-{6-[2-(4-Methyl-benzo[b]thiophen-5-yl)-ethylamino]-pyrimidin-4-yl}-2-methylsulfanyl-benzoic acid (*1) | 0.9 (D) | 436.2 |
| 205 | (2-Ethoxy-4-{6-[2-(1-methyl-naphthalen-2-yl)-ethylamino]-pyrimidin-4-yl}-phenylamino)-acetic acid | 0.8 (D) | 457.1 |
| 206 | 2-Cyclobutoxy-4-[6-(2-indan-5-yl-ethylamino)-pyrimidin-4-yl]-benzoic acid | 1.0 (D) | 430.3 |
| 207 | (2-Ethoxy-4-{6-[2-(1-methyl-1H-indol-6-yl)-ethylamino]-pyrimidin-4-yl}-phenoxy)-acetic acid | 0.7 (D) | 447 |
| 208 | 2-Cyclobutoxy-4-{6-[2-(6-methoxy-4-methyl-benzofuran-5-yl)-ethylamino]-pyrimidin-4-yl}-benzoic acid | 1.0 (D) | 474.4 |
| 209 | (4-{6-[2-(3-Cyano-benzo[b]thiophen-5-yl)-ethylamino]-pyrimidin-4-yl}-2-ethoxy-phenyl)-acetic acid (*1) | 0.7 (D) | 459.1 |
| 210 | 3-Ethoxy-5-{6-[2-(7-methoxy-1-methyl-2-oxo-1,2,3,4-tetrahydro-quinolin-6-yl)-ethylamino]-pyrimidin-4-yl}-thiophene-2-carboxylic acid | 0.8 (D) | 483 |
| 211 | 4-{6-[2-(3-Difluoromethoxy-naphthalen-2-yl)-ethylamino]-pyrimidin-4-yl}-2-ethoxy-benzoic acid (*1) | 1.0 (D) | 480 |
| 212 | 4-{6-[2-(3-Cyano-benzo[b]thiophen-5-yl)-ethylamino]-pyrimidin-4-yl}-2-methylsulfanyl-benzoic acid (*1) | 0.8 (D) | 447.4 |
| 213 | 2-Cyclobutoxy-4-{6-[2-(6-methoxy-benzo[1,3]dioxol-5-yl)-ethylamino]-pyrimidin-4-yl}-benzoic acid | 0.9 (D) | 464.3 |
| 214 | 2-(2-Ethoxy-4-{6-[2-(7-methoxy-2,3-dihydro-benzo[1,4]dioxin-6-yl)-ethylamino]-pyrimidin-4-yl}-phenyl)-propionic acid | 0.8 (D) | 480.3 |
| 215 | 4-{6-[2-(4,5-Difluoro-7-methoxy-2-methyl-benzofuran-6-yl)-ethylamino]-pyrimidin-4-yl}-2-ethoxy-benzoic acid | 1.0 (D) | 484.3 |
| 216 | 4-{6-[2-(8-Fluoro-2,3-dihydro-benzo[1,4]dioxin-6-yl)-ethylamino]-pyrimidin-4-yl}-2-methylsulfanyl-benzoic acid | 0.8 (D) | 441.9 |
| 217 | (4-{6-[2-(6-Difluoromethoxy-benzo[1,3]dioxol-5-yl)-ethylamino]-pyrimidin-4-yl}-2-ethoxy-phenoxy)-acetic acid | 0.7 (D) | 504.3 |
| 218 | 2-Ethoxy-4-{6-[2-(5-methoxy-benzo[b]thiophen-6-yl)-ethylamino]-pyrimidin-4-yl}-benzoic acid | 0.9 (D) | 450.3 |
| 219 | 2-Methylsulfanyl-4-[6-(2-naphthalen-2-yl-ethylamino)-pyrimidin-4-yl]-benzoic acid | 0.9 (D) | 416.3 |
| 220 | 3-(2-Ethoxy-4-{6-[2-(1-methyl-naphthalen-2-yl)-ethylamino]-pyrimidin-4-yl}-phenyl)-[1,2,4]oxadiazol-5(4H)-one [tautomeric form: 3-(2-ethoxy-4-(6-((2-(1-methylnaphthalen-2-yl)ethyl)amino)pyrimidin-4-yl)phenyl)-[1,2,4]oxadiazol-5-ol] | 1.0 (D) | 468 |
| 221 | 2-Ethoxy-4-{6-[2-(6-methoxy-4-methyl-benzofuran-5-yl)-ethylamino]-pyrimidin-4-yl}-benzoic acid | 0.9 (D) | 448.4 |
| 222 | 4-[6-(2-Benzo[b]thiophen-5-yl-ethylamino)-pyrimidin-4-yl]-2-ethylsulfanyl-benzoic acid | 0.9 (D) | 436.4 |
| 223 | 2-(2-Ethoxy-4-{6-[2-(1H-indol-6-yl)-ethylamino]-pyrimidin-4-yl}-phenoxy)-propionic acid | 0.7 (D) | 447 |
| 224 | (4-{6-[2-(6-Methoxy-benzo[b]thiophen-5-yl)-ethylamino]-pyrimidin-4-yl}-2-methylsulfanyl-phenyl)-acetic acid (*1) | 0.8 (D) | 466 |
| 225 | (2-Ethoxy-4-{6-[2-(1H-indol-5-yl)-ethylamino]-pyrimidin-4-yl}-phenoxy)-acetic acid | 0.6 (D) | 433.3 |
| 226 | [2-(1H-Indol-6-yl)-ethyl]-[6-(1H-indol-5-yl)-pyrimidin-4-yl]-amine | 0.6 (D) | 354.3 |
| 227 | 2-Ethoxy-4-{6-[2-(6-fluoro-benzofuran-5-yl)-ethylamino]-pyrimidin-4-yl}-benzoic acid | 0.9 (D) | 422.3 |
| 228 | 2-Cyclobutoxy-4-{6-[2-(5,7-difluoro-quinolin-6-yl)-ethylamino]-pyrimidin-4-yl}-benzoic acid (*1) | 0.9 (D) | 477.3 |
| 229 | {4-[6-(2-Benzofuran-6-yl-ethylamino)-pyrimidin-4-yl]-2-ethoxy-phenoxyl-acetic acid (*1) | 0.7 (D) | 434.4 |
| 230 | 4-{6-[2-(8-Chloro-2,3-dihydro-benzo[1,4]dioxin-6-yl)-ethylamino]-pyrimidin-4-yl}-2-methylsulfanyl-benzoic acid | 0.8 (D) | 458.2 |
| 231 | 2-Cyclobutoxy-4-{6-[2-(8-fluoro-naphthalen-2-yl)-ethylamino]-pyrimidin-4-yl}-benzoic acid (*1) | 1.0 (D) | 458.1 |
| 232 | N-(2-Ethoxy-4-{6-[2-(1-methyl-naphthalen-2-yl)-ethylamino]-pyrimidin-4-yl}-phenyl)-oxalamic acid | 0.9 (D) | 471 |
| 233 | 2-(2-Ethoxy-4-{6-[2-(6-methoxy-benzofuran-5-yl)-ethylamino]-pyrimidin-4-yl}-phenoxy)-propionic acid | 0.8 (D) | 478.1 |
| 234 | 2-(2-Hydroxy-ethoxy)-4-{6-[2-(1-methyl-naphthalen-2-yl)-ethylamino]-pyrimidin-4-yl}-benzoic acid (*1) | 0.8 (D) | 444.3 |
| 235 | 2-Cyclobutoxy-4-{6-[2-(8-methyl-quinolin-7-yl)-ethylamino]-pyrimidin-4-yl}-benzoic acid (*1) | 0.7 (D) | 455.3 |
| 236 | 2-(2-Ethoxy-4-{6-[2-(6-fluoro-benzofuran-5-yl)-ethylamino]-pyrimidin-4-yl}-phenoxy)-propionic acid | 0.8 (D) | 466 |
| 237 | 4-[6-(2-Benzothiazol-5-yl-ethylamino)-pyrimidin-4-yl]-2-methylsulfanyl-benzoic acid (*1) | 0.7 (D) | 423.1 |
| 238 | 4-{6-[2-(6-Fluoro-benzofuran-5-yl)-ethylamino]-pyrimidin-4-yl}-2-methylsulfanyl-benzoic acid | 0.9 (D) | 424.2 |

TABLE 4-continued

Examples 1-337

| Ex. Compound | t_R [min] (LC-MS) | MS Data m/z [M + H]+ |
|---|---|---|
| 239 (2-Ethoxy-4-{6-[2-(6-methoxy-benzo[1,3]dioxol-5-yl)-ethylamino]-pyrimidin-4-yl}-phenoxy)-acetic acid | 0.68 (A) | 468.05 |
| 240 2-Ethoxy-4-{6-[2-(3-methyl-naphthalen-2-yl)-ethylamino]-pyrimidin-4-yl}-benzoic acid | 1.0 (D) | 428.3 |
| 241 4-[6-(2-Benzofuran-5-yl-ethylamino)-pyrimidin-4-yl]-2-cyclobutoxy-benzoic acid (*1) | 0.9 (D) | 430.3 |
| 242 3-Ethoxy-5-{6-[2-(1-ethyl-1H-indol-6-yl)-ethylamino]-pyrimidin-4-yl}-thiophene-2-carboxylic acid | 1.0 (D) | 437.2 |
| 243 4-{6-[2-(8-Fluoro-naphthalen-2-yl)-ethylamino]-pyrimidin-4-yl}-2-methylsulfanyl-benzoic acid (*1) | 0.9 (D) | 434.1 |
| 244 2-Cyclobutoxy-4-{6-[2-(2,3-dihydro-benzo[1,4]dioxin-6-yl)-ethylamino]-pyrimidin-4-yl}-benzoic acid | 0.8 (D) | 448.3 |
| 245 2-(2-Ethoxy-4-{6-[2-(3-ethoxy-naphthalen-2-yl)-ethylamino]-pyrimidin-4-yl}-phenoxy)-2-methyl-propionic acid | 1.0 (D) | 516 |
| 246 4-{6-[2-(8-Chloro-2,3-dihydro-benzo[1,4]dioxin-6-yl)-ethylamino]-pyrimidin-4-yl}-2-cyclobutoxy-benzoic acid | 0.9 (D) | 482.3 |
| 247 (4-{6-[2-(3-Chloro-naphthalen-2-yl)-ethylamino]-pyrimidin-4-yl}-2-ethoxy-phenoxy)-acetic acid (*1) | 0.9 (D) | 478.1 |
| 248 4-[6-(2-Benzofuran-5-yl-ethylamino)-pyrimidin-4-yl]-2-methylsulfanyl-benzoic acid | 0.8 (D) | 406.2 |
| 249 6-{6-[2-(1H-Indol-6-yl)-ethylamino]-pyrimidin-4-yl}-1-methyl-1,2-dihydro-indazol-3-one | 0.6 (D) | 385.3 |
| 250 4-[6-(2-Benzofuran-6-yl-ethylamino)-pyrimidin-4-yl]-2-methylsulfanyl-benzoic acid | 0.8 (D) | 406.2 |
| 251 3-Ethoxy-5-{6-[2-(5-methoxy-1-methyl-1H-indazol-6-yl)-ethylamino]-pyrimidin-4-yl}-thiophene-2-carboxylic acid (*1) | 1.2 (D) | 454.2 |
| 252 4-[6-(2-Benzofuran-6-yl-ethylamino)-pyrimidin-4-yl]-2-cyclobutoxy-benzoic acid (*1 ) | 0.9 (D) | 430.3 |
| 253 4-{6-[2-(3-Cyano-benzo[b]thiophen-5-yl)-ethylamino]-pyrimidin-4-yl}-2-ethoxy-benzoic acid (*1) | 0.8 (D) | 445.3 |
| 254 2-Ethoxy-4-{6-[2-(6-methyl-benzo[b]thiophen-5-yl)-ethylamino]-pyrimidin-4-yl}-benzoic acid | 0.9 (D) | 434.1 |
| 255 4-{6-[2-(2,3-Dihydro-benzo[b]thiophen-5-yl)-ethylamino]-pyrimidin-4-yl}-2-ethoxy-benzoic acid (*1) | 0.9 (D) | 422.3 |
| 256 (2-Ethoxy-4-{6-[2-(5-methoxy-benzofuran-6-yl)-ethylamino]-pyrimidin-4-yl}-phenyl)-acetic acid | 0.8 (D) | 448 |
| 257 4-[6-(2-Chroman-6-yl-ethylamino)-pyrimidin-4-yl]-2-methylsulfanyl-benzoic acid | 0.8 (D) | 422.1 |
| 258 (2-Ethoxy-4-{6-[2-(3-isopropoxy-naphthalen-2-yl)-ethylamino]-pyrimidin-4-yl}-phenyl)-acetic acid (*1) | 1.0 (D) | 486 |
| 259 2-Ethoxy-4-{6-[2-(1H-indol-6-yl)-ethylamino]-pyrimidin-4-yl}-benzoic acid | 0.7 (D) | 403.3 |
| 260 4-{6-[2-(1-Chloro-naphthalen-2-yl)-ethylamino]-pyrimidin-4-yl}-2-ethoxy-benzoic acid | 1.0 (D) | 448.2 |
| 261 2-Ethoxy-4-{6-[2-(7-ethoxy-2,3-dihydro-benzo[1,4]dioxin-6-yl)-ethylamino]-pyrimidin-4-yl}-benzoic acid | 0.8 (D) | 466.4 |
| 262 2-Cyclobutoxy-4-{6-[2-(4,5-difluoro-7-methoxy-2-methyl-benzofuran-6-yl)-ethylamino]-pyrimidin-4-yl}-6-fluoro-benzoic acid (*1) | 1.2 (D) | 528 |
| 263 4-{6-[2-(7-Chloro-8-methyl-quinolin-6-yl)-ethylamino]-pyrimidin-4-yl}-2-cyclobutoxy-benzoic acid (*1) | 1.0 (D) | 489.3 |
| 264 2-Cyclobutoxy-4-{6-[2-(3-isopropoxy-naphthalen-2-yl)-ethylamino]-pyrimidin-4-yl}-benzoic acid | 1.2 (D) | 498.4 |
| 265 4-[6-(2-Chroman-7-yl-ethylamino)-pyrimidin-4-yl]-2-cyclobutoxy-benzoic acid | 0.9 (D) | 446 |
| 266 4-[6-(2-Chroman-6-yl-ethylamino)-pyrimidin-4-yl]-2-cyclobutoxy-benzoic acid | 0.9 (D) | 446.3 |
| 267 [2-(1H-Indol-6-yl)-ethyl]-[6-(1H-indol-6-yl)-pyrimidin-4-yl]-amine | 0.7 (D) | 354.3 |
| 268 2-Cyclobutoxy-4-{6-[2-(4-methyl-benzo[b]thiophen-5-yl)-ethylamino]-pyrimidin-4-yl}-benzoic acid (*1) | 1.0 (D) | 460.4 |
| 269 2-Ethoxy-4-{6-[2-(8-fluoro-naphthalen-2-yl)-ethylamino]-pyrimidin-4-yl}-benzoic acid (*1) | 0.9 (D) | 432.2 |
| 270 (4-{6-[2-(1,3-Difluoro-naphthalen-2-yl)-ethylamino]-pyrimidin-4-yl}-2-methylsulfanyl-phenyl)-acetic acid (*1) | 0.9 (D) | 466.3 |
| 271 (2-Ethoxy-4-{6-[2-(1H-indol-6-yl)-ethylamino]-pyrimidin-4-yl}-phenyl)-acetic acid | 0.7 (D) | 417.3 |
| 272 646-(2-Benzo[b]thiophen-5-yl-ethylamino)-pyrimidin-4-yl]-1H-indole-3-carboxylic acid | 0.7 (D) | 415.2 |
| 273 4-{6-[2-(3-Cyano-benzo[b]thiophen-5-yl)-ethylamino]-pyrimidin-4-yl}-2-cyclobutoxy-benzoic acid (*1) | 0.9 (D) | 471.3 |
| 274 (2-Ethoxy-4-{6-[2-(3-methylamino-naphthalen-2-yl)-ethylamino]-pyrimidin-4-yl}-phenoxy)-acetic acid (1) | 0.8 (D) | 472 |
| 275 2-Ethylsulfanyl-4-{6-[2-(6-fluoro-benzofuran-5-yl)-ethylamino]-pyrimidin-4-yl}-benzoic acid | 0.9 (D) | 438.3 |
| 276 4-{6-[2-(6-Methoxy-benzo[b]thiophen-5-yl)-ethylamino]-pyrimidin-4-yl}-benzoic acid | 0.8 (D) | 406.2 |
| 277 4-{6-[2-(6-Methoxy-benzo[1,3]dioxol-5-yl)-ethylamino]-pyrimidin-4-yl}-2-methylsulfanyl-benzoic acid | 0.8 (D) | 440 |
| 278 2-Cyclobutoxy-4-{6-[2-(1H-indol-6-yl)-ethylamino]-pyrimidin-4-yl}-benzoic acid | 0.8 (D) | 429.3 |
| 279 4-{6-[2-(3-Chloro-naphthalen-2-yl)-ethylamino]-pyrimidin-4-yl}-2-ethoxy-benzoic acid (*1) | 1.0 (D) | 448.4 |
| 280 2-Cyclobutoxy-4-{6-[2-(2-fluoro-5-methoxy-benzofuran-6-yl)-ethylamino]-pyrimidin-4-yl}-benzoic acid | 1.0 (D) | 478.3 |

TABLE 4-continued

Examples 1-337

| Ex. Compound | $t_R$ [min] (LC-MS) | MS Data m/z [M + H]$^+$ |
|---|---|---|
| 281 3-Hydroxy-4-(4-{6-[2-(1H-indol-6-yl)-ethylamino]-pyrimidin-4-yl}-phenyl)-cyclobut-3-ene-1,2-dione | 0.7 (D) | 411.2 |
| 282 2-Ethoxy-6-methoxy-4-{6-[2-(3-methoxy-naphthalen-2-yl)-ethylamino]-pyrimidin-4-yl}-benzoic acid (*1) | 0.9 (D) | 474.3 |
| 283 3-(5-{6-[2-(7-Fluoro-quinolin-6-yl)-ethylamino]-pyrimidin-4-yl}-3-methoxy-thiophen-2-yl)-oxetan-3-ol | 0.6 (D) | 453.3 |
| 284 2-Ethoxy-4-{6-[2-(3-isopropoxy-naphthalen-2-yl)-ethylamino]-pyrimidin-4-yl}-benzoic acid (*1) | 1.1 (D) | 472.4 |
| 285 4-[6-(2-Chroman-7-yl-ethylamino)-pyrimidin-4-yl]-2-methylsulfanyl-benzoic acid | 0.8 (D) | 422.1 |
| 286 2-Ethoxy-4-{6-[2-(7-methoxy-2,3-dihydro-benzo[1,4]dioxin-6-yl)-ethylamino]-pyrimidin-4-yl}-benzoic acid (*1) | 0.8 (D) | 452.3 |
| 287 2-Cyclobutoxy-4-{6-[2-(1-methyl-1H-indol-6-yl)-ethylamino]-pyrimidin-4-yl}-benzoic acid | 0.9 (D) | 443.3 |
| 288 2-Cyclobutoxy-4-{6-[2-(7-methyl-2,3-2,3-benzo[1,4]dioxin-6-yl)-ethylamino]-pyrimidin-4-yl}-benzoic acid | 0.9 (D) | 462.1 |
| 289 (2-Ethoxy-4-{6-[2-(4-methyl-benzo[b]thiophen-5-yl)-ethylamino]-pyrimidin-4-yl}-phenyl)-acetic acid (*1) | 0.8 (D) | 448 |
| 290 (2-Ethoxy-4-{6-[2-(6-methyl-benzo[b]thiophen-5-yl)-ethylamino]-pyrimidin-4-yl}-phenyl)-acetic acid | 0.8 (D) | 448 |
| 291 4-[6-(2-Benzothiazol-5-yl-ethylamino)-pyrimidin-4-yl]-2-cyclobutoxy-benzoic acid (*1) | 0.8 (D) | 447.3 |
| 292 4-{6-[2-(8-Methyl-2,3-dihydro-benzo[1,4]dioxin-6-yl)-ethylamino]-pyrimidin-4-yl}-2-methylsulfanyl-benzoic acid | 0.8 (D) | 438 |
| 293 4-[6-(2-Benzofuran-6-yl-ethylamino)-pyrimidin-4-yl]-2-ethoxy-benzoic acid (*1) | 0.8 (D) | 404.3 |
| 294 5-{6-[2-(1H-Indol-6-yl)-ethylamino]-pyrimidin-4-yl}-thiophene-2-carboxylic acid amide | 0.7 (D) | 364.2 |
| 295 2-Cyclobutoxy-4-{6-[2-(2,3-dihydro-benzofuran-6-yl)-ethylamino]-pyrimidin-4-yl}-benzoic acid | 0.9 (D) | 432.3 |
| 296 2-Ethoxy-4-{6-[2-(4-methyl-benzo[b]thiophen-5-yl)-ethylamino]-pyrimidin-4-yl}-benzoic acid (*1) | 0.9 (D) | 434.3 |
| 297 (2-Ethoxy-4-{6-[2-(3-methyl-benzo[b]thiophen-5-yl)-ethylamino]-pyrimidin-4-yl}-phenyl)-acetic acid | 0.8 (D) | 448.4 |
| 298 (2-Ethoxy-4-{6-[2-(5-methoxy-1-methyl-1H-indazol-6-yl)-ethylamino]-pyrimidin-4-yl}-phenoxy)-acetic acid (*1) | 1.1 (D) | 478.3 |
| 299 (2-Ethoxy-4-{6-[2-(6-methoxy-benzo[1,3]dioxol-5-yl)-ethylamino]-pyrimidin-4-yl}-phenyl)-acetic acid | 0.7 (D) | 452.3 |
| 300 2,6-Dimethoxy-4-{6-[2-(3-methoxy-naphthalen-2-yl)-ethylamino]-pyrimidin-4-yl}-benzoic acid (*1) | 0.8 (D) | 460.2 |
| 301 (4-{6-[2-(7-Chloro-8-fluoro-quinolin-6-yl)-ethylamino]-pyrimidin-4-yl}-2-ethoxy-phenoxy)-acetic acid (*1) | 0.7 (D) | 497.3 |
| 302 5-(4-{6-[2-(1-Methyl-naphthalen-2-yl)-ethylamino]-pyrimidin-4-yl}-phenyl)-[1,2,4]oxadiazol-3(2H)-one [tautomeric form: 5-(4-(6-((2-(1-methylnaphthalen-2-yl)ethyl)amino)pyrimidin-4-yl)phenyl)-[1,2,4]oxadiazol-3-ol] | 0.9 (D) | 424.3 |
| 303 {4-[6-(2-Benzo[b]thiophen-5-yl-ethylamino)-pyrimidin-4-yl]-2-methylsulfanyl-phenyl}-acetic acid (*1) | 0.8 (D) | 436.2 |
| 304 4-{6-[2-(5,7-Difluoro-quinolin-6-yl)-ethylamino]-pyrimidin-4-yl}-2-ethoxy-benzoic acid (*1) | 0.8 (D) | 451.3 |
| 305 (4-{6-[2-(6-Methyl-benzo[b]thiophen-5-yl)-ethylamino]-pyrimidin-4-yl}-2-methylsulfanyl-phenyl)-acetic acid (*1) | 0.9 (D) | 450.1 |
| 306 2-Cyclobutoxy-4-{6-[2-(3-methyl-benzo[b]thiophen-5-yl)-ethylamino]-pyrimidin-4-yl}-benzoic acid | 1.0 (D) | 460.1 |
| 307 2,6-Difluoro-4-{6-[2-(1H-indol-6-yl)-ethylamino]-pyrimidin-4-yl}-phenol | 0.7 (D) | 367.4 |
| 308 {4-[6-(2-Benzo[b]thiophen-5-yl-ethylamino)-2-methyl-pyrimidin-4-yl]-2-ethoxy-phenyl}-acetic acid (*1) | 0.8 (D) | 448.3 |
| 309 4-[6-(2-Chroman-7-yl-ethylamino)-pyrimidin-4-yl]-2-ethoxy-benzoic acid | 0.8 (D) | 420.3 |
| 310 4-{6-[2-(2,3-Dihydro-benzo[1,4]dioxin-6-yl)-ethylamino]-pyrimidin-4-yl}-2-methylsulfanyl-benzoic acid | 0.7 (D) | 424.3 |
| 311 {4-[6-(2-Benzofuran-5-yl-ethylamino)-pyrimidin-4-yl]-2-ethoxy-phenyl}-acetic acid | 0.7 (D) | 418 |
| 312 2-Ethoxy-4-{6-[2-(3-methylamino-naphthalen-2-yl)-ethylamino]-pyrimidin-4-yl}-benzoic acid (*1) | 0.9 (D) | 443 |
| 313 2-(2-Ethoxy-4-{6-[2-(7-methoxy-2,3-dihydro-benzo[1,4]dioxin-6-yl)-ethylamino]-pyrimidin-4-yl}-phenoxy)-2-methyl-propionic acid | 0.8 (D) | 510 |
| 314 (2-Ethoxy-4-{6-[2-(8-fluoro-naphthalen-2-yl)-ethylamino]-pyrimidin-4-yl}-phenyl)-acetic acid (*1) | 0.8 (D) | 446 |
| 315 2-Ethoxy-4-{6-[2-(6-methoxy-benzo[1,3]dioxol-5-yl)-ethylamino]-pyrimidin-4-yl}-benzoic acid | 0.8 (D) | 438.3 |
| 316 (3-Ethoxy-5-{6-[2-(1-methyl-naphthalen-2-yl)-ethylamino]-pyrimidin-4-yl}-thiophen-2-yl)-acetic acid methyl ester | 1.2 (D) | 462.3 |
| 317 4-[6-(2-Benzofuran-5-yl-ethylamino)-pyrimidin-4-yl]-2-ethoxy-benzoic acid (*1) | 0.8 (D) | 404.3 |
| 318 [2-(5,7-Difluoro-quinolin-6-yl)-ethyl]-(6-isoquinolin-6-yl-pyrimidin-4-yl)-amine | 0.6 (D) | 414.1 |
| 319 4-{6-[2-(1H-Indol-5-yl)-ethylamino]-pyrimidin-4-yl}-2-methylsulfanyl-benzoic acid | 0.7 (D) | 405 |
| 320 4-[6-(2-Benzo[b]thiophen-5-yl-ethylamino)-pyrimidin-4-yl]-2,6-dimethoxy-benzoic acid | 0.8 (D) | 436.1 |
| 321 2-{4-[6-(2-Benzo[b]thiophen-5-yl-ethylamino)-pyrimidin-4-yl]-2-ethoxy-phenoxy}-2-methyl-propionic acid | 0.9 (D) | 478.3 |

TABLE 4-continued

Examples 1-337

| Ex. Compound | $t_R$ [min] (LC-MS) | MS Data m/z $[M + H]^+$ |
|---|---|---|
| 322 2-Cyclobutoxy-4-{6-[2-(1H-indol-5-yl)-ethylamino]-pyrimidin-4-yl}-benzoic acid | 0.8 (D) | 429.4 |
| 323 6-{6-[2-(7-Methoxy-2,3-dihydro-benzo[1,4]dioxin-6-yl)-ethylamino]-pyrimidin-4-yl}-1H-indole-3-carboxylic acid | 0.6 (D) | 447 |
| 324 4-{6-[2-(8-Chloro-2,3-dihydro-benzo[1,4]dioxin-6-yl)-ethylamino]-pyrimidin-4-yl}-2-ethoxy-benzoic acid | 0.8 (D) | 456.4 |
| 325 4-{6-[2-(6-Difluoromethoxy-benzo[1,3]dioxol-5-yl)-ethylamino]-pyrimidin-4-yl}-2-ethoxy-benzoic acid | 0.8 (D) | 474.3 |
| 326 (4-{6-[2-(4-Methyl-benzo[b]thiophen-5-yl)-ethylamino]-pyrimidin-4-yl}-2-methylsulfanyl-phenyl)-acetic acid (*1) | 0.8 (D) | 450.4 |
| 327 2-Ethoxy-4-{6-[2-(7-methyl-2,3-dihydro-benzo[1,4]dioxin-6-yl)-ethylamino]-pyrimidin-4-yl}-benzoic acid | 0.8 (D) | 436 |
| 328 4-{6-[2-(1H-Indol-6-yl)-ethylamino]-pyrimidin-4-yl}-2-methylsulfanyl-benzoic acid | 0.7 (D) | 405.3 |
| 329 4-{6-[2-(7-Methoxy-1,2,3,4-tetrahydro-quinolin-6-yl)-ethylamino]-pyrimidin-4-yl}-2-methylsulfanyl-benzoic acid (*1) | 0.6 (D) | 450.2 |
| 330 [2-(5,7-Difluoro-quinolin-6-yl)-ethyl]-[6-(1H-indol-5-yl)-pyrimidin-4-yl]-amine | 0.6 (D) | 402.1 |
| 331 2-{6-[2-(1-Methyl-naphthalen-2-yl)-ethylamino]-pyrimidin-4-yl}-1H-indole-6-carboxylic acid | 1.0 (D) | 423.3 |
| 332 {4-[6-(2-Chroman-7-yl-ethylamino)-pyrimidin-4-yl]-2-ethoxy-phenyl}-acetic acid | 0.8 (D) | 434.3 |
| 333 2-Cyclobutoxy-4-{6-[2-(1,3-difluoro-naphthalen-2-yl)-ethylamino]-pyrimidin-4-yl}-benzoic acid (*1) | 1.1 (D) | 476.1 |
| 334 4-{6-[2-(1,3-Difluoro-naphthalen-2-yl)-ethylamino]-pyrimidin-4-yl}-2-ethoxy-benzoic acid (*1) | 1.0 (D) | 450.1 |
| 335 5-{6-[2-(1,3-Difluoro-naphthalen-2-yl)-ethylamino]-pyrimidin-4-yl}-3-ethoxy-thiophene-2-carboxylic acid (*1) | 1.1 (D) | 455.9 |
| 336 4-{6-[2-(1,3-Difluoro-naphthalen-2-yl)-ethylamino]-pyrimidin-4-yl}-2-methylsulfanyl-benzoic acid (*1) | 1.0 (D) | 452.3 |
| 337 2-(4-{6-[2-(7-Methoxy-2,3-dihydro-benzo[1,4]dioxin-6-yl)-ethylamino]-pyrimidin-4-yl}-phenyl)-acrylic acid | 0.7 (D) | 434 |

Example 338: 3-{3-Ethoxy-5-[6-(2-quinolin-6-yl-ethylamino)-pyrimidin-4-y]-thiophen-2-yl}-[1,2,4] oxadiazol-5(4H)-one [tautomeric form: 3-(3-ethoxy-5-(6-((2-(quinolin-6-yl)ethyl)amino)pyrimidin-4-yl) thiophen-2-yl)-[1,2,4]oxadiazol-5-ol]

Following the general procedure with 3-(3-ethoxy-5-(6-hydroxypyrimidin-4-yl)thiophen-2-yl)-[1,2,4]oxadiazol-5-ol and 2-(quinolin-6-yl) ethan-1-amine di-hydrochloride, the title compound is obtained as a pale yellow solid. L-MS B: $t_R$=0.67 min; $[M+H]^+$=461.07.

a) 3-(3-Ethoxy-5-(6-hydroxypyrimidin-4-yl)thiophen-2-yl)-[1,2,4]oxadiazol-5-ol

A suspension of 3-(3-ethoxy-5-(6-methoxypyrimidin-4-yl)thiophen-2-yl)-[1,2,4]oxadiazol-5-ol(5180 mg, 12.1 mmol) in HCl(4M in dioxane, 100 mL) is heated at 10000 overnight, cooled down to RT, and the solvent is partially removed. The solid residue is filtered off washing with water, and dried under high vacuum, affording the title compound as alight yellow solid. LC-MS B: $t_R$=0.66 min; $[M+H]^+$=307.01.

b) 3-(3-Ethoxy-5-(6-methoxypyrimidin-4-yl)thiophen-2-yl)-[1,2,4]oxadiazol-5-ol

To a mixture of 3-ethoxy-N'-hydroxy-5-(6-methoxypyrimidin-4-yl)thiophene-2-carboximidamide (6930 mg, 22.6 mmol) and DBU (8.62 mL, 56.5 mmol) in Dioxane/DMSO (3:2, 220 ml) is added CDI (5498 mg, 33.9 mmol). The RM is stirred at 100° C. for 30 min, then cooled to RT. Evaporation of the solvent and trituration in 2N HCl affords the title compound as a yellow solid (7.15 g, 99%). LC-MS A: $t_R$=0.89 min; $[M+H]^+$=321.14.

c) 3-Ethoxy-N'-hydroxy-5-(6-methoxypyrimidin-4-yl)thiophene-2-carboximidamide

A suspension of 3-ethoxy-5-(6-methoxypyrimidin-4-yl) thiophene-2-carbonitrile (6860 mg, 24.7 mmol), TEA (10.3 mL, 74 mmol) and hydroxylamine hydrochloride (2.59 mL, 61.7 mmol) in EtOH (220 mL) is refluxed for 3 h, then cooled to RT and treated with water (30 mL) The yellow solid is filtered off and dried under high vacuum. The filtrate is concentrated and the solid is triturated in water, filtered off and combined with the first crop. The title compound is obtained as a yellow solid (6.93 g, 95%). LC-MS B: $t_R$=0.62 min; $[M+H]^+$=295.23.

d) 3-Ethoxy-5-(6-methoxypyrimidin-4-yl)thiophene-2-carbonitrile

Cyanuric chloride (6248 mg, 33.5 mmol) is added portionwise at 0° C. to a suspension of 3-ethoxy-5-(6-methoxy-pyrimidin-4-yl)thiophene-2-carboxamide (6940 mg, 22.4 mmol) in DMF (130 mL). The RM is then stirred at RT for 45 min. It is cooled at 0° C. and diluted with water. The solid is filtered off, washing with water and then EtOAc, and dried under high vacuum. The filtrate is extracted twice with EtOAc, combined organic layers are washed with brine, dried over MgSO$_4$, filtered and concentrated under reduced pressure. Both solids are combined to afford the title compound as a beige solid (5.49 g, 94%). LC-MS B: $t_R$=1.00 min; $[M+H]^+$=262.26.

e) 3-Ethoxy-5-(6-methoxypyrimidin-4-yl)thiophene-2-carboxamide

CDI (4861 mg, 29.1 mmol) is added to a solution of 3-ethoxy-5-(6-methoxypyrimidin-4-yl)thiophene-2-carboxylic acid (7410 mg, 26.4 mmol) in THF (140 mL) at RT. The RM is stirred for 30 min, then NH$_4$OH (25% solution, 61.1 mL, 397 mmol) is added, and the RM is stirred at RT for 30 min, then concentrated under reduced pressure, and the residue is triturated in 2N HCl. The title compound is filtered off, dried under high vacuum, and obtained as a yellow solid (6.94 g, 94%). LC-MS B: $t_R$=0.79 min; [M+H]$^+$=280.22.

f) 3-Ethoxy-5-(6-methoxypyrimidin-4-yl)thiophene-2-carboxylic acid

A suspension of methyl 3-ethoxy-5-(6-methoxypyrimidin-4-yl)thiophene-2-carboxylate (7870 mg, 26.2 mmol) in MeOH (210 mL) and NaOH 2M (38.8 mL, 419 mmol) is stirred overnight at RT. It is then acidified with HCl 24.5% (8N) (60 mL), MeOH is removed under vacuum and the slurry is filtered, to afford the title compound as a yellow solid (7.41 g, 99%). LC-MS B: $t_R$=0.77 min; [M+H]$^+$=281.19.

g) Methyl 3-ethoxy-5-(6-methoxypyrimidin-4-yl)thiophene-2-carboxylate

A mixture of methyl 3-ethoxy-5-(4,4,5,5-tetramethyl-1,3,2-dioxaboroan-2-yl)thiophene-2-carboxylate (10520 mg, 30 mmol), 4-chloro-6-methoxypyrimidine (4645 mg, 31.5 mmol), Pd(dppf)Cl$_2$DCM (2449 mg, 3 mmol) and potassium phosphate tribasic monohydrate (20719 mg, 90 mmol) in water (4 mL) and DMF (150 mL) is degassed for 20 min under a nitrogen stream, then stirred at RT for 1 h15. The RM is filtered through celite, the filtrate is concentrated under vacuum, the residue is partitioned between water and EtOAc. The organic layer is further washed with brine, dried over MgSO$_4$, filtered and concentrated. Purification by FC (heptane/EtOAc, from 1:0 to 0:1) affords the title compound as a yellow solid (7.87 g, 89%). LC-MS B: $t_R$=0.93 min; [M+H]$^+$=295.18.

h) Methyl 3-ethoxy-5-(4,4,5,5-tetramethyl-1,3,2-dioxaborolan-2-yl)thiophene-2-carboxylate The title compound is prepared according to the synthesis of A.2.9. using methyl 3-ethoxythiophene-2-carboxylate, and obtained as a white solid; LC-MS B: $t_R$=0.63 min; [M+H]$^+$=313.13.

Example 339: 3-(3-Ethoxy-5-{6-[2-(1H-indol-5-yl)-ethylamino]-pyrimidin-4-yl}-thiophen-2-yl)-[1,2,4]oxadiazol-5(4H)-one [tautomeric form: 3-(5-(6-((2-(1H-indol-5-yl)ethyl)amino)pyrimidin-4-yl)-3-ethoxythiophen-2-yl)-[1,2,4]oxadiazol-5-ol] (*2)

Following the general procedure D with 3-(3-ethoxy-5-(6-hydroxypyrimidin-4-yl)thiophen-2-yl)-[1,2,4]oxadiazol-5-ol (Example 338-a) and 2-(1H-indol-5-yl)ethan-1-amine, the title compound is obtained as a very pale yellow solid. LC-MS B: $t_R$=0.86 min; [M+H]$^+$=449.04.

Example 340: 3-{5-[6-(2-Benzo[b]thiophen-5-yl-ethylamino)-pyrimidin-4-yl]-3-ethoxy-thiophen-2-yl}-[1,2,4]oxadiazol-5(4H)-one [tautomeric form: 3-(5-(6-((2-(benzo[b]thiophen-5-yl)ethyl)amino)pyrimidin-4-yl)-3-ethoxythiophen-2-yl)-[1,2,4]oxadiazol-5-ol]

Following the general procedure D with 3-(3-ethoxy-5-(6-hydroxypyrimidin-4-yl)thiophen-2-yl)-[1,2,4]oxadiazol-5-ol (Example 338-a) and 2-(benzo[b]thiophen-5-yl)ethan-1-amine hydrochloride (A.1.26.1.), the title compound is obtained as a beige solid. LC-MS B: $t_R$=0.94 min; [M+H]$^+$=465.72.

Example 341: 3-(3-Ethoxy-5-{6-[2-(7-methyl-2,3-dihydro-benzo[1,4]dioxin-6-yl)-ethylamino]-pyrimidin-4-yl}-thiophen-2-yl)-[1,2,4]oxadiazol-5(4H)-one [tautomeric form: 3-(3-ethoxy-5-(6-((2-(7-methyl-2,3-dihydrobenzo[b][1,4]dioxin-6-yl)ethyl)amino)pyrimidin-4-yl)thiophen-2-yl)-[1,2,4]oxadiazol-5-ol]

Following the general procedure D with 3-(3-ethoxy-5-(6-hydroxypyrimidin-4-yl)thiophen-2-yl)-[1,2,4]oxadiazol-5-ol (Example 338-a) and 2-(7-methyl-2,3-dihydrobenzo[b][1,4]dioxin-6-yl)ethan-1-amine (A.1.71.1.), the title compound is obtained as a beige solid. LC-MS B: $t_R$=0.90 min; [M+H]$^+$=481.73.

Example 342: 3-(3-Ethoxy-5-{6-[2-(6-methoxy-benzo[b]thiophen-5-yl)-ethylamino]-pyrimidin-4-yl}-thiophen-2-yl)-[1,2,4]oxadiazol-5(4H)-one [tautomeric form: 3-(3-ethoxy-5-(6-((2-(6-methoxybenzo[b]thiophen-5-yl)ethyl)amino)pyrimidin-4-yl)thiophen-2-yl)-[1,2,4]oxadiazol-5-ol]

Following the general procedure D with 3-(3-ethoxy-5-(6-hydroxypyrimidin-4-yl)thiophen-2-yl)-[1,2,4]oxadiazol-5-ol (Example 338-a) and 2-(6-methoxybenzo[b]thiophen-5-yl)ethan-1-amine hydrochloride (A.1.31.1.), the title compound is obtained as a beige solid. LC-MS B: $t_R$=0.96 min; [M+H]$^+$=495.97.

Example 343: 3-(3-Ethoxy-5-{6-[2-(1H-indol-6-yl)-ethylamino]-pyrimidin-4-yl}-thiophen-2-yl)-[1,2,4]oxadiazol-5(4H)-one [tautomeric form: 3-(5-(6-((2-(1H-indol-6-yl)ethyl)amino)pyrimidin-4-yl)-3-ethoxythiophen-2-yl)-[1,2,4]oxadiazol-5-ol]

Following the general procedure D with 3-(3-ethoxy-5-(6-hydroxypyrimidin-4-yl)thiophen-2-yl)-[1,2,4]oxadiazol-5-ol (Example 338-a) and 2-(1H-indol-6-yl)ethan-1-amine (A.1.41.1.), the title compound is obtained as an off-white solid. LC-MS B: $t_R$=0.86 min: [M+H]$^+$=449.08.

Example 344: 3-{5-[6-(2-Benzo[1,3]dioxol-5-yl-ethylamino)-pyrimidin-4-yl]-3-ethoxy-thiophen-2-yl}-[1,2,4]oxadiazol-5(4H)-one [tautomeric form: 3-(5-(6-((2-(benzo[d][1,3]dioxol-5-yl)ethyl)amino)pyrimidin-4-yl)-3-ethoxythiophen-2-yl)-[1,2,4]oxadiazol-5-ol]

Following the general procedure D with 3-(3-ethoxy-5-(6-hydroxypyrimidin-4-yl)thiophen-2-yl)-[1,2,4]oxadiazol-5-ol (Example 338-a) and 2-(benzo[d][1,3]dioxol-5-yl)ethan-1-amine (A.1.80.1.), the title compound is obtained as a white solid. LC-MS B: $t_R$=0.88 min; [M+H]$^+$=454.02.

Example 345: 3-{3-Ethoxy-5-[6-(2-naphthalen-2-yl-ethylamino)-pyrimidin-4-yl]-thiophen-2-yl}-[1,2,4]oxadiazol-5(4H)-one [tautomeric form: 3-(3-ethoxy-5-(6-((2-(naphthalen-2-yl)ethyl)amino)pyrimidin-4-yl)thiophen-2-yl)-[1,2,4]oxadiazol-5-ol]

Following the general procedure D with 3-(3-ethoxy-5-(6-hydroxypyrimidin-4-yl)thiophen-2-yl)-[1,2,4]oxadiazol-5-ol (Example 338-a) and 2-(naphthalen-2-yl)ethan-1-amine (A.1.5.1.), the title compound is obtained as a yellow solid. LC-MS B: $t_R$=0.97 min; [M+H]$^+$=460.05.

Example 346: 3-(5-{6-[2-(5,7-Difluoro-quinolin-6-yl)-ethylamino]-pyrimidin-4-yl}-3-ethoxy-thiophen-2-yl)-[1,2,4]oxadiazol-5(4H)-one [tautomeric form: 3-(5-(6-((2-(5,7-difluoroquinolin-6-yl)ethyl)amino)pyrimidin-4-yl)-3-ethoxythiophen-2-yl)-[1,2,4]oxadiazol-5-ol]

Following the general procedure D with 3-(3-ethoxy-5-(6-hydroxypyrimidin-4-yl)thiophen-2-yl)-[1,2,4]oxadiazol-5-ol (Example 338-a) and 2-(5,7-difluoroquinolin-6-yl)ethan-1-amine hydrochloride (A.1.55.1.), the title compound is obtained as a white solid. LC-MS B: $t_R$=0.90 min; [M+H]$^+$=496.70.

Example 347: 3-Ethoxy-5-{6-[2-(7-fluoro-quinolin-6-yl)-ethylamino]-pyrimidin-4-yl}-N-hydroxy-thiophene-2-carboxamidine A mixture of 3-ethoxy-5-(6-((2-(7-fluoroquinolin-6-yl)ethyl)amino)pyrimidin-4-yl)thiophene-2-carbonitrile (50 mg, 0.119 mmol), hydroxyamine hydrochloride (16.7 mg, 0.238 mmol) and NaHCO$_3$ (25 mg, 0.298 mmol) in water (0.026 mL) and EtOH (1.00 mL) is stirred in a sealed tube at 90° C. for 1.5 h. Once at RT, it is diluted with water and extracted with EtOAc. The organic layer is then washed twice with brine, dried over MgSO$_4$, filtered and concentrated. The residue is purified by prep LC-MS to the title compound as a yellow solid. (17.3 mg, 32%). LC-MS A: $t_R$=0.70 min; [M+H]$^+$=479.02.

a) 3-Ethoxy-5-(6-((2-(7-fluoroquinolin-6-yl)ethyl)amino)pyrimidin-4-yl)thiophene-2-carbonitrile Following the general procedure D with 3-ethoxy-5-(6-hydroxypyrimidin-4-yl)thiophene-2-carbonitrile and 2-(7-fluoroquinolin-6-yl)ethan-1-amine hydrochloride (A.1.54.1.), the title compound is obtained as a beige solid. LC-MS A: $t_R$=0.78 min; [M+H]$^+$=420.16.

b) 3-Ethoxy-5-(6-hydroxypyrimidin-4-yl)thiophene-2-carbonitrile

Following the procedure described for Example 338-a with 3-ethoxy-5-(6-methoxypyrimidin-4-yl)thiophene-2-carbonitrile (Example 338-d), the title compound is obtained as a white solid. LC-MS A: $t_R$=0.69 min; [M+H]$^+$=289.01.

Example 348: 3-(3-Ethoxy-5-{6-[2-(7-fluoro-quinolin-6-yl)-ethylamino]-pyrimidin-4-yl}-thiophen-2-yl)-[1,2,4]oxadiazol-5(4H)-one [tautomeric form: 3-(3-ethoxy-5-(6-((2-(7-fluoroquinolin-6-yl)ethyl)amino)pyrimidin-4-yl)thiophen-2-yl)-[1,2,4]oxadiazol-5-ol]

Following the procedure described for Example 338-b with 3-ethoxy-5-{6-[2-(7-fluoro-quinolin-6-yl)-ethylamino]-pyrimidin-4-yl}-N-hydroxy-thiophene-2-carboxamidine (Example 347), the title compound is obtained as a white solid. LC-MS A: $t_R$=0.70 min; [M+H]$^+$=479.02.

Example 349: {6-[4-Ethoxy-5-(1H-tetrazol-5-yl)-thiophen-2-yl]-pyrimidin-4-yl}-[2-(7-fluoro-quinolin-6-yl)-ethyl]-amine To a suspension of 3-ethoxy-5-(6-((2-(7-fluoroquinolin-6-yl)ethyl)amino)pyrimidin-4-yl)thiophene-2-carbonitrile (Example 347-a, 35 mg, 0.0834 mmol) in toluene (0.63 mL) is added trimethylsilylazide (0.0173 mL, 0.125 mmol) and dibutyltin oxide (2.08 mg, 0.00834 mmol). The RM is stirred at 110° C. for 16 h in a sealed tube, cooled to RT and partitioned between brine and EtOAc. The organic extracts are dried over MgSO$_4$, filtered and concentrated under reduced pressure. The residue is purified by prep. HPLC to afford the title compound as a white solid (6 mg, 15%). LC-MS A: $t_R$=0.66 min; [M+H]$^+$=463.06.

Example 350: 4-Ethoxy-2-{6-[2-(1-methyl-naphthalen-2-yl)-ethylamino]-pyrimidin-4-yl}-thiazole-5-carboxylic acid To a solution of ethyl 4-ethoxy-2-(6-hydroxypyrimidin-4-yl)thiazole-5-carboxylate (59 mg, 0.2 mmol) in DMF (2 mL) are added TEA (0.14 mL, 1.0 mmol) and PyBop (156 mg, 0.3 mmol). The RM is stirred at RT for a few minutes until complete dissolution and 2-(1-methylnaphthalen-2-yl)ethan-1-amine hydrochloride (A.1.2.1., 56 mg, 0.25 mmol) is added. The RM is heated at 100° C. for 30 min in the microwave apparatus. NaOH 10% (0.721 mL, 2 mmol) is added and the RM is stirred at 70° C. overnight. Purification by prep. LC-MS affords the title compound as a yellow solid. LC-MS B: $t_R$=0.97 min; [M+H]$^+$=435.21.

a) Ethyl 4-ethoxy-2-(6-hydroxypyrimidin-4-yl)thiazole-5-carboxylate

Following the procedure described for the synthesis of Example 338-a with ethyl 4-ethoxy-2-(6-methoxypyrimidin-4-yl)thiazole-5-carboxylate, the title compound is obtained as a yellow solid. LC-MS B: $t_R$=0.78 min; [M+H]$^+$=296.15.

b) Ethyl 4-ethoxy-2-(6-methoxypyrimidin-4-yl)thiazole-5-carboxylate

To a solution of ethyl 4-hydroxy-2-(6-methoxypyrimidin-4-yl)thiazole-5-carboxylate (1730 mg, 6.15 mmol) in DMF (40 mL) at RT under argon is added K$_2$CO (2168 mg, 15.4 mmol), and the RM is heated at 60° C. Iodoethane (0.749 mL, 9.23 mmol) is added and the RM is stirred at 75° C. overnight. It is then cooled to RT, and water (75 mL) is added. The aq layer is extracted with DCM, the organic extracts are dried (MgSO$_4$), filtered and concentrated under reduced pressure, affording the crude title compound as an orange solid (1.75 g, 76%). LC-MS B: $t_R$=1.04 min; [M+H]$^+$=310.24.

c) Ethyl 4-hydroxy-2-(6-methoxypyrimidin-4-yl)thiazole-5-carboxylate

To a solution of 6-methoxypyrimidine-4-carbothioamide (1000 mg, 5.85 mmol) in toluene (40 mL) is added pyridine (1.9 mL, 23.4 mmol) at RT, followed by diethyl bromomalonate (1.52 mL, 8.19 mmol). The RM is heated at reflux overnight, then cooled to RT and treated with HCl 2N. The product is filtered off. The layers of the filtrate are separated and the aq layer is extracted twice with EtOAC. The combined organic layers are dried over MgSO$_4$, filtered, evaporated to dryness. The residue is combined with the first crop, yielding the title compound as a brown solid (1.73 g, 99%). LC-MS B: $t_R$=0.89 min; [M+H]$^+$=282.18.

Example 351: 4-Ethyl-2-{6-[2-(1-methyl-naphthalen-2-yl)-ethylamino]-pyrimidin-4-yl}-thiazole-5-carboxylic acid Following the procedure described for the synthesis of Example 350, using 2-(1-methylnaphthalen-2-yl)ethan-1-amine hydrochloride (A.1.2.1.) and ethyl 4-ethyl-2-(6-hydroxypyrimidin-4-yl)thiazole-5-carboxylate, the title compound is obtained as a yellow solid. LC-MS B: $t_R$=0.97 min; $[M+H]^+$=419.05.

a) Ethyl 4-ethyl-2-(6-hydroxypyrimidin-4-yl)thiazole-5-carboxylate

Following the procedure described for the synthesis of Example 350-a with ethyl 4-ethyl-2-(6-ethoxypyrimidin-4-yl)thiazole-5-carboxylate, the title compound is obtained as a beige solid. LC-MS B: $t_R$=0.73 min; $[M+H]^+$=266.26.

b) Ethyl 4-ethyl-2-(6-ethoxypyrimidin-4-yl)thiazole-5-carboxylate

To a solution of methyl 2-chloro-3-oxovalerate (0.96 mL, 6.5 mmol) in EtOH (30 mL) is added 6-methoxypyrimidine-4-carbothioamide (1000 mg, 5.91 mmol) and the mixture is refluxed overnight. Methyl 2-chloro-3-oxovalerate (1.31 mL, 8.86 mmol) is added and the RM is further refluxed for 24 h, then cooled at RT and treated with water (15 mL), cooled down to 0° C. The precipitate is filtered off, rinsed with MeOH and dried under high vacuum, affording the title compound as a pinkish solid (485 mg, 28%). LC-MS B: $t_R$=1.07 min; $[M+H]^+$=294.20.

Example 352: 3-(4-Ethoxy-2-{6-[2-(1-methyl-naphthalen-2-yl)-ethylamino]-pyrimidin-4-yl}-thiazol-5-yl)-[1,2,4]oxadiazol-5(4H)-one [tautomeric form: 3-(4-ethoxy-2-(6-((2-(1-methylnaphthalen-2-yl)ethyl)amino)pyrimidin-4-yl)thiazol-5-yl)-[1,2,4]oxadiazol-5-ol] (*1)

Following the general procedure D with 2-(1-methyl-naphthalen-2-yl)ethan-1-amine hydrochloride (A.1.2.1.) and 3-(4-ethoxy-2-(6-hydroxypyrimidin-4-yl)thiazol-5-yl)-[1,2,4]oxadiazol-5-ol, the title compound is obtained as a yellow solid. LC-MS B: $t_R$=1.11 min; $[M+H]^+$=475.16.

a) 3-(4-Ethoxy-2-(6-hydroxypyrimidin-4-yl)thiazol-5-yl)-[1,2,4]oxadiazol-5-ol Following the procedure described for the synthesis of Example 338-a with 3-(4-ethoxy-2-(6-methoxypyrimidin-4-yl)thiazol-5-yl)-[1,2,4]oxadiazol-5-ol, the title compound is obtained as a yellowish solid. LC-MS B: $t_R$=0.68 min; $[M+H]^+$=308.17.

b) 3-(4-Ethoxy-2-(6-methoxypyrimidin-4-yl)thiazol-5-yl)-[1,2,4]oxadiazol-5-ol Following the procedure described for the synthesis of Example 338-b with 4-ethoxy-N'-hydroxy-2-(6-methoxypyrimidin-4-yl)thiazole-5-carboximidamide, the title compound is obtained as a beige solid. LC-MS B: $t_R$=0.94 min; $[M+H]^+$=321.93.

c) 4-Ethoxy-N'-hydroxy-2-(6-methoxypyrimidin-4-yl)thiazole-5-carboximidamide Following the procedure described for the synthesis of Example 338-c with 4-ethoxy-2-(6-methoxypyrimidin-4-yl)thiazole-5-carbonitrile, the title compound is obtained as a deep yellow solid. LC-MS B: $t_R$=0.67 min; $[M+H]^+$=296.17.

d) 4-Ethoxy-2-(6-methoxypyrimidin-4-yl)thiazole-5-carbonitrile

NH$_4$OH (25%, 4.05 mL, 26.3 mmol) and I$_2$ (1824 mg, 7.19 mmol) are added at 0° C. to a solution of 4-ethoxy-2-(6-methoxypyrimidin-4-yl)thiazole-5-carbaldehyde (465 mg, 1.75 mmol) in THF (15 mL) and the RM is stirred at RT for 3 h. It is then poured in 10 mL of NaHSO$_3$ 40% (15 mL) and extracted with EtOAc, dried over MgSO$_4$ and concentrated under vacuum, to afford the title compound as an orange solid. LC-MS B: $t_R$=1.02 min; $[M+H]^+$=263.25.

e) 4-Ethoxy-2-(6-methoxypyrimidin-4-yl)thiazole-5-carbaldehyde

A mixture of ethyl 4-ethoxy-2-(6-methoxypyrimidin-4-yl)thiazole-5-carboxylate (Example 350-b, 706 mg, 2.64 mmol) in THF (20 mL) is cooled down to −78° C. and DiBAl-H (1M in THF, 5.28 mL, 5.28 mmol) is added dropwise. The mixture is stirred at RT overnight. The mixture is quenched at 0° C. by dropwise addition of water (200 uL), then NaOH 10% (400 uL) and finally water (600 uL). The aluminium precipitate is filtered over a pad of Celite and rinsed with EtOAc. The filtrate is dried over MgSO$_4$, filtered and concentrated under reduced pressure. The residue is dissolved in DCM (20 mL) and MnO$_2$ (2701 mg, 26.4 mmol) is added. The mixture is stirred 5 h at RT, then filtered over a pad of Celite and rinsed with EtOAc. The filtrate is concentrated under reduced pressure, affording the title compound as a light orange solid. LC-MS B: $t_R$=0.97 min; $[M+H]^+$=266.25.

Example 353: 3-(4-Ethyl-2-{6-[2-(1-methyl-naphthalen-2-yl)-ethylamino]-pyrimidin-4-yl}-thiazol-5-yl)-[1,2,4]oxadiazol-5(4H)-one [tautomeric form: 3-(4-ethyl-2-(6-((2-(1-methylnaphthalen-2-yl)ethyl)amino)pyrimidin-4-yl)thiazol-5-yl)-[1,2,4]oxadiazol-5-ol]

Following the general procedure D, using 3-(4-ethyl-2-(6-hydroxypyrimidin-4-yl)thiazol-5-yl)-[1,2,4]oxadiazol-5-ol and 2-(1-methylnaphthalen-2-yl)ethan-1-amine hydrochloride (A.1.2.1.), the title compound is obtained as a yellow solid. LC-MS B: $t_R$=1.05 min; $[M+H]^+$=459.16.

a) 3-(4-Ethyl-2-(6-hydroxypyrimidin-4-yl)thiazol-5-yl)-[1,2,4]oxadiazol-5-ol Following the procedure described for the synthesis of Example 338-a with 3-(4-ethyl-2-(6-ethoxypyrimidin-4-yl)thiazol-5-yl)-[1,2,4]oxadiazol-5-ol, the title compound is obtained as a grey solid. LC-MS B: $t_R$=0.64 min; $[M+H]^+$=292.17.

b) 3-(4-Ethyl-2-(6-ethoxypyrimidin-4-yl)thiazol-5-yl)-[1,2,4]oxadiazol-5-ol Following the procedure described for the synthesis of Example 338-b with 4-ethyl-N'-hydroxy-2-(6-ethoxypyrimidin-4-yl)thiazole-5-carboximidamide, the title compound is obtained as a light orange solid. LC-MS B: $t_R$=0.92 min; $[M+H]^+$=320.21.

c) 4-Ethyl-N'-hydroxy-2-(6-ethoxypyrimidin-4-yl)thiazole-5-carboximidamide

Following the procedure described for the synthesis of Example 338-c with 4-ethyl-2-(6-ethoxypyrimidin-4-yl)thiazole-5-carbonitrile, the title compound is obtained as a light yellow solid. LC-MS B: $t_R$=0.66 min; [M+H]$^+$=294.21.

d) 4-Ethyl-2-(6-ethoxypyrimidin-4-yl)thiazole-5-carbonitrile

Following the procedure described for the synthesis of Example 338-d with 2-(6-ethoxypyrimidin-4-yl)-4-ethylthiazole-5-carboxamide, the title compound is obtained as a beige solid. LC-MS B: $t_R$=1.04 min; [M+H]$^+$=261.29.

e) 2-(6-Ethoxypyrimidin-4-yl)-4-ethylthiazole-5-carboxamide

Following the procedure described for the synthesis of Example 338-e with 2-(6-ethoxypyrimidin-4-yl)-4-ethylthiazole-5-carboxylic acid, the title compound is obtained as an orange solid. LC-MS B: $t_R$=0.79 min; [M+H]$^+$=279.25.

f) 2-(6-Ethoxypyrimidin-4-yl)-4-ethylthiazole-5-carboxylic acid

An ice-chilled solution of ethyl 4-ethyl-2-(6-ethoxypyrimidin-4-yl)thiazole-5-carboxylate (Example 351-b, 1000 mg, 3.09 mmol) in THF/MeOH 1:1 (15 mL) is treated with NaOH 10% (5.58 mL, 15.5 mmol) and stirred at RT for 20 h. The solvents are removed under reduced pressure, the aqueous phase is extracted once with Et$_2$O. The aqueous phase is then acidified with 2N HCl and extracted with EtOAc (3×). The combined organic extracts are dried over MgSO$_4$, filtered and concentrated under reduced pressure, yielding the title compound as a greenish solid (522 mg, 64%). LC-MS B: $t_R$=0.88 min; [M+H]$^+$=280.24.

Example 354: 3-Ethoxy-5-(6-((2-(1-methylnaphthalen-2-yl)ethyl)amino)pyrimidin-4-yl)-N-sulfamoyl-thiophene-2-carboxamide 3-Ethoxy-5-{6-[2-(1-methyl-naphthalen-2-yl)-ethylamino]-pyrimidin-4-yl}-thiophene-2-carboxylic acid (Example 7, 50 mg, 0.15 mmol) is dissolved in DMSO/THF (2:1) (3.3 mL) and CDI (28.1 mg, 0.173 mmol) is added. The RM is heated at 60° C. for 1 h, cooled to RT and treated with sulfamide (24.4 mg, 0.254 mmol) and DBU (0.0431 mL, 0.288 mmol). The RM is stirred at RT for 1 h. HCl 2M (5 mL) is added, the precipitate is filtered, then purified by prep HPLC to yield the title compound as a white solid (52 mg, 88%). LC-MS B: $t_R$=0.93 min; [M+H]$^+$=512.13.

Example 355: N-(3-Ethoxy-5-{6-[2-(1-methyl-naphthalen-2-yl)-ethylamino]-pyrimidin-4-yl}-thiophene-2-carbonyl)-methanesulfonamide Following the procedure described for the synthesis of Example 354, with 3-ethoxy-5-{6-[2-(1-methyl-naphthalen-2-yl)-ethylamino]-pyrimidin-4-yl}-thiophene-2-carboxylic acid (Example 7) and methanesulfonamide, the title compound is obtained as a white solid. LC-MS B: $t_R$=1.06 min; [M+H]$^+$=511.16.

Compounds of Examples 356-456 listed in Table 5 below are prepared by applying either one of the above-mentioned procedures A, B or C to the pyrimidine halide derivatives A.1.1.-A.1.xx. coupled with commercially available boronic acid derivatives or with boronic acid derivatives A.2.1.-A.2.45.

TABLE 5

Examples 356-456

| Ex. | Compound | $t_R$ [min] (LC-MS C) | MS Data m/z [M + H]$^+$ |
|---|---|---|---|
| 356 | 5-{6-[2-(5,7-Difluoro-quinolin-6-yl)-ethylamino]-pyrimidin-4-yl}-thiophene-2-carboxylic acid amide | 0.738 | 412.2 |
| 357 | (4-{6-[2-(3-Cyano-1-methyl-naphthalen-2-yl)-ethylamino]-pyrimidin-4-yl}-2-ethoxy-phenyl)-acetic acid (1*) | 0.862 | 465.2 |
| 358 | 4-{6-[2-(7-Chloro-benzo[b]thiophen-5-yl)-ethylamino]-pyrimidin-4-yl}-2-ethoxy-benzoic acid (1*) | 0.999 | 454.2 |
| 359 | 5-{6-[2-(7-Chloro-benzo[b]thiophen-5-yl)-ethylamino]-pyrimidin-4-yl}-3-ethoxy-thiophene-2-carboxylic acid | 1.147 | 460.2 |
| 360 | 4-{6-[2-(7-Chloro-benzo[b]thiophen-5-yl)-ethylamino]-pyrimidin-4-yl}-2-methylsulfanyl-benzoic acid | 1.013 | 456.2 |
| 361 | 2-Ethoxy-4-{6-[2-(7-fluoro-benzo[b]thiophen-5-yl)-ethylamino]-pyrimidin-4-yl}-benzoic acid | 0.944 | 436.1 |
| 362 | 3-Ethoxy-5-{6-[2-(7-fluoro-benzo[b]thiophen-5-yl)-ethylamino]-pyrimidin-4-yl}-thiophene-2-carboxylic acid (1*) | 1.091 | 442.1 |
| 363 | (2-Ethoxy-4-{6-[2-(7-fluoro-benzo[b]thiophen-5-yl)-ethylamino]-pyrimidin-4-yl}-phenyl)-acetic acid (1*) | 0.855 | 450.1 |
| 364 | 4-{6-[2-(7-Fluoro-benzo[b]thiophen-5-yl)-ethylamino]-pyrimidin-4-yl}-2-methylsulfanyl-benzoic acid (1*) | 0.954 | 438.1 |
| 365 | 2-Ethoxy-4-{6-[2-(4-fluoro-benzo[b]thiophen-5-yl)-ethylamino]-pyrimidin-4-yl}-benzoic acid (1*) | 0.937 | 436.1 |
| 366 | 2-Cyclobutoxy-4-{6-[2-(4-fluoro-benzo[b]thiophen-5-yl)-ethylamino]-pyrimidin-4-yl}-benzoic acid (1*) | 1.039 | 462.1 |
| 367 | 3-Ethoxy-5-{6-[2-(4-fluoro-benzo[b]thiophen-5-yl)-ethylamino]-pyrimidin-4-yl}-thiophene-2-carboxylic acid (1*) | 1.085 | 442 |
| 368 | (2-Ethoxy-4-{6-[2-(4-fluoro-benzo[b]thiophen-5-yl)-ethylamino]-pyrimidin-4-yl}-phenyl)-acetic acid (1*) | 0.845 | 450.1 |
| 369 | 4-{6-[2-(4-Fluoro-benzo[b]thiophen-5-yl)-ethylamino]-pyrimidin-4-yl}-2-methylsulfanyl-benzoic acid (1*) | 0.945 | 438.1 |
| 370 | {4-[6-(2-Benzo[b]thiophen-5-yl-ethylamino)-pyrimidin-4-yl]-2-ethoxy-6-fluoro-phenyl}-acetic acid (1*) | 0.941 | 450.2 |

TABLE 5-continued

Examples 356-456

| Ex. | Compound | $t_R$ [min] (LC-MS C) | MS Data m/z [M + H]+ |
|---|---|---|---|
| 371 | (2-Ethoxy-6-fluoro-4-{6-[2-(6-methoxy-benzo[b]thiophen-5-yl)-ethylamino]-pyrimidin-4-yl}-phenyl)-acetic acid (1*) | 0.957 | 480.1 |
| 372 | (2-Ethoxy-6-fluoro-4-{6-[2-(4-methyl-benzo[b]thiophen-5-yl)-ethylamino]-pyrimidin-4-yl}-phenyl)-acetic acid (1*) | 0.977 | 464.3 |
| 373 | (2-Ethoxy-6-fluoro-4-{6-[2-(7-methoxy-2,3-dihydro-benzo[1,4]dioxin-6-yl)-ethylamino]-pyrimidin-4-yl}-phenyl)-acetic acid (1*) | 0.826 | 482.2 |
| 374 | (2-Ethoxy-6-fluoro-4-{6-[2-(3-methoxy-1-methyl-naphthalen-2-yl)-ethylamino]-pyrimidin-4-yl}-phenyl)-acetic acid (1*) | 1.03 | 488.4 |
| 375 | (2-Ethoxy-6-fluoro-4-{6-[2-(4-fluoro-benzo[b]thiophen-5-yl)-ethylamino]-pyrimidin-4-yl}-phenyl)-acetic acid (1*) | 0.976 | 468.2 |
| 376 | 3-Ethoxy-5-{6-[2-(7-methyl-benzo[b]thiophen-6-yl)-ethylamino]-pyrimidin-4-yl}-thiophene-2-carboxylic acid (1*) | 1.114 | 438 |
| 377 | 4-{6-[2-(6-Methoxy-benzo[b]thiophen-5-yl)-ethylamino]-pyrimidin-4-yl}-2-propyl-benzoic acid (1*) | 0.977 | 446.4 |
| 378 | 4-{6-[2-(4-Fluoro-benzo[b]thiophen-5-yl)-ethylamino]-pyrimidin-4-yl}-2-propyl-benzoic acid (1*) | 0.997 | 434.1 |
| 379 | 4-{6-[2-(7-Methoxy-2,3-dihydro-benzo[1,4]dioxin-6-yl)-ethylamino]-pyrimidin-4-yl}-2-propyl-benzoic acid (1*) | 0.842 | 448 |
| 380 | 4-{6-[2-(3-Methoxy-1-methyl-naphthalen-2-yl)-ethylamino]-pyrimidin-4-yl}-2-propyl-benzoic acid (1*) | 1.049 | 454.1 |
| 381 | (2-Methoxy-4-{6-[2-(6-methoxy-benzo[b]thiophen-5-yl)-ethylamino]-pyrimidin-4-yl}-phenyl)-acetic acid (1*) | 0.797 | 448.1 |
| 382 | (4-{6-[2-(4-Fluoro-benzo[b]thiophen-5-yl)-ethylamino]-pyrimidin-4-yl}-2-methoxy-phenyl)-acetic acid (1*) | 0.797 | 436.2 |
| 383 | (2-Methoxy-4-{6-[2-(7-methoxy-2,3-dihydro-benzo[1,4]dioxin-6-yl)-ethylamino]-pyrimidin-4-yl}-phenyl)-acetic acid (1*) | 1.059 | 450.1 |
| 384 | (2-Methoxy-4-{6-[2-(3-methoxy-1-methyl-naphthalen-2-yl)-ethylamino]-pyrimidin-4-yl}-phenyl)-acetic acid (1*) | 0.861 | 456.3 |
| 385 | (4-{6-[2-(6-Methoxy-benzo[b]thiophen-5-yl)-ethylamino]-pyrimidin-4-yl}-2-propyl-phenyl)-acetic acid (1*) | 0.885 | 460.1 |
| 386 | (4-{6-[2-(4-Fluoro-benzo[b]thiophen-5-yl)-ethylamino]-pyrimidin-4-yl}-2-propyl-phenyl)-acetic acid (1*) | 0.89 | 448.1 |
| 387 | (4-{6-[2-(7-Methoxy-2,3-dihydro-benzo[1,4]dioxin-6-yl)-ethylamino]-pyrimidin-4-yl}-2-propyl-phenyl)-acetic acid (1*) | 0.777 | 462.2 |
| 388 | (4-{6-[2-(3-Methoxy-1-methyl-naphthalen-2-yl)-ethylamino]-pyrimidin-4-yl}-2-propyl-phenyl)-acetic acid (1*) | 0.95 | 468.2 |
| 389 | 4-{6-[2-(7-Fluoro-benzo[b]thiophen-5-yl)-ethylamino]-pyrimidin-4-yl}-2-propyl-benzoic acid | 0.996 | 434.1 |
| 390 | (4-{6-[2-(7-Fluoro-benzo[b]thiophen-5-yl)-ethylamino]-pyrimidin-4-yl}-2-propyl-phenyl)-acetic acid (1*) | 0.897 | 448.2 |
| 391 | 3-Ethoxy-5-{6-[2-(7-methyl-benzo[b]thiophen-5-yl)-ethylamino]-pyrimidin-4-yl}-thiophene-2-carboxylic acid (1*) | 1.12 | 438.2 |
| 392 | (4-{6-[2-(6-Methoxy-benzo[b]thiophen-5-yl)-ethylamino]-pyrimidin-4-yl}-2-propoxy-phenyl)-acetic acid (1*) | 0.894 | 476 |
| 393 | (4-{6-[2-(4-Fluoro-benzo[b]thiophen-5-yl)-ethylamino]-pyrimidin-4-yl}-2-propoxy-phenyl)-acetic acid (1*) | 0.905 | 464.1 |
| 394 | (4-{6-[2-(3-Methoxy-1-methyl-naphthalen-2-yl)-ethylamino]-pyrimidin-4-yl}-2-propoxy-phenyl)-acetic acid (1*) | 0.958 | 484.2 |
| 395 | 2-Ethoxy-4-{6-[2-(7-methoxy-5-methyl-2,3-dihydro-benzo[1,4]dioxin-6-yl)-ethylamino]-pyrimidin-4-yl}-benzoic acid (1*) | 0.84 | 466.2 |
| 396 | 2-Cyclobutoxy-4-{6-[2-(7-methoxy-5-methyl-2,3-dihydro-benzo[1,4]dioxin-6-yl)-ethylamino]-pyrimidin-4-yl}-benzoic acid (1*) | 0.934 | 490 |
| 397 | (4-{6-[2-(7-Methoxy-5-methyl-2,3-dihydro-benzo[1,4]dioxin-6-yl)-ethylamino]-pyrimidin-4-yl}-2-propyl-phenyl)-acetic acid (1*) | 0.823 | 476.1 |
| 398 | (2-Ethoxy-6-fluoro-4-{6-[2-(7-methoxy-5-methyl-2,3-dihydro-benzo[1,4]dioxin-6-yl)-ethylamino]-pyrimidin-4-yl}-phenyl)-acetic acid (1*) | 0.888 | 496.1 |
| 399 | (2-Ethoxy-4-{6-[2-(7-methoxy-5-methyl-2,3-dihydro-benzo[1,4]dioxin-6-yl)-ethylamino]-pyrimidin-4-yl}-phenyl)-acetic acid (1*) | 0.776 | 478.1 |
| 400 | 4-{6-[2-(7-Methoxy-5-methyl-2,3-dihydro-benzo[1,4]dioxin-6-yl)-ethylamino]-pyrimidin-4-yl}-2-methylsulfanyl-benzoic acid (1*) | 0.845 | 466.2 |
| 401 | rac-2-(4-{6-[2-(7-Methoxy-2,3-dihydro-benzo[1,4]dioxin-6-yl)-ethylamino]-pyrimidin-4-yl}-2-propyl-phenyl)-propionic acid (1*) | 0.83 | 476.1 |
| 402 | (4-{6-[2-(7-Ethoxy-2,3-dihydro-benzo[1,4]dioxin-6-yl)-ethylamino]-pyrimidin-4-yl}-2-propyl-phenyl)-acetic acid (1*) | 0.831 | 476.2 |
| 403 | (2-Ethoxy-4-{6-[2-(7-ethoxy-2,3-dihydro-benzo[1,4]dioxin-6-yl)-ethylamino]-pyrimidin-4-yl}-6-fluoro-phenyl)-acetic acid (1*) | 0.889 | 496.2 |
| 404 | 2-Ethoxy-4-{6-[2-(7-fluoro-6-methoxy-benzo[b]thiophen-5-yl)-ethylamino]-pyrimidin-4-yl}-benzoic acid (1*) | 0.968 | 466 |
| 405 | 4-{6-[2-(7-Fluoro-6-methoxy-benzo[b]thiophen-5-yl)-ethylamino]-pyrimidin-4-yl}-2-methylsulfanyl-benzoic acid (1*) | 0.976 | 468.2 |
| 406 | (2-Ethoxy-4-{6-[2-(7-fluoro-6-methoxy-benzo[b]thiophen-5-yl)-ethylamino]-pyrimidin-4-yl}-phenyl)-acetic acid (1*) | 0.876 | 480.3 |
| 407 | 2-Cyclobutoxy-4-≡6-[2-(7-fluoro-6-methoxy-benzo[b]thiophen-5-yl)-ethylamino]-pyrimidin-4-yl}-benzoic acid (1*) | 1.064 | 492 |

TABLE 5-continued

Examples 356-456

| Ex. | Compound | $t_R$ [min] (LC-MS C) | MS Data m/z [M + H]+ |
|---|---|---|---|
| 408 | (4-{6-[2-(5-Fluoro-7-methoxy-2,3-dihydro-benzo[1,4]dioxin-6-yl)-ethylamino]-pyrimidin-4-yl}-2-propyl-phenyl)-acetic acid (1*) | 0.8 | 480.1 |
| 409 | (4-{6-[2-(4-Fluoro-benzo[b]thiophen-5-yl)-ethylamino]-pyrimidin-4-yl}-2-isobutyl-phenyl)-acetic acid (1*) | 0.939 | 462 |
| 410 | (4-{6-[2-(7-Fluoro-6-methoxy-benzo[b]thiophen-5-yl)-ethylamino]-pyrimidin-4-yl}-2-isobutyl-phenyl)-acetic acid (1*) | 0.968 | 492.1 |
| 411 | (2-Isobutyl-4-{6-[2-(7-methoxy-2,3-dihydro-benzo[1,4]dioxin-6-yl)-ethylamino]-pyrimidin-4-yl}-phenyl)-acetic acid (1*) | 0.821 | 476.1 |
| 412 | (4-{6-[2-(7-Ethoxy-2,3-dihydro-benzo[1,4]dioxin-6-yl)-ethylamino]-pyrimidin-4-yl}-2-isobutyl-phenyl)-acetic acid (1*) | 0.88 | 490.2 |
| 413 | 4-{6-[2-(4-Fluoro-benzo[b]thiophen-5-yl)-ethylamino]-pyrimidin-4-yl}-2-isobutyl-benzoic acid (1*) | 1.052 | 448.2 |
| 414 | 4-{6-[2-(7-Fluoro-benzo[b]thiophen-5-yl)-ethylamino]-pyrimidin-4-yl}-2-isobutyl-benzoic acid (1*) | 1.056 | 448.1 |
| 415 | 4-{6-[2-(7-Fluoro-6-methoxy-benzo[b]thiophen-5-yl)-ethylamino]-pyrimidin-4-yl}-2-isobutyl-benzoic acid (1*) | 1.075 | 478 |
| 416 | 2-Isobutyl-4-}6-[2-(7-methoxy-2,3-dihydro-benzo[1,4]dioxin-6-yl)-ethylamino]-pyrimidin-4-yl}-benzoic acid (1*) | 0.899 | 462 |
| 417 | 4-{6-[2-(7-Ethoxy-2,3-dihydro-benzo[1,4]dioxin-6-yl)-ethylamino]-pyrimidin-4-yl}-2-isobutyl-benzoic acid (1*) | 0.961 | 476 |
| 418 | 2-Ethoxy-4-{6-[2-(3-ethoxy-1-methyl-naphthalen-2-yl)-ethylamino]-pyrimidin-4-yl}-benzoic acid (1*) | 1.07 | 472.3 |
| 419 | 4-{6-[2-(3-Ethoxy-1-methyl-naphthalen-2-yl)-ethylamino]-pyrimidin-4-yl}-2-methylsulfanyl-benzoic acid (1*) | 1.075 | 474.3 |
| 420 | (2-Ethoxy-4-{6-[2-(3-ethoxy-1-methyl-naphthalen-2-yl)-ethylamino]-pyrimidin-4-yl}-phenyl)-acetic acid (1*) | 0.969 | 486 |
| 421 | 3-(2-Ethoxy-4-{6-[2-(4-fluoro-benzo[b]thiophen-5-yl)-ethylamino]-pyrimidin-4-yl}-phenoxy)-propionic acid (1*) | 0.812 | 480.1 |
| 422 | 3-(2-Ethoxy-4-{6-[2-(7-fluoro-benzo[b]thiophen-5-yl)-ethylamino]-pyrimidin-4-yl}-phenoxy)-propionic acid (1*) | 0.821 | 480.1 |
| 423 | 3-(2-Ethoxy-4-{6-[2-(3-methoxy-1-methyl-naphthalen-2-yl)-ethylamino]-pyrimidin-4-yl}-phenoxy)-propionic acid (1*) | 0.87 | 500.2 |
| 424 | (4-{6-[2-(4-Fluoro-benzo[b]thiophen-5-yl)-ethylamino]-pyrimidin-4-yl}-2-isopropoxy-phenyl)-acetic acid (1*) | 0.885 | 464 |
| 425 | (4-{6-[2-(7-Ethoxy-2,3-dihydro-benzo[1,4]dioxin-6-yl)-ethylamino]-pyrimidin-4-yl}-2-isopropoxy-phenyl)-acetic acid (1*) | 0.822 | 492.1 |
| 426 | (2-Isopropoxy-4-{6-[2-(7-methoxy-5-methyl-2,3-dihydro-benzo[1,4]dioxin-6-yl)-ethylamino]-pyrimidin-4-yl}-phenyl)-acetic acid (1*) | 0.807 | 492.1 |
| 427 | (4-{6-[2-(7-Ethoxy-2,3-dihydro-benzo[1,4]dioxin-6-yl)-ethylamino]-pyrimidin-4-yl}-2-trifluoromethoxy-phenyl)-acetic acid (1*) | 0.948 | 518.2 |
| 428 | (4-{6-[2-(7-Methoxy-5-methyl-2,3-dihydro-benzo[1,4]dioxin-6-yl)-ethylamino]-pyrimidin-4-yl}-2-trifluoromethoxy-phenyl)-acetic acid (1*) | 0.938 | 518 |
| 429 | 4-{6-[2-(3-Chloro-benzo[b]thiophen-5-yl)-ethylamino]-pyrimidin-4-yl}-2-methylsulfanyl-benzoic acid (1*) | 0.992 | 454.1 |
| 430 | 4-{6-[2-(3-Chloro-benzo[b]thiophen-5-yl)-ethylamino]-pyrimidin-4-yl}-2-cyclobutoxy-benzoic acid (1*) | 1.086 | 478.1 |
| 431 | (4-{6-[2-(3-Chloro-benzo[b]thiophen-5-yl)-ethylamino]-pyrimidin-4-yl}-2-ethoxy-phenyl)-acetic acid (1*) | 0.886 | 466.4 |
| 432 | 2-Isopropoxy-4-{6-[2-(7-methoxy-5-methyl-2,3-dihydro-benzo[1,4]dioxin-6-yl)-ethylamino]-pyrimidin-4-yl}-benzoic acid (1*) | 0.904 | 478.1 |
| 433 | 5-{6-[2-(7-Difluoromethoxy-2,3-dihydro-benzo[1,4]dioxin-6-yl)-ethylamino}-pyrimidin-4-yl}-3-ethoxy-thiophene-2-carboxylic acid (1*) | 0.987 | 492 |
| 434 | (2-Methoxy-4-{6-[2-(7-methoxy-5-methyl-2,3-dihydro-benzo[1,4]dioxin-6-yl)-ethylamino]-pyrimidin-4-yl}-phenyl)-acetic acid (1*) | 0.734 | 464.1 |
| 435 | 2-Ethoxy-4-{6-[2-(5-fluoro-7-methoxy-2,3-dihydro-benzo[1,4]dioxin-6-yl)-ethylamino]-pyrimidin-4-yl}-benzoic acid (1*) | 0.812 | 468.1 |
| 436 | 2-Ethoxy-4-{6-[2-(3-ethoxy-1-fluoro-naphthalen-2-yl)-ethylamino]-pyrimidin-4-yl}-benzoic acid (1*) | 1.075 | 476.3 |
| 437 | 3-(4-{6-[2-(4-Fluoro-benzo[b]thiophen-5-yl)-ethylamino]-pyrimidin-4-yl}-2-methoxy-phenoxy)-propionic acid (1*) | 0.77 | 466.2 |
| 438 | 3-(4-{6-[2-(7-Fluoro-benzo[b]thiophen-5-yl)-ethylamino]-pyrimidin-4-yl}-2-methoxy-phenoxy)-propionic acid (1*) | 0.781 | 466.1 |
| 439 | 2-Ethoxy-4-{6-[2-(7-ethynyl-2,3-dihydro-benzo[1,4]dioxin-6-yl)-ethylamino]-pyrimidin-4-yl}-benzoic acid (1*) | 0.739 | 447.4 |
| 440 | (4-{6-[2-(7-Ethynyl-2,3-dihydro-benzo[1,4]dioxin-6-yl)-ethylamino]-pyrimidin-4-yl}-2-propyl-phenyl)-acetic acid (1*) | 0.8 | 459 |
| 441 | (2-Difluoromethoxy-4-{6-[2-(7-methoxy-5-methyl-2,3-dihydro-benzo[1,4]dioxin-6-yl)-ethylamino]-pyrimidin-4-yl}-phenyl)-acetic acid (1*) | 0.835 | 500.1 |
| 442 | (2-Difluoromethoxy-4-{6-[2-(5-fluoro-7-methoxy-2,3-dihydro-benzo[1,4]dioxin-6-yl)-ethylamino]-pyrimidin-4-yl}-phenyl)-acetic acid (1*) | 0.816 | 504.1 |
| 443 | (2-Difluoromethoxy-4-{6-[2-(3-methoxy-1-methyl-naphthalen-2-yl)-ethylamino]-pyrimidin-4-yl}-phenyl)-acetic acid (1*) | 0.987 | 492.4 |
| 444 | (2-Ethyl-4-{6-[2-(7-methoxy-5-methyl-2,3-dihydro-benzo[1,4]dioxin-6-yl)-ethylamino]-pyrimidin-4-yl}-phenyl)-acetic acid (1*) | 0.772 | 462 |

TABLE 5-continued

Examples 356-456

| Ex. | Compound | $t_R$ [min] (LC-MS C) | MS Data m/z [M + H]+ |
|---|---|---|---|
| 445 | (2-Ethyl-4-{6-[2-(3-methoxy-1-methyl-naphthalen-2-yl)-ethylamino]-pyrimidin-4-yl}-phenyl)-acetic acid (1*) | 0.893 | 454.2 |
| 446 | 2-Ethyl-4-{6-[2-(3-methoxy-1-methyl-naphthalen-2-yl)-ethylamino]-pyrimidin-4-yl}-benzoic acid (1*) | 0.985 | 440.1 |
| 447 | 2-Cyclopropoxy-4-{6-[2-(7-ethoxy-2,3-dihydro-benzo[1,4]dioxin-6-yl)-ethylamino]-pyrimidin-4-yl}-benzoic acid (1*) | 0.861 | 476 |
| 448 | 2-Cyclopropoxy-4-{6-[2-(3-methoxy-1-methyl-naphthalen-2-yl)-ethylamino]-pyrimidin-4-yl}-benzoic acid (1*) | 1.001 | 468 |
| 449 | 2-Cyclopropoxy-4-{6-[2-(7-fluoro-benzo[b]thiophen-5-yl)-ethylamino]-pyrimidin-4-yl}-benzoic acid (1*) | 0.952 | 448.2 |
| 450 | (4-{6-[2-(7-Methoxy-2,3-dihydro-benzo[1,4]dioxin-6-yl)-ethylamino]-pyrimidin-4-yl}-2-trifluoromethoxy-phenyl)-acetic acid (1*) | 0.879 | 504 |
| 451 | 3-(2-Ethoxy-4-{6-[2-(7-fluoro-benzo[b]thiophen-5-yl)-ethylamino]-pyrimidin-4-yl}-phenyl)-[1,2,4]oxadiazol-5(4H)-one [tautomeric form: 3-(2-ethoxy-4-{6-[2-(7-fluoro-benzo[b]thiophen-5-yl)-ethylamino]-pyrimidin-4-yl}-phenyl)-[1,2,4]oxadiazol-5-ol] | 1.024 | 478.2 |
| 452 | {6-[3-Ethoxy-4-(1H-tetrazol-5-yl)-phenyl]-pyrimidin-4-yl}-[2-(7-fluoro-benzo[b]thiophen-5-yl)-ethyl]-amine | 0.961 | 462.3 |
| 453 | 4-{6-[2-(7-Fluoro-benzo[b]thiophen-5-yl)-ethylamino]-pyrimidin-4-yl}-2-isobutoxy-benzoic acid (1*) | 1.084 | 466.1 |
| 454 | 2-Butoxy-4-{6-[2-(7-fluoro-benzo[b]thiophen-5-yl)-ethylamino]-pyrimidin-4-yl}-benzoic acid (1*) | 1.088 | 466.3 |
| 455 | 3-Ethyl-5-{6-[2-(7-fluoro-benzo[b]thiophen-5-yl)-ethylamino]-pyrimidin-4-yl}-thiophene-2-carboxylic acid (1*) | 1.174 | 428.2 |
| 456 | (3-Ethoxy-5-{6-[2-(7-fluoro-benzo[b]thiophen-5-yl)-ethylamino]-pyrimidin-4-yl}-thiophen-2-yl)-acetic acid (1*) | 1.015 | 458.2 |

Example 457: 4-{6-[2-(7-Fluoro-benzo[b]thiophen-5-yl)-ethylamino]-pyrimidin-4-yl}-2-propyl-benzamide To a solution of 4-{6-[2-(7-fluoro-benzo[b]thiophen-5-yl)-ethylamino]-pyrimidin-4-yl}-2-propyl-benzoic acid (Example 389, 0.08 mmol), ammonium chloride (5.7 mg, 0.096 mmol), DIPEA (0.0438 mL, 0.256 mmol) in DMF (0.6 mL) is added a solution of HATU (31.9 mg, 0.084 mmol) in DMF (0.2 mL). The RM is stirred for 3d at RT, then directly purified by prep LC-MS, affording the title compound as a white solid (16 mg, 46%). LC-MS C: $t_R$=0.834 min; [M+H]+=435.0.

Following the procedure described for Example 457, with 4-{6-[2-(7-fluoro-benzo[b]thiophen-5-yl)-ethylamino]-pyrimidin-4-yl}-2-propyl-benzoic acid (Example 389) or 2-ethoxy-4-{6-[2-(7-fluoro-benzo[b]thiophen-5-yl)-ethylamino]-pyrimidin-4-yl}-benzoic acid(Example 361) and the corresponding commercially available amines, the following examples are synthesized:

| Ex. | Compound | $t_R$ [min] (LC-MS C) | MS Data m/z [M + H]+ |
|---|---|---|---|
| 458 | 4-{6-[2-(7-Fluoro-benzo[b]thiophen-5-yl)-ethylamino]-pyrimidin-4-yl}-N-methyl-2-propyl-benzamide | 0.869 | 449.3 |
| 459 | 4-{6-[2-(7-Fluoro-benzo[b]thiophen-5-yl)-ethylamino]-pyrimidin-4-yl}-N-(2-hydroxy-2-methyl-propyl)-2-propyl-benzamide | 0.885 | 507.2 |
| 460 | 4-{6-[2-(7-Fluoro-benzo[b]thiophen-5-yl)-ethylamino]-pyrimidin-4-yl}-N-(2-hydroxy-ethyl)-2-propyl-benzamide | 0.814 | 479.1 |
| 461 | 2-Ethoxy-4-{6-[2-(7-fluoro-benzo[b]thiophen-5-yl)-ethylamino]-pyrimidin-4-yl}benzamide | 0.869 | 437.1 |
| 462 | 2-Ethoxy-4-{6-[2-(7-fluoro-benzo[b]thiophen-5-yl)-ethylamino]-pyrimidin-4-yl}-N-methyl-benzamide | 0.91 | 451.3 |
| 463 | 2-Ethoxy-4-{6-[2-(7-fluoro-benzo[b]thiophen-5-yl)-ethylamino]-pyrimidin-4-yl}-N-(2-hydroxy-2-methyl-propylbenzamide | 0.92 | 509.3 |
| 464 | 2-Ethoxy-4-{6-[2-(7-fluoro-benzo[b]thiophen-5-yl)-ethylamino]-pyrimidin-4-yl}-N-(2-hydroxy-ethyl)-benzamide | 0.844 | 481.3 |

Compounds of Examples 465-564 listed in Table 6 below are prepared by applying either one of the above-mentioned procedures A, B or C to the pyrimidine halide derivatives A.1.1-A.1.xx. coupled with commercially available boronic acid derivatives or with boronic acid derivatives A.2.1.-A.2.xx.

TABLE 6

| Ex. | Compound | $t_R$ [min] (LC-MS C) | MS Data m/z [M +H]+ |
|---|---|---|---|
| 465 | 2-Ethoxy-4-{6-[2-(3-methyl-benzo[b]thiophen-5-yl)-ethylamino]-pyrimidin-4-yl}-benzoic acid | 0.95 | 434.3 |
| 466 | (2-Ethoxy-4-{6-[2-(3-methyl-benzo[b]thiophen-5-yl)-ethylamino]-pyrimidin-4-yl}-phenoxy)-acetic acid | 0.829 | 464 |
| 467 | 6-[6-(2-Benzo[b]thiophen-5-yl-ethylamino)-pyrimidin-4-yl]-benzofuran-3-carboxylic acid | 0.844 | 416.2 |
| 468 | 3-Hydroxy-5-{6-[2-(1-methyl-naphthalen-2-yl)-ethylamino]-pyrimidin-4-yl}-thiophene-2-carboxylic acid methyl ester | 1.303 | 420.3 |
| 469 | (2-Ethoxy-6-fluoro-4-{6-[2-(6-methyl-benzo[b]thiophen-5-yl)-ethylamino]-pyrimidin-4-yl}-phenyl)-acetic acid (*1) | 0.996 | 464.3 |
| 470 | 2-Ethoxy-4-{6-[2-(7-methyl-benzo[b]thiophen-6-yl)-ethylamino]-pyrimidin-4-yl}-benzoic acid (*1) | 0.945 | 432.2 |
| 471 | 2-Cyclobutoxy-4-{6-[2-(7-methyl-benzo[b]thiophen-6-yl)-ethylamino]-pyrimidin-4-yl}-benzoic acid (*1) | 1.051 | 457.9 |
| 472 | (2-Ethoxy-4-{6-[2-(7-methyl-benzo[b]thiophen-6-yl)-ethylamino]-pyrimidin-4-yl}-phenyl)-acetic acid (*1) | 0.844 | 446.2 |
| 473 | 4-{6-[2-(7-Methyl-benzo[b]thiophen-6-yl)-ethylamino]-pyrimidin-4-yl}-2-methylsulfanyl-benzoic acid (*1) | 0.95 | 434 |
| 474 | rac-5-[6-(2-Benzo[b]thiophen-5-yl-ethylamino)-pyrimidin-4-yl]-2,3-dihydro-benzofuran-2-carboxylic acid (*1) | 0.733 | 416.1 |
| 475 | (4-{6-[2-(7-Fluoro-benzo[b]thiophen-5-yl)-ethylamino]-pyrimidin-4-yl}-2-methoxy-phenyl)-acetic acid (*1) | 0.804 | 436.1 |
| 476 | 2-Ethoxy-4-{6-[2-(7-methyl-benzo[b]thiophen-5-yl)-ethylamino]-pyrimidin-4-yl}-benzoic acid (*1) | 0.95 | 432.3 |
| 477 | 4-{6-[2-(7-Methyl-benzo[b]thiophen-5-yl)-ethylamino]-pyrimidin-4-yl}-2-methylsulfanyl-benzoic acid (*1) | 0.955 | 433.9 |
| 478 | 4-{6-[2-(7-Methyl-benzo[b]thiophen-5-yl)-ethylamino]-pyrimidin-4-yl}-2-propyl-benzoic acid (*1) | 1.006 | 430.1 |
| 479 | {4-[6-(2-Benzo[b]thiophen-5-yl-ethylamino)-pyrimidin-4-yl]-2-propoxy-phenyl}-acetic acid (*1) | 0.859 | 446.3 |
| 480 | (4-{6-[2-(7-Methoxy-2,3-dihydro-benzo[1,4]dioxin-6-yl)-ethylamino]-pyrimidin-4-yl}-2-propoxy-phenyl)-acetic acid (*1) | 0.774 | 478.1 |
| 481 | rac-2-{4-[6-(2-Benzo[b]thiophen-5-yl-ethylamino)-pyrimidin-4-yl]-2-propyl-phenyl}-propionic acid (*1) | 0.905 | 444.3 |
| 482 | rac-2-(4 -{6-[2-(4-Fluoro-benzo[b]thiophen-5-yl)-ethylamino]-pyrimidin-4-yl}-2-propyl-phenyl)-propionic acid (*1) | 0.935 | 462.2 |
| 483 | 4-{6-[2-(7-Fluoro-6-methoxy-benzo[b]thiophen-5-yl)-ethylamino]-pyrimidin-4-yl}-2-propyl-benzoic acid (*1) | 1.015 | 464.1 |
| 484 | 3-Ethoxy-5-{6-[2-(7-fluoro-6-methoxy-benzo[b]thiophen-5-yl)-ethylamino]-pyrimidin-4-yl}-thiophene-2-carboxylic acid (*1) | 1.116 | 472.1 |
| 485 | (4-{6-[2-(7-Fluoro-6-methoxy-benzo[b]thiophen-5-yl)-ethylamino]-pyrimidin-4-yl}-2-methoxy-phenyl)-acetic acid (*1) | 0.824 | 466.1 |
| 486 | (4-{6-[2-(7-Fluoro-6-methoxy-benzo[b]thiophen-5-yl)-ethylamino]-pyrimidin-4-yl}-2-propyl-phenyl)-acetic acid (*1) | 0.91 | 478.2 |
| 487 | rac-2-(4-{6-[2-(7-Ethoxy-2,3-dihydro-benzo[1,4]dioxin-6-yl)-ethylamino]-pyrimidin-4-yl}-2-propyl-phenyl)-propionic acid (*1) | 0.87 | 490 |
| 488 | 3-Ethoxy-5-{6-[2-(7-trifluoromethyl-benzo[b]thiophen-5-yl)-ethylamino]-pyrimidin-4-yl}-thiophene-2-carboxylic acid (*1) | 1.162 | 492.1 |
| 489 | (4-{6-[2-(4-Fluoro-benzo[b]thiophen-5-yl)-ethylamino]-pyrimidin-4-yl}-2-trifluoromethoxy-phenyl)-acetic acid (*1) | 1.036 | 446.1 |
| 490 | 4-{6-[2-(3-Chloro-benzo[b]thiophen-5-yl)-ethylamino]-pyrimidin-4-yl}-2-ethoxy-benzoic acid (*1) | 0.975 | 452.1 |
| 491 | 4-{6-[2-(7-Fluoro-benzo[b]thiophen-5-yl)-ethylamino]-pyrimidin-4-yl}-2-isopropoxy-benzoic acid (*1) | 1.01 | 450 |
| 492 | 4-{6-[2-(4-Fluoro-benzo[b]thiophen-5-yl)-ethylamino]-pyrimidin-4-yl}-2-isopropoxy-benzoic acid (*1) | 1.001 | 450 |
| 493 | 2-Isopropoxy-4-{6-[2-(7-methoxy-2,3-dihydro-benzo[1,4]dioxin-6-yl)-ethylamino]-pyrimidin-4-yl}-benzoic acid (*1) | 0.844 | 464.1 |
| 494 | 2-Cyclobutoxy-4-{6-[2-(7-difluoromethoxy-2,3-dihydro-benzo[1,4]dioxin-6-yl)-ethylamino]-pyrimidin-4-yl}-benzoic acid (*1) | 0.93 | 512.3 |
| 495 | 4-{6-[2-(7-Difluoromethoxy-2,3-dihydro-benzo[1,4]dioxin-6-yl)-ethylamino]-pyrimidin-4-yl}-2-methylsulfanyl-benzoic acid (*1) | 0.844 | 488.2 |
| 496 | 4-{6-[2-(7-Fluoro-benzo[b]thiophen-5-yl)-ethylamino]-pyrimidin-4-yl}-benzoic acid (*1) | 0.87 | 392.1 |
| 497 | 4-{6-[2-(7-Fluoro-benzo[b]thiophen-5-yl)-ethylamino]-pyrimidin-4-yl}-2-methoxy-benzoic acid (*1) | 0.869 | 422.1 |
| 498 | (4-{6-[2-(3-Chloro-benzo[b]thiophen-5-yl)-ethylamino]-pyrimidin-4-yl}-2-propyl-phenyl)-acetic acid (*1) | 0.92 | 464.1 |
| 499 | (4-{6-[2-(3-Chloro-benzo[b]thiophen-5-yl)-ethylamino]-pyrimidin-4-yl}-2-trifluoromethoxy-phenyl)-acetic acid (*1) | 1.081 | 506.3 |
| 500 | (4-{6-[2-(3-Methoxy-1-methyl-naphthalen-2-yl)-ethylamino]-pyrimidin-4-yl}-2-trifluoromethoxy-phenyl)-acetic acid (*1) | 1.086 | 510.1 |

TABLE 6-continued

| Ex. | Compound | $t_R$ [min] (LC-MS C) | MS Data m/z [M +H]$^+$ |
|---|---|---|---|
| 501 | (4-{6-[2-(3-Chloro-7-fluoro-benzo[b]thiophen-5-yl)-ethylamino]-pyrimidin-4-yl}-2-propyl-phenyl)-acetic acid (*1) | 0.945 | 482.2 |
| 502 | (4-{6-[2-(3-Chloro-7-fluoro-benzo[b]thiophen-5-yl)-ethylamino]-pyrimidin-4-yl}-2-ethoxy-phenyl)-acetic acid (*1) | 0.9 | 484.3 |
| 503 | (4-{6-[2-(7-Ethynyl-2,3-dihydro-benzo[1,4]dioxin-6-yl)-ethylamino]-pyrimidin-4-yl}-2-methoxy-phenyl)-acetic acid (*1) | 0.73 (LC-MS B) | 446.2 |
| 504 | (4-{6-[2-(5-Methyl-2,3-dihydro-benzo[1,4]dioxin-6-yl)-ethylamino]-pyrimidin-4-yl}-2-propyl-phenyl)-acetic acid (*1) | 0.789 | 446.1 |
| 505 | (2-Methoxy-4-{6-[2-(5-methyl-2,3-dihydro-benzo[1,4]dioxin-6-yl)-ethylamino]-pyrimidin-4-yl}-phenyl)-acetic acid (*1) | 0.698 | 434.1 |
| 506 | (2-Ethoxy-4-{6-[2-(5-methyl-2,3-dihydro-benzo[1,4]dioxin-6-yl)-ethylamino]-pyrimidin-4-yl}-phenyl)-acetic acid (*1) | 0.743 | 448.2 |
| 507 | 3-(2-Methoxy-4-{6-[2-(5-methyl-2,3-dihydro-benzo[1,4]dioxin-6-yl)-ethylamino]-pyrimidin-4-yl}-phenoxy)-propionic acid (*1) | 0.678 | 464 |
| 508 | 2-Ethoxy-4-{6-[2-(5-methyl-2,3-dihydro-benzo[1,4]dioxin-6-yl)-ethylamino]-pyrimidin-4-yl}-benzoic acid (*1) | 0.809 | 434 |
| 509 | (4-{6-[2-(5-Methyl-2,3-dihydro-benzo[1,4]dioxin-6-yl)-ethylamino]-pyrimidin-4-yl}-2-trifluoromethoxy-phenyl)-acetic acid (*1) | 0.91 | 488.2 |
| 510 | (2-Difluoromethoxy-4-{6-[2-(7-ethoxy-2,3-dihydro-benzo[1,4]dioxin-6-yl)-ethylamino]-pyrimidin-4-yl}-phenyl)-acetic acid (*1) | 0.844 | 500.1 |
| 511 | (2-Difluoromethoxy-4-{6-[2-(5-methyl-2,3-dihydro-benzo[1,4]dioxin-6-yl)-ethylamino]-pyrimidin-4-yl}-phenyl)-acetic acid (*1) | 0.809 | 470.1 |
| 512 | (4-{6-[2-(7-Ethoxy-2,3-dihydro-benzo[1,4]dioxin-6-yl)-ethylamino]-pyrimidin-4-yl}-2-ethyl-phenyl)-acetic acid (*1) | 0.769 | 462.1 |
| 513 | (2-Ethyl-4-{6-[2-(5-methyl-2,3-dihydro-benzo[1,4]dioxin-6-yl)-ethylamino]-pyrimidin-4-yl}-phenyl)-acetic acid (*1) | 0.734 | 432.2 |
| 514 | (2-Ethyl-4-{6-[2-(4-fluoro-benzo[b]thiophen-5-yl)-ethylamino]-pyrimidin-4-yl}-phenyl)-acetic acid (*1) | 0.824 | 434.1 |
| 515 | 2-Ethyl-4-{6-[2-(5-methyl-2,3-dihydro-benzo[1,4]dioxin-6-yl)-ethylamino]-pyrimidin-4-yl}-benzoic acid (*1) | 0.804 | 418.1 |
| 516 | 4-{6-[2-(7-Ethoxy-2,3-dihydro-benzo[1,4]dioxin-6-yl)-ethylamino]-pyrimidin-4-yl}-2-ethyl-benzoic acid (*1) | 0.839 | 448 |
| 517 | 2-Ethyl-4-{6-[2-(1-methyl-naphthalen-2-yl)-ethylamino]-pyrimidin-4-yl}-benzoic acid (*1) | 0.955 | 410 |
| 518 | 2-Ethyl-4-{6-[2-(7-fluoro-benzo[b]thiophen-5-yl)-ethylamino]-pyrimidin-4-yl}-benzoic acid (*1) | 0.93 | 420 |
| 519 | 2-Cyclopropoxy-4-{6-[2-(5-methyl-2,3-dihydro-benzo[1,4]dioxin-6-yl)-ethylamino]-pyrimidin-4-yl}-benzoic acid (*1) | 0.819 | 446.1 |
| 520 | 2-Cyclopropoxy-4-{6-[2-(7-methoxy-2,3-dihydro-benzo[1,4]dioxin-6-yl)-ethylamino]-pyrimidin-4-yl}-benzoic acid (*1) | 0.784 | 461.9 |
| 521 | 2-Cyclopropoxy-4-{6-[2-(1-methyl-naphthalen-2-yl)-ethylamino]-pyrimidin-4-yl}-benzoic acid (*1) | 0.98 | 438 |
| 522 | (2-Difluoromethoxy-4-{6-[2-(7-methoxy-2,3-dihydro-benzo[1,4]dioxin-6-yl)-ethylamino]-pyrimidin-4-yl}-phenyl)-acetic acid (*1) | 0.779 | 486.2 |
| 523 | (2-Isopropoxy-4-{6-[2-(7-methoxy-2,3-dihydro-benzo[1,4]dioxin-6-yl)-ethylamino]-pyrimidin-4-yl}-phenyl)-acetic acid (*1) | 0.759 | 478 |
| 524 | (2-Ethyl-4-{6-[2-(7-methoxy-2,3-dihydro-benzo[1,4]dioxin-6-yl)-ethylamino]-pyrimidin-4-yl}-phenyl)-acetic acid (*1) | 0.718 | 448.2 |
| 525 | (4-{6-[2-(7-Methoxy-2,3-dihydro-benzo[1,4]dioxin-6-yl)-ethylamino]-pyrimidin-4-yl}-2-trifluoromethyl-phenyl)-acetic acid (*1) | 0.849 | 488.2 |
| 526 | (4-{6-[2-(7-Methyl-2,3-dihydro-benzo[1,4]dioxin-6-yl)-ethylamino]-pyrimidin-4-yl}-2-propyl-phenyl)-acetic acid (*1) | 0.784 | 446.1 |
| 527 | (4-{6-[2-(2,3-Dihydro-benzo[1,4]dioxin-6-yl)-ethylamino]-pyrimidin-4-yl}-2-propyl-phenyl)-acetic acid (*1) | 0.744 | 432.2 |
| 528 | (4-{6-[2-(7-Fluoro-2,3-dihydro-benzo[1,4]dioxin-6-yl)-ethylamino]-pyrimidin-4-yl}-2-propyl-phenyl)-acetic acid (*1) | 0.784 | 450.3 |
| 529 | 3-(4-(6-((2-(7-fluorobenzo[b]thiophen-5-yl)ethyl)amino)pyrimidin-4-yl)phenyl)-[1,2,4]oxadiazol-5(4H)-one [tautomeric form: 3-(4-{6-[2-(7-fluoro-benzo[b]thiophen-5-yl)-ethylamino]-pyrimidin-4-yl}-phenyl)-[1,2,4]oxadiazol-5-ol] | 0.92 | 434.2 |
| 530 | 7-{6-[2-(7-Fluoro-benzo[b]thiophen-5-yl)-ethylamino]-pyrimidin-4-yl}-1-methyl-3,4-dihydro-1H-quinazolin-2-one | 0.774 | 434.3 |
| 531 | 2-{6-[2-(7-Fluoro-benzo[b]thiophen-5-yl)-ethylamino]-pyrimidin-4-yl}-1H-indole-4-carboxylic acid (*1) | 0.93 | 433 |
| 532 | 4-{6-[2-(7-Fluoro-benzo[b]thiophen-5-yl)-ethylamino]-pyrimidin-4-yl}-2,6-dimethyl-phenol | 0.794 | 394.3 |
| 533 | 2-Ethylsulfanyl-4-{6-[2-(7-fluoro-benzo[b]thiophen-5-yl)-ethylamino]-pyrimidin-4-yl}-benzoic acid (*1) | 1.006 | 454.1 |
| 534 | 2-Cyclobutoxy-4-{6-[2-(7-fluoro-benzo[b]thiophen-5-yl)-ethylamino]-pyrimidin-4-yl}-benzoic acid (*1) | 1.041 | 464.3 |
| 535 | 3-(3-Ethoxy-5-{6-[2-(7-fluoro-benzo[b]thiophen-5-yl)-ethylamino]-pyrimidin-4-yl}-thiophen-2-yl)-propionic acid (*1) | 1.187 | 472.2 |
| 536 | 3-(4-{6-[2-(7-Fluoro-benzo[b]thiophen-5-yl)-ethylamino]-pyrimidin-4-yl}-phenyl)-4-hydroxy-cyclobut-3-ene-1,2-dione | 0.908 | 446.1 |
| 537 | (2-Ethoxy-4-{6-[2-(7-fluoro-benzo[b]thiophen-5-yl)-ethylamino]-pyrimidin-4-yl}-phenyl)-oxo-acetic acid | 0.915 | 466.3 |

TABLE 6-continued

| Ex. | Compound | $t_R$ [min] (LC-MS C) | MS Data m/z [M +H]+ |
|---|---|---|---|
| 538 | 2-Cyclopropoxy-4-{6-[2-(7-fluoro-benzo[b]thiophen-5-yl)-ethylamino]-pyrimidin-4-yl}-benzoic acid methyl ester | 1.086 | 464.3 |
| 539 | [2-(7-Fluoro-benzo[b]thiophen-5-yl)-ethyl]-[6-(1H-indol-5-yl)-pyrimidin-4-yl]amine | 0.779 | 389.4 |
| 540 | (2-Difluoromethoxy-4-{6-[2-(7-fluoro-benzo[b]thiophen-5-yl)-ethylamino]-pyrimidin-4-yl}-phenyl)-acetic acid (*1) | 0.935 | 474.3 |
| 541 | (2-Chloro-6-ethyl-4-{6-[2-(7-fluoro-benzo[b]thiophen-5-yl)-ethylamino]-pyrimidin-4-yl}-phenyl)-acetic acid (*1) | 0.991 | 470.1 |
| 542 | (2-Ethyl-4-{6-[2-(7-fluoro-benzo[b]thiophen-5-yl)-ethylamino]-pyrimidin-4-yl}-6-methyl-phenyl)-acetic acid (*1) | 0.854 | 450.3 |
| 543 | 5-(4-(6-((2-(7-fluorobenzo[b]thiophen-5-yl)ethyl)amino)pyrimidin-4-yl)phenyl)-[1,2,4]oxadiazol-3(2H)-one [tautomeric form: 5-(4-{6-[2-(7-fluoro-benzo[b]thiophen-5-yl)-ethylamino]-pyrimidin-4-yl}-phenyl)-[1,2,4]oxadiazol-3-ol] | 0.854 | 433.9 |
| 544 | (4-{6-[2-(7-Fluoro-benzo[b]thiophen-5-yl)-ethylamino]-pyrimidin-4-yl}-2-methyl-phenyl)-acetic acid (*1) | 0.789 | 422.3 |
| 545 | (3-Ethyl-5-{6-[2-(7-fluoro-benzo[b]thiophen-5-yl)-ethylamino]-pyrimidin-4-yl}-thiophen-2-yl)-acetic acid (*1) | 0.981 | 442.4 |
| 546 | (2-Chloro-4-{6-[2-(7-fluoro-benzo[b]thiophen-5-yl)-ethylamino]-pyrimidin-4-yl}-6-methyl-phenyl)-acetic acid (*1) | 0.945 | 456.2 |
| 547 | 1-Ethyl-4-{6-[2-(7-fluoro-benzo[b]thiophen-5-yl)-ethylamino]-pyrimidin-4-yl}-1H-pyrrole-2-carboxylic acid (*1) | 0.749 | 411.3 |
| 548 | 4-{6-[2-(7-Fluoro-benzo[b]thiophen-5-yl)-ethylamino]-pyrimidin-4-yl}-1-propyl-1H-pyrrole-2-carboxylic acid (*1) | 0.794 | 425.1 |
| 549 | 6-{6-[2-(7-Fluoro-benzo[b]thiophen-5-yl)-ethylamino]-pyrimidin-4-yl}-benzofuran-3-carboxylic acid (*1) | 0.89 | 434.1 |
| 550 | 5-(2-Ethoxy-4-{6-[2-(7-fluoro-benzo[b]thiophen-5-yl)-ethylamino]-pyrimidin-4-yl}-phenyl)-isoxazol-3-ol [tautomeric form: 5-(2-ethoxy-4-(6-((2-(7-fluorobenzo[b]thiophen-5-yl)ethyl)amino)pyrimidin-4-yl)phenyl)isoxazol-3(2H)-one] | 1.001 | 477.3 |
| 551 | 2-Ethoxy-4-{6-[2-(7-fluoro-benzo[b]thiophen-5-yl)-ethylamino]-pyrimidin-4-yl}-6-propyl-benzoic acid (*1) | 0.981 | 480.3 |
| 552 | 2-Ethoxy-3-fluoro-4-{6-[2-(7-fluoro-benzo[b]thiophen-5-yl)-ethylamino]-pyrimidin-4-yl}-benzoic acid (*1) | 0.99 | 456.3 |
| 553 | 5-(4-{6-[2-(7-Fluoro-benzo[b]thiophen-5-yl)-ethylamino]-pyrimidin-4-yl}-2-methoxy-phenyl)-isoxazol-3-ol [tautomeric form: 5-(4-(6-((2-(7-fluorobenzo[b]thiophen-5-yl)ethyl)amino)pyrimidin-4-yl)-2-methoxyphenyl)isoxazol-3(2H)-one] | 0.945 | 463.3 |
| 554 | 2-Fluoro-4-{6-[2-(7-fluoro-benzo[b]thiophen-5-yl)-ethylamino]-pyrimidin-4-yl}-benzoic acid (*1) | 0.965 | 412.2 |
| 555 | 4-{6-[2-(7-Fluoro-benzo[b]thiophen-5-yl)-ethylamino]-pyrimidin-4-yl}-2-methyl-benzoic acid (*1) | 0.874 | 408.3 |
| 556 | (5-{6-[2-(7-Fluoro-benzo[b]thiophen-5-yl)-ethylamino]-pyrimidin-4-yl}-3-propyl-thiophen-2-yl)-acetic acid (*1) | 1.046 | 456.3 |
| 557 | 1-(4-{6-[2-(7-Fluoro-benzo[b]thiophen-5-yl)-ethylamino]-pyrimidin-4-yl}-2-propyl-phenyl)-cyclopropanecarboxylic acid (*1) | 0.95 | 476.1 |
| 558 | 4-{6-[2-(7-Fluoro-benzo[b]thiophen-5-yl)-ethylamino]-pyrimidin-4-yl}-1H-indole-7-carboxylic acid (*1) | 0.804 | 433.4 |
| 559 | (3-Difluoromethoxy-5-{6-[2-(7-fluoro-benzo[b]thiophen-5-yl)-ethylamino]-pyrimidin-4-yl}-thiophen-2-yl)-acetic acid (*1) | 1.096 | 480.2 |
| 560 | 3-(4-{6-[2-(7-Fluoro-benzo[b]thiophen-5-yl)-ethylamino]-pyrimidin-4-yl}-2-methoxy-phenyl)-propionic acid (*1) | 0.829 | 452.1 |
| 561 | 2-{6-[2-(7-Fluoro-benzo[b]thiophen-5-yl)-ethylamino]-pyrimidin-4-yl}-1H-indole-7-carboxylic acid (*1) | 1.096 | 432.9 |
| 562 | 6-{6-[2-(7-Fluoro-benzo[b]thiophen-5-yl)-ethylamino]-pyrimidin-4-yl}-1H-indazole-3-carboxylic acid (*1) | 0.779 | 434.3 |
| 563 | 4-{6-[2-(7-Fluoro-benzo[b]thiophen-5-yl)-ethylamino]-pyrimidin-4-yl}-2-hydroxy-benzoic acid (*1) | 0.91 | 410.2 |
| 564 | (2-Ethoxy-3-fluoro-4-{6-[2-(7-fluoro-benzo[b]thiophen-5-yl)-ethylamino]-pyrimidin-4-yl}-phenyl)-acetic acid (*1) | 0.91 | 470 |

Example 565: 3-(2-Ethoxy-4-{6-[2-(1-methyl-naphthalen-2-yl)-ethylamino]-pyrimidin-4-yl}-phenyl)-[1,2,4]oxadiazole-5(4H)-thione (tautomeric form: 3-(2-ethoxy-4-{6-[2-(1-methyl-naphthalen-2-yl)-ethylamino]-pyrimidin-4-yl}-phenyl)-[1,2,4]oxadiazole-5-thiol)

To a solution of (E/Z)-2-ethoxy-N'-hydroxy-4-(6-((2-(1-methylnaphthalen-2-yl)ethyl)amino)pyrimidin-4-yl)benzimidamide (79 mg, 0.166 mmol) in dioxane (0.8 ml) and DMSO (0.8 ml) are added 1,1'-thiocarbonyldiimidazole (46.8 mg, 0.25 mmol) and DBU (0.0989 mL, 0.649 mmol). The RM is heated at 9000 and stirred overnight. Dioxane is removed under vacuo then the solution is filtered through a PTFE filter, washing with MeCN and DMF, and purified by prep. LC-MS, affording the title compound as a pale yellow powder (45 mg, 56%). LC-MS C: $t_R$=1.141 min; [M+H]+ 484.1.

a) (E/Z)-2-Ethoxy-N'-hydroxy-4-(6-((2-(1-methyl naphthalen-2-yl)ethyl)amino)pyrimidin-4-yl)benzimidamide A solution of 2-ethoxy-4-(6-((2-(1-methylnaphthalen-2-yl)ethyl)amino)pyrimidin-4-yl)benzonitrile (87 mg, 0.213 mmol), hydroxylamine hydrochloride (0.0224 mL, 0.532 mmol), TEA (0.0745 mL, 0.532 mmol) and EtOH (2 ml) is heated at 9000 and stirred overnight. The RM is cooled to RT, and the precipitate is collected by filtration, washed with water, EtOH and finally Et2O, and dried under high vacuum, yielding the title compound as a beige powder (79 mg, 84%). LC-MS B: $t_R$=0.68 min; [M+H]$^+$=442.0.

b) 2-Ethoxy-4-(6-((2-(1-methylnaphthalen-2-yl)ethyl)amino)pyrimidin-4-yl)benzonitrile Following the General Procedure A, with 6-chloro-N-(2-(1-methylnaphthalen-2-yl)ethyl)pyrimidin-4-amine (A.1.2.) and 4-cyano-3-ethoxyphenylboronic acid, the title compound is obtained as a white solid. LC-MS B: $t_R$=0.93 min; [M+H]$^+$=408.97.

Example 566: 3-(2-Ethoxy-4-{6-[2-(1-methyl-naphthalen-2-yl)-ethylamino]-pyrimidin-4-yl}-benzyl)-[1,2,4]oxadiazol-5(4H)-one (tautomeric form: 3-(2-ethoxy-4-{6-[2-(1-methyl-naphthalen-2-yl)-ethylamino]-pyrimidin-4-yl}-benzyl)-[1,2,4]oxadiazol-5-ol)

A MW vial is charged with (E/Z)-2-(2-ethoxy-4-(6-((2-(1-methylnaphthalen-2-yl)ethyl)amino)pyrimidin-4-yl)phenyl)-N'-hydroxyacetimidamide (35 mg, 0.077 mmol), DBU (0.035 mL, 0.23 mmol) and 1,1'-carbonyldiimidazole (26 mg, 0.154 mmol), dioxane (1 mL) and DMSO (1 mL). The vial is capped and heated at 110° C. for 30 min in the microwave apparatus. Once at RT the dioxane is removed and the mixture is purified by prep LC-MS, affording the title compound as a white solid (23 mg, 62%). LC-MS C: $t_R$=0.91 min; [M+H]$^+$=482.2.

a) (E/Z)-2-(2-Ethoxy-4-(6-((2-(1-methylnaphthalen-2-yl)ethyl)amino)pyrimidin-4-yl)phenyl)-N'-hydroxyacetimidamide 2-(2-Ethoxy-4-(6-((2-(1-methylnaphthalen-2-yl)ethyl)amino)pyrimidin-4-yl)phenyl)acetonitrile (32 mg, 0.076 mmol) is dissolved in EtOH (1 mL) then hydroxylamine solution (50% in H$_2$O, 0.023 mL, 0.379 mmol) is added. The mixture is heated at 120° C. for 30 min in the microwave apparatus, cooled to RT, and concentrated under reduced pressure, affording the title compound as a brown solid (35 mg, quant.). LC-MS B: $t_R$=0.68 min; [M+H]$^+$=456.5.

b) 2-(2-Ethoxy-4-(6-((2-(1-methylnaphthalen-2-yl)ethyl)amino)pyrimidin-4-yl)phenyl)acetonitrile Following the General Procedure A, with 6-chloro-N-(2-(1-methylnaphthalen-2-yl)ethyl)pyrimidin-4-amine (A.1.2.) and 2-(2-ethoxy-4-(4,4,5,5-tetramethyl-1,3,2-dioxaborolan-2-yl)phenyl)acetonitrile, the title compound is obtained as a white solid. LC-MS B: $t_R$=0.90 min; [M+H]$^+$=423.4.

c) 2-(2-ethoxy-4-(4,4,5,5-tetramethyl-1,3,2-dioxaborolan-2-yl)phenyl)acetonitrile The title compound is prepared according to the procedure described for A.2.12., starting with 2-(4-bromo-2-ethoxyphenyl)acetonitrile. LC-MS B: $t_R$=1.05 min; [M+H]$^+$=288.4.

d) 2-(4-Bromo-2-ethoxyphenyl)acetonitrile

The title compound is prepared according to the procedure described for Example 338-d, starting with 2-(4-bromo-2-ethoxyphenyl)acetamide. LC-MS B: $t_R$=0.97 min: no ionization. $^1$H NMR (400 MHz, d6-DMSO) δ: 7.22-7.42 (m, 2H), 6.96-7.21 (m, 1H), 4.13 (q, J=6.9 Hz, 2H), 3.78-3.86 (m, 2H), 1.36 (m, 3H).

e) 2-(4-bromo-2-ethoxyphenyl)acetamide

The title compound is prepared according to the procedure described for Example 338-e, starting with 2-(4-bromo-2-ethoxyphenyl)acetic acid. LC-MS B: $t_R$=0.76 min; [M+H]$^+$=257.85.

Example 567: 3-(2-Ethoxy-4-{6-[2-(1-methyl-naphthalen-2-yl)-ethylamino]-pyrimidin-4-yl}-benzyl)-[1,2,4]oxadiazole-5(4H)-thione (tautomeric form: 3-(2-ethoxy-4-{6-[2-(1-methyl-naphthalen-2-yl)-ethylamino]-pyrimidin-4-yl}-benzyl)-[1,2,4]oxadiazole-5-thiol)

The title compound is prepared according to the procedure described for Example 566, using (E/Z)-2-(2-ethoxy-4-(6-((2-(1-methylnaphthalen-2-yl)ethyl)amino)pyrimidin-4-yl)phenyl)-N'-hydroxyacetimidamide (Example 566-a) and 1,1'-thiocarbonyldiimidazole. LC-MS C: $t_R$=0.995 min; [M+H]$^+$=498.2.

II. Biological Assays

Compounds of the present invention may be further characterized with regard to their general pharmacokinetic and pharmacological properties using conventional assays well known in the art such as angiogenesis assays or tumor growth inhibition assays, or for example relating to their bioavailability in different species (such as rat or dog); or for their properties with regard to drug safety and/or toxicological properties using conventional assays well known in the art, for example relating to cytochrome P450 enzyme inhibition and time dependent inhibition, pregnane X receptor (PXR) activation, glutathione binding, or phototoxic behavior.

EMT-6 Mouse Tumor Model

The EMT-6 cell line is established from a transplantable murine mammary carcinoma that arose in a BALB/cCRGL mouse after implantation of a hyperplastic mammary alveolar nodule (Volence F J, et al, J Surg Oncol. 1980, 13(1): 39-44), obtained from ATCC (American Type culture collection, Manassas, Virginia, USA).

EMT-6 tumour cells are grown as monolayer at 37° C. in a humidified atmosphere (5% CO2, 95% air) in RPMI 1640 containing 2 mM L glutamine supplemented with 10% fetal bovine serum. For experimental use, tumour cells are detached from the culture flask with trypsin. The cells are counted in a hemocytometer and their viability is assessed by trypan blue exclusion.

Tumours are induced in female BALB/c mice by either subcutaneous injection of 1×10$^6$ EMT-6 cells in 200 μL of RPMI 1640 into the right flank or by injection of 2.5×10$^5$ EMT-6 cells in 50 μL of RPMI1640 into the mammary fat pad tissue. For the latter injection, female BALB/c mice are anaesthetized with Isoflurane and a 5 mm incision is made in the skin over the lateral thorax to expose the mammary fat pad tissue. After tumor cell injection the thoracic surface is gently dabbed with a 95% ethanol-dampened cotton-swab to kill tumor cells that may leak from the injection site. The skin of mice is closed with 4-0 crinerce sutures.

Animals are monitored daily for behavior and survival and twice weekly for body weight and tumor growth. Tumor size is measured with calipers and tumor volume is calculated according to the following formula: Tumor volume= (width$^2$×length)/2.

When tumors reach between 60 and 100 mm$^3$ (depending on the experiment), treatment with EP2 and/or EP4 antagonists is started and compound is given daily for at least 3 weeks.

Tumor weight is measured at the end of the study.

Biological In Vitro Assays

The antagonistic activities of the compounds of formula (I) on the EP2 and EP4 receptors are determined in accordance with the following experimental method.

The assay is using the PathHunter™ HEK 293 PTGER2 and PTGER4 b-arrestin cell lines from DiscoverX. The system is based on the Enzyme Fragment Complementation Technology. Two complementing fragments of the b-galactosidase enzyme are expressed within stably transfected cells. The larger portion of b-gal, termed EA for Enzyme Acceptor, is fused to the C-terminus of b-arrestin 2. The smaller fragment, termed ProLink™ tag, is fused to PTGER2 (EP2) or PTRGER4 (EP4) at the C-terminus. Upon activation, b-arrestin is recruited which forces the interaction of ProLink and EA, allowing complementation of the two fragments of b-gal and the formation of a functional enzyme which is capable of hydrolysing the substrate and generating a chemiluminescent signal.

hEP2 b-Arrestin Assay:

The HEK 293 PTGER2 b-arrestin cells (DiscoverX 93-021-4C1) are detached from culture dishes with a cell dissociation buffer (Invitrogen, 13151-014), and collected in growing medium (GM: DMEM+Glutamax-I (Invitrogen 32430)/10% FCS, 1% Penicilin/streptomycin). 5000 cells per well of a 384 well plate (white with white bottom Greiner 781080) are seeded in 20 ul per well of GM. Plate is incubated at 37° C., 5% CO2 for 24 hours.

Stock solutions of test compounds are made at a concentration of 10 mM in DMSO, and serially diluted in DMSO to concentrations required for inhibition dose response curves (tested concentration range 10 µM-2 nM or 1 µM-0.2 nM).

PGE2 (Cayman 14010, stock solution: 10 mM in DMSO) is used as agonist at 5 µM final concentration, corresponding to EC80.

Five microliters of diluted compounds are transferred into the assay plate. Plate is pre-incubated 15 minutes at 37° C. Then five microliters of PGE2 (final conc. 5 µM) are transferred into the assay plate. Plate is incubated 120 minutes at 37° C.

PathHunter Glo Detection Kit components are thawed and mix according to manufacturer's instructions: 1 part Galacton Star Substrate with 5 parts Emerald II™ Solution, and 19 parts of PathHunter Cell Assay Buffer, respectively. Twelve µl of reagent are transferred to the assay plate and incubate for 1 hour at RT in the dark. Luminescence counts are read on a BMG Fluostar Optima reader according to manufacturer's instructions.

For each compound concentration calculate of the percentage of activity compared to DMSO control value as average ±STDEV. (each concentration is measured in duplicate)

IC$_{50}$ values and curves are generated with XLfit software (IDBS) using Dose-Response One Site model 203. When compounds were measured multiple times, mean values are given.

hEP4 b-Arrestin Assay:

The HEK 293 PTGER4 b-arrestin cells (DiscoverX 93-030-4C1) are detached from culture dishes with a cell dissociation buffer (Invitrogen, 13151-014), and collected in growing medium (GM: DMEM+Glutamax-I (Invitrogen 32430)/10% FCS, 1% Penicilin/streptomycin). 5000 cells per well of a 384 well plate (white with white bottom Greiner 781080) are seeded in 20 ul per well of GM. Plate is incubated at 37° C., 5% CO2 for 24 hours.

Stock solutions of test compounds are made at a concentration of 10 mM in DMSO, and serially diluted in DMSO to concentrations required for inhibition dose response curves (tested concentration range 10 µM-2 nM or 1 µM-0.2 nM).

PGE2 (Cayman 14010, stock solution: 100 uM in DMSO) is used as agonist at 20 nM final concentration, corresponding to EC80.

Five microliters of diluted compounds are transferred into the assay plate. Plate is pre-incubated 15 minutes at 37° C. Then five microliters of PGE2 (final conc. 20 nM) are transferred into the assay plate. Plate is incubated 120 minutes at 37° C.

PathHunter Glo Detection Kit components are thawed and mix according to manufacturer's instructions: 1 part Galacton Star Substrate with 5 parts Emerald II™ Solution, and 19 parts of PathHunter Cell Assay Buffer, respectively. Twelve l of reagent are transferred to the assay plate and incubate for 1 hour at RT in the dark. Luminescence counts are read on a BMG Fluostar Optima reader according to manufacturer's instructions.

For each compound concentration calculate of the percentage of activity compared to DMSO control value as average ±STDEV. (each concentration is measured in duplicate)

IC$_{50}$ values and curves are generated with XLfit software (IDBS) using Dose-Response One Site model 203. When compounds were measured multiple times, mean values are given.

The antagonistic activities of the compounds of formula (I) on the EP2 and EP4 receptors are also determined in accordance with the following experimental method.

Human tumor cell lines expressing endogenously either EP4 or EP2 are used and cAMP accumulation in cells upon PGE$_2$ stimulation is monitored. SF295 glioblastoma cells express high endogenous EP2 and no EP4, whereas BT549 breast cancer cells, express high endogenous EP4 levels and very low EP2 levels.

As a detection method for cAMP the HTRF (homogeneous time resolved fluorescence) Cisbio kit (HTRF cAMP dynamic 2 kit 20'000 tests Cisbio Cat. #62AM4PEC) was used, which is based on a competitive immunoassay using a Cryptate-labeled anti-cAMP antibody and d2-labeled cAMP. Native cAMP produced by cells or unlabeled cAMP (for the standard curve) compete with exogenously added d2-labeled cAMP (acceptor) for binding to monoclonal anti-cAMP-Eu3+Cryptate (donor). A FRET signal (Fluorescence Resonance Energy Transfer) is obtained only if the labeled anti-cAMP antibody binds the d2 labelled cAMP, thus the specific signal (i.e. energy transfer) is inversely proportional to the concentration of cAMP in the standard or sample.

hEP2 cAMP Assay:

The SF295 cells (NCI/No. 0503170) are detached from culture dishes with a cell dissociation buffer (Invitrogen, 13151-014), and collected in growing medium (GM: RPMI1640 (Invitrogen 21875)/10% FCS, 1% Penicilin/streptomycin). Cells are counted washed and resuspended in assay buffer (AB; HBSS, 20 mM HEPES, 0.2% BSA; 2 mM IBMX). 4'000 cells in 5 µl of AB are seeded per well of a small volume 384 well plate (black with flat bottom, Greiner 784076).

Stock solutions of test compounds are made at a concentration of 10 mM in DMSO, and serially diluted in DMSO to concentrations required for inhibition dose response curves (tested concentration range 30 µM-0.4 nM; 30 µM-0.015 nM or 1 µM-0.01 nM).

PGE$_2$ (Cayman 14010, stock solution: 75 µM in DMSO) is used as agonist at 75 nM final concentration, corresponding to EC80.

Two point five microliters of diluted compounds are transferred into the assay plate. Plate is pre-incubated 45 minutes at RT. Subsequently, 2.5 microliters of PGE$_2$ (final conc. 75 nM) are transferred into the assay plate. Plate is incubated 30 minutes at RT. Five µl of each donor (anti-cAMP cryptate) and acceptor (cAMP-d2) are added and the plate is incubated another hour at RT in the dark and then read using a BMG LABTECH PHERAstar reader (Excitation: 337 nm, Emission: 620 and 665 nm).

The obtained Delta F (fluorescence) values (665 nm/620 nM) are converted into % cAMP values using the measurements of the cAMP calibrator provided in the kit. For each compound concentration the percentage of cAMP compared to DMSO control value as average ±STDEV (each concentration is measured in duplicate) is calculated.

IC$_{50}$ values and curves are generated with XLfit software (IDBS) using Dose-Response One Site model 203. When compounds were measured multiple times, mean values are given.

hEP4 cAMP Assay:

The BT549 cells (NCI/No. 0507282) are detached from culture dishes with a cell dissociation buffer (Invitrogen, 13151-014), and collected in growing medium (GM: RPMI1640 (Invitrogen 21875)/10% FCS, 1% Penicilin/streptomycin). Cells are counted washed and resuspended in assay buffer (AB; HBSS, 20 mM HEPES, 0.2% BSA; 2 mM IBMX). 4'000 cells in 5 µl of AB are seeded per well of a small volume 384 well plate (black with flat bottom, Greiner 784076).

Stock solutions of test compounds are made at a concentration of 10 mM in DMSO, and serially diluted in DMSO to concentrations required for inhibition dose response curves (tested concentration range 30 µM-0.4 nM; 30 µM-0.015 nM or 1 µM-0.01 nM).

PGE$_2$ (Cayman 14010, stock solution: 6 µM in DMSO) is used as agonist at 6 nM final concentration, corresponding to EC80.

Two point five microliters of diluted compounds are transferred into the assay plate. Plate is pre-incubated 45 minutes at RT. Subsequently, 2.5 microliters of PGE$_2$ (final conc. 6 nM) are transferred into the assay plate. Plate is incubated 30 minutes at RT. Five µl of each donor (anti-cAMP cryptate) and acceptor (cAMP-d2) are added and the plate is incubated another hour at RT in the dark and then read using a BMG LABTECH PHERAstar reader (Excitation: 337 nm, Emission: 620 and 665 nm).

The obtained Delta F (fluorescence) values (665 nm/620 nM) are converted into % cAMP values using the measurements of the cAMP calibrator provided in the kit. For each compound concentration the percentage of cAMP compared to DMSO control value as average ±STDEV (each concentration is measured in duplicate) is calculated.

IC$_{50}$ values and curves are generated with XLfit software (IDBS) using Dose-Response One Site model 203. When compounds were measured multiple times, mean values are given.

Antagonistic activities (IC$_{50}$ in nM) in the beta-arrestin and cAMP assays of exemplified compounds are displayed in Table 7:

TABLE 7

| Ex | hEP2 b-arr IC$_{50}$ | hEP4 b-arr IC$_{50}$ | hEP2 cAMP IC$_{50}$ | hEP4 cAMP IC$_{50}$ |
|---|---|---|---|---|
| 1 | 6 | 2 | 8 | 1 |
| 2 | 113 | 3 | 79 | 1 |
| 3 |  | 1 | 26 | 2 |
| 4 | 11 | 4 | 2 | 3 |
| 5 | 39 | 5 | 28 | 3 |
| 6 | 11 | 6 | 37 | 4 |
| 7 | 21 | 14 | 12 | 5 |
| 8 | 5 | 22 | 1 | 6 |
| 9 | 59 | 6 | 67 | 6 |
| 10 | 237 | 21 | 145 | 6 |
| 11 |  | 13 | 277 | 7 |
| 12 | 7 | 20 | 3 | 7 |
| 13 | 12 | 9 | 15 | 8 |
| 14 | 23 | 22 | 55 | 8 |
| 15 | 177 | 12 | 28 | 8 |
| 16 |  | 5 | 269 | 8 |
| 17 | 108 | 8 | 171 | 9 |
| 18 | 6 | 70 | 4 | 10 |
| 19 |  | 16 | 249 | 11 |
| 20 | 27 | 74 | 11 | 12 |
| 21 |  | 58 | 912 | 12 |
| 22 |  | 20 | 395 | 13 |
| 23 | 15 | 3 | 19 | 14 |
| 24 | 72 | 18 | 52 | 15 |
| 25 | 96 | 16 | 98 | 22 |
| 26 | 19 | 22 | 19 | 16 |
| 27 | 75 | 16 | 19 | 17 |
| 28 | 135 | 96 | 74 | 61 |
| 29 | 53 | 33 | 52 | 17 |
| 30 | 29 | 51 | 14 | 17 |
| 31 |  | 6 | 7740 | 18 |
| 32 | 199 | 56 | 161 | 18 |
| 33 |  | 11 | 537 | 18 |
| 34 | 6 | 25 | 8 | 18 |
| 35 | 359 | 23 | 194 | 18 |
| 36 |  | 20 | 557 | 18 |
| 37 |  | 16 | 281 | 22 |
| 38 | 226 | 123 | 210 | 28 |
| 39 | 4 | 14 | 2 | 19 |
| 40 | 126 | 25 | 228 | 20 |
| 41 | 405 | 30 | 164 | 21 |
| 42 | 240 | 25 | 137 | 21 |
| 43 | 54 | 44 | 43 | 21 |
| 44 |  | 24 | 283 | 21 |
| 45 | 127 | 5 | 185 | 21 |
| 46 | 47 | 19 | 45 | 22 |
| 47 | 45 | 85 | 91 | 22 |
| 48 |  |  | 66 | 22 |
| 49 | 10 | 223 | 8 | 23 |
| 50 | 61 | 27 | 52 | 24 |
| 51 | 230 | 22 | 207 | 25 |
| 52 | 318 | 63 | 158 | 25 |
| 53 | 5 | 12 | 12 | 25 |
| 54 |  | 68 | 331 | 27 |
| 55 | 844 | 25 | 335 | 16 |
| 56 | 538 | 27 | 190 | 28 |
| 57 | 195 | 34 | 191 | 28 |
| 58 |  | 13 | 9390 | 30 |
| 59 | 37 | 94 | 18 | 30 |
| 60 |  | 3 | 320 | 31 |
| 61 | 148 | 28 | 214 | 46 |
| 62 |  | 16 | 301 | 32 |
| 63 | 16 | 50 | 12 | 33 |
| 64 | 25 | 41 | 28 | 33 |
| 65 |  | 33 | 304 | 35 |
| 66 |  | 21 | 1220 | 35 |
| 67 | 123 | 40 | 110 | 36 |
| 68 | 65 | 70 | 46 | 49 |
| 69 | 438 | 59 | 222 | 38 |
| 70 |  | 209 | 441 | 38 |
| 71 |  | 24 | 301 | 39 |
| 72 |  | 37 | 892 | 39 |
| 73 | 809 | 91 | 1770 | 39 |
| 74 | 450 | 257 | 151 | 40 |
| 75 |  | 86 | 483 | 41 |
| 76 | 360 | 120 | 221 | 42 |

TABLE 7-continued

| Ex | hEP2 b-arr IC$_{50}$ | hEP4 b-arr IC$_{50}$ | hEP2 cAMP IC$_{50}$ | hEP4 cAMP IC$_{50}$ |
|---|---|---|---|---|
| 77 | 47 | 154 | 25 | 43 |
| 78 | 141 | 21 | 219 | 44 |
| 79 | 43 | 56 | 83 | 44 |
| 80 | 17 | 32 | 37 | 45 |
| 81 | 122 | 1840 | 123 | 164 |
| 82 |  | 128 | 251 | 46 |
| 83 | 274 | 255 | 70 | 47 |
| 84 |  | 19 | 1280 | 47 |
| 85 |  |  | 87 | 49 |
| 86 |  | 79 | 445 | 49 |
| 87 | 173 | 85 | 134 | 51 |
| 88 | 107 | 59 | 64 | 53 |
| 89 |  | 17 | 19400 | 54 |
| 90 |  | 26 | 378 | 55 |
| 91 |  | 40 | 586 | 56 |
| 92 |  | 105 | 1680 | 57 |
| 93 | 275 | 1260 | 85 | 118 |
| 94 | 423 | 49 | 528 | 59 |
| 95 |  | 25 | 447 | 59 |
| 96 | 148 | 92 | 57 | 61 |
| 97 | 192 | 147 | 78 | 63 |
| 98 |  | 33 | 314 | 64 |
| 99 | 16 | 60 | 13 | 67 |
| 100 | 35 | 176 | 29 | 67 |
| 101 |  | 30 | 102 | 35 |
| 102 | 9 | 141 | 6 | 70 |
| 103 | 51 | 18 | 89 | 71 |
| 104 | 12 | 91 | 13 | 71 |
| 105 | 40 | 53 | 76 | 73 |
| 106 |  | 135 | 831 | 74 |
| 107 |  |  | 950 | 76 |
| 108 |  | 66 | 740 | 77 |
| 109 | 34 | 101 | 12 | 78 |
| 110 | 56 | 179 | 61 | 81 |
| 111 | 115 | 89 | 49 | 81 |
| 112 | 40 | 127 | 69 | 82 |
| 113 |  | 179 | 251 | 82 |
| 114 | 222 | 640 | 222 | 85 |
| 115 | 243 | 53 | 682 | 85 |
| 116 | 76 | 135 | 23 | 86 |
| 117 | 53 | 131 | 61 | 88 |
| 118 | 34 | 74 | 66 | 88 |
| 119 | 32 | 113 | 41 | 90 |
| 120 | 114 | 61 | 111 | 92 |
| 121 |  | 42 | 283 | 93 |
| 122 |  | 19 | 324 | 95 |
| 123 |  | 353 | 588 | 97 |
| 124 | 113 | 215 | 95 | 99 |
| 125 | 116 | 226 | 129 | 99 |
| 126 | 8 | 66 | 6 | 101 |
| 127 | 181 | 109 | 101 | 103 |
| 128 | 151 | 192 | 76 | 103 |
| 129 |  | 35 | 494 | 104 |
| 130 |  | 23 | 423 | 106 |
| 131 |  | 68 | 353 | 106 |
| 132 | 82 | 161 | 66 | 107 |
| 133 |  | 42 | 482 | 109 |
| 134 |  | 63 | 358 | 84 |
| 135 | 198 | 172 | 171 | 115 |
| 136 |  | 29 | 677 | 120 |
| 137 | 14 | 124 | 4 | 120 |
| 138 | 74 | 358 | 61 | 120 |
| 139 | 85 | 157 | 131 | 121 |
| 140 |  | 95 | 459 | 121 |
| 141 |  | 131 | 328 | 122 |
| 142 | 121 | 180 | 177 | 127 |
| 143 |  | 22 | 787 | 128 |
| 144 |  | 91 | 751 | 132 |
| 145 |  | 90 | 519 | 134 |
| 146 | 258 | 361 | 115 | 137 |
| 147 |  | 219 | 571 | 141 |
| 148 | 174 | 46 | 126 | 141 |
| 149 |  | 194 | 619 | 144 |
| 150 | 230 | 222 | 219 | 144 |
| 151 | 32 | 618 | 35 | 145 |
| 152 | 119 | 352 | 111 | 145 |
| 153 |  | 757 | 340 | 146 |
| 154 |  | 99 | 25000 | 147 |
| 155 | 232 | 301 | 161 | 151 |
| 156 | 107 | 36 | 221 | 154 |
| 157 | 7 | 89 | 22 | 156 |
| 158 | 23 | 185 | 16 | 157 |
| 159 | 180 | 140 | 179 | 157 |
| 160 | 35 | 24 | 93 | 158 |
| 161 |  | 199 | 524 | 130 |
| 162 |  | 134 | 371 | 158 |
| 163 | 85 | 98 | 246 | 158 |
| 164 | 269 | 93 | 149 | 163 |
| 165 |  | 188 | 333 | 164 |
| 166 |  | 49 | 297 | 165 |
| 167 |  | 361 | 714 | 166 |
| 168 | 151 | 128 | 214 | 168 |
| 169 | 141 | 269 | 125 | 168 |
| 170 | 241 | 124 | 94 | 168 |
| 171 | 83 | 62 | 120 | 181 |
| 172 | 157 | 287 | 137 | 181 |
| 173 |  | 128 | 769 | 183 |
| 174 | 409 | 88 | 269 | 90 |
| 175 |  | 179 | 301 | 185 |
| 176 |  | 179 | 293 | 185 |
| 177 |  | 156 | 280 | 186 |
| 178 | 30 | 164 | 54 | 188 |
| 179 |  | 309 | 568 | 188 |
| 180 |  | 55 | 692 | 188 |
| 181 |  | 376 | 384 | 192 |
| 182 |  | 79 | 645 | 195 |
| 183 | 115 | 223 | 67 | 178 |
| 184 | 171 | 378 | 164 | 200 |
| 185 |  | 258 | 452 | 200 |
| 186 |  | 194 | 811 | 202 |
| 187 | 74 | 144 | 64 | 206 |
| 188 | 45 | 105 | 142 | 206 |
| 189 | 158 | 108 | 530 | 208 |
| 190 | 38 | 609 | 18 | 149 |
| 191 |  | 279 | 329 | 208 |
| 192 | 76 | 153 | 69 | 210 |
| 193 | 10 | 349 | 12 | 211 |
| 194 |  | 325 | 295 | 212 |
| 195 |  | 245 | 373 | 217 |
| 196 | 21 | 199 | 37 | 217 |
| 197 | 127 | 300 | 176 | 224 |
| 198 |  | 226 | 366 | 225 |
| 199 | 177 | 2160 | 62 | 138 |
| 200 | 57 | 510 | 108 | 227 |
| 201 | 83 | 111 | 133 | 229 |
| 202 |  | 77 | 277 | 234 |
| 203 |  | 352 | 687 | 237 |
| 204 | 12 | 633 | 29 | 186 |
| 205 | 118 | 47 | 190 | 244 |
| 206 |  | 304 | 572 | 248 |
| 207 |  | 234 | 673 | 248 |
| 208 | 8 | 130 | 5 | 248 |
| 209 | 832 | 143 | 248 | 249 |
| 210 |  |  | 794 | 252 |
| 211 |  |  | 571 | 253 |
| 212 | 255 | 340 | 50 | 253 |
| 213 | 59 |  | 46 | 256 |
| 214 |  | 216 | 674 | 258 |
| 215 | 1590 | 379 | 650 | 259 |
| 216 |  | 307 | 490 | 267 |
| 217 | 238 |  | 321 | 272 |
| 218 | 160 | 651 | 405 | 278 |
| 219 |  | 202 | 486 | 129 |
| 220 | 113 |  | 141 | 283 |
| 221 | 8 |  | 2 | 285 |
| 222 |  |  | 279 | 287 |
| 223 | 329 |  | 199 | 288 |
| 224 | 84 | 260 | 61 | 173 |
| 225 |  |  | 923 | 289 |
| 226 | 151 |  | 250 | 291 |
| 227 | 142 |  | 88 | 293 |
| 228 | 392 |  | 194 | 300 |

TABLE 7-continued

| Ex | hEP2 b-arr IC$_{50}$ | hEP4 b-arr IC$_{50}$ | hEP2 cAMP IC$_{50}$ | hEP4 cAMP IC$_{50}$ |
|---|---|---|---|---|
| 229 | | | 483 | 304 |
| 230 | | 831 | 508 | 311 |
| 231 | | 286 | 5650 | 315 |
| 232 | | | 382 | 321 |
| 233 | 29 | | 76 | 322 |
| 234 | | | 113 | 325 |
| 235 | | | 772 | 325 |
| 236 | 121 | | 147 | 327 |
| 237 | 388 | 908 | 160 | 335 |
| 238 | 55 | | 75 | 343 |
| 239 | 134 | | 222 | 346 |
| 240 | | 598 | 816 | 346 |
| 241 | 168 | | 193 | 351 |
| 242 | | 495 | 443 | 351 |
| 243 | 493 | 147 | 2100 | 355 |
| 244 | | | 552 | 356 |
| 245 | | | 304 | 358 |
| 246 | | | 534 | 364 |
| 247 | | | 797 | 365 |
| 248 | 132 | 270 | 50 | 366 |
| 249 | 196 | | 171 | 368 |
| 250 | 112 | 609 | 77 | 287 |
| 251 | 105 | | 132 | 369 |
| 252 | 212 | | 186 | 373 |
| 253 | 521 | 671 | 158 | 373 |
| 254 | 45 | 864 | 70 | 379 |
| 255 | | 788 | 272 | 380 |
| 256 | | | 296 | 381 |
| 257 | | 417 | 282 | 389 |
| 258 | | | 3610 | 390 |
| 259 | | | 302 | 394 |
| 260 | | | 880 | 404 |
| 261 | 53 | 396 | 20 | 406 |
| 262 | 1300 | 186 | 855 | 424 |
| 263 | | | 524 | 425 |
| 264 | | | 11800 | 425 |
| 265 | | | 11400 | 428 |
| 266 | | 444 | 537 | 428 |
| 267 | | | 306 | 431 |
| 268 | 25 | 688 | 47 | 342 |
| 269 | 1640 | 588 | 6510 | 434 |
| 270 | 1520 | 404 | 5660 | 435 |
| 271 | | | 638 | 439 |
| 272 | | 679 | 458 | 295 |
| 273 | 289 | 221 | 140 | 455 |
| 274 | | | 1180 | 462 |
| 275 | 67 | | 102 | 468 |
| 276 | 79 | 1820 | 47 | 474 |
| 277 | 51 | 437 | 14 | 324 |
| 278 | 281 | | 187 | 477 |
| 279 | | 743 | 559 | 489 |
| 280 | | | 514 | 491 |
| 281 | | | 524 | 494 |
| 282 | | | 296 | 498 |
| 283 | | | 618 | 502 |
| 284 | | 125 | >28100 | 509 |
| 285 | | 341 | 7520 | 513 |
| 286 | 198 | | 86 | 515 |
| 287 | | | 515 | 520 |
| 288 | 156 | | 85 | 523 |
| 289 | 144 | 964 | 358 | 525 |
| 290 | 163 | 438 | 194 | 527 |
| 291 | | 815 | 269 | 538 |
| 292 | | 1510 | 688 | 538 |
| 293 | | | 255 | 540 |
| 294 | | | 786 | 561 |
| 295 | | 603 | 520 | 568 |
| 296 | 34 | 1600 | 61 | 583 |
| 297 | | 2120 | 782 | 592 |
| 298 | | | 716 | 613 |
| 299 | 307 | 367 | 250 | 444 |
| 300 | | | 312 | 624 |
| 301 | | | 425 | 626 |
| 302 | | | 384 | 520 |
| 303 | 313 | 384 | 746 | 633 |
| 304 | | | 408 | 652 |
| 305 | 57 | 1350 | 232 | 653 |
| 306 | | 610 | 274 | 654 |
| 307 | | | 677 | 658 |
| 308 | | 866 | 926 | 674 |
| 309 | | | >27700 | 677 |
| 310 | | 937 | 564 | 683 |
| 311 | | 310 | 538 | 685 |
| 312 | | 556 | 2490 | 689 |
| 313 | | | 273 | 691 |
| 314 | 3460 | 378 | 9230 | 701 |
| 315 | 134 | | 73 | 703 |
| 316 | | | 792 | 729 |
| 317 | 501 | | 233 | 751 |
| 318 | 408 | | 247 | 753 |
| 319 | | 1180 | 354 | 559 |
| 320 | | | 440 | 766 |
| 321 | | | 562 | 772 |
| 322 | | | 809 | 814 |
| 323 | 438 | 1900 | 114 | 835 |
| 324 | | | 899 | 858 |
| 325 | 441 | | 332 | 887 |
| 326 | 126 | 1070 | 160 | 910 |
| 327 | 296 | | 159 | 920 |
| 328 | 287 | 919 | 108 | 938 |
| 329 | | 798 | 755 | 956 |
| 330 | 158 | | 249 | 1040 |
| 331 | 69 | | 135 | 1180 |
| 332 | | 415 | 12200 | 1510 |
| 333 | 359 | 128 | | |
| 334 | 791 | 408 | 1630 | 230 |
| 335 | 100 | 12 | 268 | 3 |
| 336 | 225 | 113 | | |
| 337 | 664 | 1320 | 1310 | 1430 |
| 338 | | 15 | 459 | 64 |
| 339 | 66 | 10 | 90 | 22 |
| 340 | 12 | 3 | 104 | 11 |
| 341 | 12 | 14 | 41 | 36 |
| 342 | 7 | 3 | 20 | 19 |
| 343 | 9 | 2 | 23 | 12 |
| 344 | 33 | 39 | 33 | 14 |
| 345 | | 6 | 683 | 30 |
| 346 | | 57 | 282 | 110 |
| 347 | | 31 | 495 | 172 |
| 348 | 172 | 2 | 113 | 8 |
| 349 | 109 | 4 | 103 | 14 |
| 350 | 83 | 21 | 51 | 10 |
| 351 | 475 | 79 | 236 | 167 |
| 352 | 42 | 5 | 142 | 24 |
| 353 | 237 | 9 | 115 | 109 |
| 354 | 41 | 32 | 27 | 56 |
| 355 | 55 | 29 | 46 | 95 |
| 356 | | | 2340 | 828 |
| 357 | | 22 | 967 | 17 |
| 358 | 538 | 138 | 219 | 90 |
| 359 | 40 | 9 | 61 | 2 |
| 360 | 137 | 69 | 183 | 44 |
| 361 | 187 | 116 | 270 | 68 |
| 362 | 20 | 6 | 21 | 1 |
| 363 | 479 | 59 | 534 | 35 |
| 364 | 151 | 52 | 37 | 18 |
| 365 | 77 | 149 | 29 | 55 |
| 366 | 84 | 119 | 30 | 47 |
| 367 | 7 | 2 | 6 | 1 |
| 368 | 221 | 66 | 119 | 37 |
| 369 | 66 | 91 | 9 | 31 |
| 370 | 438 | 105 | 312 | 81 |
| 371 | 86 | 88 | 48 | 68 |
| 372 | 75 | 195 | 111 | 200 |
| 373 | 257 | 118 | 286 | 117 |
| 374 | 334 | 52 | 304 | 45 |
| 375 | 229 | 46 | 294 | 66 |
| 376 | 50 | 13 | 188 | 11 |
| 377 | 8 | 68 | 27 | 92 |
| 378 | 20 | 36 | 110 | 66 |
| 379 | 51 | 155 | 87 | 245 |
| 380 | 16 | 17 | 124 | 54 |

TABLE 7-continued

| Ex | hEP2 b-arr IC$_{50}$ | hEP4 b-arr IC$_{50}$ | hEP2 cAMP IC$_{50}$ | hEP4 cAMP IC$_{50}$ |
|---|---|---|---|---|
| 381 | 51 | 126 | 165 | 119 |
| 382 | 160 | 81 | 675 | 222 |
| 383 | 177 | 194 | 650 | 270 |
| 384 | 145 | 28 | 577 | 59 |
| 385 | 30 | 71 | 180 | 134 |
| 386 | 64 | 28 | 453 | 54 |
| 387 | 61 | 49 | 205 | 62 |
| 388 | 45 | 13 | 626 | 51 |
| 389 | 51 | 25 | 231 | 57 |
| 390 | 264 | 29 | 590 | 32 |
| 391 | 131 | 19 | 243 | 6 |
| 392 | 66 | 292 | 156 | 111 |
| 393 | 155 | 166 | 439 | 81 |
| 394 | 163 | 80 | 639 | 70 |
| 395 | 4 | 98 | 5 | 128 |
| 396 | 2 | 44 | 1 | 20 |
| 397 | 7 | 35 | 25 | 34 |
| 398 | 9 | 26 | 30 | 18 |
| 399 | 10 | 30 | 40 | 48 |
| 400 | 2 | 44 | 2 | 37 |
| 401 | 331 | 114 | 739 | 236 |
| 402 | 22 | 61 | 48 | 131 |
| 403 | 57 | 65 | 135 | 112 |
| 404 | 20 | 80 | 27 | 71 |
| 405 | 9 | 79 | 7 | 18 |
| 406 | 45 | 62 | 220 | 101 |
| 407 | 22 | 66 | 21 | 44 |
| 408 | 29 | 24 | 126 | 20 |
| 409 | 260 | 57 | 486 | 87 |
| 410 | 153 | 113 | 665 | 170 |
| 411 | 97 | 31 | 325 | 94 |
| 412 | 20 | 40 | 57 | 79 |
| 413 | 62 | 41 | 119 | 38 |
| 414 | 219 | 48 | 505 | 88 |
| 415 | 63 | 52 | 106 | 57 |
| 416 | 245 | 82 | 123 | 83 |
| 417 | 38 | 174 | 31 | 240 |
| 418 | 10 | 54 | 45 | 148 |
| 419 | 3 | 30 | 29 | 85 |
| 420 | 27 | 30 | 257 | 119 |
| 421 | 84 | 22 | 247 | 27 |
| 422 | 249 | 23 | 492 | 18 |
| 423 | 49 | 10 | 230 | 6 |
| 424 | 424 | 80 | 782 | 89 |
| 425 | 65 | 152 | 226 | 356 |
| 426 | 9 | 46 | 22 | 48 |
| 427 | 17 | 90 | 17 | 190 |
| 428 | 7 | 41 | 7 | 50 |
| 429 | 52 | 60 | 66 | 38 |
| 430 | 69 | 66 | 185 | 40 |
| 431 | 179 | 52 | 460 | 43 |
| 432 | 20 | 87 | 10 | 72 |
| 433 | 30 | 19 | 57 | 13 |
| 434 | 26 | 58 | 25 | 95 |
| 435 | 46 | 110 | 28 | 80 |
| 436 | 16 | 31 | 110 | 57 |
| 437 | 104 | 41 | 227 | 37 |
| 438 | 519 | 49 | 708 | 29 |
| 439 | 17 | 197 | 33 | 139 |
| 440 | 11 | 51 | 25 | 65 |
| 441 | 10 | 53 | 21 | 31 |
| 442 | 82 | 27 | 224 | 81 |
| 443 | 107 | 29 | 549 | 43 |
| 444 | 15 | 43 | 22 | 80 |
| 445 | 88 | 38 | 525 | 104 |
| 446 | 32 | 108 | 160 | 98 |
| 447 | 2 | 130 | 16 | 136 |
| 448 | 15 | 46 | 55 | 26 |
| 449 | 83 | 46 | 131 | 21 |
| 450 | 66 | 97 | 165 | 80 |
| 451 | 71 | 21 | 660 | 16 |
| 452 | 103 | 21 | 371 | 18 |
| 453 | 102 | 70 | 281 | 118 |
| 454 | 88 | 212 | 608 | 225 |
| 455 | 271 | 18 | 250 | 38 |
| 456 | 129 | 21 | 311 | 14 |
| 457 | 200 | 176 | | |
| 458 | 550 | 104 | | |
| 459 | 683 | 236 | | |
| 460 | 207 | 161 | | |
| 461 | 231 | 121 | | |
| 462 | 325 | 197 | | |
| 463 | 934 | 223 | | |
| 464 | 300 | 87 | | |
| 465 | 313 | 827 | 245 | 1400 |
| 466 | 206 | 171 | 190 | 1210 |
| 467 | 417 | 187 | | 155 |
| 468 | 564 | 571 | | |
| 469 | 502 | 480 | | |
| 470 | 343 | 420 | | |
| 471 | 207 | 300 | | |
| 472 | 680 | 246 | | |
| 473 | 137 | 275 | | |
| 474 | 272 | 914 | | |
| 475 | 663 | 62 | | 114 |
| 476 | 428 | 264 | | |
| 477 | 316 | 210 | | |
| 478 | 788 | 242 | | |
| 479 | 345 | 158 | | |
| 480 | 170 | 207 | | |
| 481 | 328 | 63 | | 329 |
| 482 | 444 | 91 | | 323 |
| 483 | 26 | 115 | | |
| 484 | 3 | 3 | | |
| 485 | 125 | 122 | | |
| 486 | 95 | 136 | | |
| 487 | 59 | 136 | | |
| 488 | 723 | 45 | | |
| 489 | 231 | 128 | | |
| 490 | 90 | 144 | | |
| 491 | 372 | 148 | | |
| 492 | 204 | 142 | | |
| 493 | 642 | 497 | | |
| 494 | 340 | 209 | | |
| 495 | 77 | 193 | | |
| 496 | 588 | 908 | | |
| 497 | 449 | 443 | | |
| 498 | 163 | 107 | | |
| 499 | 180 | 169 | | |
| 500 | 88 | 99 | | |
| 501 | 196 | 808 | | |
| 502 | 103 | 903 | | |
| 503 | 102 | 157 | | |
| 504 | 108 | 167 | | |
| 505 | 427 | 929 | | |
| 506 | 172 | 332 | | |
| 507 | 170 | 209 | | |
| 508 | 85 | 748 | | |
| 509 | 29 | 356 | | |
| 510 | 45 | 194 | | |
| 511 | 304 | 423 | | |
| 512 | 67 | 220 | | |
| 513 | 158 | 347 | | |
| 514 | 262 | 112 | | |
| 515 | 67 | 893 | | |
| 516 | 23 | 930 | | |
| 517 | 108 | 288 | | |
| 518 | 116 | 176 | | |
| 519 | 19 | 262 | | |
| 520 | 19 | 107 | | |
| 521 | 31 | 78 | | |
| 522 | 131 | 204 | | |
| 523 | 227 | 195 | | |
| 524 | 231 | 257 | | |
| 525 | 160 | 349 | | |
| 526 | 96 | 269 | | |
| 527 | 892 | 337 | | |
| 528 | 513 | 198 | | |
| 529 | 699 | 55 | | |
| 530 | 514 | 44 | | |
| 531 | 624 | 110 | | |
| 532 | 293 | 69 | | |

TABLE 7-continued

| Ex | hEP2 b-arr IC$_{50}$ | hEP4 b-arr IC$_{50}$ | hEP2 cAMP IC$_{50}$ | hEP4 cAMP IC$_{50}$ |
|---|---|---|---|---|
| 533 | 211 | 53 | | |
| 534 | 332 | 70 | | |
| 535 | 871 | 42 | | |
| 536 | 203 | 28 | | |
| 537 | 670 | 76 | | |
| 538 | 685 | 99 | | |
| 539 | 452 | 225 | | |
| 540 | 339 | 146 | | |
| 541 | 604 | 88 | | |
| 542 | 609 | 91 | | |
| 543 | 612 | 124 | | |
| 544 | 851 | 452 | | |
| 545 | 394 | 25 | | |
| 546 | 980 | 166 | | |
| 547 | 825 | 322 | | |
| 548 | 933 | 295 | | |
| 549 | 560 | 190 | | |
| 550 | 371 | 63 | | |
| 551 | 900 | 867 | | |
| 552 | 577 | 385 | | |
| 553 | 302 | 80 | | |
| 554 | 739 | 884 | | |
| 555 | 887 | 835 | | |
| 556 | 246 | 19 | | |
| 557 | 994 | 117 | | |
| 558 | 684 | 539 | | |
| 559 | 168 | 67 | 372 | 19 |
| 560 | 476 | 134 | | |
| 561 | 388 | 103 | | |
| 562 | 803 | 689 | | |
| 563 | 985 | 582 | | |
| 564 | 817 | 212 | | |
| 565 | 58 | 23 | | |
| 566 | 297 | 159 | | |
| 567 | 255 | 264 | | |

The invention claimed is:

1. A compound of formula (II)

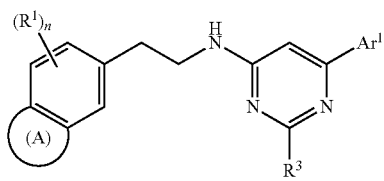

Formula (II)

wherein in compounds of the formula (II) ring (A) in the fragment:

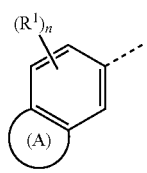

represents an aromatic 5- or 6-membered ring or a non-aromatic 5- to 7-membered ring, which ring (A) is fused to the phenyl group, wherein said ring (A) optionally contains one or two heteroatoms independently selected from nitrogen, oxygen, and sulfur; wherein said fragment is optionally substituted with $(R^1)_n$; wherein $(R^1)_n$ represents one, two, three, or four optional substituents, wherein said substituents $R^1$ are independently selected from $(C_{1-3})$alkyl, $(C_{2-3})$alkenyl, $(C_{2-3})$alkynyl, $(C_{1-3})$alkoxy, halogen, —S—$(C_{1-3})$alkyl, $(C_{1-3})$fluoroalkyl, $(C_{1-3})$fluoroalkoxy, cyano, oxo, and —NR$^{N7}$R$^{N8}$ wherein R$^{N7}$ and R$^{N8}$ independently represent hydrogen or $(C_{1-4})$alkyl;

R$^3$ represents hydrogen, or methyl;

Ar$^1$ represents a phenyl group of the structure (Ar-I):

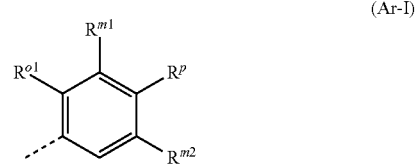

(Ar-I)

wherein

R$^p$ represents $(C_{4-6})$cycloalkyl containing a ring oxygen atom, wherein said $(C_{4-6})$cycloalkyl containing a ring oxygen atom is unsubstituted or mono-substituted with hydroxy;

hydroxy;

—X$^1$—CO—R$^{O1}$, wherein

X$^1$ represents a direct bond, $(C_{1-3})$alkylene, —O—$(C_{1-3})$alkylene-*, —NH—$(C_{1-3})$alkylene-*, —S—CH$_2$—*, —CF$_2$—, —CH=CH—, ethen-1,1-diyl, —C≡C—, —NH—CO—*, —CO—, or $(C_{3-5})$cycloalkylene; wherein the asterisks indicate the bond that is linked to the —CO—R$^{O1}$ group; and R$^{O1}$ represents

—OH;

—O—$(C_{1-4})$alkyl;

—NH—SO$_2$—R$^{S3}$ wherein R$^{S3}$ represents $(C_{1-4})$alkyl, $(C_{3-6})$cycloalkyl wherein the $(C_{3-6})$cycloalkyl optionally contains a ring oxygen atom, $(C_{3-6})$cycloalkyl-$(C_{1-3})$alkylene wherein the $(C_{3-6})$cycloalkyl optionally contains a ring oxygen atom, $(C_{1-3})$fluoroalkyl, or —NH$_2$;

—O—CH$_2$—CO—R$^{O4}$, wherein R$^{O4}$ represents hydroxy, or $(C_{1-4})$alkoxy, or —N[$(C_{1-4})$alkyl]$_2$;

—O—CH$_2$—O—CO—R$^{O5}$, wherein R$^{O5}$ represents $(C_{1-4})$alkyl or $(C_{1-4})$alkoxy;

—O—CH$_2$—CH$_2$—N[$(C_{1-4})$alkyl]$_2$; or (5-methyl-2-oxo-[1,3]dioxol-4-yl)-methyloxy-;

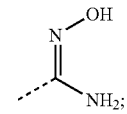

2-hydroxy-3,4-dioxo-cyclobut-1-enyl;

hydroxy-$(C_{1-4})$alkyl;

hydroxy-$(C_{2-4})$alkoxy;

—(CH$_2$)$_r$—CO—NR$^{N3}$R$^{N4}$ wherein r represents the integer 0 or 1; and wherein R$^{N3}$ and R$^{N4}$ independently represent hydrogen, $(C_{1-4})$alkyl, hydroxy-$(C_{2-4})$alkyl, $(C_{1-3})$alkoxy-$(C_{2-4})$alkyl, or hydroxy;

—NR$^{N1}$R$^{N2}$, wherein R$^{N1}$ independently represents hydrogen or $(C_{1-4})$alkyl, and R$^{N2}$ independently represents —CO—H, —CO—($C_{1-3}$)alkyl, or —CO—($C_{1-3}$)alkylene-OH;
—NH—CO—NR$^{N5}$R$^{N6}$ wherein R$^{N5}$ and R$^{N6}$ independently represent hydrogen or ($C_{1-4}$)alkyl;
—SO$_2$—R$^{S1}$ wherein R$^{S1}$ represents ($C_{1-4}$)alkyl, or —NR$^{N7}$R$^{N8}$ wherein R$^{N7}$ and R$^{N8}$ independently represent hydrogen or ($C_{1-3}$)alkyl;
—(CH$_2$)$_q$-HET$^1$, wherein q represents the integer 0, 1 or 2; and wherein HET$^1$ represents 5-oxo-4,5-dihydro-[1,2,4]oxadiazol-3-yl, 3-oxo-2,3-dihydro-[1,2,4]oxadiazol-5-yl, or 5-thioxo-4,5-dihydro-[1,2,4]oxadiazol-3-yl; or
—(CH$_2$)$_p$-HET, wherein p represents the integer 0 or 1; and wherein HET represents a 5-membered heteroaryl, wherein said 5-membered heteroaryl is unsubstituted, or mono- or di-substituted, wherein the substituents are independently selected from ($C_{1-4}$)alkyl, ($C_{1-4}$)alkoxy, —COOH, hydroxy, hydroxy-($C_{1-3}$)alkyl, ($C_{3-5}$)cycloalkyl optionally containing one ring oxygen atom, or —NR$^{N9}$R$^{N10}$ wherein R$^{N9}$ and R$^{N10}$ independently represent hydrogen, ($C_{1-3}$)alkyl, or hydroxy-($C_{2-4}$)alkyl;

R$^{m1}$ represents
hydrogen;
($C_{1-6}$)alkyl;
($C_{1-4}$)alkoxy;
($C_{1-3}$)fluoroalkyl;
($C_{1-3}$)fluoroalkoxy;
halogen;
($C_{3-6}$)cycloalkyl;
($C_{3-6}$)cycloalkyl-oxy;
hydroxy;
hydroxy-($C_{2-4}$)alkoxy;
—X$^2$—NR$^{N1}$R$^{N2}$, wherein X$^2$ represents a direct bond; or X$^2$ represents —O—CH$_2$—CH$_2$—*, wherein the asterisk indicates the bond that is linked to the —NR$^{N1}$R$^{N2}$ group; and wherein R$^{N1}$ and R$^{N2}$ independently represent hydrogen, ($C_{1-4}$)alkyl, or ($C_{3-6}$)cycloalkyl; or
—S—R$^{S2}$ wherein R$^{S2}$ represents ($C_{1-4}$)alkyl, or ($C_{3-6}$)cycloalkyl optionally containing one ring oxygen atom;

R$^{m2}$ represents hydrogen, methyl, fluoro, or chloro; and

R$^{o1}$ represents hydrogen; or, in case R$^{m2}$ represents hydrogen, R$^{o1}$ represents hydrogen or fluoro;
or Ar$^1$ represents a 5-membered heteroaryl group of the structure (Ar-II):

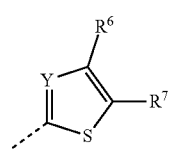

(Ar-II)

wherein
Y represents CR$^8$ wherein R$^8$ represents hydrogen or halogen; or Y represents N;
R$^7$ represents
($C_{4-6}$)cycloalkyl containing a ring oxygen atom, wherein said ($C_{4-6}$)cycloalkyl containing a ring oxygen atom is unsubstituted or mono-substituted with hydroxy;

—X$^1$—CO—R$^{O1}$, wherein
X$^1$ represents a direct bond, ($C_{1-3}$)alkylene, —O—($C_{1-3}$)alkylene-*, —NH—($C_{1-3}$)alkylene-*, —S—CH$_2$—*, —CF$_2$—, —CH=CH—, —C≡C—, —NH—CO—*, —CO—, or ($C_{3-5}$)cycloalkylene; wherein the asterisks indicate the bond that is linked to the —CO—R$^{O1}$ group; and
R$^{O1}$ represents
—OH;
—O—($C_{1-4}$)alkyl;
—NH—SO$_2$—R$^{S3}$ wherein R$^{S3}$ represents ($C_{1-4}$)alkyl, ($C_{3-6}$)cycloalkyl wherein the ($C_{3-6}$)cycloalkyl optionally contains a ring oxygen atom, ($C_{3-6}$)cycloalkyl-($C_{1-3}$)alkylene wherein the ($C_{3-6}$)cycloalkyl optionally contains a ring oxygen atom, ($C_{1-3}$)fluoroalkyl, or —NH$_2$;
—O—CH$_2$—CO—R$^{O4}$, wherein R$^{O4}$ represents hydroxy, or ($C_{1-4}$)alkoxy, or —N[($C_{1-4}$)alkyl]$_2$;
—O—CH$_2$—O—CO—R$^{O5}$, wherein R$^{O5}$ represents ($C_{1-4}$)alkyl or ($C_{1-4}$)alkoxy;
—O—CH$_2$—CH$_2$—N[($C_{1-4}$)alkyl]2; or
(5-methyl-2-oxo-[1,3]dioxol-4-yl)-methyloxy-;

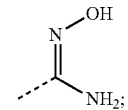

2-hydroxy-3,4-dioxo-cyclobut-1-enyl;
hydroxy-($C_{1-4}$)alkyl;
hydroxy-($C_{2-4}$)alkoxy;
—(CH$_2$)$_r$—CO—NR$^{N3}$R$^{N4}$ wherein r represents the integer 0 or 1; and wherein R$^{N3}$ and R$^{N4}$ independently represent hydrogen, ($C_{1-4}$)alkyl, hydroxy-($C_{2-4}$)alkyl, ($C_{1-3}$)alkoxy-($C_{2-4}$)alkyl, or hydroxy;
—NR$^{N1}$R$^{N2}$, wherein R$^{N1}$ independently represents hydrogen or ($C_{1-4}$)alkyl, and R$^{N2}$ independently represents —CO—H, —CO—($C_{1-3}$)alkyl, or —CO—($C_{1-3}$)alkylene-OH;
—NH—CO—NR$^{N5}$R$^{N6}$ wherein R$^{N5}$ and R$^{N6}$ independently represent hydrogen or ($C_{1-4}$)alkyl;
—SO$_2$—R$^{S1}$ wherein RSI represents ($C_{1-4}$)alkyl, or —NR$^{N7}$R$^{N8}$ wherein R$^{N7}$ and R$^{N8}$ independently represent hydrogen or ($C_{1-3}$)alkyl;
—(CH$_2$)$_q$-HET$^1$, wherein q represents the integer 0, 1 or 2; and wherein HET$^1$ represents 5-oxo-4,5-dihydro-[1,2,4]oxadiazol-3-yl, 3-oxo-2,3-dihydro-[1,2,4]oxadiazol-5-yl, or 5-thioxo-4,5-dihydro-[1,2,4]oxadiazol-3-yl; or
—(CH$_2$)$_p$-HET, wherein p represents the integer 0 or 1; and wherein HET represents a 5-membered heteroaryl, wherein said 5-membered heteroaryl is unsubstituted, or mono- or di-substituted, wherein the substituents are independently selected from ($C_{1-4}$)alkyl, ($C_{1-4}$)alkoxy, —COOH, hydroxy, hydroxy-($C_{1-3}$)alkyl, ($C_{3-5}$)cycloalkyl optionally containing one ring oxygen atom, or —NR$^{N9}$R$^{N10}$ wherein R$^{N9}$ and R$^{N10}$ independently represent hydrogen, ($C_{1-3}$)alkyl, or hydroxy-($C_{2-4}$)alkyl;

R⁶ represents
- (C$_{1-6}$)alkyl;
- (C$_{1-4}$)alkoxy;
- (C$_{1-3}$)fluoroalkyl;
- (C$_{1-3}$)fluoroalkoxy;
- halogen;
- hydroxy;
- (C$_{3-6}$)cycloalkyl;
- (C$_{3-6}$)cycloalkyl-oxy;
- hydroxy-(C$_{2-4}$)alkoxy;
  - —X²—NR$^{N1}$R$^{N2}$, wherein X² represents a direct bond; or X² represents -O—CH$_2$—CH$_2$—*, wherein the asterisk indicates the bond that is linked to the —NR$^{N1}$R$^{N2}$ group; and wherein R$^{N1}$ and R$^{N2}$ independently represent hydrogen, (C$_{1-4}$)alkyl, or (C$_{3-6}$)cycloalkyl; or
  - —S—R$^{S2}$ wherein R$^{S2}$ represents (C$_{1-4}$)alkyl, or (C$_{3-6}$)cycloalkyl optionally containing one ring oxygen atom;
- or Ar¹ represents 8- to 10-membered bicyclic heteroaryl; wherein said 8- to 10-membered bicyclic heteroaryl independently is mono-substituted with —(C$_{0-3}$)alkylene-COOR$^{O2}$ wherein R$^{O2}$ represents hydrogen or (C$_{1-4}$)alkyl;
- or Ar¹ represents a group of the structure (Ar-III):

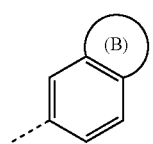

(Ar-III)

which is selected from 2-oxo-2,3-dihydro-benzooxazol-6-yl, 3-methyl-2-oxo-2,3-dihydro-benzooxazol-5-yl, 1-methyl-3-oxo-2,3-dihydro-1H-indazol-6-yl, 2-oxo-1,2,3,4-tetrahydro-quinazolin-6-yl, 1-methyl-2-oxo-1,2,3,4-tetrahydro-quinazolin-6-yl, 1-oxo-1,2,3,4-tetrahydro-isoquinolin-6-yl, 1-methyl-2-oxo-1,2,3,4-tetrahydro-quinazolin-7-yl, and 1-oxo-1,2,3,4-tetrahydro-isoquinolin-7-yl;

or a pharmaceutically acceptable salt thereof.

2. The compound according to claim 1; wherein Ar¹ represents a group selected from:

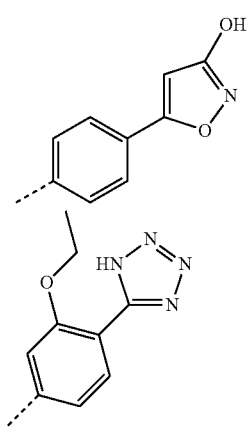

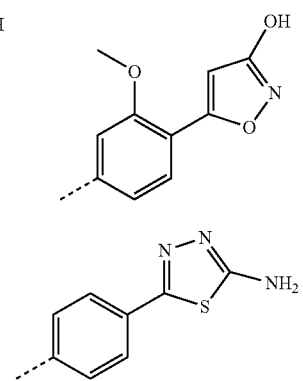

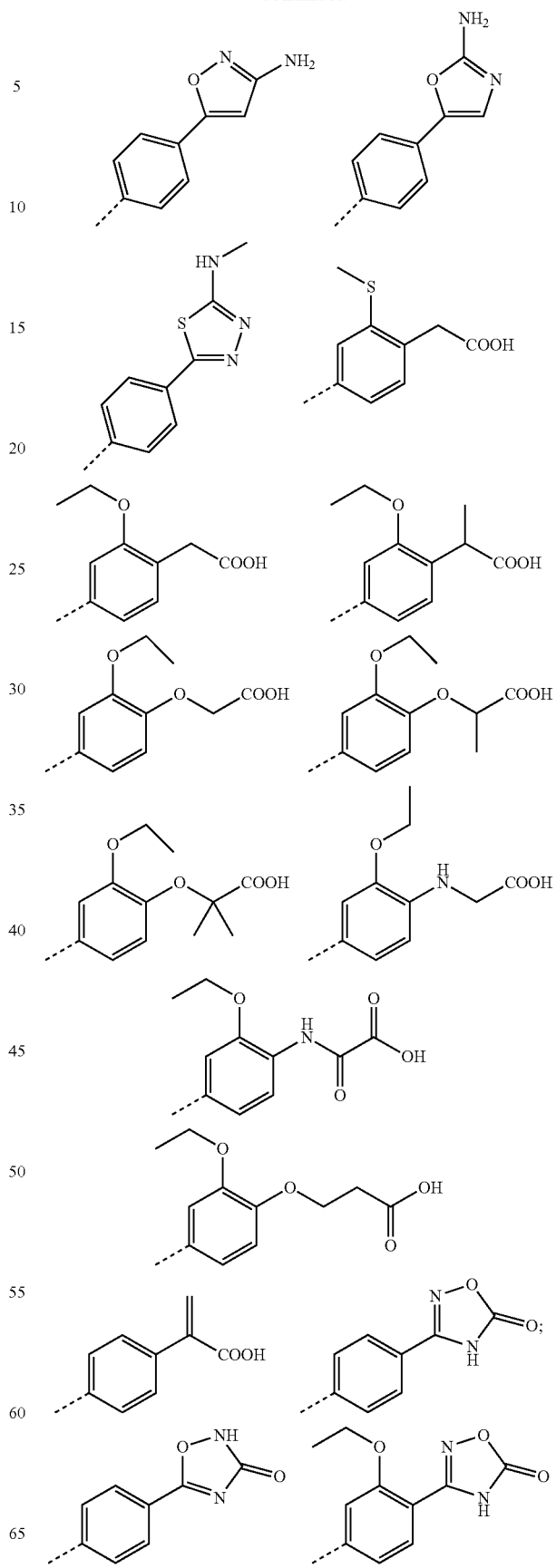

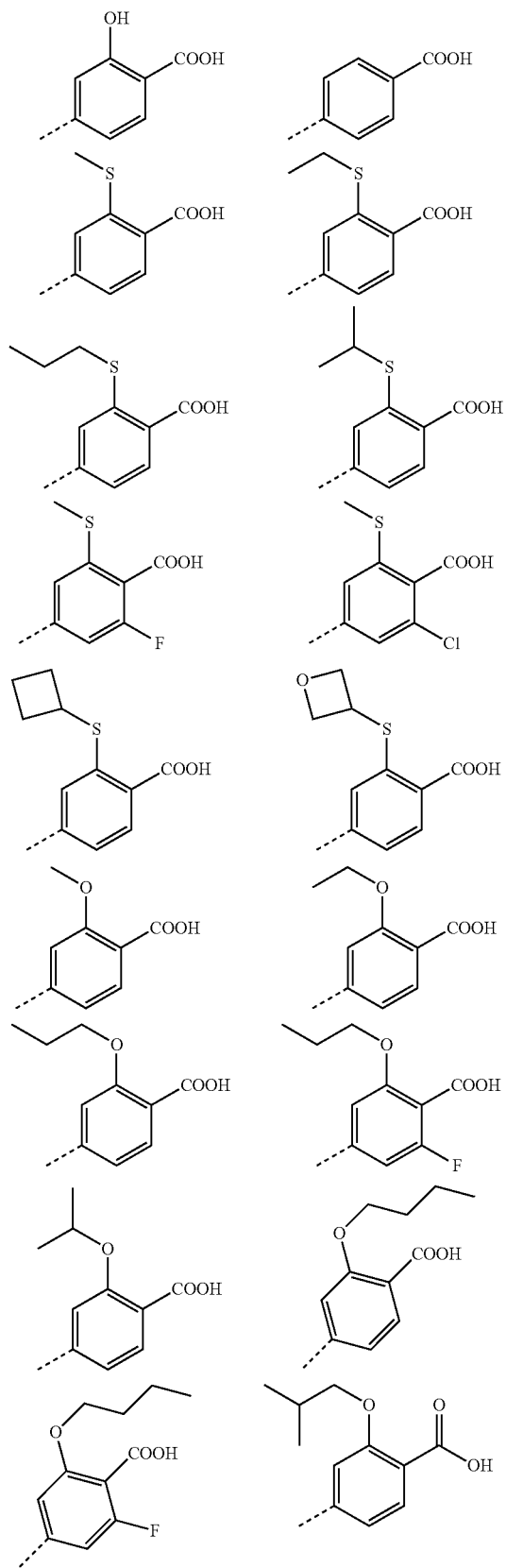
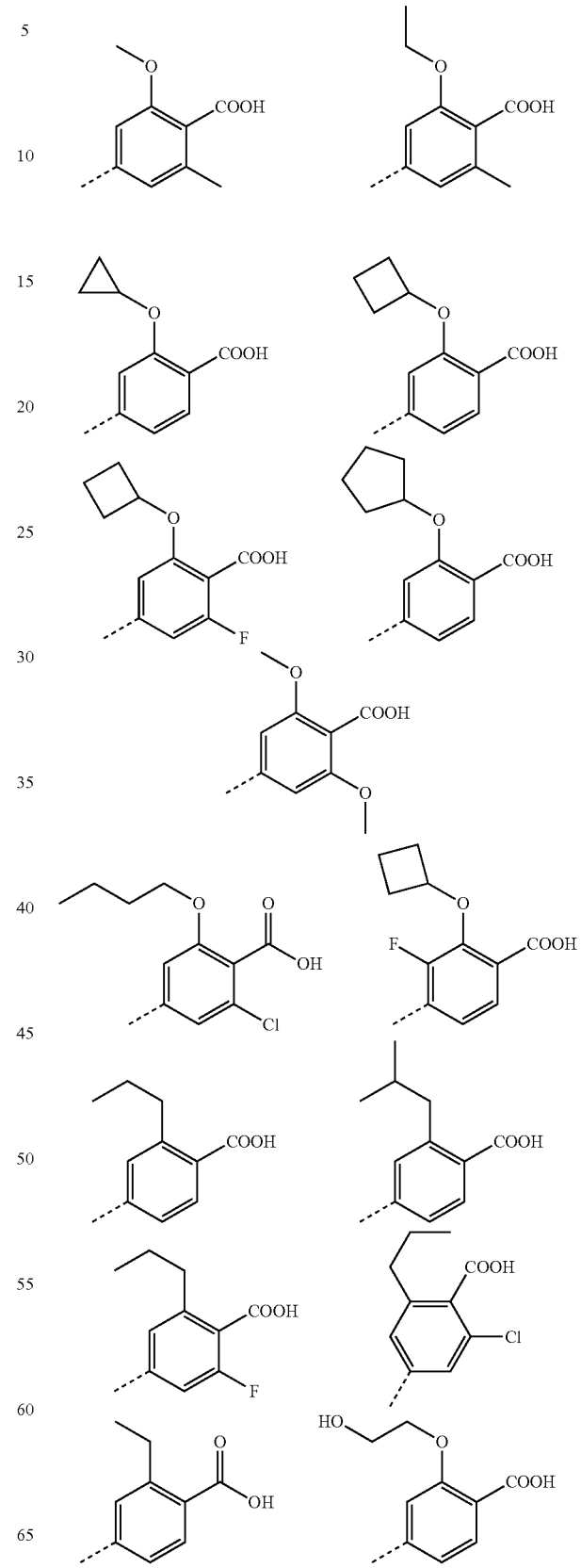

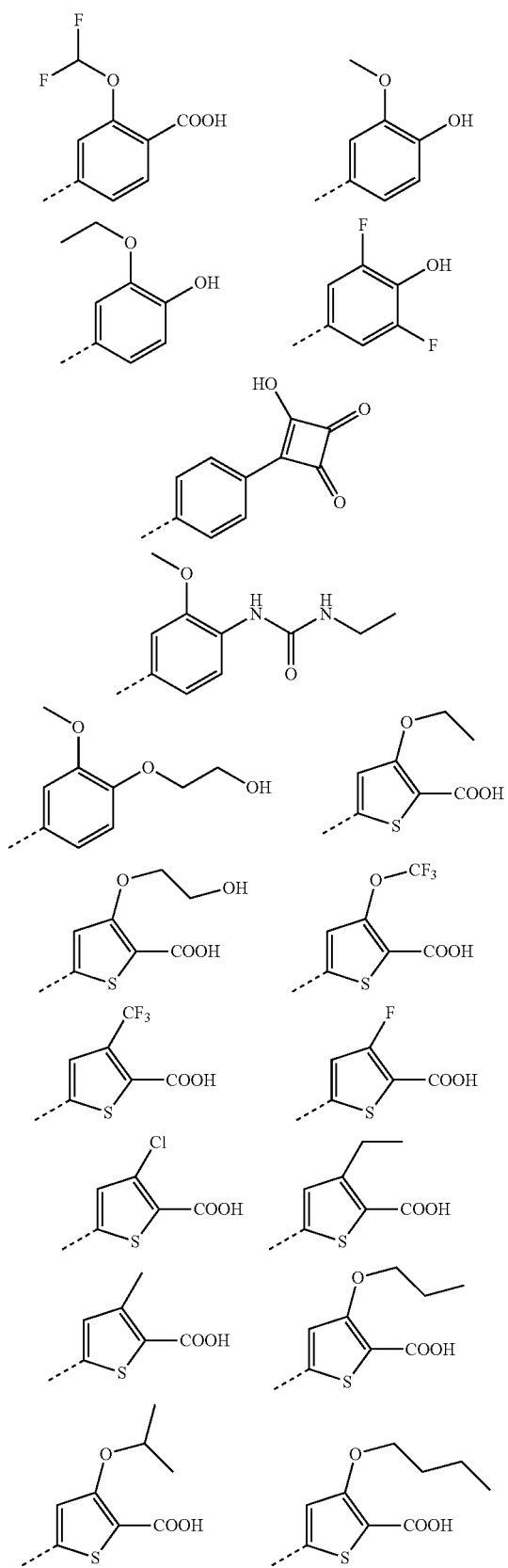
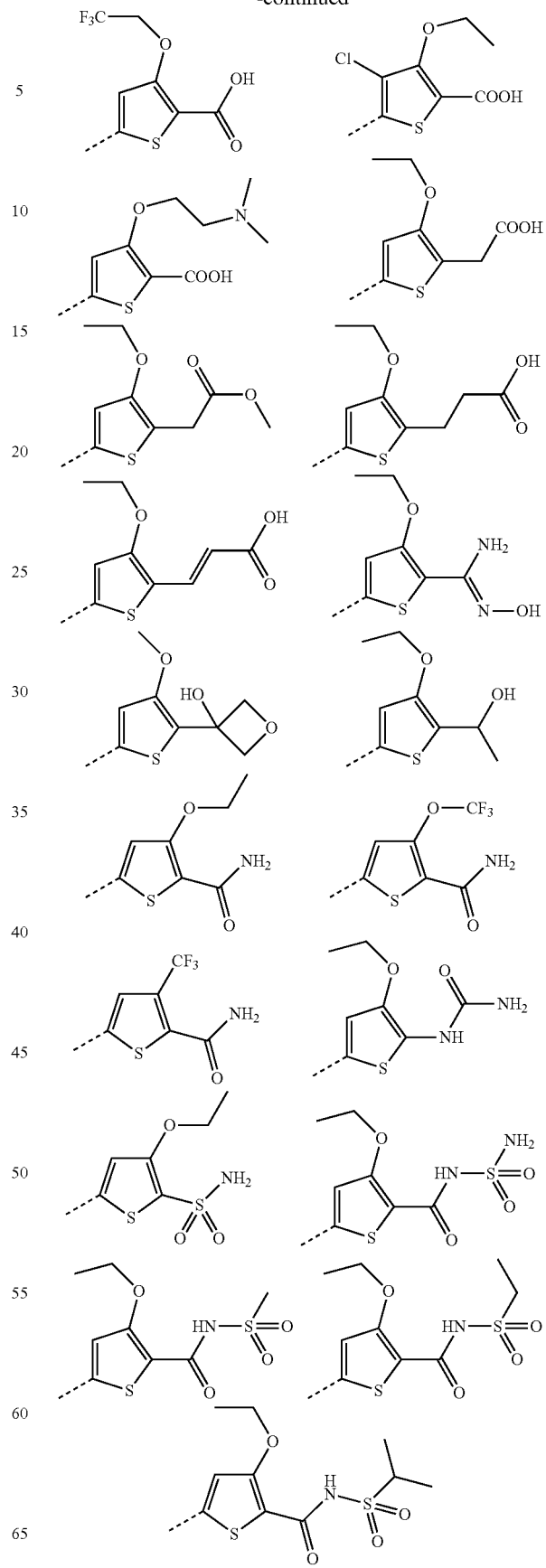

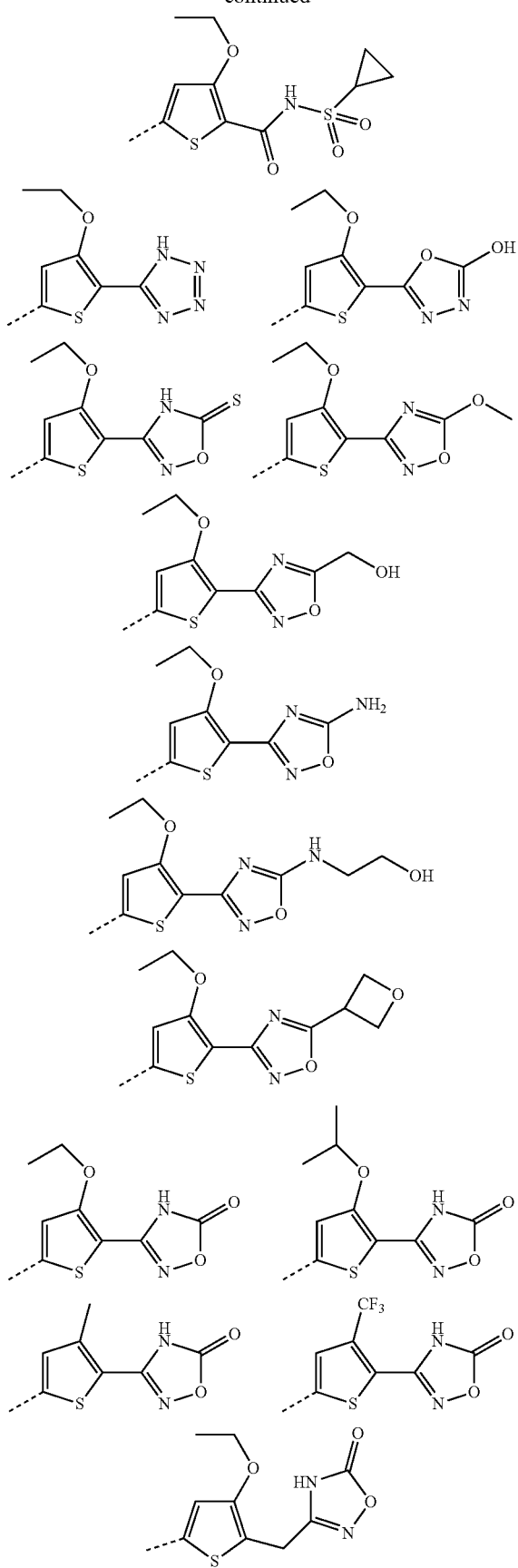
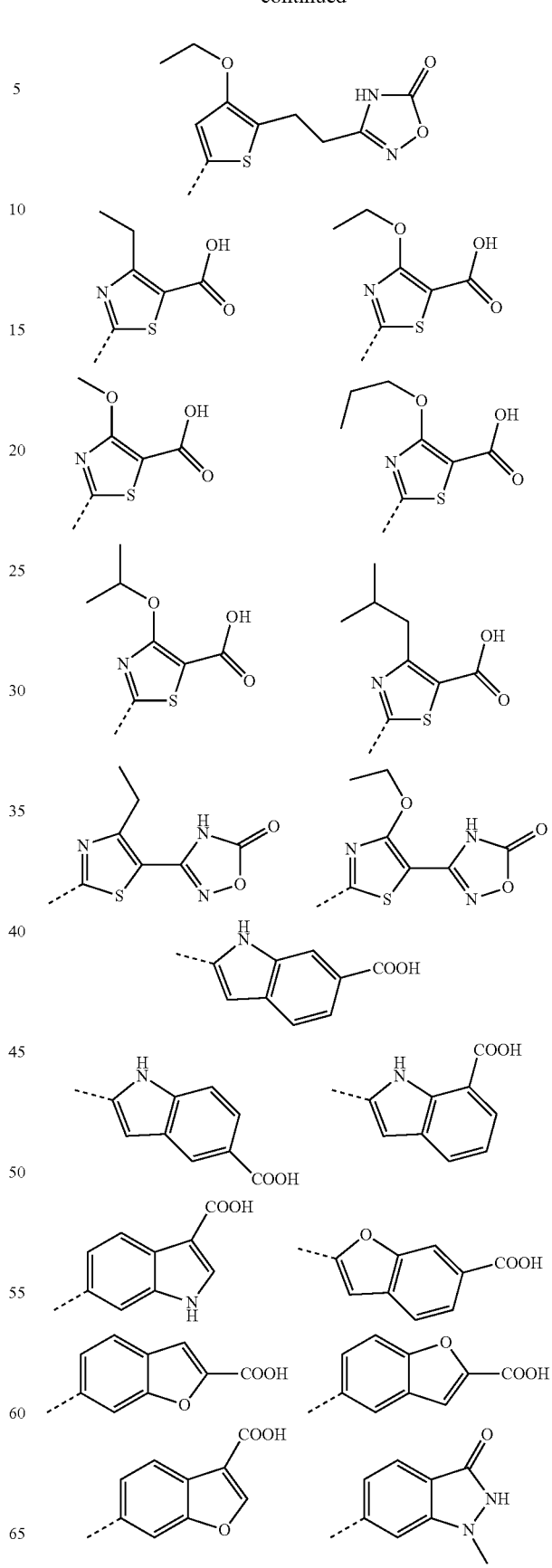

301
-continued
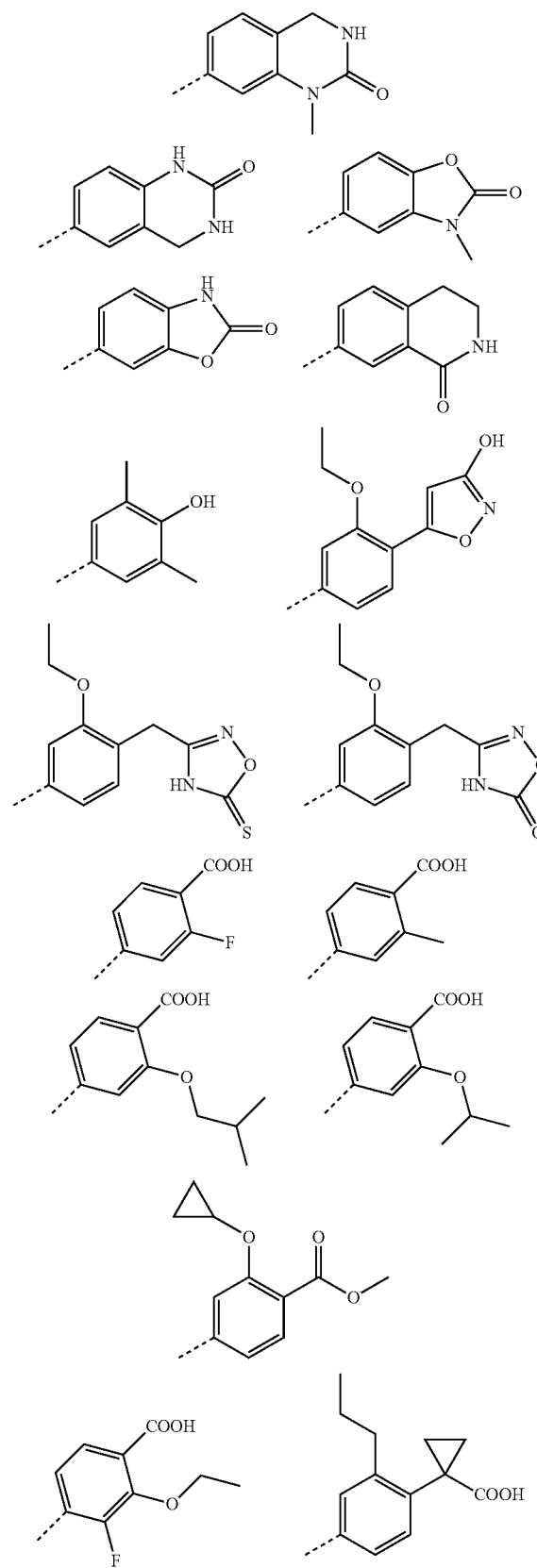
302
-continued
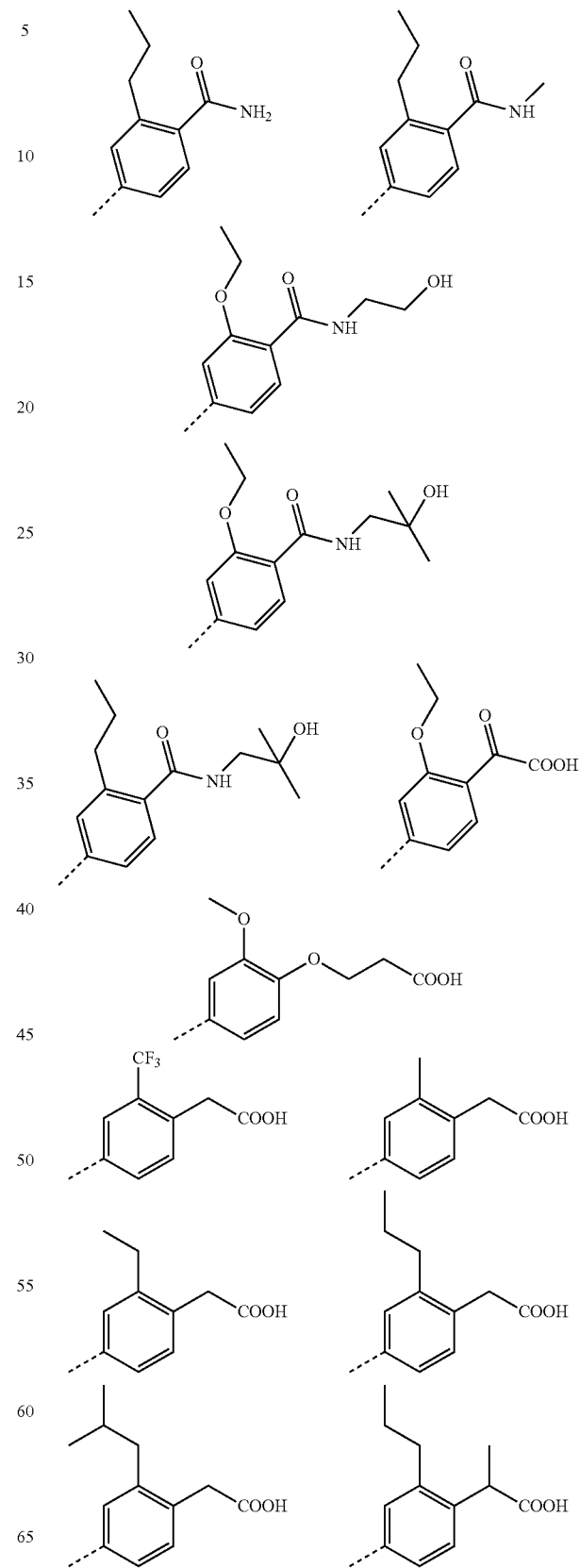

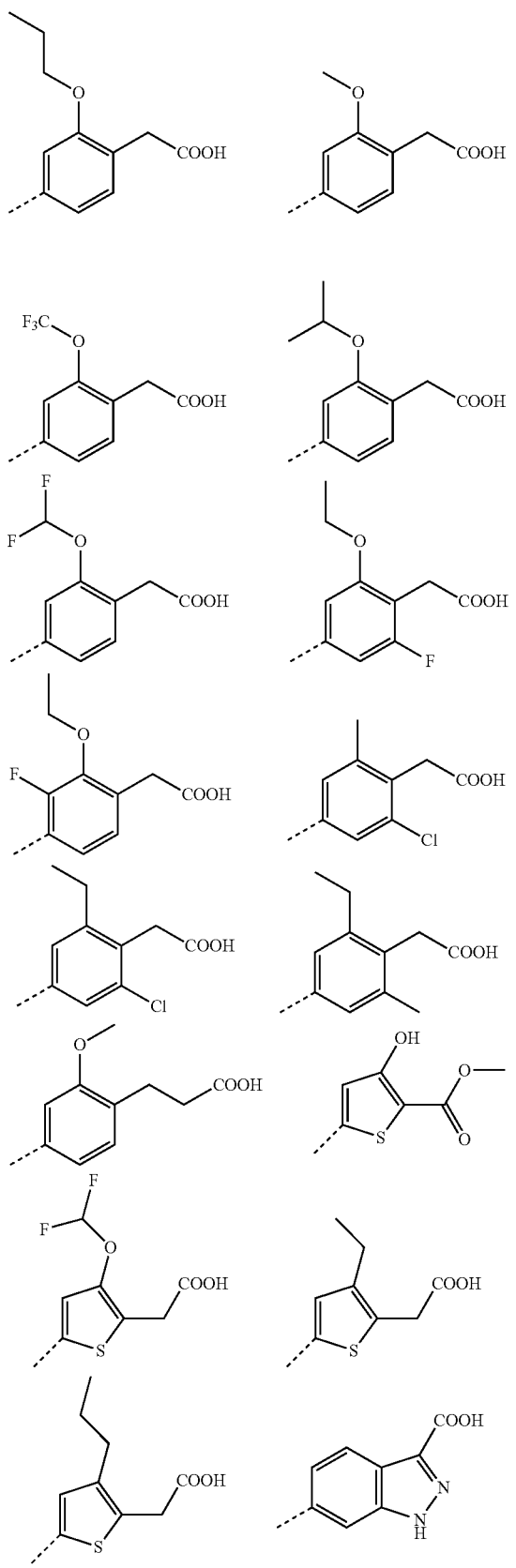
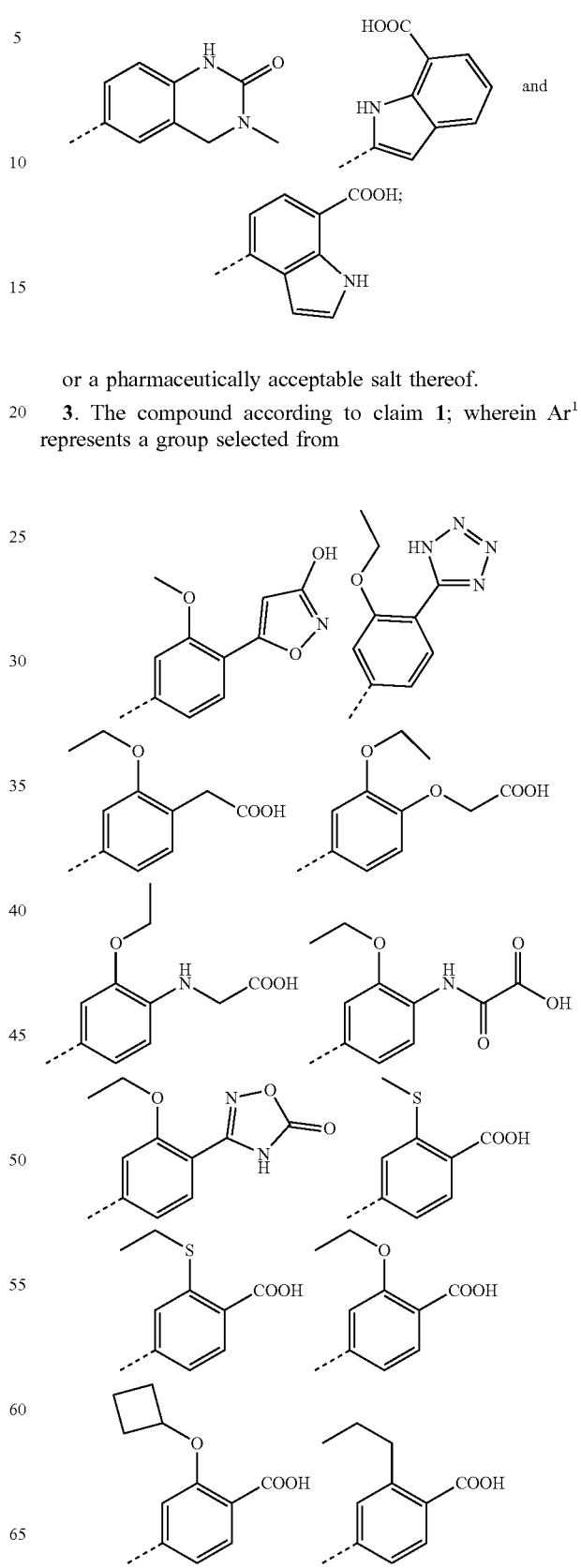
or a pharmaceutically acceptable salt thereof.
3. The compound according to claim 1; wherein Ar¹ represents a group selected from

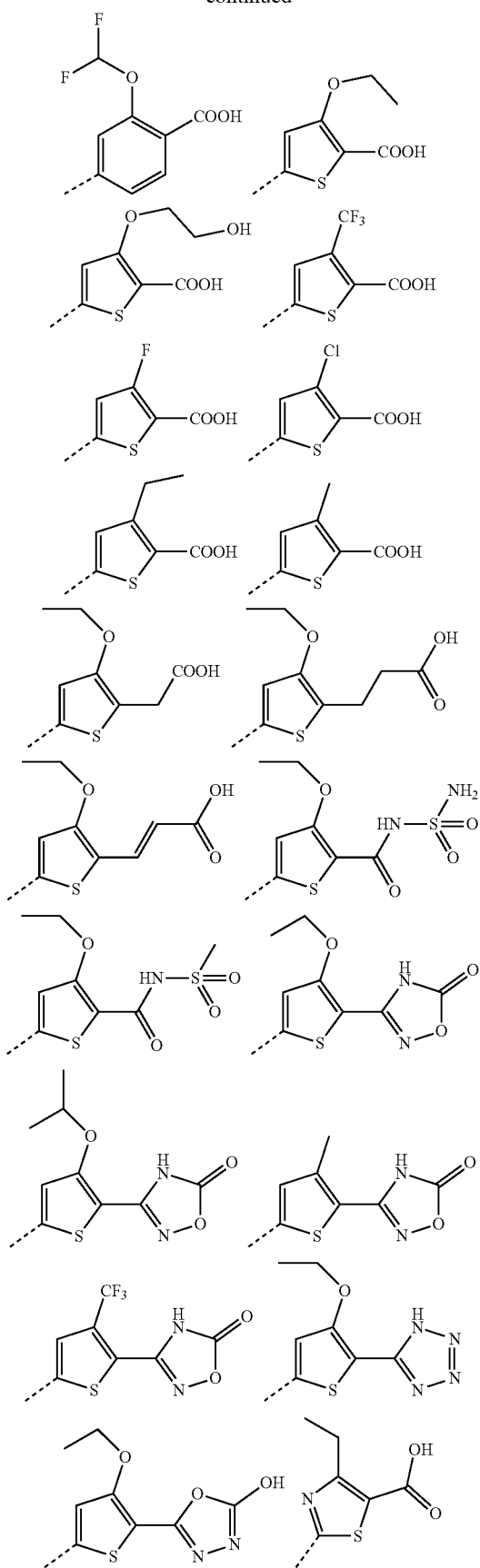
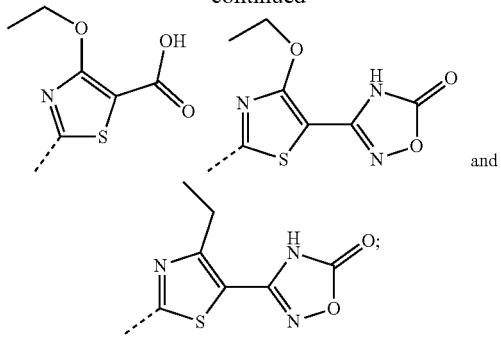

or a pharmaceutically acceptable salt thereof.

4. The compound according to claim 1; wherein the fragment

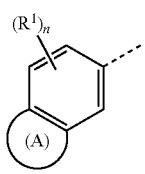

represents a group selected from benzofuranyl, benzothiophenyl, benzothiazolyl, benzoisothiazolyl, indolyl, indazolyl, naphthyl, quinolinyl, and isoquinolinyl; which group independently is unsubstituted or substituted with $(R^1)_n$; wherein $(R^1)_n$ represents one, two, three, or four substituents, wherein said substituents $R^1$ are independently selected from $(C_{1-3})$alkyl, $(C_{2-3})$alkenyl, $(C_{2-3})$alkynyl, $(C_{1-3})$alkoxy, halogen, —S—$(C_{1-3})$alkyl, $(C_{1-3})$fluoroalkyl, $(C_{1-3})$fluoroalkoxy, cyano, or —NR$^{N7}$R$^{N8}$ wherein R$^{N7}$ and R$^{N8}$ independently represent hydrogen or $(C_{1-4})$alkyl; or a group selected from 2,3-dihydro-benzo[b]thiophenyl, benzo[1,3]dioxolyl, 1,3-dihydro-isobenzofuranyl, 2,3-dihydro-benzofuranyl, indanyl, 5,6,7,8-tetrahydro-naphthalenyl, 2,3-dihydro-benzo[1,4]dioxinyl, chromanyl, 3,4-dihydro-2H-benzo[1,4]oxazinyl, 1,2,3,4-tetrahydro-quinolinyl, and 3,4-dihydro-2H-benzo[b][1,4]dioxepinyl; which group independently is unsubstituted, or substituted with $(R^1)_n$; wherein $(R^1)_n$ represents one, two, or three substituents, wherein said substituents $R^1$ are independently selected from $(C_{1-3})$alkyl, $(C_{2-3})$alkenyl, $(C_{2-3})$alkynyl, $(C_{1-3})$alkoxy, halogen, —S—$(C_{1-3})$alkyl, $(C_{1-3})$fluoroalkyl, $(C_{1-3})$fluoroalkoxy, cyano, oxo, or —NR$^{N7}$R$^{N8}$ wherein R$^{N7}$ and R$^{N8}$ independently represent hydrogen or $(C_{1-4})$alkyl;

or a pharmaceutically acceptable salt thereof.

5. The compound according to claim 2; wherein the fragment

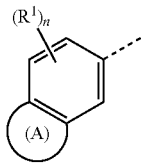

represents a group selected from the following groups a), b), c), and d), or the following groups e), f) and g):

a) benzothiophen-5-yl, benzothiophen-6-yl, 6-methyl-benzothiophen-5-yl, 3-methyl-benzothiophen-5-yl, 4-methyl-benzothiophen-5-yl, 6-methoxy-benzothiophen-5-yl, 5-methoxy-benzothiophen-6-yl, 6-cyano-benzothiophen-5-yl, 3-cyano-benzothiophen-5-yl, 6-ethoxy-benzothiophen-5-yl, 4-fluoro-7-methoxy-2-methyl-benzothiophen-6-yl, benzoisothiazol-5-yl, benzothiazol-5-yl, benzothiazol-6-yl, benzofuran-5-yl, benzofuran-6-yl, 6-fluoro-benzofuran-5-yl, 6-methoxy-benzofuran-5-yl, 5-methoxy-benzofuran-6-yl, 2-fluoro-5-methoxy-benzofuran-6-yl, 6-methoxy-4-methyl-benzofuran-5-yl, 4,5-difluoro-7-methoxy-2-methyl-benzofuran-6-yl, benzooxazol-6-yl, 1H-indol-5-yl, 1H-indol-6-yl, 1-methyl-1H-indol-6-yl, 1-methyl-1H-indol-5-yl, 6-fluoro-1-methyl-1H-indol-5-yl, 1,3-dimethyl-1H-indol-5-yl, 1-ethyl-1H-indol-6-yl, or 5-methoxy-1-methyl-1H-indazol-6-yl;

b) naphthalen-2-yl, 3-chloro-naphthalen-2-yl, 1-chloro-naphthalen-2-yl, 8-fluoro-naphthalen-2-yl, 1-fluoro-naphthalen-2-yl, 3-methyl-naphthalen-2-yl, 1-methyl-naphthalen-2-yl, 1-amino-naphthalen-2-yl, 3-ethynyl-naphthalen-2-yl, 1-ethynyl-naphthalen-2-yl, 1-vinyl-naphthalen-2-yl, 1,3-difluoro-naphthalen-2-yl, 3-methoxy-naphthalen-2-yl, 3-cyano-naphthalen-2-yl, 1-cyano-naphthalen-2-yl, 3-methylamino-naphthalen-2-yl, 1-fluoro-3-methoxy-naphthalen-2-yl, 4-chloro-3-methoxy-naphthalen-2-yl, 4-fluoro-3-methoxy-naphthalen-2-yl, 3-ethoxy-naphthalen-2-yl, 3-methoxy-1-methyl-naphthalen-2-yl, 3-cyano-1-fluoro-naphthalen-2-yl, 3-cyano-1-methyl-naphthalen-2-yl, 3-isopropoxy-naphthalen-2-yl, or 3-difluoromethoxy-naphthalen-2-yl;

c) quinolin-6-yl, 6-fluoro-isoquinolin-7-yl, 7-fluoro-isoquinolin-6-yl, 5-fluoro-quinolin-6-yl, 7-methyl-quinolin-6-yl, 8-methyl-quinolin-7-yl, 4-chloro-7-methyl-quinolin-6-yl, 7-chloro-8-methyl-quinolin-6-yl, 5,8-difluoro-quinolin-6-yl, or 7-chloro-8-fluoro-quinolin-6-yl, 5,7-difluoro-quinolin-6-yl;

d) 2,3-dihydro-benzo[b]thiophen-5-yl, benzo[1,3]dioxol-5-yl, 6-methoxy-benzo[1,3]dioxol-5-yl, 6-cyano-benzo[1,3]dioxol-5-yl, 6-chloro-2,2-difluoro-benzo[1,3]dioxol-5-yl, 6-difluoromethoxy-benzo[1,3]dioxol-5-yl, 1,3-dihydro-isobenzofuran-5-yl, 2,3-dihydro-benzofuran-5-yl, 2,3-dihydro-benzofuran-6-yl, indan-5-yl, 3-methoxy-5,6,7,8-tetrahydro-naphthalen-2-yl, 2,3-dihydro-benzo[1,4]dioxin-6-yl, 8-chloro-2,3-dihydro-benzo[1,4]dioxin-6-yl, 8-fluoro-2,3-dihydro-benzo[1,4]dioxin-6-yl, 8-methyl-2,3-dihydro-benzo[1,4]dioxin-6-yl, 7-methyl-2,3-dihydro-benzo[1,4]dioxin-6-yl, 7-methylsulfanyl-2,3-dihydro-benzo[1,4]dioxin-6-yl, 7-methoxy-2,3-dihydro-benzo[1,4]dioxin-6-yl, 7-cyano-2,3-dihydro-benzo[1,4]dioxin-6-yl, 7-ethoxy-2,3-dihydro-benzo[1,4]dioxin-6-yl, chroman-7-yl, chroman-6-yl, 6-chloro-3,4-dihydro-2H-benzo[1,4]oxazin-7-yl, 7-fluoro-4-methyl-3,4-dihydro-2H-benzo[1,4]oxazin-6-yl, 7-fluoro-1-methyl-1,2,3,4-tetrahydro-quinolin-6-yl, 7-methoxy-1,2,3,4-tetrahydro-quinolin-6-yl, 7-methoxy-1-methyl-2-oxo-1,2,3,4-tetrahydro-quinolin-6-yl, or 8-methoxy-3,4-dihydro-2H-benzo[b][1,4]dioxepin-7-yl;

e) 7-methyl-benzothiophen-5-yl, 7-methyl-benzothiophen-6-yl, 4-fluoro-benzothiophen-5-yl, 7-fluoro-benzothiophen-5-yl, 7-chloro-benzothiophen-5-yl, 3-chloro-benzothiophen-5-yl, 3-chloro-7-fluoro-benzothiophen-5-yl, 7-fluoro-6-methoxy-benzothiophen-5-yl, 7-trifluoromethyl-benzothiophen-5-yl;

f) 3-ethoxy-1-fluoro-naphthalen-2-yl, 3-ethoxy-1-methyl-naphthalen-2-yl; and g) 7-fluoro-2,3-dihydro-benzo[1,4]dioxin-6-yl, 5-methyl-2,3-dihydro-benzo[1,4]dioxin-6-yl, 7-ethynyl-2,3-dihydro-benzo[1,4]dioxin-6-yl, 5-fluoro-7-methoxy-2,3-dihydro-benzo[1,4]dioxin-6-yl, 7-methoxy-5-methyl-2,3-dihydro-benzo[1,4]dioxin-6-yl, 7-difluoromethoxy-2,3-dihydro-benzo[1,4]dioxin-6-yl;

or a pharmaceutically acceptable salt thereof.

6. The compound according to claim 3; wherein the fragment

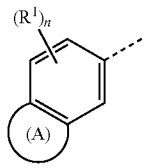

represents a group selected from the following groups a), b), c), and d):

a) benzothiophen-5-yl, 6-methyl-benzothiophen-5-yl, 4-methyl-benzothiophen-5-yl, 6-methoxy-benzothiophen-5-yl, 5-methoxy-benzothiophen-6-yl, 3-cyano-benzothiophen-5-yl, 6-ethoxy-benzothiophen-5-yl, benzothiazol-5-yl, benzofuran-5-yl, 6-fluoro-benzofuran-5-yl, 6-methoxy-benzofuran-5-yl, 5-methoxy-benzofuran-6-yl, 6-methoxy-4-methyl-benzofuran-5-yl, 1H-indol-5-yl, or 1H-indol-6-yl;

b) 1-methyl-naphthalen-2-yl, 1-ethynyl-naphthalen-2-yl, 3-methoxy-naphthalen-2-yl, 1-fluoro-3-methoxy-naphthalen-2-yl, 3-ethoxy-naphthalen-2-yl, 3-methoxy-1-methyl-naphthalen-2-yl, or 3-cyano-1-methyl-naphthalen-2-yl;

c) 7-chloro-8-fluoro-quinolin-6-yl, or 5,7-difluoro-quinolin-6-yl;

d) 2,3-dihydro-benzo[b]thiophen-5-yl, benzo[1,3]dioxol-5-yl, 6-methoxy-benzo[1,3]dioxol-5-yl, 6-cyano-benzo[1,3]dioxol-5-yl, 6-difluoromethoxy-benzo[1,3]dioxol-5-yl, 7-methyl-2,3-dihydro-benzo[1,4]dioxin-6-yl, 7-methoxy-2,3-dihydro-benzo[1,4]dioxin-6-yl, 7-cyano-2,3-dihydro-benzo[1,4]dioxin-6-yl, 7-ethoxy-2,3-dihydro-benzo[1,4]dioxin-6-yl, or 7-fluoro-4-methyl-3,4-dihydro-2H-benzo[1,4]oxazin-6-yl;

or a pharmaceutically acceptable salt thereof.

7. A compound selected from the group consisting of:

3-Ethoxy-5-{6-[2-(3-methoxy-1-methyl-naphthalen-2-yl)-ethylamino]-pyrimidin-4-yl}-thiophene-2-carboxylic acid;

5-{6-[2-(3-Cyano-1-methyl-naphthalen-2-yl)-ethylamino]-pyrimidin-4-yl}-3-ethoxy-thiophene-2-carboxylic acid;

3-Ethoxy-5-{6-[2-(1-fluoro-3-methoxy-naphthalen-2-yl)-ethylamino]-pyrimidin-4-yl}-thiophene-2-carboxylic acid;

3-Ethoxy-5-{6-[2-(6-methoxy-benzo[b]thiophen-5-yl)-ethylamino]-pyrimidin-4-yl}-thiophene-2-carboxylic acid;

5-[6-(2-Benzo[b]thiophen-5-yl-ethylamino)-pyrimidin-4-yl]-3-ethoxy-thiophene-2-carboxylic acid;

5-{6-[2-(7-Cyano-2,3-dihydro-benzo[1,4]dioxin-6-yl)-ethylamino]-pyrimidin-4-yl}-3-ethoxy-thiophene-2-carboxylic acid;

3-Ethoxy-5-{6-[2-(1-methyl-naphthalen-2-yl)-ethylamino]-pyrimidin-4-yl}-thiophene-2-carboxylic acid;
3-Ethoxy-5-{6-[2-(6-methoxy-4-methyl-benzofuran-5-yl)-ethylamino]-pyrimidin-4-yl}-thiophene-2-carboxylic acid;
3-Ethoxy-5-{6-[2-(3-methoxy-naphthalen-2-yl)-ethylamino]-pyrimidin-4-yl}-thiophene-2-carboxylic acid;
5-[6-(2-Benzo[b]thiophen-6-yl-ethylamino)-pyrimidin-4-yl]-3-ethoxy-thiophene-2-carboxylic acid;
3-Ethoxy-5-{6-[2-(6-methoxy-benzofuran-5-yl)-ethylamino]-pyrimidin-4-yl}-thiophene-2-carboxylic acid;
3-Ethoxy-5-{6-[2-(6-fluoro-benzofuran-5-yl)-ethylamino]-pyrimidin-4-yl}-thiophene-2-carboxylic acid;
3-Ethoxy-5-{6-[2-(5-methoxy-benzo[b]thiophen-6-yl)-ethylamino]-pyrimidin-4-yl}-thiophene-2-carboxylic acid;
5-{6-[2-(2,3-Dihydro-benzo[b]thiophen-5-yl)-ethylamino]-pyrimidin-4-yl}-3-ethoxy-thiophene-2-carboxylic acid;
3-Ethoxy-5-{6-[2-(1-ethynyl-naphthalen-2-yl)-ethylamino]-pyrimidin-4-yl}-thiophene-2-carboxylic acid;
4-{6-[2-(6-Methoxy-benzo[b]thiophen-5-yl)-ethylamino]-pyrimidin-4-yl}-2-methylsulfanyl-benzoic acid;
3-Ethoxy-5-{6-[2-(4-methyl-benzo[b]thiophen-5-yl)-ethylamino]-pyrimidin-4-yl}-thiophene-2-carboxylic acid;
3-Ethoxy-5-{6-[2-(3-ethoxy-naphthalen-2-yl)-ethylamino]-pyrimidin-4-yl}-thiophene-2-carboxylic acid;
3-Ethoxy-5-{6-[2-(1H-indol-6-yl)-ethylamino]-pyrimidin-4-yl}-thiophene-2-carboxylic acid;
2-Cyclobutoxy-4-{6-[2-(1-fluoro-3-methoxy-naphthalen-2-yl)-ethylamino]-pyrimidin-4-yl}-benzoic acid;
3-Ethoxy-5-{6-[2-(7-methoxy-2,3-dihydro-benzo[1,4]dioxin-6-yl)-ethylamino]-pyrimidin-4-yl}-thiophene-2-carboxylic acid;
5-{6-[2-(3-Cyano-benzo[b]thiophen-5-yl)-ethylamino]-pyrimidin-4-yl}-3-ethoxy-thiophene-2-carboxylic acid;
4-{6-[2-(1-Methyl-naphthalen-2-yl)-ethylamino]-pyrimidin-4-yl}-2-propyl-benzoic acid;
4-{6-[2-(1-Fluoro-3-methoxy-naphthalen-2-yl)-ethylamino]-pyrimidin-4-yl}-2-methylsulfanyl-benzoic acid;
3-Ethoxy-5-{6-[2-(7-methyl-2,3-dihydro-benzo[1,4]dioxin-6-yl)-ethylamino]-pyrimidin-4-yl}-thiophene-2-carboxylic acid;
3-Ethoxy-5-{6-[2-(1H-indol-5-yl)-ethylamino]-pyrimidin-4-yl}-thiophene-2-carboxylic acid;
3-Ethoxy-5-{6-[2-(6-methyl-benzo[b]thiophen-5-yl)-ethylamino]-pyrimidin-4-yl}-thiophene-2-carboxylic acid;
3-Ethoxy-5-{6-[2-(8-fluoro-2,3-dihydro-benzo[1,4]dioxin-6-yl)-ethylamino]-pyrimidin-4-yl}-thiophene-2-carboxylic acid;
5-[6-(2-Benzo[b]thiophen-5-yl-ethylamino)-pyrimidin-4-yl]-benzofuran-2-carboxylic acid;
3-Ethoxy-5-{6-[2-(7-ethoxy-2,3-dihydro-benzo[1,4]dioxin-6-yl)-ethylamino]-pyrimidin-4-yl}-thiophene-2-carboxylic acid;
5-{6-[2-(2,3-Dihydro-benzo[1,4]dioxin-6-yl)-ethylamino]-pyrimidin-4-yl}-3-ethoxy-thiophene-2-carboxylic acid;
3-Ethoxy-5-{6-[2-(1-methyl-1H-indol-6-yl)-ethylamino]-pyrimidin-4-yl}-thiophene-2-carboxylic acid;
5-{6-[2-(5,7-Difluoro-quinolin-6-yl)-ethylamino]-pyrimidin-4-yl}-3-ethoxy-thiophene-2-carboxylic acid;
5-{6-[2-(3-Difluoromethoxy-naphthalen-2-yl)-ethylamino]-pyrimidin-4-yl}-3-ethoxy-thiophene-2-carboxylic acid;
5-[6-(2-Benzofuran-6-yl-ethylamino)-pyrimidin-4-yl]-3-ethoxy-thiophene-2-carboxylic acid;
3-Ethoxy-5-{6-[2-(3-methyl-benzo[b]thiophen-5-yl)-ethylamino]-pyrimidin-4-yl}-thiophene-2-carboxylic acid;
3-(2-Hydroxy-ethoxy)-5-{6-[2-(1-methyl-naphthalen-2-yl)-ethylamino]-pyrimidin-4-yl}-thiophene-2-carboxylic acid;
3-Ethoxy-5-{6-[2-(6-methoxy-benzo[1,3]dioxol-5-yl)-ethylamino]-pyrimidin-4-yl}-thiophene-2-carboxylic acid;
5-[6-(2-Benzofuran-5-yl-ethylamino)-pyrimidin-4-yl]-3-ethoxy-thiophene-2-carboxylic acid;
4-{6-[2-(3-Cyano-1-methyl-naphthalen-2-yl)-ethylamino]-pyrimidin-4-yl}-2-methylsulfanyl-benzoic acid;
(2-Ethoxy-4-{6-[2-(6-ethoxy-benzo[b]thiophen-5-yl)-ethylamino]-pyrimidin-4-yl}-phenoxy)-acetic acid;
5-[6-(2-Chroman-6-yl-ethylamino)-pyrimidin-4-yl]-3-ethoxy-thiophene-2-carboxylic acid;
3-(3-Ethoxy-5-{6-[2-(1-methyl-naphthalen-2-yl)-ethylamino]-pyrimidin-4-yl}-thiophen-2-yl)-propionic acid;
4-{6-[2-(3-Methoxy-1-methyl-naphthalen-2-yl)-ethylamino]-pyrimidin-4-yl}-2-methylsulfanyl-benzoic acid;
2-Cyclobutoxy-4-{6-[2-(6-methoxy-benzo[b]thiophen-5-yl)-ethylamino]-pyrimidin-4-yl}-benzoic acid;
5-{6-[2-(6-Cyano-benzo[1,3]dioxol-5-yl)-ethylamino]-pyrimidin-4-yl}-3-ethoxy-thiophene-2-carboxylic acid;
5-{6-[2-(2,3-Dihydro-benzofuran-6-yl)-ethylamino]-pyrimidin-4-yl}-3-ethoxy-thiophene-2-carboxylic acid;
2-Ethoxy-4-{6-[2-(3-methoxy-1-methyl-naphthalen-2-yl)-ethylamino]-pyrimidin-4-yl}-benzoic acid;
2-Fluoro-4-{6-[2-(1-methyl-naphthalen-2-yl)-ethylamino]-pyrimidin-4-yl}-6-propyl-benzoic acid;
4-{6-[2-(6-Cyano-benzo[b]thiophen-5-yl)-ethylamino]-pyrimidin-4-yl}-2-methylsulfanyl-benzoic acid;
2-Cyclobutoxy-4-{6-[2-(3-methoxy-1-methyl-naphthalen-2-yl)-ethylamino]-pyrimidin-4-yl}-benzoic acid;
(2-Ethoxy-4-{6-[2-(6-methoxy-benzo[b]thiophen-5-yl)-ethylamino]-pyrimidin-4-yl}-phenoxy)-acetic acid;
6-{6-[2-(7-Methoxy-2,3-dihydro-benzo[1,4]dioxin-6-yl)-ethylamino]-pyrimidin-4-yl}-benzofuran-2-carboxylic acid;
2-Difluoromethoxy-4-{6-[2-(1-methyl-naphthalen-2-yl)-ethylamino]-pyrimidin-4-yl}-benzoic acid;
6-[6-(2-Benzo[b]thiophen-5-yl-ethylamino)-pyrimidin-4-yl]-benzofuran-2-carboxylic acid;
5-{6-[2-(7-Chloro-8-methyl-quinolin-6-yl)-ethylamino]-pyrimidin-4-yl}-3-ethoxy-thiophene-2-carboxylic acid;
5-[6-(2-Benzothiazol-5-yl-ethylamino)-pyrimidin-4-yl]-3-ethoxy-thiophene-2-carboxylic acid;
5-{6-[2-(7-Methoxy-2,3-dihydro-benzo[1,4]dioxin-6-yl)-ethylamino]-pyrimidin-4-yl}-benzofuran-2-carboxylic acid;
5-[6-(2-Benzo[b]thiophen-5-yl-ethylamino)-2-methyl-pyrimidin-4-yl]-3-ethoxy-thiophene-2-carboxylic acid;
4-{6-[2-(7-Cyano-2,3-dihydro-benzo[1,4]dioxin-6-yl)-ethylamino]-pyrimidin-4-yl}-2-methylsulfanyl-benzoic acid;

(2-Ethoxy-4-{6-[2-(7-ethoxy-2,3-dihydro-benzo[1,4]dioxin-6-yl)-ethylamino]-pyrimidin-4-yl}-phenoxy)-acetic acid;
2-Cyclobutoxy-4-{6-[2-(6-methoxy-benzofuran-5-yl)-ethylamino]-pyrimidin-4-yl}-benzoic acid;
2-Ethoxy-4-{6-[2-(1-fluoro-3-methoxy-naphthalen-2-yl)-ethylamino]-pyrimidin-4-yl}-benzoic acid;
(2-Ethoxy-4-{6-[2-(6-methoxy-4-methyl-benzofuran-5-yl)-ethylamino]-pyrimidin-4-yl}-phenoxy)-acetic acid;
(2-Ethoxy-4-{6-[2-(3-ethynyl-naphthalen-2-yl)-ethylamino]-pyrimidin-4-yl}-phenoxy)-acetic acid;
3-Ethoxy-5-{6-[2-(7-fluoro-4-methyl-3,4-dihydro-2H-benzo[1,4]oxazin-6-yl)-ethylamino]-pyrimidin-4-yl}-thiophene-2-carboxylic acid;
2-Ethoxy-4-{6-[2-(3-ethynyl-naphthalen-2-yl)-ethylamino]-pyrimidin-4-yl}-benzoic acid;
2-Ethoxy-4-{6-[2-(6-methoxy-benzo[b]thiophen-5-yl)-ethylamino]-pyrimidin-4-yl}-benzoic acid;
2-Ethylsulfanyl-4-{6-[2-(7-methoxy-2,3-dihydro-benzo[1,4]dioxin-6-yl)-ethylamino]-pyrimidin-4-yl}-benzoic acid;
5-[6-(2-Benzo[1,3]dioxol-5-yl-ethylamino)-pyrimidin-4-yl]-3-ethoxy-thiophene-2-carboxylic acid;
(2-Ethoxy-4-{6-[2-(6-methoxy-benzofuran-5-yl)-ethylamino]-pyrimidin-4-yl}-phenoxy)-acetic acid;
4-{6-[2-(7-Methoxy-2,3-dihydro-benzo[1,4]dioxin-6-yl)-ethylamino]-pyrimidin-4-yl}-2-methylsulfanyl-benzoic acid;
5-{6-[2-(7-Chloro-8-fluoro-quinolin-6-yl)-ethylamino]-pyrimidin-4-yl}-3-ethoxy-thiophene-2-carboxylic acid;
(2-Ethoxy-4-{6-[2-(6-methoxy-benzo[b]thiophen-5-yl)-ethylamino]-pyrimidin-4-yl}-phenyl)-acetic acid;
5-{6-[2-(6-Difluoromethoxy-benzo[1,3]dioxol-5-yl)-ethylamino]-pyrimidin-4-yl}-3-ethoxy-thiophene-2-carboxylic acid;
(2-Ethoxy-4-{6-[2-(7-methoxy-2,3-dihydro-benzo[1,4]dioxin-6-yl)-ethylamino]-pyrimidin-4-yl}-phenoxy)-acetic acid;
2-Cyclobutoxy-4-{6-[2-(5-methoxy-benzofuran-6-yl)-ethylamino]-pyrimidin-4-yl}-benzoic acid;
4-[6-(2-Benzo[b]thiophen-5-yl-ethylamino)-pyrimidin-4-yl]-2-cyclobutoxy-benzoic acid;
2-Ethoxy-4-{6-[2-(6-ethoxy-benzo[b]thiophen-5-yl)-ethylamino]-pyrimidin-4-yl}-benzoic acid;
2-{6-[2-(1-Methyl-naphthalen-2-yl)-ethylamino]-pyrimidin-4-yl}-1H-indole-4-carboxylic acid;
4-{6-[2-(6-Cyano-benzo[b]thiophen-5-yl)-ethylamino]-pyrimidin-4-yl}-2-ethoxy-benzoic acid;
4-[6-(2-Benzo[b]thiophen-5-yl-ethylamino)-pyrimidin-4-yl]-2-methylsulfanyl-benzoic acid;
5-[6-(2-Benzo[d]isothiazol-5-yl-ethylamino)-pyrimidin-4-yl]-3-ethoxy-thiophene-2-carboxylic acid;
4-{6-[2-(7-Ethoxy-2,3-dihydro-benzo[1,4]dioxin-6-yl)-ethylamino]-pyrimidin-4-yl}-2-methylsulfanyl-benzoic acid;
4-{6-[2-(2,3-Dihydro-benzo[b]thiophen-5-yl)-ethylamino]-pyrimidin-4-yl}-2-methylsulfanyl-benzoic acid;
(2-Ethoxy-4-{6-[2-(6-methoxy-benzofuran-5-yl)-ethylamino]-pyrimidin-4-yl}-phenyl)-acetic acid;
(2-Ethoxy-4-{6-[2-(6-fluoro-benzofuran-5-yl)-ethylamino]-pyrimidin-4-yl}-phenoxy)-acetic acid;
5-[6-(2-Benzooxazol-6-yl-ethylamino)-pyrimidin-4-yl]-3-ethoxy-thiophene-2-carboxylic acid;
(3-Ethoxy-5-{6-[2-(1-methyl-naphthalen-2-yl)-ethylamino]-pyrimidin-4-yl}-thiophen-2-yl)-acetic acid;
2-Ethoxy-4-{6-[2-(6-methoxy-benzofuran-5-yl)-ethylamino]-pyrimidin-4-yl}-benzoic acid;
4-{6-[2-(5-Methoxy-benzo[b]thiophen-6-yl)-ethylamino]-pyrimidin-4-yl}-2-methylsulfanyl-benzoic acid;
4-[6-(2-Benzo[b]thiophen-5-yl-ethylamino)-pyrimidin-4-yl]-2-ethoxy-benzoic acid;
(2-Ethoxy-4-{6-[2-(6-methoxy-4-methyl-benzofuran-5-yl)-ethylamino]-pyrimidin-4-yl}-phenyl)-acetic acid;
2-Ethylsulfanyl-4-{6-[2-(6-methoxy-benzofuran-5-yl)-ethylamino]-pyrimidin-4-yl}-benzoic acid;
(2-Ethoxy-4-{6-[2-(5-methoxy-benzofuran-6-yl)-ethylamino]-pyrimidin-4-yl}-phenoxy)-acetic acid;
(2-Ethoxy-4-{6-[2-(3-ethoxy-naphthalen-2-yl)-ethylamino]-pyrimidin-4-yl}-phenoxy)-acetic acid;
5-{6-[2-(1,3-Dihydro-isobenzofuran-5-yl)-ethylamino]-pyrimidin-4-yl}-3-ethoxy-thiophene-2-carboxylic acid;
2-Butoxy-4-{6-[2-(1-methyl-naphthalen-2-yl)-ethylamino]-pyrimidin-4-yl}-benzoic acid;
2-Cyclobutoxy-4-{6-[2-(2,3-dihydro-benzo[b]thiophen-5-yl)-ethylamino]-pyrimidin-4-yl}-benzoic acid;
2-Cyclobutoxy-4-{6-[2-(3-ethoxy-naphthalen-2-yl)-ethylamino]-pyrimidin-4-yl}-benzoic acid;
2-Ethoxy-4-{6-[2-(1-methyl-naphthalen-2-yl)-ethylamino]-pyrimidin-4-yl}-benzoic acid;
5-{6-[2-(4-Chloro-7-methyl-quinolin-6-yl)-ethylamino]-pyrimidin-4-yl}-3-ethoxy-thiophene-2-carboxylic acid;
4-{6-[2-(1-Methyl-naphthalen-2-yl)-ethylamino]-pyrimidin-4-yl}-2-propoxy-benzoic acid;
(2-Ethoxy-4-{6-[2-(7-methyl-2,3-dihydro-benzo[1,4]dioxin-6-yl)-ethylamino]-pyrimidin-4-yl}-phenoxy)-acetic acid;
3-(3-Ethoxy-5-{6-[2-(1H-indol-5-yl)-ethylamino]-pyrimidin-4-yl}-thiophen-2-yl)-[1,2,4]oxadiazol-5(4H)-one;
3-(5-(6-((2-(1H-indol-5-yl)ethyl)amino)pyrimidin-4-yl)-3-ethoxythiophen-2-yl)-[1,2,4]oxadiazol-5-ol;
3-{5-[6-(2-Benzo[b]thiophen-5-yl-ethylamino)-pyrimidin-4-yl]-3-ethoxy-thiophen-2-yl}-[1,2,4]oxadiazol-5(4H)-one;
3-(5-(6-((2-(Benzo[b]thiophen-5-yl)ethyl)amino)pyrimidin-4-yl)-3-ethoxythiophen-2-yl)-[1,2,4]oxadiazol-5-ol;
3-(3-Ethoxy-5-{6-[2-(7-methyl-2,3-dihydro-benzo[1,4]dioxin-6-yl)-ethylamino]-pyrimidin-4-yl}-thiophen-2-yl)-[1,2,4]oxadiazol-5(4H)-one;
3-(3-Ethoxy-5-(6-((2-(7-methyl-2,3-dihydrobenzo[b][1,4]dioxin-6-yl)ethyl)amino)pyrimidin-4-yl)thiophen-2-yl)-[1,2,4]oxadiazol-5-ol;
3-(3-Ethoxy-5-{6-[2-(6-methoxy-benzo[b]thiophen-5-yl)-ethylamino]-pyrimidin-4-yl}-thiophen-2-yl)-[1,2,4]oxadiazol-5(4H)-one;
3-(3-Ethoxy-5-(6-((2-(6-methoxybenzo[b]thiophen-5-yl)ethyl)amino)pyrimidin-4-yl)thiophen-2-yl)-[1,2,4]oxadiazol-5-ol;
3-(3-Ethoxy-5-{6-[2-(1H-indol-6-yl)-ethylamino]-pyrimidin-4-yl}-thiophen-2-yl)-[1,2,4]oxadiazol-5(4H)-one;
3-(5-(6-((2-(1H-indol-6-yl)ethyl)amino)pyrimidin-4-yl)-3-ethoxythiophen-2-yl)-[1,2,4]oxadiazol-5-ol;
3-{5-[6-(2-Benzo[1,3]dioxol-5-yl-ethylamino)-pyrimidin-4-yl]-3-ethoxy-thiophen-2-yl}-[1,2,4]oxadiazol-5(4H)-one;

3-(5-(6-((2-(Benzo[d][1,3]dioxol-5-yl)ethyl)amino)pyrimidin-4-yl)-3-ethoxythiophen-2-yl)-[1,2,4]oxadiazol-5-ol;
3-(3-Ethoxy-5-{6-[2-(7-fluoro-quinolin-6-yl)-ethylamino]-pyrimidin-4-yl}-thiophen-2-yl)-[1,2,4]oxadiazol-5(4H)-one;
3-(3-Ethoxy-5-(6-((2-(7-fluoroquinolin-6-yl)ethyl)amino)pyrimidin-4-yl)thiophen-2-yl)-[1,2,4]oxadiazol-5-ol;
{6-[4-Ethoxy-5-(1H-tetrazol-5-yl)-thiophen-2-yl]-pyrimidin-4-yl}-[2-(7-fluoro-quinolin-6-yl)-ethyl]-amine;
4-Ethoxy-2-{6-[2-(1-methyl-naphthalen-2-yl)-ethylamino]-pyrimidin-4-yl}-thiazole-5-carboxylic acid;
3-(4-Ethoxy-2-{6-[2-(1-methyl-naphthalen-2-yl)-ethylamino]-pyrimidin-4-yl}-thiazol-5-yl)-[1,2,4]oxadiazol-5(4H)-one;
3-(4-Ethoxy-2-(6-((2-(1-methylnaphthalen-2-yl)ethyl)amino)pyrimidin-4-yl)thiazol-5-yl)-[1,2,4]oxadiazol-5-ol;
3-(4-Ethyl-2-{6-[2-(1-methyl-naphthalen-2-yl)-ethylamino]-pyrimidin-4-yl}-thiazol-5-yl)-[1,2,4]oxadiazol-5(4H)-one;
3-(4-Ethyl-2-(6-((2-(1-methylnaphthalen-2-yl)ethyl)amino)pyrimidin-4-yl)thiazol-5-yl)-[1,2,4]oxadiazol-5-ol;
3-Ethoxy-5-(6-((2-(1-methylnaphthalen-2-yl)ethyl)amino)pyrimidin-4-yl)-N-sulfamoylthiophene-2-carboxamide;
N-(3-Ethoxy-5-{6-[2-(1-methyl-naphthalen-2-yl)-ethylamino]-pyrimidin-4-yl}-thiophene-2-carbonyl)-methanesulfonamide;
2-Cyclobutoxy-4-{6-[2-(7-methoxy-2,3-dihydro-benzo[1,4]dioxin-6-yl)-ethylamino]-pyrimidin-4-yl}-benzoic acid;
4-{6-[2-(6-Methyl-benzo[b]thiophen-5-yl)-ethylamino]-pyrimidin-4-yl}-2-methylsulfanyl-benzoic acid;
(2-Ethoxy-4-{6-[2-(7-ethoxy-2,3-dihydro-benzo[1,4]dioxin-6-yl)-ethylamino]-pyrimidin-4-yl}-phenyl)-acetic acid;
4-{6-[2-(6-Methoxy-benzofuran-5-yl)-ethylamino]-pyrimidin-4-yl}-2-methylsulfanyl-benzoic acid;
2-Cyclobutoxy-4-{6-[2-(7-ethoxy-2,3-dihydro-benzo[1,4]dioxin-6-yl)-ethylamino]-pyrimidin-4-yl}-benzoic acid;
6-{6-[2-(7-Methoxy-2,3-dihydro-benzo[1,4]dioxin-6-yl)-ethylamino]-pyrimidin-4-yl}-benzofuran-3-carboxylic acid;
4-{6-[2-(4-Methyl-benzo[b]thiophen-5-yl)-ethylamino]-pyrimidin-4-yl}-2-methylsulfanyl-benzoic acid;
2-Cyclobutoxy-4-{6-[2-(6-methoxy-4-methyl-benzofuran-5-yl)-ethylamino]-pyrimidin-4-yl}-benzoic acid;
4-{6-[2-(3-Cyano-benzo[b]thiophen-5-yl)-ethylamino]-pyrimidin-4-yl}-2-methylsulfanyl-benzoic acid;
2-Cyclobutoxy-4-{6-[2-(6-methoxy-benzo[1,3]dioxol-5-yl)-ethylamino]-pyrimidin-4-yl}-benzoic acid;
2-Ethoxy-4-{6-[2-(6-methoxy-4-methyl-benzofuran-5-yl)-ethylamino]-pyrimidin-4-yl}-benzoic acid;
(4-{6-[2-(6-Methoxy-benzo[b]thiophen-5-yl)-ethylamino]-pyrimidin-4-yl}-2-methylsulfanyl-phenyl)-acetic acid;
2-Ethoxy-4-{6-[2-(6-fluoro-benzofuran-5-yl)-ethylamino]-pyrimidin-4-yl}-benzoic acid;
2-(2-Ethoxy-4-{6-[2-(6-methoxy-benzofuran-5-yl)-ethylamino]-pyrimidin-4-yl}-phenoxy)-propionic acid;
4-{6-[2-(6-Fluoro-benzofuran-5-yl)-ethylamino]-pyrimidin-4-yl}-2-methylsulfanyl-benzoic acid;
4-[6-(2-Benzofuran-5-yl-ethylamino)-pyrimidin-4-yl]-2-methylsulfanyl-benzoic acid;
4-[6-(2-Benzofuran-6-yl-ethylamino)-pyrimidin-4-yl]-2-methylsulfanyl-benzoic acid;
2-Ethoxy-4-{6-[2-(6-methyl-benzo[b]thiophen-5-yl)-ethylamino]-pyrimidin-4-yl}-benzoic acid;
2-Ethoxy-4-{6-[2-(7-ethoxy-2,3-dihydro-benzo[1,4]dioxin-6-yl)-ethylamino]-pyrimidin-4-yl}-benzoic acid;
2-Cyclobutoxy-4-{6-[2-(4-methyl-benzo[b]thiophen-5-yl)-ethylamino]-pyrimidin-4-yl}-benzoic acid;
4-{6-[2-(6-Methoxy-benzo[b]thiophen-5-yl)-ethylamino]-pyrimidin-4-yl}-benzoic acid;
4-{6-[2-(6-Methoxy-benzo[1,3]dioxol-5-yl)-ethylamino]-pyrimidin-4-yl}-2-methylsulfanyl-benzoic acid;
2-Ethoxy-4-{6-[2-(7-methoxy-2,3-dihydro-benzo[1,4]dioxin-6-yl)-ethylamino]-pyrimidin-4-yl}-benzoic acid;
2-Cyclobutoxy-4-{6-[2-(7-methyl-2,3-dihydro-benzo[1,4]dioxin-6-yl)-ethylamino]-pyrimidin-4-yl}-benzoic acid;
2-Ethoxy-4-{6-[2-(4-methyl-benzo[b]thiophen-5-yl)-ethylamino]-pyrimidin-4-yl}-benzoic acid;
2-Ethoxy-4-{6-[2-(6-methoxy-benzo[1,3]dioxol-5-yl)-ethylamino]-pyrimidin-4-yl}-benzoic acid;
3-Ethoxy-5-{6-[2-(1-fluoro-naphthalen-2-yl)-ethylamino]-pyrimidin-4-yl}-thiophene-2-carboxylic acid;
3-Ethoxy-5-{6-[2-(6-fluoro-1-methyl-1H-indol-5-yl)-ethylamino]-pyrimidin-4-yl}-thiophene-2-carboxylic acid;
5-{6-[2-(4-Chloro-3-methoxy-naphthalen-2-yl)-ethylamino]-pyrimidin-4-yl}-3-ethoxy-thiophene-2-carboxylic acid;
3-Ethoxy-5-{6-[2-(8-methoxy-3,4-dihydro-2H-benzo[b][1,4]dioxepin-7-yl)-ethylamino]-pyrimidin-4-yl}-thiophene-2-carboxylic acid;
3-Ethoxy-5-{6-[2-(8-methyl-quinolin-7-yl)-ethylamino]-pyrimidin-4-yl}-thiophene-2-carboxylic acid;
3-Ethoxy-5-{6-[2-(3-isopropoxy-naphthalen-2-yl)-ethylamino]-pyrimidin-4-yl}-thiophene-2-carboxylic acid;
5-{6-[2-(1-Cyano-naphthalen-2-yl)-ethylamino]-pyrimidin-4-yl}-3-ethoxy-thiophene-2-carboxylic acid;
3-Ethoxy-5-[6-(2-naphthalen-2-yl-ethylamino)-pyrimidin-4-yl]-thiophene-2-carboxylic acid;
(2-Ethoxy-4-{6-[2-(1-fluoro-3-methoxy-naphthalen-2-yl)-ethylamino]-pyrimidin-4-yl}-phenyl)-acetic acid;
3-Ethoxy-5-{6-[2-(3-methyl-naphthalen-2-yl)-ethylamino]-pyrimidin-4-yl}-thiophene-2-carboxylic acid;
3-Ethoxy-5-[6-(2-indan-5-yl-ethylamino)-pyrimidin-4-yl]-thiophene-2-carboxylic acid;
5-{6-[2-(8-Chloro-2,3-dihydro-benzo[1,4]dioxin-6-yl)-ethylamino]-pyrimidin-4-yl}-3-ethoxy-thiophene-2-carboxylic acid;
4-{6-[2-(3-Cyano-1-methyl-naphthalen-2-yl)-ethylamino]-pyrimidin-4-yl}-2-ethoxy-benzoic acid;
5-{6-[2-(4,5-Difluoro-7-methoxy-2-methyl-benzofuran-6-yl)-ethylamino]-pyrimidin-4-yl}-3-ethoxy-thiophene-2-carboxylic acid;
5-[6-(2-Chroman-7-yl-ethylamino)-pyrimidin-4-yl]-3-ethoxy-thiophene-2-carboxylic acid;
3-Ethoxy-5-{6-[2-(3-methoxy-5,6,7,8-tetrahydro-naphthalen-2-yl)-ethylamino]-pyrimidin-4-yl}-thiophene-2-carboxylic acid;
(2-Ethoxy-4-{6-[2-(3-methoxy-1-methyl-naphthalen-2-yl)-ethylamino]-pyrimidin-4-yl}-phenyl)-acetic acid;
5-{6-[2-(3-Chloro-naphthalen-2-yl)-ethylamino]-pyrimidin-4-yl}-3-ethoxy-thiophene-2-carboxylic acid;

3-Ethoxy-5-{6-[2-(1-methyl-1H-indol-5-yl)-ethyl-amino]-pyrimidin-4-yl}-thiophene-2-carboxylic acid;
3-Ethoxy-5-{6-[2-(8-fluoro-naphthalen-2-yl)-ethyl-amino]-pyrimidin-4-yl}-thiophene-2-carboxylic acid;
3-Ethoxy-5-{6-[2-(5-fluoro-quinolin-6-yl)-ethylamino]-pyrimidin-4-yl}-thiophene-2-carboxylic acid;
2-Cyclobutoxy-4-{6-[2-(7-methylsulfanyl-2,3-dihydro-benzo[1,4]dioxin-6-yl)-ethylamino-pyrimidin-4-yl}-benzoic acid;
5-{6-[2-(1-Amino-naphthalen-2-yl)-ethylamino]-pyrimidin-4-yl}-3-ethoxy-thiophene-2-carboxylic acid;
5-{6-[2-(7-Fluoro-1-methyl-1,2,3,4-tetrahydro-quinolin-6-yl)-ethylamino]-pyrimidin-4-yl}-3-trifluoromethyl-thiophene-2-carboxylic acid;
4-{6-[2-(3-Cyano-1-fluoro-naphthalen-2-yl)-ethyl-amino]-pyrimidin-4-yl}-2-ethoxy-benzoic acid;
3-Ethoxy-5-{6-[2-(1-vinyl-naphthalen-2-yl)-ethyl-amino]-pyrimidin-4-yl}-thiophene-2-carboxylic acid;
2-Isobutyl-4-{6-[2-(1-methyl-naphthalen-2-yl)-ethyl-amino]-pyrimidin-4-yl}-benzoic acid;
3-Ethoxy-5-{6-[2-(7-methylsulfanyl-2,3-dihydro-benzo[1,4]dioxin-6-yl)-ethylamino]-pyrimidin-4-yl}-thiophene-2-carboxylic acid;
(4-{6-[2-(6-Cyano-benzo[b]thiophen-5-yl)-ethylamino]-pyrimidin-4-yl}-2-ethoxy-phenyl)-acetic acid;
(4-{6-[2-(3-Cyano-naphthalen-2-yl)-ethylamino]-pyrimidin-4-yl}-2-ethoxy-phenoxy)-acetic acid;
5-{6-[2-(5,8-Difluoro-quinolin-6-yl)-ethylamino]-pyrimidin-4-yl}-3-ethoxy-thiophene-2-carboxylic acid;
(2-Ethoxy-4-{6-[2-(3-isopropoxy-naphthalen-2-yl)-ethylamino]-pyrimidin-4-yl}-phenoxy)-acetic acid;
5-{6-[2-(1-Chloro-naphthalen-2-yl)-ethylamino]-pyrimidin-4-yl}-3-ethoxy-thiophene-2-carboxylic acid;
5-[6-(2-Benzothiazol-6-yl-ethylamino)-pyrimidin-4-yl]-3-ethoxy-thiophene-2-carboxylic acid;
4-{6-[2-(3-Cyano-naphthalen-2-yl)-ethylamino]-pyrimidin-4-yl}-2-ethoxy-benzoic acid;
3-Ethoxy-5-{6-[2-(4-fluoro-7-methoxy-2-methyl-benzo[b]thiophen-6-yl)-ethylamino]-pyrimidin-4-yl}-thiophene-2-carboxylic acid;
3-Ethoxy-5-{6-[2-(8-methyl-2,3-dihydro-benzo[1,4]dioxin-6-yl)-ethylamino]-pyrimidin-4-yl}-thiophene-2-carboxylic acid;
3-Ethoxy-5-{6-[2-(7-fluoro-quinolin-6-yl)-ethylamino]-pyrimidin-4-yl}-thiophene-2-carboxylic acid;
3-Ethoxy-5-{6-[2-(6-fluoro-isoquinolin-7-yl)-ethyl-amino]-pyrimidin-4-yl}-thiophene-2-carboxylic acid;
(4-{6-[2-(1,3-Difluoro-naphthalen-2-yl)-ethylamino]-pyrimidin-4-yl}-2-ethoxy-phenyl)-acetic acid;
5-{6-[2-(7-Fluoro-isoquinolin-6-yl)-ethylamino]-pyrimidin-4-yl}-3-trifluoromethyl-thiophene-2-carboxylic acid;
4-{6-[2-(7-Cyano-2,3-dihydro-benzo[1,4]dioxin-6-yl)-ethylamino]-pyrimidin-4-yl}-2-cyclobutoxy-benzoic acid;
5-{6-[2-(2,3-Dihydro-benzofuran-5-yl)-ethylamino]-pyrimidin-4-yl}-3-ethoxy-thiophene-2-carboxylic acid;
(4-{6-[2-(1-Fluoro-3-methoxy-naphthalen-2-yl)-ethyl-amino]-pyrimidin-4-yl}-2-methylsulfanyl-phenyl)-acetic acid;
{4-[6-(2-Benzo[b]thiophen-5-yl-ethylamino)-pyrimidin-4-yl]-2-ethoxy-phenoxy}-acetic acid;
(2-Ethoxy-4-{6-[2-(3-methoxy-naphthalen-2-yl)-ethyl-amino]-pyrimidin-4-yl}-phenoxy)-acetic acid;
2-Ethoxy-4-{6-[2-(4-fluoro-3-methoxy-naphthalen-2-yl)-ethylamino]-pyrimidin-4-yl}-benzoic acid;
5-{6-[2-(1,3-Difluoro-naphthalen-2-yl)-ethylamino]-pyrimidin-4-yl}-3-ethoxy-thiophene-2-carboxylic acid;
3-{3-Ethoxy-5-[6-(2-quinolin-6-yl-ethylamino)-pyrimidin-4-yl]-thiophen-2-yl}-[1,2,4]oxadiazol-5(4H)-one;
3-(3-Ethoxy-5-(6-((2-(quinolin-6-yl)ethyl)amino)pyrimidin-4-yl)thiophen-2-yl)-[1,2,4]oxadiazol-5-ol;
3-{3-Ethoxy-5-[6-(2-naphthalen-2-yl-ethylamino)-pyrimidin-4-yl]-thiophen-2-yl}-[1,2,4]oxadiazol-5(4H)-one; and
3-(3-Ethoxy-5-(6-((2-(naphthalen-2-yl)ethyl)amino)pyrimidin-4-yl)thiophen-2-yl)-[1,2,4]oxadiazol-5-ol;
or a pharmaceutically acceptable salt thereof.

8. A compound selected from the group consisting of:
5-{6-[2-(7-Chloro-benzo[b]thiophen-5-yl)-ethylamino]-pyrimidin-4-yl}-3-ethoxy-thiophene-2-carboxylic acid;
4-{6-[2-(7-Chloro-benzo[b]thiophen-5-yl)-ethylamino]-pyrimidin-4-yl}-2-methylsulfanyl-benzoic acid;
2-Ethoxy-4-{6-[2-(7-fluoro-benzo[b]thiophen-5-yl)-ethylamino]-pyrimidin-4-yl}-benzoic acid;
3-Ethoxy-5-{6-[2-(7-fluoro-benzo[b]thiophen-5-yl)-ethylamino]-pyrimidin-4-yl}-thiophene-2-carboxylic acid;
4-{6-[2-(7-Fluoro-benzo[b]thiophen-5-yl)-ethylamino]-pyrimidin-4-yl}-2-methylsulfanyl-benzoic acid;
2-Ethoxy-4-{6-[2-(4-fluoro-benzo[b]thiophen-5-yl)-ethylamino]-pyrimidin-4-yl}-benzoic acid;
2-Cyclobutoxy-4-{6-[2-(4-fluoro-benzo[b]thiophen-5-yl)-ethylamino]-pyrimidin-4-yl}-benzoic acid;
3-Ethoxy-5-{6-[2-(4-fluoro-benzo[b]thiophen-5-yl)-ethylamino]-pyrimidin-4-yl}-thiophene-2-carboxylic acid;
4-{6-[2-(4-Fluoro-benzo[b]thiophen-5-yl)-ethylamino]-pyrimidin-4-yl}-2-methylsulfanyl-benzoic acid;
(2-Ethoxy-6-fluoro-4-{6-[2-(6-methoxy-benzo[b]thiophen-5-yl)-ethylamino]-pyrimidin-4-yl}-phenyl)-acetic acid;
(2-Ethoxy-6-fluoro-4-{6-[2-(4-methyl-benzo[b]thiophen-5-yl)-ethylamino]-pyrimidin-4-yl}-phenyl)-acetic acid;
3-Ethoxy-5-{6-[2-(7-methyl-benzo[b]thiophen-6-yl)-ethylamino]-pyrimidin-4-yl}-thiophene-2-carboxylic acid;
4-{6-[2-(6-Methoxy-benzo[b]thiophen-5-yl)-ethyl-amino]-pyrimidin-4-yl}-2-propyl-benzoic acid;
4-{6-[2-(4-Fluoro-benzo[b]thiophen-5-yl)-ethylamino]-pyrimidin-4-yl}-2-propyl-benzoic acid;
4-{6-[2-(7-Methoxy-2,3-dihydro-benzo[1,4]dioxin-6-yl)-ethylamino]-pyrimidin-4-yl}-2-propyl-benzoic acid;
4-{6-[2-(3-Methoxy-1-methyl-naphthalen-2-yl)-ethyl-amino]-pyrimidin-4-yl}-2-propyl-benzoic acid;
(2-Methoxy-4-{6-[2-(6-methoxy-benzo[b]thiophen-5-yl)-ethylamino]-pyrimidin-4-yl}-phenyl)-acetic acid;
(4-{6-[2-(4-Fluoro-benzo[b]thiophen-5-yl)-ethylamino]-pyrimidin-4-yl}-2-methoxy-phenyl)-acetic acid;
(2-Methoxy-4-{6-[2-(7-methoxy-2,3-dihydro-benzo[1,4]dioxin-6-yl)-ethylamino]-pyrimidin-4-yl}-phenyl)-acetic acid;
(2-Methoxy-4-{6-[2-(3-methoxy-1-methyl-naphthalen-2-yl)-ethylamino]-pyrimidin-4-yl}-phenyl)-acetic acid;
(4-{6-[2-(6-Methoxy-benzo[b]thiophen-5-yl)-ethyl-amino]-pyrimidin-4-yl}-2-propyl-phenyl)-acetic acid;
(4-{6-[2-(4-Fluoro-benzo[b]thiophen-5-yl)-ethylamino]-pyrimidin-4-yl}-2-propyl-phenyl)-acetic acid;
(4-{6-[2-(7-Methoxy-2,3-dihydro-benzo[1,4]dioxin-6-yl)-ethylamino]-pyrimidin-4-yl}-2-propyl-phenyl)-acetic acid;

(4-{6-[2-(3-Methoxy-1-methyl-naphthalen-2-yl)-ethylamino]-pyrimidin-4-yl}-2-propyl-phenyl)-acetic acid;
4-{6-[2-(7-Fluoro-benzo[b]thiophen-5-yl)-ethylamino]-pyrimidin-4-yl}-2-propyl-benzoic acid;
3-Ethoxy-5-{6-[2-(7-methyl-benzo[b]thiophen-5-yl)-ethylamino]-pyrimidin-4-yl}-thiophene-2-carboxylic acid;
(4-{6-[2-(4-Fluoro-benzo[b]thiophen-5-yl)-ethylamino]-pyrimidin-4-yl}-2-propoxy-phenyl)-acetic acid;
(4-{6-[2-(3-Methoxy-1-methyl-naphthalen-2-yl)-ethylamino]-pyrimidin-4-yl}-2-propoxy-phenyl)-acetic acid;
2-Ethoxy-4-{6-[2-(7-methoxy-5-methyl-2,3-dihydro-benzo[1,4]dioxin-6-yl)-ethylamino]-pyrimidin-4-yl}-benzoic acid;
2-Cyclobutoxy-4-{6-[2-(7-methoxy-5-methyl-2,3-dihydro-benzo[1,4]dioxin-6-yl)-ethylamino]-pyrimidin-4-yl}-benzoic acid;
(4-{6-[2-(7-Methoxy-5-methyl-2,3-dihydro-benzo[1,4]dioxin-6-yl)-ethylamino]-pyrimidin-4-yl}-2-propyl-phenyl)-acetic acid;
(2-Ethoxy-6-fluoro-4-{6-[2-(7-methoxy-5-methyl-2,3-dihydro-benzo[1,4]dioxin-6-yl)-ethylamino]-pyrimidin-4-yl}-phenyl)-acetic acid;
(2-Ethoxy-4-{6-[2-(7-methoxy-5-methyl-2,3-dihydro-benzo[1,4]dioxin-6-yl)-ethylamino]-pyrimidin-4-yl}-phenyl)-acetic acid;
4-{6-[2-(7-Methoxy-5-methyl-2,3-dihydro-benzo[1,4]dioxin-6-yl)-ethylamino]-pyrimidin-4-yl}-2-methylsulfanyl-benzoic acid;
(4-{6-[2-(7-Ethoxy-2,3-dihydro-benzo[1,4]dioxin-6-yl)-ethylamino]-pyrimidin-4-yl}-2-propyl-phenyl)-acetic acid;
(2-Ethoxy-4-{6-[2-(7-ethoxy-2,3-dihydro-benzo[1,4]dioxin-6-yl)-ethylamino]-pyrimidin-4-yl}-6-fluoro-phenyl)-acetic acid;
2-Ethoxy-4-{6-[2-(7-fluoro-6-methoxy-benzo[b]thiophen-5-yl)-ethylamino]-pyrimidin-4-yl}-benzoic acid;
4-{6-[2-(7-Fluoro-6-methoxy-benzo[b]thiophen-5-yl)-ethylamino]-pyrimidin-4-yl}-2-methylsulfanyl-benzoic acid;
(2-Ethoxy-4-{6-[2-(7-fluoro-6-methoxy-benzo[b]thiophen-5-yl)-ethylamino]-pyrimidin-4-yl}-phenyl)-acetic acid;
2-Cyclobutoxy-4-{6-[2-(7-fluoro-6-methoxy-benzo[b]thiophen-5-yl)-ethylamino]-pyrimidin-4-yl}-benzoic acid;
(4-{6-[2-(5-Fluoro-7-methoxy-2,3-dihydro-benzo[1,4]dioxin-6-yl)-ethylamino]-pyrimidin-4-yl}-2-propyl-phenyl)-acetic acid;
(4-{6-[2-(7-Fluoro-6-methoxy-benzo[b]thiophen-5-yl)-ethylamino]-pyrimidin-4-yl}-2-isobutyl-phenyl)-acetic acid;
(2-Isobutyl-4-{6-[2-(7-methoxy-2,3-dihydro-benzo[1,4]dioxin-6-yl)-ethylamino]-pyrimidin-4-yl}-phenyl)-acetic acid;
(4-{6-[2-(7-Ethoxy-2,3-dihydro-benzo[1,4]dioxin-6-yl)-ethylamino]-pyrimidin-4-yl}-2-isobutyl-phenyl)-acetic acid;
4-{6-[2-(4-Fluoro-benzo[b]thiophen-5-yl)-ethylamino]-pyrimidin-4-yl}-2-isobutyl-benzoic acid;
4-{6-[2-(7-Fluoro-6-methoxy-benzo[b]thiophen-5-yl)-ethylamino]-pyrimidin-4-yl}-2-isobutyl-benzoic acid;
4-{6-[2-(7-Ethoxy-2,3-dihydro-benzo[1,4]dioxin-6-yl)-ethylamino]-pyrimidin-4-yl}-2-isobutyl-benzoic acid;
2-Ethoxy-4-{6-[2-(3-ethoxy-1-methyl-naphthalen-2-yl)-ethylamino]-pyrimidin-4-yl}-benzoic acid;
4-{6-[2-(3-Ethoxy-1-methyl-naphthalen-2-yl)-ethylamino]-pyrimidin-4-yl}-2-methylsulfanyl-benzoic acid;
(2-Ethoxy-4-{6-[2-(3-ethoxy-1-methyl-naphthalen-2-yl)-ethylamino]-pyrimidin-4-yl}-phenyl)-acetic acid;
3-(2-Ethoxy-4-{6-[2-(4-fluoro-benzo[b]thiophen-5-yl)-ethylamino]-pyrimidin-4-yl}-phenoxy)-propionic acid;
3-(2-Ethoxy-4-{6-[2-(3-methoxy-1-methyl-naphthalen-2-yl)-ethylamino]-pyrimidin-4-yl}-phenoxy)-propionic acid;
(4-{6-[2-(7-Ethoxy-2,3-dihydro-benzo[1,4]dioxin-6-yl)-ethylamino]-pyrimidin-4-yl}-2-isopropoxy-phenyl)-acetic acid;
(2-Isopropoxy-4-{6-[2-(7-methoxy-5-methyl-2,3-dihydro-benzo[1,4]dioxin-6-yl)-ethylamino]-pyrimidin-4-yl}-phenyl)-acetic acid;
(4-{6-[2-(7-Ethoxy-2,3-dihydro-benzo[1,4]dioxin-6-yl)-ethylamino]-pyrimidin-4-yl}-2-trifluoromethoxy-phenyl)-acetic acid;
(4-{6-[2-(7-Methoxy-5-methyl-2,3-dihydro-benzo[1,4]dioxin-6-yl)-ethylamino]-pyrimidin-4-yl}-2-trifluoromethoxy-phenyl)-acetic acid;
4-{6-[2-(3-Chloro-benzo[b]thiophen-5-yl)-ethylamino]-pyrimidin-4-yl}-2-methylsulfanyl-benzoic acid;
4-{6-[2-(3-Chloro-benzo[b]thiophen-5-yl)-ethylamino]-pyrimidin-4-yl}-2-cyclobutoxy-benzoic acid;
(4-{6-[2-(3-Chloro-benzo[b]thiophen-5-yl)-ethylamino]-pyrimidin-4-yl}-2-ethoxy-phenyl)-acetic acid;
2-Isopropoxy-4-{6-[2-(7-methoxy-5-methyl-2,3-dihydro-benzo[1,4]dioxin-6-yl)-ethylamino]-pyrimidin-4-yl}-benzoic acid;
5-{6-[2-(7-Difluoromethoxy-2,3-dihydro-benzo[1,4]dioxin-6-yl)-ethylamino]-pyrimidin-4-yl}-3-ethoxy-thiophene-2-carboxylic acid;
(2-Methoxy-4-{6-[2-(7-methoxy-5-methyl-2,3-dihydro-benzo[1,4]dioxin-6-yl)-ethylamino]-pyrimidin-4-yl}-phenyl)-acetic acid;
2-Ethoxy-4-{6-[2-(5-fluoro-7-methoxy-2,3-dihydro-benzo[1,4]dioxin-6-yl)-ethylamino]-pyrimidin-4-yl}-benzoic acid;
2-Ethoxy-4-{6-[2-(3-ethoxy-1-fluoro-naphthalen-2-yl)-ethylamino]-pyrimidin-4-yl}-benzoic acid;
3-(4-{6-[2-(4-Fluoro-benzo[b]thiophen-5-yl)-ethylamino]-pyrimidin-4-yl}-2-methoxy-phenoxy)-propionic acid;
2-Ethoxy-4-{6-[2-(7-ethynyl-2,3-dihydro-benzo[1,4]dioxin-6-yl)-ethylamino]-pyrimidin-4-yl}-benzoic acid;
(4-{6-[2-(7-Ethynyl-2,3-dihydro-benzo[1,4]dioxin-6-yl)-ethylamino]-pyrimidin-4-yl}-2-propyl-phenyl)-acetic acid;
(2-Difluoromethoxy-4-{6-[2-(7-methoxy-5-methyl-2,3-dihydro-benzo[1,4]dioxin-6-yl)-ethylamino]-pyrimidin-4-yl}-phenyl)-acetic acid;
(2-Difluoromethoxy-4-{6-[2-(5-fluoro-7-methoxy-2,3-dihydro-benzo[1,4]dioxin-6-yl)-ethylamino]-pyrimidin-4-yl}-phenyl)-acetic acid;
(2-Difluoromethoxy-4-{6-[2-(3-methoxy-1-methyl-naphthalen-2-yl)-ethylamino]-pyrimidin-4-yl}-phenyl)-acetic acid;
(2-Ethyl-4-{6-[2-(7-methoxy-5-methyl-2,3-dihydro-benzo[1,4]dioxin-6-yl)-ethylamino]-pyrimidin-4-yl}-phenyl)-acetic acid;
(2-Ethyl-4-{6-[2-(3-methoxy-1-methyl-naphthalen-2-yl)-ethylamino]-pyrimidin-4-yl}-phenyl)-acetic acid;
2-Ethyl-4-{6-[2-(3-methoxy-1-methyl-naphthalen-2-yl)-ethylamino]-pyrimidin-4-yl}-benzoic acid;

2-Cyclopropoxy-4-{6-[2-(7-ethoxy-2,3-dihydro-benzo[1,4]dioxin-6-yl)-ethylamino]-pyrimidin-4-yl}-benzoic acid;
2-Cyclopropoxy-4-{6-[2-(3-methoxy-1-methyl-naphthalen-2-yl)-ethylamino]-pyrimidin-4-yl}-benzoic acid;
2-Cyclopropoxy-4-{6-[2-(7-fluoro-benzo[b]thiophen-5-yl)-ethylamino]-pyrimidin-4-yl}-benzoic acid;
(4-{6-[2-(7-Methoxy-2,3-dihydro-benzo[1,4]dioxin-6-yl)-ethylamino]-pyrimidin-4-yl}-2-trifluoromethoxy-phenyl)-acetic acid;
3-(2-Ethoxy-4-{6-[2-(7-fluoro-benzo[b]thiophen-5-yl)-ethylamino]-pyrimidin-4-yl}-phenyl)-[1,2,4]oxadiazol-5(4H)-one;
3-(2-Ethoxy-4-{6-[2-(7-fluoro-benzo[b]thiophen-5-yl)-ethylamino]-pyrimidin-4-yl}-phenyl)-[1,2,4]oxadiazol-5-ol;
{6-[3-Ethoxy-4-(1H-tetrazol-5-yl)-phenyl]-pyrimidin-4-yl}-[2-(7-fluoro-benzo[b]thiophen-5-yl)-ethyl]-amine;
4-{6-[2-(7-Fluoro-benzo[b]thiophen-5-yl)-ethylamino]-pyrimidin-4-yl}-2-isobutoxy-benzoic acid;
(3-Ethoxy-5-{6-[2-(7-fluoro-benzo[b]thiophen-5-yl)-ethylamino]-pyrimidin-4-yl}-thiophen-2-yl)-acetic acid;
4-{6-[2-(7-Fluoro-benzo[b]thiophen-5-yl)-ethylamino]-pyrimidin-4-yl}-2-propyl-benzamide;
4-{6-[2-(7-Fluoro-6-methoxy-benzo[b]thiophen-5-yl)-ethylamino]-pyrimidin-4-yl}-2-propyl-benzoic acid;
3-Ethoxy-5-{6-[2-(7-fluoro-6-methoxy-benzo[b]thiophen-5-yl)-ethylamino]-pyrimidin-4-yl}-thiophene-2-carboxylic acid;
(4-{6-[2-(7-Fluoro-6-methoxy-benzo[b]thiophen-5-yl)-ethylamino]-pyrimidin-4-yl}-2-methoxy-phenyl)-acetic acid;
(4-{6-[2-(7-Fluoro-6-methoxy-benzo[b]thiophen-5-yl)-ethylamino]-pyrimidin-4-yl}-2-propyl-phenyl)-acetic acid;
2-(4-{6-[2-(7-Ethoxy-2,3-dihydro-benzo[1,4]dioxin-6-yl)-ethylamino]-pyrimidin-4-yl}-2-propyl-phenyl)-propionic acid;
4-{6-[2-(3-Chloro-benzo[b]thiophen-5-yl)-ethylamino]-pyrimidin-4-yl}-2-ethoxy-benzoic acid;
4-{6-[2-(7-Difluoromethoxy-2,3-dihydro-benzo[1,4]dioxin-6-yl)-ethylamino]-pyrimidin-4-yl}-2-methylsulfanyl-benzoic acid;
(4-{6-[2-(3-Chloro-benzo[b]thiophen-5-yl)-ethylamino]-pyrimidin-4-yl}-2-propyl-phenyl)-acetic acid;
(4-{6-[2-(3-Chloro-benzo[b]thiophen-5-yl)-ethylamino]-pyrimidin-4-yl}-2-trifluoromethoxy-phenyl)-acetic acid;
(4-{6-[2-(3-Methoxy-1-methyl-naphthalen-2-yl)-ethylamino]-pyrimidin-4-yl}-2-trifluoromethoxy-phenyl)-acetic acid;
(4-{6-[2-(7-Ethynyl-2,3-dihydro-benzo[1,4]dioxin-6-yl)-ethylamino]-pyrimidin-4-yl}-2-methoxy-phenyl)-acetic acid;
(4-{6-[2-(5-Methyl-2,3-dihydro-benzo[1,4]dioxin-6-yl)-ethylamino]-pyrimidin-4-yl}-2-propyl-phenyl)-acetic acid;
(2-Difluoromethoxy-4-{6-[2-(7-ethoxy-2,3-dihydro-benzo[1,4]dioxin-6-yl)-ethylamino]-pyrimidin-4-yl}-phenyl)-acetic acid;
2-Ethyl-4-{6-[2-(7-fluoro-benzo[b]thiophen-5-yl)-ethylamino]-pyrimidin-4-yl}-benzoic acid;
2-Cyclopropoxy-4-{6-[2-(7-methoxy-2,3-dihydro-benzo[1,4]dioxin-6-yl)-ethylamino]-pyrimidin-4-yl}-benzoic acid;
2-Cyclopropoxy-4-{6-[2-(1-methyl-naphthalen-2-yl)-ethylamino]-pyrimidin-4-yl}-benzoic acid;
(3-Difluoromethoxy-5-{6-[2-(7-fluoro-benzo[b]thiophen-5-yl)-ethylamino]-pyrimidin-4-yl}-thiophen-2-yl)-acetic acid;
3-(2-Ethoxy-4-{6-[2-(1-methyl-naphthalen-2-yl)-ethylamino]-pyrimidin-4-yl}-phenyl)-[1,2,4]oxadiazole-5(4H)-thione;
3-(2-Ethoxy-4-{6-[2-(1-methyl-naphthalen-2-yl)-ethylamino]-pyrimidin-4-yl}-phenyl)-[1,2,4]oxadiazole-5-thiol;
(4-{6-[2-(6-Methoxy-benzo[b]thiophen-5-yl)-ethylamino]-pyrimidin-4-yl}-2-propoxy-phenyl)-acetic acid;
2-Butoxy-4-{6-[2-(7-fluoro-benzo[b]thiophen-5-yl)-ethylamino]-pyrimidin-4-yl}-benzoic acid;
2-Ethoxy-4-{6-[2-(5-methyl-2,3-dihydro-benzo[1,4]dioxin-6-yl)-ethylamino]-pyrimidin-4-yl}-benzoic acid;
(4-{6-[2-(5-Methyl-2,3-dihydro-benzo[1,4]dioxin-6-yl)-ethylamino]-pyrimidin-4-yl}-2-trifluoromethoxy-phenyl)-acetic acid;
(4-{6-[2-(7-Ethoxy-2,3-dihydro-benzo[1,4]dioxin-6-yl)-ethylamino]-pyrimidin-4-yl}-2-ethyl-phenyl)-acetic acid;
2-Ethyl-4-{6-[2-(5-methyl-2,3-dihydro-benzo[1,4]dioxin-6-yl)-ethylamino]-pyrimidin-4-yl}-benzoic acid;
4-{6-[2-(7-Ethoxy-2,3-dihydro-benzo[1,4]dioxin-6-yl)-ethylamino]-pyrimidin-4-yl}-2-ethyl-benzoic acid;
2-Cyclopropoxy-4-{6-[2-(5-methyl-2,3-dihydro-benzo[1,4]dioxin-6-yl)-ethylamino]-pyrimidin-4-yl}-benzoic acid;
(4-{6-[2-(7-Methyl-2,3-dihydro-benzo[1,4]dioxin-6-yl)-ethylamino]-pyrimidin-4-yl}-2-propyl-phenyl)-acetic acid;
(4-{6-[2-(3-Cyano-1-methyl-naphthalen-2-yl)-ethylamino]-pyrimidin-4-yl}-2-ethoxy-phenyl)-acetic acid;
(2-Ethoxy-4-{6-[2-(7-fluoro-benzo[b]thiophen-5-yl)-ethylamino]-pyrimidin-4-yl}-phenyl)-acetic acid;
(2-Ethoxy-4-{6-[2-(4-fluoro-benzo[b]thiophen-5-yl)-ethylamino]-pyrimidin-4-yl}-phenyl)-acetic acid;
(2-Ethoxy-6-fluoro-4-{6-[2-(3-methoxy-1-methyl-naphthalen-2-yl)-ethylamino]-pyrimidin-4-yl}-phenyl)-acetic acid;
(2-Ethoxy-6-fluoro-4-{6-[2-(4-fluoro-benzo[b]thiophen-5-yl)-ethylamino]-pyrimidin-4-yl}-phenyl)-acetic acid;
(4-{6-[2-(7-Fluoro-benzo[b]thiophen-5-yl)-ethylamino]-pyrimidin-4-yl}-2-propyl-phenyl)-acetic acid;
(4-{6-[2-(4-Fluoro-benzo[b]thiophen-5-yl)-ethylamino]-pyrimidin-4-yl}-2-isobutyl-phenyl)-acetic acid;
4-{6-[2-(7-Fluoro-benzo[b]thiophen-5-yl)-ethylamino]-pyrimidin-4-yl}-2-isobutyl-benzoic acid;
2-Isobutyl-4-{6-[2-(7-methoxy-2,3-dihydro-benzo[1,4]dioxin-6-yl)-ethylamino]-pyrimidin-4-yl}-benzoic acid;
3-(2-Ethoxy-4-{6-[2-(7-fluoro-benzo[b]thiophen-5-yl)-ethylamino]-pyrimidin-4-yl}-phenoxy)-propionic acid;
(4-{6-[2-(4-Fluoro-benzo[b]thiophen-5-yl)-ethylamino]-pyrimidin-4-yl}-2-isopropoxy-phenyl)-acetic acid;
3-(4-{6-[2-(7-Fluoro-benzo[b]thiophen-5-yl)-ethylamino]-pyrimidin-4-yl}-2-methoxy-phenoxy)-propionic acid;
3-Ethyl-5-{6-[2-(7-fluoro-benzo[b]thiophen-5-yl)-ethylamino]-pyrimidin-4-yl}-thiophene-2-carboxylic acid;
2-Ethoxy-4-{6-[2-(7-fluoro-benzo[b]thiophen-5-yl)-ethylamino]-pyrimidin-4-yl}-N-(2-hydroxy-ethyl)-benzamide;
(4-{6-[2-(7-Fluoro-benzo[b]thiophen-5-yl)-ethylamino]-pyrimidin-4-yl}-2-methoxy-phenyl)-acetic acid;

2-{4-[6-(2-Benzo[b]thiophen-5-yl-ethylamino)-pyrimidin-4-yl]-2-propyl-phenyl}-propionic acid;
2-(4-{6-[2-(4-Fluoro-benzo[b]thiophen-5-yl)-ethylamino]-pyrimidin-4-yl}-2-propyl-phenyl)-propionic acid;
3-Ethoxy-5-{6-[2-(7-trifluoromethyl-benzo[b]thiophen-5-yl)-ethylamino]-pyrimidin-4-yl}-thiophene-2-carboxylic acid;
3-(4-(6-((2-(7-fluorobenzo[b]thiophen-5-yl)ethyl)amino)pyrimidin-4-yl)phenyl)-[1,2,4]oxadiazol-5(4H)-one;
3-(4-{6-[2-(7-Fluoro-benzo[b]thiophen-5-yl)-ethylamino]-pyrimidin-4-yl}-phenyl)-[1,2,4]oxadiazol-5-ol;
7-{6-[2-(7-Fluoro-benzo[b]thiophen-5-yl)-ethylamino]-pyrimidin-4-yl}-1-methyl-3,4-dihydro-1H-quinazolin-2-one;
4-{6-[2-(7-Fluoro-benzo[b]thiophen-5-yl)-ethylamino]-pyrimidin-4-yl}-2,6-dimethyl-phenol;
2-Ethylsulfanyl-4-{6-[2-(7-fluoro-benzo[b]thiophen-5-yl)-ethylamino]-pyrimidin-4-yl}-benzoic acid;
2-Cyclobutoxy-4-{6-[2-(7-fluoro-benzo[b]thiophen-5-yl)-ethylamino]-pyrimidin-4-yl}-benzoic acid;
3-(3-Ethoxy-5-{6-[2-(7-fluoro-benzo[b]thiophen-5-yl)-ethylamino]-pyrimidin-4-yl}-thiophen-2-yl)-propionic acid;
3-(4-{6-[2-(7-Fluoro-benzo[b]thiophen-5-yl)-ethylamino]-pyrimidin-4-yl}-phenyl)-4-hydroxy-cyclobut-3-ene-1,2-dione;
(2-Ethoxy-4-{6-[2-(7-fluoro-benzo[b]thiophen-5-yl)-ethylamino]-pyrimidin-4-yl}-phenyl)-oxo-acetic acid;
2-Cyclopropoxy-4-{6-[2-(7-fluoro-benzo[b]thiophen-5-yl)-ethylamino]-pyrimidin-4-yl}-benzoic acid methyl ester;
(2-Chloro-6-ethyl-4-{6-[2-(7-fluoro-benzo[b]thiophen-5-yl)-ethylamino]-pyrimidin-4-yl}-phenyl)-acetic acid;
(2-Ethyl-4-{6-[2-(7-fluoro-benzo[b]thiophen-5-yl)-ethylamino]-pyrimidin-4-yl}-6-methyl-phenyl)-acetic acid;
(3-Ethyl-5-{6-[2-(7-fluoro-benzo[b]thiophen-5-yl)-ethylamino]-pyrimidin-4-yl}-thiophen-2-yl)-acetic acid;
5-(2-Ethoxy-4-{6-[2-(7-fluoro-benzo[b]thiophen-5-yl)-ethylamino]-pyrimidin-4-yl}-phenyl)-isoxazol-3-ol;
5-(2-ethoxy-4-(6-((2-(7-fluorobenzo[b]thiophen-5-yl)ethyl)amino)pyrimidin-4-yl)phenyl)isoxazol-3(2H)-one;
5-(4-{6-[2-(7-Fluoro-benzo[b]thiophen-5-yl)-ethylamino]-pyrimidin-4-yl}-2-methoxy-phenyl)-isoxazol-3-ol;
5-(4-(6-((2-(7-fluorobenzo[b]thiophen-5-yl)ethyl)amino)pyrimidin-4-yl)-2-methoxyphenyl)isoxazol-3(2H)-one; and
(5-{6-[2-(7-Fluoro-benzo[b]thiophen-5-yl)-ethylamino]-pyrimidin-4-yl}-3-propyl-thiophen-2-yl)-acetic acid;
or a pharmaceutically acceptable salt thereof.

9. A pharmaceutical composition comprising, as active principle, a compound according claim 1, or a pharmaceutically acceptable salt thereof, and at least one therapeutically inert excipient.

10. A method of modulating an immune response in a subject having a tumor, comprising administering to a subject in need thereof an effective amount of a compound of formula (II) according to claim 1, or a pharmaceutically acceptable salt thereof, wherein said effective amount reactivates the subject's immune system in the tumor.

11. A method of treatment of cancer; pain; endometriosis; autosomal dominant polycystic kidney disease; an acute ischemic syndrome in an atherosclerotic patient; pneumonia; or a neurodegenerative disease; or for control of female fertility; comprising administering to a subject in need thereof an effective amount of a compound of formula (II) according to claim 1, or a pharmaceutically acceptable salt thereof.

12. A method of treatment of a cancer selected from melanoma; lung cancer; bladder cancer; renal carcinomas; gastro-intestinal cancers; endometrial cancer; ovarian cancer; cervical cancer; neuroblastoma; and prostate cancer; comprising administering to a subject in need thereof an effective amount of a compound of formula (II) according to claim 1, or a pharmaceutically acceptable salt thereof.

13. A method of treatment of a cancer in a subject in need thereof, wherein said cancer is treated by modulating an immune response comprising a reactivation of subject's immune system in tumor; comprising administering to the subject an effective amount of a compound of formula (II) according to claim 1, or a pharmaceutically acceptable salt thereof, and optionally administering one or more chemotherapy agents and/or radiotherapy and/or targeted therapy.

14. A pharmaceutical composition comprising, as active principle, a compound according claim 7, or a pharmaceutically acceptable salt thereof, and at least one therapeutically inert excipient.

15. A method of treatment of cancer; pain; endometriosis; autosomal dominant polycystic kidney disease; an acute ischemic syndrome in an atherosclerotic patient; pneumonia; or a neurodegenerative disease; or for control of female fertility; comprising administering to a subject in need thereof an effective amount of a compound according to claim 7, or a pharmaceutically acceptable salt thereof.

16. A method of treatment of a cancer in a subject in need thereof, wherein said cancer is treated by modulating an immune response comprising a reactivation of subject's immune system in tumor; comprising administering to the subject an effective amount of a compound according to claim 7, or a pharmaceutically acceptable salt thereof, and optionally administering one or more chemotherapy agents and/or radiotherapy and/or targeted therapy.

17. A pharmaceutical composition comprising, as active principle, a compound according claim 8, or a pharmaceutically acceptable salt thereof, and at least one therapeutically inert excipient.

18. A method of treatment of a cancer selected from melanoma; lung cancer; bladder cancer; renal carcinomas; gastro-intestinal cancers; endometrial cancer; ovarian cancer; cervical cancer; neuroblastoma; and prostate cancer; comprising administering to a subject in need thereof an effective amount of a compound according to claim 8, or a pharmaceutically acceptable salt thereof.

19. A method of treatment of cancer; pain; endometriosis; autosomal dominant polycystic kidney disease; an acute ischemic syndrome in an atherosclerotic patient; pneumonia; or a neurodegenerative disease; or for control of female fertility; comprising administering to a subject in need thereof an effective amount of a compound according to claim 8, or a pharmaceutically acceptable salt thereof.

20. A method of treatment of a cancer in a subject in need thereof, wherein said cancer is treated by modulating an immune response comprising a reactivation of subject's immune system in tumor; comprising administering to the subject an effective amount of a compound according to claim 8, or a pharmaceutically acceptable salt thereof, and optionally administering one or more chemotherapy agents and/or radiotherapy and/or targeted therapy.

* * * * *